United States Patent
Wu et al.

(10) Patent No.: US 10,301,280 B2
(45) Date of Patent: May 28, 2019

(54) COMPOUNDS AND METHODS FOR KINASE MODULATION, AND INDICATIONS THEREFOR

(71) Applicant: Plexxikon Inc., Berkeley, CA (US)

(72) Inventors: Guoxian Wu, Foster City, CA (US);
Katrina Chan, Fremont, CA (US);
Todd Ewing, Walnut Creek, CA (US);
Prabha N. Ibrahim, Mountain View, CA (US); Jack Lin, Hercules, CA (US);
Marika Nespi, Berkeley, CA (US);
Wayne Spevak, Berkeley, CA (US);
Ying Zhang, Fremont, CA (US)

(73) Assignee: Plexxikon Inc., Berkeley, CA (US)

( * ) Notice: Subject to any disclaimer, the term of this patent is extended or adjusted under 35 U.S.C. 154(b) by 0 days.

(21) Appl. No.: 15/620,396

(22) Filed: Jun. 12, 2017

(65) Prior Publication Data

US 2017/0349572 A1    Dec. 7, 2017

Related U.S. Application Data

(62) Division of application No. 14/137,438, filed on Dec. 20, 2013, now Pat. No. 9,676,748.

(60) Provisional application No. 61/784,928, filed on Mar. 14, 2013, provisional application No. 61/745,409, filed on Dec. 21, 2012.

(51) Int. Cl.
| | |
|---|---|
| *C07D 403/12* | (2006.01) |
| *C07D 401/12* | (2006.01) |
| *C07D 471/04* | (2006.01) |
| *C07D 487/04* | (2006.01) |
| *C07D 513/04* | (2006.01) |
| *A61K 31/519* | (2006.01) |
| *A61K 31/506* | (2006.01) |
| *A61K 31/437* | (2006.01) |
| *A61K 31/675* | (2006.01) |
| *C07F 5/02* | (2006.01) |
| *A61K 31/5377* | (2006.01) |
| *C07F 9/6561* | (2006.01) |

(52) U.S. Cl.
CPC .......... *C07D 401/12* (2013.01); *A61K 31/437* (2013.01); *A61K 31/506* (2013.01); *A61K 31/519* (2013.01); *A61K 31/5377* (2013.01); *A61K 31/675* (2013.01); *C07D 403/12* (2013.01); *C07D 471/04* (2013.01); *C07D 487/04* (2013.01); *C07D 513/04* (2013.01); *C07F 5/025* (2013.01); *C07F 9/65616* (2013.01)

(58) Field of Classification Search
CPC .. C07D 403/12; C07D 401/12; C07D 471/04; C07D 487/04; C07D 513/04; A61K 31/519; A61K 31/506; A61K 31/437; A61K 31/675; C07F 5/02
See application file for complete search history.

(56) References Cited

U.S. PATENT DOCUMENTS

| | | | |
|---|---|---|---|
| 7,202,266 B2 | 4/2007 | Arnold et al. | |
| 7,348,338 B2 | 3/2008 | Arnold et al. | |
| 7,476,746 B2 | 1/2009 | Artis et al. | |
| 7,491,831 B2 | 2/2009 | Artis et al. | |
| 7,498,342 B2 | 3/2009 | Ibrahim et al. | |
| 7,504,509 B2 | 3/2009 | Ibrahim et al. | |
| 7,517,970 B2 | 4/2009 | West | |
| 7,531,568 B2 | 5/2009 | Lin et al. | |
| 7,572,806 B2 | 8/2009 | Arnold et al. | |
| 7,585,859 B2 | 9/2009 | Ibrahim et al. | |
| 7,605,168 B2 | 10/2009 | Ibrahim et al. | |
| 7,723,374 B2 | 5/2010 | Artis et al. | |
| 7,728,140 B2 | 6/2010 | Salom et al. | |
| 7,759,475 B2 | 7/2010 | West | |
| 7,846,941 B2 | 12/2010 | Zhang et al. | |
| 7,863,288 B2 | 1/2011 | Ibrahim et al. | |
| 7,863,289 B2 | 1/2011 | Spevak et al. | |
| 7,872,018 B2 | 1/2011 | Ibrahim et al. | |
| 7,893,075 B2 | 2/2011 | Zhang et al. | |
| 7,947,708 B2 | 5/2011 | Ibrahim et al. | |
| 8,053,463 B2 | 11/2011 | Lin et al. | |
| 8,067,434 B2 | 11/2011 | Ibrahim et al. | |
| 8,110,576 B2 | 2/2012 | Ibrahim et al. | |
| 8,119,637 B2 | 2/2012 | Ibrahim et al. | |
| 8,129,404 B2 | 3/2012 | Ibrahim et al. | |
| 8,143,271 B2 | 3/2012 | Ibrahim et al. | |
| 8,153,641 B2 | 4/2012 | Ibrahim et al. | |
| 8,158,636 B2 | 4/2012 | Ibrahim et al. | |
| 8,198,273 B2 | 6/2012 | Ibrahim et al. | |
| 8,268,858 B2 | 9/2012 | Wu et al. | |
| 8,367,828 B2 | 2/2013 | Arnold et al. | |
| 8,404,700 B2 | 3/2013 | Ibrahim et al. | |
| 8,415,469 B2 | 4/2013 | Ibrahim et al. | |
| 8,461,169 B2 | 6/2013 | Zhang et al. | |
| 8,470,818 B2 | 6/2013 | Ibrahim et al. | |
| 8,470,821 B2 | 6/2013 | Ibrahim et al. | |

(Continued)

FOREIGN PATENT DOCUMENTS

| | | |
|---|---|---|
| EP | 2522658 | 11/2012 |
| JP | 2006-504711 | 2/2006 |

(Continued)

OTHER PUBLICATIONS

Appel et al., Publ Jul. 6, 2017, www.nature.com/scientificreports, 7:4792, p. 1-14.*

(Continued)

*Primary Examiner* — Sun Jae Yoo
(74) *Attorney, Agent, or Firm* — Sheppard Mullin Richter & Hampton LLP

(57) ABSTRACT

Compounds active on c-kit protein kinases or mutant c-kit protein kinases having any mutations are described, as well as methods of making and using such compounds to treat diseases and conditions associated with aberrant activity of the c-kit protein kinases and/or mutant c-kit protein kinases.

21 Claims, No Drawings
Specification includes a Sequence Listing.

(56) References Cited

U.S. PATENT DOCUMENTS

| | | | |
|---|---|---|---|
| 8,580,815 B2* | 11/2013 | Yasri | C07D 471/04 514/300 |
| 8,642,606 B2 | 2/2014 | Ibrahim et al. | |
| 8,673,928 B2 | 3/2014 | Ibrahim et al. | |
| 8,722,702 B2 | 5/2014 | Zhang et al. | |
| 8,865,735 B2 | 10/2014 | Ibrahim et al. | |
| 8,901,118 B2 | 12/2014 | Zhang et al. | |
| 8,901,301 B2 | 12/2014 | Ibrahim et al. | |
| 8,912,204 B2 | 12/2014 | Ibrahim et al. | |
| 9,096,593 B2 | 8/2015 | Zhang et al. | |
| 9,150,570 B2 | 10/2015 | Ibrahim et al. | |
| 9,169,250 B2 | 10/2015 | Zhang et al. | |
| 9,260,437 B2 | 2/2016 | Ibrahim et al. | |
| 9,358,235 B2 | 6/2016 | Bollag et al. | |
| 9,440,969 B2 | 9/2016 | Ibrahim et al. | |
| 9,447,089 B2 | 9/2016 | Desai et al. | |
| 9,469,640 B2 | 10/2016 | Wu et al. | |
| 9,487,515 B2 | 11/2016 | Zhang et al. | |
| 9,550,768 B2 | 1/2017 | Zhang et al. | |
| 9,617,267 B2 | 4/2017 | Ibrahim et al. | |
| 9,624,213 B2 | 4/2017 | Ibrahim et al. | |
| 9,663,517 B2 | 5/2017 | Desai et al. | |
| 9,676,748 B2 | 6/2017 | Wu et al. | |
| 9,682,981 B2 | 6/2017 | Zhang et al. | |
| 2004/0002534 A1 | 1/2004 | Lipson et al. | |
| 2004/0077585 A1 | 4/2004 | Peterson et al. | |
| 2004/0077595 A1 | 4/2004 | Cheng et al. | |
| 2004/0142864 A1 | 7/2004 | Bremer et al. | |
| 2004/0171062 A1 | 9/2004 | Hirth et al. | |
| 2005/0048573 A1 | 3/2005 | Artis et al. | |
| 2005/0079548 A1 | 4/2005 | Artis et al. | |
| 2005/0164300 A1 | 7/2005 | Artis et al. | |
| 2005/0170431 A1 | 8/2005 | Ibrahim et al. | |
| 2006/0035921 A1 | 2/2006 | Castelhano et al. | |
| 2006/0058339 A1 | 3/2006 | Ibrahim et al. | |
| 2006/0058340 A1 | 3/2006 | Ibrahim et al. | |
| 2006/0135540 A1 | 6/2006 | Lin et al. | |
| 2006/0160135 A1 | 7/2006 | Wang et al. | |
| 2007/0032519 A1 | 2/2007 | Zhang et al. | |
| 2007/0066641 A1 | 3/2007 | Ibrahim et al. | |
| 2007/0072862 A1 | 3/2007 | Dimauro et al. | |
| 2007/0072904 A1 | 3/2007 | Lin et al. | |
| 2008/0221127 A1 | 9/2008 | Lin et al. | |
| 2008/0234349 A1 | 9/2008 | Lin et al. | |
| 2008/0249137 A1 | 10/2008 | Lin et al. | |
| 2009/0076275 A1 | 3/2009 | Bolin et al. | |
| 2009/0155202 A1 | 6/2009 | Dervan et al. | |
| 2010/0190777 A1 | 7/2010 | Wu et al. | |
| 2010/0234379 A1 | 9/2010 | Bahr et al. | |
| 2010/0310659 A1 | 12/2010 | Desai et al. | |
| 2011/0092538 A1 | 4/2011 | Spevak et al. | |
| 2011/0112127 A1 | 5/2011 | Zhang et al. | |
| 2011/0166174 A1 | 7/2011 | Zhang et al. | |
| 2011/0183988 A1 | 7/2011 | Ibrahim et al. | |
| 2012/0015966 A1 | 1/2012 | Lin et al. | |
| 2012/0053177 A1 | 3/2012 | Ibrahim et al. | |
| 2012/0122860 A1 | 5/2012 | Visor et al. | |
| 2012/0165366 A1 | 6/2012 | Ibrahim et al. | |
| 2012/0245174 A1 | 9/2012 | Ibrahim et al. | |
| 2013/0237531 A1 | 9/2013 | Wu et al. | |
| 2013/0261117 A1 | 10/2013 | Ibrahim et al. | |
| 2013/0274259 A1 | 10/2013 | Zhang et al. | |
| 2013/0303534 A1 | 11/2013 | Ibrahim et al. | |
| 2014/0037617 A1 | 2/2014 | Bollag et al. | |
| 2014/0038948 A1 | 2/2014 | Wu et al. | |
| 2014/0045840 A1 | 2/2014 | Zhang et al. | |
| 2014/0094611 A1 | 4/2014 | Ibrahim | |
| 2014/0128373 A1 | 5/2014 | Ibrahim et al. | |
| 2014/0128390 A1 | 5/2014 | Lin et al. | |
| 2014/0243365 A1 | 8/2014 | Zhang et al. | |
| 2014/0288070 A1 | 9/2014 | Ibrahim et al. | |
| 2014/0303121 A1 | 10/2014 | Zhang et al. | |
| 2014/0303187 A1 | 10/2014 | Wu et al. | |
| 2014/0357612 A1 | 12/2014 | Zhang et al. | |
| 2015/0080372 A1 | 3/2015 | Ibrahim et al. | |
| 2015/0133400 A1 | 5/2015 | Zhang et al. | |
| 2015/0166547 A1 | 6/2015 | Ibrahim et al. | |
| 2015/0183793 A1 | 7/2015 | Zhang et al. | |
| 2015/0284397 A1 | 10/2015 | Lin et al. | |
| 2015/0290205 A1 | 10/2015 | Ibrahim et al. | |
| 2015/0368243 A1 | 12/2015 | Ibrahim | |
| 2016/0045505 A1* | 2/2016 | Jiricek | C07D 491/08 514/63 |
| 2016/0068528 A1 | 3/2016 | Zhang et al. | |
| 2016/0075712 A1 | 3/2016 | Shi et al. | |
| 2016/0176865 A1 | 6/2016 | Ibrahim et al. | |
| 2016/0243092 A1 | 8/2016 | Bollag et al. | |
| 2016/0326162 A1 | 11/2016 | Lin et al. | |
| 2016/0326168 A1 | 11/2016 | Ibrahim et al. | |
| 2016/0326169 A1 | 11/2016 | Ibrahim et al. | |
| 2016/0339025 A1 | 11/2016 | Ibrahim et al. | |
| 2016/0340357 A1 | 11/2016 | Ibrahim et al. | |
| 2016/0340358 A1 | 11/2016 | Ibrahim et al. | |
| 2017/0029413 A1 | 2/2017 | Holladay et al. | |
| 2017/0056382 A1 | 3/2017 | Wu et al. | |
| 2017/0081326 A1 | 3/2017 | Ibrahim et al. | |
| 2017/0157120 A1 | 6/2017 | Ibrahim et al. | |
| 2017/0158690 A1 | 6/2017 | Wu et al. | |
| 2017/0247370 A1 | 8/2017 | Zhang et al. | |
| 2017/0267660 A1 | 9/2017 | Lin et al. | |
| 2017/0283423 A1 | 10/2017 | Zhang et al. | |
| 2017/0319559 A1 | 11/2017 | Wu et al. | |
| 2017/0320899 A1 | 11/2017 | Zhang et al. | |
| 2017/0334909 A1 | 11/2017 | Ibrahim et al. | |
| 2017/0349572 A1 | 12/2017 | Wu et al. | |
| 2017/0362231 A1 | 12/2017 | Ibrahim et al. | |
| 2018/0002332 A1 | 1/2018 | Ibrahim et al. | |
| 2018/0030051 A1 | 2/2018 | Ibrahim et al. | |
| 2018/0055828 A1 | 3/2018 | Bollag et al. | |
| 2018/0072722 A1 | 3/2018 | Zhang et al. | |
| 2018/0099939 A1 | 4/2018 | Zhang et al. | |
| 2018/0099975 A1 | 4/2018 | Zhang et al. | |
| 2018/0111929 A1 | 4/2018 | Ibrahim et al. | |
| 2018/0111930 A1 | 4/2018 | Desai et al. | |

FOREIGN PATENT DOCUMENTS

| | | |
|---|---|---|
| JP | 2007-502822 | 2/2007 |
| JP | 2008-528469 | 7/2008 |
| WO | WO-2000/027394 | 5/2000 |
| WO | WO-2002/020480 | 3/2002 |
| WO | WO-2003/087087 | 10/2003 |
| WO | WO-2004/014864 | 2/2004 |
| WO | WO-2004/108133 | 12/2004 |
| WO | WO-2005/094805 | 10/2005 |
| WO | WO-2006/032851 | 3/2006 |
| WO | WO-2007/013896 A2 | 2/2007 |
| WO | WO-2007/051981 | 5/2007 |
| WO | WO-2008/048991 | 4/2008 |
| WO | WO-2008/079346 | 7/2008 |
| WO | WO-2008/112695 | 9/2008 |
| WO | WO-2008/144253 | 11/2008 |
| WO | WO-2009/073788 | 6/2009 |
| WO | WO-2009/112445 | 9/2009 |
| WO | WO-2010/092489 | 8/2010 |
| WO | WO-2010/111527 A1 | 9/2010 |
| WO | WO-2010/129467 A1 | 11/2010 |
| WO | WO-2011/024869 | 3/2011 |
| WO | WO-2011/116176 | 9/2011 |
| WO | WO-2013/040215 | 3/2013 |

OTHER PUBLICATIONS

Epilepsy and Seizure Medications List, 2018, https://www.healthline.com/health/epilepsy/medications-list#Introduction1.*
Mehdi et al., 2016, International Journal of Molecular Sciences, 17, 1585, p. 1-12.*
Gagalo et al., Current Neuropharmacology, 2015, 13, 836-844.*
Babaei et al., 2016, 10, 2443-2459.*
PolycysticKidneyDisease, 2017, https://www.gstatic.com/healthricherkp/pdf/polycystic_kidney_disease.pdf.*

(56) References Cited

OTHER PUBLICATIONS

New Treatments for Your Chronic Pain, 2018, https://www.webmd.com/pain-management/features/chronic-pain-relief-new-treatments#1.*
ProteinKinaseInhibitor, 2018, https://en.wikipedia.org/wiki/Protein_kinase_inhibitor.*
Ohashi et al., 2011, caplus an 2011:262243.*
U.S. Appl. No. 15/605,856, filed May 25, 2017, Ibrahim.
U.S. Appl. No. 15/606,682, filed May 26, 2017, Desai.
U.S. Appl. No. 15/669,353, filed Aug. 4, 2017, Bollag.
U.S. Appl. No. 15/713,502, filed Sep. 22, 2017, Zhang et al.
U.S. Appl. No. 15/725,197, filed Oct. 4, 2017, Ibrahim et al.
U.S. Appl. No. 15/814,179, filed Nov. 15, 2017, Zhang et al.
U.S. Appl. No. 15/838,268, filed Dec. 11, 2017, Zhang.
U.S. Appl. No. 15/851,639, filed Dec. 21, 2017, Wu et al.
Cheve et al., 2012, caplus an 2012:940201.
Clemence, et al., "4-Hydroxy-3-quinolinecarboxamides with antiarthritic and analgesic activities," Journal of Medicinal Chemistry, 31(7):1453-1462 (1988).
Database Registry [Online] Chemical Abstracts Service, Database accession No. 1253912-30-9; XP002724645, Nov. 22, 2010).
Francois et al., "4-Hydroxy-3-quinolinecarboxamides with antiarthritic and analgesic activities", Journal of Medicinal Chemistry, vol. 31, No. 7, Jul. 1, 1988, pp. 1453-1462.
Haddach et al., 2011, caplus an 2011:720871.
International Search Report and Written Opinion for PCT/US2013/076995, dated Jul. 2, 2014.
Jiricek et al., 2014, caplus an 2014:1593138.
Kiselyov et al., "Novel inhibitors of VEGF receptors-1 and -2 based on azole-5-carboxamide templates", Bioorganic & Medicinal Chemistry Letters, Pergamon, Amsterdam, NL, vol. 17, No. 13, Jul. 1, 2007, pp. 3550-3557.
Pelcman et al., caplus an 2006:295967, 2006.
Selwood, et al., "Solution-Phase parallel synthesis of 5-carboxamido 1-benzyl-3-(3-dimethylaminopropyloxy)-1H-pyrazoles as activators of soluble guanylate cyclase with improved oral bioavailability," Bioorganic & Medicinal Chemistry Letters, 11(8):1089-1092 (2001).
Yasri et al., 2010, caplus an2010:1040663.
U.S. Appl. No. 15/925,270, filed Mar. 19, 2018, Lin et al.
U.S. Appl. No. 15/977,772, filed May 11, 2018, Ibrahim et al.
U.S. Appl. No. 16/001,534, filed Jun. 6, 2018, Zhang et al.
International Preliminary Report on Patentability for International Application No. PCT/US2013/076995 dated Jun. 23, 2015. (9 pages).
Verstovsek, S., "Advanced systemic mastocytosis: the impact of KIT mutations in diagnosis, treatment, and progression", European Journal of Haematology, 2012, 90, pp. 89-98.

\* cited by examiner

COMPOUNDS AND METHODS FOR KINASE MODULATION, AND INDICATIONS THEREFOR

CROSS REFERENCE TO RELATED APPLICATIONS

This application is a divisional of U.S. application Ser. No. 14/137,438, filed Dec. 20, 2013, now U.S. Pat. No. 9,676,748, which claims the benefit of 35 U.S.C. § 119(e) of U.S. Provisional Application Nos. 61/745,409, filed Dec. 21, 2012 and 61/784,928, filed Mar. 14, 2013, each of which is hereby incorporated by reference in its entirety.

FIELD

The present disclosure relates to protein kinases and compounds which selectively modulate kinases, and uses therefor. Particular embodiments contemplate disease indications which are amenable to treatment by modulation of kinase activity by the compounds of the present disclosure.

BACKGROUND

Receptor protein tyrosine kinases (RPTKs) regulate key signal transduction cascades that control cellular growth and proliferation. The Stem Cell Factor (SCF) receptor c-kit is a type III transmembrane RPTK that includes five extracellular immunoglobulin (IG) domains, a single transmembrane domain, and a split cytoplasmic kinase domain separated by a kinase insert segment. C-kit plays an important role in the development of melanocytes, mast, germ, and hematopoietic cells.

Stem Cell Factor (SCF) is a protein encoded by the S1 locus, and has also been called kit ligand (KL) and mast cell growth factor (MGF), based on the biological properties used to identify it (reviewed in Tsujimura, *Pathol Int* 1996, 46:933-938; Loveland, et al., *J. Endocrinol* 1997, 153:337-344; Vliagoftis, et al., *Clin Immunol* 1997, 100:435-440; Broudy, Blood 1997, 90:1345-1364; Pignon, *Hermatol Cell Ther* 1997, 39:114-116; and Lyman, et al., *Blood* 1998, 91:1101-1134.). Herein we use the abbreviation SCF to refer to the ligand for the c-Kit RTK (receptor tyrosine kinase).

SCF is synthesized as a transmembrane protein with a molecular weight of 220 or 248 Dalton, depending on alternative splicing of the mRNA to encode exon 6. The larger protein can be proteolytically cleaved to form a soluble, glycosylated protein which noncovalently dimerizes. Both the soluble and membrane-bound forms of SCF can bind to and activate c-Kit. For example, in the skin, SCF is predominantly expressed by fibroblasts, keratinocytes, and endothelial cells, which modulate the activity of melanocytes and mast cells expressing c-Kit. In bone, marrow stromal cells express SCF and regulate hematopoiesis of c-Kit expressing stem cells. In the gastrointestinal tract, intestinal epithelial cells express SCF and affect the interstitial cells of Cajal and intraepithelial lymphocytes. In the testis, sertoli cells and granulosa cells express SCF which regulates spermatogenesis by interaction with c-Kit on germ cells.

Aberrant expression and/or activation of c-Kit and/or a mutant form(s) of c-kit has been implicated in a variety of pathologic states (Roskoski, 2005, *Biochemical and Biophysical Research Comm.* 338: 1307-1315). For example, evidence for a contribution of c-Kit to neoplastic pathology includes its association with leukemias and mast cell tumors, small cell lung cancer, testicular cancer, and some cancers of the gastrointestinal tract and central nervous system. In addition, c-Kit has been implicated in playing a role in carcinogenesis of the female genital tract sarcomas of neuroectodermal origin, and Schwann cell neoplasia associated with neurofibromatosis. It was found that mast cells are involved in modifying the tumor microenvironment and enhancing tumor growth (Yang et al., *J Clin Invest.* 2003, 112:1851-1861; Viskochil, *J Clin Invest.* 2003, 112:1791-1793). Accordingly, there is a need in the art for compounds and methods of use thereof for the modulation of receptor protein kinases. The present disclosure meets this and other needs.

SUMMARY

In one aspect, the present disclosure provides a compound of formula (I'):

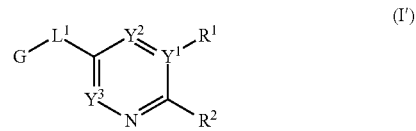

or a pharmaceutically acceptable salt, a solvate, a tautomer, an isomer, or a deuterated analog thereof, wherein:

(i) $R^1$ and $R^2$ are taken together to form an optionally substituted 5- or 6-membered fused ring having from 0-3 heteroatoms as ring members selected from N, O or S, wherein one or two ring carbon atoms are optionally replaced by —C(=O)—; or (ii) $R^1$ is H, halogen, $C_{1-4}$ alkyl, $C_{1-4}$haloalkyl, $C_{1-4}$haloalkoxy, cyclopropyl or a lone pair of electrons and $R^2$ is —NH-$L^2$-$R^6$, wherein $R^6$ is H, optionally substituted aryl, optionally substituted aryl-$C_{1-4}$alkyl, optionally substituted heteroaryl, optionally substituted heteroaryl-$C_{1-4}$ alkyl, optionally substituted heterocycloalkyl, optionally substituted $C_{1-6}$alkyl, optionally substituted cycloalkyl, optionally substituted cycloalkyl-$C_{1-4}$alkyl, optionally substituted heterocyclyl or optionally substituted heterocyclyl-$C_{1-4}$alkyl; and wherein $L^2$ is selected from a bond, —C(O)—, —C(O)N($R^f$)—, —SO$_2$N($R^f$)—, —SO$_2$—, —C(O)O—, —C(=N$R^f$)N($R^f$)—, wherein each $R^f$ is independently H or $C_{1-4}$alkyl;

G is an optionally substituted $C_{1-6}$alkyl, an optionally substituted aryl or an optionally substituted 5- or 6-membered heteroaryl having one or more nitrogen atoms as ring members, wherein the aryl or heteroaryl is optionally fused with an optionally substituted 5- to 8-membered ring having from 0-2 heteroatoms as ring members selected from O, N or S;

$L^1$ is selected from —CH(OH)—, —C(O)NR$^5$—, —NR$^5$C(O)—, —CH$_2$N(R$^5$)—, —SO$_2$N(R$^5$)—, —N(R$^5$)C(O)N(R$^5$)—, —N(R$^5$)SO$_2$—, —N(R$^5$)CH$_2$—, —OC$_{1-4}$alkylene-, —C$_{1-4}$alkylene-O—, —C(O)—, —NR$^5$C(O)—, —SO$_2$—, —SON(R$^5$)—, —N(R$^5$)SO$_2$N(R$^5$)—, or —S(O)—, wherein each $R^5$ is independently H or $C_{1-4}$alkyl;

$Y^1$ is N or C;

$Y^2$ is N or optionally substituted =C—; and $Y^3$ is N or CH; with the proviso that $Y^1$, $Y^2$ and $Y^3$ are not simultaneously N.

In another aspect, the disclosure provides a composition. The composition includes a compound of any of formulas (I'), (I'a), (I), (II), (III), (IV), (V) or (V') or any of the formulas and subformulas as described herein, or a compound as recited in any of the claims and described herein, or a pharmaceutically acceptable salt, solvate, tautomer or isomers thereof, and a pharmaceutically acceptable excipient or carrier. The disclosure also provides a composition, which includes a compound as recited in the claims and described herein, a pharmaceutically acceptable excipient or carrier, and another therapeutic agent.

In another aspect, the disclosure provides a method for preparing a compound of formula (IV), (V') and any of the subgeneric formulas.

In another aspect, the disclosure provides a method for modulating a protein kinase. The method includes administering to a subject in need thereof a compound of any of formulas (I'), (I'a), (I), (II), (III), (IV), (V) or (V'), or any of the formulas and subformulas as described herein, or a compound as recited in any of the claims and described herein, or a pharmaceutically acceptable salt, solvate, tautomer or isomers thereof, or a pharmaceutical composition as described herein. In some embodiments, the protein kinase is a c-kit protein kinase or a mutant c-kit protein kinase.

In still another aspect, the disclosure provides a method for treating a subject suffering from or at risk of diseases or conditions mediated by a protein kinase. The method includes administering to the subject an effective amount of a compound of any of formulas (I'), (I'a), (I), (II), (III), (IV), (V) or (V') or any of the subformulas, or a compound as recited in any of the claims and described herein, or a pharmaceutically acceptable salt, solvate, tautomer or isomer thereof, or a composition comprising a compound of any of formulas (I'), (I'a), (I), (II), (III), (IV), (V) or (V') or any of the subformulas described herein, or a compound as recited in any of the claims or described herein, or a pharmaceutically acceptable salt, solvate, tautomer or isomer thereof.

DETAILED DESCRIPTION

I. Definitions

As used herein the following definitions apply unless clearly indicated otherwise:

It is noted here that as used in this specification and the appended claims, the singular forms "a," "an," and "the" include plural reference unless the context clearly dictates otherwise.

"Halogen" or "halo" refers to all halogens, that is, chloro (Cl), fluoro (F), bromo (Br), or iodo (I).

"Hydroxyl" or "hydroxy" refers to the group —OH.

"Thiol" refers to the group —SH.

"Heteroatom" is meant to include oxygen (O), nitrogen (N), and sulfur (S).

The term "alkyl", by itself or as part of another substituent, means, unless otherwise stated, a straight or branched chain hydrocarbon, having the number of carbon atoms designated (i.e. $C_{1-6}$ means one to six carbons). Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms. Examples of alkyl groups include, but are not limited to, methyl, ethyl, n-propyl, isopropyl, n-butyl, t-butyl, isobutyl, sec-butyl, but-2-enyl (e.g. —CH$_2$CH=CHCH$_3$), cis-2-buten-1-yl, n-pentyl, n-hexyl, n-heptyl, n-octyl, and the like. For each of the definitions herein (e.g., alkyl, alkoxy, alkylamino, alkylthio, alkylene, haloalkyl, arylalkyl, cycloalkylalkyl, heterocycloalkylalkyl, heteroarylalkyl), when a prefix is not included to indicate the number of carbon atoms in an alkyl portion, the alkyl moiety or portion thereof will have 12 or fewer main chain carbon atoms or 8 or fewer main chain carbon atoms or 6 or fewer main chain carbon atoms. For example, $C_{1-6}$ alkyl refers to a straight or branched hydrocarbon having 1, 2, 3, 4, 5 or 6 carbon atoms and includes, but is not limited to, $C_{1-2}$ alkyl, $C_{1-4}$ alkyl, $C_{2-6}$ alkyl, $C_{2-4}$ alkyl, $C_{1-6}$ alkyl, $C_{2-8}$ alkyl, $C_{1-7}$ alkyl, $C_{2-7}$ alkyl and $C_{3-6}$ alkyl. "Fluoro substituted alkyl" denotes an alkyl group substituted with one or more fluoro atoms, such as perfluoroalkyl, where preferably the lower alkyl is substituted with 1, 2, 3, 4 or 5 fluoro atoms, also 1, 2, or 3 fluoro atoms. While it is understood that substitutions are attached at any available atom to produce a stable compound, when optionally substituted alkyl is an R group of a moiety such as —OR (e.g. alkoxy), —SR (e.g. thioalkyl), —NHR (e.g. alkylamino), —C(O)NHR, and the like, substitution of the alkyl R group is such that substitution of the alkyl carbon bound to any O, S, or N of the moiety (except where N is a heteroaryl ring atom) excludes substituents that would result in any O, S, or N of the substituent (except where N is a heteroaryl ring atom) being bound to the alkyl carbon bound to any O, S, or N of the moiety. As used herein, "deuterated $C_{1-6}$alkyl" is meant to include partially deuterated or perdeuterated $C_{1-6}$alkyl groups. Non-limiting examples include —CD$_3$, CD$_3$CH$_2$—, CD$_3$CD$_2$-, -CD(CD$_3$)$_2$, —CD(CH$_3$)$_2$, and the like.

The term "alkylene" by itself or as part of another substituent means a linear or branched saturated divalent hydrocarbon moiety derived from an alkane having the number of carbon atoms indicated in the prefix. For example, (i.e., $C_{1-6}$ means one to six carbons; $C_{1-6}$ alkylene is meant to include methylene, ethylene, propylene, 2-methylpropylene, pentylene, hexylene and the like). $C_{1-4}$ alkylene includes methylene —CH$_2$—, ethylene —CH$_2$CH$_2$—, propylene —CH$_2$CH$_2$CH$_2$—, and isopropylene —CH(CH$_3$)CH$_2$—, —CH$_2$CH(CH$_3$)—, —CH$_2$—(CH$_2$)$_2$CH$_2$—, —CH$_2$—CH(CH$_3$)CH$_2$—, —CH$_2$—C(CH$_3$)$_2$—, —CH$_2$—CH$_2$CH(CH$_3$)—. Typically, an alkyl (or alkylene) group will have from 1 to 24 carbon atoms, with those groups having 10 or fewer, 8 or fewer, or 6 or fewer carbon atoms being preferred in the present disclosure. When a prefix is not included to indicate the number of carbon atoms in an alkylene portion, the alkylene moiety or portion thereof will have 12 or fewer main chain carbon atoms or 8 or fewer main chain carbon atoms, 6 or fewer main chain carbon atoms or 4 or fewer main chain carbon atoms.

The term "alkenyl" refers to a linear monovalent hydrocarbon radical or a branched monovalent hydrocarbon radical having the number of carbon atoms indicated in the prefix and containing at least one double bond. For example, (C$_2$-C$_6$)alkenyl is meant to include ethenyl, propenyl, —CH=C(H)(CH$_3$), —CH=C(CH$_3$)$_2$, —C(CH$_3$)=C(H)$_2$, —C(CH$_3$)=C(H)(CH$_3$), —C(CH$_2$CH$_3$)=CH$_2$, butadienyl e.g. 2-(butadienyl), pentadienyl e.g. 2,4-pentadienyl and 3-(1,4-pentadienyl), and hexadienyl, and the like, among others, and higher homologs and stereoisomers thereof. Similarly, the term "alkynyl" refers to a linear monovalent hydrocarbon radical or a branched monovalent hydrocarbon radical containing at least one triple bond and having the number of carbon atoms indicated in the prefix. Examples include, but are not limited to, ethynyl e.g. —C≡C(H), 1-propynyl e.g. —C≡C(CH$_3$), —C≡C(CH$_2$CH$_3$), —C(H$_2$)C≡C(H), —C(H)$_2$C≡C(CH$_3$), and —C(H)$_2$C≡C(CH$_2$CH$_3$), among others, and higher homologs and isomers thereof. When a prefix is not included to indicate the number of carbon atoms in an alkenyl or alkynyl portion, the alkenyl or alkynyl moiety or portion thereof will have 12 or fewer main chain carbon atoms, or 8 or fewer main chain carbon atoms, or 6 or fewer main chain carbon atoms, or 4 or fewer main chain carbon atoms.

The term "alkenylene" refers to a linear bivalent hydrocarbon moiety or a branched divalent hydrocarbon moiety having the number of carbon atoms indicated in the prefix and containing at least one double bond. For example, i.e., $C_{2-6}$ means two to six carbons; $C_{2-6}$ alkenylene is meant to include, but are not limited to, —CH=CH—, —CH$_2$—CH=CH—, —CH$_2$—CH=C(CH$_3$)—, —CH=CH—CH=CH—, and the like). Similarly, the term "alkynylene" refers to a linear bivalent hydrocarbon moiety or a branched divalent hydrocarbon moiety containing at least one triple bond and having the number of carbon atoms indicated in the prefix. For example, (i.e., $C_{2-6}$ means two to six carbons; $C_{2-6}$ alkynlene is meant to include, but are not limited to, —C≡C—, —C≡CCH$_2$—, —CH$_2$C≡CCH$_2$—, —C≡CCH(CH$_3$)—, and the like. When a prefix is not included to indicate the number of carbon atoms in an alkenylene or alkynlene portion, the alkenylene moiety or portion thereof will have 12 or fewer main chain carbon atoms, or 8 or fewer main chain carbon atoms, or 6 or fewer main chain carbon atoms, or 4 or fewer main chain carbon atoms.

"Cycloalkyl" or "Carbocycle" by itself or as part of another substituent, refers to saturated or unsaturated, non-aromatic monocyclic, bicyclic or tricyclic carbon ring systems having the number of carbon atoms indicated in the prefix or if unspecified having 3-10, also 3-8, more preferably 3-6, ring members per ring, such as cyclopropyl, cyclopentyl, cyclohexyl, 1-cyclohexenyl, adamantyl, and the like, where one or two ring carbon atoms may optionally be replaced by a carbonyl. Cycloalkyl refers to hydrocarbon rings having the indicated number of ring atoms (e.g., $C_{3-8}$ cycloalkyl means three to eight ring carbon atoms). "Cycloalkyl" or "carbocycle" refers to a mono-bicyclic or polycyclic group such as, for example, bicyclo[2.2.1]heptane, bicyclo[2.2.2]octane, etc. When used in connection with cycloalkyl substituents, the term "polycyclic" refers herein to fused and non-fused alkyl cyclic structures. "Cycloalkyl" or "carbocycle" may form a bridged ring or a spiro ring. The cycloalkyl group may have one or more double or triple bond(s).

"Cycloalkylene" by itself or as part of another substituent, refers to a divalent cycloalkyl, where the cycloalkyl as defined above having 3-10, also 3-8, more preferably 3-6, ring members per ring. Exemplary cycloalkylene includes, e.g., 1,2-, 1,3-, or 1,4-cis or trans-cyclohexylene, 2-methyl-1,4-cyclohexylene, 2,2-dimethyl-1,4-cyclohexylene, and the like.

"Cycloalkylalkyl" refers to an -(alkylene)-cycloalkyl group where alkylene as defined herein has the indicated number of carbon atoms or if unspecified having six or fewer, preferably four or fewer main chain carbon atoms; and cycloalkyl is as defined herein has the indicated number of carbon atoms or if unspecified having 3-10, also 3-8, more preferably 3-6, ring members per ring. $C_{3-8}$cycloalkyl-$C_{1-2}$ alkyl is meant to have 3 to 8 ring carbon atoms and 1 to 2 alkylene chain carbon atoms. Exemplary cycloalkylalkyl includes, e.g., cyclopropylmethylene, cyclobutylethylene, cyclobutylmethylene, and the like.

"Cycloalkylalkenyl" refers to an -(alkenylene)-cycloalkyl group where alkenylene as defined herein has the indicated number of carbon atoms or if unspecified having six or fewer, preferably four or fewer main chain carbon atoms; and cycloalkyl is as defined herein has the indicated number of carbon atoms or if unspecified having 3-10, also 3-8, more preferably 3-6, ring members per ring. $C_{3-8}$cycloalkyl-$C_{2-4}$alkenyl is meant to have 3 to 8 ring carbon atoms and 2 to 4 alkenylene chain carbon atoms. Exemplary cycloalkylalkenyl includes, e.g., 2-cyclopropylvinyl, 2-cyclopentylvinyl, and the like.

"Cycloalkylalkynyl" refers to an -(alkynylene)-cycloalkyl group where alkynylene as defined herein has the indicated number of carbon atoms or if unspecified having six or fewer, preferably four or fewer main chain carbon atoms; and cycloalkyl is as defined herein has the indicated number of carbon atoms or if unspecified having 3-10, also 3-8, more preferably 3-6, ring members per ring. $C_{3-8}$cycloalkyl-$C_{2-4}$alkynyl is meant to have 3 to 8 ring carbon atoms and 2 to 4 alkynylene chain carbon atoms. Exemplary cycloalkylalkynyl includes, e.g., 2-cyclopropylethynyl, 2-cyclobutylethynyl, 2-cyclopentylethynyl and the like.

"Cycloalkenyl" by itself or as part of another substituent, refers to a non-aromatic monocyclic, bicyclic or tricyclic carbon ring system having the number of carbon atoms indicated in the prefix or if unspecified having 3-10, also 3-8, more preferably 3-6, ring members per ring, which contains at least one carbon-carbon double bond. Exemplary cycloalkenyl includes, e.g., 1-cyclohexenyl, 4-cyclohexenyl, 1-cyclopentenyl, 2-cyclopentenyl and the like.

"Cycloalkenylene" by itself or as part of another substituent, refers to a divalent cycloalkenyl, where the cycloalkenyl as defined herein having 3-10, also 3-8, more preferably 3-6, ring members per ring. Exemplary cycloalkenylene includes, e.g., cyclohexene-1,4-diyl, 2-methyl-cyclohexene-1,4-diyl, 3-methyl-cyclohexene-1,4-diyl, 3,3-dimethyl-cyclohexene-1,4-diyl, cyclohexene-1,2-diyl, cyclohexene-1,3-diyl, and the like.

"Haloalkyl," is meant to include alkyl substituted by one to seven halogen atoms. Haloalkyl includes monohaloalkyl and polyhaloalkyl. For example, the term "$C_{1-6}$ haloalkyl" is meant to include trifluoromethyl, difluoromethyl, fluoromethyl, 2,2,2-trifluoroethyl, 4-chlorobutyl, 3-bromopropyl, and the like.

"Haloalkoxy" refers to a —O-haloalkyl group, where haloalkyl is as defined herein, e.g., trifluoromethoxy, 2,2,2-trifluoroethoxy, difluoromethoxy, and the like.

"Alkoxy" refers to a —O-alkyl group, where alkyl is as defined herein. "Cycloalkoxy" refers to a —O-cycloalkyl group, where cycloalkyl is as defined herein. "Fluoro substituted alkoxy" denotes alkoxy in which the alkyl is substituted with one or more fluoro atoms, where preferably the alkoxy is substituted with 1, 2, 3, 4 or 5 fluoro atoms, also 1, 2, or 3 fluoro atoms. While it is understood that substitutions on alkoxy are attached at any available atom to produce a stable compound, substitution of alkoxy is such that O, S, or N (except where N is a heteroaryl ring atom), are not bound to the alkyl carbon bound to the alkoxy O. Further, where alkoxy is described as a substituent of another moiety, the alkoxy oxygen is not bound to a carbon atom that is bound to an O, S, or N of the other moiety (except where N is a heteroaryl ring atom), or to an alkene or alkyne carbon of the other moiety.

"Amino" or "amine" denotes the group —NH$_2$.

"Alkylamino" refers to a —NH-alkyl group, where alkyl is as defined herein. Exemplary alkylamino groups include CH$_3$NH—, ethylamino, and the like.

"Dialkylamino" refers to a —N(alkyl)(alkyl) group, where each alkyl is independently as defined herein. Exemplary dialkylamino groups include dimethylamino, diethylamino, ethylmethylamino, and the like.

"Cycloalkylamino" denotes the group —NR$^{dd}$R$^{ee}$, where R$^{dd}$ and R$^{ee}$ combine with the nitrogen to form a 5-7 membered heterocycloalkyl ring, where the heterocycloalkyl may contain an additional heteroatom within the ring, such as O, N, or S, and may also be further substituted with alkyl. Alternatively, "cycloalkylamino" refers to a —NH-cycloalkyl group, where cycloalkyl is as defined herein.

"Alkylthio" refers to —S-alkyl, where alkyl is as defined herein. Exemplary alkylthio groups include $CH_3S—$, ethylthio, and the like.

"Aryl" by itself or as part of another substituent refers to a monocyclic, bicyclic or polycyclic polyunsaturated aromatic hydrocarbon radical containing 6 to 14 ring carbon atoms, which can be a single ring or multiple rings (up to three rings) which are fused together or linked covalently. Non-limiting examples of unsubstituted aryl groups include phenyl, 1-naphthyl, 2-naphthyl and 4-biphenyl. Exemplary aryl groups, such as phenyl or naphthyl, may be optionally fused with a cycloalkyl of preferably 5-7, more preferably 5-6, ring members.

"Arylene" by itself or as part of another substituent, refers to a divalent aryl, where the aryl is as defined herein. Exemplary arylene includes, e.g., phenylene, biphenylene, and the like.

"Arylalkyl" refers to -(alkylene)-aryl, where the alkylene group is as defined herein and has the indicated number of carbon atoms, or if unspecified having six or fewer main chain carbon atoms or four or fewer main chain carbon atoms; and aryl is as defined herein. Examples of arylalkyl include benzyl, phenethyl, 1-methylbenzyl, and the like.

"Arylalkoxy" refers to —O-(alkylene)-aryl, where the alkylene group is as defined herein and has the indicated number of carbon atoms, or if unspecified having six or fewer main chain carbon atoms or four or fewer main chain carbon atoms; and aryl is as defined herein. Examples of arylalkoxy include benzyloxy, phenethyloxy, and the like.

"Aryloxy" refers to —O-aryl, where the aryl group is as defined herein. Exemplary aryloxy includes, e.g., phenoxy.

"Arylthio" refers to —S-aryl, where the aryl group is as defined herein. Exemplary arylthio includes, e.g., phenylthio.

"Heteroaryl" by itself or as part of another substituent refers to a monocyclic aromatic ring radical containing 5 or 6 ring atoms, or a bicyclic aromatic radical having 8 to 10 atoms, containing one or more, preferably 1-4, more preferably 1-3, even more preferably 1-2, heteroatoms independently selected from the group consisting of O, S, and N. Heteroaryl is also intended to include oxidized S or N, such as sulfinyl, sulfonyl and N-oxide of a tertiary ring nitrogen. A carbon or nitrogen atom is the point of attachment of the heteroaryl ring structure such that a stable compound is produced. Examples of heteroaryl groups include, but are not limited to, pyridinyl, pyridazinyl, pyrazinyl, indolizinyl, benzo[b]thienyl, quinazolinyl, purinyl, indolyl, quinolinyl, pyrimidinyl, pyrrolyl, pyrazolyl, oxazolyl, thiazolyl, thienyl, isoxazolyl, oxathiadiazolyl, isothiazolyl, tetrazolyl, imidazolyl, triazolyl, furanyl, benzofuryl, indolyl, triazinyl, quinoxalinyl, cinnolinyl, phthalaziniyl, benzotriazinyl, benzimidazolyl, benzopyrazolyl, benzotriazolyl, benzisoxazolyl, isobenzofuryl, isoindolyl, indolizinyl, benzotriazinyl, thienopyridinyl, thienopyrimidinyl, pyrazolopyrimidinyl, imidazopyridines, benzothiaxolyl, benzothienyl, quinolyl, isoquinolyl, indazolyl, pteridinyl and thiadiazolyl. "Nitrogen containing heteroaryl" refers to heteroaryl wherein any of the heteroatoms is N. As used herein, "heterocyclic aromatic ring" is meant to be a heteroaryl ring.

"Heteroarylene" by itself or as part of another substituent, refers to a divalent heteroaryl, where the heteroaryl is as defined herein. Exemplary heteroarylene includes, e.g., pyridine-2,5-diyl, pyrimidine-2,5-diyl, pyridazine-3,5-diyl, pyrazine-2,5-diyl, and the like.

"Heteroarylalkyl" refers to -(alkylene)-heteroaryl, where the alkylene group is as defined herein and has the indicated number of carbon atoms, or if unspecified having six or fewer main chain carbon atoms or four or fewer main chain carbon atoms; and heteroaryl is as defined herein. Non-limiting examples of heteroarylalkyl include 2-pyridylmethyl, 4-pyridylmethyl, 2-thiazolylethyl, and the like.

"Heterocyclyl", "Heterocycle" or "Heterocyclic" refers to a saturated or unsaturated non-aromatic mono- or bicyclic radical group containing at least one heteroatom independently selected from oxygen (O), nitrogen (N) or sulfur (S). Each heterocycle can be attached at any available ring carbon or heteroatom. Each heterocycle may have one or more rings. When multiple rings are present, they can be fused together or linked covalently. Each heterocycle typically contains 1, 2, 3, 4 or 5, independently selected heteroatoms. Preferably, these groups contain 1, 2, 3, 4, 5, 6, 7, 8, 9 or 10 carbon atoms, 0, 1, 2, 3, 4 or 5 nitrogen atoms, 0, 1 or 2 sulfur atoms and 0, 1 or 2 oxygen atoms. More preferably, these groups contain 1, 2 or 3 nitrogen atoms, 0-1 sulfur atoms and 0-1 oxygen atoms. Non-limiting examples of heterocyclyl groups include morpholin-3-one, piperazine-2-one, piperazin-1-oxide, pyridine-2-one, piperidine, morpholine, piperazinyl, isoxazoline, pyrazoline, imidazoline, pyrazol-5-one, pyrrolidine-2,5-dione, imidazolidine-2,4-dione, pyrrolidine, tetrahydroquinolinyl, decahydroquinolinyl, tetrahydrobenzooxazepinyl dihydrodibenzooxepin and the like.

"Heterocyclylene" by itself or as part of another substituent, refers to a divalent heterocyclyl, where the heterocyclyl is as defined herein. Exemplary heterocyclylene includes, e.g., piperazine-1,4-diyl, piperidine-1,4-diyl, 1,2,3,6-tetrahydropyridine-1,4-diyl, 3-azabicyclo[3.2.1]octane-3,8-diyl, 3,8-diazabicyclo[3.2.1]octane-3,8-diyl, 8-azabicyclo[3.2.1] octane-3,8-diyl, 2-azabicyclo[2.2.2]octane-2,5-diyl, 2,5-diazabicyclo[2.2.2]octane-2,5-diyl, 2,3,6,7-tetrahydro-1H-azepine-1,4-diyl, 2,3,6,7-tetrahydro-1H-azepine-1,5-diyl, 2,5-dihydro-1H-pyrrole-1,3-diyl and the like.

"Heterocyclylalkyl" refers to -(alkylene)-heterocyclyl, where the alkylene group is as defined herein and has the indicated number of carbon atoms, or if unspecified having six or fewer main chain carbon atoms or four or fewer main chain carbon atoms; and heterocyclyl is as defined herein. Exemplary heterocyclylalkyl includes, e.g., pyrrolidin-1-ylmethyl, 2-piperidinylmethyl, and the like.

"Heterocycloalkyl" refers to a saturated or unsaturated non-aromatic cycloalkyl group that contains from one to five heteroatoms selected from N, O, and S, wherein the nitrogen and sulfur atoms are optionally oxidized, and the nitrogen atom(s) are optionally quaternized, the remaining ring atoms being C, where one or two C atoms may optionally be replaced by a carbonyl. The heterocycloalkyl may be a monocyclic, a bicyclic or a polycyclic ring system of 3 to 12, preferably 4 to 10 ring atoms, more preferably 5 to 8 ring atoms in which one to five ring atoms are heteroatoms selected from —N=, —N—, —O—, —S—, —S(O)—, or —S(O)$_2$— and further wherein one or two ring atoms are optionally replaced by a —C(O)— group. The heterocycloalkyl can also be a heterocyclic alkyl ring fused with a cycloalkyl, an aryl or a heteroaryl ring. Non limiting examples of heterocycloalkyl groups include pyrrolidinyl, piperidinyl, imidazolidinyl, pyrazolidinyl, butyrolactam moiety, valerolactam moiety, imidazolidinone moiety, hydantoin, dioxolane moiety, phthalimide moiety, piperidine, 1,4-dioxane moiety, morpholinyl, thiomorpholinyl, thiomorpholinyl-S-oxide, thiomorpholinyl-S,S-oxide, piperazinyl, pyranyl, pyridine moiety, 3-pyrrolinyl, thiopyranyl, pyrone moiety, tetrahydrofuranyl, tetrahydrothiophenyl, quinuclidinyl, and the like. A heterocycloalkyl group can be attached to the remainder of the molecule through a ring carbon or a heteroatom. As used herein, the term "Heterocycloalkylene" by itself or as part of another substituent, refers to a divalent heterocycloalkyl, where the heterocycloalkyl is as defined herein. Non-limiting examples of heterocycloalkylene include piperidine-1,4-diyl, 1,2,3,6-tetrahydropyridine-1,4-diyl, 1,2,3,6-tetrahydropyridine-1,5-diyl, 2,3,6,7-tetrahydro-1H-azepine-1,4-diyl, 2,3,6,7-tetrahydro-1H-azepine-1,5-diyl, 2,5-dihydro-1H-pyrrole-1,3-diyl and the like.

"Heterocycloalkylalkyl" refers to -(alkylene)-heterocycloalkyl, where the alkylene group is as defined herein and has the indicated number of carbon atoms, or if unspecified having six or fewer main chain carbon atoms or four or fewer main chain carbon atoms; and heterocycloalkyl is as defined herein. Non-limiting examples of heterocycloalkylalkyl include 2-pyridylmethyl, 2-thiazolylethyl, and the like.

The substituents for alkyl, alkoxy, haloalkyl, haloalkoxy, cycloalkyl, cycloalkylalkyl, heterocycloalkyl, heterocycloalkylalkyl, heterocyclyl, alkylene, alkenylene, or alkynlene include, but are not limited to, R',
halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR', —SR', —OC(O)R', —OC(S)R', —C(O)R', —C(S) R', —C(O)OR', —C(S)OR', —S(O)R', —S(O)$_2$R', —C(O)NHR', —C(S)NHR', —C(O)NR'R", —C(S)NR'R", —S(O)$_2$NH R', —S(O)$_2$NR'R", —C(NH)NHR', —C(NH)NR'R", —NHC(O)R', —NHC(S)R', —NR"C(O)R', —NR'C(S)R", —NHS(O)$_2$R', —NR'S(O)$_2$R", —NHC(O)NHR', —NHC(S)NHR', —NR'C(O)NH$_2$, —NR'C(S)NH$_2$, —NR'C(O) NHR", —NR'C(S)NHR", —NHC(O)NR'R", —NHC(S)NR'R", —NR'C(O)NR'R'", —NR'"C(S)NR'R", —NH S(O)$_2$NHR', —NR'S(O)$_2$NH$_2$, —NR'S(O)$_2$NHR", —NHS(O)$_2$NR'R", —NR'S(O)$_2$NR'R'", —NHR', and —NR'R" in a number ranging from zero to (2m'+1), where m' is the total number of carbon atoms in such group. R', R" and R'" each independently refer to hydrogen, C$_{1-8}$ alkyl, heterocycloalkyl, aryl, heteroaryl, arylalkyl, heteroarylalkyl, aryl substituted with 1-3 halogens, C$_{1-8}$ alkoxy, haloalkyl, haloalkoxy or C$_{1-8}$ thioalkoxy groups, or unsubstituted aryl-C$_{1-4}$ alkyl groups. When R' and R" are attached to the same nitrogen atom, they can be combined with the nitrogen atom to form a 3-, 4-, 5-, 6-, or 7-membered ring. For example, —NR'R" is meant to include 1-pyrrolidinyl and 4-morpholinyl. R', R" and R'" can be further substituted with R$^{a1}$,
halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)N H$_2$, —NHC(S)NH$_2$, —NHS(O)$_2$NH$_2$, —C(NH)NH$_2$, —OR$^{a1}$, —SR$^{a1}$, —OC(O)R$^{a1}$, —OC(S)R$^{a1}$, —C(O)R$^{a1}$, —C(S) R$^{a1}$, —C(O)OR$^{a1}$, —C(S)OR$^{a1}$, —S(O)R$^{a1}$, —S(O)$_2$R$^{a1}$, —C(O)NHR$^{a1}$, —C(S)NHR$^{a1}$, —C(O)NR$^{a1}$R$^{a2}$, —C(S)NR$^{a1}$R$^{a2}$, —S(O)$_2$NHR$^{a1}$, —S(O)$_2$NR$^{a1}$R$^{a2}$, —C(NH)NHR$^{a1}$, —C(NH)NR$^{a1}$R$^{a2}$, —NHC(O)R$^{a1}$, —NHC(S)R$^{a1}$, —NR$^{a2}$C(O)R$^{a1}$, —NR$^{a1}$C(S)R$^{a2}$, —NHS(O)$_2$R$^{a1}$, —NR$^{a1}$S(O)$_2$R$^{a2}$, —NHC(O)NHR$^{a1}$, —NHC(S)NHR$^{a1}$, —NR$^{a1}$C(O)N H$_2$, —NR$^{a1}$C(S)NH$_2$, —NR$^{a1}$C(O)NHR$^{a2}$, —NR$^{a1}$C(S)NHR$^{a2}$, —NHC(O)NR$^{a1}$R$^{a2}$, —NHC(S)NR$^{a1}$R$^{a2}$, —NR$^{a1}$C(O)NR$^{a2}$R$^{a3}$, —NR$^{a3}$C(S)NR$^{a1}$R$^{a2}$, —NHS(O)$_2$NHR$^{a1}$, —NR$^{a1}$S(O)$_2$NH$_2$, —NR$^{a1}$S(O)$_2$NHR$^{a2}$, —NHS(O)$_2$NR$^{a1}$R$^{a2}$, —NR$^{a1}$S(O)$_2$NR$^{a2}$R$^{a3}$, —NHR$^{a1}$, and —NR$^{a1}$R$^{a2}$ in a number ranging from zero to (2n'+1), where n' is the total number of carbon atoms in such group. R$^{a1}$, R$^{a2}$ and R$^{a3}$ each independently refer to hydrogen, C$_{1-8}$ alkyl, heterocycloalkyl, aryl, heteroaryl, arylalkyl, heteroarylalkyl, aryl substituted with 1-3 halogens, C$_{1-8}$ alkoxy, haloalkyl, haloalkoxy or C$_{1-8}$ thioalkoxy groups, or unsubstituted aryl-C$_{1-4}$ alkyl groups. R$^{a1}$, R$^{a2}$ and R$^{a3}$ can be further substituted with R$^{b1}$, halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)N H$_2$, —NHC(S)NH$_2$, —NHS(O)$_2$NH$_2$, —C(NH)NH$_2$, —OR$^{b1}$, —SR$^{b1}$, —OC(O)R$^{b1}$, —OC(S)R$^{b1}$, —C(O)R$^{b1}$, —C(S) R$^{b1}$, —C(O)OR$^{b1}$, —C(S)OR$^{b1}$, —S(O)R$^{b1}$, —S(O)$_2$R$^{b1}$, —C(O)NHR$^{b1}$, —C(S)NHR$^{b1}$, —C(O)NR$^{b1}$R$^{b2}$, —C(S)NR$^{b1}$R$^{b2}$, S(O)$_2$NHR$^{b1}$, —S(O)$_2$NR$^{b1}$R$^{b2}$, —C(NH)NHR$^{b1}$, —C(NH)NR$^{b1}$R$^{b2}$, —NHC(O)R$^{b1}$, —NHC(S)R$^{b1}$, —NR$^{b2}$C(O)R$^{b1}$, —NR$^{b1}$C(S)R$^{b2}$, —NHS(O)$_2$R$^{b1}$, —NR$^{b1}$S(O)$_2$R$^{b2}$, —NHC(O)NHR$^{b1}$, —NHC(S)NHR$^{b1}$, —NR$^{b1}$C(O)NH$_2$, —NR$^{b1}$C(S)NH$_2$, —NR$^{b1}$C(O)NHR$^{b2}$, —NR$^{b1}$C(S)NHR$^{b2}$, —NHC(O)NR$^{b1}$R$^{b2}$, —NHC(S)NR$^{b1}$R$^{b2}$, —NR$^{b1}$C(O)NR$^{b2}$R$^{b3}$, —NR$^{b3}$C(S)NR$^{b1}$R$^{b2}$, —NHS(O)$_2$NHR$^{b1}$, —NR$^{b1}$S(O)$_2$NH$_2$, —NR$^{b1}$S(O)$_2$NHR$^{b2}$, —NHS(O)$_2$NR$^{b1}$R$^{b2}$, —NR$^{b1}$S(O)$_2$NR$^{b2}$R$^{b3}$, —NHR$^{b1}$, and —NR$^{b1}$R$^{b2}$ in a number ranging from zero to (2p'+1), where p' is the total number of carbon atoms in such group. R$^{b1}$, R$^{b2}$ and R$^{b3}$ each independently refer to hydrogen, C$_{1-8}$ alkyl, heterocycloalkyl, aryl, heteroaryl, arylalkyl, heteroarylalkyl, aryl substituted with 1-3 halogens, C$_{1-8}$ alkoxy, haloalkyl, haloalkoxy or C$_{1-s}$ thioalkoxy groups, or unsubstituted aryl-C$_{1-4}$ alkyl groups.

Substituents for the aryl and heteroaryl groups are varied and are generally selected from: R', halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)N H$_2$, —NHC(S)NH$_2$, —NHS(O)$_2$NH$_2$, —C(NH)NH$_2$, —OR, —SR, —OC(O)R', —OC(S)R', —C(O)R', —C(S)R', —C(O)OR', —C(S)OR', —S(O)R', —S(O)$_2$R', —C(O)NHR', —C(S)NHR', —C(O)NR'R", —C(S)NR'R", —S(O)$_2$NH R', —S(O)$_2$NR'R", —C(NH)NHR', —C(NH)NR'R", —NHC(O)R', —NHC(S)R', —NR"C(O)R', —NR'C(S)R", —NHS(O)$_2$R', —NR'S(O)$_2$R", —NHC(O)NHR', —NHC(S)NHR', —NR'C(O)NH$_2$, —NR'C(S)NH$_2$, —NR'C(O) NHR", —NR'C(S)NHR", —NHC(O)NR'R", —NHC(S)NR'R", —NR'C(O)NR'R'", —NR'"C(S)NR'R", —NH S(O)$_2$NHR', —NR'S(O)$_2$NH$_2$, —NR'S(O)$_2$NHR", —NHS(O)$_2$NR'R", —NR'S(O)$_2$NR'R'", —NHR', —NR'R", —N$_3$, perfluoro (C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, haloalkyl, haloalkoxy, C$_{1-s}$ alkyl, C$_{3-6}$ cycloalkyl, cycloalkylalkyl, C$_{2-8}$ alkenyl, C$_{2-8}$ alkynyl, aryl, arylalkyl, heteroaryl, heteroarylalkyl, aryl-C$_{1-4}$ alkyl, and aryloxy-C$_{1-4}$ alkyl. Other suitable substituents include each of the above aryl substituents attached to a ring atom by an alkylene tether of from 1-4 carbon atoms. R', R" and R'" can be further substituted with R$^{a1}$, halogen, —OH, —NH$_2$, —NO$_2$, —CN, —C(O)OH, —C(S)OH, —C(O)NH$_2$, —C(S)NH$_2$, —S(O)$_2$NH$_2$, —NHC(O)N H$_2$, —NHC(S)NH$_2$, —NHS(O)$_2$NH$_2$, —C(NH)NH$_2$, —OR$^{a1}$, —SR$^{a1}$, —OC(O)R$^{a1}$, —OC(S) R$^{a1}$, —C(O)R$^{a1}$, —C(S) R$^{a1}$, —C(O)OR$^{a1}$, —C(S)OR$^{a1}$, —S(O)R$^{a1}$, —S(O)$_2$R$^{a1}$, —C(O)NHR$^{a1}$, —C(S)NHR$^{a1}$, —C(O)NR$^{a1}$R$^{a2}$, —C(S)NR$^{a1}$R$^{a2}$, —S(O)$_2$NHR$^{a1}$, —S(O)$_2$NR$^{a1}$R$^{a2}$, —C(NH)NHR$^{a1}$, —C(NH)NR$^{a1}$R$^{a2}$, —NHC(O)R$^{a1}$, —NHC(S)R$^{a1}$, —NR$^{a2}$C(O)R$^{a1}$, —NR$^{a1}$C(S)R$^{a2}$, —NHS(O)$_2$R$^{a1}$, —NR$^{a1}$S(O)$_2$R$^{a2}$, —NHC(O) NHR$^{a1}$, —NHC(S)NHR$^{a1}$, —NR$^{a1}$C(O)N H$_2$, —NR$^{a1}$C(S) NH$_2$, —NR$^{a1}$C(O)NHR$^{a2}$, —NR$^{a1}$C(S)NHR$^{a2}$, —NHC(O)

NR$^{a1}$R$^{a2}$, —NHC(S)NR$^{a1}$R$^{a2}$, —NR$^{a1}$C(O)NR$^{a2}$R$^{a3}$, —NR$^{a3}$C(S)NR$^{a}$R$^{a2}$, —NHS(O)$_2$NHR$^{a1}$, —NR$^{a1}$S(O)$_2$NH$_2$, —NR$^{a1}$S(O)$_2$NHR$^{a2}$, —NHS(O)$_2$NR$^{a1}$R$^{a2}$, —NR$^{a1}$S(O)$_2$NR$^{a2}$R$^{a3}$, —NHR$^{a1}$, —NR$^{a1}$R$^{a2}$, —N$_3$, perfluoro(C$_1$-C$_4$)alkoxy, and perfluoro(C$_1$-C$_4$)alkyl, in a number ranging from zero to the total number of open valences on the aromatic ring system; and where R$^{a1}$, R$^{a2}$ and R$^{a3}$ are each independently selected from hydrogen, haloalkyl, haloalkoxy, C$_{1-8}$ alkyl, C$_{3-6}$ cycloalkyl, cycloalkylalkyl, C$_{2-8}$ alkenyl, C$_{2-8}$ alkynyl, aryl, arylalkyl, heteroaryl, heteroarylalkyl, aryl-C$_{1-4}$ alkyl, or aryloxy-C$_{1-4}$ alkyl. Other suitable substituents include each of the above aryl substituents attached to a ring atom by an alkylene tether of from 1-4 carbon atoms.

When two substituents are present on adjacent atoms of a substituted aryl or a substituted heteroaryl ring, such substituents may optionally be replaced with a substituent of the formula -T-C(O)—(CH$_2$)$_q$-U-, wherein T and U are independently —NH—, —O—, —CH$_2$— or a single bond, and q is an integer of from 0 to 2. Alternatively, when two substituents are present on adjacent atoms of a substituted aryl or a substituted heteroaryl ring, such substituents may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, when two substituents are present on adjacent atoms of a substituted aryl or a substituted heteroaryl ring, such substituents may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted C$_{1-6}$ alkyl.

"Protecting group" refers to a grouping of atoms that when attached to a reactive group in a molecule masks, reduces or prevents that reactivity. Examples of protecting groups can be found in T. W. Greene and P. G. Wuts, PROTECTIVE GROUPS IN ORGANIC CHEMISTRY, (Wiley, 4th ed. 2006), Beaucage and Iyer, Tetrahedron 48:2223-2311 (1992), and Harrison and Harrison et al., COMPENDIUM OF SYNTHETIC ORGANIC METHODS, Vols. 1-8 (John Wiley and Sons. 1971-1996). Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), tri-isopropylsilyl (TIPS), phenylsulphonyl and the like (see also, Boyle, A. L. (Editor), carbamates, amides, N-sulfonyl derivatives, groups of formula —C(O)OR, wherein R is, for example, methyl, ethyl, t-butyl, benzyl, phenylethyl, CH$_2$=CHCH$_2$—, and the like, groups of the formula —C(O)R', wherein R' is, for example, methyl, phenyl, trifluoromethyl, and the like, groups of the formula —SO$_2$R", wherein R" is, for example, tolyl, phenyl, trifluoromethyl, 2,2,5,7,8-pentamethylchroman-6-yl, 2,3,6-trimethyl-4-methoxyphenyl, and the like, and silanyl containing groups, such as 2-trimethylsilylethoxymethyl, t-butyldimethylsilyl, triisopropylsilyl, and the like, CURRENT PROTOCOLS IN NUCLEIC ACID CHEMISTRY, John Wiley and Sons, New York, Volume 1, 2000).

"Optional" or "Optionally" as used throughout the specification means that the subsequently described event or circumstance may or may not occur, and that the description includes instances where the event or circumstance occurs and instances in which it does not. For example, the phrase "the aromatic group is optionally substituted with one or two alkyl substituents" means that the alkyl may but need not be present, and the description includes situations where the aromatic group is substituted with an alkyl group and situations where the aromatic group is not substituted with the alkyl group.

As used herein, the term "composition" refers to a formulation suitable for administration to an intended animal subject for therapeutic purposes that contains at least one pharmaceutically active compound and at least one pharmaceutically acceptable carrier or excipient.

The term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile, e.g., for injectables.

"Pharmaceutically acceptable salt" refers to a salt which is acceptable for administration to a patient, such as a mammal (e.g., salts having acceptable mammalian safety for a given dosage regime). Such salts can be derived from pharmaceutically acceptable inorganic or organic bases and from pharmaceutically-acceptable inorganic or organic acids, depending on the particular substituents found on the compounds described herein. When compounds of the present disclosure contain relatively acidic functionalities, base addition salts can be obtained by contacting the neutral form of such compounds with a sufficient amount of the desired base, either neat or in a suitable inert solvent. Salts derived from pharmaceutically acceptable inorganic bases include aluminum, ammonium, calcium, copper, ferric, ferrous, lithium, magnesium, manganic, manganous, potassium, sodium, zinc and the like. Salts derived from pharmaceutically acceptable organic bases include salts of primary, secondary, tertiary and quaternary amines, including substituted amines, cyclic amines, naturally-occurring amines and the like, such as arginine, betaine, caffeine, choline, N, N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, N,N'-dibenzylethylenediamine, chloroprocaine, choline, diethanolamine, meglumine (N-methyl-glucamine) and the like. When compounds of the present disclosure contain relatively basic functionalities, acid addition salts can be obtained by contacting the neutral form of such compounds with a sufficient amount of the desired acid, either neat or in a suitable inert solvent. Salts derived from pharmaceutically acceptable acids include acetic, trifluoroacetic, propionic, ascorbic, benzenesulfonic, benzoic, camphosulfonic, citric, ethanesulfonic, fumaric, glycolic, gluconic, glucoronic, glutamic, hippuric, hydrobromic, hydrochloric, isethionic, lactic, lactobionic, maleic, malic, mandelic, methanesulfonic, mucic, naphthalenesulfonic, nicotinic, nitric, pamoic, pantothenic, phosphoric, succinic, sulfuric, hydroiodic, carbonic, tartaric, p-toluenesulfonic, pyruvic, aspartic, benzoic, anthranilic, mesylic, salicylic, p-hydroxybenzoic, phenylacetic, embonic (pamoic), ethanesulfonic, benzenesulfonic, 2-hydroxyethanesulfonic, sulfanilic, stearic, cyclohexylaminosulfonic, algenic, hydroxybutyric, galactaric and galacturonic acid and the like.

Also included are salts of amino acids such as arginate and the like, and salts of organic acids like glucuronic or galactunoric acids and the like (see, for example, Berge, S. M. et al, "Pharmaceutical Salts", J. Pharmaceutical Science, 1977, 66:1-19). Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

In the present context, the term "therapeutically effective" or "effective amount" indicates that a compound or amount of the compound when administered is sufficient or effective to prevent, alleviate, or ameliorate one or more symptoms of a disease, disorder or medical condition being treated, and/or to prolong the survival of the subject being treated. The therapeutically effective amount will vary depending on the compound, the disease, disorder or condition and its severity and the age, weight, etc., of the mammal to be treated. In general, satisfactory results in subjects are indicated to be obtained at a daily dosage of from about 0.1 to about 10 g/kg subject body weight. In some embodiments, a daily dose ranges from about 0.10 to 10.0 mg/kg of body weight, from about 1.0 to 3.0 mg/kg of body weight, from about 3 to 10 mg/kg of body weight, from about 3 to 150 mg/kg of body weight, from about 3 to 100 mg/kg of body weight, from about 10 to 100 mg/kg of body weight, from about 10 to 150 mg/kg of body weight, or from about 150 to 1000 mg/kg of body weight. The dosage can be conveniently administered, e.g., in divided doses up to four times a day or in sustained-release form.

Reference to particular amino acid residues in human c-kit polypeptide is defined by the numbering corresponding to the Kit sequence in GenBank NP_000213 (SEQ ID NO: 1). Reference to particular nucleotide positions in a nucleotide sequence encoding all or a portion of c-kit is defined by the numbering corresponding to the sequence provided in GenBank NM_000222 (SEQ ID NO: 2).

The terms "kit", "c-kit", and "c-Kit" mean an enzymatically active kinase that contains a portion with greater than 90% amino acid sequence identity to amino acid residues including the ATP binding site of full-length c-kit (e.g., human c-kit, e.g., the sequence NP_000213, SEQ ID NO: 1), for a maximal alignment over an equal length segment; or that contains a portion with greater than 90% amino acid sequence identity to at least 200 contiguous amino acids of native c-kit and retains kinase activity. Preferably the sequence identity is at least 95, 97, 98, 99, or even 100%. Preferably the specified level of sequence identity is over a sequence at least 100-500, at least 200-400, or at least 300 contiguous amino acid residues in length. Unless indicated to the contrary, the term includes reference to wild-type c-kit, allelic variants, and mutated forms (e.g., having activating mutations).

In the present context, the terms "synergistically effective" or "synergistic effect" indicate that two or more compounds that are therapeutically effective, when used in combination, provide improved therapeutic effects greater than the additive effect that would be expected based on the effect of each compound used by itself.

By "assaying" is meant the creation of experimental conditions and the gathering of data regarding a particular result of the exposure to specific experimental conditions. For example, enzymes can be assayed based on their ability to act upon a detectable substrate. A compound can be assayed based on its ability to bind to a particular target molecule or molecules.

As used herein, the terms "ligand" and "modulator" are used equivalently to refer to a compound that changes (i.e., increases or decreases) the activity of a target biomolecule, e.g., an enzyme such as a kinase. Generally a ligand or modulator will be a small molecule, where "small molecule refers to a compound with a molecular weight of 1500 Daltons or less, or preferably 1000 Daltons or less, 800 Daltons or less, or 600 Daltons or less. Thus, an "improved ligand" is one that possesses better pharmacological and/or pharmacokinetic properties than a reference compound, where "better" can be defined by one skilled in the relevant art for a particular biological system or therapeutic use.

The term "binds" in connection with the interaction between a target and a potential binding compound indicates that the potential binding compound associates with the target to a statistically significant degree as compared to association with proteins generally (i.e., non-specific binding). Thus, the term "binding compound" refers to a compound that has a statistically significant association with a target molecule. Preferably a binding compound interacts with a specified target with a dissociation constant ($K_D$) of 1 mM or less, 1 µM or less, 100 nM or less, 10 nM or less, or 1 nM or less.

In the context of compounds binding to a target, the terms "greater affinity" and "selective" indicates that the compound binds more tightly than a reference compound, or than the same compound in a reference condition, i.e., with a lower dissociation constant. In some embodiments, the greater affinity is at least 2, 3, 4, 5, 8, 10, 50, 100, 200, 400, 500, 1000, or 10,000-fold greater affinity.

As used herein in connection with compounds of the disclosure, the term "synthesizing" and like terms means chemical synthesis from one or more precursor materials. Further, by "assaying" is meant the creation of experimental conditions and the gathering of data regarding a particular result of the experimental conditions. For example, enzymes can be assayed based on their ability to act upon a detectable substrate. A compound or ligand can be assayed based on its ability to bind to a particular target molecule or molecules.

As used herein, the term "lone pair" or "lone pair of electrons" refers to a pair of electrons in the outermost shell of an atom, in particular a nitrogen atom, that are not used in bonding As used herein, the term "modulating" or "modulate" refers to an effect of altering a biological activity, especially a biological activity associated with a particular biomolecule such as a protein kinase. For example, an agonist or antagonist of a particular biomolecule modulates the activity of that biomolecule, e.g., an enzyme, by either increasing (e.g. agonist, activator), or decreasing (e.g. antagonist, inhibitor) the activity of the biomolecule, such as an enzyme. Such activity is typically indicated in terms of an inhibitory concentration ($IC_{50}$) or excitation concentration ($EC_{50}$) of the compound for an inhibitor or activator, respectively, with respect to, for example, an enzyme.

"Prodrugs" means any compound which releases an active parent drug according to Formula I in vivo when such prodrug is administered to a mammalian subject. Prodrugs of a compound of Formula I are prepared by modifying functional groups present in the compound of Formula I in such a way that the modifications may be cleaved in vivo to release the parent compound. Prodrugs may be prepared by modifying functional groups present in the compounds in such a way that the modifications are cleaved, either in routine manipulation or in vivo, to the parent compounds. Prodrugs include compounds of Formula I wherein a hydroxy, amino, carboxyl or sulfhydryl group in a compound of Formula I is bonded to any group that may be cleaved in vivo to regenerate the free hydroxyl, amino, or sulfhydryl group, respectively. Examples of prodrugs include, but are not limited to esters (e.g., acetate, formate, and benzoate derivatives), amides, guanidines, carbamates (e.g., N,N-dimethylaminocarbonyl) of hydroxy functional groups in compounds of Formula I, and the like. Preparation, selection, and use of prodrugs is discussed in T. Higuchi and V. Stella, "Pro-drugs as Novel Delivery Systems," Vol. 14 of the A.C.S. Symposium Series; "Design of Prodrugs", ed. H. Bundgaard, Elsevier, 1985; and in Bioreversible Carriers in Drug Design, ed. Edward B. Roche, American Pharmaceutical Association and Pergamon Press, 1987, each of which are hereby incorporated by reference in their entirety.

"Tautomer" means compounds produced by the phenomenon wherein a proton of one atom of a molecule shifts to another atom. See, Jerry March, *Advanced Organic Chemistry: Reactions, Mechanisms and Structures*, Fourth Edition, John Wiley & Sons, pages 69-74 (1992). The tautomers also refer to one of two or more structural isomers that exist in equilibrium and are readily converted from one isomeric form to another. Examples of include keto-enol tautomers, such as acetone/propen-2-ol, imine-enamine tautomers and the like, ring-chain tautomers, such as glucose/2,3,4,5,6-pentahydroxy-hexanal and the like, the tautomeric forms of heteroaryl groups containing a —N=C(H)—NH— ring atom arrangement, such as pyrazoles, imidazoles, benzimidazoles, triazoles, and tetrazoles. Where the compound contains, for example, a keto or oxime group or an aromatic moiety, tautomeric isomerism ('tautomerism') can occur. The compounds described herein may have one or more tautomers and therefore include various isomers. A person of ordinary skill in the art would recognize that other tautomeric ring atom arrangements are possible. All such isomeric forms of these compounds are expressly included in the present disclosure.

"Isomers" mean compounds having identical molecular formulae but differ in the nature or sequence of bonding of their atoms or in the arrangement of their atoms in space. Isomers that differ in the arrangement of their atoms in space are termed "stereoisomers". "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 6th edition J. March, John Wiley and Sons, New York, 2007) differ in the chirality of one or more stereocenters.

Certain compounds of the present disclosure can exist in unsolvated forms as well as solvated forms, including hydrated forms. "Hydrate" refers to a complex formed by combination of water molecules with molecules or ions of the solute. "Solvate" refers to a complex formed by combination of solvent molecules with molecules or ions of the solute. The solvent can be an organic compound, an inorganic compound, or a mixture of both. Solvate is meant to include hydrate. Some examples of solvents include, but are not limited to, methanol, N,N-dimethylformamide, tetrahydrofuran, dimethylsulfoxide, and water. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In the context of the use, testing, or screening of compounds that are or may be modulators, the term "contacting" means that the compound(s) are caused to be in sufficient proximity to a particular molecule, complex, cell, tissue, organism, or other specified material that potential binding interactions and/or chemical reaction between the compound and other specified material can occur.

As used herein, the term "subject" refers to a living organism that is treated with compounds as described herein, including, but not limited to, any mammal, such as a human, other primates, sports animals, animals of commercial interest such as cattle, farm animals such as horses, or pets such as dogs and cats.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

"Solid form" refers to a solid preparation (i.e. a preparation that is neither gas nor liquid) of a pharmaceutically active compound that is suitable for administration to an intended animal subject for therapeutic purposes. The solid form includes any complex, such as a salt, co-crystal or an amorphous complex, as well as any polymorph of the compound. The solid form may be substantially crystalline, semi-crystalline or substantially amorphous. The solid form may be administered directly or used in the preparation of a suitable composition having improved pharmaceutical properties. For example, the solid form may be used in a formulation comprising at least one pharmaceutically acceptable carrier or excipient.

The terms "prevent", "preventing", "prevention" and grammatical variations thereof as used herein, refers to a method of partially or completely delaying or precluding the onset or recurrence of a disease, disorder or condition and/or one or more of its attendant symptoms or barring a subject from acquiring or reacquiring a disorder or condition or reducing a subject's risk of acquiring or reacquiring a disorder or condition or one or more of its attendant symptoms.

"Pain" or a "pain condition" can be acute and/or chronic pain, including, without limitation, arachnoiditis; arthritis (e.g. osteoarthritis, rheumatoid arthritis, ankylosing spondylitis, gout); back pain (e.g. sciatica, ruptured disc, spondylolisthesis, radiculopathy); burn pain; cancer pain; dysmenorrhea; headaches (e.g. migraine, cluster headaches, tension headaches); head and facial pain (e.g. cranial neuralgia, trigeminal neuralgia); hyperalgesia; hyperpathia; inflammatory pain (e.g. pain associated with irritable bowel syndrome, inflammatory bowel disease, ulcerative colitis, Crohn's disease, cystitis, pain from bacterial, fungal or viral infection); keloid or scar tissue formation; labor or delivery pain; muscle pain (e.g. as a result of polymyositis, dermatomyositis, inclusion body myositis, repetitive stress injury (e.g. writer's cramp, carpal tunnel syndrome, tendonitis, tenosynovitis)); myofascial pain syndromes (e.g. fibromyalgia); neuropathic pain (e.g. diabetic neuropathy, causalgia, entrapment neuropathy, brachial plexus avulsion, occipital neuralgia, gout, reflex sympathetic dystrophy syndrome, phantom limb or post-amputation pain, postherpetic neuralgia, central pain syndrome, or nerve pain resulting from trauma (e.g. nerve injury), disease (e.g. diabetes, multiple sclerosis, Guillan-Barre Syndrome, myasthenia gravis, neurodegenerative diseases such as Parkinson's disease, Alzheimer's disease, amyotrophic lateral sclerosis, or cancer treatment); pain associated with skin disorders (e.g. shingles, herpes simplex, skin tumors, cysts, neurofibromatosis); sports injuries (e.g. cuts, sprains, strains, bruises, dislocations, fractures, spinal cord, head); spinal stenosis; surgical pain; tactile allodynia; temporomandibular disorders; vascular disease or injury (e.g. vasculitis, coronary artery disease, reperfusion injury (e.g. following ischemia, stroke, or myocardial infarcts)); other specific organ or tissue pain (e.g. ocular pain, corneal pain, bone pain, heart pain, visceral pain (e.g. kidney, gallbladder, gastrointestinal), joint pain, dental pain, pelvic hypersensitivity, pelvic pain, renal colic, urinary incontinence); other disease associated pain (e.g. sickle cell anemia, AIDS, herpes zoster, psoriasis, endometriosis, asthma, chronic obstructive pulmonary disease (COPD), silicosis, pulmonary sarcoidosis, esophagitis, heart burn, gastroesophageal reflux disorder, stomach and duodenal ulcers, functional dyspepsia, bone resorption disease, osteoporosis, cerebral malaria, bacterial meningitis); or pain due to graft v. host rejection or allograft rejections.

"Unit dosage form" refers to a composition intended for a single administration to treat a subject suffering from a disease or medical condition. Each unit dosage form typically comprises each of the active ingredients of this disclosure plus pharmaceutically acceptable excipients. Examples of unit dosage forms are individual tablets, individual capsules, bulk powders, liquid solutions, ointments, creams, eye drops, suppositories, emulsions or suspensions. Treatment of the disease or condition may require periodic administration of unit dosage forms, for example: one unit dosage form two or more times a day, one with each meal, one every four hours or other interval, or only one per day.

The expression "oral unit dosage form" indicates a unit dosage form designed to be taken orally.

As used herein, the term c-kit-mediated disease or condition or kit-mediated disease or condition or KIT-mediated disease or condition refers to a disease or condition in which the biological function of c-kit and/or mutant c-kit affects the development and/or course of the disease or condition, and/or in which modulation of c-kit and/or mutant c-kit alters the development, course, and/or symptoms. For example, mutations in the c-kit gene such as the W42, Wv, and W41 mutations reported by Herbst et al (J. Biol. Chem., 1992, 267: 13210-13216) confer severe, intermediate, and mild phenotypic characteristics, respectively. These mutations attenuate the intrinsic tyrosine kinase activity of the receptor to different degrees and are models for the effect of modulation of c-kit activity. A c-kit mediated disease or condition includes a disease or condition for which c-kit and/or mutant c-kit inhibition provides a therapeutic benefit, e.g. wherein treatment with c-kit inhibitors, including compounds described herein, provides a therapeutic benefit to the subject suffering from or at risk of the disease or condition. As used herein, mutant c-kit, kit or KIT includes kit having one or more of the mutations selected from D816F, D816H, D816N, D816Y, D816V, K642E, Y823D, Del 550-558, Del 557-561, N822K, V654A, N822H, Del 550-558+V654A, Del 557-561+V654A, Ins503AY, V560G, 558NP, Del 557-558, Del W559-560, F522C, Del 579, R634W, K642E, T801I, C809G, D820Y, N822K, N822H, Y823D, Y823C and T670I. In some instances, KIT mutations include D816F, D816H, D816N, D816Y, D816V, T670I and V654A. In other instances, KIT mutations include D816V and or V560G.

The compounds of the present disclosure may also contain unnatural proportions of atomic isotopes at one or more of the atoms that constitute such compounds. For example, the compounds may be radiolabelled with radioactive isotopes, such as for example tritium ($^3$H), iodine-125 ($^{125}$I), carbon-14 ($^{14}$C), carbon-11 ($^{11}$C) or fluorine-18 ($^{18}$F). All isotopic variations of the compounds of the present disclosure, whether radioactive or not, are intended to be encompassed within the scope of the present disclosure.

The term "deuterated" as used herein alone or as part of a group, means substituted deuterium atoms. When a particular position is designated as holding deuterium (stated as "D" or "deuterium"), it is understood that the abundance of deuterium at that position is substantially greater than the natural abundance of deuterium, which is 0.015% (i.e., at least 50.1% incorporation of deuterium).

The term "deuterated analog" as used herein alone or as part of a group, means substituted deuterium atoms in place of hydrogen. The deuterated analog of the disclosure may be a fully or partially deuterium substituted derivative. Preferably the deuterium substituted compound of the disclosure holds a fully or partially deuterium substituted alkyl, aryl or heteroaryl group. In one embodiment, the deuterium substituted compound of the disclosure holds a fully or partially deuterium substituted alkyl group, e.g., —CD$_3$, CD$_2$CD$_3$, —CD$_2$CD$_2$CD$_3$ (n-propyl-D7), —CD(CD$_3$)$_2$(iso-propyl-D7), —CD$_2$CD$_2$CD$_2$CD$_3$ (n-butyl-D9), —CD$_2$-CD(CD$_3$)$_2$ (iso-butyl-D9) and the like. In another embodiment, the deuterium substituted compound of the disclosure holds a fully or partially deuterium substituted aryl, such as phenyl, e.g., C$_6$D$_5$ or a fully or partially deuterium substituted heteroaryl, e.g., pyrazoly-d$_2$, thiazoly-d$_2$, pyridyl-d$_3$, and the like.

As used herein in connection with amino acid or nucleic acid sequence, the term "isolate" indicates that the sequence is separated from at least a portion of the amino acid and/or nucleic acid sequences with which it would normally be associated.

In connection with amino acid or nucleic sequences, the term "purified" indicates that the subject molecule constitutes a significantly greater proportion of the biomolecules in a composition than the proportion observed in a prior composition, e.g., in a cell culture. The greater proportion can be 2-fold, 5-fold, 10-fold, or more than 10-fold, with respect to the proportion found in the prior composition.

The disclosure also embraces isotopically-labeled compounds of the present disclosure which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine, and chlorine, such as, but not limited to $^2$H (deuterium, D), $^3$H (tritium), $^{11}$C, $^{13}$C, 14C, $^{15}$N, $^{18}$F, $^{31}$P, $^{32}$P, $^{35}$S, $^{36}$Cl, and $^{125}$I. Unless otherwise stated, when a position is designated specifically as "H" or "hydrogen", the position is understood to have hydrogen at its natural abundance isotopic composition or its isotopes, such as deuterium (D) or tritium ($^3$H). Certain isotopically-labeled compounds of the present disclosure (e.g., those labeled with $^3$H and 14C) are useful in compound and/or substrate tissue distribution assays. Tritiated (i.e., $^3$H) and carbon-14 (i.e., 14C) and fluorine-18 ($^{18}$F) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Isotopically labeled compounds of the present disclosure can generally be prepared by following procedures analogous to those disclosed in the Schemes and in the Examples herein below, by substituting an isotopically labeled reagent for a non-isotopically labeled reagent.

II. General

The present disclosure concerns compounds of Formulas (I'), (I), (II), (III), (IV), (V) or (V') and all sub-generic formulae, compounds as recited in the claims, and compounds described herein that are modulators of protein kinases, for example without limitation, the compounds are modulators of wild type KIT and/or mutant forms of KIT protein kinases and the use of such compounds in the treatment of diseases or conditions.

III. Compounds

In one aspect, the present disclosure provides compounds of formula (I'):

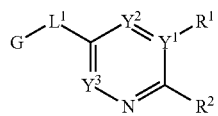

or pharmaceutically acceptable salts, hydrates, solvates, tautomers and isomers thereof; wherein the variables and substituents are as defined in the Summary.

In some embodiments of compounds of formula (I'), the compounds have molecular weights less than 600. In some preferred embodiments, the compounds have molecular weights less than 500. In other preferred embodiments, the compounds have molecular weights less than 450. In other preferred embodiments, the compounds have molecular weights less than 400. In yet other preferred embodiments, the compounds have molecular weights less than 350. In still other preferred embodiments, the compounds have molecular weights less than 300.

In some embodiments of compounds of formula (I'), G is an optionally substituted aryl or an optionally substituted 5- or 6-membered heteroaryl having from one to three nitrogen atoms as ring members, wherein the aryl or heteroaryl is optionally fused with an optionally substituted 5 to 8-membered ring having from 0-2 heteroatoms as ring members selected from O, N or S. $R^1$ and $R^2$ are taken together to form an optionally substituted aryl or an optionally substituted 5- or 6-membered fused heteroaryl ring having from 0-3 heteroatoms as ring members selected from N, O or S, wherein one or two ring carbon atoms are optionally replaced by —C(=O)—.

In some embodiments of compounds of formula (I'), the disclosure provides compounds having formula (I):

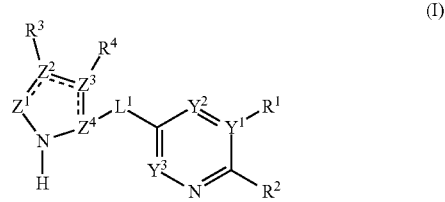

or pharmaceutically acceptable salts, hydrates, solvates, tautomers and isomers thereof; wherein:

(i) $R^1$ and $R^2$ are taken together to form an optionally substituted 5- or 6-membered fused ring having from 0-3 heteroatoms as ring members selected from N, O or S, wherein one or two ring carbon atoms are optionally replaced by —C(=O)—; or (ii) $R^1$ is H, halogen, $C_{1-4}$ alkyl, $C_{1-4}$haloalkyl, $C_{1-4}$haloalkoxy, cyclopropyl or a lone pair of electrons and $R^2$ is —NH-$L^2$-$R^6$, wherein $R^6$ is H, optionally substituted aryl, optionally substituted aryl-$C_{1-4}$alkyl, optionally substituted heteroaryl, optionally substituted heteroaryl-$C_{1-4}$ alkyl, optionally substituted heterocycloalkyl, optionally substituted $C_{1-6}$alkyl, optionally substituted cycloalkyl, optionally substituted cycloalkyl-$C_{1-4}$alkyl, optionally substituted heterocyclyl or optionally substituted heterocyclyl-$C_{1-4}$alkyl; and wherein $L^2$ is selected from a bond, —C(O)—, —C(O)N($R^f$)—, —SO$_2$N($R^f$)—, —SO$_2$—, —C(O)O—, —C(=N$R^f$)N($R^f$)—, wherein each $R^f$, is independently H or $C_{1-4}$alkyl;

$R^3$ and $R^4$ are each independently selected from H, halogen, $C_{1-4}$ alkyl, $C_{1-4}$haloalkyl, $C_{1-4}$haloalkoxy, cyclopropyl, phenyl, CN, CN—CH$_2$—, $C_{1-4}$alkoxy, $R^g$ or a lone pair of electrons; or $R^3$ and $R^4$ are taken together with the atoms to which they are attached form an optionally substituted 5 to 8-membered ring having from 0-2 heteroatoms as ring members selected from O, N or S; wherein $R^g$ is —OH, —NH$_2$, —NO$_2$, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^h$, —SR$^h$, —OC(O) R$^h$, —OC(S)R$^h$, —C(O)R$^h$, —C(S)R$^h$, —C(O)OR$^h$, —C(S) OR$^h$, —S(O)R$^h$, —S(O)$_2$R$^h$, —C(O)NHR$^h$, —C(S)NHR$^h$, —C(O)NR$^h$R$^h$, —C(S)NR$^h$R$^h$, —S(O)$_2$NHR$^h$, —S(O)$_2$ NR$^h$R$^h$, —C(NH)NHR$^h$, —C(NH)NR$^h$R$^h$, —NHC(O)R$^h$, —NHC(S)R$^h$, —NR$^h$C(O)R$^h$, —NR$^h$C(S)R$^h$, —NHS(O)$_2$ $R^h$, —$NR^hS(O)_2R^h$, —NHC(O)NH $R^h$, —NHC(S)NH$R^h$, —$NR^hC(O)NH_2$, —$NR^hC(S)NH_2$, —$NR^hC(O)NHR^h$, —$NR^hC(S)NHR^h$, —NHC(O)$NR^hR^h$, —NHC(S)$NR^hR^h$, —$NR^hC(O)NR^hR^h$, —$NR^hC(S)NR^hR^h$, —NHS(O)$_2$NH$R^h$, —$NR^hS(O)_2NH_2$, —$NR^hS(O)_2N$ H$R^h$, —NHS(O)$_2NR^hR^h$, —$NR^hS(O)_2NR^hR^h$, —NH$R^h$ or —$NR^hR^h$, wherein each $R^h$ is independently H or $C_{1-2}$alkyl; In certain instances, $R^3$ and $R^4$ are not simultaneously hydrogen;

$L^1$ is selected from —C(O)$NR^5$—, —CH$_2$N($R^5$)—, —SO$_2$N($R^5$)—, —N($R^5$)C(O)N($R^5$)—, —N($R^5$)SO$_2$—, —N($R^5$)CH$_2$—, —OC$_{1-4}$alkylene-, —C$_{1-4}$alkylene-O—, —C(O)—, —$NR^5$C(O)—, —SO$_2$—, —SON($R^5$)— or —S(O)—, wherein each $R^5$ is independently H or C$_{1-4}$alkyl;

$Y^1$ is N or C;

$Y^2$ is N or optionally substituted =C—;

$Y^3$ is N or CH; with the proviso that $Y^1$, $Y^2$ and $Y^3$ are not simultaneously N;

$Z^1$ is N or CH;

$Z^3$ is N, C or CH;

$Z^2$ and $Z^4$ are each independently N or C, with the proviso that $Z^1$, $Z^2$, $Z^3$ and $Z^4$ are not simultaneously N; and ----- is a single or a double bond. In some embodiments of compounds of Formula (I), $Z^2$ and $Z^3$ are C. In certain instances, moiety

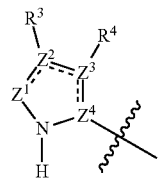

in compounds of formula (I) can exist in a tautomeric form:

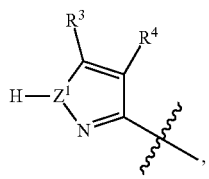

where the wavy line indicates the point of attachment to the rest of the molecule.

In some embodiments of compounds of Formula (I), $Z^1$ is N, $Z^2$, $Z^3$ and $Z^4$ are C. In other embodiments of compounds of Formula (I), $Z^1$ is N, $Z^2$ is C, $Z^3$ and $Z^4$ are N. In yet other embodiments of compounds of Formula (I), $Z^1$ is N, $Z^2$ is C, $Z^3$ is CH and $Z^4$ is N. In still other embodiments of compounds of Formula (I), $Z^1$ is N, $Z^2$ is C, $Z^3$ is N and $Z^4$ is C. In other embodiments of compounds of Formula (I), $Z^1$ is N, $Z^2$ is N, $Z^3$ is N and $Z^4$ is C. In other embodiments of compounds of Formula (I), $Z^1$ is N, $Z^2$ is N, $Z^3$ is CH and $Z^4$ is N. In other embodiments of compounds of Formula (I), $Z^1$ is N, $Z^2$ is N, $Z^3$ and $Z^4$ are C. In other embodiments of compounds of Formula (I), $Z^1$ is CH, $Z^2$, $Z^3$ and $Z^4$ are C. In other embodiments of compounds of Formula (I), $Z^1$ is CH, $Z^2$ is C, $Z^3$ is N and $Z^4$ is C. In other embodiments of compounds of Formula (I), $Z^1$ is CH, $Z^2$ is C, $Z^3$ is C and $Z^4$ is N. In other embodiments of compounds of Formula (I), $Z^1$ is CH, $Z^2$ is C, $Z^3$ and $Z^4$ are N. In other embodiments of compounds of Formula (I), $Z^1$ is CH, $Z^2$ is N, $Z^3$ is C and $Z^4$ is C. In other embodiments of compounds of Formula (I), $Z^1$ is CH, $Z^2$ is N, $Z^3$ is N and $Z^4$ is C. In other embodiments of compounds of Formula (I), $Z^1$ is CH, $Z^2$ is N, $Z^3$ is CH and $Z^4$ is N. In other embodiments of compounds of Formula (I), $Z^1$ is CH, $Z^2$, $Z^3$ and $Z^4$ are N. All the other variables and substituents $Y^1$, $Y^2$, $Y^3$, $R^1$, $R^2$, $L^1$, $R^3$ and $R^4$ are as defined in any of the subgeneric formulas of formula (I) or in any the embodiments of compounds of formula (I) as described herein.

In some embodiments of compounds of Formulas (I') or (I), the disclosure provides compounds of Formula (II):

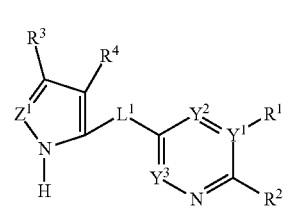

(II)

The variables $Y^1$, $Y^2$, $Y^3$, $R^1$, $R^2$, $Z^1$, $L^1$, $R^3$ and $R^4$ are as defined in any of the embodiments of compounds of Formulas (I'), (I) or (IV), or any of the subgeneric formulas of Formulas (I'), (I), (II) or (IV). In one instance, $Z^1$ is N. In another instance, $Z^1$ is CH. In certain instances, moiety

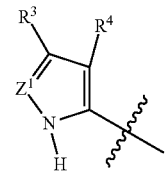

in compounds of formula (II) exist in a tautomeric form:

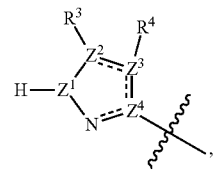

where the wavy line indicates the point of attachment to the rest of the molecule.

In some embodiments of compounds of Formulas (I'), (I) or (II), $L^1$ is selected from —C(O)$NR^5$—, —CH$_2$N($R^5$)—, —SO$_2$N($R^5$)—, —N($R^5$)C(O)N($R^5$)—, —N($R^5$)SO$_2$—, —N($R^5$)CH$_2$—, —OC$_{1-4}$alkylene-, —C$_{1-4}$alkylene-O—, —C(O)—, —SO$_2$—, —SON($R^5$)— or —S(O)—. In other embodiments, $L^1$ is selected from —C(O)N($R^5$)—, —SO$_2$N ($R^5$)—, —C(O)—, —SO$_2$—, —CH$_2$O—, —CH$_2$N($R^5$)— or —SON($R^5$)—. In other embodiments, $L^1$ is C(O)N($R^5$)—. In yet other embodiments, $L^1$ is —C(O)NH— or —SO$_2$NH—. In one embodiment, $L^1$ is —C(O)NH—. In certain instances, $R^5$ is H. In other instances, $R^5$ is C$_{1-4}$alkyl. In yet other instances, $R^5$ is H, C$_{1-4}$alkyl or C$_{1-4}$haloalkyl. In one instance, $R^5$ is H, —CH$_3$, —CHF$_2$, —CH$_2$F or —CF$_3$. All the other variables and substituents $Y^1$, $Y^2$, $Y^3$, $R^1$, $R^2$, $Z^1$, $Z^2$, $Z^3$, $Z^4$, $R^3$ and $R^4$ are as defined in any of the subgeneric formulas of formulas (I'), (I) or (II) or in any of the embodiments of compounds of formulas formula (I'), (I) or (II) as described herein.

In some embodiments of compounds of Formulas (I'), (I) or (II), $L^1$ is —NHSO$_2$—, —SO$_2$NH—, —NHC(O)NH—, —NHC(O)—, —CH$_2$O—, —OCH$_2$—, —C(O)NH—, —SO$_2$—, —C(O)O—, —C(O)—, —C(=NH)NH— or —NHC(=NH)—. In certain embodiments, $L^1$ is —NHSO$_2$—, —SO$_2$NH—, —NHC(O)NH—, —NHC(O)—, —C(O)NH—, —SO$_2$—, —C(O)O—, —OC(O)—, —C(O)— or —C(=NH)NH—. In certain instances, $L^1$ is —NHSO$_2$—, —SO$_2$NH—, —NHC(O)NH— or —NHC(O)—. In other instances, $L^1$ is —C(O)NH—, —SO$_2$—, —SO$_2$NH—, —C(O)O— or —C(O)—. In other instances, $L^1$ is —NHSO$_2$— or —SO$_2$NH—. In yet other instances, $L^1$ is —C(O)NH—, —NHSO$_2$—, —SO$_2$NH— or —C(=NH)NH—. In still other instances, $L^1$ is —NHSO$_2$—, —SO$_2$NH— or —SO$_2$—. In other instances, $L^1$ is —NH—C(O)—. All the other variables and substituents $Y^1$, $Y^2$, $Y^3$, $R^1$, $R^2$, $Z^1$, $Z^2$, $Z^3$, $Z^4$, $R^3$ and $R^4$ are as defined in any of the embodiments as described herein.

In some embodiments of compounds of Formulas (I'), (I) (II), the disclosure provides compounds of Formula (III):

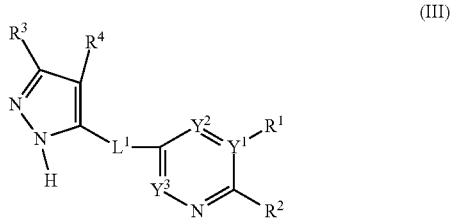

(III)

The variables $Y^1$, $Y^2$, $Y^3$, $R^1$, $R^2$, $R^3$, $R^4$ and $L^1$ are as defined in any of the embodiments of compounds of Formulas (I'), (I), (II) or (IV) as described herein or in any of the subgeneric formulas of Formulas (I'), (I), (II) or (IV). In some instances of compounds of formula (III), $L^1$ is —C(O)NR$^5$—, wherein the carbonyl group in $L^1$ is covalently linked to the pyrazole ring and the nitrogen atom in $L^1$ is covalently bonded to the 6-membered aromatic ring in formula (III).

In some embodiments of compounds of formulas (I'), (I), (II) or (III), $R^1$ and $R^2$ taken together with the atoms to which they attach form an optionally substituted 5- or 6-membered fused heterocyclic aromatic ring having from 1-3 heteroatoms as ring members selected from O, N or S; or an optionally substituted fused benzene ring. In some instances, the substituents for the fused aromatic ring are $R^7$ groups as defined in any of the embodiments of compounds of formula (I'), (I), (II), (III), (IV) as described herein or in any of the subgeneric formulas of Formulas (I'), (I), (II), (III) or (IV).

In some embodiments of compounds of formula (I'), the disclosure provides compounds having formula (I'a):

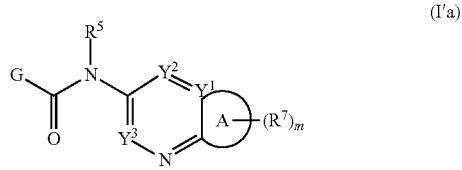

(I'a)

The substituent G is as defined in any of the embodiments of compounds of formula (I'). $R^5$ is H, $C_{1-4}$alkyl or $C_{1-4}$haloalkyl. Ring A is a 5- or 6-membered fused heterocyclic aromatic ring having from 1-3 heteroatoms as ring members selected from O, N or S; or a fused benzene ring;

each $R^7$ is independently selected from $C_{1-6}$alkyl, $C_{1-6}$alkoxy, $C_{2-6}$alkenyl, $C_{2-6}$alkynyl, —X$^1$-aryl, aryl-$C_{1-4}$alkyl-X$^1$—, heteroaryl-X$^1$—, heteroaryl-$C_{1-4}$ alkyl-X$^1$—, $C_{3-6}$cycloalkyl-X$^1$—, $C_{3-6}$cycloalkyl-$C_{1-4}$alkyl-X$^1$—, $C_{3-6}$cycloalkenyl-X$^1$—, CH$_2$=CH—X$^1$, $C_{3-6}$cycloalkyl-$C_{2-4}$alkenyl-X$^1$, $C_{3-6}$cycloalkyl-$C_{2-4}$alkynyl-X$^1$, heterocyclyl-X$^1$—, heterocyclyl-$C_4$alkyl-X$^1$— or $R^8$, wherein $R^8$ is selected from halogen, CN, —OH, —NH$_2$, —NO$_2$, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$—OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O) NHR$^a$, —C(S)NHR$^a$, —C(O)NR$^{a1}$R$^a$, —C(S)NR$^{a1}$R$^a$, —S(O)$_2$NHR$^a$, —S(O)$_2$NR$^{a1}$R$^a$, —C(NH)NHR$^a$, —C(NH)NR$^a$R$^a$, —NHC(O)R$^a$, —NHC(S)R$^a$, —NR$^a$C(O)R$^a$, —NR$^a$C(S)R$^a$, —NHS(O)$_2$R$^a$, —NR$^{a1}$S(O)$_2$R$^a$, —NHC(O)NHR$^a$, —NHC(S)NHR$^a$, —NR$^a$C(O) NH$_2$, —NR$^a$C(S)NH$_2$, —NR$^a$C(O)NHR$^a$, —NR$^a$C(S) NHR$^a$, —NHC(O)NR$^a$R$^a$, —NHC(S)NR$^a$R$^a$, —NR$^a$C(O) NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$ or —NR$^a$R$^a$, wherein each R$^a$ is independently selected from $C_{1-6}$alkyl, aryl, aryl-$C_{1-2}$alkyl, $C_{3-6}$cycloalkyl, $C_{3-6}$cycloalkyl-$C_{1-4}$alkyl, heteroaryl, heteroaryl-$C_{1-4}$alkyl, heterocycloalkyl or heterocycloalkyl-$C_{1-4}$alkyl, wherein each R$^a$ is further optionally substituted with 1-3 R$^b$ substituents independently selected from $C_{1-6}$alkyl, $C_{1-6}$alkoxy, halogen, $C_{1-6}$ haloalkyl or $C_{1-6}$ haloalkoxy; wherein $X^1$ is a bond or —C(O)— and wherein $R^7$ is optionally substituted with from 1-5 $R^9$ members selected from halogen, —CH=CH$_2$, CN, —OH, —NH$_2$, —NO$_2$, —C(O)OH, —C(S)OH, —C(O)NH$_2$, —C(S)NH$_2$, —S(O)$_2$NH$_2$, —NHC(O)NH$_2$, —NHC(S)NH$_2$, —NH S(O)$_2$NH$_2$, —C(NH)NH$_2$, —OR$^c$, —SR$^c$, —OC(O)R$^c$, —OC(S)R$^c$, —P(=O)HR$^c$, —P(=O)R$^c$R$^c$, —PH(=O) OR$^c$, —P(=O)(OR$^c$)$_2$, —OP(=O)(OR$^c$)$_2$, —C(O)R$^c$, —C(S)R$^c$, —C(O)OR$^c$, —C(S)OR$^c$, —S(O)R$^c$, —S(O)$_2$R$^c$, —C(O)NHR$^c$, —C(S)NHR$^c$, —C(O)NR$^c$R$^c$, —C(S)NR$^c$R$^c$, —S(O)$_2$NHR$^c$, —S(O)$_2$NR$^c$R$^c$, —C(NH)NHR$^c$, —C(NH) NR$^c$R$^c$, —NHC(O)R$^c$, —N HC(S)R$^c$, —NR$^c$C(O)R$^c$, —NR$^c$C(S)R$^c$, —NHS(O)$_2$R$^c$, —NR$^c$S(O)$_2$R$^c$, —NHC(O) NHR$^c$, —NHC(S)NHR$^c$, —NR$^c$C(O)NH$_2$, —NR$^c$C(S)NH$_2$, —NR$^c$C(O)NHR$^c$, —NR$^c$C(S)NHR$^c$, —NHC(O)NR$^c$R$^c$, —NHC(S)NR$^c$R$^c$, —NR$^c$C(O)NR$^c$R$^c$, —NR$^c$C(S)NR$^c$R$^c$, —NHS(O)$_2$NHR$^c$, —NR$^c$S(O)$_2$NH$_2$, —NR$^c$S(O)$_2$NHR$^c$, —NHS(O)$_2$NR$^c$R$^c$, —NR$^c$S(O)$_2$NR$^c$R$^c$, —NHR$^c$, R$^c$ or —NR$^c$R$^c$, wherein each R$^c$ is independently selected from $C_{1-6}$alkyl, aryl, aryl-$C_{1-2}$alkyl, $C_{3-6}$cycloalkyl, $C_{3-6}$cycloalkyl-$C_{1-4}$alkyl, heteroaryl, heteroaryl-$C_{1-4}$alkyl, heterocycloalkyl or heterocycloalkyl-$C_{1-4}$alkyl, wherein each R$^c$ is further optionally substituted with from 1-3 R$^d$ groups independently selected from CN, —OH, —N(R$^e$)(R$^e$), —NO$_2$, —C(O)OH, —P(=O)HR$^e$, —P(=O)R$^e$R$^e$, —PH(=O) OR$^e$, —P(=O)(OR$^e$)$_2$, —OP(=O)(OR$^e$)$_2$, —C(O)NH$_2$, —S(O)$_2$NH$_2$, —NHC(O)NH$_2$, —C(NH)NH$_2$, —OC(O)R$^e$, —OC(S)R$^e$, —C(O)R$^e$, —C(S)R$^e$, —C(O)OR$^e$, —S(O)$_2$R$^e$, —C(O)NHR$^e$, $C_{1-6}$alkyl, $C_{1-6}$alkoxy, halogen, $C_{1-6}$ haloalkyl or $C_{1-6}$ haloalkoxy, wherein each R$^e$ is independently $C_{1-6}$alkyl; or two adjacent R$^7$ substituents together with the atoms to which they are attached form a 4-, 5- or 6-membered carbocyclic ring or heterocyclic ring having from 1-2 heteroatoms as ring members selected from O, N or S;

$Y^2$ is C—R$^{10}$, wherein R$^{10}$ is H, $C_{1-6}$alkyl, $C_{1-6}$alkoxy, $C_{2-6}$alkenyl, $C_{2-6}$alkynyl, aryl-$C_{1-4}$alkyl-, heteroaryl-$C_{1-4}$ alkyl-, C$_{3-6}$cycloalkyl-C$_{1-4}$alkyl-, C$_{3-6}$cycloalkenyl-C$_{1-4}$alkyl-, CH$_2$=CH—X$^2$—, C$_{3-6}$cycloalkyl-C$_{2-4}$alkenyl-X$^2$—, C$_{3-6}$cycloalkyl-C$_{2-4}$alkynyl-X$^2$—, heterocyclyl-C$_{1-4}$alkyl- or R$^8$, each of which is optionally substituted with from 1-5 R$^g$ groups or 1-5 R$^c$ groups or 1-5 R$^d$ groups or 1-5 R$^e$ groups; wherein X$^2$ is C$_{1-4}$alkylene, —O—, —S— or —NH—; Y$^1$ is N or C; and the subscript m is 0, 1 or 2. In some embodiments, R$^{10}$ is H. In some embodiments, R$^{10}$ is H, halogen, C$_{1-4}$alkyl, C$_{1-2}$alkoxy, CN, NH$_2$, C$_{1-2}$alkylNH, (C$_{1-2}$alkyl)$_2$N. In some embodiments, R$^{10}$ is C$_{1-4}$ alkyl, halogen, —NH$_2$, —CN, —OCH$_3$, CF$_3$, CN, —OCF$_3$, —CHF$_2$, —CH$_2$F, —OCH$_2$F or —OCHF$_2$. In other embodiments, R$^{10}$ is C$_{1-4}$alkyl. In other embodiments, R$^7$ is C$_{1-4}$ alkyl, halogen, —CN, —OCH$_3$, CF$_3$, CN, —OCF$_3$, —CHF$_2$, —CH$_2$F, —OCH$_2$F or —OCHF$_2$. In other embodiments, R$^7$ is C$_{1-4}$alkyl. In some embodiments, the subscript m is 0, 1, 2 or 3. In one embodiment, Y$^1$ is N or C. In another embodiment, Y$^3$ is CH.

In some embodiments, the variables and substituents G, Y$^1$, Y$^2$, Y$^3$, A, R$^7$ and the subscript m are as defined in any of the subgeneric formulas of (I'), (I'a) or (IV), or any of the embodiments of compounds of formula (IV). In any of the embodiments of compounds of formulas (I'a), the hydrogen atoms in G are optionally replaced by 1 to 12, or 1 to 8, or 1 to 6, or 1 to 3 or 1, 2, 3, 4, 5, 6, 7, 8, 9, 10, 11 and 12 deuterium atoms with at least 52.5%, 60%, 70%, 75%, 80%, 90%, 95%, 99%, 99.5% or 99.9% deuterium incorporation for each deuterium. In certain embodiments, each hydrogen atom in G is optionally replaced by a deuterium atom with at least 52.5%, 60%, 70%, 75%, 80%, 90%, 95%, 99%, 99.5% or 99.9% deuterium incorporation for each deuterium.

In some embodiments of compounds of formulas (I') or (I'a), G is an optionally substituted C$_{1-6}$ alkyl. In other embodiments, G is an optionally substituted aryl or an optionally substituted 5- or 6-membered heteroaryl having one or more nitrogen atoms as ring members, wherein the aryl or heteroaryl is optionally fused with an optionally substituted 5 to 8-membered ring having from 0-2 heteroatoms as ring members selected from O, N or S. In certain instances, the alkyl or aromatic portion of G is optionally substituted with 1-3 R$^7$; or 1-3 R$^8$; or 1-3 R$^9$; or 1-3 R$^a$; or 1-3 R$^c$; or 1-3 R$^d$; or 1-3 R$^g$ substituents. In other instances, the alkyl or aromatic portion of G is optionally substituted with from 1-3 R$^{21}$ groups selected from halogen, C$_{1-4}$ alkyl, C$_{1-4}$haloalkyl, C$_{1-4}$haloalkoxy, cyclopropyl, phenyl, CN, CN—CH$_2$—, C$_{1-4}$alkoxy, —OH, —NH$_2$, —NO$_2$, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^i$, —SR$^i$, —OC(O)R$^i$, —OC(S)R$^i$, —C(O)R$^i$, —C(S)R$^i$, —C(O)OR$^i$, —C(S)OR$^i$, —S(O)R$^i$, —S(O)$_2$R$^i$, —C(O)N HR$^i$, —C(S)NHR$^i$, —C(O)NR$^i$R$^i$, —C(S)NR$^i$R$^i$, —S(O)$_2$NHR$^i$, —S(O)$_2$NR$^i$R$^i$, —C(NH)NHR$^i$, —C(NH)NR$^i$R$^i$, —NHC(O)R$^i$, —NHC(S)R$^i$, —NR$^i$C(O)R$^i$, —NR$^i$C(S)R$^i$, —NHS(O)$_2$R$^i$, —NR'S(O)$_2$R$^1$, —NHC(O)NHR$^1$, —NHC(S)NHR$^i$, —NR$^i$C(O)NH$_2$, —NR$^i$C(S)NH$_2$, —NR$^i$C(O)NHR$^1$, —NR$^i$C(S)NHR$^1$, —NHC(O)NR$^i$R$^i$, —NHC(S)NR$^i$R$^i$, —NR$^i$C(O)NR$^i$R$^i$, —NR$^i$C(S)NR$^i$R$^i$, —NHS(O)$_2$NHR$^1$, —NR'S(O)$_2$NH$_2$, —NR'S(O)$_2$NHR$^1$, —NHS(O)$_2$NR$^i$R$^i$, —NR'S(O)$_2$NR$^i$R$^i$, —NHR$^1$ or —NR$^i$R$^i$, wherein R$^1$ is C$_{1-2}$alkyl or optionally substituted phenyl.

In some embodiments of compounds of formula (I') or (I'a), G is phenyl, 2-pyridyl, 3-pyridyl, 4-pyridyl, 2-pyrazinyl, 2-pyrimidinyl, 4-pyrimidinyl, 5-pyrimidinyl, 3-isoxazolyl, 4-isoxazolyl, 5-isoxazolyl, 1H-1,2,4-triazol-5-yl, 1H-1,2,4-triazol-3-yl, 1H-1,2,5-triazol-3-yl, 1H-5-pyrazolyl, 1H-4-pyrazolyl, 1H-3-pyrazolyl, 3-pyridazinyl, 4-pyridazinyl, 1H-indazol-3-yl, 1H-indazol-4-yl, 1H-indazol-5-yl, 1H-indazol-6-yl, 1H-indazol-7-yl,

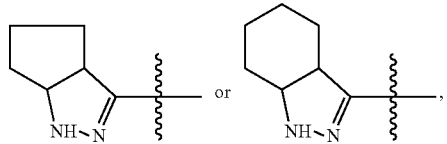 [SMILES: *C1=NNC2CCCC12 ; *C1=NNC2CCCCC12]

each of which is optionally substituted with from 1-3 R$^{22}$ groups independently selected from halogen, C$_{1-4}$ alkyl, C$_{1-4}$haloalkyl, C$_{1-4}$haloalkoxy, cyclopropyl, phenyl, CN, CN—CH$_2$—, C$_{1-4}$alkoxy or R$^g$; or 1-3 R$^g$ groups, wherein the hydrogen atoms in R$^{22}$ are optionally replaced with from 1-8 deuterium atoms. In some embodiments, G is 2-pyridyl, 3-pyridyl or 4-pyridyl, each of which is optionally substituted with from 1-3 R$^{22}$ groups independently selected from halogen, C$_{1-4}$ alkyl, C$_{1-4}$haloalkyl, C$_{1-4}$haloalkoxy, cyclopropyl, phenyl, CN, CN—CH$_2$—, C$_{1-4}$alkoxy or R$^g$; or 1-3 R$^g$ groups. In other instances, G is 1H-5-pyrazolyl, 1H-4-pyrazolyl or 1H-3-pyrazolyl, each of which is optionally substituted with from 1-3 R$^{22}$ groups independently selected from halogen, C$_{1-4}$ alkyl, C$_{1-4}$haloalkyl, C$_{1-4}$haloalkoxy, cyclopropyl, phenyl, CN, CN—CH$_2$—, C$_{1-4}$alkoxy or R$^g$; or 1-3 R$^g$ groups. In yet other instances, G is 1H-5-pyrazolyl, which is optionally substituted with from 1-3 R$^{22}$ groups independently selected from halogen, C$_{1-4}$ alkyl, C$_{1-4}$haloalkyl, C$_{1-4}$haloalkoxy, cyclopropyl, phenyl, CN, CN—CH$_2$—, C$_{1-4}$alkoxy or R$^g$; or 1-3 R$^g$ groups. In some instances, R$^{22}$ is —CD$_3$, —C$_6$D5, partially deuterated C$_{1-6}$alkyl or perdeuterated C$_{1-6}$alkyl.

In some embodiments of compounds of Formulas (I'), (I'a), (I), (II) or (III), the disclosure provides compounds of Formula (IV):

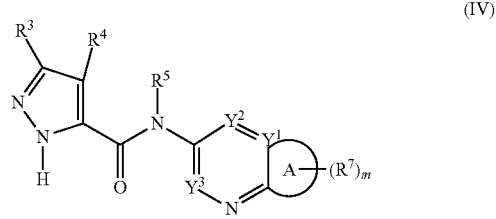

(IV)

ring A is a 5- or 6-membered fused heterocyclic aromatic ring having from 1-3 heteroatoms as ring members selected from O, N or S; or a fused benzene ring;

each R$^7$ is independently selected from C$_{1-6}$alkyl, C$_{1-6}$alkoxy, C$_{2-6}$alkenyl, C$_{2-6}$alkynyl, —X$^1$-aryl, aryl-C$_{1-4}$ alkyl-X—, heteroaryl-X$^1$—, heteroaryl-C$_{1-4}$ alkyl-X$^1$—, C$_{3-6}$cycloalkyl-X—, C$_{3-6}$cycloalkyl-C$_{1-4}$alkyl-X—, C$_{3-6}$cycloalkenyl-X—, CH$_2$=CH—X$^1$, C$_{3-6}$cycloalkyl-C$_{2-4}$alkenyl-X$^1$, C$_{3-6}$cycloalkyl-C$_{2-4}$alkynyl-X$^1$, heterocyclyl-X$^1$—, heterocyclyl-C$_{1-4}$alkyl-X— or R$^8$, wherein R$^8$ is selected from halogen, CN, —OH, —NH$_2$, —NO$_2$, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O) NHR$^a$, —C(S)NHR$^a$, —C(O)NR$^a$R$^a$, —C(S)NR$^a$R$^a$, —S(O)$_2$NHR$^a$, —S(O)$_2$NR$^a$R$^a$, —C(NH) NHR$^a$, —C(NH)NR$^a$R$^a$, —NHC(O)R$^a$, —NHC(S)R$^a$, —NR$^a$C(O)R$^a$, —NR$^a$C(S)R$^a$, —NHS(O)$_2$R$^a$, —NR$^a$S(O)$_2$R$^a$, —NHC(O)NHR$^a$, —NHC(S)NHR$^a$, —NR$^a$C(O)NH$_2$, —NR$^a$C(S)NH$_2$, —NR$^a$C(O)NHR$^a$, —NR$^a$C(S)NHR$^a$, —NHC(O)NR$^a$R$^a$, —N HC(S)NR$^a$R$^a$, —NR$^a$C(O)NR$^a$R$^a$, —NHC(O)NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$ or —NR$^a$R$^a$, wherein each R$^a$ is independently selected from C$_{1-6}$alkyl, aryl, aryl-C$_{1-2}$alkyl, C$_{3-6}$cycloalkyl, C$_{3-6}$cycloalkyl-C$_{1-4}$alkyl, heteroaryl, heteroaryl-C$_{1-4}$alkyl, heterocycloalkyl or heterocycloalkyl-C$_{1-4}$alkyl, wherein each R$^a$ is further optionally substituted with 1-3 R$^b$ substituents independently selected from C$_{1-6}$alkyl, C$_{1-6}$alkoxy, halogen, C$_{1-6}$ haloalkyl or C$_{1-6}$ haloalkoxy; wherein X$^1$ is a bond or —(O)— and wherein R$^7$ is optionally substituted with from 1-5 R$^9$ members selected from halogen, —CH=CH$_2$, CN, —OH, —NH$_2$, —NO$_2$, —C(O)OH, —C(S)OH, —C(O)NH$_2$, —C(S)NH$_2$, —S(O)$_2$NH$_2$, —NHC(O)NH$_2$, —NHC(S)NH$_2$, —NH S(O)$_2$NH$_2$, —C(NH)NH$_2$, —OR$^c$, —SR$^c$, —OC(O)R$^c$, —OC(S)R$^c$, —P(=O)HR$^c$, —P(=O)R$^c$R$^c$, —PH(=O) OR$^c$, —P(=O)(OR$^c$)$_2$, —OP(=O)(OR$^c$)$_2$, —C(O)R$^c$, —C(S)R$^c$, —C(O)OR$^c$, —C(S)OR$^c$, —S(O)R$^c$, —S(O)$_2$R$^c$, —C(O)NHR$^c$, —C(S)NHR$^c$, —C(O)NR$^c$R$^c$, —C(S)NR$^c$R$^c$, —S(O)$_2$NHR$^c$, —S(O)$_2$NR$^c$R$^c$, —C(NH)NHR$^c$, —C(NH) NR$^c$R$^c$, —NHC(O)R$^c$, —N HC(S)R$^c$, —NR$^c$C(O)R$^c$, —NR$^c$C(S)R$^c$, —NHS(O)$_2$R$^c$, —NR$^c$S(O)$_2$R$^c$, —NHC(O) NHR$^c$, —NHC(S)NHR$^c$, —NR$^c$C(O)NH$_2$, —NR$^c$C(S)NH$_2$, —NR$^c$C(O)NHR$^c$, —NR$^c$C(S)NHR$^c$, —NHC(O)NR$^c$R$^c$, —NHC(S)NR$^c$R$^c$, —NR$^c$C(O)NR$^c$R$^c$, —NR$^c$C(S)NR$^c$R$^c$, —NHS(O)$_2$NHR$^c$, —NR$^c$S(O)$_2$NH$_2$, —NR$^c$S(O)$_2$NHR$^c$, —NHS(O)$_2$NR$^c$R$^c$, —NR$^c$S(O)$_2$NR$^c$R$^c$, —NHR$^c$, R$^c$ or —NR$^c$R$^c$, wherein each R$^c$ is independently selected from C$_{1-6}$alkyl, aryl, aryl-C$_{1-2}$alkyl, C$_{3-6}$cycloalkyl, C$_{3-6}$cycloalkyl-C$_{1-4}$alkyl, heteroaryl, heteroaryl-C$_{1-4}$alkyl, heterocycloalkyl or heterocycloalkyl-C$_{1-4}$alkyl, wherein each R$^c$ is further optionally substituted with from 1-3 R$^d$ groups independently selected from CN, —OH, —N(R$^e$)(R$^e$), —NO$_2$, —C(O)OH, —C(O)NH$_2$, —S(O)$_2$NH$_2$, —NHC(O)NH$_2$, —C(NH)NH$_2$, —P(=O)HR$^e$, —P(=O)R$^e$R$^e$, —PH(=O) OR$^e$, —P(=O)(OR$^e$)$_2$, —OP(=O)(OR$^e$)$_2$, —OC(O)R$^e$, —OC(S)R$^e$, —C(O)R$^e$, —C(S)R$^e$, —C(O)OR$^e$, —S(O)$_2$R$^e$, —C(O)NHR$^e$, C$_{1-6}$alkyl, C$_{1-6}$alkoxy, halogen, C$_{1-6}$ haloalkyl or C$_{1-6}$ haloalkoxy, wherein each R$^e$ is independently C$_{1-6}$alkyl; or two adjacent R$^7$ substituents together with the atoms to which they are attached form a 4-, 5- or 6-membered carbocyclic ring or heterocyclic ring having from 1-2 heteroatoms as ring members selected from O, N or S;

Y$^2$ is C—R$^{10}$, wherein R$^{10}$ is H, C$_{1-6}$alkyl, C$_{1-6}$alkoxy, C$_{2-6}$alkenyl, C$_{2-6}$alkynyl, aryl-C$_{1-4}$alkyl-, heteroaryl-C$_{1-4}$alkyl-, C$_{3-6}$cycloalkyl-C$_{1-4}$alkyl-, C$_{3-6}$cycloalkenyl-C$_{1-4}$alkyl-, CH$_2$=CH—X$^2$—, C$_{3-6}$cycloalkyl-C$_{2-4}$alkenyl-X$^2$—, C$_{3-6}$cycloalkyl-C$_{2-4}$alkynyl-X$^2$—, heterocyclyl-C$_{1-4}$alkyl- or R$^8$, each of which is optionally substituted with from 1-5 R$^9$ groups or 1-5 R$^c$ groups or 1-5 R$^d$ groups or 1-5 Re groups; wherein X$^2$ is C$_{1-4}$alkylene, —O—, —S— or —NH—; Y$^1$ is N or C; and the subscript m is 0, 1 or 2. In some embodiments, R$^{10}$ is H. In other embodiments, R$^{10}$ is H, halogen, C$_{1-4}$alkyl, C$_{1-2}$alkoxy, CN, NH$_2$, C$_{1-2}$alkylNH, (C$_{1-2}$alkyl)$_2$N. In other embodiments, R$^{10}$ is C$_{1-4}$ alkyl, halogen, —CN, —NH$_2$, —OCH$_3$, CF$_3$, CN, —OCF$_3$, —CHF$_2$, —CH$_2$F, —OCH$_2$F or —OCHF$_2$. In other embodiments, R$^{10}$ is C$_{1-4}$alkyl. In other embodiments, R$^7$ is C$_{1-4}$ alkyl, halogen, —CN, —OCH$_3$, CF$_3$, CN, —OCF$_3$, —CHF$_2$, —CH$_2$F, —OCH$_2$F or —OCHF$_2$. In other embodiments, R$^7$ is C$_{1-4}$alkyl. In one embodiment, Y$^1$ is C. In one embodiment, Y$^3$ is CH.

In some embodiments of compounds of formula (IV) or (I'a), the subscript m is 1 or 2 and all the other substituents of formula (IV) are as defined in any of the embodiments described herein. In one instance, the subscript m is 1. In another instance, the subscript m is 2. In yet another instance, the subscript m is 0. All the other variables Y$^1$, Y$^2$, Y$^3$, R$^3$, R$^4$, R$^5$ and R$^7$ of formula (IV) are as defined in any of the embodiments described herein.

In some embodiments of compounds of formula (IV) or (I'a), R$^7$ is independently selected from C$_{1-6}$alkyl, deuterated C$_{1-6}$alkyl, C$_{1-6}$alkoxy, C$_{2-6}$alkenyl, C$_{2-6}$alkynyl, —X$^1$-aryl, aryl-C$_{1-4}$alkyl-X$^1$—, heteroaryl-X$^1$—, heteroaryl-C$_{1-4}$alkyl-X$^1$—, C$_{3-6}$cycloalkyl-X$^1$—, C$_{3-6}$cycloalkenyl-X$^1$—, C$_{3-6}$cycloalkyl-C$_{1-4}$alkyl-X$^1$—, heterocyclyl-X$^1$—, heterocyclyl-C$_{1-4}$alkyl-X$^1$—, CH$_2$=CH—X$^1$, C$_{3-6}$cycloalkyl-C$_{2-4}$alkenyl-X$^1$, C$_{3-6}$cycloalkyl-C$_{2-4}$alkynyl-X$^1$, halogen, CN, —OH, —NH$_2$, —NO$_2$, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^a$, —SR$^a$, —OC(O)R$^a$, —OC(S)R$^a$, —C(O)R$^a$, —C(S)R$^a$, —C(O)OR$^a$, —C(S)OR$^a$, —S(O)R$^a$, —S(O)$_2$R$^a$, —C(O)NHR$^a$, —C(S)NHR$^a$, —C(O)NR$^a$R$^a$, —C(S)NR$^a$R$^a$, —S(O)$_2$NHR$^a$, —S(O)$_2$NR$^a$R$^a$, —C(NH)NHR$^a$, —C(NH)NR$^a$R$^a$, —NHC(O)R$^a$, —NHC(S)R$^a$, —NR$^a$C(O)R$^a$, —NR$^a$C(S)R$^a$, —NHS(O)$_2$R$^a$, —NR$^a$S(O)$_2$R$^a$, —NHC(O)NHR$^a$, —NHC(S)NHR$^a$, —NR$^a$C(O)NH$_2$, —NR$^a$C(S)NH$_2$, —NR$^a$C(O)NHR$^a$, —NR$^a$C(S)NHR$^a$, —NHC(O)NR$^a$R$^a$, —N HC(S)NR$^a$R$^a$, —NR$^a$C(O)NR$^a$R$^a$, —NR$^a$C(S)NR$^a$R$^a$, —NHS(O)$_2$NHR$^a$, —NR$^a$S(O)$_2$NH$_2$, —NR$^a$S(O)$_2$NHR$^a$, —NHS(O)$_2$NR$^a$R$^a$, —NR$^a$S(O)$_2$NR$^a$R$^a$, —NHR$^a$ or —NR$^a$R$^a$, wherein each R$^a$ is independently C$_{1-6}$alkyl, aryl, aryl-C$_{1-2}$alkyl, C$_{3-6}$cycloalkyl, C$_{3-6}$cycloalkyl-C$_{1-4}$alkyl, heteroaryl, heteroaryl-C$_{1-4}$alkyl, heterocycloalkyl or heterocycloalkyl-C$_{1-4}$alkyl, wherein each R$^a$ is further optionally substituted with 1-3 R$^b$ substituents independently selected from C$_{1-6}$alkyl, —OCH$_3$, —OCH$_2$CH$_3$, —O—CH(CH$_3$)$_2$, —Cl, —F, —CH$_2$F, —CHF$_2$, CF$_3$, —OCF$_3$, —OCHF$_2$ or —OCH$_2$F; wherein X$^1$ is a bond or —C(O)— and wherein the aliphatic or aromatic portion of R$^7$ is optionally substituted with from 1-5 R$^9$ members selected from halogen, CN, —OH, —NH$_2$, —NO$_2$, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^c$, —SR$^c$, —P(=O)HR$^c$, —P(=O) R$^c$R$^c$, —PH(=O)OR$^c$, —P(=O)(OR$^c$)$_2$, —OP(=O)(OR$^c$)$_2$, —OC(O)R$^c$, —OC(S)R$^c$, —C(O)R$^c$, —C(S)R$^c$, —C(O) OR$^c$, —C(S)OR$^c$, —S(O)R$^c$, —S(O)$_2$R$^c$, —C(O)NHR$^c$, —C(S)NHR$^c$, —C(O)NR$^c$R$^c$, —C(S)NR$^c$R$^c$, —S(O)$_2$NHR$^c$, —S(O)$_2$NR$^c$R$^c$, —C(NH)NHR$^c$, —C(NH)NR$^c$R$^c$, —NHC(O)R$^c$, —NHC(S)R$^c$, —NR$^c$C(O)R$^c$, —NR$^c$C(S)R$^c$, —NHS(O)$_2$R$^c$, —NR$^c$S(O)$_2$R$^c$, —NHC(O)NHR c, —NHC(S)NHR$^c$, —NR$^c$C(O)NH$_2$, —NR$^c$C(S)NH$_2$, —NR$^c$C(O)NHR$^c$, —NR$^c$C(S)NHR$^c$, —NHC(O)NR$^c$R$^c$, —NHC(S)NR$^c$R$^c$, —NR$^c$C(O)NR$^c$R$^c$, —NR$^c$C(S)NR$^c$R$^c$, —NH S(O)$_2$NHR$^c$, —NR$^c$S(O)$_2$NH$_2$, —NR$^c$S(O)$_2$NHR$^c$, —NHS(O)$_2$NR$^c$R$^c$, —NR$^c$S(O)$_2$NR$^c$R$^c$, —NHR$^c$, R$^c$ or —NR$^c$R$^c$, wherein each R$^c$ is independently C$_{1-6}$alkyl, aryl, aryl-C$_{1-2}$alkyl, C$_{3-6}$cycloalkyl, C$_{3-6}$cycloalkyl-C$_{1-4}$alkyl, heteroaryl, heteroaryl-C$_{1-4}$alkyl, heterocycloalkyl or heterocycloalkyl-C$_{1-4}$alkyl, wherein each R$^c$ is further optionally substituted with from 1-3 R$^d$ groups independently selected from CN, —OH, —N(R$^e$)(R$^e$), —NO$_2$, —C(O)OH, —C(O) NH$_2$, —S(O)$_2$NH$_2$, —NHC(O)NH$_2$, —C(NH)NH$_2$, —P(=O)HR$^e$, —P(=O)R$^e$R$^e$, —PH(=O)OR$^e$, —P(=O)(OR$^e$)$_2$, —OP(=O)(OR$^e$)$_2$, —OC(O)R$^e$, —OC(S)R$^e$, —C(O)R$^e$, —C(S)R$^e$, —C(O)OR$^e$, —S(O)$_2$R$^e$, —C(O)NHR$^e$, C$_{1-6}$alkyl, C$_{1-6}$alkoxy, halogen, C$_{1-6}$ haloalkyl or C$_{1-6}$ haloalkoxy, wherein $R^e$ is $C_{1-6}$alkyl; or two adjacent $R^7$ substituents together with the atom to which they are attached form a 4-, 5- or 6-membered carbocyclic ring or heterocyclic ring having from 1-2 heteroatoms as ring members selected from O, N or S; and the subscript m is 0, 1 or 2. In some instances, $X^1$ is a bond. In other instances, $X^1$ is —C(O)—. In some instances, $R^9$ is CN, —CH$_3$, —OCH$_3$, —OCH$_2$CH$_3$, —O—CH(CH$_3$)$_2$, —Cl, —F, —CH$_2$F, —CHF$_2$, CF$_3$, —OCF$_3$, —OCHF$_2$ or —OCH$_2$F, —P(=O)CH$_3$, —P(=O)(CH$_3$)$_2$, —PH(=O)O(C$_{1-4}$alkyl), —P(=O)(OC$_{1-4}$alkyl)$_2$, —OP(=O)(OC$_{1-4}$alkyl)$_2$, $C_{1-6}$alkyl, phenyl, perdeuterated phenyl, benzyl, cyclopropyl, cyclobutyl, cyclopentyl, cyclohexyl, cyclopropylmethyl, cyclobutylmethyl, cyclopentylmethyl, cyclohexylmethyl, 2-pyridyl, 3-pyridyl, 4-pyridyl, 2-thiazolyl, 4-thiazolyl, 5-thiazolyl, 3-pyrazolyl, 4-pyrazolyl, 2-pyrimidinyl, 4-pyrimidinyl, 5-pyrimidinyl, 2-oxazolyl, 5-oxazolyl, 4-oxazolyl, 2-thiophenyl, 3-thiophenyl, 1-piperidinyl, 4-piperidinyl or 4-morpholinyl, 4-morpholinylcarbonyl, cyclopropylcarbonyl, 1-piperazinyl, 4-methyl-1-piperazinyl, 1-pyrrolidinyl, 1-piperazinylcarbonyl, 1-piperidinylcarbonyl, 1-pyrrolidinylcarbonyl, dimethylamino, 2-(4-morpholinyl)ethoxy, 3-methoxypropoxy, dimethylcarbamoyl, acetamido, propanoyl, thiomorpholino, 1, pyrrolidinyl, methylsofonylamino, methylsulfonyl, propanoylamino, 1-cyclopentenyl, 1-cyclohexenyl, 1,2,3,6-tetrahydropyridin-4-yl, 1,2,3,6-tetrahydropyridin-5-yl, 2,5-dihydro-1H-pyrrol-3-yl, 2,5-dihydro-pyrrol-1-yl, each of which is optionally substituted with 1-3 R groups independently selected from OH, NH$_2$, CN, —CH$_3$, —OCH$_3$, —OCH$_2$CH$_3$, —O—CH(CH$_3$)$_2$, —Cl, —F, —CH$_2$F, —CHF$_2$, CF$_3$, —OCF$_3$, —OCHF$_2$, —OCH$_2$F, $C_{1-6}$alkyl, 4-morpholinyl, 4-morpholinylcarbonyl, cyclopropyl, cyclopropylmethyl, cyclopropylcarbonyl, 1-piperazinyl, 4-methyl-1-piperazinyl, 1-pyrrolidinyl, 1-piperazinylcarbonyl, 1-piperidinylcarbonyl, 1-pyrrolidinylcarbonyl, dimethylamino, 2-(4-morpholinyl)ethoxy, 3-methoxypropoxy, acetamido, propanoyl, methylsofonylamino, methylsulfonyl, propanoylamino, dimethylcarbamoyl or ethoxycarbonylamino. In other instances, $R^a$ is $C_{1-6}$alkyl, phenyl, perdeuterated phenyl, benzyl, cyclopropyl, cyclobutyl, cyclopentyl, cyclohexyl, cyclopropylmethyl, cyclobutylmethyl, cyclopentylmethyl, cyclohexylmethyl, 2-pyridyl, 3-pyridyl, 4-pyridyl, 2-thiazolyl, 4-thiazolyl, 5-thiazolyl, 3-pyrazolyl, 4-pyrazolyl, 2-pyrimidinyl, 4-pyrimidinyl, 5-pyrimidinyl, 2-oxazolyl, 5-oxazolyl, 4-oxazolyl, 2-thiophenyl, 3-thiophenyl, 1-piperidinyl, 4-piperidinyl or 4-morpholinyl, 4-morpholinylcarbonyl, cyclopropylcarbonyl, 1-piperazinyl, 4-methyl-1-piperazinyl, 1-pyrrolidinyl, 1-piperazinylcarbonyl, 1-piperidinylcarbonyl, 1-pyrrolidinylcarbonyl, dimethylamino, 2-(4-morpholinyl)ethoxy, 3-methoxypropoxy, dimethylcarbamoyl, acetamido, propanoyl, thiomorpholino, 1-pyrrolidinyl, methylsulfonylamino, methylsulfonyl, propanoylamino, 1-cyclopentenyl, 1-cyclohexenyl, 1,2,3,6-tetrahydropyridin-4-yl, 1,2,3,6-tetrahydropyridin-5-yl, 2,5-dihydro-1H-pyrrol-3-yl, 2,5-dihydro-pyrrol-1-yl, each of which is optionally substituted with 1-3 $R^j$groups. In other instances, $R^a$, $R^c$ or $R^9$ is each independently $C_{1-6}$alkyl or $C_{1-4}$alkoxy, each of which is optionally substituted with a member selected from $C_{1-6}$alkyl, methoxy, phenyl, cyclopropyl, cyclobutyl, cyclopentyl, cyclohexyl, 2-pyridyl, 3-pyridyl, 4-pyridyl, 2-thiazolyl, 4-thiazolyl, 5-thiazolyl, 3-pyrazolyl, 4-pyrazolyl, 2-pyrimidinyl, 4-pyrimidinyl, 5-pyrimidinyl, 2-oxazolyl, 5-oxazolyl, 4-oxazolyl, 2-thiophenyl, 3-thiophenyl, 1-piperidinyl, 4-piperidinyl or 4-morpholinyl. In yet other instances, $R^d$ is selected from $C_{1-6}$alkyl, —CN, —OCH$_3$, —OCH$_2$CH$_3$, —O—CH(CH$_3$)$_2$, —Cl, —F, —CH$_2$F, —CHF$_2$, CF$_3$, —OCF$_3$, —OCHF$_2$, —OCH$_2$F, —NH—C$_{1-6}$alkyl, —N(C$_{1-6}$alkyl)(C$_{1-6}$alkyl). All the other variables $Y^1$, $Y^2$, $Y^3$, $R^3$, $R^4$, $R^5$ and the subscript m of formulas (I'a) or (IV) are as defined in any of the embodiments described herein.

In some embodiments of compounds of formula (IV) or (I'a), $R^7$ is selected from halogen, —CN, vinyl-$X^1$, $C_{1-6}$alkyl-$X^1$, $C_{1-6}$alkoxy-X, $C_{2-6}$ alkynyl-$X^1$, $C_{3-6}$ cycloalkyl-$X^1$, $C_{3-6}$cycloalkenyl-$X^1$—, $C_{3-6}$ cycloalkyl-$C_{1-4}$ alkyl-$X^1$, $C_{3-6}$ cycloalkyl-$C_{2-4}$alkynyl-$X^1$, aryl-$X^1$, aryl-$C_{1-4}$ alkyl-$X^1$, heteroaryl-$X^1$, heteroaryl-$C_{1-4}$ alkyl-$X^1$, heterocyclyl-$X^1$, heterocyclyl-$C_{1-4}$alkyl, —C(O)—$R^a$, —C(O)NHR$^a$, —C(O)NR$^a$R$^a$, —NHC(O)R$^a$, —NHC(O)OR$^a$, —NHC(O)NHR$^a$, —NHC(O)NR$^a$R$^a$, —NR$^a$R$^a$, —NHR$^a$, —C(O)OR$^a$, —OC(O)R$^a$, —SO$_2$R$^a$, —NHSO$_2$R$^a$, —NHSO$_2$NHR$^a$, —NHSO$_2$NR$^a$R$^a$, —SO$_2$NHR$^a$ or —SO$_2$NR$^a$R$^a$, wherein at each occurrence $R^7$ is optionally substituted with from 1-4 $R^9$ members. In some instances, each $R^9$ is independently selected from halogen, —CN, $C_{1-6}$alkyl, $C_{1-6}$alkoxy, $C_{1-6}$ haloalkyl, $C_{1-6}$ haloalkoxy, $C_{3-6}$cycloalkyl, $C_{3-6}$ cycloalkyl-$C_{1-4}$alkyl, aryl, aryl-$C_{1-4}$ alkyl, heteroaryl, heteroaryl-$C_{1-4}$ alkyl, heterocyclyl or heterocyclyl-$C_{1-4}$alkyl or $R^8$. In one instance, $R^7$ is H. In other instances, two adjacent $R^9$ substituents on an aromatic ring are taken together to form a 5 or 6-membered ring having from 0-2 heteroatoms selected from O, N or S. All the other variables $Y^1$, $Y^2$, $Y^3$, $R^3$, $R^4$, $R^5$ and the subscript m of formulas (I'a) or (IV) are as defined in any of the embodiments described herein.

In some embodiments of compounds of formula (IV) or (I'a), $R^7$ is selected from halogen, CN, vinyl, $C_{1-6}$alkyl, $C_{1-6}$alkoxy, $C_{2-6}$ alkynyl, $C_{3-6}$ cycloalkyl, $C_{3-6}$cycloalkenyl, $C_{3-6}$ cycloalkyl-$C_{1-4}$alkyl, $C_{3-6}$ cycloalkyl-$C_{2-4}$alkynyl, aryl, aryl-$C_{1-4}$alkyl, heteroaryl, heteroaryl-$C_{1-4}$ alkyl, heterocloalkyl, heterocycloalkyl-$C_{1-4}$alkyl, —C(O)—$R^a$, —C(O)NHR$^a$, —C(O)NR$^a$R$^a$, —NHC(O)R$^a$, —NHC(O)OR$^a$, —NHC(O)NHR$^a$, —NHC(O)NR$^a$R$^a$, —NR$^a$R$^a$, —NHR$^a$, —C(O)OR$^a$, —OC(O)R$^a$, —SO$_2$R$^a$, —NHSO$_2$R$^a$, —NHSO$_2$NHR$^a$, —NHSO$_2$NR$^a$R$^a$, —SO$_2$NHR$^a$ or —SO$_2$NR$^a$R$^a$, each of which is optionally independently substituted with from 1-4 $R^9$ substituents; or optionally independently substituted with from 1-4 $R^e$ substituents; or optionally independently substituted with from 1-4 $R^d$ substituents; or optionally substituted with from 1-4 $R^{15}$ substituents selected from halogen, —CN, $C_{1-6}$alkyl, $C_{1-6}$alkoxy, $C_{1-6}$ haloalkyl, $C_{1-6}$ haloalkoxy, $C_{3-6}$cycloalkyl, $C_{3-6}$cycloalkyl-$C_{1-4}$alkyl, heterocycloalkyl-$C_{1-4}$alkyl, —C(O)—$R^c$, —C(O)NHR$^c$, —C(O)NR$^c$R$^c$, —NHC(O)R$^c$, —P(=O)HR$^c$, —P(=O)R$^c$R$^c$, —PH(=O)OR$^c$, —P(=O)(OR$^c$)$_2$, —OP(=O)(OR$^c$)$_2$, —NHC(O)OR$^c$, —NHC(O)NHR$^c$, —NR$^c$R$^c$, —NHR$^c$, —C(O)OR$^c$, —OC(O)R$^c$, —OC(O)NHR$^c$, —SO$_2$R$^c$, —NHSO$_2$R$^c$, —SO$_2$NHR$^c$ or —SO$_2$NR$^c$R$^c$; or optionally independently substituted with from 1-4 $R^{16}$ substituents selected from $C_{1-6}$alkyl, —OH, —CN, —NO$_2$, —NH$_2$, —NHCH$_3$, —N(CH$_3$)$_2$, —OCH$_3$, —OCH$_2$CH$_3$, —O—CH(CH$_3$)$_2$, —Cl, —F, —CH$_2$F, —CHF$_2$, CF$_3$, —OCF$_3$, —OCHF$_2$, —OCH$_2$F, 4-morpholinyl, cyclopropyl, cyclopropoxy, cyclopropylmethyl, 1-pyrrolidinyl, 1-pyrrolidinylcarbonyl, 1-piperidinylcarbonyl, acetyl, methoxycarbonyl, acetamido, dimethylcarbamoyl, methylcarbamoyl, methylsulfonyl or methylsulfonylamino. In some instances, $R^c$ is $C_{3-6}$cycloalkyl, $C_{3-6}$cycloalkyl-$C_{1-4}$ alkyl, heterocycloalkyl or heterocycloalkyl-$C_{1-4}$alkyl. All the other variables $Y^1$, $Y^2$, $Y^3$, $R^3$, $R^4$, $R^5$ and the subscript m of formulas (I'a) or (IV) are as defined in any of the embodiments as described herein.

In some embodiments of compounds of formula (IV) or (I'a), $R^7$ is selected from aryl, heteroaryl, $C_{2-6}$ alkynyl, $C_{3-6}$cycloalkenyl, heterocycloalkyl, —C(O)—$R^a$, —C(O)NH$R^a$, —C(O)N$R^aR^a$, —C(O)O$R^a$, —SO$_2$NH$R^a$ or —SO$_2$N$R^aR^a$, each of which is optionally substituted with from (i) 1-4 $R^9$ substituents; or (ii) 1-4 $R^c$ substituents; or (iii) 1-4 $R^d$ substituents; or (iv) 1-4 $R^{15}$ substituents selected from halogen, —CN, $C_{1-6}$alkyl, $C_{1-6}$alkoxy, $C_{1-6}$ haloalkyl, $C_{1-6}$ haloalkoxy, $C_{3-6}$cycloalkyl, $C_{3-6}$cycloalkyl-$C_{1-4}$alkyl, heterocycloalkyl-$C_{1-4}$alkyl, —C(O)—$R^c$, —C(O)NH$R^c$, —C(O)N$R^cR^c$, —NHC(O)$R^c$, —NHC(O)O$R^c$, —NHC(O)NH$R^c$, —N$R^cR^c$, —NH$R^c$, —C(O)O$R^c$, —P(=O)H$R^c$, —P(=O)$R^cR^c$, —PH(=O)O$R^c$, —P(=O)(O$R^c$)$_2$, —OP(=O)(O$R^c$)$_2$, —OC(O)$R^c$, —OC(O)NH$R^c$, —SO$_2R^c$, —NHSO$_2R^c$, —SO$_2$NH$R^c$ or —SO$_2$N$R^cR^c$; or (v) 1-4 $R^{16}$ groups; or (vi) 1-4 $R^{17}$ substituents independently selected from $C_{1-6}$alkyl, —OH, —CN, —NO$_2$, —NH$_2$, —NHCH$_3$, —N(CH$_3$)$_2$, —OCH$_3$, —OCH$_2$CH$_3$, —O—CH(CH$_3$)$_2$, —Cl, —F, —CH$_2$F, —CHF$_2$, CF$_3$, —OCF$_3$, —OCHF$_2$, —OCH$_2$F, 4-morpholinyl, thiomorpholino, 1-piperidinyl, cyclopropyl, 1-cyanocyclopropyl, cyclopropoxy, cyclopropylmethyl, 1-pyrrolidinyl, 1-piperazinyl, 1-piperazinylcarbonyl, 1-pyrrolidinylcarbonyl, 1-piperidinylcarbonyl, acetyl, methoxycarbonyl, acetamido, dimethylcarbamoyl, methylcarbamoyl, methylsulfonyl, methylsulfonylamino, —$C_{1-2}$alkyl-$R^k$, —C(O)—$R^k$, —C(O)NH$R^k$, —C(O)N$R^kR^k$, —NHC(O)$R^k$, —P(=O)H$R^k$, —P(=O)$R^kR^k$, —PH(=O)O$R^k$, —P(=O)(O$R^k$)$_2$, —OP(=O)(O$R^k$)$_2$, —C(O)O$R^k$, —OC(O)$R^k$, —SO$_2R^k$, —NHSO$_2R^k$, —SO$_2$NH$R^k$, —SO$_2$N$R^kR^k$, wherein each $R^k$ is independently $C_{1-6}$alkyl, $C_{3-6}$cycloalkyl, phenyl or heterocycloalkyl, wherein $R^k$ is further optionally substituted with from 1-3 $R^d$, $R^e$ or $R^j$ group; or (vii) 1-4 $R^{18}$ substituents selected from F, Cl, I, —CH$_3$, —OCH$_3$, OCH$_2$CH$_3$, —O—CH(CH$_3$)$_2$, —OH, —CN, —NO$_2$, —NH$_2$, —NHCH$_3$, —N(CH$_3$)$_2$, —CH$_2$F, —CHF$_2$, CF$_3$, —OCF$_3$, —OCHF$_2$, —OCH$_2$F, cyclopropyl, cyclopropylmethyl, 1-cyanocyclopropyl, cyclobutyl, cyclopentyl, cyclohexyl, —PH(=O)—$C_{1-6}$alkyl, —P(=O)($C_{1-6}$alkyl)$_2$, —PH(=O)O($C_{1-6}$alkyl), —P(=O)(O$C_{1-6}$alkyl)$_2$, —OP(=O)(O$C_{1-6}$alkyl)$_2$, —NHSO$_2$—$C_{1-6}$alkyl, —SO$_2$NH—$C_{1-6}$alkyl, —NHC(O)—$C_{1-6}$alkyl, —C(O)NH—$C_{1-6}$alkyl, —NHC(O)NH—$C_{1-6}$alkyl, NHC(O)O—$C_{1-6}$alkyl, —C(O)—$C_{1-6}$alkyl, —C(O)O—$C_{1-6}$alkyl, —OC(O)—$C_{1-6}$alkyl, —NHSO$_2$CH$_3$, NH$_2$C(O)—, CH$_3$NHC(O)—, NH$_2$SO$_2$—, CH$_3$SO$_2$—, (CH$_3$)$_2$NC(O)—, CH$_3$C(O)NH—, CH$_3$SO$_2$NH—, benzyl, benzyl-C(O), ($C_{1-4}$alkyl)OC(O)—, cyclopropyl-C(O)—, cyclopropylethyl-C(O)—, cyclobutyl-C(O)—, cyclobutylmethyl-C(O)—, Ph-NH—C(O)—, 4-morpholinyl, 4-morpholinylmethyl, 4-morpholinylethyl, thiomorpholino, 4-thiomorpholinyl-C(O)—, 4-morpholinyl-C(O)—, 1-piperidinyl, 1-piperidinyl-C(O)—, p-CH$_3$-Ph-SO$_2$NH—, Ph-SO$_2$NH—, propyl-SO$_2$NH—, cyclopropyl-SO$_2$NH—, cyclobutyl-SO$_2$NH—, butylSO$_2$NH—, ethoxycarbonyl-NH—, methoxycarbonyl-NH—, cyclopropoxy, cyclopropylmethyl, 1-pyrrolidinyl, 1-piperazinyl, 1-piperazinylcarbonyl, 4-methyl-1-piperazinylcarbonyl, 1-pyrrolidinylcarbonyl, 1-piperidinylcarbonyl, acetyl, methoxycarbonyl, acetamido, dimethylcarbamoyl, methylcarbamoyl, ethoxycarbonylamino, 1-azetidinyl, 2-azetidinyl, 3-azetidinyl, 2-oxetanyl, 3-oxetanyl, 1-morpholinylethyl, 3-methoxypropoxy, 2-(4-morpholinyl)ethoxy, 4-morpholinylmethylcarbonyl or 4-morpholinylethylcarbonyl, wherein at each occurrence, $R^{18}$ is further optionally substituted with from 1-3 substituents independently selected from —CN, F, Cl, I, —OCH$_3$, $C_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH— or CH$_3$SO$_2$. All the other variables $Y^1$, $Y^2$, $Y^3$, $R^3$, $R^4$, $R^5$ and the subscript m of formulas (I'a) or (IV) are as defined in any of the embodiments of compounds of formulas (I'a) or (IV) as described herein.

In some embodiments of compounds of formula (IV) or (I'a), $R^7$ is selected from aryl, heteroaryl, $C_{2-6}$ alkynyl, $C_{3-6}$cycloalkenyl or heterocycloalkyl, each of which is optionally substituted with (i) 1-4 $R^9$ substituents; or (ii) 1-4 $R^c$ substituents; or (iii) 1-4 $R^d$ substituents; or (iv) 1-4 $R^{15}$ substituents; or (v) 1-4 $R^{16}$ groups; or (vi) 1-4 $R^7$ substituents independently selected from $C_{1-6}$alkyl, —OH, —CN, —NO$_2$, —NH$_2$, —NHCH$_3$, —N(CH$_3$)$_2$, —OCH$_3$, —OCH$_2$CH$_3$, —O—CH(CH$_3$)$_2$, —Cl, —F, —CH$_2$F, —CHF$_2$, CF$_3$, —OCF$_3$, —OCHF$_2$, —OCH$_2$F, 4-morpholinyl, 1-piperidinyl, cyclopropyl, 1-cyanocyclopropyl, cyclopropoxy, cyclopropylmethyl, 1-pyrrolidinyl, 1-piperazinyl, 1-piperazinylcarbonyl, 1-pyrrolidinylcarbonyl, 1-piperidinylcarbonyl, acetyl, methoxycarbonyl, acetamido, dimethylcarbamoyl, methylcarbamoyl, methylsulfonyl, methylsulfonylamino, —$C_{1-2}$alkyl-$R^k$, —C(O)—$R^k$, —P(=O)H$R^k$, —P(=O)$R^kR^k$, —PH(=O)O$R^k$, —P(=O)(O$R^k$)$_2$, —OP(=O)(O$R^k$)$_2$, —C(O)NH$R^k$, —C(O)N$R^kR^k$, —NHC(O)$R^k$, —C(O)O$R^k$, —OC(O)$R^k$, —SO$_2R^k$, —NHSO$_2R^k$, —SO$_2$NH$R^k$, —SO$_2$N$R^kR^k$, wherein each $R^k$ is independently $C_{1-6}$alkyl, $C_{3-6}$cycloalkyl, phenyl or heterocycloalkyl, wherein $R^k$ is further optionally substituted with from 1-3 $R^d$, $R^e$ or $R^j$ group; or (vii) 1-4 $R^{18}$ substituents selected from F, Cl, I, —CH$_3$, —OCH$_3$, OCH$_2$CH$_3$, —O—CH(CH$_3$)$_2$, —OH, —CN, —NO$_2$, —NH$_2$, —NHCH$_3$, —N(CH$_3$)$_2$, —CH$_2$F, —CHF$_2$, CF$_3$, —OCF$_3$, —OCHF$_2$, —OCH$_2$F, cyclopropyl, 1-cyanocyclopropyl, cyclobutyl, cyclopentyl, cyclohexyl, —NHSO$_2$CH$_3$, NH$_2$C(O)—, CH$_3$NHC(O)—, NH$_2$SO$_2$—, CH$_3$SO$_2$—, —PH(=O)—$C_{1-6}$alkyl, —P(=O)($C_{1-6}$alkyl)$_2$, —PH(=O)(O$C_{1-6}$alkyl), —P(=O)(O$C_{1-6}$alkyl)$_2$, —OP(=O)(O$C_{1-6}$alkyl)$_2$, (CH$_3$)$_2$NC(O)—, CH$_3$C(O)NH—, CH$_3$SO$_2$NH—, benzyl, benzyl-C(O), ($C_{1-4}$alkyl)OC(O)—, cyclopropyl-C(O)—, cyclopropylethyl-C(O)—, cyclobutyl-C(O)—, cyclobutylmethyl-C(O)—, Ph-NH—C(O)—, 4-morpholinyl, 4-morpholinylmethyl, 4-morpholinylethyl, 4-morpholinyl-C(O)—, 1-piperidinyl, 1-piperidinyl-C(O)—, p-CH$_3$-Ph-SO$_2$NH—, Ph-SO$_2$NH—, propyl-SO$_2$NH—, cyclopropyl-SO$_2$NH—, cyclobutyl-SO$_2$NH—, butylSO$_2$NH—, ethoxycarbonyl-NH—, methoxycarbonyl-NH—, cyclopropoxy, cyclopropylmethyl, 1-pyrrolidinyl, 1-piperazinyl, 1-piperazinylcarbonyl, 4-methyl-1-piperazinylcarbonyl, 1-azetidinyl, 2-azetidinyl, 3-azetidinyl, 2-oxetanyl, 3-oxetanyl, 1-pyrrolidinylcarbonyl, 1-piperidinylcarbonyl, acetyl, methoxycarbonyl, acetamido, dimethylcarbamoyl, methylcarbamoyl, ethoxycarbonylamino, 1-morpholinylethyl, 3-methoxypropoxy, 2-(4-morpholinyl)ethoxy, 4-morpholinylmethylcarbonyl or 4-morpholinylethylcarbonyl, wherein at each occurrence, $R^8$ is further optionally substituted with from 1-3 substituents independently selected from —CN, F, Cl, I, —OCH$_3$, $C_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH— or CH$_3$SO$_2$. All the other variables $Y^1$, $Y^2$, $Y^3$, $R^3$, $R^4$, $R^5$ and the subscript m of formulas (I'a) or (IV) are as defined in any of the embodiments of compounds of formulas (I'a) or (IV) as described herein.

In some embodiments of compounds of formula (IV) or (I'a), $R^7$ is selected from halogen, —CN, $C_{1-6}$alkyl, $C_{1-6}$alkoxy, 2-pyridyl, 3-pyridyl, 4-pyridyl, perdeuterated pyridyl, phenyl, perdeuterated phenyl, 1-pyrazolyl, 3-1H-pyrazolyl, 4-1H-pyrazolyl, vinyl, ethynyl, propynyl, 3-fluoropropynyl, cyclopropyl-ethynyl, cyclobutyl-ethynyl, cyclopentyl-ethynyl, cyclohexyl-ethynyl, 1-cyclopentenyl-ethynyl, 2-thiazolyl, 4-thiazolyl, 5-thiazolyl, cyclopropyl, cyclobutyl, cyclopentyl, cyclohexyl, cyclopropylmethyl, cyclobutylmethyl, cyclopentylmethyl, cyclohexylmethyl, 1-piperazinyl, 1-piperidinyl, morpholinyl, 1,2,5,6-tetrahydropyridin-4-yl, 1,2,5,6-tetrahydropyridin-3-yl, 2,3-dihydro-1,4-benzodioxin-5-yl, 1,3-benzodioxol-4-yl, 1,3-benzodioxol-5-yl, indanyl, 1,2-benzoxazolyl, 1,3-benzoxazolyl, 1-cyclohexenyl, 1-cyclopentenyl, 1-cyclooctenyl, 2-pyrimidinyl, 4-pyrimidinyl, 5-pyrimidinyl, 2-pyrazinyl, 3-pyridazinyl, 4-pyridazinyl, 5,6-dihydro-2H-pyran-4-yl, 5,6-dihydro-2H-pyran-3-yl, 1-pyrrolyl, 2-pyrrolyl, 3-pyrrolyl, 2-imidazolyl, 4-imidazolyl, 1-pyrazolyl, 2-pyrazolyl, 3-pyrazolyl, 2-oxazolyl, 4-oxazolyl, 5-oxazolyl, 3-isoxazolyl, 4-isoxazolyl, 5-isoxazolyl, 3-isothiazolyl, 4-isothiazolyl, 5-isothiazolyl, 1,2,3-triazol-1-yl, 1,2,3-triazol-2-yl, 1,2,3-triazol-3-yl, 1,2,3-triazol-4-yl, 1,2,3-triazol-5-yl, 1,2,4-triazol-1-yl, 1,2,4-triazol-2-yl, 1,2,4-triazol-3-yl, 1,2,4-triazol-4-yl, 1,2,4-triazol-5-yl, 1-oxa-2,3-diazol-4-yl, 1-oxa-2,3-diazol-5-yl, 1-oxa-2,4-diazol-3-yl, 1-oxa-2,4-diazol-5-yl, 1-oxa-2,5-diazol-3-yl, 1-oxa-2,5-diazol-4-yl, 1-thia-2,3-diazol-4-yl, 1-thia-2,3-diazol-5-yl, 1-thia-2,4-diazol-3-yl, 1-thia-2,4-diazol-5-yl, 1-thia-2,5-diazol-3-yl, 1-thia-2,5-diazol-4-yl, 1-tetrazolyl, 3-tetrazolyl, 1H-5-tetrazolyl, 3H-5-tetrazolyl, 2-furanyl, 3-furanyl, 2-thiophenyl or 3-thiophenyl, each of which is optionally substituted with from (i) 1-4 $R^9$ substituents; or (ii) 1-4 $R^c$ substituents; or (iii) 1-4 $R^d$ substituents; or (iv) 1-4 $R^{15}$ substituents selected from halogen, —CN, $C_{1-6}$alkyl, $C_{1-6}$alkoxy, $C_{1-6}$ haloalkyl, $C_{1-6}$ haloalkoxy, $C_{3-6}$cycloalkyl, $C_{3-6}$cycloalkyl-$C_{1-4}$alkyl, heterocycloalkyl-$C_{1-4}$alkyl, —C(O)—$R^c$, —C(O)NHR$^c$, —C(O)NR$^c$R$^c$, —NHC(O)R$^c$, —NHC(O)OR$^c$, —NHC(O)NHR$^c$, —NR$^c$R$^c$, —NHR$^c$, —C(O)OR$^c$, —OC(O)R$^c$, —OC(O)NHR$^c$, —SO$_2$R$^c$, —NHSO$_2$R$^c$, —SO$_2$NHR$^c$ or —SO$_2$NR$^c$R$^c$; or (v) 1-4 $R^{16}$ groups; or (vi) 1-4 $R^{17}$ substituents independently selected from $C_{1-6}$alkyl, —OH, —CN, —NO$_2$, —NH$_2$, —NHCH$_3$, —N(CH$_3$)$_2$, —OCH$_3$, —OCH$_2$CH$_3$, —O—CH(CH$_3$)$_2$, —Cl, —F, —CH$_2$F, —CHF$_2$, CF$_3$, —OCF$_3$, —OCHF$_2$, —OCH$_2$F, 4-morpholinyl, thiomorpholino, 1-piperidinyl, cyclopropyl, 1-cyanocyclopropyl, cyclopropoxy, cyclopropylmethyl, 1-pyrrolidinyl, 1-piperazinyl, 1-piperazinylcarbonyl, 1-pyrrolidinylcarbonyl, 1-piperidinylcarbonyl, acetyl, methoxycarbonyl, acetamido, dimethylcarbamoyl, methylcarbamoyl, methylsulfonyl, methylsulfonylamino, —C$_{1-2}$alkyl-R$^k$, —C(O)—R$^k$, —C(O)NHR$^k$, —C(O)NR$^k$R$^k$, —NHC(O)R$^k$, —C(O)OR$^k$, —PH(=O)R$^k$, —P(=O)R$^k$R$^k$, —PH(=O)OR$^k$, —P(=O)(OR$^k$)$_2$, —OP(=O)(OR$^k$)$_2$, —OC(O)R$^k$, —SO$_2$R$^k$, —NHSO$_2$R$^k$, —SO$_2$NHR$^k$, —SO$_2$NR$^k$R$^k$, wherein each R$^k$ is independently $C_{1-6}$alkyl, $C_{3-6}$cycloalkyl, phenyl or heterocycloalkyl, wherein R$^k$ is further optionally substituted with from 1-3 R$^d$, R$^e$ or R$^j$ group; or (vii) 1-4 $R^{18}$ substituents selected from F, Cl, I, —CH$_3$, —OCH$_3$, OCH$_2$CH$_3$, —O—CH(CH$_3$)$_2$, —OH, —CN, —NO$_2$, —NH$_2$, —NHCH$_3$, —N(CH$_3$)$_2$, —CH$_2$F, —CHF$_2$, CF$_3$, —OCF$_3$, —OCHF$_2$, —OCH$_2$F, cyclopropyl, 1-cyanocyclopropyl, cyclobutyl, cyclopentyl, cyclohexyl, —NHSO$_2$CH$_3$, NH$_2$C(O)—, CH$_3$NHC(O)—, NH$_2$SO$_2$—, CH$_3$SO$_2$—, (CH$_3$)$_2$NC(O)—, CH$_3$C(O)NH—, CH$_3$SO$_2$NH—, benzyl, benzyl-C(O), (C$_{1-4}$alkyl)OC(O)—, cyclopropyl-C(O)—, cyclopropylethyl-C(O)—, cyclobutyl-C(O)—, cyclobutylmethyl-C(O)—, Ph-NH—C(O)—, thiomrpholino, 4-thiomorpholinyl-C(O)—, —PH(=O)—C$_{1-6}$alkyl, —P(=O)(C$_{1-6}$alkyl)$_2$, —PH(=O)(OC$_{1-6}$alkyl), —P(=O)(OC$_{1-6}$alkyl)$_2$, —OP(=O)(OC$_{1-6}$alkyl)$_2$, 4-morpholinyl, 4-morpholinylmethyl, 4-morpholinylethyl, 4-morpholinyl-C(O)—, 1-piperidinyl, 1-piperidinyl-C(O)—, p-CH$_3$-Ph-SO$_2$NH—, Ph-SO$_2$NH—, propyl-SO$_2$NH—, cyclopropyl-SO$_2$NH—, cyclobutyl-SO$_2$NH—, butylSO$_2$NH—, ethoxycarbonyl-NH—, methoxycarbonyl-NH—, cyclopropoxy, cyclopropylmethyl, 1-pyrrolidinyl, 1-piperazinyl, 1-piperazinylcarbonyl, 4-methyl-1-piperazinylcarbonyl, 1-azetidinyl, 2-azetidinyl, 3-azetidinyl, 2-oxetanyl, 3-oxetanyl, 1-pyrrolidinylcarbonyl, 1-piperidinylcarbonyl, acetyl, methoxycarbonyl, acetamido, dimethylcarbamoyl, methylcarbamoyl, ethoxycarbonylamino, 1-morpholinylethyl, 3-methoxypropoxy, 2-(4-morpholinyl)ethoxy, 4-morpholinylmethylcarbonyl or 4-morpholinylethylcarbonyl, wherein at each occurrence, $R^{18}$ is further optionally substituted with from 1-3 substituents independently selected from —CN, F, Cl, I, —OCH$_3$, $C_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH— or CH$_3$SO$_2$. In certain embodiments, the hydrogen atoms in $R^7$ are optionally replaced by 1 to 12, or 1 to 8, or 1 to 6, or 1 to 3 or 1, 2, 3, 4, 5, 6, 7, 8, 9, 10, 11 and 12 deuterium atoms with at least 52.5%, 60%, 70%, 75%, 80%, 90%, 95%, 99%, 99.5% or 99.9% deuterium incorporation for each deuterium. In certain embodiments, each hydrogen atom in $R^7$ is optionally replaced by a deuterium atom with at least 52.5%, 60%, 70%, 75%, 80%, 90%, 95%, 99%, 99.5% or 99.9% deuterium incorporation for each deuterium. All the other variables $Y^1$, $Y^2$, $Y^3$, $R^3$, $R^4$, $R^5$ and the subscript m of formulas (I'a) or (IV) are as defined in any of the embodiments of compounds of formulas (I'a) or (IV) as described herein.

In some embodiments of compounds of formula (IV) or (I'a), $R^7$ is selected from halogen, —CN, $C_{1-6}$alkyl, $C_{1-6}$alkoxy, 2-pyridyl, 3-pyridyl, 4-pyridyl, 2-methoxy-4-pyridyl, phenyl, 1-pyrazolyl, 3-1H-pyrazolyl, 4-1H-pyrazolyl, 1-methyl-4-pyrazolyl, 1,3-dimethyl-5-pyrazolyl, vinyl, ethynyl, propynyl, 3-fluoropropynyl, cyclopropyl-ethynyl, cyclobutyl-ethynyl, cyclopentyl-ethynyl, cyclohexyl-ethynyl, 1-cyclopentenyl-ethynyl, 2-thiazolyl, 4-thiazolyl, 5-thiazolyl, cyclopropyl, cyclobutyl, cyclopentyl, cyclohexyl, cyclopropylmethyl, cyclobutylmethyl, cyclopentylmethyl, cyclohexylmethyl, 2-cyclopropylethyl, 2-cyclobutylethyl, 1-methyl-1-cyclopropyl, 1-cyclopropylethyl, 1-methyl-1-cyclobutyl, 1-cyclobutylethyl, methoxymethoxy, 4-morpholinylmethoxy, 1-piperidinylmethoxy, 4,4-difluoropiperidinyl, 4-ethoxycarbonyl-1-piperazinyl, 1-piperazinyl, 1-piperidinyl, 4-morpholinyl, 1,2,3,6-tetrahydropyridin-4-yl, 1,2,3,6-tetrahydropyridin-5-yl, 1-cyclopropylcarbonyl-2,3,6-trihydropyridin-4-yl, 2,2,6,6-tetramethyl-1,5-dihydropyridin-4-yl, 2,2,6,6-tetramethyl-1,5-dihydropyridin-3-yl, 1-cyclopropylcarbonyl-2,3,6-trihydropyridin-5-yl, 1-methylsulfonyl-2,3,6-trihydropyridin-4-yl, 1-methylsulfonyl-2,3,6-trihydropyridin-5-yl, 1-(4-morpholinylcarbonyl)-2,3,6-trihydropyridin-4-yl, 1-(4-morpholinylcarbonyl)-2,3,6-trihydropyridin-5-yl, 1-t-butoxycarbonyl-2,3,6-trihydropyridin-4-yl, 1-t-butoxycarbonyl-2,3,6-trihydropyridin-5-yl, 2,3-dihydro-1,4-benzodioxin-5-yl, 1,3-benzodioxol-4-yl, 1,3-benzodioxol-5-yl, indanyl, 1,2-benzoxazolyl, 1,3-benzoxazolyl, 1-cyclohexenyl, 1-cyclopentenyl, 1-cyclooctenyl, 2-pyrimidinyl, 4-pyrimidinyl, 5-pyrimidinyl, 2-cyclopropyl-5-pyrimidinyl, 2-cyclopropyl-pyrimidin-5-yl, 2-pyrazinyl, 3-pyridazinyl, 4-pyridazinyl, 5,6-dihydro-2H-pyran-4-yl, 5,6-dihydro-2H-pyran-3-yl, 1-pyrrolyl, 2-pyrrolyl, 3-pyrrolyl, 2-imidazolyl, 4-imidazolyl, 1-pyrazolyl, 2-pyrazolyl, 3-pyrazolyl, 2-oxazolyl, 4-oxazolyl, 5-oxazolyl, 3-isoxazolyl, 4-isoxazolyl, 5-isoxazolyl, 3-isothiazolyl, 4-isothiazolyl, 5-isothiazolyl, 1,2,3-triazol-1-yl, 1,2,3-triazol-2-yl, 1,2,3-triazol-3-yl, 1,2,3-triazol-4-yl, 1,2,3-triazol-5-yl, 1,2,4-triazol-1-yl, 1,2,4-triazol-2-yl, 1,2,4-triazol-3-yl, 1,2,4-triazol-4-yl, 1,2,4-triazol-5-yl, 1-oxa-2,3-diazol-4-yl, 1-oxa-2,3-diazol-5-yl, 1-oxa-2,4-diazol-3-yl, 1-oxa-2,4-diazol-5-yl, 1-oxa-2,5-diazol-3-yl, 1-oxa-2,5-diazol-4-yl, 1-thia-2,3-diazol-4-yl, 1-thia-2,3-diazol-5-yl, 1-thia-2,4-diazol-3-yl, 1-thia-2,4-diazol-5-yl, 1-thia-2,5-diazol-3-yl, 1-thia-2,5-diazol-4-yl, 1-tetrazolyl, 3-tetrazolyl, 1H-5-tetrazolyl, 3H-5-tetrazolyl, 2-furanyl, 3-furanyl, 2-thiophenyl, 3-thiophenyl, 3-chloro-5-thiophenyl or 1-cyclopropylcarbonyl-piperidin-4-yl, each of which is optionally substituted with from 1-4 $R^{16}$ or $R^1$ substituents; or 1-4 $R^{18}$ substituents, wherein at each occurrence, $R^8$ is further optionally substituted with from 1-3 $R^{19}$ substituents selected from CN, F, Cl, I, —OCH$_3$, C$_{1-6}$alkyl, cyclopropyl, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH— or CH$_3$SO$_2$—. In some instances, $R^k$ is C$_{1-6}$alkyl, C$_{3-6}$cycloalkyl, C$_{3-6}$cycloalkyl-C$_{1-2}$alkyl, 4-morpholinyl, 1-pyrrolidinyl, 2-pyrrolidinyl, 3-pyrrolidinyl, 1-azetidinyl, 2-azetidinyl, 3-azetidinyl, 2-oxatanyl, 3-oxatanyl, 2-oxo-1-pyrrolidinyl, 1-piperidinyl, 2-piperidinyl, 3-piperidinyl, 4-piperidinyl, piperazinyl, phenyl or benzyl, each of which is optionally substituted with 1-3 substituents selected from —CH$_3$, —OCH$_3$, F, Cl, CN, CF$_3$, CHF$_2$, CH$_2$F, —OCF$_3$, —N(CH$_3$)$_2$, —NHCH$_3$. All the other variables $Y^1$, $Y^2$, $Y^3$, $R^3$, $R^4$, $R^5$ and the subscript m of formulas (I'a) or (IV) are as defined in any of the embodiments as described herein.

In some embodiments of compounds of formula (IV) or (I'a), $R^7$ is selected from 3-fluoropropynyl, 2-pyridyl, 3-pyridyl, 4-pyridyl, 2-methoxy-4-pyridyl, phenyl, 1-pyrazolyl, 3-1H-pyrazolyl, 4-1H-pyrazolyl, 1-methyl-4-pyrazolyl, 1,3-dimethyl-5-pyrazolyl, 4-morpholinyl, 3-isoxazolyl, 4-isoxazolyl, 5-isoxazolyl, 2,5-dimethyl-4-isoxazolyl, 2-thiazolyl, 4-thiazolyl, 5-thiazolyl, 2-methyl-5-thiazolyl, 1-isopropyl-pyrazol-4-yl, 1-cyclohexenyl, 1-cyclopentenyl, 1-cyclooctenyl, 1,2,3,6-tetrahydropyridin-4-yl, 1,2,3,6-tetrahydropyridin-5-yl, cyclopropyl, 2,5-dihydro-1H-pyrrol-3-yl, 2,5-dihydro-1H-pyrrol-2-yl or 2,5-dihydropyrrol-1-yl, each of which is optionally substituted with from 1-4 $R^{16}$ or $R^{17}$ substituents; or 1-4 $R^{s8}$ substituents, wherein at each occurrence, $R^{18}$ is further optionally substituted with from 1-3 $R^{19}$ substituents selected from CN, F, Cl, I, —OCH$_3$, C$_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH— or CH$_3$SO$_2$—. In some instances, $R^k$ is C$_{1-6}$alkyl, C$_{3-6}$cycloalkyl, C$_{3-6}$cycloalkyl-C$_{1-2}$alkyl, 4-morpholinyl, 1-pyrrolidinyl, 2-pyrrolidinyl, 3-pyrrolidinyl, 2-oxo-1-pyrrolidinyl, 1-piperidinyl, 2-piperidinyl, 3-piperidinyl, 4-piperidinyl, piperazinyl, phenyl or benzyl, each of which is optionally substituted with 1-3 substituents selected from —CH$_3$, —OCH$_3$, F, Cl, CN, CF$_3$, CHF$_2$, CH$_2$F, —OCF$_3$, —N(CH$_3$)$_2$, —NHCH$_3$. All the other variables $Y^1$, $Y^2$, $Y^3$, $R^3$, $R^4$, $R^5$ and the subscript m of formulas (I'a) or (IV) are as defined in any of the embodiments as described herein.

In some embodiments of compounds of formula (IV) or (I'a), $R^7$ is H, CN, vinyl, C$_{1-6}$alkyl, deuterated C$_{1-6}$alkyl, perdeuterated C$_{1-6}$alkyl, halogen, C$_{1-6}$alkoxy, 2-cyclopropylethynyl, pyridyl, phenyl, benzyl, pyrazolyl, oxazolyl, thiozolyl, pyrimidinyl, pyrazinyl, pyridazinyl, cyclopropyl, cyclopropylmethyl, cyclopropylcarbonyl, cyclobutyl, cyclobutylmethyl, cyclopentyl, cyclopentylmethyl, cyclohexyl, cyclohexylmethyl, benzoyl, phenylcarbamoyl, piperidinyl, piperazinyl, morpholinyl, cyclopentenyl, cyclohexenyl, 1,2,3,6-tetrahydropyridin-4-yl, 2,3-dihydro-1,4-benzodioxin-5-yl, 1,3-benzodioxol-4-yl, 1,3-benzodioxol-5-yl, indanyl, 1,2-benzoxazolyl, 1,3-benzoxazolyl, each of which is optionally substituted with from 1-4 members independently selected from halogen, —CH$_3$, CD$_3$, —OCH$_3$, CN, CF$_3$, CF$_3$O—, —CF$_2$H, CHF$_2$O—, —N(CH$_3$)$_2$, —NHCH$_3$, CH$_3$CONH—, NH$_2$C(O)—, CH$_3$NHC(O)—, (CH$_3$)$_2$NC(O)—, cyclopropyl, 1-cyanocyclopropyl, CH$_3$SO$_2$NH—, cyclopropyl-SO$_2$NH—, butyl-SO$_2$NH—, p-CH$_3$C$_6$H$_4$SO$_2$NH—, NH$_2$SO$_2$—, CH$_3$NHSO$_2$—, (CH$_3$)$_2$NSO$_2$—, 4-morpholinyl, piperidinyl, 4-methyl-1-piperazinyl, cyclopropylcarbonyl, cyclobutylcarbonyl, cyclopentylcarbonyl, cyclohexylcarbonyl, 4-morpholinylcarbonyl, piperdinylcarbonyl, piperazinylcarbonyl, t-butoxycarbonyl or 2-(4-morpholinyl)-ethyl. All the other variables $Y^1$, $Y^2$, $Y^3$, $R^3$, $R^4$, $R^5$ and the subscript m of formulas (I'a) or (IV) are as defined in any of the embodiments as described herein.

In some embodiments of compounds of formula (IV) or (I'a), $R^7$ is selected from Cl, Br, phenyl, 4-fluorophenyl, 2-fluorophenyl, 3-fluorophenyl, 2-pyridyl, 3-pyridyl, 4-pyridyl, 1-cyclopropylcarbonyl-1,2,3,6-tetrahydropyridin-4-yl, 1-morpholinocarbonyl, 1,2,3,6-tetrahydropyridin-4-yl, 1,2,3,6-tetrahydropyridin-5-yl, 1,3-dimethyl-pyrazol-4-yl or 1-(4-piperidinyl)pyrazol-4-yl, 3,4-dimethyl-1H-pyrazol-5-yl, 1-(cyclopropylcarbonyl)-2,5-dihydro-pyrrol-3-yl, 3-fluoro-propynyl, 3,5-dimethyl-isoxazol-4-yl, 5-thiazolyl, each of which is optionally substituted with from 1-3 $R^{14}$ substituents independently selected from F, Cl, —CH$_3$, -Et, propyl, isopropyl, 2-methylpropyl, CD$_3$, —OCH$_3$, CN, CH$_2$F, —CF$_2$H, CF$_3$, CF$_3$O—, CHF$_2$O—, CH$_2$FO—, NH$_2$, —N(CH$_3$)$_2$, —NHCH$_3$, CH$_3$CONH—, NH$_2$C(O)—, CH$_3$NHC(O)—, (CH$_3$)$_2$NC(O)—, —PH(=O)(C$_{1-4}$alkyl), —P(=O)(C$_{1-4}$alkyl)$_2$, —PH=O)CH$_3$, —P(=O)(CH$_3$)$_2$, cyclopropyl, 1-cyanocyclopropyl, 4-morpholinyl, 4-morpholinylmethyl, 4-thiomorpholinyl, 4-morpholinylcarbonyl, 4-thiomorpholinylcarbonyl, 4-morpholinylmethylcarbonyl, 4-thiomorpholinylmethylcarbonyl, cyclopropylcarbonyl, cyclobuylcarbonyl, cyclopentylcarbonyl, cyclohexylcarbonyl, 4-piperidinyl, 4-piperidinylcarbonyl, 1-piperidinylcarbonyl, 1-piperazinylcarbonyl, t-butoxycarbonyl, 2-(4-morpholinyl)-ethyl, 2-(4-morpholinyl)-ethoxy, 1,2-dihydroxyethylcarbonyl, 3-methoxypropoxy, 1-pyrrolidinyl, PhSO$_2$NH—, C$_{1-4}$alkyl-SO$_2$NH—, cyclopropyl-SO$_2$NH—, p-CH$_3$C6H$_4$SO$_2$NH—, NH$_2$SO$_2$—, C$_{1-4}$alkyl-NHSO$_2$—, (C$_{1-4}$alkyl)$_2$NSO$_2$—, C$_{1-4}$alkyl-NHC(O)—, C$_{1-4}$alkyl-C(O)—, C$_{1-4}$alkyl-SO$_2$—, 4-morpholinyl-C$_{1-4}$alkoxy, or 1-pyrrolidinylcarbonyl, each of which is optionally substituted with from 1-2 C$_{1-4}$alkyl groups. All the other variables $Y^1$, $Y^2$, $Y^3$, $R^3$, $R^4$, $R^5$ and the subscript m of formulas (I'a) or (IV) are as defined in any of the embodiments as described herein.

In some embodiments of compounds of formula (IV) or (I'a), $R^7$ is aryl optionally substituted with from: (i) 1-3 $R^9$ substituents; or two adjacent $R^9$ substituents on $R^7$, together with the atoms to which they are attached, form a 5- or 6-membered ring having from 0-2 additional heteroatoms selected from O, N or S and optionally substituted with from 1-3 $R^d$ substituents; or (ii) 1-3 $R^c$ substituents; or (iii) 1-3 $R^d$ substituents; or (iv) 1-3 $R^{15}$ substituents; or (v) 1-3 $R^{16}$ or $R^{17}$ substituents; or (vi) 1-3 $R^{18}$ substituents, wherein each of $R^7$, $R^9$, $R^c$, $R^d$, $R^{15}$, $R^{16}$, $R^{17}$ or $R^{18}$ substituent is further optionally substituted with from 1-3 $R^{19}$ substituents independently selected from —CN, F, Cl, I, —OCH$_3$, $C_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH— or CH$_3$SO$_2$. In some instances, $R^7$ is phenyl or perdeuterated phenyl (C$_6$D5), each of which is optionally substituted with from 1-3 $R^{16}$ or $R^{17}$ substituents; or 1-3 $R^{18}$ substituents, wherein $R^{16}$, $R^{17}$ and $R^{18}$ are each further optionally substituted with 1-3 $R^{19}$ groups. In other instances, $R^7$ is phenyl optionally substituted with from 1-3 substituents independently selected from F, Cl, CH$_3$, —OCH$_3$, CF$_3$, CF$_3$O—, —CFH$_2$, —CF$_2$H, CHF$_2$O—, CH$_2$FO—, —NHCH$_3$, —N(CH$_3$)$_2$, —CN, 4-morpholinyl, 4-morpholinylmethyl, 1-piperidinyl, 4-methyl-1-piperazinyl, 1-pyrrolidinyl, 1-pyrrolidinylcarbonyl, 4-morpholinylcarbonyl, 1-piperidinylcarbonyl, 4-methyl-1-piperazinylcarbonyl, 1-pyrrolidinylcarbonyl, cyclopropyl, cyclopropylcarbonyl, 4-morpholinylethyl, CH$_3$SO$_2$, CH$_3$SO$_2$NH—, CH$_3$C(O)—, 4-morpholinylmethylcarbonyl, 1,2-dihydroxypropanoyl, (CH$_3$)$_2$NC(O)— or methoxycarbonylamino, each of which is optionally substituted with 1-2 groups independently selected from $C_{1-6}$alkyl, $C_{1-4}$alkoxy, 4-morphilinyl or 4-morpholinylmethyl. In other instances, $R^7$ is 1-naphthyl, or 2-naphthyl, each of which is optionally substituted with from 11-3 $R^{16}$ or $R^{17}$ substituents; or 1-3 $R^{18}$ substituents, wherein $R^{16}$, $R^{17}$ and $R^{18}$ are each further optionally substituted with 1-3 $R^{19}$ groups. In certain embodiments, the hydrogen atoms in $R^7$ are optionally replaced by 1 to 12, or 1 to 8, or 1 to 6, or 1 to 3 or 1, 2, 3, 4, 5, 6, 7, 8, 9, 10, 11 and 12 deuterium atoms with at least 52.5%, 60%, 70%, 75%, 80%, 90%, 95%, 99%, 99.5% or 99.9% deuterium incorporation for each deuterium. In certain embodiments, each hydrogen atom in $R^7$ is optionally replaced by a deuterium atom with at least 52.5%, 60%, 70%, 75%, 80%, 90%, 95%, 99%, 99.5% or 99.9% deuterium incorporation for each deuterium. All the other variables $Y^1$, $Y^2$, $Y^3$, $R^3$, $R^4$, $R^5$ and the subscript m of formulas (I'a) or (IV) are as defined in any of the embodiments as described herein.

In some embodiments of compounds of formula (IV) or (I'a), $R^7$ is 1H-4-benzotriazolyl, 1H-5-benzotriazolyl, 1H-4-benzimidazolyl, 1H-5-benzimidazolyl, 1H-4-indazolyl, 1H-5-indazolyl, 1H-6-indazolyl, 1H-7-indazolyl, 1H-4-indolyl, 1H-5-indolyl, 1H-6-indolyl, 1H-7-indolyl, 2-oxo-6-indolinyl, 2-oxo-4-indolinyl, 2-oxo-5-indolinyl, 2-oxo-7-indolinyl, 1,2-benzoxazol-4-yl, 1,2-benzoxazol-5-yl, 1,2-benzoxazol-6-yl, 1,2-benzoxazol-7-yl, 1,3-benzoxazol-4-yl, 1,3-benzoxazol-5-yl, 1,3-benzoxazol-6-yl, 1,3-benzoxazol-7-yl, 1,2-benzothiazol-4-yl, 1,2-benzothiazol-5-yl, 1,2-benzothiazol-6-yl, 1,2-benzothiazol-7-yl, 5-quinolinyl, 6-quinolinyl, 7-quinolinyl, 8-quinolinyl, 5-isoquinolinyl, 6-isoquinolinyl, 7-isoquinolinyl, 8-isoquinolinyl, 5-cinnolinyl, 6-cinnolinyl, 7-cinnolinyl, 8-cinnolinyl, 5-quinazolinyl, 6-quinazolinyl, 7-quinazolinyl, 8-quinazolinyl, 5-quinoxalinyl, 6-quinoxalinyl, 7-quinoxalinyl, 8-quinoxalinyl, 4-indanyl, 5-indanyl, 5-tetralinyl, 6-tetralinyl, 1,3-dihydroisobenzofuran-4-yl, 1,3-dihydroisobenzofuran-5-yl, 2,3-dihydrobenzofuran-4-yl, 2,3-dihydrobenzofuran-5-yl, 2,3-dihydrobenzofuran-6-yl, 2,3-dihydrobenzofuran-7-yl, 1,3-dihydroisobenzothiophen-4-yl, 1,3-dihydroisobenzothiophen-5-yl, 2,3-dihydrobenzothiophen-4-yl, 2,3-dihydrobenzothiophen-5-yl, 2,3-dihydrobenzothiophen-6-yl, 2,3-dihydrobenzothiophen-7-yl, 4-indolinyl, 5-indolinyl, 6-indolinyl, 7-indolinyl, 5-isochromanyl, 6-isochromanyl, 7-isochromanyl, 8-isochromanyl, 5-chromanyl, 6-chromanyl, 7-chromanyl, 8-chromanyl, 2,3-dihydro-1,3-benzothiazo-4-yl, 2,3-dihydro-1,3-benzothiazo-5-yl, 2,3-dihydro-1,3-benzothiazo-6-yl, 2,3-dihydro-1,3-benzothiazo-7-yl, 2,3-dihydro-1,2-benzothiazo-4-yl, 2,3-dihydro-1,2-benzothiazo-5-yl, 2,3-dihydro-1,2-benzothiazo-6-yl, 2,3-dihydro-1,2-benzothiazo-7-yl, 2,3-dihydro-1,3-benzoxazol-4-yl, 2,3-dihydro-1,3-benzoxazol-5-yl, 2,3-dihydro-1,3-benzoxazol-6-yl, 2,3-dihydro-1,3-benzoxazol-7-yl, 2,3-dihydro-1,2-benzoxazol-4-yl, 2,3-dihydro-1,2-benzoxazol-5-yl, 2,3-dihydro-1,2-benzoxazol-6-yl, 2,3-dihydro-1,2-benzoxazol-7-yl, 4-benzofuranyl, 5-benzofuranyl, 6-benzofuranyl, 7-benzofuranyl, 4-benzo[b]thiophenyl, 5-benzo[b]thiophenyl, 6-benzo[b]thiophenyl, 7-benzo[b]thiophenyl, 4-benzo[c]thiophenyl, 5-benzo[c]thiophenyl 2,3-dihydro-1,4-benzodioxin-5-yl, 1,3-benzodioxol-4-yl, 1,3-benzodioxol-5-yl, indanyl, 1,2-benzoxazol-4-yl, 1,2-benzoxazol-5-yl, 1,2-benzoxazol-6-yl, 1,2-benzoxazol-7-yl, 1,3-benzoxazol-4-yl, 1,3-benzoxazol-5-yl, 1,3-benzoxazol-6-yl or 1,3-benzoxazol-7-yl, each of which is optionally substituted with from: (i) 1-3 $R^9$ substituents; or (ii) 1-3 $R^c$ substituents; or (iii) 1-3 $R^d$ substituents; or (iv) 1-3 $R^{15}$ substituents; or (v) 1-3 $R^{16}$ substituents; or (vi) 1-3 $R^{17}$ substituents; or (vii) 1-3 $R^{18}$ substituents, wherein each of $R^9$, $R^c$, $R^d$, $R^{15}$, $R^{16}$, $R^{17}$ or $R^{18}$ substituent is further optionally substituted with from 1-3 $R^{19}$ substituents independently selected from —CN, F, Cl, I, —OCH$_3$, $C_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —PH(=O)CH$_3$, —P(=O)(CH$_3$)$_2$, —PH(=O)OCH$_3$, —P(=O)(OCH$_3$)$_2$, —OP(=O)(OCH$_3$)$_2$, —N(CH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH— or CH$_3$SO$_2$. All the other variables $Y^1$, $Y^2$, $Y^3$, $R^3$, $R^4$, $R^5$ and the subscript m of formulas (I'a) or (IV) are as defined in any of the embodiments as described herein.

In some embodiments of compounds of formula (IV) or (I'a), $R^7$ is a heteroaryl optionally substituted with from: (i) 1-3 $R^9$ substituents; or two adjacent $R^9$ substituents on $R^7$, together with the atoms to which they are attached, form a 5- or 6-membered ring having from 0-2 additional heteroatoms selected from O, N or S and optionally substituted with from 1-3 $R^d$ substituents; or (ii) 1-3 $R^c$ substituents; or (iii) 1-3 $R^d$ substituents; or (iv) 1-3 $R^{15}$ substituents; or (v) 1-3 $R^{16}$ substituents; or (vi) 1-3 $R^{17}$ substituents; or (vii) 1-3 $R^{18}$ substituents, wherein each of $R^9$, $R^c$, $R^d$, $R^{15}$, $R^{16}$, $R^{17}$ or $R^{18}$ substituent is further optionally substituted with from 1-3 $R^{19}$ substituents independently selected from —CN, F, Cl, I, —OCH$_3$, $C_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —N(CH$_3$)$_2$, —PH(=O)CH$_3$, —P(=O)(CH$_3$)$_2$, —PH(=O)OCH$_3$, —P(=O)(OCH$_3$)$_2$, —OP(=O)(OCH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH— or CH$_3$SO$_2$. In some instances, $R^7$ is an optionally substituted 5- or 6-membered heteroaryl. All the other variables $Y^1$, $Y^2$, $Y^3$, $R^3$, $R^4$, $R^5$ and the subscript m of formulas (I'a) or (IV) are as defined in any of the embodiments as described herein.

In some embodiments of compounds of formula (IV) or (I'a), $R^7$ is 5-pyrimidinyl, 2-pyrimidinyl, 4-pyrimidinyl, 2-pyridyl, 3-pyridyl, 4-pyridyl, 2-pyrazinyl, 2-pyridazinyl, 3-pyridazinyl, 1-pyrrolyl, 2-pyrrolyl, 3-pyrrolyl, 2-imidazolyl, 4-imidazolyl, 1-pyrazolyl, 2-pyrazolyl, 3-pyrazolyl, 2-oxazolyl, 4-oxazolyl, 5-oxazolyl, 2-thiazolyl, 4-thiazolyl, 5-thiazolyl, 3-isoxazolyl, 4-isoxazolyl, 5-isoxazolyl, 3-isothiazolyl, 4-isothiazolyl, 5-isothiazolyl, 1,2,3-triazol-1-yl, 1,2,3-triazol-2-yl, 1,2,3-triazol-3-yl, 1,2,3-triazol-4-yl, 1,2,3-triazol-5-yl, 1,2,4-triazol-1-yl, 1,2,4-triazol-2-yl, 1,2,4-triazol-3-yl, 1,2,4-triazol-4-yl, 1,2,4-triazol-5-yl, 1-oxa-2,3-diazol-4-yl, 1-oxa-2,3-diazol-5-yl, 1-oxa-2,4-diazol-3-yl, 1-oxa-2,4-diazol-5-yl, 1-oxa-2,5-diazol-3-yl, 1-oxa-2,5-diazol-4-yl, 1-thia-2,3-diazol-4-yl, 1-thia-2,3-diazol-5-yl, 1-thia-2,4-diazol-3-yl, 1-thia-2,4-diazol-5-yl, 1-thia-2,5-diazol-3-yl, 1-thia-2,5-diazol-4-yl, 1-tetrazolyl, 3-tetrazolyl, 1H-5-tetrazolyl, 3H-5-tetrazolyl, 2-furanyl, 3-furanyl, 2-thiophenyl or 3-thiophenyl, each of which is optionally substituted with from: (i) 1-3 $R^9$ substituents; or (ii) 1-3 $R^c$ substituents; or (iii) 1-3 $R^d$ substituents; or (iv) 1-3 $R^{15}$ substituents; or (v) 1-3 $R^{16}$ substituents; or (vi) 1-3 $R^{17}$ substituents; or (vii) 1-3 $R^{18}$ substituents, wherein each of $R^9$, $R^c$, $R^d$, $R^{15}$, $R^{16}$, $R^{17}$ or $R^{18}$ substituent is further optionally substituted with from 1-3 $R^{19}$ substituents independently selected from —CN, F, Cl, I, —OCH$_3$, C$_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —N(CH$_3$)$_2$, —CH$_2$F, —CHF$_2$, CF$_3$, —PH(=O)CH$_3$, —P(=O)(CH$_3$)$_2$, —PH(=O)OCH$_3$, —P(=O)(OCH$_3$)$_2$, —OP(=O)(OCH$_3$)$_2$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH— or CH$_3$SO$_2$. All the other variables $Y^1$, $Y^2$, $Y^3$, $R^3$, $R^4$, $R^5$ and the subscript m of formulas (I'a) or (IV) are as defined in any of the embodiments as described herein.

In some embodiments of compounds of formula (IV) or (I'a), $R^7$ is selected from 1-benzotriazolyl, 1-benzimidazolyl, 1H-2-benzimidazolyl, 1-indazolyl, 1H-3-indazolyl, 1-indolyl, 1H-2-indolyl, 1H-3-indolyl, 1,2-benzoxazol-3-yl, 1,3-benzoxazol-2-yl, 1,2-benzothiazol-3-yl, 1,3-benzothiazol-2-yl, 2-quinolinyl, 3-quinolinyl, 4-quinolinyl, 1-isoquinolinyl, 3-isoquinolinyl, 4-isoquinolinyl, 3-cinnolinyl, 4-cinnolinyl, 2-quinazolinyl, 4-quinazolinyl, 2-quinoxalinyl, 2-benzofuranyl, 3-benzofuranyl, 2-benzo[b]thiophenyl, 3-benzo[b]thiophenyl or 1-benzo[c]thiophenyl each of which is optionally substituted with from: (i) 1-3 $R^9$ substituents; or (ii) 1-3 $R^c$ substituents; or (iii) 1-3 $R^d$ substituents; or (iv) 1-3 $R^{15}$ substituents; or (v) 1-3 $R^{16}$ substituents; or (vi) 1-3 $R^{17}$ substituents; or (vii) 1-3 $R^{18}$ substituents, wherein each of $R^9$, $R^c$, $R^d$, $R^{15}$, $R^{16}$, $R^{17}$ or $R^{18}$ substituents is further optionally substituted with from 1-3 $R^{19}$ substituents. All the other variables $Y^1$, $Y^2$, $Y^3$, $R^3$, $R^4$, $R^5$ and the subscript m of formulas (I'a) or (IV) are as defined in any of the embodiments as described herein.

In some embodiments of compounds of formula (IV) or (I'a), $R^7$ is selected from:

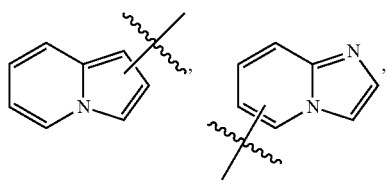

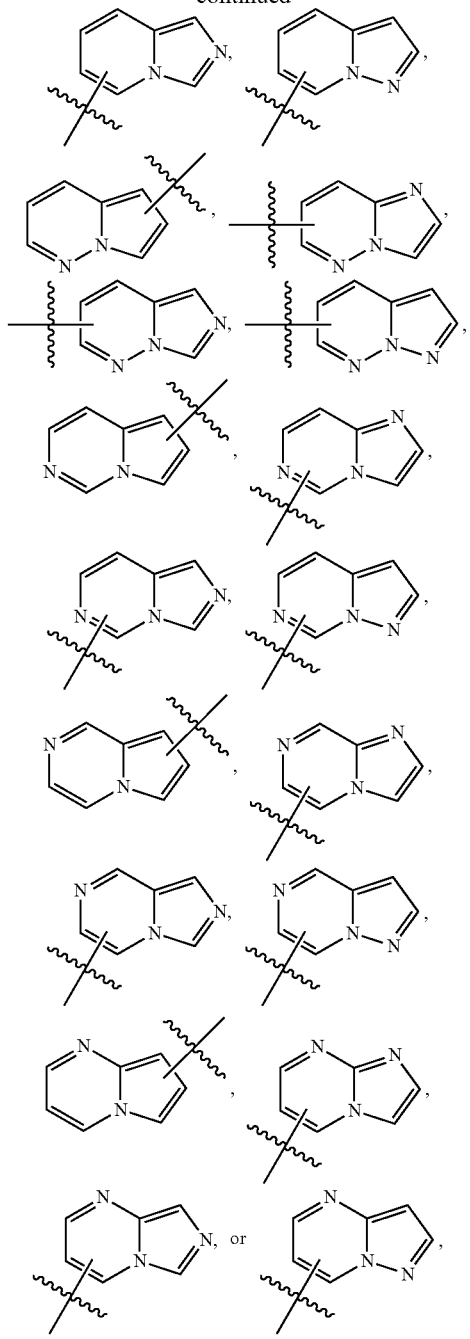

each of which is optionally substituted with from (i) 1-3 $R^9$ substituents; or (ii) 1-3 $R^c$ substituents; or (iii) 1-3 $R^d$substituents; or (iv) 1-3 $R^{15}$ substituents; or (v) 1-3 $R^{16}$ substituents; or (vi) 1-3 $R^{17}$ substituents; or (vii) 1-3 $R^{18}$ substituents, wherein each of $R^9$, $R^c$, $R^d$, $R^{15}$, $R^{16}$, $R^{17}$ or $R^{18}$ substituent is further optionally substituted with from 1-3 $R^{19}$ substituents independently selected from —CN, F, Cl, I, —OCH$_3$, C$_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —N(CH$_3$)$_2$, —CH$_2$F, —PH(=O)CH$_3$, —P(=O)(CH$_3$)$_2$, —PH(=O)(OC$_{1-6}$alkyl), —P(=O)(OC$_{1-6}$alkyl)$_2$, —OP(=O)(OC$_{1-6}$alkyl)$_2$, —CHF$_2$, CF$_3$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC (O)—, (CH$_3$)$_2$NS(O)$_2$—, (CH$_3$)$_2$S(O)$_2$NH— or CH$_3$SO$_2$, where the wavy line indicate the point of attachment to the rest of the molecule. The notation

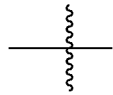

means R$^7$ can be attached to the rest of the molecule at any of the available positions of the R$^7$ group set forth above. For example,

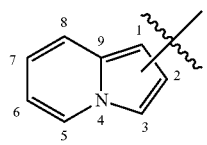

is meant to include 1-indolizinyl, 2-indolizinyl, 3-indolizinyl, 4-indolizinyl, 5-indolizinyl, 6-indolizinyl, 7-indolizinyl, and 8-indolizinyl (i.e., substitutions can be at 1, 2, 3, 5, 6, 7 or 8 positions of the indolizine ring).

In some embodiments of compounds of formula (IV) or (I'a), R$^7$ is selected from:

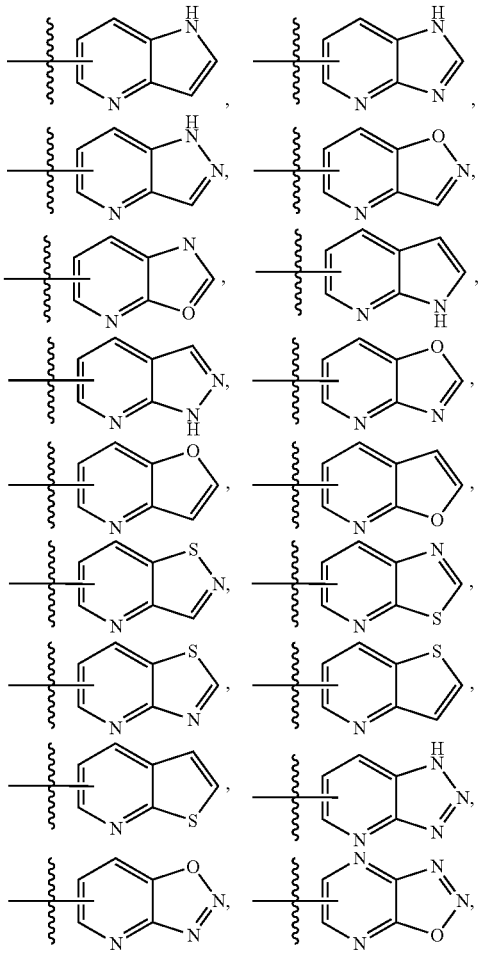

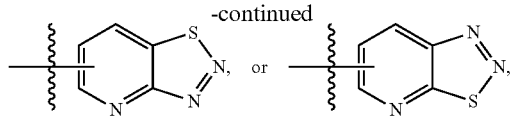

each of which is optionally substituted with from (i) 1-3 R$^9$ substituents; or (ii) 1-3 R$^d$ substituents; or (iii) 1-3 R$^d$ substituents; or (iv) 1-3 R$^{15}$ substituents; or (v) 1-3 R$^{16}$ substituents; or (vi) 1-3 R$^{17}$ substituents; or (vii) 1-3 R$^8$ substituents, wherein each of R$^9$, R$^c$, R$^d$, R$^{15}$, R$^{16}$, R$^{17}$ or R$^{18}$ substituent is further optionally substituted with from 1-3 R$^{19}$ substituents independently selected from —CN, F, Cl, I, —OCH$_3$, C$_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, —PH(=O)CH$_3$, —P(=O)(CH$_3$)$_2$, —PH(=O)(OC$_{1-6}$alkyl), —P(=O)(OC$_{1-6}$alkyl)$_2$, —OP(=O)(OC$_{1-6}$alkyl)$_2$, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH— or CH$_3$SO$_2$, where the wavy line indicates the point of attachment to the rest of the molecule. The notation

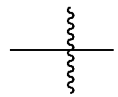

means R$^7$ can be attached to the rest of the molecule at any of the available positions of the R$^7$ group set forth above. For example,

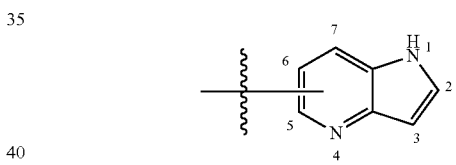

is meant to include 1H-pyrrolo[3,2-b]pyridin-1-yl, 1H-pyrrolo[3,2-b]pyridin-2-yl, 1H-pyrrolo[3,2-b]pyridin-3-yl, 1H-pyrrolo[3,2-b]pyridin-5-yl, 1H-pyrrolo[3,2-b]pyridin-6-yl and 1H-pyrrolo[3,2-b]pyridin-7-yl (i.e., substitutions can be at 1, 2, 3, 5, 6, or 7 positions of the pyrrolo[3,2-b]pyridine ring). All the other variables Y$^1$, Y$^2$, Y$^3$, R$^3$, R$^4$, R$^5$ and the subscript m of formulas (I'a) or (IV) are as defined in any of the embodiments as described herein.

In some embodiments of compounds of formula (IV) or (I'a), R$^7$ is selected from:

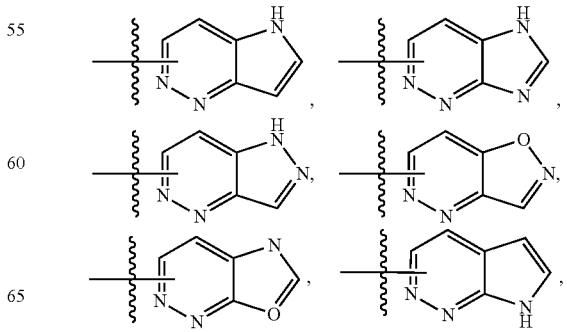

-continued

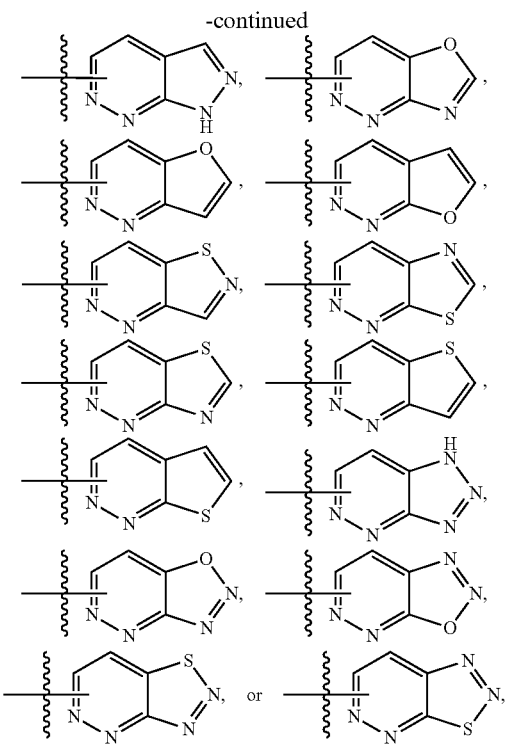

each of which is optionally substituted with from (i) 1-3 $R^9$ substituents; or (ii) 1-3 $R^c$ substituents; or (iii) 1-3 $R^d$ substituents; or (iv) 1-3 $R^{15}$ substituents; or (v) 1-3 $R^{16}$ substituents; or (vi) 1-3 $R^{17}$ substituents; or (vii) 1-3 $R^{18}$ substituents, wherein each of $R^9$, $R^c$, $R^d$, $R^{15}$, $R^{16}$, $R^{17}$ or $R^{18}$ substituent is further optionally substituted with from 1-3 $R^{19}$ substituents independently selected from —CN, F, Cl, I, —OCH$_3$, C$_{1-6}$alkyl, cyclopropyl, 1-azetidinyl, 2-azetidinyl, 3-azetidinyl, 2-oxetanyl, 3-oxetanyl, —PH(=O)CH$_3$, —P(=O)(CH$_3$)$_2$, —PH(=O)(OC$_{1-6}$alkyl), —P(=O)(OC$_{1-6}$alkyl)$_2$, —OP(=O)(OC$_{1-6}$alkyl)$_2$, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH— or CH$_3$SO$_2$, where the wavy line indicates the point of attachment to the rest of the molecule. The notation

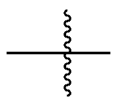

means $R^7$ can be attached to the rest of the molecule at any of the available positions of the $R^7$ group set forth above. For example,

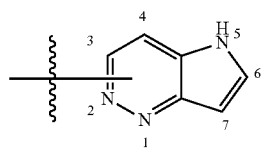

is meant to include 5H-pyrrolo[3,2-c]pyridazin-3-yl, 5H-pyrrolo[3,2-c]pyridazin-4-yl, 5H-pyrrolo[3,2-c]pyridazin-5-yl, 5H-pyrrolo[3,2-c]pyridazin-6-yl, 5H-pyrrolo[3,2-c]pyridazin-7-yl (i.e., substitutions can be at 3, 4, 5, 6, or 7 positions of the 5H-pyrrolo[3,2-c]pyridazine ring). All the other variables $Y^1$, $Y^2$, $Y^3$, $R^3$, $R^4$, $R^5$ and the subscript m of formulas (I'a) or (IV) are as defined in any of the embodiments as described herein.

In some embodiments of compounds of formula (IV) or (I'a), $R^7$ is selected from:

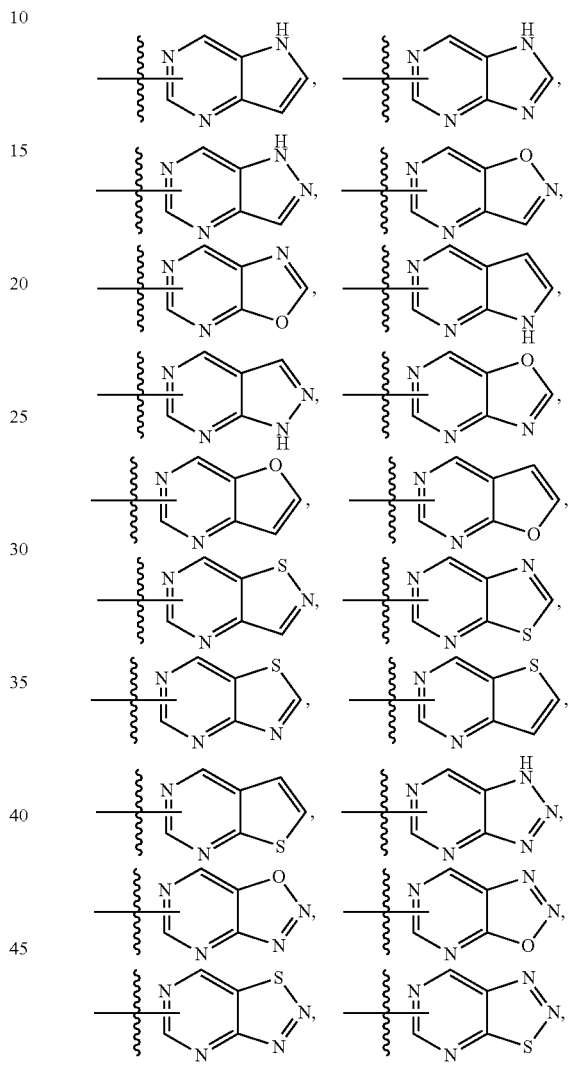

each of which is optionally substituted with from (i) 1-3 $R^9$ substituents; or (ii) 1-3 $R^c$ substituents; or (iii) 1-3 $R^d$ substituents; or (iv) 1-3 $R^{15}$ substituents; or (v) 1-3 $R^{16}$ substituents; or (vi) 1-3 $R^{17}$ substituents; or (vii) 1-3 $R^{18}$ substituents, wherein each of $R^9$, $R^c$, $R^d$, $R^{15}$, $R^{16}$, $R^{17}$ or $R^{18}$ substituent is further optionally substituted with from 1-3 $R^{19}$ substituents independently selected from —CN, F, Cl, I, —OCH$_3$, C$_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, —PH(=O)CH$_3$, —P(=O)(CH$_3$)$_2$, —PH(=O)(OC$_{1-6}$alkyl), —P(=O)(OC$_{1-6}$alkyl)$_2$, —OP(=O)(OC$_{1-6}$alkyl)$_2$, CH$_3$OC(O)—, CH$_3$NHC(O)—, CH$_3$C(O)NH—, (CH$_3$)$_2$NC(O)— (CH$_3$)$_2$NS(O)$_2$—, (CH$_3$)$_2$S(O)$_2$NH— or CH$_3$SO$_2$, where the wavy line indicates the point of attachment to the rest of the molecule. The notation

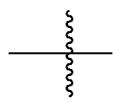

means $R^7$ can be attached to the rest of the molecule at any of the available positions of the $R^7$ group set forth above. For example

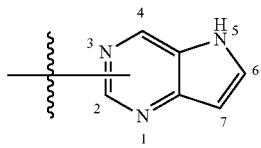

is meant to include 5H-pyrrolo[3,2-c]pyrimidin-2-yl, 5H-pyrrolo[3,2-c]pyrimidin-4-yl, 5H-pyrrolo[3,2-c]pyrimidin-5-yl, 5H-pyrrolo[3,2-c]pyrimidin-6-yl and 5H-pyrrolo[3,2-c]pyrimidin-7-yl (i.e., substitutions can be at 2, 4, 5, 6, or 7 positions of the 5H-pyrrolo[3,2-c]pyrimidine ring). All the other variables $Y^1$, $Y^2$, $Y^3$, $R^3$, $R^4$, $R^5$ and the subscript m of formulas (I'a) or (IV) are as defined in any of the embodiments as described herein.

In some embodiments of compounds of formula (IV) or (I'a), $R^7$ is selected from:

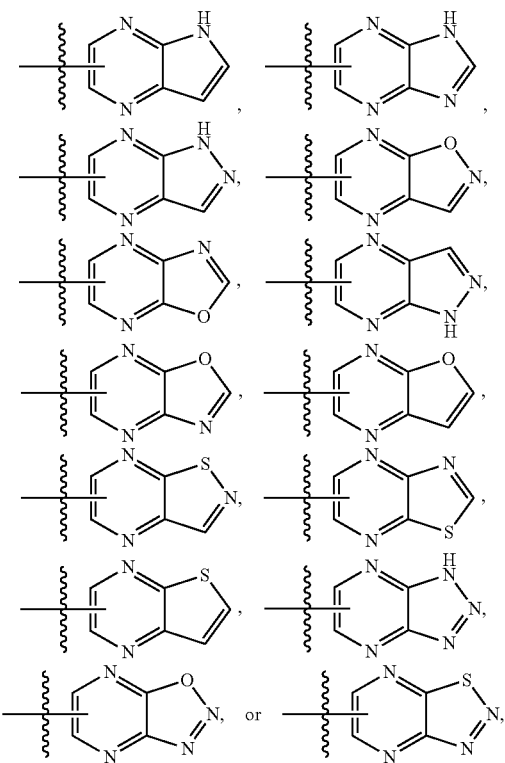

each of which is optionally substituted with from (i) 1-3 $R^9$ substituents; or (ii) 1-3 $R^c$ substituents; or (iii) 1-3 $R^d$ substituents; or (iv) 1-3 $R^{15}$ substituents; or (v) 1-3 $R^{16}$ substituents; or (vi) 1-3 $R^{17}$ substituents; or (vii) 1-3 $R^{18}$ substituents, wherein each of $R^9$, $R^c$, $R^d$, $R^{15}$, $R^{16}$, $R^{17}$ or $R^{18}$ substituent is further optionally substituted with from 1-3 $R^{19}$ substituents independently selected from —CN, F, Cl, I, —OCH$_3$, C$_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)—, —PH(=O)CH$_3$, —P(=O)(CH$_3$)$_2$, —PH(=O)(OC$_{1-6}$alkyl), —P(=O)(OC$_{1-6}$alkyl)$_2$, —OP(=O)(OC$_{1-6}$alkyl)$_2$, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH— or CH$_3$SO$_2$, where the wavy line indicates the point of attachment to the rest of the molecule. The notation

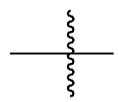

means $R^7$ can be attached to the rest of the molecule at any of the available positions of the $R^7$ group set forth above. For example,

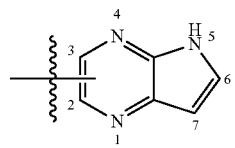

is meant to include 5H-pyrrolo[2,3-b]pyrazin-2-yl, 5H-pyrrolo[2,3-b]pyrazin-3-yl, 5H-pyrrolo[2,3-b]pyrazin-5-yl, 5H-pyrrolo[2,3-b]pyrazin-6-yl, 5H-pyrrolo[2,3-b]pyrazin-7-yl, (i.e., substitutions can be at 2, 3, 5, 6, or 7 positions of the 5H-pyrrolo[2,3-b]pyrazine ring). All the other variables $Y^1$, $Y^2$, $Y^3$, $R^3$, $R^4$, $R^5$ and the subscript m of formulas (I'a) or (IV) are as defined in any of the embodiments as described herein.

In some embodiments of compounds of formula (IV) or (I'a), $R^7$ is cycloalkyl or cycloalkenyl, each of which is optionally substituted with from: (i) 1-3 $R^9$ substituents; or (ii) 1-3 $R^c$ substituents; or (iii) 1-3 $R^d$ substituents; or (iv) 1-3 $R^{15}$ substituents; or (v) 1-3 $R^{16}$ substituents; or (vi) 1-3 $R^{17}$ substituents; or (vii) 1-3 $R^{18}$ substituents, wherein each of $R^9$, $R^c$, $R^d$, $R^{15}$, $R^{16}$, $R^{17}$ or $R^{18}$ substituent is further optionally substituted with from 1-3 $R^{19}$ substituents. All the other variables $Y^1$, $Y^2$, $Y^3$, $R^3$, $R^4$, $R^5$ and the subscript m of formulas (I'a) or (IV) are as defined in any of the embodiments as described herein.

In some embodiments of compounds of formula (IV) or (I'a), $R^7$ is cyclopropyl, cyclobutyl, cyclopentyl, cyclohexyl, cycloheptyl, cyclooctyl, 1-cyclopentenyl, 3-cyclopentenyl, 4-cyclopentenyl, 1-cyclohexenyl, 3-cyclohexenyl, 4-cyclohexenyl, 1-cyclohexenyl, 1-octenyl, 1,4-cyclohexadienyl, 1,4-cyclohexadien-3-yl or cyclooctatetraene, each of which is optionally substituted with from: (i) 1-3 $R^9$ substituents; or (ii) 1-3 $R^c$ substituents; or (iii) 1-3 $R^d$ substituents; or (iv) 1-3 $R^{15}$ substituents; or (v) 1-3 $R^{16}$ substituents; or (vi) 1-3 $R^{17}$ substituents; or (vii) 1-3 $R^{18}$ substituents, wherein each of $R^9$, $R^c$, $R^d$, $R^{15}$, $R^{16}$, $R^{17}$ or $R^{18}$ substituent is further optionally substituted with from 1-3 $R^{19}$ substituents. In some instances, $R^7$ is cyclopentenyl, cyclohexenyl or cyclopropyl, each of which is optionally substituted with from (i) 1-3 $R^9$ substituents; or (ii) 1-3 $R^c$ substituents; or (iii) 1-3 $R^d$ substituents; or (iv) 1-3 $R^{15}$ substituents; or (v) 1-3 $R^{16}$ substituents; or (vi) 1-3 $R^{17}$ substituents; or (vii) 1-3 $R^{18}$, wherein each of $R^9$, $R^c$, $R^d$, $R^{15}$, $R^{16}$, $R^{17}$ or $R^{18}$ substituent is further optionally substituted with from 1-3 $R^{19}$ substituents. All the other variables $Y^1$, $Y^2$, $Y^3$, $R^3$, $R^4$, $R^5$ and the subscript m of formula (IV) are as defined in any of the embodiments as described herein.

In some embodiments of compounds of formula (IV) or (I'a), $R^7$ is heterocycloalkyl, optionally substituted with from: (i) 1-3 $R^9$ substituents; or (ii) 1-3 $R^c$ substituents; or (iii) 1-3 $R^d$ substituents; or (iv) 1-3 $R^{15}$ substituents; or (v) 1-3 $R^{16}$ substituents; or (vi) 1-3 $R^{17}$ substituents; or (vii) 1-3 $R^{18}$, wherein each of $R^9$, $R^c$, $R^d$, $R^{15}$, $R^{16}$, $R^{17}$ or $R^{18}$ substituent is further optionally substituted with from 1-3 $R^{19}$ substituents. All the other variables $Y^1$, $Y^2$, $Y^3$, $R^3$, $R^4$, $R^5$ and the subscript m of formulas (I'a) or (IV) are as defined in any of the embodiments as described herein.

In some embodiments of compounds of formula (IV) or (I'a), $R^7$ is 1-aziridinyl, 2-aziridinyl, 1-1-azetidinyl, 2-azetidinyl, 3-azetidinyl, 1-pyrrolidinyl, 2-pyrrolidinyl, 3-pyrrolidinyl, 2,3-dihydro-1H-pyrrol-1-yl, 2,3-dihydro-1H-pyrrol-2-yl, 2,3-dihydro-1H-pyrrol-3-yl, 2,3-dihydro-1H-pyrrol-4-yl, 2,3-dihydro-1H-pyrrol-5-yl, 2,5-dihydro-1H-pyrrol-1-yl, 2,5-dihydro-1H-pyrrol-2-yl, 2,5-dihydro-1H-pyrrol-3-yl, 2,3-dihydro-1H-imidazol-1-yl, 2,3-dihydro-1H-imidazol-2-yl, 2,3-dihydro-1H-imidazol-4-yl, 2,3-dihydrothiazol-2-yl, 2,3-dihydrothiazol-4-yl, 2,3-dihydrothiazol-5-yl, 2,3-dihydrofuran-2-yl, 2,3-dihydrofuran-3-yl, 2,3-dihydrofuran-4-yl, 2,3-dihydrofuran-5-yl, 2,5-dihydrofuran-2-yl, 2,5-dihydrofuran-3-yl, 2,3-dihydropyran-2-yl, 2,3-dihydropyran-3-yl, 2,3-dihydropyran-4-yl, 2,3-dihydropyran-5-yl, 2,3-dihydropyran-6-yl, 3,6-dihydro-2H-pyran-2-yl, 3,6-dihydro-2H-pyran-3-yl, 3,6-dihydro-2H-pyran-4-yl, 3,6-dihydro-2H-pyran-5-yl, 3,6-dihydro-2H-pyran-6-yl, 1-piperidinyl, 2-piperidinyl, 3-piperidinyl, 4-piperidinyl, 1-piperazinyl, 2-piperazinyl, 2-morpholinyl, 3-morpholinyl, 4-morpholinyl, 1,2,3,6-tetrahydropyridin-1-yl, 1,2,3,6-tetrahydropyridin-1-yl, 1,2,3,6-tetrahydropyridin-2-yl, 1,2,3,6-tetrahydropyridin-3-yl, 1,2,3,6-tetrahydropyridin-4-yl, 1,2,3,6-tetrahydropyridin-5-yl, or 1,2,3,6-tetrahydropyridin-6-yl, each of which is optionally substituted with from: (i) 1-3 $R^9$ substituents; or (ii) 1-3 $R^c$ substituents; or (iii) 1-3 $R^d$ substituents; or (iv) 1-3 $R^{15}$ substituents; or (v) 1-3 $R^{16}$ substituents; or (vi) 1-3 $R^{17}$ substituents; or (vii) 1-3 $R^{18}$, wherein each of $R^9$, $R^c$, $R^d$, $R^{15}$, $R^{16}$, $R^{17}$ or $R^{18}$ substituent is further optionally substituted with from 1-3 $R^{19}$ substituents. In some instances, $R^7$ is 1-aziridinyl, 2-aziridinyl, 2,3-dihydro-1H-pyrrol-5-yl, 2,5-dihydro-1H-pyrrol-3-yl, 2,3-dihydro-1H-imidazol-4-yl, 2,3-dihydrofuran-4-yl, 2,3-dihydrofuran-5-yl, 2,3-dihydrofuran-4-yl, 2,3-dihydrofuran-5-yl, 2,5-dihydrofuran-3-yl, 2,3-dihydropyran-5-yl, 2,3-dihydropyran-6-yl, 3,6-dihydro-2H-pyran-4-yl, 3,6-dihydro-2H-pyran-5-yl, 1,2,3,6-tetrahydropyridin-4-yl or 1,2,3,6-tetrahydropyridin-5-yl, each of which is optionally substituted with from (i) 1-3 $R^9$ substituents; or (ii) 1-3 $R^c$ substituents; or (iii) 1-3 $R^d$ substituents; or (iv) 1-3 $R^{15}$ substituents; or (v) 1-3 $R^{16}$ substituents; or (vi) 1-3 $R^{17}$ substituents; or (vii) 1-3 $R^{18}$, wherein each of $R^9$, $R^c$, $R^d$, $R^{15}$, $R^{16}$, $R^{17}$ or $R^{18}$ substituent is further optionally substituted with from 1-3 $R^{19}$ substituents. In other instances, $R^7$ is 1,2,3,6-tetrahydropyridin-4-yl or 1,2,3,6-tetrahydropyridin-5-yl, 2,5-dihydro-1H-pyrrol-1-yl, 2,5-dihydro-1H-pyrrol-2-yl or 2,5-dihydro-1H-pyrrol-3-yl, each of which is optionally substituted with from (i) 1-3 $R^9$ substituents; or (ii) 1-3 $R^c$ substituents; or (iii) 1-3 $R^d$ substituents; or (iv) 1-3 $R^{15}$ substituents; or (v) 1-3 $R^{16}$ substituents; or (vi) 1-3 $R^{17}$ substituents; or (vii) 1-3 $R^{18}$, wherein each of $R^9$, $R^c$, $R^d$, $R^{15}$, $R^{16}$, $R^{17}$ or $R^{18}$ substituent is further optionally substituted with from 1-3 $R^{19}$ substituents. All the other variables $Y^1$, $Y^2$, $Y^3$, $R^3$, $R^4$, $R^5$ and the subscript m of formulas (I'a) or (IV) are as defined in any of the embodiments as described herein.

In some embodiments of compounds of formula (IV) or (I'a), $R^7$ is $C_{2-4}$alkenyl or $C_{2-4}$alkynyl, each of which is optionally substituted with from: each of which is optionally substituted with from (i) 1-3 $R^9$ substituents; or (ii) 1-3 $R^c$ substituents; or (iii) 1-3 $R^d$ substituents; or (iv) 1-3 $R^{15}$ substituents; or (v) 1-3 $R^{16}$ substituents; or (vi) 1-3 $R^{17}$ substituents; or (vii) 1-3 $R^{18}$, wherein each of $R^9$, $R^c$, $R^d$, $R^{15}$, $R^{16}$, $R^{17}$ or $R^{18}$ substituent is further optionally substituted with from 1-3 $R^{19}$ substituents. All the other variables $Y^1$, $Y^2$, $Y^3$, $R^3$, $R^4$, $R^5$ and the subscript m of formulas (I'a) or (IV) are as defined in any of the embodiments as described herein.

In some embodiments of compounds of formula (IV) or (I'a), $R^7$ is vinyl, ethynyl, 1-propynyl, 3-fluoro-propynyl or cyclopropylethynyl, each of which is optionally substituted with from: (i) 1-3 $R^9$ substituents; or (ii) 1-3 $R^c$ substituents; or (iii) 1-3 $R^d$ substituents; or (iv) 1-3 $R^{15}$ substituents; or (v) 1-3 $R^{16}$ substituents; or (vi) 1-3 $R^{17}$ substituents; or (vii) 1-3 $R^{18}$, wherein each of $R^9$, $R^c$, $R^d$, $R^{15}$, $R^{16}$, $R^{17}$ or $R^{18}$ substituent is further optionally substituted with from 1-3 $R^{19}$ substituents. In some instances, $R^7$ is ethynyl, 1-propynyl, 3-fluoro-propynyl or cyclopropylethynyl, each of which is optionally substituted with from: (i) 1-3 $R^9$ substituents; or (ii) 1-3 $R^c$ substituents; or (iii) 1-3 $R^d$ substituents; or (iv) 1-3 $R^{15}$ substituents; or (v) 1-3 $R^{16}$ substituents; or (vi) 1-3 $R^{17}$ substituents; or (vii) 1-3 $R^{18}$, wherein each of $R^9$, $R^c$, $R^d$, $R^{15}$, $R^{16}$, $R^{17}$ or $R^{18}$ substituent is further optionally substituted with from 1-3 $R^{19}$ substituents. All the other variables $Y^1$, $Y^2$, $Y^3$, $R^3$, $R^4$, $R^5$ and the subscript m of formulas (I'a) or (IV) are as defined in any of the embodiments as described herein.

In some embodiments of compounds of formula (IV) or (I'a), $R^7$ is halogen, $C_{1-6}$alkyl, CN, —$C_{1-2}$alkyl-$R^k$, —C(O)—$R^k$, —C(O)NH$R^k$, —C(O)N$R^k R^k$, —NHC(O)$R^k$, —C(O)O$R^k$, —OC(O)$R^k$, —SO$_2 R^k$, —NHSO$_2 R^k$, —SO$_2$NH$R^k$, —SO$_2$N$R^k R^k$, wherein each $R^k$ is independently $C_{1-6}$alkyl, $C_{3-6}$cycloalkyl, phenyl or heterocycloalkyl, wherein $R^k$ is further optionally substituted with from 1-3 $R^d$ groups. In some instances, $R^k$ is $C_{1-6}$alkyl, $C_{3-6}$cycloalkyl, phenyl, 4-morpholinyl, 1-piperidinyl, 3-piperidinyl, 4-piperidinyl, 1-piperazinyl or 2-piperazinyl, wherein $R^k$ is further optionally substituted with from 1-3 $R^d$ group. All the other variables $Y^1$, $Y^2$, $Y^3$, $R^3$, $R^4$, $R^5$ and the subscript m of formulas (I'a) or (IV) are as defined in any of the embodiments as described herein.

In some embodiments of compounds of formula (IV) or (I'a), two adjacent $R^7$ substituents together with the atoms to which they are attached form a 5- or 6-membered ring having from 0-2 heteroatoms selected from N, O or S, wherein in the ring is optionally substituted with from (i) 1-3 $R^9$ substituents; or (ii) 1-3 $R^c$ substituents; or (iii) 1-3 $R^d$ substituents; or (iv) 1-3 $R^{15}$ substituents; or (v) 1-3 $R^{16}$ substituents; or (vi) 1-3 $R^{17}$ substituents; or (vii) 1-3 $R^{18}$, wherein each of $R^9$, $R^c$, $R^d$, $R^{15}$, $R^{16}$, $R^{17}$ or $R^{18}$ substituent is further optionally substituted with from 1-3 $R^{19}$ substituents. In certain embodiments, the 5- or 6-membered ring is selected from cyclopentane, cyclohexane, pyrrolidine, pyrrole, pyrazole, imidazole, oxazole, isoxazole, thiazole, isothiazole, tetrahydrofuran, tetrahydropyran, 1,4-dioxane, pyridine, pyrazine, piperidine, piperazine, pyrimidine or pyridazine ring system, each of which is optionally substituted with from 1-3 $R^{16}$; or 1-3 $R^{17}$; or 1-3 $R^{18}$ substituents wherein $R^{16}$, $R^{17}$ or $R^{18}$ substituent is further optionally substituted with from 1-3 $R^{19}$ substituents. All the other variables $Y^1$, $Y^2$, $Y^3$, $R^3$, $R^4$, $R^5$ and the subscript m of formulas (I'a) or (IV) are as defined in any of the embodiments as described herein.

In some embodiments of compounds of formula (IV) or (I'a), ring A is an optionally substituted 5-membered fused heterocyclic aromatic ring having from 1-3 heteroatoms as ring members selected from O, N or S; or an optionally substituted fused benzene ring; or when ring A is substituted with two or more substituents, two such substituents, together with the atoms to which they are attached, optionally form a 5- or 6-membered ring. All the other variables $Y^1$, $Y^2$, $Y^3$, $R^3$, $R^4$, $R^5$ of formulas (I'a) or (IV) are as defined in any of the embodiments as described herein.

In any of the embodiments of compounds of formulas (I'a) or (IV), the hydrogen atoms in $R^7$ are optionally replaced by 1 to 12, or 1 to 8, or 1 to 6, or 1 to 3 or 1, 2, 3, 4, 5, 6, 7, 8, 9, 10, 11 and 12 deuterium atoms with at least 52.5%, 60%, 70%, 75%, 80%, 90%, 95%, 99%, 99.5% or 99.9% deuterium incorporation for each deuterium. In certain embodiments, each hydrogen atom in $R^7$ is optionally replaced by a deuterium atom with at least 52.5%, 60%, 70%, 75%, 80%, 90%, 95%, 99%, 99.5% or 99.9% deuterium incorporation for each deuterium.

In some embodiments of compounds of formulas (I'a) or (IV), ring A is 5-membered fused heterocyclic aromatic ring having from 1-3 heteroatoms as ring members selected from O, N or S; or a fused benzene ring. All the other variables $Y^1$, $Y^2$, $Y^3$, $R^3$, $R^4$, $R^5$ of formula (IV) are as defined in any of the embodiments as described herein. In certain instances, ring A is a fused pyrrole, pyrazole, 1,2,3-triazole, 1,2,4-triazole, imidazole, thiophene or benzene ring.

In certain embodiments of compounds of formula (IV), the moiety:

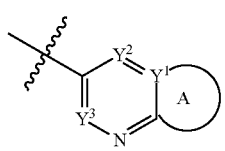

is selected from

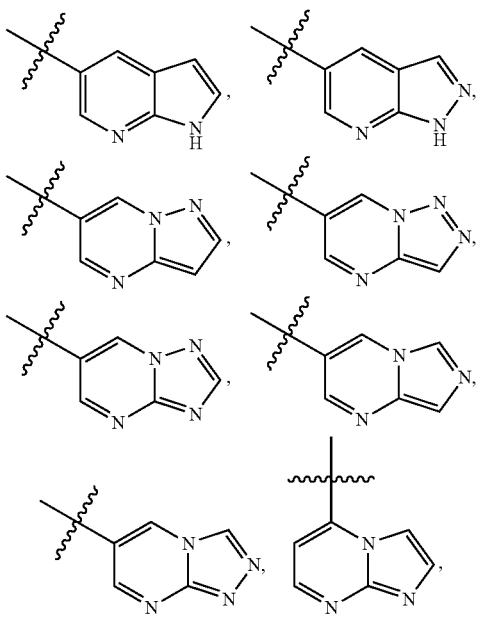

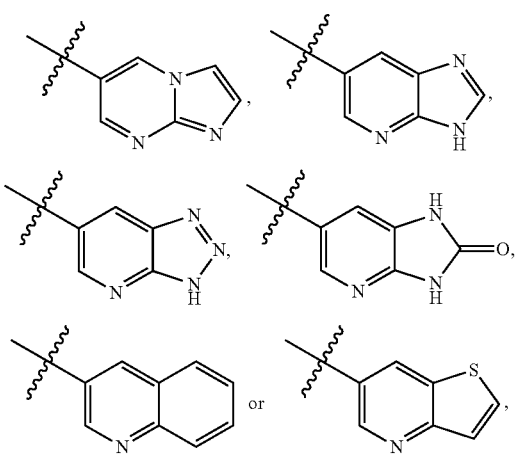

each of which is optionally substituted with from 1-2 $R^7$ groups and the wavy line indicates the point of attachment to the rest of the molecule. In some embodiments,

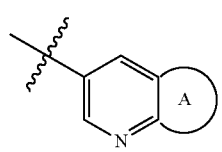

is substituted with from 1-2 $R^7$ groups. In one embodiment,

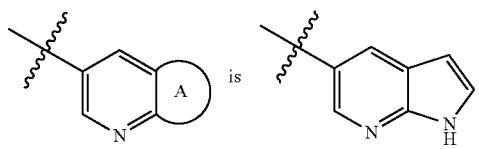

(pyrrolo[2,3-b]pyridine moiety), optionally substituted with from 1-2 $R^7$ groups. In other embodiments,

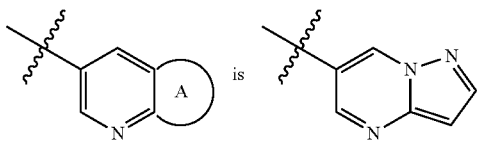

(pyrazolo[1,5-a]pyrimidine moiety, optionally substituted with from 1-2 $R^7$ groups. In other embodiments,

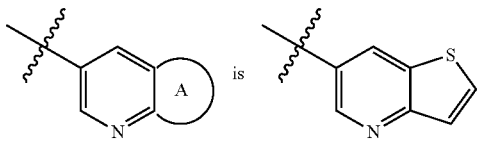

(thieno[2,3-b]pyridine moiety), optionally substituted with from 1-2 $R^7$ groups. In yet other embodiments,

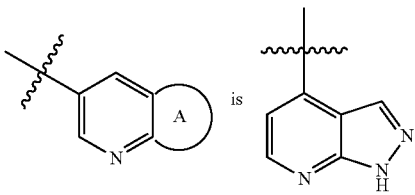 is (pyrazolo[3,4-b]pyridine moiety), optionally substituted with from $R^7$ group. In still other embodiments,

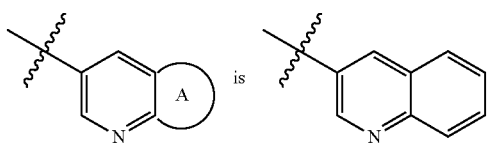 is (quinoline moiety), optionally substituted with from 1-2 $R^7$ groups. All the other variables $R^3$, $R^4$ and $R^5$ of formula (IV) are as defined in any of the embodiments as described herein. In some embodiments, the hydrogen atoms in

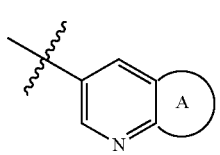

are optionally replaced with from 1 to 6 deuteriums with at least 52.5%, 60%, 70%, 75%, 80%, 90%, 95%, 99%, 99.5% or 99.9% deuterium incorporation for each deuterium. In some embodiments, each hydrogen atom in

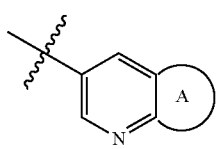

is optionally replaced by a deuterium atom with at least 52.5%, 60%, 70%, 75%, 80%, 90%, 95%, 99%, 99.5% or 99.9% deuterium incorporation for each deuterium.

In certain embodiments of compounds of formula (IV), the moiety:

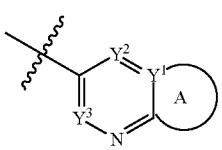

is selected from

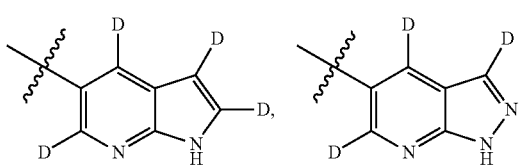

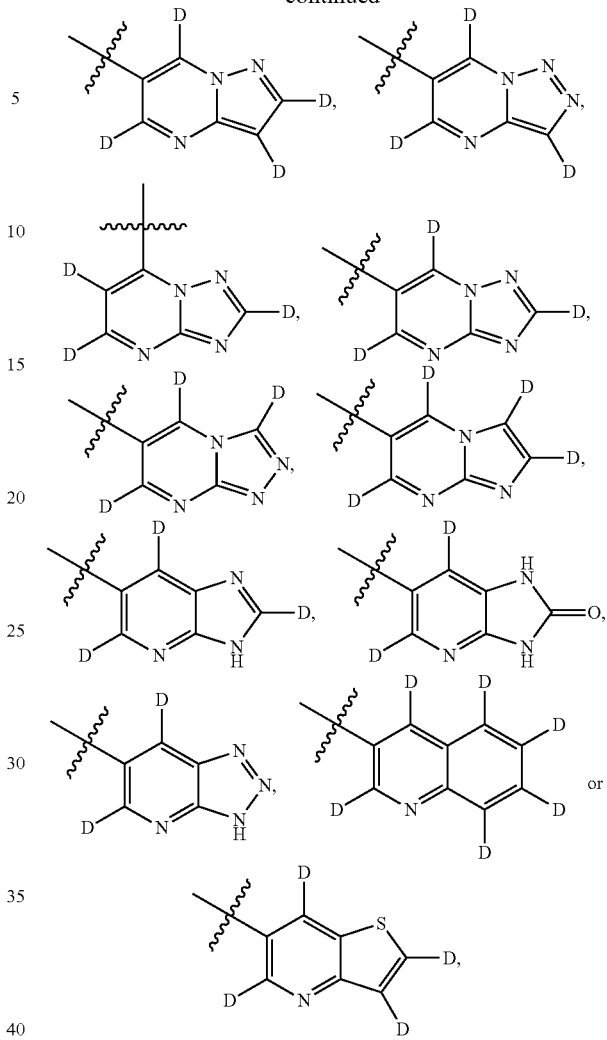

each of which is optionally substituted with from 1-2 $R^7$ groups and the wavy line indicates the point of attachment to the rest of the molecule.

In some embodiments of compounds of compounds of formulas (I'), (I'a), (I), (II) or (III), the disclosure provides compounds of formula (V):

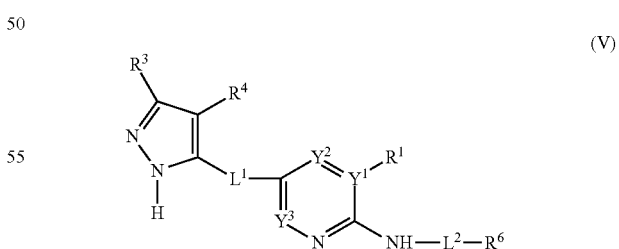

(V)

In certain embodiments, $R^1$ is H, halogen, $C_{1-4}$ alkyl, $C_{1-4}$haloalkyl, $C_{1-4}$haloalkoxy, cyclopropyl or a lone pair of electrons; $L^2$ is a bond, —$CH_2$—, —C(O)— or —$SO_2$; $R^6$ is alkyl, aryl or heteroaryl, each of which is optionally substituted with from 1-3 $R^9$ members independently selected from $C_{1-6}$alkyl, $C_{1-6}$alkoxy, $C_{2-6}$alkenyl, $C_{2-6}$alkynyl, —$X^1$-aryl, aryl-$C_{1-4}$alkyl-$X^1$—, heteroaryl-$X^1$—, heteroaryl-$C_{1-4}$ alkyl-X$^1$—, C$_{3-6}$cycloalkyl-X$^1$—, C$_{3-6}$cycloalkyl-C$_{1-4}$alkyl-X$^1$—, C$_{3-6}$cycloalkenyl-X$^1$—, CH$_2$=CH—X$^1$—, C$_{3-6}$cycloalkyl-C$_{2-4}$alkenyl-X$^1$—, C$_{3-6}$cycloalkyl-C$_{2-4}$alkynyl-X$^1$—, heterocyclyl-X$^1$—, heterocyclyl-C$_{1-4}$alkyl-X$^1$— or R$^s$; or two adjacent R$^9$ members together with the atoms to which they are attached form a 5- or 6-membered fused ring having 0-2 heteroatoms as ring members selected from O, N or S. In some instances, R$^1$ is H or a lone pair of electron. In one instance, R$^1$ is H. In other instance, Y$^1$ is N and R$^1$ is a lone pair of electron. The other variables Y$^1$, Y$^2$, Y$^3$, R$^3$, R$^4$, L$^1$ and L$^2$ of formula (V) are as defined in any of the embodiments as described herein. In some embodiments of compounds of formula (V), L$^1$ is —C(O)NR$^5$—, wherein the carbonyl group in L$^1$ is covalently linked to the pyrazole ring and the nitrogen atom in L$^1$ is covalently bonded to the 6-membered aromatic ring in formula (V).

In some embodiments of compounds of compounds of formulas (I'), (I'a), (I), (II), (III) or (V), the disclosure provides compounds of formula (V'):

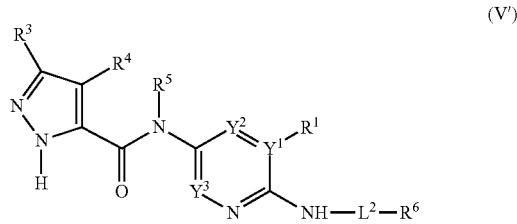
(V')

In certain embodiments, R$^1$ is H, halogen, C$_{1-4}$ alkyl, C$_{1-4}$haloalkyl, C$_{1-4}$haloalkoxy, cyclopropyl or a lone pair of electrons; L$^2$ is a bond, —CH$_2$—, —C(O)— or —SO$_2$; R$^6$ is alkyl, aryl or heteroaryl, each of which is optionally substituted with from 1-3 R$^9$ members independently selected from C$_{1-6}$alkyl, C$_{1-6}$alkoxy, C$_{2-6}$alkenyl, C$_{2-6}$alkynyl, —X$^1$-aryl, aryl-C$_{1-4}$alkyl-X—, heteroaryl-X$^1$—, heteroaryl-C$_{1-4}$alkyl-X$^1$—, C$_{3-6}$cycloalkyl-X$^1$—, C$_{3-6}$cycloalkyl-C$_{1-4}$alkyl-X$^1$—, C$_{3-6}$cycloalkenyl-X$^1$—, CH$_2$=CH—X$^1$—, C$_{3-6}$cycloalkyl-C$_{2-4}$alkenyl-X—, C$_{3-6}$cycloalkyl-C$_{2-4}$alkynyl-X$^1$—, heterocyclyl-X$^1$—, heterocyclyl-C$_{1-4}$alkyl-X— or R$^8$; or two adjacent R$^9$ members together with the atoms to which they are attached form a 5- or 6-membered fused ring having 0-2 heteroatoms as ring members selected from O, N or S. In some instances, R$^1$ is H or a lone pair of electron. In one instance, R$^1$ is H. In other instance, Y$^1$ is N and R$^1$ is a lone pair of electron. The other variables Y$^1$, Y$^2$, Y$^3$, R$^3$, R$^4$ and L$^2$ of formula (V') are as defined in any of the embodiments as described herein.

In some embodiments of compounds of compounds of formula (V) or (V'), R$^6$ is aryl or heteroaryl, each of which is optionally substituted with from (i) 1-3 R$^9$ substituents; or (ii) 1-3 R$^c$ substituents; or (iii) 1-3 R$^d$ substituents; or (iv) 1-3 R$^{15}$ substituents; or (v) 1-3 R$^{16}$ substituents; or (vi) 1-3 R$^{17}$ substituents; or (vii) 1-3 R$^{18}$ substituents, wherein each of R$^9$, R$^c$, R$^d$, R$^{15}$, R$^{16}$, R$^{17}$ or R$^{18}$ substituent is further optionally substituted with from 1-3 R$^{19}$ substituents independently selected from —CN, F, Cl, I, —OCH$_3$, C$_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH— or CH$_3$SO$_2$. In certain instances, R$^6$ is phenyl, 1-naphthyl or 2-naphthyl, each of which is optionally substituted with from (i) 1-3 R$^9$ substituents; or (ii) 1-3 R$^c$ substituents; or (iii) 1-3 R$^d$ substituents; or (iv) 1-3 R$^{15}$ substituents; or (v) 1-3 R$^{16}$ substituents; or (vi) 1-3 R$^{17}$ substituents; or (vii) 1-3 R$^{18}$ substituents, wherein each of R$^9$, R$^c$, R$^d$, R$^{15}$, R$^{16}$, R$^{17}$ or R$^{18}$ substituent is further optionally substituted with from 1-3 R$^{19}$ substituents independently selected from —CN, F, Cl, I, —OCH$_3$, C$_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH— or CH$_3$SO$_2$. In some instances, R$^6$ is a heteroaryl having from 1-3 heteroatoms as ring members selected from O, N or S. In other instances, R$^6$ is a heteroaryl having from 1-2 heteroatoms as ring members selected from N. The other variables Y$^1$, Y$^2$, Y$^3$, R$^1$, R$^3$, R$^4$, R$^5$ and L$^2$ of formula (V) are as defined in any of the embodiments as described herein.

In some embodiments of compounds of formula (V) or (V'), R$^6$ is phenyl, which is optionally substituted with from (i) 1-3 R$^9$ substituents; or (ii) 1-3 R$^c$ substituents; or (iii) 1-3 R$^d$ substituents; or (iv) 1-3 R$^{15}$ substituents; or (v) 1-3 R$^{16}$ substituents; or (vi) 1-3 R$^{17}$ substituents; or (vii) 1-3 R$^{18}$ substituents; or (viii) 1-3 R$^{19}$ substituents, wherein each of R$^9$, R$^c$, R$^d$, R$^{15}$, R$^{16}$, R$^{17}$ or R$^{18}$ substituent is further optionally substituted with from 1-3 R$^{19}$ substituents independently selected from —CN, F, Cl, I, —OCH$_3$, C$_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH— or CH$_3$SO$_2$. The other variables Y$^1$, Y$^2$, Y$^3$, R$^1$, R$^3$, R$^4$, R$^5$ and L$^2$ of formula (V) are as defined in any of the embodiments as described herein.

In some embodiments of compounds of formula (V) or (V'), R$^6$ is 2-pyridyl, 3-pyridyl, 4-pyridyl, 2-pyrimidinyl, 4-pyrimidinyl, 5-pyrimidinyl, 2-pyrazinyl, 3-pyridazinyl or 4-pyridazinyl, each of which is optionally substituted with from (i) 1-3 R$^9$ substituents; or (ii) 1-3 R$^c$ substituents; or (iii) 1-3 R$^d$ substituents; or (iv) 1-3 R$^{15}$ substituents; or (v) 1-3 R$^{16}$ substituents; or (vi) 1-3 R$^{17}$ substituents; or (vii) 1-3 R$^{18}$ substituents; or (viii) 1-3 R$^{19}$ substituents, wherein each of R$^9$, R$^c$, R$^d$, R$^{15}$, R$^{16}$, R$^{17}$ or R$^{18}$ substituent is further optionally substituted with from 1-3 R$^{19}$ substituents independently selected from —CN, F, Cl, I, —OCH$_3$, C$_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH— or CH$_3$SO$_2$. The other variables Y$^1$, Y$^2$, Y$^3$, R$^1$, R$^3$, R$^4$, R$^5$ and L$^2$ of formula (V) or (V') are as defined in any of the embodiments as described herein.

In some embodiments of compounds of formulas (I), (II), (III), (IV), (V) or (V') and any of the subformulas thereof, R$^3$ and R$^4$ are each independently selected from H, halogen, C$_{1-4}$ alkyl, C$_{1-4}$haloalkyl, C$_{1-4}$haloalkoxy, cyclopropyl, phenyl, CN, CN—CH$_2$—, C$_{1-4}$alkoxy, R$^g$ or a lone pair of electrons; or R$^3$ and R$^4$ are taken together with the atoms to which they are attached form an optionally substituted 5 to 8-membered ring having from 0-2 heteroatoms as ring members selected from O, N or S; wherein R$^g$ is —OH, —NH$_2$, —NO$_2$, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OR$^h$, —SR$^h$, —OC(O)R$^h$, —OC(S)R$^h$, —C(O)R$^h$, —C(S)R$^h$, —C(O)OR$^h$, —C(S)OR$^h$, —S(O)R$^h$, —S(O)$_2$R$^h$, —C(O)NHR$^h$, —C(S)NHR$^h$, —C(O)NR$^h$R$^h$, —C(S)NR$^h$R$^h$, —S(O)$_2$NHR$^h$, —S(O)$_2$NR$^h$R$^h$, —C(NH)NHR$^h$, —C(NH)NR$^h$R$^h$, —NHC(O)R$^h$, —NHC(S)R$^h$, —NR$^h$C(O)R$^h$, —NR$^h$C(S)R$^h$, —NHS(O)$_2$R$^h$, —NR$^h$S(O)$_2$R$^h$, —NHC(O)NH R$^h$, —NHC(S)NHR$^h$, —NR$^h$C(O)NH$_2$, —NR$^h$C(S)NH$_2$, —NR$^h$C(O)NHR$^h$, —NR$^h$C(S)NHR$^h$, —NHC(O)NR$^h$R$^h$, —NHC(S)NR$^h$R$^h$, —NR$^h$C(O)NR$^h$R$^h$, —NR$^h$C(S)NR$^h$R$^h$, —NHS(O)$_2$NHR$^h$, —NR$^h$S(O)$_2$NH$_2$, —NR$^h$S(O)$_2$N HR$^h$, —NHS(O)$_2$NR$^h$R$^h$, —NR$^h$S(O)$_2$NR$^h$R$^h$, —NHR$^h$ or —NR$^h$R$^h$, wherein each R$^h$ is independently H or C$_{1-2}$alkyl. In certain embodiments, R$^3$ and R$^4$ are not simultaneously hydrogen. In some instances, R$^3$ and R$^4$ are each independently selected from H, C$_{1-6}$alkyl, halogen, CN, cyclopropyl, CN—CH$_2$—, phenyl, cyclopropylmethyl, C$_{1-6}$alkoxy, C$_{1-6}$haloalkyl, C$_{1-6}$haloalkoxy or R$^g$. In some embodiments, R$^3$ and R$^4$ are each independently halogen, C$_{1-6}$alkyl, C$_{1-6}$alkoxy, cyclopropyl, —CN, C$_{1-4}$haloalkyl or C$_{1-4}$haloalkoxy. In other embodiments, R$^3$ and R$^4$ are each independently selected from Br, Cl, methyl, ethyl, cyclopropyl, —CN, CF$_3$, CHF$_2$, CH$_2$F, —OCH$_3$, —OCF$_3$, —OCHF$_2$ or —OCH$_2$F, CNCH$_2$—, NH$_2$C(O)—, CH$_3$NHCO— or CH$_3$C(O)NH—. In other instances, R$^3$ and R$^4$ are each independently selected from H, —CH$_3$, —CD$_3$, —C$_6$D5, —CF$_3$, —CHF$_2$, —CH$_2$F, —OCF$_3$, —OCHF$_2$, —OCH$_2$F halogen, CN, cyclopropyl, CN—CH$_2$—, phenyl, cyclopropylmethyl or —OCH$_3$. In yet other instances, R$^3$ and R$^4$ are each independently H, F, Cl, Br, NH$_2$C(O)—, CH$_3$, CD$_3$, Et, cyclopropyl, CN, CH$_2$CH$_2$— or CH$_3$C(O)NH—. In other instances, R$^3$ and R$^4$ are each independently selected from H, —OH, —NH$_2$, —NO$_2$, —C(O)OH, —C(S)OH, —C(O)NH$_2$, —C(S)NH$_2$, —S(O)$_2$NH$_2$, —NHC(O)NH$_2$, —NHC(S)NH$_2$, —NHS(O)$_2$NH$_2$, —C(NH)NH$_2$, —OC(O)R$^h$, —C(O)R$^h$, —C(O)OR$^h$, —S(O)R$^h$, —S(O)$_2$R$^h$, —C(O)NHR$^h$, —C(O)NR$^h$R$^h$, —C(S)NR$^h$R$^h$, —S(O)$_2$NHR$^h$, —S(O)$_2$NR$^h$R$^h$, —C(NH)NHR$^h$, —C(NH)NR$^h$R$^h$, —NHC(O)R$^h$, —NHC(S)R$^h$, —NR$^h$C(O)R$^h$, —NHC(O)NHR$^h$, —NHC(S)NHR$^h$, —NR$^h$C(O)NH$_2$, —NR$^h$C(O)NHR$^h$, —NHC(O)NR$^h$R$^h$, —NR$^h$C(O)NR$^h$R$^h$, —NHS(O)$_2$NHR$^h$, —NR$^h$S(O)$_2$NH$_2$, —NR$^h$S(O)$_2$NHR$^h$, —NHS(O)$_2$NR$^h$R$^h$, —NR$^h$S(O)$_2$ NR$^h$R$^h$, —NHR$^h$ or —NR$^h$R$^h$, wherein R$^h$ is H or C$_{1-6}$alkyl. In some embodiments, R$^3$ and R$^4$ are H. In other embodiments, R$^3$ is H and R$^4$ is a substituent other than hydrogen as described herein. In yet other embodiments, R$^4$ is H and R$^3$ is a substituent other than hydrogen as described herein. In other embodiments, both R$^3$ and R$^4$ are a substituent other than hydrogen as described herein. The other variables and substituents are as defined in any of the embodiments as described herein.

In some embodiments of compounds of Formulas (I'), (I'a), (I), (II), (III), (IV), (V) or (V'), or any of the subgeneric formulas thereof, Y$^1$ is C, Y$^2$ is CR$^{10}$ and Y$^3$ are CH. In other embodiments, Y$^1$ is C and Y$^2$ and Y$^3$ are N. In yet other embodiments, Y$^1$ is C, Y$^2$ is N and Y$^3$ is CH. In still other embodiments, Y$^1$ is C, Y$^2$ is CR$^{10}$ and Y$^3$ is N. In other embodiments, Y$^1$ is N, Y$^2$ is N and Y$^3$ is N. In other embodiments, Y$^1$ is N, Y$^2$ is CR$^{10}$ and Y$^3$. In other embodiments, Y$^1$ is N, Y$^2$ is CR$^{10}$ and Y$^3$ is N. In other embodiments, Y$^1$ is N, Y$^2$ is CR$^{10}$ and Y$^3$ is CH. In other embodiments, Y$^1$ is N, Y$^2$ is N and Y$^3$ is CH. In certain instances, R$^{10}$ is H, CN, C$_{1-4}$alkyl, halogen, C$_{1-4}$haloalkyl, C$_{1-4}$haloalkoxy, C$_{1-4}$alkoxy. In one embodiment, R$^{10}$ is H. All the other variables R$^1$, R$^2$, Z$^1$, Z$^2$, Z$^3$, Z$^4$, R$^3$, R$^4$, R$^5$, L$^1$ or L$^2$ are as defined in any of the embodiments as described herein.

In certain embodiments of compounds of Formula (I'), (I'a), (I), (II), (III), (IV), (V) or (V') or any of the subformulas thereof, Y$^1$ is C, Y$^3$ is CH and Y$^2$ is H, C$_{1-6}$alkyl, C$_{1-6}$alkoxy, vinyl, ethynyl, phenyl-C$_{1-4}$alkyl-, heteroaryl-C$_{1-4}$alkyl-, C$_{3-6}$cycloalkyl-C$_{1-4}$alkyl-, C$_{3-6}$cycloalkenyl-C$_{1-4}$akyl-, CH$_2$=CH—X$^2$—, C$_{3-6}$cycloalkyl-C$_{2-4}$alkenyl-X$^2$—, C$_{3-6}$cycloalkyl-C$_{2-4}$alkynyl-X$^2$—, heterocyclyl-C$_{1-4}$alkyl- or R$^8$, each of which is optionally substituted with from 1-5 R$^9$ groups or 1-5 R$^c$ groups or 1-5 R$^d$groups or 1-5 R$^e$ groups. All the other variables R$^1$, R$^2$, Z$^1$, Z$^2$, Z$^3$, Z$^4$, R$^3$, R$^4$, R$^5$, L$^1$ or L$^2$ are as defined in any of the embodiments as described herein.

In certain embodiments of compounds of formulas (IV), (V), (V') or any subgeneric formulas thereof, or any embodiments of compounds of formulas (IV), (V), (V') as described herein, or any of the compounds as described in the Examples, the moiety

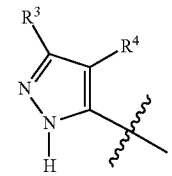

can exist in a tautomeric form:

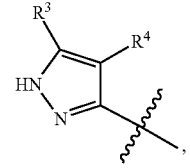

where the wavy line indicates the point of attachment to the rest of the molecule.

Subformulae of Formulas (I'), (I'a), (I), (II), (III), (IV), (V) or (V')

In one group of embodiments of the disclosure, compounds of formulas (I'), (I), (II) or (III) have subformulas (IIIa), (IIIb), (IIIc), (IIId) or (IIIe):

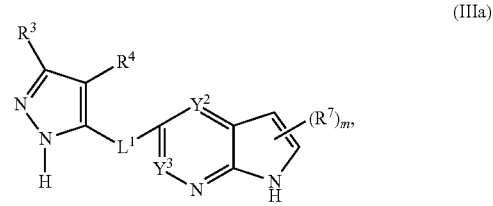

(IIIa)

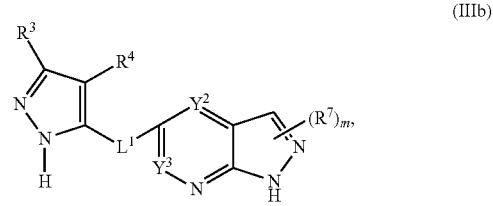

(IIIb)

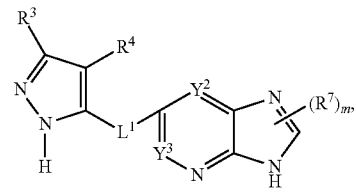

(IIIc)

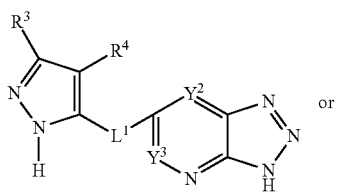
(IIId)

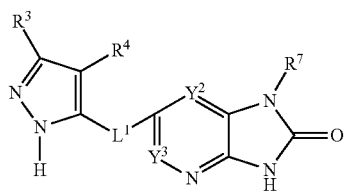
(IIIe)

The variables and substituents $R^3$, $R^4$, $R^7$, $L^1$, $Y^2$ and $Y^3$ in subformulas (IIIa), (IIIb), (IIIc), (IIId) or (IIIe) are as defined in any of the embodiments of compounds of formulas (I'), (I'a), (I), (II) or (III) and in any of the embodiments as disclosed herein. In some embodiments, $R^7$ is as defined in any of the embodiments of compounds of formula (IV) as described herein. In some embodiments, $L^1$ is as defined in the embodiments of compounds of formulas (I'), (I'a), (I) or (II) as disclosed herein. In some embodiments, $R^5$ is H. In certain instances, $L^1$ is —NHSO$_2$—, —SO$_2$NH—, —NHC(O)NH—, —NHC(O)—, —CH$_2$O—, —OCH$_2$—, —C(O)NH—, —SO$_2$—, —C(O)O—, —C(O)—, —C(=NH)NH— or —NHC(=NH)—. In some instances, $L^1$ is —SO$_2$NH—, —CH$_2$O—, —OCH$_2$— or —C(O)NH—. In other instances $L^1$ is —C(O)NH—. In one embodiment, the disclosure provides compounds of formula (IIIa). In another embodiment, the disclosure provides compounds of formula (IIIb). In another embodiment, the disclosure provides compounds of formula (IIIc). In another embodiment, the disclosure provides compounds of formula (IIId). In another embodiment, the disclosure provides compounds of formula (IIIe). In some embodiments of compounds of formulas (IIIa), (IIIb), (IIIc), (IIId) or (IIIe), $Y^2$ and $Y^3$ are CH. In other embodiments of compounds of formulas (IIIa), (IIIb), (IIIc), (IIId) or (IIIe), $Y^2$ is N and $Y^3$ is CH. In other embodiments of compounds of formulas (IIIa), (IIIb), (IIIc), (IIId) or (IIIe), $Y^2$ is $CR^{10}$ wherein $R^{10}$ is a substituent other than hydrogen as described herein for compounds of formulas (I'), (I'a), (I), (II), (III), (IV) (V) or (V') and $Y^3$ is CH.

In a second group of embodiments of the disclosure, compounds of formulas (I'), (I), (II), (III) or (IIIa) have subformulas (IIIa-1), (IIIa-2), (IIIa-3), (IIIa-4), (IIIa-5), (IIIa-6), (IIIa-7) or (IIIa-8):

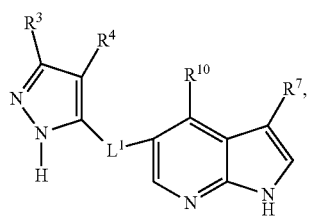
(IIIa-1)

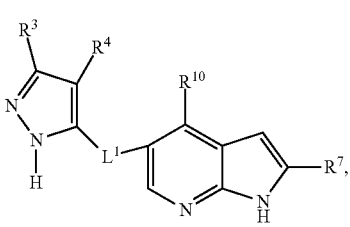
(IIIa-2)

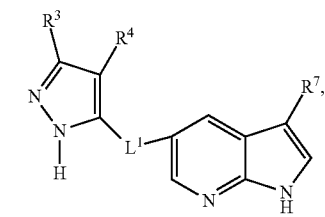
(IIIa-3)

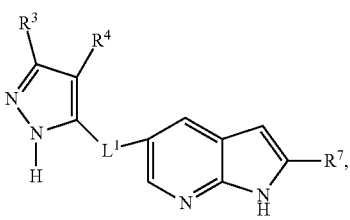
(IIIa-4)

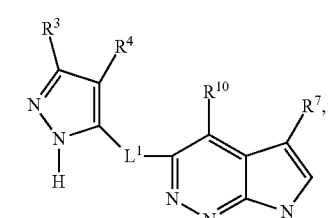
(IIIa-5)

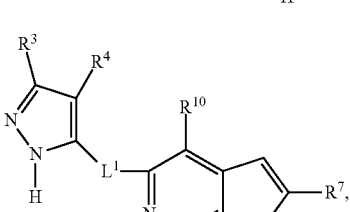
(IIIa-6)

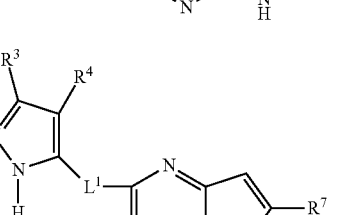
(IIIa-7)

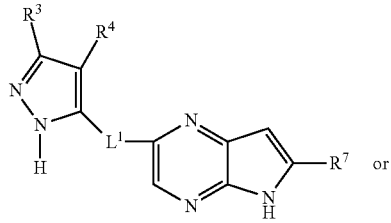
or

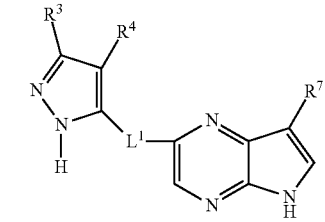
(IIIa-8)

The variables $R^3$, $R^4$, $L^1$, $R^{10}$ and $R^7$ are as defined in any of the embodiments of compounds of formulas (I'), (I'a), (I), (II), (III) or (IIIa). In some embodiments, $R^7$ is as defined in any of the embodiments of compounds of formula (IV) described herein. In some embodiments, $R^{10}$ is selected from $C_{1-6}$alkyl, $C_{1-6}$alkoxy, $C_{2-6}$alkenyl, $C_{2-6}$alkynyl, aryl-$C_{1-4}$alkyl-, heteroaryl-$C_{1-4}$ alkyl-, $C_{3-6}$cycloalkyl-$C_{1-4}$alkyl-, $C_{3-6}$cycloalkenyl-$C_{1-4}$alkyl-, $CH_2$=CH—$X^2$—, $C_{3-6}$cycloalkyl-$C_{2-4}$alkenyl-$X^2$—, $C_{3-6}$cycloalkyl-$C_{2-4}$alkynyl-$X^2$—, heterocyclyl-$C_{1-4}$alkyl- or $R^8$, each of which is optionally substituted with from 1-5 $R^9$ groups; wherein $X^2$ is $C_{1-4}$alkylene, —O—, —S— or —NH—. In other embodiments, $R^{10}$ is CN, $C_{1-4}$alkyl, halogen, $C_{1-4}$haloalkyl, $C_{1-4}$haloalkoxy or $C_{1-4}$alkoxy. In some embodiments of compounds of formulas (IIIa-1) to (IIIa-8), $L^1$ is —C(O)NH—, —SO$_2$NH—, —NHSO$_2$—, —CH$_2$O— or —OCH$_2$—. In certain embodiments of compounds of formulas (IIIa-1) to (IIIa-8), $L^1$ is —C(O)NH—. In one embodiment, the disclosure provides a compound of formula (IIIa-1). In another embodiment, the disclosure provides a compound of formula (IIIa-2). In another embodiment, the disclosure provides a compound of formula (IIIa-3). In another embodiment, the disclosure provides a compound of formula (IIIa-4). In another embodiment, the disclosure provides a compound of formula (IIIa-5). In another embodiment, the disclosure provides a compound of formula (IIIa-6). In another embodiment, the disclosure provides a compound of formula (IIIa-7). In another embodiment, the disclosure provides a compound of formula (IIIa-8).

In a third group of embodiments, of the disclosure, compounds of formulas (I'), (I), (II), (III) or (IIIb) have subformulas (IIIb-1), (IIIb-2), (IIIb-3), (IIIb-4) or (IIIb-5):

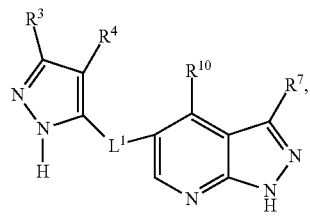
(IIIb-1)

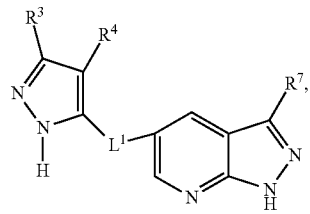
(IIIb-2)

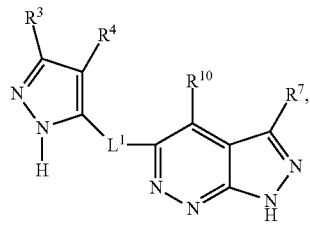
(IIIb-3)

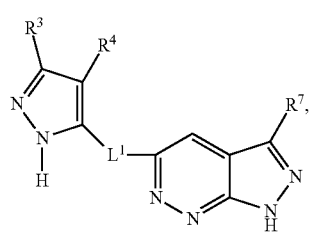
(IIIb-4)

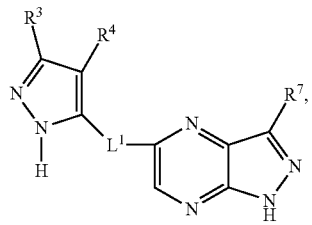
(IIIb-5)

The variables $R^3$, $R^4$, $R^{10}$, $L^1$ and $R^7$ are as defined in any of the embodiments of compounds of formulas (I'), (I'a), (I), (II), (III) or (IIIb). In some embodiments, $R^7$ is as defined in any of the embodiments of compounds of formula (IV) described herein. In some embodiments, $R^1$ is selected from $C_{1-6}$alkyl, $C_{1-6}$alkoxy, $C_{2-6}$alkenyl, $C_{2-6}$alkynyl, aryl-$C_{1-4}$alkyl-, heteroaryl-$C_{1-4}$ alkyl-, $C_{3-6}$cycloalkyl-$C_{1-4}$alkyl-, $C_{3-6}$cycloalkenyl-$C_{1-14}$alkyl-, $CH_2$=CH—$X^2$—, $C_{3-6}$cycloalkyl-$C_{2-4}$alkenyl-$X^2$—, $C_{3-6}$cycloalkyl-$C_{2-4}$alkynyl-$X^2$—, heterocyclyl-$C_{1-4}$alkyl- or $R^8$, each of which is optionally substituted with from 1-5 $R^9$ groups; wherein $X^2$ is $C_{1-4}$alkylene, —O—, —S— or —NH—. In other embodiments, $R^{10}$ is CN, $C_{1-4}$alkyl, halogen, $C_{1-4}$haloalkyl, $C_{1-4}$haloalkoxy or $C_{1-4}$alkoxy. In some embodiments of compounds of formulas (IIIb-1) to (IIIb-5), $L^1$ is —C(O)NH—, —SO$_2$NH—, —NHSO$_2$—, —CH$_2$O— or —OCH$_2$—. In certain embodiments of compounds of formulas (IIIb-1) to (IIIb-5), $L^1$ is —C(O)NH—. In one embodiment, the disclosure provides a compound of formula (IIIb-1). In another embodiment, the disclosure provides a compound of formula (IIIb-2). In another embodiment, the disclosure provides a compound of formula (IIIb-3). In another embodiment, the disclosure provides a compound of formula (IIIb-4). In another embodiment, the disclosure provides a compound of formula (IIIb-5).

In a 4th group of embodiments of the disclosure, compounds of formulas (I'), (I), (II), (III) or (IIIc) have subformulas (IIIc-1), (IIIc-2), (IIIc-3), (IIIc-4) or (IIIc-5):

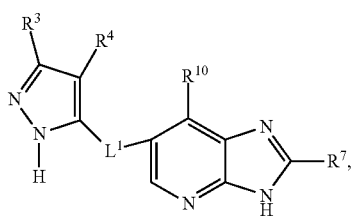
(IIIc-1)

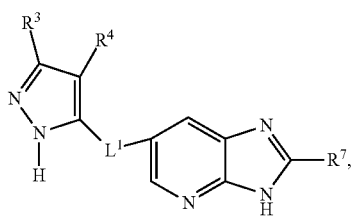
(IIIc-2)

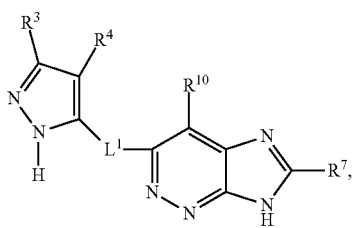
(IIIc-3)

-continued

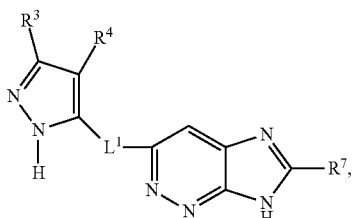
(IIIc-4)

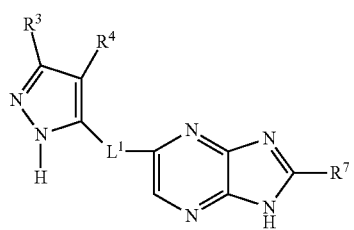
(IIIc-5)

The variables $R^3$, $R^4$, $R^{10}$, $L^1$ and $R^7$ are as defined in any of the embodiments of compounds of formulas (I'), (I'a), (I), (II), (III) or (IIIc). In some embodiments, $R^7$ is as defined in any of the embodiments of compounds of formula (IV) described herein. In some embodiments, $R^{10}$ is selected from $C_{1-6}$alkyl, $C_{1-6}$alkoxy, $C_{2-6}$alkenyl, $C_{2-6}$alkynyl, aryl-$C_{1-4}$ alkyl-, heteroaryl-$C_{1-4}$ alkyl-, $C_{3-6}$cycloalkyl-$C_{1-4}$alkyl-, $C_{3-6}$cycloalkenyl-$C_{1-4}$alkyl-, CH$_2$=CH—X$^2$—, $C_{3-6}$cycloalkyl-$C_{2-4}$alkenyl-X$^2$—, $C_{3-6}$cycloalkyl-$C_{2-4}$alkynyl-X$^2$—, heterocyclyl-$C_{1-4}$alkyl- or $R^8$, each of which is optionally substituted with from 1-5 $R^9$ groups; wherein $X^2$ is $C_{1-4}$alkylene, —O—, —S— or —NH—. In other embodiments, $R^{10}$ is CN, $C_{1-4}$alkyl, halogen, $C_{1-4}$haloalkyl, $C_{1-4}$haloalkoxy or $C_{1-4}$alkoxy. In some embodiments of compounds of formulas (IIIc-1) to (IIIc-5), $L^1$ is —C(O)NH—, —SO$_2$NH—, —NHSO$_2$—, —CH$_2$O— or —OCH$_2$—. In certain embodiments of compounds of formulas (IIIc-1) to (IIIc-5), $L^1$ is —C(O)NH—. In one embodiment, the disclosure provides a compound of formula (IIIc-1). In another embodiment, the disclosure provides a compound of formula (IIIc-2). In another embodiment, the disclosure provides a compound of formula (IIIc-3). In another embodiment, the disclosure provides a compound of formula (IIIc-4). In another embodiment, the disclosure provides a compound of formula (IIIc-5).

In a 5th group of embodiments of the disclosure, compounds of formulas (I'), (I), (II), (III) or (IIId) have subformulas (IIId-1), (IIId-2), (IIId-3), (IIId-4) or (IIId-5):

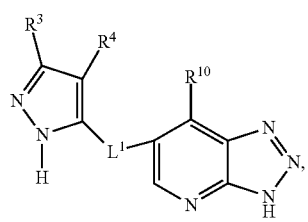
(IIId-1)

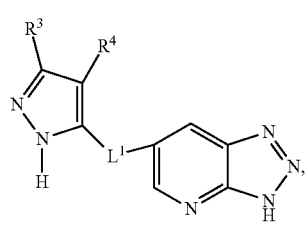
(IIId-2)

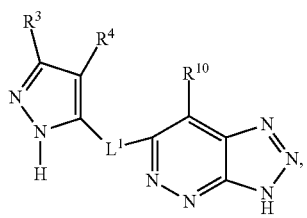
(IIId-3)

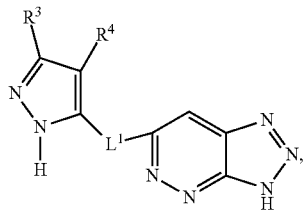
(IIId-4)

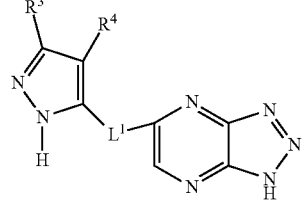
(IIId-5)

The variables $R^3$, $R^4$, $R^{10}$ and $L^1$ are as defined in any of the embodiments of compounds of formulas (I'), (I'a), (I), (II), (III) or (IIId). In some embodiments, $R^{10}$ is selected from $C_{1-6}$alkyl, $C_{1-6}$alkoxy, $C_{2-6}$alkenyl, $C_{2-6}$alkynyl, aryl-$C_{1-4}$alkyl-, heteroaryl-$C_{1-4}$ alkyl-, $C_{3-6}$cycloalkyl-$C_{1-4}$alkyl-, $C_{3-6}$cycloalkenyl-$C_{1-4}$alkyl-, CH$_2$=CH—X$^2$—, $C_{3-6}$cycloalkyl-$C_{2-4}$alkenyl-X$^2$—, $C_{3-6}$cycloalkyl-$C_{2-4}$alkynyl-X$^2$—, heterocyclyl-$C_{1-4}$alkyl- or $R^8$, each of which is optionally substituted with from 1-5 $R^9$ groups; wherein $X^2$ is $C_{1-4}$alkylene, —O—, —S— or —NH—. In other embodiments, $R^{10}$ is CN, $C_{1-4}$alkyl, halogen, $C_{1-4}$haloalkyl, $C_{1-4}$haloalkoxy or $C_{1-4}$alkoxy. In some embodiments of compounds of formulas (IIId-1) to (IIId-5), $L^1$ is —C(O)NH—, —SO$_2$NH—, —NHSO$_2$—, —CH$_2$O— or —OCH$_2$—. In certain embodiments of compounds of formulas (IIId-1) to (IIId-5), $L^1$ is —C(O)NH—. In one embodiment, the disclosure provides a compound of formula (IIId-1). In another embodiment, the disclosure provides a compound of formula (IIId-2). In another embodiment, the disclosure provides a compound of formula (IIId-3). In another embodiment, the disclosure provides a compound of formula (IIId-4). In another embodiment, the disclosure provides a compound of formula (IIId-5).

In a 6th group of embodiments of the disclosure, compounds of formulas (I'), (I), (II), (III) or (IIIe) have subformulas (IIIe-1), (IIIe-2), (IIIe-3), (IIIe-4) or (IIIe-5):

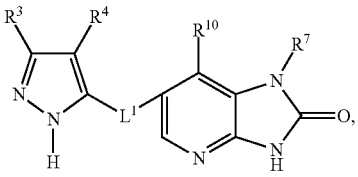
(IIIe-1)

-continued

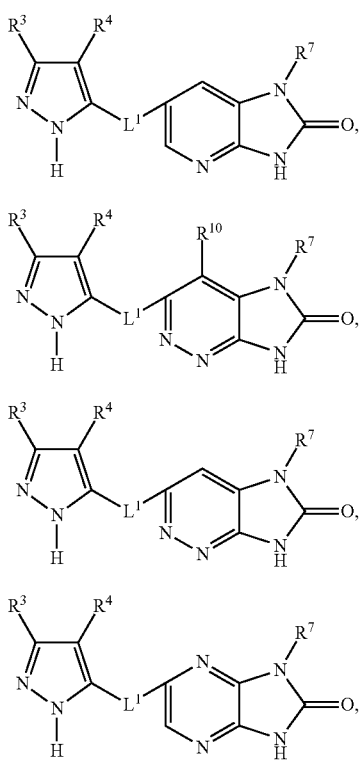

(IIIe-2)

(IIIe-3)

(IIIe-4)

(IIIe-5)

The variables $R^3$, $R^4$, $R^{10}$, $R^7$ and $L^1$ are as defined in any of the embodiments of compounds of formulas (I'), (I'a), (I), (II), (III) or (IIIe). In some embodiments, $R^7$ is as defined in any of the embodiments of compounds of formula (IV) described herein. In some embodiments, $R^{10}$ is selected from $C_{1-6}$alkyl, $C_{1-6}$alkoxy, $C_{2-6}$alkenyl, $C_{2-6}$alkynyl, aryl-$C_{1-4}$alkyl-, heteroaryl-$C_{1-4}$ alkyl-, $C_{3-6}$cycloalkyl-$C_{1-4}$alkyl-, $C_{3-6}$cycloalkenyl-$C_{1-4}$alkyl-, $CH_2$=CH—$X^2$—, $C_{3-6}$cycloalkyl-$C_{2-4}$alkenyl-$X^2$—, $C_{3-6}$cycloalkyl-$C_{2-4}$alkynyl-$X^2$—, heterocyclyl-$C_{1-4}$alkyl- or $R^8$, each of which is optionally substituted with from 1-5 $R^9$ groups; wherein $X^2$ is $C_{1-4}$alkylene, —O—, —S— or —NH—. In other embodiments, $R^{10}$ is CN, $C_{1-4}$alkyl, halogen, $C_{1-4}$haloalkyl, $C_{1-4}$haloalkoxy or $C_{1-4}$alkoxy. In some embodiments of compounds of formulas (IIIe-1) to (IIIe-5), $L^1$ is —C(O)NH—, —SO$_2$NH—, —NHSO$_2$—, —CH$_2$O— or —OCH$_2$—. In certain embodiments of compounds of formulas (IIIe-1) to (IIIe-5), $L^1$ is —C(O)NH—. In one embodiment, the disclosure provides a compound of formula (IIIe-1). In another embodiment, the disclosure provides a compound of formula (IIIe-2). In another embodiment, the disclosure provides a compound of formula (IIIe-3). In another embodiment, the disclosure provides a compound of formula (IIIe-4). In another embodiment, the disclosure provides a compound of formula (IIIe-5).

In a 7th group of embodiments of the disclosure, compounds of formulas (I'), (I'a), (I), (II), (III), (IIIa), (IV) have subformula (IVa):

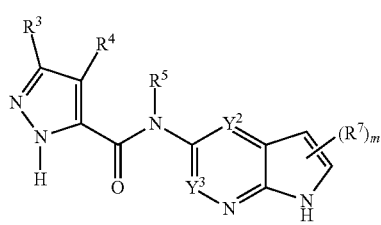

(IVa)

The variables $R^3$, $R^4$, $R^5$, $R^7$, m, $Y^2$ and $Y^3$ are as defined in any of the embodiments of compounds of formulas (I'), (I'a), (I), (II), (III), (IIIa) or (IV) or in any of the embodiments as disclosed herein. In one embodiment, $R^5$ is H or $C_{1-4}$alkyl. In another embodiment, $R^5$ is H. In some embodiments, $Y^2$ is N or $CR^{10}$ and $Y^3$ is N or CH, wherein $R^{10}$ is H, $C_{1-6}$alkyl, $C_{1-6}$alkoxy, $C_{2-6}$alkenyl, $C_{2-6}$alkynyl, aryl-$C_{1-4}$alkyl-, heteroaryl-$C_{1-4}$ alkyl-, $C_{3-6}$cycloalkyl-$C_{1-4}$alkyl-, $C_{3-6}$cycloalkenyl-$C_{1-4}$alkyl-, $CH_2$=CH—$X^2$—, $C_{3-6}$cycloalkyl-$C_{2-4}$alkenyl-$X^2$—, $C_{3-6}$cycloalkyl-$C_{2-4}$alkynyl-$X^2$—, heterocyclyl-$C_{1-4}$alkyl- or $R^8$, each of which is optionally substituted with from; (i) 1-5 $R^9$ groups; or (ii) 1-5 $R^c$ substituents; or (iii) 1-5 $R^d$substituents; or (iv) 1-5 $R^{15}$ substituents; or (v) 1-5 $R^{16}$ substituents; or (vi) 1-5 $R^7$ substituents; or (vii) 1-5 $R^{18}$ substituents; or (viii) 1-5 $R^{19}$ substituents, wherein each of $R^9$, $R^c$, $R^d$, $R^{15}$, $R^{16}$, $R^7$ or $R^1$ substituent is further optionally substituted with from 1-3 $R^{19}$ substituents independently selected from —CN, F, Cl, I, —OCH$_3$, $C_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH— or CH$_3$SO$_2$, wherein $X^2$ is $C_{1-4}$alkylene, —O—, —S— or —NH—. In some embodiments of compounds of formula (IVa), $Y^2$ and $Y^3$ are CH. In other embodiments, $Y^2$ is N and $Y^3$ is CH. In other embodiments, $Y^2$ is $CR^{10}$, wherein $R^{10}$ is a substituent other than hydrogen as described herein and $Y^3$ is CH. In certain embodiments of compounds of formula (IVa), the subscript m is 0. In other embodiments of compounds of formula (IVa), the subscript m is 1. In other embodiments of compounds of formula (IVa), the subscript m is 2.

In an 8th group of embodiments of the disclosure, compounds of formulas (I'), (I'a), (I), (II), (III), (IIIa), (IV) or (IVa) have subformula (IVa-1), (IVa-2), (IVa-3), (IVa-4), (IVa-5), (IVa-6), (IVa-7), (IVa-8), (IVa-9), (IVa-10):

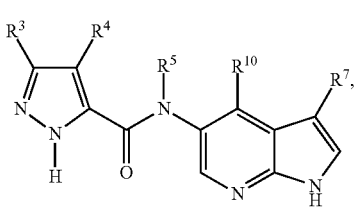

(IVa-1)

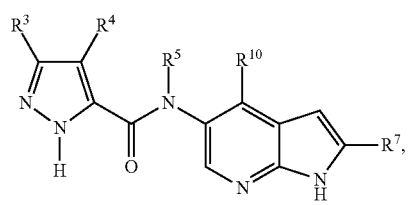

(IVa-2)

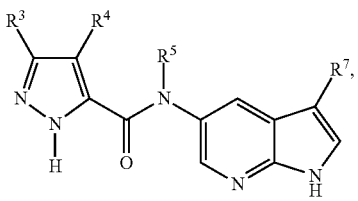

(IVa-3)

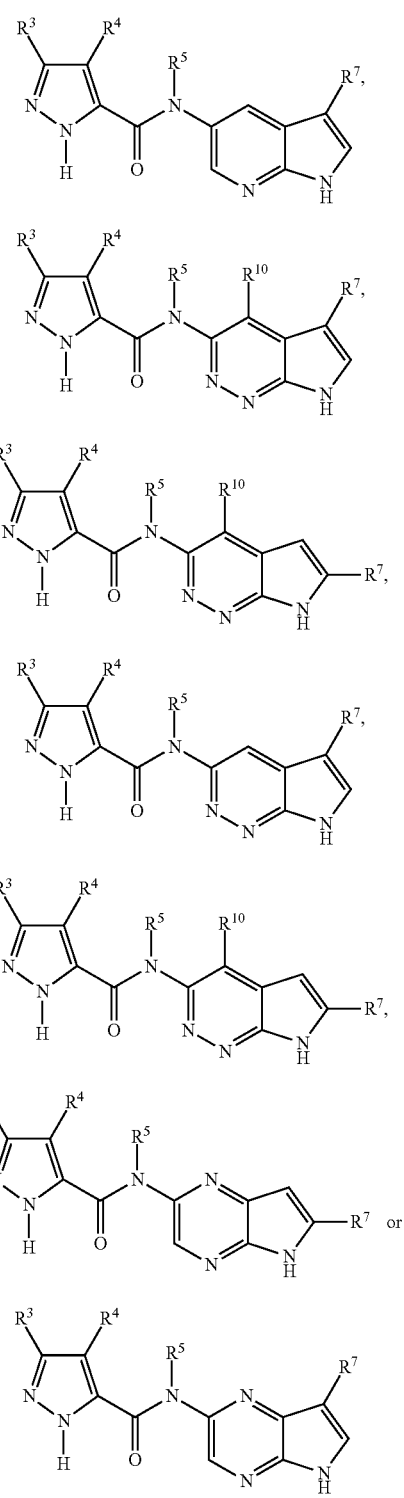

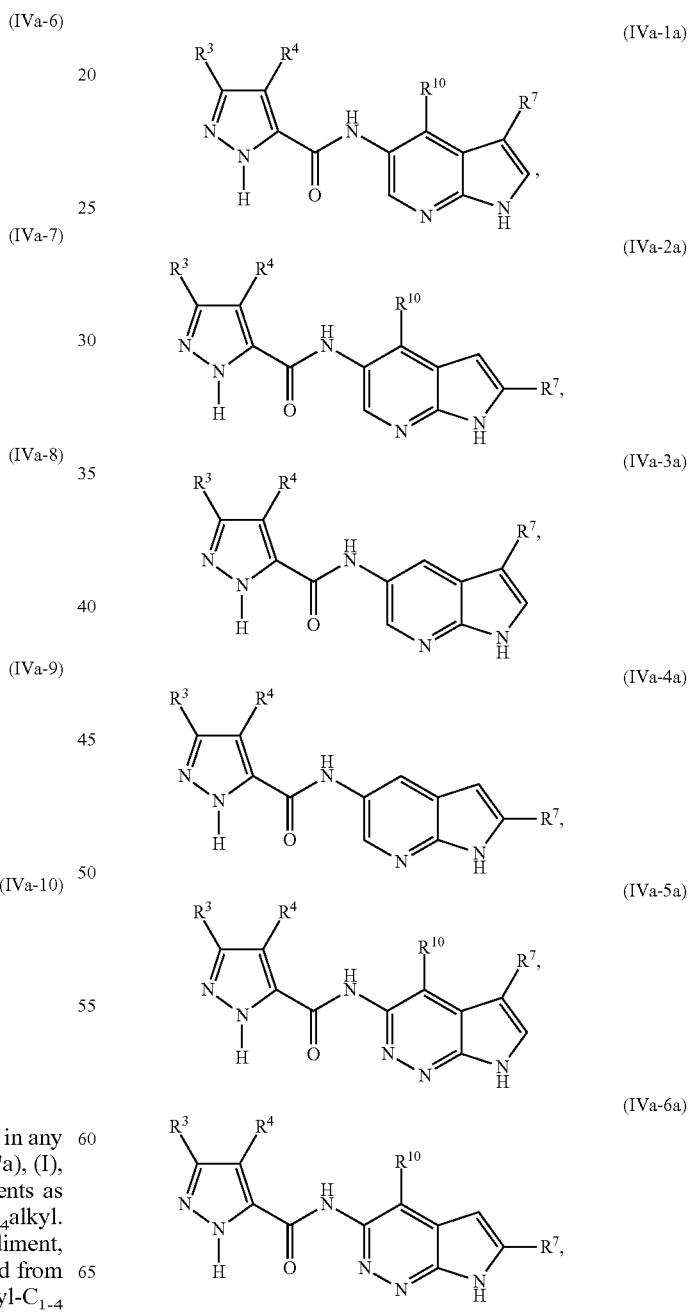

The variables $R^3$, $R^4$, $R^5$, $R^7$ and $R^{10}$ are as defined in any of the embodiments of compounds of formulas (I'), (I'a), (I), (II), (III), (IIIa) or (IV) and in any of the embodiments as disclosed herein. In one embodiment, $R^5$ is H or $C_{1-4}$alkyl. In another embodiment, $R^5$ is H. In yet another embodiment, $R^5$ is $C_{1-4}$alkyl. In some embodiments, $R^{10}$ is selected from $C_{1-6}$alkyl, $C_{1-6}$alkoxy, $C_{2-6}$alkenyl, $C_{2-6}$alkynyl, aryl-$C_{1-4}$ alkyl-, heteroaryl-$C_{1-4}$ alkyl-, $C_{3-6}$cycloalkyl-$C_{1-4}$alkyl-, $C_{3-6}$cycloalkenyl-$C_{1-4}$alkyl-, $CH_2$=CH—$X^2$—, $C_{3-6}$cycloalkyl-$C_{2-4}$alkenyl-$X^2$—, $C_{3-6}$cycloalkyl-$C_{2-4}$alkynyl-$X^2$—, heterocyclyl-$C_{1-4}$alkyl- or $R^8$, each of which is optionally substituted with from 1-5 $R^9$ groups; wherein $X^2$ is $C_{1-4}$alkylene, —O—, —S— or —NH—. In other embodiments, $R^{10}$ is CN, $C_{1-4}$alkyl, halogen, $C_{1-4}$haloalkyl, $C_{1-4}$haloalkoxy or $C_{1-4}$alkoxy. In other embodiments, $R^{10}$ is CN, $CH_3$, Et, Cl, Br, F, $CF_3$, $CF_2H$—, $CFH_2$—, $CH_3O$—, $CF_3O$—, $CF_2HO$— or $CFH_2O$—.

In a 9th group of embodiments of the disclosure, compounds of formulas (I'), (I'a), (I), (II), (III), (IIIa), (IV), (IVa), (IVa-1), (IVa-2), (IVa-3), (IVa-4), (IVa-5), (IVa-6), (IVa-7), (IVa-8), (IVa-9) or (IVa-10) have subformulas (IVa-1a), (IVa-2a), (IVa-3a), (IVa-4a), (IVa-5a), (IVa-6a), (IVa-7a), (IVa-8a), (IVa-9a) or (IVa-10a):

-continued

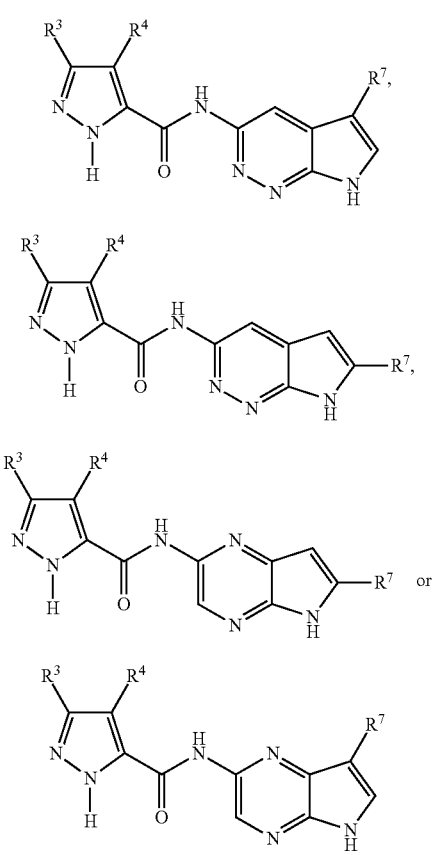

(IVa-7a)

(IVa-8a)

(IVa-9a)

(IVa-10a)

The variables $R^3$, $R^4$, $R^7$ and $R^{10}$ are as defined in any of the embodiments of compounds of formulas (I'), (I'a), (I), (II), (III), (IIIa), (IV), (IVa), (IVa-1), (IVa-2), (IVa-3), (IVa-4), (IVa-5), (IVa-6), (IVa-7), (IVa-8), (IVa-9) or (IVa-10) or in any of the embodiments as disclosed herein.

In a 10th group of embodiments of the disclosure, compounds of formulas (I'), (I'a), (I), (II), (III), (IIIa), (IV), (IVa), (IVa-1), (IVa-2), (IVa-3), (IVa-4), (IVa-5), (IVa-6), (IVa-7), (IVa-8), (IVa-9), (IVa-10), (IVa-1a), (IVa-2a), (IVa-5a) or (IVa-8a) have subformulas (IVa-1b), (IVa-2b), (IVa-5b) or (IVa-6b):

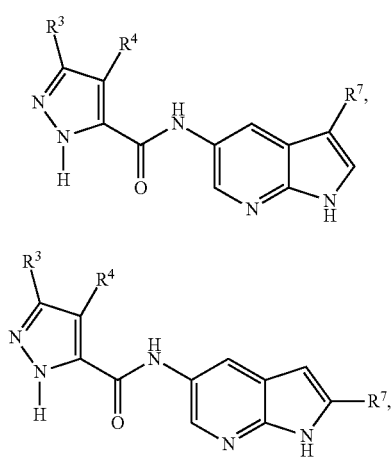

(IVa-1b)

(IVa-2b)

-continued

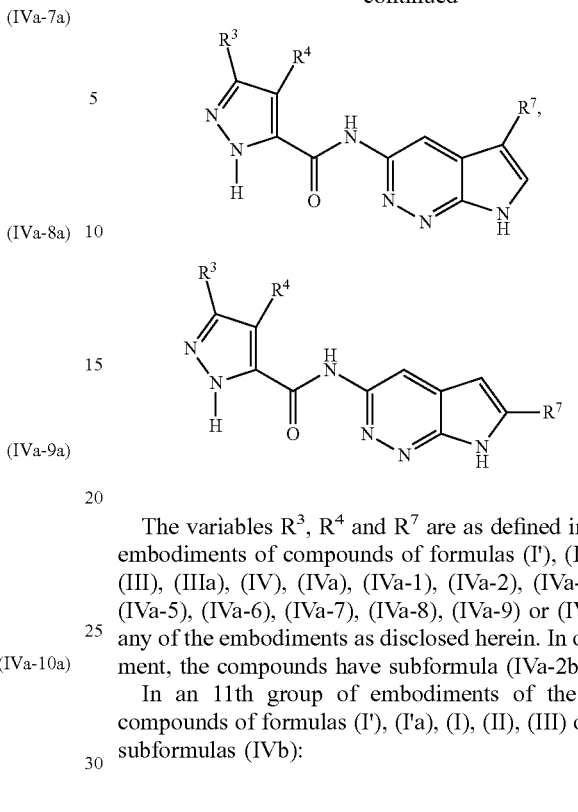

(IVa-5b)

(IVa-6b)

The variables $R^3$, $R^4$ and $R^7$ are as defined in any of the embodiments of compounds of formulas (I'), (I'a), (I), (II), (III), (IIIa), (IV), (IVa), (IVa-1), (IVa-2), (IVa-3), (IVa-4), (IVa-5), (IVa-6), (IVa-7), (IVa-8), (IVa-9) or (IVa-10) or in any of the embodiments as disclosed herein. In one embodiment, the compounds have subformula (IVa-2b).

In an 11th group of embodiments of the disclosure, compounds of formulas (I'), (I'a), (I), (II), (III) or (IV) have subformulas (IVb):

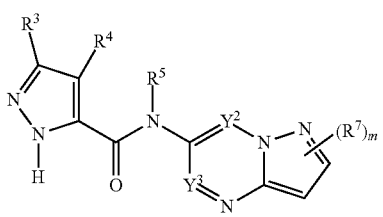

(IVb)

The variables $R^3$, $R^4$, $R^5$, $R^7$, m, $Y^2$ and $Y^3$ are as defined in any of the embodiments of compounds of formulas (I'), (I'a), (I), (II), (III) or (IV) and in any of the embodiments as disclosed herein. In one embodiment, $R^5$ is H or $C_{1-4}$alkyl. In another embodiment, $R^5$ is H. In some embodiments of compounds of formula (IVb), $Y^2$ is $CR^{10}$ and $Y^3$ is CH, wherein $R^{10}$ is H, $C_{1-6}$alkyl, $C_{1-6}$alkoxy, $C_{2-6}$alkenyl, $C_{2-6}$alkynyl, aryl-$C_{1-4}$alkyl-, heteroaryl-$C_{1-4}$ alkyl-, $C_{3-6}$cycloalkyl-$C_{1-4}$alkyl-, $C_{3-6}$cycloalkenyl-$C_{1-4}$alkyl-, $CH_2$=CH—$X^2$—, $C_{3-6}$cycloalkyl-$C_{2-4}$alkenyl-$X^2$—, $C_{3-6}$cycloalkyl-$C_{2-4}$alkynyl-$X^2$—, heterocyclyl-$C_{1-4}$alkyl- or $R^8$, each of which is optionally substituted with from; (i) 1-5 $R^9$ groups; or (ii) 1-5 $R^c$ substituents; or (iii) 1-5 $R^{15}$ substituents; or (iv) 1-5 $R^{15}$ substituents; or (v) 1-5 $R^{16}$ substituents; or (vi) 1-5 $R^{17}$ substituents; or (vii) 1-5 $R^{18}$ substituents; or (viii) 1-5 $R^{19}$ substituents, wherein each of $R^9$, $R^c$, $R^d$, $R^{15}$, $R^{16}$, $R^{17}$ or $R^{18}$ substituent is further optionally substituted with from 1-3 $R^{19}$ substituents independently selected from —CN, F, Cl, I, —OCH$_3$, $C_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH— or CH$_3$SO$_2$, wherein $X^2$ is $C_{1-4}$alkylene, —O—, —S— or —NH—. In other embodiments of compounds of formula (IVb), $Y^2$ and $Y^3$ are CH. In other embodiments, $Y^2$ is N and $Y^3$ is CH. In other embodiments, $Y^2$ is $CR^{10}$, wherein $R^{10}$ is a substituent other than hydrogen as disclosed herein and $Y^3$ is CH. In certain embodiments of compounds of formula (IVb), the subscript m is 0. In other embodiments of compounds of formula (IVb), the subscript m is 1. In other embodiments of compounds of formula (IVb), the subscript m is 2.

In a 12th group of embodiments of the disclosure, compounds of formulas (I'), (I'a), (I), (II), (III) (IV) or (IVb) have subformulas (IVb-1), (IVb-2), (IVb-3), (IVb-4), (IVb-5), (IVb-6), (IVb-7) or (IVb-8):

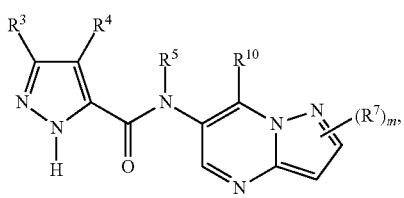
(IVb-1)

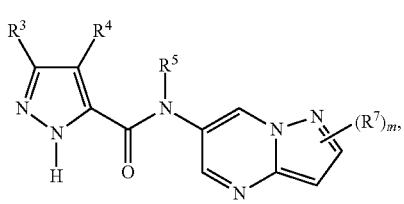
(IVb-2)

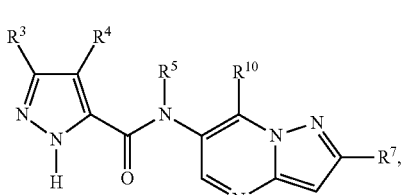
(IVb-3)

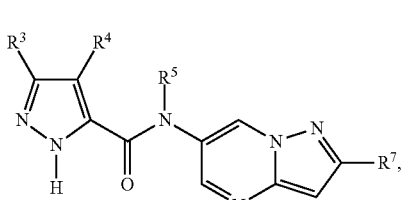
(IVb-4)

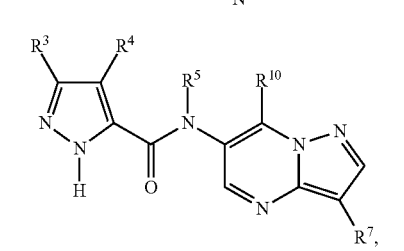
(IVb-5)

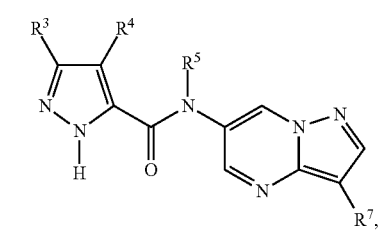
(IVb-6)

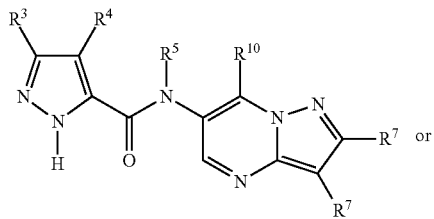
(IVb-7)

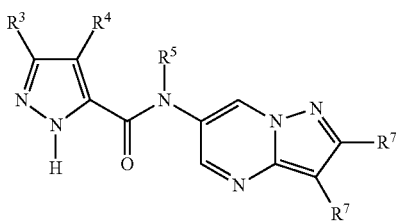
(IVb-8)

The variables $R^3$, $R^4$, $R^5$, $R^7$, m and $R^{10}$ are as defined in any of the embodiments of compounds of formulas (I'), (I'a), (I), (II), (III), (IV) or (IVb) or in any of the embodiments as disclosed herein. In some embodiments, m is 0. In formulas (IVb-7) or (IVb-8), each $R^7$ is an independently selected member. In one embodiment of compounds of formulas (IVb-1), (IVb-2), (IVb-3), (IVb-4), (IVb-5), (IVb-6), (IVb-7) or (IVb-8), $R^5$ is H or $C_{1-4}$alkyl. In another embodiment of compounds of formulas (IVb-1), (IVb-2), (IVb-3), (IVb-4), (IVb-5), (IVb-6), (IVb-7) or (IVb-8), $R^5$ is H. In yet another embodiment, $R^5$ is $C_{1-4}$alkyl. In some embodiments of compounds of formulas (IVb-1), (IVb-2), (IVb-3), (IVb-4), (IVb-5), (IVb-6), (IVb-7) or (IVb-8), $R^{10}$ is selected from $C_{1-6}$alkyl, $C_{1-6}$alkoxy, $C_{2-6}$alkenyl, $C_{2-6}$alkynyl, aryl-$C_{1-4}$ alkyl-, heteroaryl-$C_{1-4}$ alkyl-, $C_{3-6}$cycloalkyl-$C_{1-4}$alkyl-, $C_{3-6}$cycloalkenyl-$C_{1-4}$alkyl-, $CH_2$=CH—$X^2$—, $C_{3-6}$cycloalkyl-$C_{2-4}$alkenyl-$X^2$—, $C_{3-6}$cycloalkyl-$C_{2-4}$alkynyl-$X^2$—, heterocyclyl-$C_{1-4}$alkyl- or $R^8$, each of which is optionally substituted with from 1-5 $R^9$ groups; wherein $X^2$ is $C_{1-4}$alkylene, —O—, —S— or —NH—. In other embodiments of compounds of formulas (IVb-1), (IVb-2), (IVb-3), (IVb-4), (IVb-5), (IVb-6), (IVb-7) or (IVb-8), $R^{10}$ is CN, $C_{1-4}$alkyl, halogen, $C_{1-4}$haloalkyl, $C_{1-4}$haloalkoxy or $C_{1-4}$alkoxy. In other embodiments of compounds of formulas (IVb-1), (IVb-2), (IVb-3), (IVb-4), (IVb-5), (IVb-6), (IVb-7) or (IVb-8), $R^{10}$ is CN, $CH_3$, Et, Cl, Br, F, $CF_3$, $CF_2H$—, $CFH_2$—, $CH_3O$—, $CF_3O$—, $CF_2HO$— or $CFH_2O$—.

In a 13th group of embodiments of the disclosure, compounds of formulas (I'), (I'a), (I), (II), (III) or (IV) have subformulas (IVc):

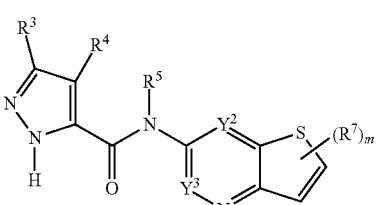
(IVc)

The variables $R^3$, $R^4$, $R^5$, $R^7$, m, $Y^2$ and $Y^3$ are as defined in any of the embodiments of compounds of formulas (I'), (I'a), (I), (II), (III) or (IV) or in any of the embodiments as disclosed herein. In one embodiment, $R^5$ is H or $C_{1-4}$alkyl. In another embodiment of compounds of formula (IVc), $R^5$ is H. In some embodiments of compounds of formula (IVc), $Y^2$ is N or $CR^{10}$ and $Y^3$ is N or CH, wherein $R^{10}$ is H, $C_{1-6}$alkyl, $C_{1-6}$alkoxy, $C_{2-6}$alkenyl, $C_{2-6}$alkynyl, aryl-$C_{1-4}$ alkyl-, heteroaryl-$C_{1-4}$ alkyl-, $C_{3-6}$cycloalkyl-$C_{1-4}$alkyl-, $C_{3-6}$cycloalkenyl-$C_{1-4}$alkyl-, $CH_2$=$CH$—$X^2$—, $C_{3-6}$cycloalkyl-$C_{2-4}$alkenyl-$X^2$—, $C_{3-6}$cycloalkyl-$C_{2-4}$alkynyl-$X^2$—, heterocyclyl-$C_{1-4}$alkyl- or $R^8$, each of which is optionally substituted with from; (i) 1-5 $R^9$ groups; or (ii) 1-5 $R^d$ substituents; or (iii) 1-5 $R^d$ substituents; or (iv) 1-5 $R^{15}$ substituents; or (v) 1-5 $R^{16}$ substituents; or (vi) 1-5 $R^7$ substituents; or (vii) 1-5 $R^{18}$ substituents; or (viii) 1-5 $R^{19}$ substituents, wherein each of $R^9$, $R^c$, $R^d$, $R^{15}$, $R^{16}$, $R^7$ or $R^{18}$ substituent is further optionally substituted with from 1-3 $R^{19}$ substituents independently selected from —CN, F, Cl, I, —$OCH_3$, $C_{1-6}$alkyl, cyclopropyl, 1-azetidinyl, 2-azetidinyl, 3-azetidinyl, 2-oxetanyl, 3-oxetanyl, —OH, —$NH_2$, —$NHCH_3$, —$N(CH_3)_2$, —$CH_2F$, —$CHF_2$, $CF_3$, —$OCF_3$, —$OCHF_2$, —$OCH_2F$, $CH_3C(O)$—, $CH_3C(O)O$—, $CH_3OC(O)$—, $CH_3NHC(O)$—, $CH_3C(O)NH$—, $(CH_3)_2NC(O)$—, $(CH_3)_2NS(O)_2$—, $(CH_3)_2S(O)_2NH$— or $CH_3SO_2$, wherein $X^2$ is $C_{1-4}$alkylene, —O—, —S— or —NH—. In other embodiments of compounds of formula (IVc), $Y^2$ and $Y^3$ are CH. In other embodiments, $Y^2$ is N and $Y^3$ is CH. In other embodiments, $Y^2$ is $CR^{10}$, wherein $R^{10}$ is a substituent other than hydrogen as disclosed herein and $Y^3$ is CH. In certain embodiments of compounds of formula (IVc), the subscript m is 0. In other embodiments of compounds of formula (IVc), the subscript m is 1. In other embodiments of compounds of formula (IVc), the subscript m is 2.

In a 14th group of embodiments of the disclosure, compounds of formulas (I'), (I'a), (I), (II), (III), (IV) or (IVc) have subformulas (IVc-1), (IVc-2), (IVc-3), (IVc-4) or (IVc-5):

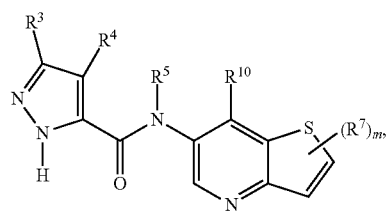
(IVc-1)

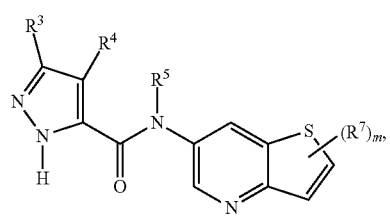
(IVc-2)

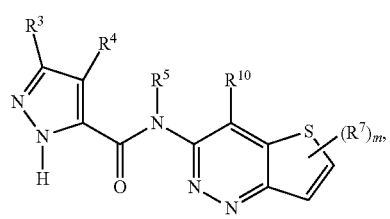
(IVc-3)

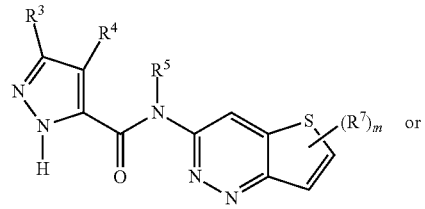
(IVc-4)

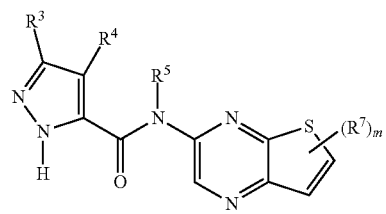
(IVc-5)

The variables $R^3$, $R^4$, $R^5$, $R^7$, m and $R^{10}$ in formulas (IVc-1), (IVc-2), (IVc-3), (IVc-4) or (IVc-5) are as defined in any of the embodiments of compounds of formulas (I'), (I'a), (I), (II), (III), (IV) or (IVc) or in any of the embodiments as disclosed herein. In one embodiment, m is 0. In another embodiment, m is 1. In yet another embodiment, m is 2 and each $R^7$ is an independently selected member. In one embodiment of compounds of formulas (IVc-1), (IVc-2), (IVc-3), (IVc-4) or (IVc-5), $R^5$ is H or $C_{1-4}$alkyl. In another embodiment of compounds of formulas (IVc-1), (IVc-2), (IVc-3), (IVc-4) or (IVc-5), $R^5$ is H. In yet another embodiment, $R^5$ is $C_{1-4}$alkyl. In some embodiments of compounds of formulas (IVc-1), (IVc-2), (IVc-3), (IVc-4) or (IVc-5), $R^{10}$ is selected from $C_{1-6}$alkyl, $C_{1-6}$alkoxy, $C_{2-6}$alkenyl, $C_{2-6}$alkynyl, aryl-$C_{1-4}$alkyl-, heteroaryl-$C_{1-4}$ alkyl-, $C_{3-6}$cycloalkyl-$C_{1-4}$alkyl-, $C_{3-6}$cycloalkenyl-$C_{1-4}$alkyl-, $CH_2$=$CH$—$X^2$—, $C_{3-6}$cycloalkyl-$C_{2-4}$alkenyl-$X^2$—, $C_{3-6}$cycloalkyl-$C_{2-4}$alkynyl-$X^2$—, heterocyclyl-$C_{1-4}$alkyl- or $R^8$, each of which is optionally substituted with from 1-5 $R^9$ groups; wherein $X^2$ is $C_{1-4}$alkylene, —O—, —S— or —NH—. In other embodiments of compounds of formulas (IVc-1), (IVc-2), (IVc-3), (IVc-4) or (IVc-5), $R^{10}$ is CN, $C_{1-4}$alkyl, halogen, $C_{1-4}$haloalkyl, $C_{1-4}$haloalkoxy or $C_{1-4}$alkoxy. In other embodiments of compounds of formulas (IVc-1), (IVc-2), (IVc-3), (IVc-4) or (IVc-5), $R^{10}$ is CN, $CH_3$, Et, Cl, Br, F, $CF_3$, $CF_2H$—, $CFH_2$—, $CH_3O$—, $CF_3O$—, $CF_2HO$— or $CFH_2O$—.

In a 15th group of embodiments of the disclosure, compounds of formulas (I'), (I'a), (I), (II), (III) or (IV) have subformulas (IVd):

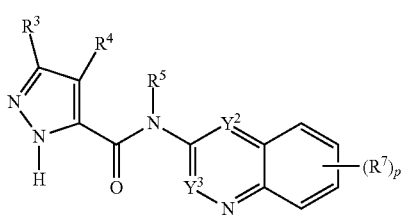
(IVd)

The variables $R^3$, $R^4$, $R^5$, $R^7$, p, $Y^2$ and $Y^3$ in formula (IVd) are as defined in any of the embodiments of compounds of formulas (I'), (I'a), (I), (II), (III) or (IV) or in any of the embodiments as disclosed herein. In one embodiment, $R^5$ is H or $C_{1-4}$alkyl. In another embodiment of compounds of formula (IVd), $R^5$ is H. In some embodiments of compounds of formula (IVd), $Y^2$ is N or $CR^{10}$ and $Y^3$ is N or CH, wherein $R^{10}$ is H, $C_{1-6}$alkyl, $C_{1-6}$alkoxy, $C_{2-6}$alkenyl, $C_{2-6}$alkynyl, aryl-$C_{1-4}$alkyl-, heteroaryl-$C_{1-4}$ alkyl-, $C_{3-6}$cycloalkyl-$C_{1-4}$alkyl-, $C_{3-6}$cycloalkenyl-$C_{1-4}$alkyl-, $CH_2$=CH—$X^2$—, $C_{3-6}$cycloalkyl-$C_{2-4}$alkenyl-$X^2$—, $C_{3-6}$cycloalkyl-$C_{2-4}$alkynyl-$X^2$—, heterocyclyl-$C_{1-4}$alkyl- or $R^8$, each of which is optionally substituted with from; (i) 1-5 $R^9$ groups; or (ii) 1-5 $R^c$ substituents; or (iii) 1-5 $R^d$ substituents; or (iv) 1-5 $R^{15}$ substituents; or (v) 1-5 $R^{16}$ substituents; or (vi) 1-5 $R^{17}$ substituents; or (vii) 1-5 $R^{18}$ substituents; or (viii) 1-5 $R^{19}$ substituents, wherein each of $R^9$, $R^c$, $R^d$, $R^{15}$, $R^{16}$, $R^{17}$ or $R^{18}$ substituent is further optionally substituted with from 1-3 $R^{19}$ substituents independently selected from —CN, F, Cl, I, —$OCH_3$, $C_{1-6}$alkyl, cyclopropyl, 1-azetidinyl, 2-azetidinyl, 3-azetidinyl, 2-oxetanyl, 3-oxetanyl, —OH, —$NH_2$, —$NHCH_3$, —$N(CH_3)_2$, —$CH_2F$, —$CHF_2$, $CF_3$, —$OCF_3$, —$OCHF_2$, —$OCH_2F$, $CH_3C(O)$—, $CH_3C(O)O$—, $CH_3OC(O)$—, $CH_3NHC(O)$—, $CH_3C(O)NH$—, $(CH_3)_2NC(O)$—, $(CH_3)_2NS(O)_2$—, $(CH_3)_2S(O)_2NH$— or $CH_3SO_2$, wherein $X^2$ is $C_{1-4}$alkylene, —O—, —S— or —NH—. In other embodiments of compounds of formula (IVd), $Y^2$ and $Y^3$ are CH. In other embodiments, $Y^2$ is N and $Y^3$ is CH. In other embodiments, $Y^2$ is $CR^{10}$, wherein $R^{10}$ is a substituent other than hydrogen as disclosed herein and $Y^3$ is CH. The subscript p is 0, 1, 2 or 3. In certain embodiments of compounds of formula (IVd), the subscript p is 0. In other embodiments of compounds of formula (IVd), the subscript p is 1. In other embodiments of compounds of formula (IVd), the subscript p is 2. In other embodiments of compounds of formula (IVd), the subscript p is 3.

In a 16th group of embodiments of the disclosure, compounds of formulas (I'), (I'a), (I), (II), (III), (IV) or (IVd) have subformulas (IVd-1), (IVd-2), (IVd-3), (IVd-4) or (IVd-5):

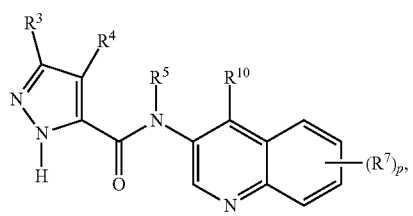

(IVd-1)

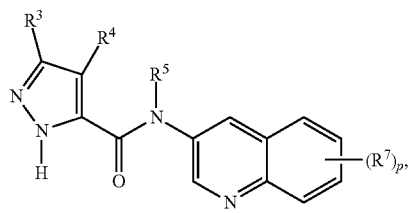

(IVd-2)

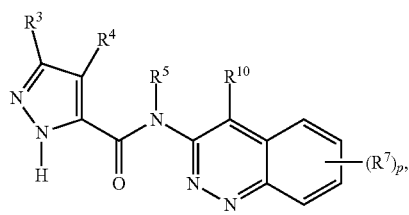

(IVd-3)

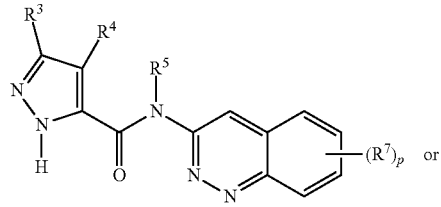

(IVd-4)

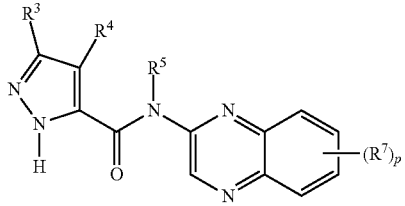

(IVd-5)

The variables $R^3$, $R^4$, $R^5$, $R^7$, m and $R^{10}$ in formulas (IVd-1), (IVd-2), (IVd-3), (IVd-4) or (IVd-5) are as defined in any of the embodiments of compounds of formulas (I'), (I'a), (I), (II), (III), (IV) or (IVd) or in any of the embodiments as disclosed herein. In one embodiment, p is 0. In another embodiment, p is 1. In yet another embodiment, p is 2 and each $R^7$ is an independently selected member. In one embodiment of compounds of formulas (IVd-1), (IVd-2), (IVd-3), (IVd-4) or (IVd-5), $R^5$ is H or $C_{1-4}$alkyl. In another embodiment of compounds of formulas (IVd-1), (IVd-2), (IVd-3), (IVd-4) or (IVd-5), $R^5$ is H. In yet another embodiment, $R^5$ is $C_{1-4}$alkyl. In some embodiments of compounds of formulas (IVd-1), (IVd-2), (IVd-3), (IVd-4) or (IVd-5), $R^{10}$ is selected from $C_{1-6}$alkyl, $C_{1-6}$alkoxy, $C_{2-6}$alkenyl, $C_{2-6}$alkynyl, aryl-$C_{1-4}$alkyl-, heteroaryl-$C_{1-4}$ alkyl-, $C_{3-6}$cycloalkyl-$C_{1-4}$alkyl-, $C_{3-6}$cycloalkenyl-$C_{1-4}$alkyl-, $CH_2$=CH—$X^2$—, $C_{3-6}$cycloalkyl-$C_{2-4}$alkenyl-$X^2$—, $C_{3-6}$cycloalkyl-$C_{2-4}$alkynyl-$X^2$—, heterocyclyl-$C_{1-4}$alkyl- or $R^8$, each of which is optionally substituted with from 1-5 $R^9$ groups; wherein $X^2$ is $C_{1-4}$alkylene, —O—, —S— or —NH—. In other embodiments of compounds of formulas (IVd-1), (IVd-2), (IVd-3), (IVd-4) or (IVd-5), $R^{10}$ is CN, $C_{1-4}$alkyl, halogen, $C_{1-4}$haloalkyl, $C_{1-4}$haloalkoxy or $C_{1-4}$alkoxy. In other embodiments of compounds of formulas (IVd-1), (IVd-2), (IVd-3), (IVd-4) or (IVd-5), $R^{10}$ is CN, $CH_3$, Et, Cl, Br, F, $CF_3$, $CF_2H$—, $CFH_2$—, $CH_3O$—, $CF_3O$—, $CF_2HO$— or $CFH_2O$—.

In a 17th group of embodiments of the disclosure, compounds of formulas (I'), (I'a), (I), (II), (III) or (IV) have subformulas (IVe):

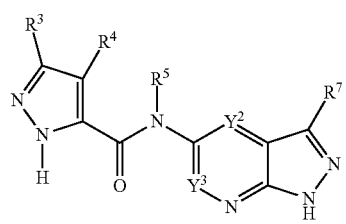

(IVe)

The variables $R^3$, $R^4$, $R^5$, $R^7$, m, $Y^2$ and $Y^3$ are as defined in any of the embodiments of compounds of formulas (I'), (I'a), (I), (II), (III) or (IV) or in any of the embodiments as disclosed herein. In one embodiment, $R^5$ is H or $C_{1-4}$alkyl. In another embodiment of compounds of formula (IVe), $R^5$ is H. In some embodiments of compounds of formula (IVe), $Y^2$ is N or $CR^{10}$ and $Y^3$ is N or CH, wherein $R^{10}$ is H, $C_{1-6}$alkyl, $C_{1-6}$alkoxy, $C_{2-6}$alkenyl, $C_{2-6}$alkynyl, aryl-$C_{1-4}$alkyl-, heteroaryl-$C_{1-4}$ alkyl-, $C_{3-6}$cycloalkyl-$C_{1-4}$alkyl-, $C_{3-6}$cycloalkyl-$C_{1-4}$alkyl-, $CH_2$=CH—$X^2$—, $C_{3-6}$cycloalkyl-$C_{2-4}$alkenyl-$X^2$—, $C_{3-6}$cycloalkyl-$C_{2-4}$alkynyl-$X^2$—, heterocyclyl-$C_{1-4}$alkyl- or $R^8$, each of which is optionally substituted with from; (i) 1-5 $R^9$ groups; or (ii) 1-5 $R^c$ substituents; or (iii) 1-5 $R^d$ substituents; or (iv) 1-5 $R^{15}$ substituents; or (v) 1-5 $R^{16}$ substituents; or (vi) 1-5 $R^{17}$ substituents; or (vii) 1-5 $R^{s8}$ substituents; or (viii) 1-5 $R^{19}$ substituents, wherein each of $R^9$, $R^c$, $R^d$, $R^{15}$, $R^{16}$, $R^{17}$ or $R^{18}$ substituent is further optionally substituted with from 1-3 $R^{19}$ substituents independently selected from —CN, F, Cl, I, —OCH$_3$, $C_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH— or CH$_3$SO$_2$, wherein $X^2$ is $C_{1-4}$alkylene, —O—, —S— or —NH—. In other embodiments of compounds of formula (IVe), $Y^2$ and $Y^3$ are CH. In other embodiments, $Y^2$ is N and $Y^3$ is CH. In other embodiments, $Y^2$ is $CR^{10}$, wherein $R^{10}$ is a substituent other than hydrogen as disclosed herein and $Y^3$ is CH.

In an 18th group of embodiments of the disclosure, compounds of formulas (I'), (I'a), (I), (II), (III), (IV) or (IVe) have subformulas (IVe-1), (IVe-2), (IVe-3), (IVe-4) or (IVe-5):

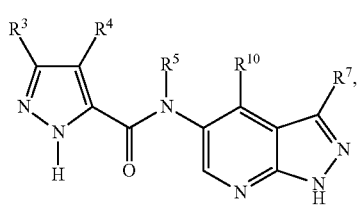

(IVe-1)

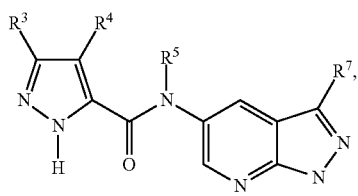

(IVe-2)

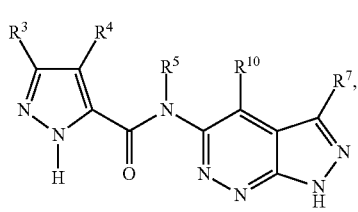

(IVe-3)

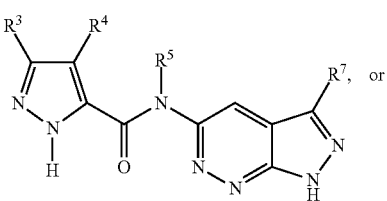

(IVe-4) or

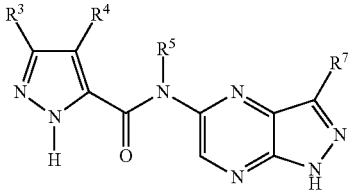

(IVe-5)

The variables $R^3$, $R^4$, $R^5$, $R^7$, m and $R^{10}$ in formulas (IVe-1), (IVe-2), (IVe-3), (IVe-4) or (IVe-5) are as defined in any of the embodiments of compounds of formulas (I'), (I'a), (I), (II), (III), (IV) or (IVe) or in any of the embodiments as disclosed herein. In one embodiment of compounds of formulas (IVe-1), (IVe-2), (IVe-3), (IVe-4) or (IVe-5), $R^5$ is H or $C_{1-4}$alkyl. In another embodiment of compounds of formulas (IVe-1), (IVe-2), (IVe-3), (IVe-4) or (IVe-5), $R^5$ is H. In yet another embodiment, $R^5$ is $C_{1-4}$alkyl. In some embodiments of compounds of formulas (IVe-1), (IVe-2), (IVe-3), (IVe-4) or (IVe-5), $R^{10}$ is selected from $C_{1-6}$alkyl, $C_{1-6}$alkoxy, $C_{2-6}$alkenyl, $C_{2-6}$alkynyl, aryl-$C_{1-4}$alkyl-, heteroaryl-$C_{1-4}$ alkyl-, $C_{3-6}$cycloalkyl-$C_{1-4}$ alkyl-, $C_{3-6}$cycloalkenyl-$C_{1-4}$alkyl-, $CH_2$=CH—$X^2$—, $C_{3-6}$cycloalkyl-$C_{2-4}$alkenyl-$X^2$—, $C_{3-6}$cycloalkyl-$C_{2-4}$alkynyl-$X^2$—, heterocyclyl-$C_{1-4}$alkyl- or $R^8$, each of which is optionally substituted with from 1-5 $R^9$ groups; wherein $X^2$ is $C_{1-4}$alkylene, —O—, —S— or —NH—. In other embodiments of compounds of formulas (IVe-1), (IVe-2), (IVe-3), (IVe-4) or (IVe-5), $R^{10}$ is CN, $C_{1-4}$alkyl, halogen, $C_{1-4}$haloalkyl, $C_{1-4}$haloalkoxy or $C_{1-4}$alkoxy. In other embodiments of compounds of formulas (IVe-1), (IVe-2), (IVe-3), (IVe-4) or (IVe-5), $R^{10}$ is CN, CH$_3$, Et, Cl, Br, F, CF$_3$, CF$_2$H—, CFH$_2$—, CH$_3$O—, CF$_3$O—, CF$_2$HO— or CFH$_2$O—.

In a 19$^{th}$ group of embodiments of the disclosure, compounds of formulas (I'), (I), (II), (III), (V) or (V') have subformula (Va):

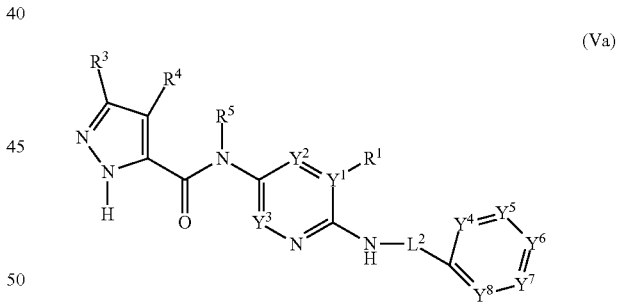

(Va)

each of the $Y^4$, $Y^5$, $Y^6$, $Y^7$ and $Y^8$ substituents is independently selected from CH, $CR^9$ or N, wherein at each occurrence, at least two of the $Y^4$, $Y^5$, $Y^6$, $Y^7$ and $Y^8$ substituents are independently selected from CH or $CR^9$, wherein $R^9$ is as defined in any of the embodiments of compounds of formulas (I'), (I), (II), (III), (V) or (V') as described herein. In certain embodiments, $R^9$ is $R^c$, or $R^d$, or $R^e$ substituent. In some embodiments, $L^2$ is a bond, —CH$_2$—, —C(O)— or —SO$_2$—. In one instance, $L^2$ is a bond. In other another instance, $L^2$ is —CH$_2$—, —C(O)— or —SO$_2$—. In some embodiments of compounds of formula (Va), $Y^4$, $Y^5$, $Y^6$, $Y^7$ and $Y^8$ are each independently CH or $CR^9$. In other embodiments, $Y^4$ is N and $Y^5$, $Y^6$, $Y^7$ and $Y^8$ are each independently CH or $CR^9$. In other embodiments, $Y^4$ is N, $Y^5$ is N and $Y^6$, $Y^7$ and $Y^8$ are each independently CH or $CR^9$. In other embodiments, $Y^4$ is N, $Y^6$ is N and $Y^5$, $Y^7$ and $Y^8$ are each independently CH or $CR^9$. $Y^4$ is N, $Y^7$ is N and $Y^5$, $Y^6$ and $Y^8$ are each independently CH or $CR^9$. $Y^4$ is N, $Y^8$ is N and $Y^5$, $Y^6$ and $Y^7$ are each independently CH or $CR^9$. $Y^5$ is N and $Y^4$, $Y^6$, $Y^7$ and $Y^8$ are each independently CH or $CR^9$. $Y^6$ is N and $Y^4$, $Y^5$, $Y^7$ and $Y^8$ are each independently CH or $CR^9$. In certain embodiments of compounds of formula (Va), the aromatic ring containing $Y^4$, $Y^5$, $Y^6$, $Y^7$ and $Y^8$ is optionally substituted with from: (i) 1-3 $R^9$ groups; or (ii) 1-3 $R^c$ substituents; or (iii) 1-3 $R^d$ substituents; or (iv) 1-3 $R^{15}$ substituents; or (v) 1-3 $R^{16}$ substituents; or (vi) 1-3 $R^{17}$ substituents; or (vii) 1-3 $R^{18}$ substituents; or (viii) 1-3 $R^{19}$ substituents; or (ix) 1-3 $R^{20}$ substituents independently selected from —CN, F, Cl, I, —$OCH_3$, $C_{1-6}$alkyl, cyclopropyl, 1-azetidinyl, 2-azetidinyl, 3-azetidinyl, 2-oxetanyl, 3-oxetanyl, —OH, —$NH_2$, —$NHCH_3$, —$N(CH_3)_2$, —$CH_2F$, —$CHF_2$, $CF_3$, —$OCF_3$, —$OCHF_2$, —$OCH_2F$, $CH_3C(O)$—, $CH_3C(O)O$—, $CH_3OC(O)$—, —PH(=O)$CH_3$, —P(=O)$(CH_3)_2$, —PH(=O)(O$C_{1-6}$alkyl), —P(=O)(O$C_{1-6}$alkyl)$_2$, —OP(=O)(O$C_{1-6}$alkyl)$_2$, $CH_3NHC(O)$—, $CH_3C(O)NH$—, $(CH_3)_2NC(O)$—, $(CH_3)_2NS(O)_2$—, $(CH_3)_2S(O)_2NH$—, EtNHSO$_2$—, PhNHSO$_2$—, $CH_3SO_2NH$—, EtSO$_2NH$—, PhSO$_2NH$—, $CH_3SO_2$—, EtSO$_2$—, PhSO$_2$—, 4-morpholinyl, EtOC(O)NH—, $CH_3OC(O)NH$—, EtNHC(O)NH—, $CH_3NHC(O)NH$—, EtOC(O)O— or $CH_3OC(O)O$—, wherein each of $R^9$, $R^c$, $R^d$, $R^{15}$, $R^{16}$, $R^{17}$, $R^{18}$, $R^{19}$ or $R^{20}$ substituent is further optionally substituted with from 1-3 $R^{19}$ substituents independently selected from —CN, F, Cl, I, —$OCH_3$, $C_{1-6}$alkyl, cyclopropyl, —OH, —$NH_2$, —$NHCH_3$, —$N(CH_3)_2$, —$CH_2F$, —$CHF_2$, $CF_3$, —$OCF_3$, —$OCHF_2$, —$OCH_2F$, $CH_3C(O)$—, $CH_3C(O)O$—, $CH_3OC(O)$—, $CH_3NHC(O)$—, $CH_3C(O)NH$—, $(CH_3)_2NC(O)$—, $(CH_3)_2NS(O)_2$—, $(CH_3)_2S(O)_2NH$— or $CH_3SO_2$. In one embodiment, $R^5$ is H. In some embodiments, $Y^1$ is N and $R^1$ is a lone pair of electron. In certain embodiments, $Y^1$ is C and $R^1$ is H, halogen, $C_{1-4}$ alkyl, $C_{1-4}$ haloalkoxy or cyclopropyl. In one embodiment, $Y^1$ is C and $R^1$ is H. The variables $R^1$, $R^3$, $R^4$, $R^5$, $Y^1$, $Y^2$, $Y^3$ and $L^2$ and are as defined in any of the embodiments of compounds of formulas (I'), (I'a), (I), (II), (III), (IIIa) or (IV) and in any of the embodiments as disclosed herein.

In a 20$^{th}$ group of embodiments of the disclosure, compounds of formulas (I'), (I), (II), (III), (V), (V') or (Va) have subformulas (Va-1), (Va-2) or (Va-3):

(Va-1)

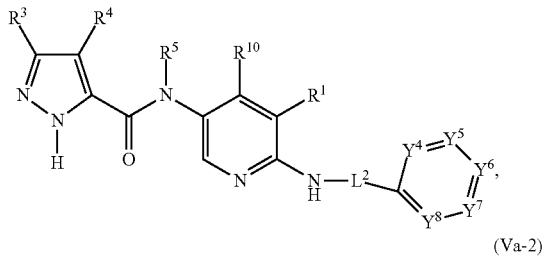

(Va-2)

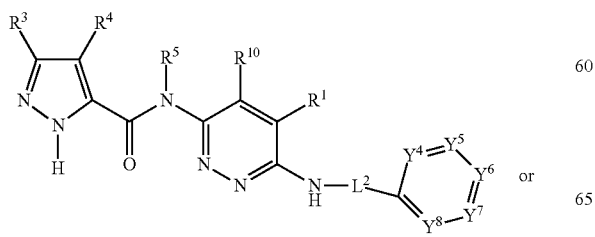

or (Va-3)

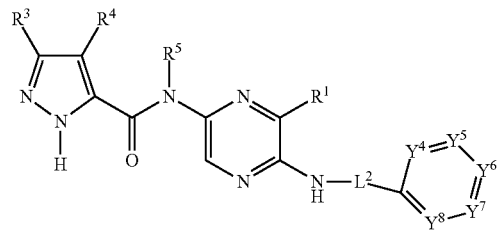

The variables, $R^3$, $R^4$, $R^5$, $R^{10}$, $R^1$, $L^2$, $Y^4$, $Y^5$, $Y^6$, $Y^7$ or $Y^8$ in formulas (Va-1), (Va-2) or (Va-3) are as defined in any of the embodiments of compounds of formulas (I'), (I), (II), (III), (V), (V') or (Va). In some instances of compounds of formulas (Va-1), (Va-2) or (Va-3), $R^5$ is H. In other instances of compounds of formulas (Va-1), (Va-2) or (Va-3), $R^1$ is H. In other instances of compounds of formulas (Va-1), (Va-2) or (Va-3), $L^2$ is a bond. In still other instances of compounds of formulas (Va-1), (Va-2) or (Va-3), $R^{10}$ is H. In one embodiment of compounds of formulas (Va-1), (Va-2) or (Va-3), $R^1$, $R^5$ and $R^{10}$ are H and $L^2$ is a bond.

In a 21$^{st}$ group of embodiments of the disclosure, compounds of formulas (I'), (I), (II), (III), (V), (V'), (Va), (Va-1), (Va-2) or (Va-3) have subformulas (Va-1a), (Va-1a-1), (Va-2a), (Va-2a-1) or (Va-3a):

(Va-1a)

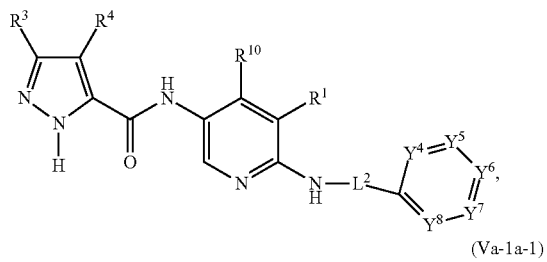

(Va-1a-1)

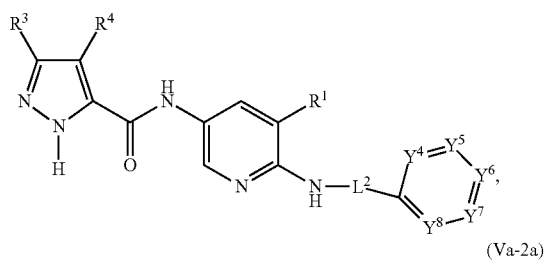

(Va-2a)

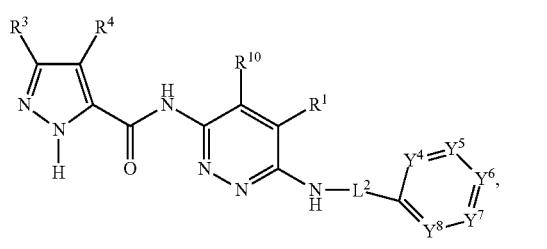

(Va-2a-1)

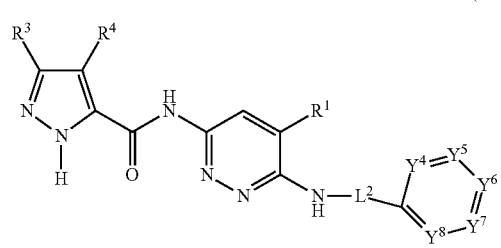

-continued

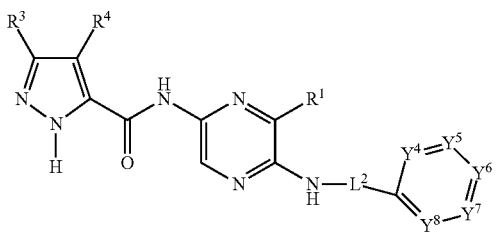
(Va-3a)

The variables, $R^3$, $R^4$, $R^{10}$, $R^1$, $L^2$, $Y^4$, $Y^5$, $Y^6$, $Y^7$ or $Y^8$ in formulas (Va-1a), (Va-1a-1), (Va-2a), (Va-2a-1) or (Va-3a) are as defined in any of the embodiments of compounds of formulas (I'), (I), (II), (III), (V), (V'), (Va), (Va-1), (Va-2) or (Va-3).

In a 22$^{nd}$ group of embodiments of the disclosure, compounds of formulas (I'), (I), (II), (III), (V), (V'), (Va), (Va-1), (Va-2), (Va-3), (Va-1a), (Va-1a-1), (Va-2a), (Va-2a-1) or (Va-3a) have subformulas (Va-1b), (Va-1b-1), (Va-2b), (Va-2b-1) or (Va-3b):

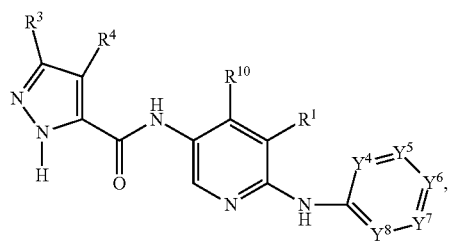
(Va-1b)

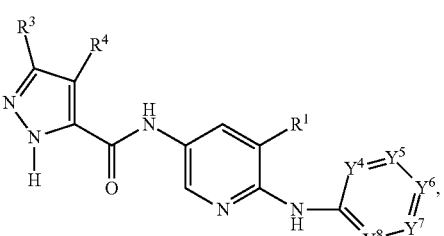
(Va-1b-1)

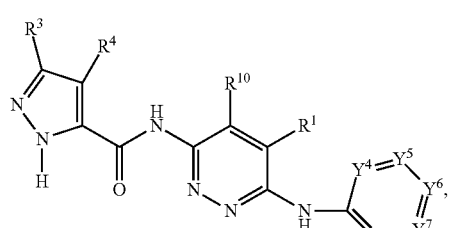
(Va-2b)

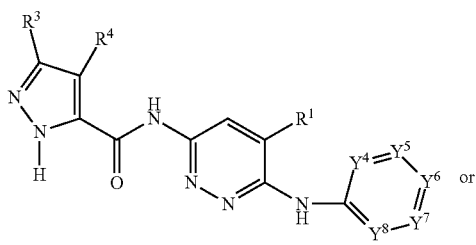
(Va-2b-1)

or

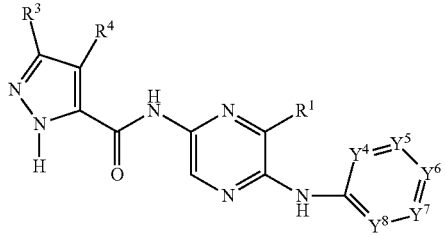
(Va-3b)

The variables, $R^3$, $R^4$, $R^1$, $Y^4$, $Y^5$, $Y^6$, $Y^7$ or $Y^8$ in formulas (Va-1b), (Va-1b-1), (Va-2b), (Va-2b-1) or (Va-3b) are as defined in any of the embodiments of compounds of formulas (I'), (I), (II), (III), (V), (V'), (Va), (Va-1), (Va-2), (Va-3, (Va-1a), (Va-1a-1), (Va-2a) or (Va-2a-1).

In a 23rd group of embodiments of the disclosure, compounds of formulas (I'), (I), (II), (III), (V), (V') or (Va) have subformula (Va-4):

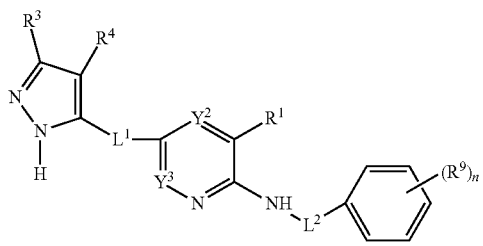
(Va-4)

The variables $R^3$, $R^4$, $L^1$, $Y^2$, $Y^3$, $R^1$, $L^2$ and $R^9$ in formula (Va-4) are as defined in any of the embodiments of compounds of formulas (I'), (I), (II), (III), (V), (V') or (Va). The subscript n is 0, 1, 2 or 3. In some embodiments of compounds of formula (Va-4), $L^1$ is —C(O)N($R^5$)—, wherein $R^5$ is H or $C_{1-4}$alkyl. In some embodiments of compounds of formula (Va-4), $L^2$ is a bond. In some embodiments of compounds of formula (Va-4), $Y^3$ is N and $Y^2$ is $CR^{10}$. In other embodiments of compounds of formula (Va-4), $Y^3$ is N and $Y^2$ is CH. In other embodiments of compounds of formula (Va-4), $Y^3$ and $Y^2$ are CH. In other embodiments of compounds of formula (Va-4), $Y^3$ is CH and $Y^2$ is N. In some embodiments of compounds of formula (Va-4), $R^9$ is a $R^c$; or $R^d$; or $R^e$; or $R^{15}$; or $R^{16}$; or $R^1$; or $R^{19}$; or $R^{20}$ group.

In a 24th group of embodiments of the disclosure, compounds of formulas (I'), (I), (II), (III), (V), (V'), (Va) or (Va-4) have subformula (Va-4a):

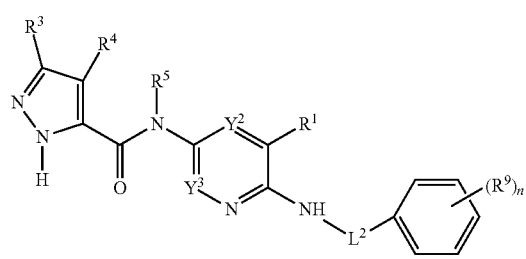
(Va-4a)

The variables $R^3$, $R^4$, $R^5$, $Y^2$, $Y^3$, $R^1$, $L^2$ and $R^9$ are as defined in any of the embodiments of compounds of formulas (I'), (I), (II), (III), (V), (V'), (Va) or (Va-4a). The subscript n is 0, 1, 2 or 3. In some embodiments of compounds of formula (Va-4a), $R^5$ is H. In other embodiments of compounds of formula (Va-4a), $R^5$ is $C_{1-4}$alkyl. In some embodiments of compounds of formula (Va-4a), $L^2$ is a bond, —$CH_2$—, —C(O)— or —$SO_2$. In some embodiments of compounds of formula (Va-4a), $L^2$ is a bond. In some embodiments of compounds of formula (Va-4a), $Y^3$ is N and $Y^2$ is $CR^{10}$. In other embodiments of compounds of formula (Va-4a), $Y^3$ is N and $Y^2$ is CH. In other embodiments of compounds of formula (Va-4a), $Y^3$ and $Y^2$ are CH. In other embodiments of compounds of formula (Va-4a), $Y^3$ is CH and $Y^2$ is N. In some embodiments of compounds of formula (Va-4a), $R^9$ is a $R^c$; or $R^d$; or $R^e$; or $R^{15}$; or $R^{16}$; or $R^{17}$; or $R^{19}$; or $R^{20}$ group.

In a 25th group of embodiments of the disclosure, compounds of formulas (I'), (I), (II), (III), (V), (V'), (Va), (Va-4) or (Va-4a) have subformula (Va-4a-1):

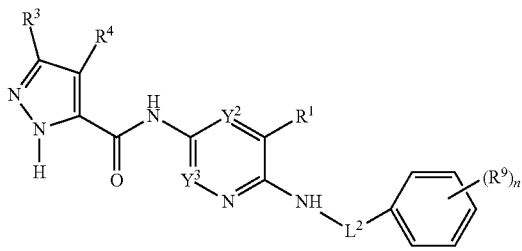

(Va-4a-1)

The variables $R^3$, $R^4$, $R^5$, $Y^2$, $Y^3$, $R^1$, $L^2$, $R^9$ and the script n are as defined in any of the embodiments of compounds of formulas (I'), (I), (II), (III), (V), (V'), (Va), (Va-4) or (Va-4a). In some embodiments of compounds of formula (Va-4a-1), $L^2$ is a bond, —$CH_2$—, —C(O)— or —$SO_2$.

In a 26th group of embodiments of the disclosure, compounds of formulas (I'), (I), (II), (III), (V), (V'), (Va), (Va-4), (Va-4a) or (Va-4a-1) have subformula (Va-4a-1a):

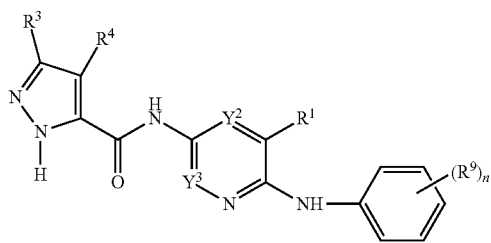

(Va-4a-1a)

The variables $R^3$, $R^4$, $R^5$, $Y^2$, $Y^3$, $R^1$, $R^9$ and the script n are as defined in any of the embodiments of compounds of formulas (I'), (I), (II), (III), (V), (V'), (Va), (Va-4), (Va-4a) or (Va-4a-1). In some embodiments of compounds of formula (Va-4a-1), $Y^3$ is N and $Y^2$ is $CR^{10}$. In other embodiments of compounds of formula (Va-4a-1), $Y^3$ is N and $Y^2$ is CH. In other embodiments of compounds of formula (Va-4a-1), $Y^3$ and $Y^2$ are CH. In other embodiments of compounds of formula (Va-4a-1), $Y^3$ is CH and $Y^2$ is N.

In a 27th group of embodiments of the disclosure, compounds of formulas (I'), (I), (II), (III), (V), (V') or (Va) have subformulas (Va-5a), (Va-5b) or (Va-5c):

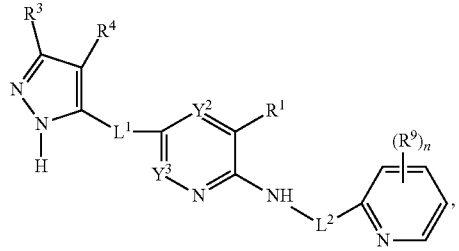

(Va-5a)

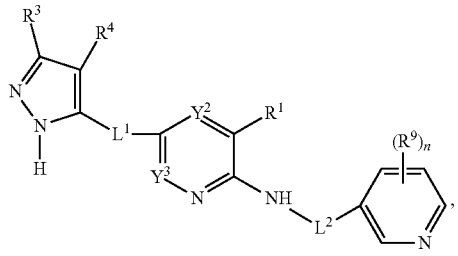

(Va-5b)

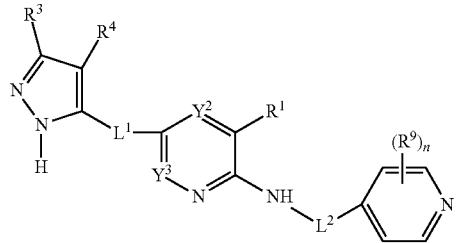

(Va-5c)

The variables $R^3$, $R^4$, $L^1$, $Y^2$, $Y^3$, $R^1$, $L^2$ and $R^9$ are as defined in any of the embodiments of compounds of formulas (I'), (I), (II), (III), (V), (V') or (Va). The subscript n is 0, 1, 2 or 3. In some embodiments of compounds of formulas (Va-5a), (Va-5b) or (Va-5c), $L^1$ is —C(O)N($R^5$)—, wherein $R^5$ is H or $C_{1-4}$alkyl. In some embodiments of compounds of formula (Vb), $L^2$ is a bond. In some embodiments of compounds of formulas (Va-5a), (Va-5b) or (Va-5c), $Y^3$ is N and $Y^2$ is $CR^{10}$. In other embodiments of compounds of formulas (Va-5a), (Va-5b) or (Va-5c), $Y^3$ is N and $Y^2$ is CH. In other embodiments of compounds of formulas (Va-5a), (Va-5b) or (Va-5c), $Y^3$ and $Y^2$ are CH. In other embodiments of compounds of formula (Va-5a), (Va-5b) or (Va-5c), $Y^3$ is CH and $Y^2$ is N. In some embodiments of compounds of formulas (Va-5a), (Va-5b) or (Va-5c), $R^9$ is a $R^c$; or $R^d$; or $R^e$; or $R^{15}$; or $R^{16}$; or $R^{17}$; or $R^{19}$; or $R^{20}$ group.

In a 28th group of embodiments of the disclosure, compounds of formulas (I'), (I), (II), (III), (V), (V') or (Va) have subformula (Va-6):

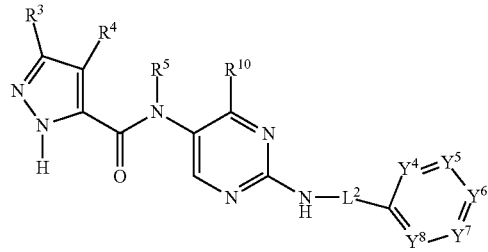

(Va-6)

The variables, $R^3$, $R^4$, $R^5$, $R^{10}$, $L^2$, $Y^4$, $Y^5$, $Y^6$, $Y^7$ or $Y^8$ in formula (Va-6) are as defined in any of the embodiments of compounds of formulas (I'), (I), (II), (III), (V), (V') or (Va). In some instances of compounds of formula (Va-6), $R^5$ is H. In other instances of compounds of formula (Va-6), $R^1$ is H. In other instances of compounds of formulas (Va-6), $L^2$ is a bond. In still other instances of compounds of formulas (Va-6), $R^{10}$ is H. In other instances of compounds of formulas (Va-6), $Y^4$, $Y^5$, $Y^6$, $Y^7$ and $Y^8$ are CH, each of which is optionally substituted with from (i) a $R^9$ group; or (ii) a $R^c$ substituent; or (iii) a $R^d$ substituent; or (iv) a $R^{15}$ substituent; or (v) a $R^{16}$ substituent; or (vi) a $R^{17}$ substituent; or (vii) a $R^{18}$ substituent; (viii) a $R^{19}$ substituent; or (ix) a $R^{20}$ substituent selected from —CN, F, Cl, I, —OCH$_3$, C$_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH—, EtNHSO$_2$—, PhNHSO$_2$—, CH$_3$SO$_2$NH—, EtSO$_2$NH—, PhSO$_2$NH—, CH$_3$SO$_2$, EtSO$_2$, PhSO$_2$—, 4-morpholinyl, EtOC(O)NH—, CH$_3$OC(O)NH—, EtNHC(O)NH—, CH$_3$NHC(O)NH—, EtOC(O)O— or CH$_3$OC(O)O—, wherein each of $R^9$, $R^c$, $R^d$, $R^{15}$, $R^{16}$, $R^{17}$, $R^{18}$, $R^{19}$ or $R^{20}$ substituent is further optionally substituted with from 1-3 $R^{19}$ substituents independently selected from —CN, F, Cl, I, —OCH$_3$, C$_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH— or CH$_3$SO$_2$. In some embodiments of compounds of formulas (Va-1), (Va-2) or (Va-3), $R^1$, $R^5$ and $R^{10}$ are H; $L^2$ is a bond; and $Y^4$, $Y^5$, $Y^6$, $Y^7$ and $Y^8$ are CH, each of which is optionally substituted with from (i) a $R^9$ group; or (ii) a $R^c$ substituent; or (iii) a $R^d$ substituent; or (iv) a $R^{15}$ substituent; or (v) a $R^{16}$ substituent; or (vi) a $R^{17}$ substituent; or (vii) a $R^{18}$ substituent; (viii) a $R^{19}$ substituent; or (ix) a $R^{20}$ substituent selected from —CN, F, Cl, I, —OCH$_3$, C$_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH—, EtNHSO$_2$—, PhNHSO$_2$—, CH$_3$SO$_2$NH—, EtSO$_2$NH—, PhSO$_2$NH—, CH$_3$SO$_2$, EtSO$_2$, PhSO$_2$—, 4-morpholinyl, EtOC(O)NH—, CH$_3$OC(O)NH—, EtNHC(O)NH—, CH$_3$NHC(O)NH—, EtOC(O)O— or CH$_3$OC(O)O—, wherein each of $R^9$, $R^c$, $R^d$, $R^{15}$, $R^{16}$, $R^{17}$, $R^{18}$, $R^{19}$ or $R^{20}$ substituent is further optionally substituted with from 1-3 $R^{19}$ substituents independently selected from —CN, F, Cl, I, —OCH$_3$, C$_{1-6}$alkyl, cyclopropyl, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH— or CH$_3$SO$_2$.

In a 29th group of embodiments of the disclosure, compounds of formulas (I'), (I), (II), (III), (V), (V'), (Va) or (Va-6) have subformulas (Va-6a), (Va-6b), (Va-6c) or (Va-6d):

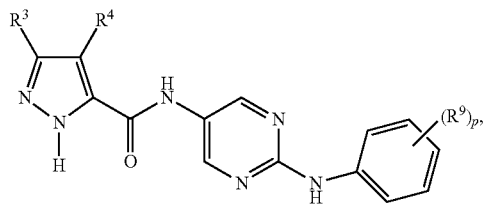
(Va-6a)

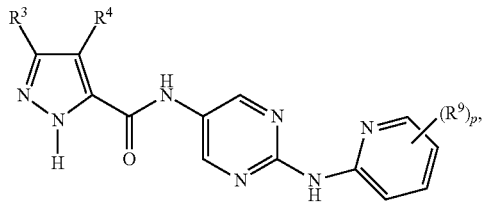
(Va-6b)

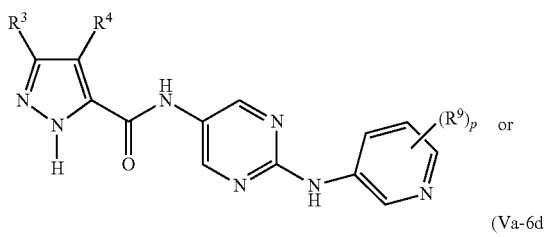
(Va-6c)

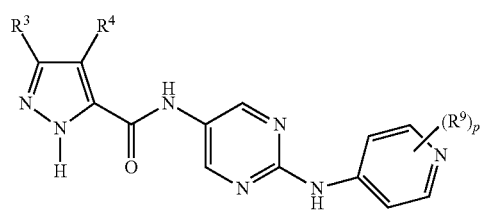
(Va-6d)

The variables, $R^3$, $R^4$ and $R^9$ in formulas (Va-6a), (Va-6b), (Va-6c) or (Va-6d) are as defined in any of the embodiments of compounds of formulas (I'), (I), (II), (III), (V), (V'), (Va) or (Va-6). The subscript p is 0, 1, 2 or 3. In some embodiments of compounds of formulas (Va-6a), (Va-6b), (Va-6c) or (Va-6d), $R^9$ is $R^{20}$.

In some embodiments of compounds of any of formulas (Va), (Va-1), (Va-2), (Va-3), (Va-1a), (Va-2a), (Va-3a), (Va-1a-1), (Va-2a-1), (Va-1b), (Va-2b), (Va-3b), (Va-1b-1), (Va-2b-1), (Va-6), (Va-6a), (Va-6b), (Va-6c) or (Va-6d), wherein the aromatic ring containing $Y^4$, $Y^5$, $Y^6$, $Y^7$ and $Y^8$ is optionally substituted with from (i) 1-3 $R^9$ groups; or (ii) 1-3 $R^c$ substituents; or (iii) 1-3 $R^d$ substituents; or (iv) 1-3 $R^{15}$ substituents; or (v) 1-3 $R^{16}$ substituents; or (vi) 1-3 $R^7$ substituents; or (vii) 1-3 $R^{18}$ substituents; (viii) 1-3 $R^{19}$ substituents; or (ix) 1-3 $R^{20}$ substituents independently selected from —CN, F, Cl, I, —OCH$_3$, C$_{1-6}$alkyl, cyclopropyl, 1-azetidinyl, 2-azetidinyl, 3-azetidinyl, 2-oxetanyl, 3-oxetanyl, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH—, EtNHSO$_2$—, PhNHSO$_2$—, CH$_3$SO$_2$NH—, EtSO$_2$NH—, PhSO$_2$NH—, CH$_3$SO$_2$, EtSO$_2$, PhSO$_2$—, 4-morpholinyl, EtOC(O)NH—, CH$_3$OC(O)NH—, EtNHC(O)NH—, CH$_3$NHC(O)NH—, EtOC(O)O— or CH$_3$OC(O)O—, wherein each of $R^9$, $R^c$, $R^d$, $R^{15}$, $R^{16}$, $R^{17}$, $R^{18}$, $R^{19}$ or $R^{20}$ substituent is further optionally substituted with from 1-3 $R^{19}$ substituents independently selected from —CN, F, Cl, I, —OCH$_3$, C$_{1-6}$alkyl, cyclopropyl, 2-oxetanyl, 3-oxetanyl, —OH, —NH$_2$, —NHCH$_3$, —N(CH$_3$)$_2$, —CH$_2$F, —CHF$_2$, CF$_3$, —OCF$_3$, —OCHF$_2$, —OCH$_2$F, CH$_3$C(O)—, CH$_3$C(O)O—, CH$_3$OC(O)—, CH$_3$NHC(O)—, CH$_3$C(O)NH—, (CH$_3$)$_2$NC(O)—, (CH$_3$)$_2$NS(O)$_2$—, (CH$_3$)$_2$S(O)$_2$NH— or CH$_3$SO$_2$. In some instances, the aromatic ring containing $Y^4$, $Y^5$, $Y^6$, $Y^7$ and $Y^8$ is an optionally substituted benzene ring. In other instances, the aromatic ring containing $Y^4$, $Y^5$, $Y^6$, $Y^7$ and $Y^8$ is an optionally substituted pyridine ring, wherein $Y^4$ is N; or $Y^5$ is N or $Y^6$ is N. In other instances, the aromatic ring containing $Y^4$, $Y^5$, $Y^6$, $Y^7$ and $Y^8$ is an optionally substituted pyrimidine ring, wherein $Y^4$ and $Y^6$ are N; or $Y^4$ and $Y^8$ are N; or $Y^5$ and $Y^7$ are N. In other instances, the aromatic ring containing $Y^4$, $Y^5$, $Y^6$, $Y^7$ and $Y^8$ is an optionally substituted pyrazine ring, wherein $Y^4$ and $Y^7$ are N. In other instances, the aromatic ring containing $Y^4$, $Y^5$, $Y^6$, $Y^7$ and $Y^8$ is an optionally substituted pyridazine ring, wherein $Y^4$ and $Y^5$ are N; or $Y^5$ and $Y^6$ are N. In some embodiments, the optional substituents for the benzene, pyridine, pyrimidine, pyrazine or pyridazine rings are (i) 1-3 $R^9$ groups; or (ii) 1-3 $R^c$ substituents; or (iii) 1-3 $R^d$ substituents; or (iv) 1-3 $R^{15}$ substituents; or (v) 1-3 $R^{16}$ substituents; or (vi) 1-3 $R^7$ substituents; or (vii) 1-3 $R^{18}$ substituents; (viii) 1-3 $R^{19}$ substituents; or (ix) 1-3 $R^{20}$ substituents.

In some embodiments of compounds of any of formulas (IIIa), (IIIb), (IIIc), (IIId), (IIId), (IIIe), (IIIa-1), (IIIa-2), (IIIa-3), (IIIa-4), (IIIa-5), (IIIa-6), (IIIa-7), (IIIa-8), (IIIb-1), (IIIb-2), (IIIb-3), (IIIb-4), (IIIb-5), (IIIc-1), (IIIc-2), (IIIc-3), (IIIc-4), (IIIc-5), (IIId-1), (IIId-2), (IIId-3), (IIId-4), (IIId-5), (IIIe-1), (IIIe-2), (IIIe-3), (IIIe-4), (IIIe-5), (IVa), (IVa-1), (IVa-2), (IVa-3), (IVa-4), (IVa-5), (IVa-6), (IVa-7), (IVa-8), (IVa-9), (IVa-10), (IVa-1a), (IVa-2a), (IVa-3a), (IVa-4a), (IVa-5a), (IVa-6a), (IVa-7a), (IVa-8a), (IVa-9a), (IVa-10a), (IVa-1b), (IVa-2b), (IVa-5b), (IVa-6b), (IVb), (IVb-1), (IVb-2), (IVb-3), (IVb-4), (IVb-5), (IVb-6), (IVb-7), (IVb-8), (IVc), (IVc-1), (IVc-2), (IVc-3), (IVc-4), (IVc-5), (IVd), (IVd-1), (IVd-2), (IVd-3), (IVd-4), (IVd-5), (IVe), (IVe-1), (IVe-2), (IVe-3), (IVe-4), (IVe-5), (V), (V'), (Va), (Va-1), (Va-2), (Va-3), (Va-1a), (Va-2a), (Va-3a), (Va-1a-1), (Va-2a-1), (Va-1b), (Va-2b), (Va-3b), (Va-1b-1), (Va-2b-1), (Va-6), (Va-6a), (Va-6b), (Va-6c) or (Va-6d), $R^3$ and $R^4$ are each independently selected from H, $C_{1-6}$alkyl, halogen, CN, cyclopropyl, CN—$CH_2$—, phenyl, cyclopropylmethyl, $C_{1-6}$alkoxy, $C_{1-6}$haloalkyl, $C_{1-6}$haloalkoxy or $R^g$. In other instances, $R^3$ and $R^4$ are each independently selected from H, —$CH_3$, —$CD_3$, —$C_6D5$, —$CF_3$, —$CHF_2$, —$CH_2F$, —$OCF_3$, —$OCHF_2$, —$OCH_2F$ halogen, CN, cyclopropyl, CN—$CH_2$—, phenyl, cyclopropylmethyl or —$OCH_3$. In yet other instances, $R^3$ and $R^4$ are each independently H, F, Cl, Br, $NH_2C(O)$—, $CH_3$, $CD_3$, Et, cyclopropyl, CN, $CH_2CH_2$— or $CH_3C(O)NH$—. In other instances, $R^3$ and $R^4$ are D. In other instances, $R^3$ and $R^4$ are $C_{1-6}$alkyl. In other instances, $R^3$ and $R^4$ are $C_{1-4}$alkoxy.

In some embodiments, the disclosure provides any of the compounds set forth in Table 1, or pharmaceutically acceptable salts, hydrates, solvates, tautomers or isomers thereof. In certain embodiments, the disclosure provides the above selected compounds and pharmaceutically acceptable salts thereof. In certain embodiments, the disclosure provides any of compounds P-2001 to P-2273 and P-2274 to P-2307 as described herein or pharmaceutically acceptable salts, hydrates, solvates, tautomers or isomers thereof. In certain embodiments, the disclosure provides any of the compounds described in formulas (I'), (I'a), (I), (II), (III), (IV), or any of the subformulas as described herein, any of the compounds described in the examples and any of the compounds described herein, or pharmaceutically acceptable salts, hydrates, solvates, tautomers or isomers thereof.

In some embodiments, the disclosure provides a compound selected from:
(2-phenyl-1H-pyrrolo[2,3-b]pyridin-5-yl)-(3-pyridyl)methanol (P-2001),
(2-phenyl-1H-pyrrolo[2,3-b]pyridin-5-yl)-(3-pyridyl)methanone (P-2002),
N-(3-carbamoylphenyl)-2-phenyl-1H-pyrrolo[2,3-b]pyridine-5-carboxamide (P-2003),
2-phenyl-N-(1H-pyrazol-3-yl)-1H-pyrrolo[2,3-b]pyridine-5-carboxamide (P-2004),
4-bromo-N-(2-phenyl-1H-pyrrolo[2,3-b]pyridin-5-yl)-1H-pyrazole-5-carboxamide, (P-2005),
ethyl 3-[(2-phenyl-1H-pyrrolo[2,3-b]pyridin-5-yl)carbamoylamino]propanoate, (P-2006),
3,4-dimethyl-N-(2-phenyl-1H-pyrrolo[2,3-b]pyridin-5-yl)-1H-pyrazole-5-carboxamide (P-2007),
4-methyl-3-phenyl-N-(2-phenyl-1H-pyrrolo[2,3-b]pyridin-5-yl)-1H-pyrazole-5-carboxamide, (P-2008),
3-cyclopropyl-N-(2-phenyl-1H-pyrrolo[2,3-b]pyridin-5-yl)-1H-pyrazole-5-carboxamide, (P-2009),
5-fluoro-N-(2-phenyl-1H-pyrrolo[2,3-b]pyridin-5-yl)-1H-indazole-3-carboxamide (P-2010),
N-(2-phenyl-1H-pyrrolo[2,3-b]pyridin-5-yl)pyrimidine-4-carboxamide (P-2011),
3-fluoro-N-(2-phenyl-1H-pyrrolo[2,3-b]pyridin-5-yl)pyridine-2-carboxamide (P-2012),
3,5-dimethyl-N-(2-phenyl-1H-pyrrolo[2,3-b]pyridin-5-yl)isoxazole-4-carboxamide (P-2013),
N-(2-phenyl-1H-pyrrolo[2,3-b]pyridin-5-yl)pyridazine-3-carboxamide (P-2014),
N-(2-phenyl-1H-pyrrolo[2,3-b]pyridin-5-yl)-2H-triazole-4-carboxamide (P-2015),
3-methyl-N-(2-phenyl-1H-pyrrolo[2,3-b]pyridin-5-yl)pyridine-2-carboxamide (P-2016),
4,5-dimethyl-N-(2-phenyl-1H-pyrrolo[2,3-b]pyridin-5-yl)isoxazole-3-carboxamide (P-2017),
N-(2-phenyl-1H-pyrrolo[2,3-b]pyridin-5-yl)-1H-pyrazole-4-sulfonamide (P-2018),
N-[2-(4-fluorophenyl)-1H-pyrrolo[2,3-b]pyridin-5-yl]-3-methyl-1H-pyrazole-5-carboxamide (P-2019),
N3-[2-(4-fluorophenyl)-1H-pyrrolo[2,3-b]pyridin-5-yl]benzene-1,3-dicarboxamide (P-2020),
3-(cyanomethyl)-N-[2-(4-fluorophenyl)-1H-pyrrolo[2,3-b]pyridin-5-yl]benzamide (P-2021),
2-chloro-N-[2-(4-fluorophenyl)-1H-pyrrolo[2,3-b]pyridin-5-yl]-6-methyl-benzamide (P-2022),
4-chloro-N-[2-(4-fluorophenyl)-1H-pyrrolo[2,3-b]pyridin-5-yl]-3-methyl-1H-pyrazole-5-carboxamide (P-2023),
N-[2-(4-fluorophenyl)-1H-pyrrolo[2,3-b]pyridin-5-yl]-3,4-dimethyl-1H-pyrazole-5-carboxamide(P-2024),
3-cyano-N-[2-(4-fluorophenyl)-1H-pyrrolo[2,3-b]pyridin-5-yl]benzamide (P-2025),
3-acetamido-N-[2-(4-fluorophenyl)-1H-pyrrolo[2,3-b]pyridin-5-yl]benzamide (P-2026),
N-[2-(4-fluorophenyl)-1H-pyrrolo[2,3-b]pyridin-5-yl]-2H-indazole-4-carboxamide (P-2027),
3-ethyl-N-[2-(4-fluorophenyl)-1H-pyrrolo[2,3-b]pyridin-5-yl]-4-methyl-1H-pyrazole-5-carboxamide (P-2028),
N-[2-(4-fluorophenyl)-1H-pyrrolo[2,3-b]pyridin-5-yl]-4-methyl-1H-pyrazole-3-carboxamide (P-2029),
2-ethyl-N-[2-(4-fluorophenyl)-1H-pyrrolo[2,3-b]pyridin-5-yl]pyrazole-3-sulfonamide (P-2030),
5-methyl-N-[2-[1-(morpholine-4-carbonyl)-3,6-dihydro-2H-pyridin-4-yl]-1H-pyrrolo[2,3-b]pyridin-5-yl]-1H-pyrazole-3-carboxamide (P-2031),
3,4-dimethyl-N-(1H-pyrrolo[2,3-b]pyridin-5-yl)-1H-pyrazole-5-carboxamide (P-2032),
N-[1-(benzenesulfonyl)-2-[1-(morpholine-4-carbonyl)-3,6-dihydro-2H-pyridin-4-yl]pyrrolo[2,3-b]pyridin-5-yl]-3,4-dimethyl-1H-pyrazole-5-carboxamide (P-2033),
3,4-dimethyl-N-[2-[1-(morpholine-4-carbonyl)-3,6-dihydro-2H-pyridin-4-yl]-1H-pyrrolo[2,3-b]pyridin-5-yl]-1H-pyrazole-5-carboxamide (P-2034), N-[2-(4-fluorophenyl)-1H-pyrrolo[2,3-b]pyridin-5-yl]-1H-1,2,4-triazole-5-carboxamide (P-2035), 4-chloro-3-methyl-N-[2-[1-(morpholine-4-carbonyl)-3,6-dihydro-2H-pyridin-4-yl]-1H-pyrrolo[2,3-b]pyridin-5-yl]-1H-pyrazole-5-carboxamide (P-2036), N-[2-(4-fluorophenyl)-1H-pyrrolo[2,3-b]pyridin-5-yl]-5-methyl-2H-triazole-4-carboxamide (P-2037), N-[2-(1,3-dimethylpyrazol-4-yl)-1H-pyrrolo[2,3-b]pyridin-5-yl]-3,4-dimethyl-1H-pyrazole-5-carboxamide (P-2038), 4-chloro-N-[2-[1-(cyclopropanecarbonyl)-3,6-dihydro-2H-pyridin-4-yl]-1H-pyrrolo[2,3-b]pyridin-5-yl]-5-methyl-1H-pyrazole-3-carboxamide (P-2039), 3,4-dimethyl-N-(3-methyl-1H-pyrazolo[3,4-b]pyridin-5-yl)-1H-pyrazole-5-carboxamide (P-2040), N-[3-(4-fluorophenyl)-1H-pyrazolo[3,4-b]pyridin-5-yl]-3,4-dimethyl-1H-pyrazole-5-carboxamide (P-2041), N-[2-[1-(cyclopropanecarbonyl)-3,6-dihydro-2H-pyridin-4-yl]-1H-pyrrolo[2,3-b]pyridin-5-yl]-5-methyl-1H-pyrazole-3-carboxamide (P-2042), N-[2-[1-(cyclopropanecarbonyl)-3,6-dihydro-2H-pyridin-4-yl]-1H-pyrrolo[2,3-b]pyridin-5-yl]-4,5-dimethyl-1H-pyrazole-3-carboxamide (P-2043), N-(2-anilinopyrimidin-5-yl)-3,4-dimethyl-1H-pyrazole-5-carboxamide (P-2044), N-(6-anilino-3-pyridyl)-3,4-dimethyl-1H-pyrazole-5-carboxamide (P-2045), N-[2-(4-fluorophenyl)-1H-pyrrolo[2,3-b]pyridin-5-yl]-1H-indazole-3-carboxamide (P-2046), N-[2-(4-fluorophenyl)-1H-pyrrolo[2,3-b]pyridin-5-yl]-4,5,6,7-tetrahydro-1H-indazole-3-carboxamide (P-2047), 3,4-dimethyl-N-[2-[1-(4-piperidyl)pyrazol-4-yl]-1H-pyrrolo[2,3-b]pyridin-5-yl]-1H-pyrazole-5-carboxamide (P-2048), N-(2-chloro-1H-pyrrolo[2,3-b]pyridin-5-yl)-3,4-dimethyl-1H-pyrazole-5-carboxamide (P-2049), N-[2-[3-(ethylsulfamoyl)anilino]pyrimidin-5-yl]-3,4-dimethyl-1H-pyrazole-5-carboxamide (P-2050), 3,4-dimethyl-N-[2-(3-morpholinoanilino)pyrimidin-5-yl]-1H-pyrazole-5-carboxamide (P-2051), 3,4-dimethyl-N-[2-[3-(propylsulfonylamino)anilino]pyrimidin-5-yl]-1H-pyrazole-5-carboxamide (P-2052), N-[2-[3-(benzenesulfonamido)anilino]pyrimidin-5-yl]-3,4-dimethyl-1H-pyrazole-5-carboxamide (P-2053), 3,4-dimethyl-N-[2-[3-(methylcarbamoyl)anilino]pyrimidin-5-yl]-1H-pyrazole-5-carboxamide (P-2054), ethyl N-[3-[[5-[(3,4-dimethyl-1H-pyrazole-5-carbonyl)amino]pyrimidin-2-yl]amino]phenyl]carbamate (P-2055), N-[2-(4-fluorophenyl)-1H-pyrrolo[2,3-b]pyridin-5-yl]-1,4,5,6-tetrahydrocyclopenta[c]pyrazole-3-carboxamide (P-2056), 4-chloro-3-methyl-N-[2-(1-methylsulfonyl-3,6-dihydro-2H-pyridin-4-yl)-1H-pyrrolo[2,3-b]pyridin-5-yl]-1H-pyrazole-5-carboxamide (P-2057), 3-methyl-N-(2-morpholino-1H-pyrrolo[2,3-b]pyridin-5-yl)-1H-pyrazole-5-carboxamide (P-2058), 4,5-dimethyl-N-[2-(4-morpholinophenyl)-1H-pyrrolo[2,3-b]pyridin-5-yl]-1H-pyrazole-3-carboxamide (P-2059), 4-chloro-N-[2-[1-(cyclopropanecarbonyl)-2,5-dihydropyrrol-3-yl]-1H-pyrrolo[2,3-b]pyridin-5-yl]-3-methyl-1H-pyrazole-5-carboxamide (P-2060), N-[2-(1-acetyl-3,6-dihydro-2H-pyridin-4-yl)-1H-pyrrolo[2,3-b]pyridin-5-yl]-4-chloro-3-methyl-1H-pyrazole-5-carboxamide (P-2061), 4-chloro-3-methyl-N-[2-[1-(morpholine-4-carbonyl)-2,5-dihydropyrrol-3-yl]-1H-pyrrolo[2,3-b]pyridin-5-yl]-1H-pyrazole-5-carboxamide (P-2062), N-[2-(3-fluoroprop-1-ynyl)-1H-pyrrolo[2,3-b]pyridin-5-yl]-3,4-dimethyl-1H-pyrazole-5-carboxamide (P-2063), N-[2-[3-(dimethylamino)phenyl]-1H-pyrrolo[2,3-b]pyridin-5-yl]-3,4-dimethyl-1H-pyrazole-5-carboxamide (P-2064), N-[2-(3,5-dimethylisoxazol-4-yl)-1H-pyrrolo[2,3-b]pyridin-5-yl]-3,4-dimethyl-1H-pyrazole-5-carboxamide (P-2065), 3,4-dimethyl-N-[2-[3-(2-morpholinoethoxy)phenyl]-1H-pyrrolo[2,3-b]pyridin-5-yl]-1H-pyrazole-5-carboxamide (P-2066), 3,4-dimethyl-N-[2-[4-(methylcarbamoyl)phenyl]-1H-pyrrolo[2,3-b]pyridin-5-yl]-1H-pyrazole-5-carboxamide (P-2067), N-[2-(3-fluoroprop-1-ynyl)-1H-pyrrolo[2,3-b]pyridin-5-yl]-3-methyl-1H-pyrazole-5-carboxamide (P-2068), 4,5-dimethyl-N-[2-[2-(4-methylpiperazin-1-yl)-4-pyridyl]-1H-pyrrolo[2,3-b]pyridin-5-yl]-1H-pyrazole-3-carboxamide (P-2069), 4,5-dimethyl-N-[2-(3-morpholinophenyl)-1H-pyrrolo[2,3-b]pyridin-5-yl]-1H-pyrazole-3-carboxamide (P-2070), N-(4,5-dimethyl-1H-pyrazol-3-yl)-2-phenyl-1H-pyrrolo[2,3-b]pyridine-5-carboxamide (P-2071), N-[2-(4-fluorophenyl)pyrazolo[1,5-a]pyrimidin-6-yl]-4,5-dimethyl-1H-pyrazole-3-carboxamide (P-2072), 3,4-dimethyl-N-[2-[1-(2-morpholinoacetyl)-3,6-dihydro-2H-pyridin-4-yl]-1H-pyrrolo[2,3-b]pyridin-5-yl]-1H-pyrazole-5-carboxamide (P-2073), N-[2-[1-(2,3-dihydroxypropanoyl)-3,6-dihydro-2H-pyridin-4-yl]-1H-pyrrolo[2,3-b]pyridin-5-yl]-3,4-dimethyl-1H-pyrazole-5-carboxamide (P-2074), N-[2-(2-chloro-4-methoxy-phenyl)-1H-pyrrolo[2,3-b]pyridin-5-yl]-3,4-dimethyl-1H-pyrazole-5-carboxamide (P-2075), N-[2-(2-fluoro-4-methoxy-phenyl)-1H-pyrrolo[2,3-b]pyridin-5-yl]-3,4-dimethyl-1H-pyrazole-5-carboxamide (P-2076), N-[2-(2-chloro-5-methoxy-phenyl)-1H-pyrrolo[2,3-b]pyridin-5-yl]-3,4-dimethyl-1H-pyrazole-5-carboxamide (P-2077), N-[2-(3-fluoro-5-morpholino-phenyl)-1H-pyrrolo[2,3-b]pyridin-5-yl]-3,4-dimethyl-1H-pyrazole-5-carboxamide (P-2078), 3,4-dimethyl-N-[2-(3-pyrrolidin-1-ylphenyl)-1H-pyrrolo[2,3-b]pyridin-5-yl]-1H-pyrazole-5-carboxamide (P-2079), N-[2-(4-aminocyclohexen-1-yl)-1H-pyrrolo[2,3-b]pyridin-5-yl]-3,4-dimethyl-1H-pyrazole-5-carboxamide (P-2080), N-[2-(4-cyano-3-morpholino-phenyl)-1H-pyrrolo[2,3-b]pyridin-5-yl]-3,4-dimethyl-1H-pyrazole-5-carboxamide (P-2081), N-[2-(3-fluoro-2-morpholino-4-pyridyl)-1H-pyrrolo[2,3-b]pyridin-5-yl]-3,4-dimethyl-1H-pyrazole-5-carboxamide (P-2082), N-[2-(1-isobutylpyrazol-4-yl)-1H-pyrrolo[2,3-b]pyridin-5-yl]-3,4-dimethyl-1H-pyrazole-5-carboxamide (P-2083), N-[2-(1,5-dimethylpyrazol-4-yl)-1H-pyrrolo[2,3-b]pyridin-5-yl]-3,4-dimethyl-1H-pyrazole-5-carboxamide (P-2084), N-[2-[4-(dimethylcarbamoyl)phenyl]-1H-pyrrolo[2,3-b]pyridin-5-yl]-3,4-dimethyl-1H-pyrazole-5-carboxamide (P-2085), 3,4-dimethyl-N-[2-[3-(trifluoromethoxy)phenyl]-1H-pyrrolo[2,3-b]pyridin-5-yl]-1H-pyrazole-5-carboxamide (P-2086), N-[2-[3-(dimethylcarbamoyl)phenyl]-1H-pyrrolo[2,3-b]pyridin-5-yl]-3,4-dimethyl-1H-pyrazole-5-carboxamide (P-2087), 3,4-dimethyl-N-[2-(3-pyridyl)-1H-pyrrolo[2,3-b]pyridin-5-yl]-1H-pyrazole-5-carboxamide (P-2088), 3,4-dimethyl-N-[2-(6-morpholino-3-pyridyl)-1H-pyrrolo[2,3-b]pyridin-5-yl]-1H-pyrazole-5-carboxamide (P-2089), N-[2-(6-methoxy-3-pyridyl)-1H-pyrrolo[2,3-b]pyridin-5-yl]-3,4-dimethyl-1H-pyrazole-5-carboxamide (P-2090), 3,4-dimethyl-N-[2-(2-methylthiazol-5-yl)-1H-pyrrolo[2,3-b]pyridin-5-yl]-1H-pyrazole-5-carboxamide (P-2091), N-[2-(4-cyanophenyl)-1H-pyrrolo[2,3-b]pyridin-5-yl]-3,4-dimethyl-1H-pyrazole-5-carboxamide (P-2092), N-[2-(2-fluorophenyl)-1H-pyrrolo[2,3-b]pyridin-5-yl]-3,4-dimethyl-1H-pyrazole-5-carboxamide (P-2093), N-[2-(3-fluorophenyl)-1H-pyrrolo[2,3-b]pyridin-5-yl]-3,4-dimethyl-1H-pyrazole-5-carboxamide (P-2094), N-[2-(3-chlorophenyl)-1H-pyrrolo[2,3-b]pyridin-5-yl]-3,4-dimethyl-1H-pyrazole-5-carboxamide (P-2095), N-[2-(2-chlorophenyl)-1H-pyrrolo[2,3-b]pyridin-5-yl]-3,4-dimethyl-1H-pyrazole-5-carboxamide (P-2096), 3,4-dimethyl-N-[2-(o-tolyl)-1H-pyrrolo[2,3-b]pyridin-5-yl]-1H-pyrazole-5-carboxamide (P-2097), N-[2-(3-methoxypheny)-1H-pyrrolo[2,3-b]pyridin-5-yl]-3,4-dimethyl-1H-pyrazole-5-carboxamide (P-2098), N-[2-(4-methoxypheny)-1H-pyrrolo[2,3-b]pyridin-5-yl]-3,4-dimethyl-1H-pyrazole-5-carboxamide (P-2099), N-[2-(3-acetamidophenyl)-1H-pyrrolo[2,3-b]pyridin-5-yl]-3,4-dimethyl-1H-pyrazole-5-carboxamide (P-2100), 3,4-dimethyl-N-[2-[4-(pyrrolidine-1-carbonyl)phenyl]-1H-pyrrolo[2,3-b]pyridin-5-yl]-1H-pyrazole-5-carboxamide (P-2101), N-[2-[4-(3-methoxypropoxy)phenyl]-1H-pyrrolo[2,3-b]pyridin-5-yl]-3,4-dimethyl-1H-pyrazole-5-carboxamide (P-2102), 3,4-dimethyl-N-[2-[4-(4-methylpiperazin-1-yl)phenyl]-1H-pyrrolo[2,3-b]pyridin-5-yl]-1H-pyrazole-5-carboxamide (P-2104), 3,4-dimethyl-N-[2-[4-(thiomorpholine-4-carbonyl)phenyl]-1H-pyrrolo[2,3-b]pyridin-5-yl]-1H-pyrazole-5-carboxamide (P-2105), 3,4-dimethyl-N-[2-[3-(morpholine-4-carbonyl)phenyl]-1H-pyrrolo[2,3-b]pyridin-5-yl]-1H-pyrazole-5-carboxamide (P-2106), 3,4-dimethyl-N-[2-[3-(pyrrolidine-1-carbonyl)phenyl]-1H-pyrrolo[2,3-b]pyridin-5-yl]-1H-pyrazole-5-carboxamide (P-2107), N-[2-(2-cyclopropyl-4-pyridyl)-1H-pyrrolo[2,3-b]pyridin-5-yl]-3,4-dimethyl-1H-pyrazole-5-carboxamide (P-2108), N-[2-(2-methoxy-4-pyridyl)-1H-pyrrolo[2,3-b]pyridin-5-yl]-3,4-dimethyl-1H-pyrazole-5-carboxamide (P-2109), 3,4-dimethyl-N-[2-(2-morpholino-4-pyridyl)-1H-pyrrolo[2,3-b]pyridin-5-yl]-1H-pyrazole-5-carboxamide (P-2110), N-[2-[4-(methanesulfonamido)phenyl]-1H-pyrrolo[2,3-b]pyridin-5-yl]-3,4-dimethyl-1H-pyrazole-5-carboxamide (P-2111), 3,4-dimethyl-N-(2-pyrazol-1-yl-1H-pyrrolo[2,3-b]pyridin-5-yl-1H-pyrazole-5-carboxamide (P-2112), N-[2-[2-chloro-5-(trifluoromethoxy)phenyl]-1H-pyrrolo[2,3-b]pyridin-5-yl]-3,4-dimethyl-1H-pyrazole-5-carboxamide (P-2113), 4,5-dimethyl-N-(2-methylpyrazolo[1,5-a]pyrimidin-6-yl)-1H-pyrazole-3-carboxamide (P-2114), 3,4-dimethyl-N-(2-pyrrolidin-1-yl-1H-pyrrolo[2,3-b]pyridin-5-yl)-1H-pyrazole-5-carboxamide (P-2115)

3-methyl-N-(2-pyrazol-1-yl-1H-pyrrolo[2,3-b]pyridin-5-yl)-1H-pyrazole-5-carboxamide (P-2116), N-[2-[4-(methanesulfonamido)phenyl]-1H-pyrrolo[2,3-b]pyridin-5-yl]-3,4-dimethyl-1H-pyrazole-5-carboxamide (P-2117), N-[2-[3-[4-(cyclopropanecarbonyl)piperazin-1-yl]phenyl]-1H-pyrrolo[2,3-b]pyridin-5-yl]-3,4-dimethyl-1H-pyrazole-5-carboxamide (P-2118), N-[2-(4-fluorophenyl)-1H-pyrrolo[2,3-b]pyridin-5-yl]-1,5-dimethyl-pyrazole-3-carboxamide (P-2119), N-[2-(4-cyano-3-pyrrolidin-1-yl-phenyl)-1H-pyrrolo[2,3-b]pyridin-5-yl]-3,4-dimethyl-1H-pyrazole-5-carboxamide (P-2120), 3,4-dimethyl-N-[2-[3-(methylsulfamoyl)phenyl]-1H-pyrrolo[2,3-b]pyridin-5-yl]-1H-pyrazole-5-carboxamide (P-2121), N-[2-(4-chlorophenyl)-1H-pyrrolo[2,3-b]pyridin-5-yl]-3,4-dimethyl-1H-pyrazole-5-carboxamide (P-2122), 3,4-dimethyl-N-[2-(6-methyl-3-pyridyl)-1H-pyrrolo[2,3-b]pyridin-5-yl]-1H-pyrazole-5-carboxamide (P-2123), 3,4-dimethyl-N-[2-(4-pyridyl)-1H-pyrrolo[2,3-b]pyridin-5-yl]-1H-pyrazole-5-carboxamide (P-2124), 3,4-dimethyl-N-[2-(4-pyrrolidin-1-ylphenyl)-1H-pyrrolo[2,3-b]pyridin-5-yl]-1H-pyrazole-5-carboxamide (P-2125), 3,4-dimethyl-N-[2-[3-(propylsulfonylamino)phenyl]-1H-pyrrolo[2,3-b]pyridin-5-yl]-1H-pyrazole-5-carboxamide (P-2126), N-[2-(4-dimethylphosphorylphenyl)-1H-pyrrolo[2,3-b]pyridin-5-yl]-3,4-dimethyl-1H-pyrazole-5-carboxamide (P-2127), N-[2-(3-cyanophenyl)-1H-pyrrolo[2,3-b]pyridin-5-yl]-3,4-dimethyl-1H-pyrazole-5-carboxamide (P-2128), N-[2-(2-fluoro-3-methoxy-phenyl)-1H-pyrrolo[2,3-b]pyridin-5-yl]-3,4-dimethyl-1H-pyrazole-5-carboxamide (P-2129), 3,4-dimethyl-N-[2-(m-tolyl)-1H-pyrrolo[2,3-b]pyridin-5-yl]-1H-pyrazole-5-carboxamide (P-2130), N-[2-(4-fluorophenyl)-1H-pyrrolo[2,3-b]pyridin-5-yl]-3-methyl-1H-1,2,4-triazole-5-carboxamide (P-2131), N-[2-(4-fluorophenyl)-1H-pyrrolo[2,3-b]pyridin-5-yl]-3-propyl-1H-pyrazole-5-carboxamide (P-2132), N-[2-(6-acetamido-3-pyridyl)-1H-pyrrolo[2,3-b]pyridin-5-yl]-3,4-dimethyl-1H-pyrazole-5-carboxamide (P-2133), N-[2-[3-(butylcarbamoylamino)phenyl]-1H-pyrrolo[2,3-b]pyridin-5-yl]-3,4-dimethyl-1H-pyrazole-5-carboxamide (P-2134), N-[2-(2-methoxypheny)-1H-pyrrolo[2,3-b]pyridin-5-yl]-3,4-dimethyl-1H-pyrazole-5-carboxamide (P-2135), 3,4-dimethyl-N-[2-(2-methyl-3-pyridyl)-1H-pyrrolo[2,3-b]pyridin-5-yl]-1H-pyrazole-5-carboxamide (P-2136), N-[2-(4-acetamidophenyl)-1H-pyrrolo[2,3-b]pyridin-5-yl]-3,4-dimethyl-1H-pyrazole-5-carboxamide (P-2137), 3,4-dimethyl-N-[2-[4-(morpholine-4-carbonyl)phenyl]-1H-pyrrolo[2,3-b]pyridin-5-yl]-1H-pyrazole-5-carboxamide (P-2138), N-[2-(2,4-dimethylthiazol-5-yl)-1H-pyrrolo[2,3-b]pyridin-5-yl]-3,4-dimethyl-1H-pyrazole-5-carboxamide (P-2139), N-[2-[1-(difluoromethyl)pyrazol-4-yl]-1H-pyrrolo[2,3-b]pyridin-5-yl]-3,4-dimethyl-1H-pyrazole-5-carboxamide (P-2140), N-[(4-chloro-3-methyl-1H-pyrazol-5-yl)methyl]-2-(4-fluorophenyl)-1H-pyrrolo[2,3-b]pyridin-5-amine (P-2141), 2-(4-fluorophenyl)-N-[(3-methyl-1H-pyrazol-5-yl)methyl]-1H-pyrrolo[2,3-b]pyridin-5-amine (P-2142), N-[2-(4-fluorophenyl)-1H-pyrrolo[2,3-b]pyridin-5-yl]-1H-pyrazole-5-carboxamide (P-2143), 3,4-dimethyl-N-(2-phenylthiazolo[5,4-b]pyridin-6-yl)-1H-pyrazole-5-carboxamide (P-2144), 3,4-dimethyl-N-(2-phenyl-3H-imidazo[4,5-b]pyridin-6-yl)-1H-pyrazole-5-carboxamide (P-2145), N-[2-(3-fluoro-2-methyl-phenyl)-1H-pyrrolo[2,3-b]pyridin-5-yl]-3,4-dimethyl-1H-pyrazole-5-carboxamide (P-2146), N-[2-(3-chloro-2-methyl-phenyl)-1H-pyrrolo[2,3-b]pyridin-5-yl]-3,4-dimethyl-1H-pyrazole-5-carboxamide (P-2147), N-[2-[4-(cyclopropylcarbamoyl)phenyl]-1H-pyrrolo[2,3-b]pyridin-5-yl]-3,4-dimethyl-1H-pyrazole-5-carboxamide (P-2148), 3,4-dimethyl-N-[2-[4-[(3-methyloxetan-3-yl)methoxy]phenyl]-1H-pyrrolo[2,3-b]pyridin-5-yl]-1H-pyrazole-5-carboxamide (P-2149), 4-chloro-3-methyl-N-(2-phenyl-3H-imidazo[4,5-b]pyridin-6-yl)-1H-pyrazole-5-carboxamide (P-2150), 3-methyl-N-(2-phenyl-3H-imidazo[4,5-b]pyridin-6-yl)-1H-pyrazole-5-carboxamide (P-2151), N-[2-(2-fluorophenyl)-3H-imidazo[4,5-b]pyridin-6-yl]-3,4-dimethyl-1H-pyrazole-5-carboxamide (P-2152), N-[2-(2-ethoxypyrimidin-5-yl)-1H-pyrrolo[2,3-b]pyridin-5-yl]-3,4-dimethyl-1H-pyrazole-5-carboxamide (P-2153), N-[2-(2-isopropylpyrimidin-5-yl)-1H-pyrrolo[2,3-b]pyridin-5-yl]-3,4-dimethyl-1H-pyrazole-5-carboxamide (P-2154), N-[2-(2-cyclopropylpyrimidin-5-yl)-1H-pyrrolo[2,3-b]pyridin-5-yl]-3,4-dimethyl-1H-pyrazole-5-carboxamide (P-2155), N-[2-(4-fluorophenyl)-1H-pyrrolo[2,3-b]pyridin-5-yl]-3-(trifluoromethyl)-1H-pyrazole-5-carboxamide (P-2156), N-[2-[2-(cyclopropylamino)pyrimidin-5-yl]-1H-pyrrolo[2,3-b]pyridin-5-yl]-3,4-dimethyl-1H-pyrazole-5-carboxamide (P-2157), 3,4-dimethyl-N-[2-(2-morpholinopyrimidin-5-yl)-1H-pyrrolo[2,3-b]pyridin-5-yl]-1H-pyrazole-5-carboxamide (P-2158), 3-ethyl-N-[2-(4-fluorophenyl)-1H-pyrrolo[2,3-b]pyridin-5-yl]-1H-pyrazole-5-carboxamide (P-2159), 3,4-dimethyl-N-[2-[2-(4-methylpiperazin-1-yl)pyrimidin-5-yl]-1H-pyrrolo[2,3-b]pyridin-5-yl]-1H-pyrazole-5-carboxamide (P-2160), N-[2-(4-cyano-2-methyl-phenyl)-1H-pyrrolo[2,3-b]pyridin-5-yl]-3,4-dimethyl-1H-pyrazole-5-carboxamide (P-2161), tert-butyl 4-[3-[5-[(3,4-dimethyl-1H-pyrazole-5-carbonyl)amino]-1H-pyrazolo[3,4-b]pyridin-3-yl]phenyl]piperazine-1-carboxylate (P-2162), N-[2-(2-isopropyl-4-pyridyl)-1H-pyrrolo[2,3-b]pyridin-5-yl]-3,4-dimethyl-1H-pyrazole-5-carboxamide (P-2163), 3,4-dimethyl-N-[2-(2,3,4,5,6-pentadeuteriophenyl)-1H-pyrrolo[2,3-b]pyridin-5-yl]-1H-pyrazole-5-carboxamide (P-2164), 3,4-dimethyl-N-[2-(1,3,5-trimethylpyrazol-4-yl)-1H-pyrrolo[2,3-b]pyridin-5-yl]-1H-pyrazole-5-carboxamide (P-2165), 3,4-dimethyl-N-[3-(3-piperazin-1-ylphenyl)-1H-pyrazolo[3,4-b]pyridin-5-yl]-1H-pyrazole-5-carboxamide (P-2166), N-[2-(3,5-dimethyl-1H-pyrazol-4-yl)-1H-pyrrolo[2,3-b]pyridin-5-yl]-3,4-dimethyl-1H-pyrazole-5-carboxamide (P-2167), 3,4-dimethyl-N-[2-[3-methyl-1-(oxetan-3-yl)pyrazol-4-yl]-1H-pyrrolo[2,3-b]pyridin-5-yl]-1H-pyrazole-5-carboxamide (P-2168), N-[2-(6-methoxy-2-methyl-3-pyridyl)-1H-pyrrolo[2,3-b]pyridin-5-yl]-3,4-dimethyl-1H-pyrazole-5-carboxamide (P-2169), N-[2-(2-methoxy-6-methyl-3-pyridyl)-1H-pyrrolo[2,3-b]pyridin-5-yl]-3,4-dimethyl-1H-pyrazole-5-carboxamide (P-2170), N-[2-(3-chloro-2-methoxy-4-pyridyl)-1H-pyrrolo[2,3-b]pyridin-5-yl]-3,4-dimethyl-1H-pyrazole-5-carboxamide (P-2171), 3-(difluoromethyl)-N-[2-(4-fluorophenyl)-1H-pyrrolo[2,3-b]pyridin-5-yl]-1H-pyrazole-5-carboxamide (P-2172), 4-chloro-3-ethyl-N-[2-(4-fluorophenyl)-1H-pyrrolo[2,3-b]pyridin-5-yl]-1H-pyrazole-5-carboxamide (P-2173), N-[2-[4-fluoro-3-(2H-tetrazol-5-yl)phenyl]-1H-pyrrolo[2,3-b]pyridin-5-yl]-3,4-dimethyl-1H-pyrazole-5-carboxamide (P-2174), N-cyclopropyl-4-[5-[(3,4-dimethyl-1H-pyrazole-5-carbonyl)amino]-1H-pyrrolo[2,3-b]pyridin-2-yl]pyridine-2-carboxamide (P-2175), 3,4-dimethyl-N-[2-[2-(trifluoromethyl)-3-pyridyl]-1H-pyrrolo[2,3-b]pyridin-5-yl]-1H-pyrazole-5-carboxamide (P-2176), N-[2-(2-ethyl-4-pyridyl)-1H-pyrrolo[2,3-b]pyridin-5-yl]-3,4-dimethyl-1H-pyrazole-5-carboxamide (P-2177), N-[2-(6-ethyl-3-pyridyl)-1H-pyrrolo[2,3-b]pyridin-5-yl]-3,4-dimethyl-1H-pyrazole-5-carboxamide (P-2178), N-[2-(2,3-dihydro-[1,4]dioxino[2,3-b]pyridin-8-yl)-1H-pyrrolo[2,3-b]pyridin-5-yl]-3,4-dimethyl-1H-pyrazole-5-carboxamide (P-2179), 3,4-dimethyl-N-[2-[2-(trifluoromethyl)phenyl]-1H-pyrrolo[2,3-b]pyridin-5-yl]-1H-pyrazole-5-carboxamide (P-2180), N-[2-(2,4-dimethylphenyl)-1H-pyrrolo[2,3-b]pyridin-5-yl]-3,4-dimethyl-1H-pyrazole-5-carboxamide (P-2181), 3,4-dimethyl-N-[2-[2-(trifluoromethoxy)phenyl]-1H-pyrrolo[2,3-b]pyridin-5-yl]-1H-pyrazole-5-carboxamide (P-2182), N-[2-(5-methoxy-3-pyridyl)-1H-pyrrolo[2,3-b]pyridin-5-yl]-3,4-dimethyl-1H-pyrazole-5-carboxamide (P-2183), 3,4-dimethyl-N-[2-(5-methyl-3-pyridyl)-1H-pyrrolo[2,3-b]pyridin-5-yl]-1H-pyrazole-5-carboxamide (P-2184), N-[2-(4-methoxy-3-pyridyl)-1H-pyrrolo[2,3-b]pyridin-5-yl]-3,4-dimethyl-1H-pyrazole-5-carboxamide (P-2185), 3,4-dimethyl-N-[2-[2-(4-methylsulfonylpiperazin-1-yl)-4-pyridyl]-1H-pyrrolo[2,3-b]pyridin-5-yl]-1H-pyrazole-5-carboxamide (P-2186), N-[2-[2-[4-(cyclopropanecarbonyl)piperazin-1-yl]-4-pyridyl]-1H-pyrrolo[2,3-b]pyridin-5-yl]-3,4-dimethyl-1H-pyrazole-5-carboxamide (P-2187), N-(2-iodo-1H-pyrrolo[2,3-b]pyridin-5-yl)-3,4-dimethyl-1H-pyrazole-5-carboxamide (P-2188), N-[2-[2-[4-(2-cyanoacetyl)piperazin-1-yl]-4-pyridyl]-1H-pyrrolo[2,3-b]pyridin-5-yl]-3,4-dimethyl-1H-pyrazole-5-carboxamide (P-2189), 4,5-dimethyl-N-(3-(6-(piperazin-1-yl)pyridin-2-yl)-1H-pyrrolo[2,3-b]pyridin-5-yl)-1H-pyrazole-3-carboxamide (P-2190), 4,5-dimethyl-N-(3-(6-(piperazin-1-yl)pyridin-2-yl)-1H-pyrrolo[2,3-b]pyridin-5-yl)-1H-pyrazole-3-carboxamide (P-2191), 4,5-dimethyl-N-(3-(6-morpholinopyridin-2-yl)-1H-pyrrolo[2,3-b]pyridin-5-yl)-1H-pyrazole-3-carboxamide (P-2192), 4,5-dimethyl-N-(3-(2-morpholinopyridin-4-yl)-1H-pyrrolo[2,3-b]pyridin-5-yl)-1H-pyrazole-3-carboxamide (P-2193), N-(2-(1-(1-acetylazetidin-3-yl)-3-methyl-1H-pyrazol-4-yl)-1H-pyrrolo[2,3-b]pyridin-5-yl)-4,5-dimethyl-1H-pyrazole-3-carboxamide (P-2194), N-(2-(1-(azetidin-3-yl)-3-methyl-1H-pyrazol-4-yl)-1H-pyrrolo[2,3-b]pyridin-5-yl)-4,5-dimethyl-1H-pyrazole-3-carboxamide (P-2195), 4,5-dimethyl-N-(2-(5-methyl-1-(oxetan-3-yl)-1H-pyrazol-4-yl)-1H-pyrrolo[2,3-b]pyridin-5-yl)-1H-pyrazole-3-carboxamide (P-216), N-(2-(1-(azetidin-3-yl)-5-methyl-1H-pyrazol-4-yl)-1H-pyrrolo[2,3-b]pyridin-5-yl)-4,5-dimethyl-1H-pyrazole-3-carboxamide (P-2197), 4,5-dimethyl-N-(2-(5-methyl-1-(piperidin-4-yl)-1H-pyrazol-4-yl)-1H-pyrrolo[2,3-b]pyridin-5-yl)-1H-pyrazole-3-carboxamide (P-2198), N-(2-(1-(1-acetylpiperidin-4-yl)-5-methyl-1H-pyrazol-4-yl)-1H-pyrrolo[2,3-b]pyridin-5-yl)-4,5-dimethyl-1H-pyrazole-3-carboxamide (P-2199), N-(2-(1-(1-(cyclopropanecarbonyl)piperidin-4-yl)-5-methyl-1H-pyrazol-4-yl)-1H-pyrrolo[2,3-b]pyridin-5-yl)-4,5-dimethyl-1H-pyrazole-3-carboxamide (P-2200), 4,5-dimethyl-N-(2-(3-methyl-1-(piperidin-4-yl)-1H-pyrazol-4-yl)-1H-pyrrolo[2,3-b]pyridin-5-yl)-1H-pyrazole-3-carboxamide (P-2201), N-(2-(1-(1-acetylpiperidin-4-yl)-3-methyl-1H-pyrazol-4-yl)-1H-pyrrolo[2,3-b]pyridin-5-yl)-4,5-dimethyl-1H-pyrazole-3-carboxamide (P-2202), N-(2-(1-(1-(cyclopropanecarbonyl)piperidin-4-yl)-3-methyl-1H-pyrazol-4-yl)-1H-pyrrolo[2,3-b]pyridin-5-yl)-4,5-dimethyl-1H-pyrazole-3-carboxamide (P-2203), N-(2-(2-(cyclopropylamino)pyridin-4-yl)-1H-pyrrolo[2,3-b]pyridin-5-yl)-4,5-dimethyl-1H-pyrazole-3-carboxamide (P-2204), N-(2-(3-chloro-2-(cyclopropanecarboxamido)pyridin-4-yl)-1H-pyrrolo[2,3-b]pyridin-5-yl)-4,5-dimethyl-1H-pyrazole-3-carboxamide (P-2205), N-(2-(2-(cyclopropanecarboxamido)pyridin-4-yl)-1H-pyrrolo[2,3-b]pyridin-5-yl)-4,5-dimethyl-1H-pyrazole-3-carboxamide (P-2206), N-(2-(2-(1-(cyclopropanecarbonyl)piperidin-4-yl)pyridin-4-yl)-1H-pyrrolo[2,3-b]pyridin-5-yl)-4,5-dimethyl-1H-pyrazole-3-carboxamide (P-2207), 4,5-dimethyl-N-(2-(2-(pyrrolidin-1-yl)pyridin-4-yl)-1H-pyrrolo[2,3-b]pyridin-5-yl)-1H-pyrazole-3-carboxamide (P-2208), 4,5-dimethyl-N-(2-(2-(piperidin-1-yl)pyridin-4-yl)-1H-pyrrolo[2,3-b]pyridin-5-yl)-1H-pyrazole-3-carboxamide (P-2209), 4,5-dimethyl-N-(2-(2-(4-methylpiperidin-1-yl)pyridin-4-yl)-1H-pyrrolo[2,3-b]pyridin-5-yl)-1H-pyrazole-3-carboxamide (P-2210), 4,5-dimethyl-N-(2-(2-(piperidin-4-yl)pyridin-4-yl)-1H-pyrrolo[2,3-b]pyridin-5-yl)-1H-pyrazole-3-carboxamide (P-2211), N-(2-(2-(4-hydroxypiperidin-1-yl)pyridin-4-yl)-1H-pyrrolo[2,3-b]pyridin-5-yl)-4,5-dimethyl-1H-pyrazole-3-carboxamide (P-2212), N-(2-(2-(3-hydroxypiperidin-1-yl)pyridin-4-yl)-1H-pyrrolo[2,3-b]pyridin-5-yl)-4,5-dimethyl-1H-pyrazole-3-carboxamide (P-2213), N-(2-(2-(4-acetylpiperazin-1-yl)pyridin-4-yl)-1H-pyrrolo[2,3-b]pyridin-5-yl)-4,5-dimethyl-1H-pyrazole-3-carboxamide (P-2214), 4,5-dimethyl-N-(2-(2-(4-(3-methylbut-2-enoyl)piperazin-1-yl)pyridin-4-yl)-1H-pyrrolo[2,3-b]pyridin-5-yl)-1H-pyrazole-3-carboxamide (P-2215), 4,5-dimethyl-N-(2-(2-(morpholine-4-carbonyl)pyridin-4-yl)-1H-pyrrolo[2,3-b]pyridin-5-yl)-1H-pyrazole-3-carboxamide (P-2216), 4,5-dimethyl-N-(2-(2-(4-methylpiperazine-1-carbonyl)pyridin-4-yl)-1H-pyrrolo[2,3-b]pyridin-5-yl)-1H-pyrazole-3-carboxamide (P-2217), 4,5-dimethyl-N-(2-(2-(pyrrolidine-1-carbonyl)pyridin-4-yl)-1H-pyrrolo[2,3-b]pyridin-5-yl)-1H-pyrazole-3-carboxamide (P-2218), 4,5-dimethyl-N-(2-(2-(thiomorpholine-4-carbonyl)pyridin-4-yl)-1H-pyrrolo[2,3-b]pyridin-5-yl)-1H-pyrazole-3-carboxamide (P-2219), 4-(5-(4,5-dimethyl-1H-pyrazole-3-carboxamido)-1H-pyrrolo[2,3-b]pyridin-2-yl)-N-(2-methoxyethyl)picolinamide (P-2220), 4-(5-(4,5-dimethyl-1H-pyrazole-3-carboxamido)-1H-pyrrolo[2,3-b]pyridin-2-yl)-N-(2-(dimethylamino)ethyl)picolinamide (P-2221), 4-(5-(4,5-dimethyl-1H-pyrazole-3-carboxamido)-1H-pyrrolo[2,3-b]pyridin-2-yl)-N-(2-methoxyethyl)picolinamide (P-2222), 4-(5-(4,5-dimethyl-1H-pyrazole-3-carboxamido)-1H-pyrrolo[2,3-b]pyridin-2-yl)-N-methoxypicolinamide (P-2223), 4-(5-(4,5-dimethyl-1H-pyrazole-3-carboxamido)-1H-pyrrolo[2,3-b]pyridin-2-yl)-N,N-dimethylpicolinamide (P-2224), 4-(5-(4,5-dimethyl-1H-pyrazole-3-carboxamido)-1H-pyrrolo[2,3-b]pyridin-2-yl)-N-(2-morpholinoethyl)picolinamide (P-2225), 4-(5-(4,5-dimethyl-1H-pyrazole-3-carboxamido)-1H-pyrrolo[2,3-b]pyridin-2-yl)-N-(2-(4-methylpiperazin-1-yl)ethyl)picolinamide (P-2226), N-(2-cyanoethyl)-4-(5-(4,5-dimethyl-1H-pyrazole-3-carboxamido)-1H-pyrrolo[2,3-b]pyridin-2-yl)picolinamide (P-2227), 4-(5-(4,5-dimethyl-1H-pyrazole-3-carboxamido)-1H-pyrrolo[2,3-b]pyridin-2-yl)-N-isobutylpicolinamide (P-2228), 4-(5-(4,5-dimethyl-1H-pyrazole-3-carboxamido)-1H-pyrrolo[2,3-b]pyridin-2-yl)-N-isopropylpicolinamide (P-2229), 4-(5-(4,5-dimethyl-1H-pyrazole-3-carboxamido)-1H-pyrrolo[2,3-b]pyridin-2-yl)-N,N-diethylpicolinamide (P-2230), 4-methyl-N-(2-phenyl-1H-pyrrolo[2,3-b]pyridin-5-yl)-5-(trifluoromethyl)-1H-pyrazole-3-carboxamide (P-2231), 4-chloro-N-(2-phenyl-1H-pyrrolo[2,3-b]pyridin-5-yl)-5-(trifluoromethyl)-1H-pyrazole-3-carboxamide (P-2232), 5-chloro-N-(2-phenyl-1H-pyrrolo[2,3-b]pyridin-5-yl)-4-(trifluoromethyl)-1H-pyrazole-3-carboxamide (P-2233), 5-(difluoromethyl)-4-methyl-N-(2-phenyl-1H-pyrrolo[2,3-b]pyridin-5-yl)-1H-pyrazole-3-carboxamide (P-2234), 4-(difluoromethyl)-5-methyl-N-(2-phenyl-1H-pyrrolo[2,3-b]pyridin-5-yl)-1H-pyrazole-3-carboxamide (P-2235), 5-chloro-4-(difluoromethyl)-N-(2-phenyl-1H-pyrrolo[2,3-b]pyridin-5-yl)-1H-pyrazole-3-carboxamide (P-2236), 4-chloro-5-(difluoromethyl)-N-(2-phenyl-1H-pyrrolo[2,3-b]pyridin-5-yl)-1H-pyrazole-3-carboxamide (P-2237), N-(2-(2-methoxypyridin-3-yl)-1H-pyrrolo[2,3-b]pyridin-5-yl)-4,5-dimethyl-1H-pyrazole-3-carboxamide (P-2238), N-(2-(2-ethoxypyridin-3-yl)-1H-pyrrolo[2,3-b]pyridin-5-yl)-4,5-dimethyl-1H-pyrazole-3-carboxamide (P-2239), N-(2-(2-(difluoromethoxy)pyridin-3-yl)-1H-pyrrolo[2,3-b]pyridin-5-yl)-4,5-dimethyl-1H-pyrazole-3-carboxamide (P-2240), 4,5-dimethyl-N-(2-(2-(trifluoromethyl)pyridin-3-yl)-1H-pyrrolo[2,3-b]pyridin-5-yl)-1H-pyrazole-3-carboxamide (P-2241), N-(2-(2,6-dimethoxypyridin-3-yl)-1H-pyrrolo[2,3-b]pyridin-5-yl)-4,5-dimethyl-1H-pyrazole-3-carboxamide (P-2242), N-(2-(5-cyclopropylpyridin-3-yl)-1H-pyrrolo[2,3-b]pyridin-5-yl)-4,5-dimethyl-1H-pyrazole-3-carboxamide (P-2243), N-(2-(5, 6-dimethylpyridin-3-yl)-H-pyrrolo[2,3-b]pyridin-5-yl)-4,5-dimethyl-1H-pyrazole-3-carboxamide (P-2244), N-(2-(2-fluoropyridin-4-yl)-1H-pyrrolo[2,3-b]pyridin-5-yl)-4,5-dimethyl-1H-pyrazole-3-carboxamide (P-2245), 4,5-dimethyl-N-(2-(2-methylpyridin-4-yl)-1H-pyrrolo[2,3-b]pyridin-5-yl)-1H-pyrazole-3-carboxamide (P-2246), N-(2-(2-ethoxypyridin-4-yl)-1H-pyrrolo[2,3-b]pyridin-5-yl)-4,5-dimethyl-1H-pyrazole-3-carboxamide (P-2247), N-(2-(2-isopropoxypyridin-4-yl)-1H-pyrrolo[2,3-b]pyridin-5-yl)-4,5-dimethyl-1H-pyrazole-3-carboxamide (P-2248), N-(2-(3-chloro-2-methoxypyridin-4-yl)-1H-pyrrolo[2,3-b]pyridin-5-yl)-4,5-dimethyl-1H-pyrazole-3-carboxamide (P-2249), N-(2-(3-chloropyridin-4-yl)-1H-pyrrolo[2,3-b]pyridin-5-yl)-4,5-dimethyl-1H-pyrazole-3-carboxamide (P-2250), 4,5-dimethyl-N-(2-(3-methylpyridin-4-yl)-1H-pyrrolo[2,3-b]pyridin-5-yl)-1H-pyrazole-3-carboxamide (P-2251), 4,5-dimethyl-N-(2-(2-(pyrrolidin-1-yl)pyridin-4-yl)-1H-pyrrolo[2,3-b]pyridin-5-yl)-1H-pyrazole-3-carboxamide (P-2252), N-(2-(5-fluoropyridin-3-yl)-1H-pyrrolo[2,3-b]pyridin-5-yl)-4,5-dimethyl-1H-pyrazole-3-carboxamide (P-2253), 4,5-dimethyl-N-(2-(5-(trifluoromethyl)pyridin-3-yl)-1H-pyrrolo[2,3-b]pyridin-5-yl)-1H-pyrazole-3-carboxamide (P-2254), N-(2-(6-cyclopropylpyridin-3-yl)-1H-pyrrolo[2,3-b]pyridin-5-yl)-4,5-dimethyl-1H-pyrazole-3-carboxamide (P-2255), N-(2-(5-ethylpyridin-3-yl)-1H-pyrrolo[2,3-b]pyridin-5-yl)-4,5-dimethyl-1H-pyrazole-3-carboxamide (P-2256), N-(2-(2-(difluoromethyl)phenyl)-1H-pyrrolo[2,3-b]pyridin-5-yl)-4,5-dimethyl-1H-pyrazole-3-carboxamide (P-2257), N-(2-(4-chloro-2-methylphenyl)H-pyrrolo[2,3-b]pyridin-5-yl)-4,5-dimethyl-H-pyrrolo[2,3-b]pyridin-5-yl)-4,5-dimethyl-H-pyrazole-3-carboxamide (P-2258), N-(2-(4-fluoro-2-methylphenyl)-1H-pyrrolo[2,3-b]pyridin-5-yl)-4,5-dimethyl-1H-pyrazole-3-carboxamide (P-2259), N-(2-(2,4-difluorophenyl)-1H-pyrrolo[2,3-b]pyridin-5-yl)-4,5-dimethyl-1H-pyrazole-3-carboxamide (P-2260), N-(2-(3-cyano-2,4-difluorophenyl)-1H-pyrrolo[2,3-b]pyridin-5-yl)-4,5-dimethyl-1H-pyrazole-3-carboxamide (P-2261), N-(2-(4-fluoro-2,3-dimethylphenyl)-1H-pyrrolo[2,3-b]pyridin-5-yl)-4,5-dimethyl-1H-pyrazole-3-carboxamide (P-2262), N-(2-(2-(difluoromethoxy)phenyl)-1H-pyrrolo[2,3-b]pyridin-5-yl)-4,5-dimethyl-1H-pyrazole-3-carboxamide (P-2263), N-(2-(2-(difluoromethoxy)-3-fluorophenyl)-1H-pyrrolo[2,3-b]pyridin-5-yl)-4,5-dimethyl-1H-pyrazole-3-carboxamide (P-2264), N-(2-(3,6-dihydro-2H-pyran-4-yl)-1H-pyrrolo[2,3-b]pyridin-5-yl)-4,5-dimethyl-1H-pyrazole-3-carboxamide (P-2265), 4,5-dimethyl-N-(2-(2,2,6,6-tetramethyl-1,2,3,6-tetrahydropyridin-4-yl)-1H-pyrrolo[2,3-b]pyridin-5-yl)-1H-pyrazole-3-carboxamide (P-2266), N-(2-(2,2-difluorobenzo[d][1,3]dioxol-4-yl)-1H-pyrrolo[2,3-b]pyridin-5-yl)-4,5-dimethyl-1H-pyrazole-3-carboxamide (P-2267), N-[2-[2-(difluoromethoxy)-4-fluoro-phenyl]-1H-pyrrolo[2,3-b]pyridin-5-yl]-3,4-dimethyl-1H-pyrazole-5-carboxamide (P-2268), N-[2-(6-fluoro-3-pyridyl)-1H-pyrrolo[2,3-b]pyridin-5-yl]-3,4-dimethyl-1H-pyrazole-5-carboxamide (P-2269)

N-[2-(5-cyano-3-pyridyl)-1H-pyrrolo[2,3-b]pyridin-5-yl]-3,4-dimethyl-1H-pyrazole-5-carboxamide (P-2270)

N-[2-(3,6-dihydro-2H-pyran-4-yl)-1H-pyrrolo[2,3-b]pyridin-5-yl]-3,4-dimethyl-1H-pyrazole-5-carboxamide (P-2271)

3-[5-[(3,4-dimethyl-1H-pyrazole-5-carbonyl)amino]-1H-pyrrolo[2,3-b]pyridin-2-yl]pyridine-4-carboxamide (P-2272)

N-[2-(2,3-dihydrobenzofuran-7-yl)-1H-pyrrolo[2,3-b]pyridin-5-yl]-3,4-dimethyl-H-pyrazole-5-carboxamide (P-2273)

3,4-dimethyl-N-[2-(3-piperazin-1-ylphenyl)-1H-pyrrolo[2,3-b]pyridin-5-yl]-1H-pyrazole-5-carboxamide (P-2274)

4-fluoro-N-[2-(4-fluorophenyl)-1H-pyrrolo[2,3-b]pyridin-5-yl]-3-methyl-1H-pyrazole-5-carboxamide (P-2275)

N-[2-[3-(isobutylcarbamoyl)phenyl]-1H-pyrrolo[2,3-b]pyridin-5-yl]-3,4-dimethyl-1H-pyrazole-5-carboxamide (P-2276)

N-[2-(4-chloro-2-methyl-phenyl)-1H-pyrrolo[2,3-b]pyridin-5-yl]-3,4-dimethyl-1H-pyrazole-5-carboxamide (P-2277)

N-[2-(3-chloro-4-pyridyl)-H-pyrrolo[2,3-b]pyridin-5-yl]-3,4-dimethyl-1H-pyrazole-5-carboxamide (P-2278)

N-[2-(4-fluoro-2,3-dimethyl-phenyl)-1H-pyrrolo[2,3-b]pyridin-5-yl]-3,4-dimethyl-1H-pyrazole-5-carboxamide (P-2279)

N-[2-(2,6-difluoro-3-pyridyl)-1H-pyrrolo[2,3-b]pyridin-5-yl]-3,4-dimethyl-1H-pyrazole-5-carboxamide (P-2280)

N-[2-(2,2-difluoro-1,3-benzodioxol-4-yl)-1H-pyrrolo[2,3-b]pyridin-5-yl]-3,4-dimethyl-1H-pyrazole-5-carboxamide (P-2281)

N-[2-(5,6-dimethyl-3-pyridyl)-1H-pyrrolo[2,3-b]pyridin-5-yl]-3,4-dimethyl-1H-pyrazole-5-carboxamide (P-2282)

N-[2-(6-fluoro-2-methyl-3-pyridyl)-1H-pyrrolo[2,3-b]pyridin-5-yl]-3,4-dimethyl-1H-pyrazole-5-carboxamide (P-2283)

N-[2-(4-methoxy-2,3-dimethyl-phenyl)-1H-pyrrolo[2,3-b]pyridin-5-yl]-3,4-dimethyl-1H-pyrazole-5-carboxamide (P-2284)

tert-butyl 3-[4-[5-[(3,4-dimethyl-1H-pyrazole-5-carbonyl)amino]-1H-pyrrolo[2,3-b]pyridin-2-yl]-3-methyl-pyrazol-1-yl]azetidine-1-carboxylate (P-2285)

N-[2-[1-(azetidin-3-yl)-3-methyl-pyrazol-4-yl]-1H-pyrrolo[2,3-b]pyridin-5-yl]-3,4-dimethyl-1H-pyrazole-5-carboxamide (P-2286)

3-(difluoromethyl)-N-[2-(4-fluorophenyl)-1H-pyrrolo[2,3-b]pyridin-5-yl]-4-methyl-1H-pyrazole-5-carboxamide (P-2287)

N-(2-iodo-1H-pyrrolo[2,3-b]pyridin-5-yl)-2H-indazole-4-carboxamide (P-2288)

N-(2-phenyl-1H-pyrrolo[2,3-b]pyridin-5-yl)-2H-indazole-4-carboxamide (P-2289)

methyl 3-[(2-phenyl-1H-pyrrolo[2,3-b]pyridin-5-yl)carbamoyl]benzoate (P-2290)
3-[(2-phenyl-1H-pyrrolo[2,3-b]pyridin-5-yl)carbamoyl]benzoic acid (P-2291)
4-[5-[(3,4-dimethyl-1H-pyrazole-5-carbonyl)amino]-1H-pyrrolo[2,3-b]pyridin-2-yl]-2-fluoro-benzoic acid (P-2292)
2-[3-[5-[(3,4-dimethyl-1H-pyrazole-5-carbonyl)amino]-1H-pyrrolo[2,3-b]pyridin-2-yl]phenyl]acetic acid (P-2293)
1-[4-[5-[(3,4-dimethyl-1H-pyrazole-5-carbonyl)amino]-1H-pyrrolo[2,3-b]pyridin-2-yl]phenyl]cyclopropanecarboxylic acid (P-2294)
2-[4-[5-[(3,4-dimethyl-1H-pyrazole-5-carbonyl)amino]-1H-pyrrolo[2,3-b]pyridin-2-yl]phenyl]acetic acid (P-2295)
4-[5-[(3,4-dimethyl-1H-pyrazole-5-carbonyl)amino]-1H-pyrrolo[2,3-b]pyridin-2-yl]-2-methyl-benzoic acid (P-2296)
3-[5-[(3,4-dimethyl-1H-pyrazole-5-carbonyl)amino]-1H-pyrrolo[2,3-b]pyridin-2-yl]-2-methyl-benzoic acid (P-2297)
1-methyl-N-(2-phenyl-1H-pyrrolo[2,3-b]pyridin-5-yl)indazole-4-carboxamide (P-2298)
N-(2-phenyl-1H-pyrrolo[2,3-b]pyridin-5-yl)-1H-indole-4-carboxamide (P-2299)
N-(2-phenyl-1H-pyrrolo[2,3-b]pyridin-5-yl)-1H-benzimidazole-4-carboxamide (P-2300)
N-(2-methyl-1H-pyrrolo[2,3-b]pyridin-5-yl)-2H-indazole-4-carboxamide (P-2301)
3,4-dimethyl-N-(2-methyl-1H-pyrrolo[2,3-b]pyridin-5-yl)-1H-pyrazole-5-carboxamide (P-2302)
4-[(2-phenyl-1H-pyrrolo[2,3-b]pyridin-5-yl)carbamoyl]benzoic acid (P-2303)
N,3,4-trimethyl-N-(2-phenyl-1H-pyrrolo[2,3-b]pyridin-5-yl)-1H-pyrazole-5-carboxamide (P-2304)
N-[2-(2,3-dihydro-1,4-benzodioxin-5-yl)-1H-pyrrolo[2,3-b]pyridin-5-yl]-3,4-dimethyl-1H-pyrazole-5-carboxamide (P-2305) tert-butyl 4-[4-[5-[(3,4-dimethyl-1H-pyrazole-5-carbonyl)amino]-1H-pyrrolo[2,3-b]pyridin-2-yl]pyrazol-1-yl]piperidine-1-carboxylate (P-2306) or
N-[2-(cyclohexen-1-yl)-1H-pyrrolo[2,3-b]pyridin-5-yl]-3,4-dimethyl-1H-pyrazole-5-carboxamide (P-2307),
or pharmaceutically acceptable salts, hydrates, solvates, tautomers or isomers thereof. In certain embodiments, the pyrazole ring moiety:

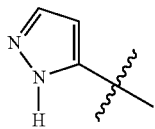

in any of compounds P-2001 to P-2273 and P-2274 to P-2307 can exist in a tautomeric form:

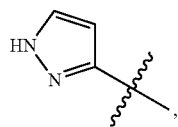

where the wavy line indicates the point of attachment to the rest of the molecule.

In some embodiments, the disclosure provides a compound of any of formulas (I'), (I'a), (I), (II), (III), (IV), (V), (V') (IIIa), (IIIb), (IIIc), (IIId), (IIId), (IIIe), (IIIa-1), (IIIa-2), (IIIa-3), (IIIa-4), (IIIa-5), (IIIa-6), (IIIa-7), (IIIa-8), (IIIb-1), (IIIb-2), (IIIb-3), (IIIb-4), (IIIb-5), (IIIc-1), (IIIc-2), (IIIc-3), (IIIc-4), (IIIc-5), (IIId-1), (IIId-2), (IIId-3), (IIId-4), (IId-5), (IIId-5), (IIe-1), (IIe-2), (IIe-3), (IIIe-4), (IIIe-5), (IVa), (IVa-1), (IVa-2), (IVa-3), (IVa-4), (IVa-5), (IVa-6), (IVa-7), (IVa-8), (IVa-9), (IVa-10), (IVa-1a), (IVa-2a), (IVa-3a), (IVa-4a), (IVa-5a), (IVa-6a), (IVa-7a), (IVa-8a), (IVa-9a), (IVa-10a), (IVa-1b), (IVa-2b), (IVa-5b), (IVa-6b), (IVb), (IVb-1), (IVb-2), (IVb-3), (IVb-4), (IVb-5), (IVb-6), (IVb-7), (IVb-8), (IVc), (IVc-1), (IVc-2), (IVc-3), (IVc-4), (IVc-5), (IVd), (IVd-1), (IVd-2), (IVd-3), (IVd-4), (IVd-5), (IVe), (IVe-1), (IVe-2), (IVe-3), (IVe-4), (IVe-5), (Va), (Va-1), (Va-2), (Va-3), (Va-1a), (Va-2a), (Va-3a), (Va-1a-1), (Va-2a-1), (Va-1b), (Va-2b), (Va-3b), (Va-1b-1), (Va-2b-1), (Va-6), (Va-6a), (Va-6b), (Va-6c) or (Va-6d), or pharmaceutically acceptable salts, hydrates, solvates, tautomers or isomers thereof.

In some embodiments, the disclosure provides any of compounds selected from P-2001 to P-2102, P-2104 to P-2273 and P-2274 to P-2307, e.g., compounds P-2001, P-2002, P-2003, P-2004, P-2005, P-2006, P-2007, P-2008, P-2009, P-2010, P-2011, P-2012, P-2013, P-2014, P-2015, P-2016, P-2017, P-2018, P-2019, P-2020, P-2021, P-2022, P-2023, P-2024, P-2025, P-2026, P-2027, P-2028, P-2029, P-2030, P-2031, P-2032, P-2033, P-2034, P-2035, P-2036, P-2037, P-2038, P-2039, P-2040, P-2041, P-2042, P-2043, P-2044, P-2045, P-2046, P-2047, P-2048, P-2049, P-2050, P-2051, P-2052, P-2053, P-2054, P-2055, P-2056, P-2057, P-2058, P-2059, P-2060, P-2061, P-2062, P-2063, P-2064, P-2065, P-2066, P-2067, P-2068, P-2069, P-2070, P-2071, P-2072, P-2073, P-2074, P-2075, P-2076, P-2077, P-2078, P-2079, P-2080, P-2081, P-2082, P-2083, P-2084, P-2085, P-2086, P-2087, P-2088, P-2089, P-2090, P-2091, P-2092, P-2093, P-2094, P-2095, P-2096, P-2097, P-2098, P-2099, P-2100, P-2101, P-2102, P-2104, P-2105, P-2106, P-2107, P-2108, P-2109, P-2110, P-2111, P-2112, P-2113, P-2114, P-2115, P-2116, P-2117, P-2118, P-2119, P-2120, P-2121, P-2122, P-2123, P-2124, P-2125, P-2126, P-2127, P-2128, P-2129, P-2130, P-2131, P-2132, P-2133, P-2134, P-2135, P-2136, P-2137, P-2138, P-2139, P-2140, P-2141, P-2142, P-2143, P-2144, P-2145, P-2146, P-2147, P-2148, P-2149, P-2150, P-2151, P-2152, P-2153, P-2154, P-2155, P-2156, P-2157, P-2158, P-2159, P-2160, P-2161, P-2162, P-2163, P-2164, P-2165, P-2166, P-2167, P-2168, P-2169, P-2170, P-2171, P-2172, P-2173, P-2174, P-2175, P-2176, P-2177, P-2178, P-2179, P-2180, P-2181, P-2182, P-2183, P-2184, P-2185, P-2186, P-2187, P-2188, P-2189, P-2190, P-2191, P-2192, P-2193, P-2194, P-2195, P-2196, P-2197, P-2198, P-2199, P-2200, P-2201, P-2202, P-2203, P-2204, P-2205, P-2206, P-2207, P-2208, P-2209, P-2210, P-2211, P-2212, P-2213, P-2214, P-2215, P-2216, P-2217, P-2218, P-2219, P-2220, P-2221, P-2222, P-2223, P-2224, P-2225, P-2226, P-2227, P-2228, P-2229, P-2230, P-2231, P-2232, P-2233, P-2234, P-2235, P-2236, P-2237, P-2238, P-2239, P-2240, P-2241, P-2242, P-2243, P-2244, P-2245, P-2246, P-2247, P-2248, P-2249, P-2250, P-2251, P-2252, P-2253, P-2254, P-2255, P-2256, P-2257, P-2258, P-2259, P-2260, P-2261, P-2262, P-2263, P-2264, P-2265, P-2266, P-2267, P-2268, P-2269, P-2270, P-2271, P-2272, P-2273, P-2274, P-2275, P-2276, P-2277, P-2278, P-2279, P-2280, P-2281, P-2282, P-2283, P-2284, P-2285, P-2286, P-2287, P-2288, P-2289, P-2290, P-2291, P-2292, P-2293, P-2294, P-2295, P-2296, P-2297, P-2298, P-2299, P-2300, P-2301, P-2302, P-2303, P-2304, P-2305, P-2306, or P-2307, or pharmaceutically acceptable salts, hydrates, solvates, tautomers or isomers thereof.

Method of Preparation

In another aspect, the present disclosure provides a method for preparing a compound of formula (IV) or any of the subformulas as described herein. The method includes contacting a compound having formula (VI) or any of subformulas thereof:

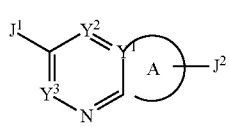

(VI)

with an agent having the formula:

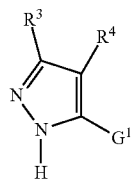

(VII)

under conditions sufficient to form a compound having formula (VIII):

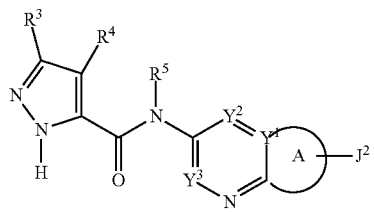

(VIII)

and reacting a compound of formula VIII with an agent having the formula: $G^2$-$(R^T)_m$ under conditions sufficient to form a compound of formula (IV), where $J^1$ is —$NR^5$, —$NH_2$, $P^1NH$—, $P^1NR^5$—, —COOH or —C(O)$Q^1$; $G^1$ is —$NH_2$, —COOH or —C(O)$Q^2$; and $J^2$ is halogen, tosylate, mesylate or triflate. $P^1$ is an amino protecting group. $Q^1$ and $Q^2$ are each independently —OH, halogen, $C_{1-4}$alkoxy or phenoxy. $G^2$ is $NH_2$, —B(OR$^{50}$)$_2$ or —Sn(Bu)$_3$, wherein $R^{50}$ is —OH, alkyl or two —OR$^{50}$ substituents together with the boron atom to which they are attached to form an optionally substituted 5 or 6-membered ring. In one instance, —B(OR$^{50}$)$_2$ is 4,4,5,5-tetramethyl-1,3,2-dioxaborolan-2-yl. The variables $R^3$, $R^4$, $R^5$, $Y^1$, $Y^2$, $Y^3$ and A are as defined in any of the embodiments and formulas and subformulas as disclosed herein. In some embodiments, A is a fused pyrrole ring together with the aromatic ring to which it is fused forms a pyrrolo[2,3-b]pyridine. In other embodiments, A is a fused thiophene ring together with the aromatic ring to which it is fused forms a thieno[3,2-b]pyridine moiety. In yet other embodiments, A is a fused pyrazole ring together with the aromatic ring to which it is fused forms a pyrazolo[3,4-b]pyridine moiety. In other embodiments, A is a fused benzene ring together with the aromatic ring to which it is fused forms a quinoline moiety. In one embodiment, $J^2$ is I, Cl or Br and $J^1$ is $NH_2$ or $NHP^1$. In another embodiment, $G^2$ is 4,4,5,5-tetramethyl-1,3,2-dioxaborolan-2-yl. In yet another embodiment, $G^1$ is —COOH. In another embodiment, $G^1$ is —$NH_2$. In certain instances, the reaction between a compound of formula (VI) and an agent of formula (VII) can be carried out in the presence of a coupling agent. Exemplary coupling agents include, but are not limited to, benzotriazol-1-yl-oxytriprrolidinophosphonium hexafluorophosphate (PyBOP), 1-ethyl-3-(3-dimethylaminopropyl)carbodiimide (EDC) and O-Benzotriazole-N, N,N',N'-tetramethyl-uronium-hexafluoro-phosphate (HBTU). In some embodiments, $R^{50}$ is H. In some embodiments, $G^2$-$(R^T)_m$ is reacted with a compound of formula (VIII) in the presence of a palladium complex. In certain instances, the palladium complexes include, but are not limited to, Pd(PPh$_3$)$_4$, palladium acetate, bis(diphenylphosphino)ferrocene]dichloropalladium, tris(dibenzylideneacetone)dipalladium(0), bis(triphenylphosphine)palladium (II) dichloride and the like. In certain embodiments, compounds of formula VI have subformulas (VI-1), (VI-2), (VI-3), (VI-4) or (VI-5):

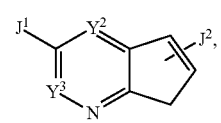

(VI-1)

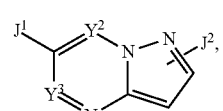

(VI-2)

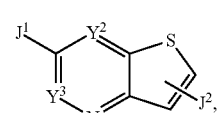

(VI-3)

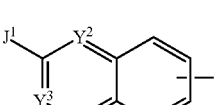

(VI-4)

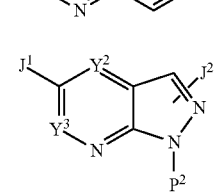

(VI-5)

where $P^2$ is H or an amino protecting group; $J^1$ and $J^2$ are as defined in any of the embodiments and formulas disclosed herein; and $Y^2$ and $Y^3$ are as defined in any of the embodiments and formulas disclosed herein. In certain embodiments, $P^1$ and $P^2$ are each independently selected from 9-fluorenylmethoxycarbonyl, t-butoxycarbonyl, trimethylsilyl, t-butyldiphenylsilyl, phenylsulfonyl, 4-methylphenylsulfonyl or 2,6-dichlorophenylcarbonyl.

In some embodiments, the method for preparing a compound of formula (IV) includes contacting a compound of formulas VI with an agent $G^2$-$(R^7)$m under conditions sufficient to form a compound of formula (IX):

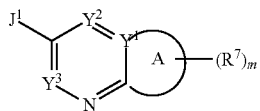
(IX)

and followed by reacting a compound of formula (IX) with an agent having the formula:

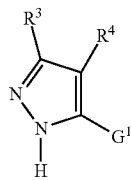

under conditions sufficient to form a compound of formula IV. In some instances, the reaction between compound of formula (IX) and agent

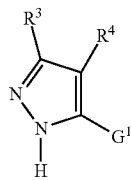

can be carried out in the presence of a coupling agent. Exemplary coupling agents include, but are not limited to, benzotriazol-1-yl-oxytripyrrolidinophosphoniumn hexafluorophosphate (PyBOP), 1-ethyl-3-(3-dimethylam-inopropyl)carbodiimide (EDC) and O-Benzotriazole-N,N,N',N'-tetramethyl-uronium-hexafluoro-phosphate (HBTU). In certain instances, the agent $G^2$-$(R^7)m$ is reacted with a compound of formula (VI) under a basic condition, e.g. in the presence of triethylamine or at a temperature greater than 100° C.

In some embodiments, the disclosure provides a method for preparing a compound of formulas (IVa), (IVb), (IVc), (IVd) or (IVe). The method includes (i) contacting a compound of any of formulas (VI-1), (VI-2), (VI-2), (VI-3), (VI-4) or (VI-5) with an agent having formula:

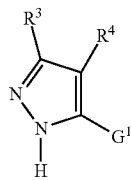

under conditions sufficient to form a compound having formulas (VI-1a), (VI-2a), (VI-3a), (VI-4a) or (VI-5a):

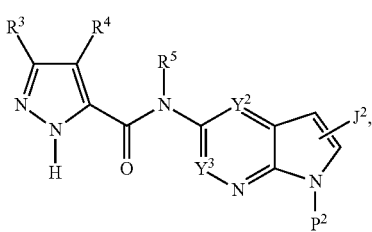
(VI-1a)

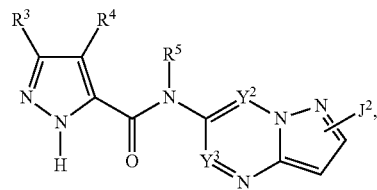
(VI-2a)

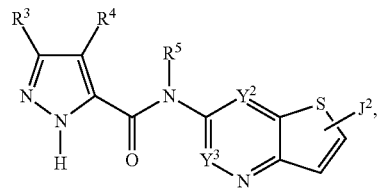
(VI-3a)

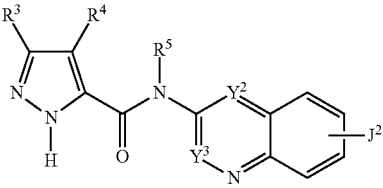
(VI-4a)

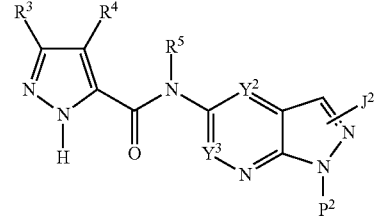
(VI-5a)

(ii) reacting a compound of any of formulas (VI-1a), (VI-2a), (VI-3a), (VI-4a) or (VI-5a): with an agent having formula: $G^2$-$(R^7)m$ under conditions sufficient to form a compound having formulas (VI-1b), (IVb), (IVc), (IVd) or (VI-5b), respectively:

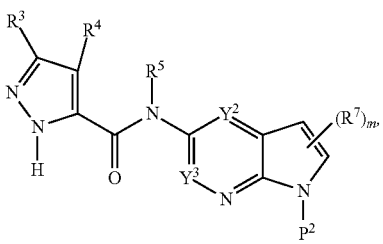
(VI-1b)

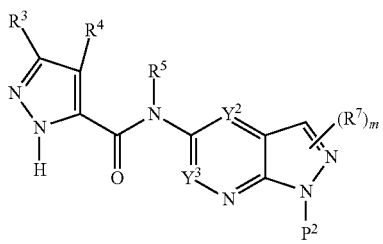
(VI-5b)

For compounds of formulas (VI-1b) or (VI-5b), the method includes a further step of removing the protecting group $P^2$ in the compounds of formulas (VI-1b) or (VI-5b) under conditions sufficient to form a compound of formulas (IVa) or (IVe), respectively. In one embodiment, the removal of the protecting group $P^2$ is carried out under a basic condition, e.g., in the presence of KOH. In certain instances, the method also includes preparing compounds of formula (IVa), (IVb), (IVc), (IVd) or (IVe) by carrying out steps (i) and (ii) above in reverse order, e.g., first reacting a compound of any of formulas (VI-1), (VI-2), (VI-2), (VI-3), (VI-4) or (VI-5) with $G^2$-$(R^7)m$ and followed by reacting with a compound of formula:

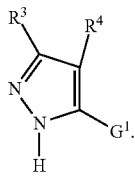

The variables $R^3$, $R^4$, $R^5$, $Y^2$, $Y^3$, m, $R^7$ and $P^2$ in subformulas (VI-1a), (VI-2a), (VI-3a), (VI-4a), (VI-5a), (VI-1b) and (VI-5b) are as defined in any of the embodiments and formulas and subformulas as disclosed herein. In one instance, m is 1.

In one embodiment, $G^2$ is —B(OH)$_2$. In another embodiment, $G^2$ is 2-hydroxy-1,3,2-benzodioxaborole or 2-hydroxy-4,4,5,5-tetramethyl-1,3,2-benzodioxaborolan-2-yl. In another embodiment, $G^2$ is —Sn(Bu)$_3$.

In another aspect, the disclosure provides a method for preparing a compound of formula (V'):

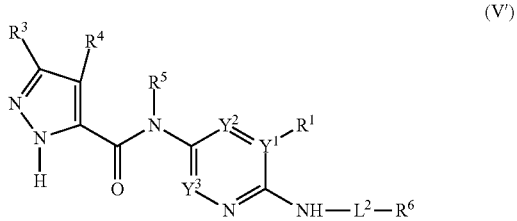

The method includes contacting a compound of formula (X):

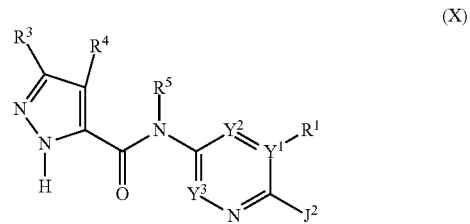

with a compound of formula: (XI): NH$_2$-L$^2$-R$^6$ under conditions sufficient to form a compound of formula (V'), where $J^2$ is halogen, tosylate, mesylate or triflate and the variables $R^3$, $R^4$, $R^5$, $Y^1$, $Y^2$, $Y^3$ and $R^1$ are as defined in any of the embodiments of compounds of formulas (I'), (I'a), (I), (II), (III), (IV), (V) or (V') as described herein. In some embodiments, the reaction is carried out at a temperature greater than 100° C. under an acidic condition. In one embodiment, the reaction can be carried out in the presence of an aqueous hydrochloric acid. In certain instances, $J^2$ is Cl or Br. In some embodiments, $Y^1$ is N and $R^1$ is a lone pair of electrons. In some instances, $L^2$ is a bond. In other instances, $R^6$ is an aryl or heteroaryl, each of which is optionally substituted with from 1-3 $R^9$; or 1-3 $R^c$; or 1-3 $R^d$; or 1-3 $R^e$; or 1-3 $R^{15}$; or 1-3 $R^{16}$; or 1-3 $R^{17}$; or 1-3 $R^{19}$; or 1-3 $R^{20}$ groups.

In other embodiments, the disclosure provides a synthetic intermediate having formula (XII):

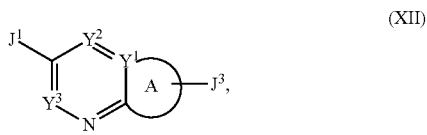

wherein $J^1$ is —NR$^5$, —NH$_2$, P$^1$NH—, (P$^1$)$_2$N— or P$^1$NR$^5$, where P$^1$ is an amino protecting group; $J^3$ is —B(OR$^{50}$)$_2$, wherein $R^{50}$ is —OH, alkyl or two —OR$^{50}$ substituents together with the boron atom to which they are attached to form an optionally substituted 5 or 6-membered ring. In certain instances, the 5 or 6-membered ring formed by two —OR$^{50}$ groups are optionally substituted with from 1-3 independently selected C$_{1-6}$alkyl groups. In one instance, —B(OR$^{50}$)$_2$ is 4,4,5,5-tetramethyl-1,3,2-dioxaborolan-2-yl, 5,5-dimethyl-1,3,2-dioxaborian-2-yl or 4,4,6-trimethyl-1,3, 2-dioxaborian-2-yl. In another instance, —B(OR$^{50}$)$_2$ is 4,4, 5,5-tetramethyl-1,3,2-dioxaborolan-2-yl. In another instance, $R^{50}$ is H. The variables $R^5$, $Y^1$, $Y^2$, $Y^3$ and A are as defined in any of the embodiments and formulas and subformulas as disclosed herein. The intermediate is useful for the preparation of compounds of formula (I'a) or (IV) or any subformulas thereof. In some embodiments, A is a fused pyrrole ring together with the aromatic ring to which it is fused forms a pyrrolo[2,3-b]pyridine. In other embodiments, A is a fused thiophene ring together with the aromatic ring to which it is fused forms a thieno[3,2-b]pyridine moiety. In yet other embodiments, A is a fused pyrazole ring together with the aromatic ring to which it is fused forms a pyrazolo [3,4-b]pyridine moiety. In other embodiments, A is a fused benzene ring together with the aromatic ring to which it is fused forms a quinoline moiety. In certain embodiments, compounds of formula (XII) have subformula (XII-1), (XII-2), (XII-3), (XII-4) or (XII-5):

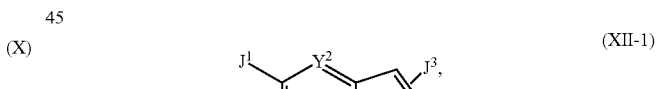

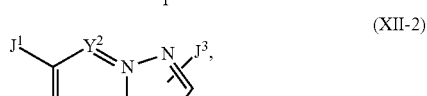

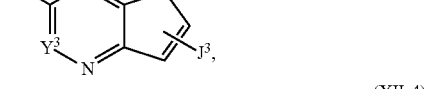

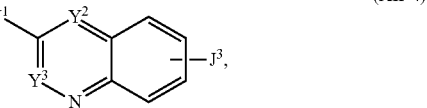

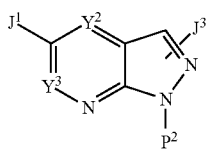
(XII-5)

where P² is H or an amino acid protecting group. In one embodiment, P² is H. In some embodiments, compounds of formula (XII) have a sub-generic formula selected from formulas (XII-6), (XII-7), (XII-8), (XII-9), (XII-10), (XII-11), (XII-12), (XII-13), (XII-14), (XII-15), (XII-16) or (XII-17):

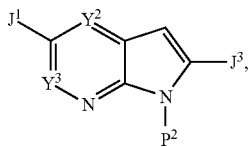
(XII-6)

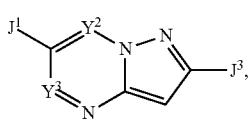
(XII-7)

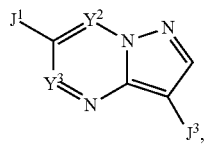
(XII-8)

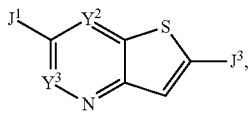
(XII-9)

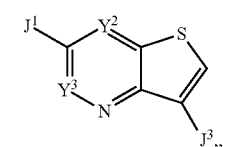
(XII-10)

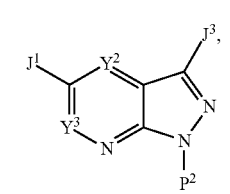
(XII-11)

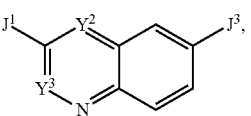
(XII-12)

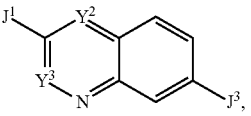
(XII-13)

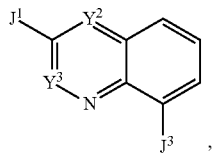
(XII-14)

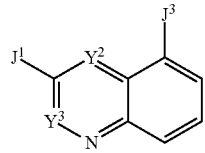
(XII-15)

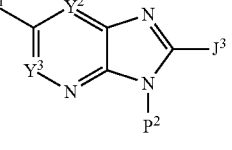
(XII-16)

or

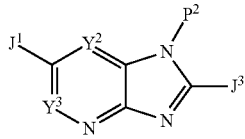
(XII-17)

where P² is H or an amino acid protecting group. In one embodiment, P² is H.

In some embodiments of compounds of formula (XII) or any of subformulas (XII-1) to (XII-17), $Y^2$ is $CR^{10}$ and $Y^3$ is CH. In certain instances, $R^{10}$ is H. In some embodiments, $Y^2$ is N and $Y^3$ is CH. In other embodiments, $Y^2$ is $CR^{10}$ and $Y^3$ is N. In some embodiments, $Y^2$ and $Y^3$ are CH. In some embodiments of compounds of formula (XII) or any of subformulas (XII-1) to (XII-17) as described herein, $J^1$ is $NH^2$. In some embodiments of compounds of formula (XII) or any of subformulas (XII-1) to (XII-17) as described herein, $J^3$ is —B(OR$^{50}$)$_2$, wherein $R^{50}$ is —OH, alkyl or two —OR$^{50}$ substituents together with the boron atom to which they are attached to form an optionally substituted 5 or 6-membered ring. In some embodiments of compounds of formula (XII) or any of subformulas (XII-1) to (XII-17) as described herein, $J^3$ is 4,4,5,5-tetramethyl-1,3,2-dioxaborolan-2-yl. In some embodiments of compounds of formula (XII) or any of subformulas (XII-1) to (XII-17) as described herein, P² is H. In one embodiment, $J^1$ is NH₂, $J^3$ is —B(OR$^{50}$)$_2$, wherein $R^{50}$ is —OH, alkyl or two —OR$^{50}$ substituents together with the boron atom to which they are attached to form an optionally substituted 5 or 6-membered ring. In one instance of compounds of formula (XII) or any of subformulas (XII-1) to (XII-17) as described herein, $J^1$ is NH₂ and $J^3$ is 4,4,5,5-tetramethyl-1,3,2-dioxaborolan-2-yl.

Organic Synthetic Techniques

A wide array of organic synthetic techniques exist in the art to facilitate the construction of potential modulators. Many of these organic synthetic methods are described in detail in standard reference sources utilized by those skilled in the art. One example of such a reference is March, 1994, Advanced Organic Chemistry; Reactions, Mechanisms and Structure, New York, McGraw Hill. Thus, the techniques useful to synthesize a potential modulator of kinase function are readily available to those skilled in the art of organic chemical synthesis.

Alternative Compound Forms or Derivatives

Compounds contemplated herein are described with reference to both generic formulae and specific compounds. In addition, disclosure compounds may exist in a number of different forms or derivatives, all within the scope of the present disclosure. Alternative forms or derivatives, include, for example, (a) prodrugs, and active metabolites (b) tautomers, isomers (including stereoisomers and regioisomers), and racemic mixtures (c) pharmaceutically acceptable salts and (d) solid forms, including different crystal forms, polymorphic or amorphous solids, including hydrates and solvates thereof, and other forms.

(a) Prodrugs and Metabolites

In addition to the present formulae and compounds described herein, the disclosure also includes prodrugs (generally pharmaceutically acceptable prodrugs), active metabolic derivatives (active metabolites), and their pharmaceutically acceptable salts.

Prodrugs are compounds or pharmaceutically acceptable salts thereof which, when metabolized under physiological conditions or when converted by solvolysis, yield the desired active compound. Prodrugs include, without limitation, esters, amides, carbamates, carbonates, ureides, solvates, or hydrates of the active compound. Typically, the prodrug is inactive, or less active than the active compound, but may provide one or more advantageous handling, administration, and/or metabolic properties. For example, some prodrugs are esters of the active compound; during metabolysis, the ester group is cleaved to yield the active drug. Esters include, for example, esters of a carboxylic acid group, or S-acyl or O-acyl derivatives of thiol, alcohol, or phenol groups. In this context, a common example is an alkyl ester of a carboxylic acid. Prodrugs may also include variants wherein an —NH group of the compound has undergone acylation, such as the 1-position of the 1H-pyrrolo[2,3-b]pyridine ring, or the nitrogen of the sulfonamide group of compounds as described herein, where cleavage of the acyl group provides the free —NH group of the active drug. Some prodrugs are activated enzymatically to yield the active compound, or a compound may undergo further chemical reaction to yield the active compound. Prodrugs may proceed from prodrug form to active form in a single step or may have one or more intermediate forms which may themselves have activity or may be inactive.

As described in *The Practice of Medicinal Chemistry*, Ch. 31-32 (Ed. Wermuth, Academic Press, San Diego, Calif., 2001), prodrugs can be conceptually divided into two non-exclusive categories, bioprecursor prodrugs and carrier prodrugs. Generally, bioprecursor prodrugs are compounds that are inactive or have low activity compared to the corresponding active drug compound, that contain one or more protective groups and are converted to an active form by metabolism or solvolysis. Both the active drug form and any released metabolic products should have acceptably low toxicity. Typically, the formation of active drug compound involves a metabolic process or reaction that is one of the following types:

Oxidative reactions: Oxidative reactions are exemplified without limitation by reactions such as oxidation of alcohol, carbonyl, and acid functionalities, hydroxylation of aliphatic carbons, hydroxylation of alicyclic carbon atoms, oxidation of aromatic carbon atoms, oxidation of carbon-carbon double bonds, oxidation of nitrogen-containing functional groups, oxidation of silicon, phosphorus, arsenic, and sulfur, oxidative N-dealkylation, oxidative O- and S-dealkylation, oxidative deamination, as well as other oxidative reactions.

Reductive reactions: Reductive reactions are exemplified without limitation by reactions such as reduction of carbonyl functionalities, reduction of alcohol functionalities and carbon-carbon double bonds, reduction of nitrogen-containing functional groups, and other reduction reactions.

Reactions without change in the oxidation state: Reactions without change in the state of oxidation are exemplified without limitation by reactions such as hydrolysis of esters and ethers, hydrolytic cleavage of carbon-nitrogen single bonds, hydrolytic cleavage of non-aromatic heterocycles, hydration and dehydration at multiple bonds, new atomic linkages resulting from dehydration reactions, hydrolytic dehalogenation, removal of hydrogen halide molecule, and other such reactions.

Carrier prodrugs are drug compounds that contain a transport moiety, e.g., that improves uptake and/or localized delivery to a site(s) of action. Desirably for such a carrier prodrug, the linkage between the drug moiety and the transport moiety is a covalent bond, the prodrug is inactive or less active than the drug compound, the prodrug and any release transport moiety are acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. (See, e.g., Cheng et al., U.S. Patent Publ. No. 20040077595, application. Ser. No. 10/656, 838, incorporated herein by reference.) Such carrier prodrugs are often advantageous for orally administered drugs. In some instances, the transport moiety provides targeted delivery of the drug, for example the drug may be conjugated to an antibody or antibody fragment. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of hydroxyl groups with lipophilic carboxylic acids, or of carboxylic acid groups with alcohols, e.g., aliphatic alcohols. Wermuth, supra.

Metabolites, e.g., active metabolites, overlap with prodrugs as described above, e.g., bioprecursor prodrugs. Thus, such metabolites are pharmacologically active compounds or compounds that further metabolize to pharmacologically active compounds that are derivatives resulting from metabolic processes in the body of a subject. Of these, active metabolites are such pharmacologically active derivative compounds. For prodrugs, the prodrug compound is generally inactive or of lower activity than the metabolic product. For active metabolites, the parent compound may be either an active compound or may be an inactive prodrug. For example, in some compounds, one or more alkoxy groups can be metabolized to hydroxyl groups while retaining pharmacologic activity and/or carboxyl groups can be esterified, e.g., glucuronidation. In some cases, there can be more than one metabolite, where an intermediate metabolite(s) is further metabolized to provide an active metabolite. For example, in some cases a derivative compound resulting from metabolic glucuronidation may be inactive or of low activity, and can be further metabolized to provide an active metabolite.

Metabolites of a compound may be identified using routine techniques known in the art, and their activities determined using tests such as those described herein. See, e.g., Bertolini et al., 1997, *J. Med. Chem.*, 40:2011-2016;

Shan et al., 1997, *J Pharm Sci* 86(7):756-757; Bagshawe, 1995, *Drug Dev. Res.*, 34:220-230; Wermuth, supra.

(b) Tautomers, Stereoisomers, and Regioisomers

It is understood that some compounds may exhibit tautomerism. In such cases, the formulae provided herein expressly depict only one of the possible tautomeric forms. It is therefore to be understood that the formulae provided herein are intended to represent any tautomeric form of the depicted compounds and are not to be limited merely to the specific tautomeric form depicted by the drawings of the formulae.

Likewise, some of the compounds according to the present disclosure may exist as stereoisomers, i.e. having the same atomic connectivity of covalently bonded atoms yet differing in the spatial orientation of the atoms. For example, compounds may be optical stereoisomers, which contain one or more chiral centers, and therefore, may exist in two or more stereoisomeric forms (e.g. enantiomers or diastereomers). Thus, such compounds may be present as single stereoisomers (i.e., essentially free of other stereoisomers), racemates, and/or mixtures of enantiomers and/or diastereomers. As another example, stereoisomers include geometric isomers, such as cis- or trans-orientation of substituents on adjacent carbons of a double bond. All such single stereoisomers, racemates and mixtures thereof are intended to be within the scope of the present disclosure. Unless specified to the contrary, all such stereoisomeric forms are included within the formulae provided herein.

In some embodiments, a chiral compound of the present disclosure is in a form that contains at least 80% of a single isomer (60% enantiomeric excess ("e.e.") or diastereomeric excess ("d.e.")), or at least 85% (70% e.e. or d.e.), 90% (80% e.e. or d.e.), 95% (90% e.e. or d.e.), 97.5% (95% e.e. or d.e.), or 99% (98% e.e. or d.e.). As generally understood by those skilled in the art, an optically pure compound having one chiral center is one that consists essentially of one of the two possible enantiomers (i.e., is enantiomerically pure), and an optically pure compound having more than one chiral center is one that is both diastereomerically pure and enantiomerically pure. In some embodiments, the compound is present in optically pure form, such optically pure form being prepared and/or isolated by methods known in the art (e.g. by recrystallization techniques, chiral synthetic techniques (including synthesis from optically pure starting materials), and chromatographic separation using a chiral column.

(c) Pharmaceutically Acceptable Salts

Unless specified to the contrary, specification of a compound herein includes pharmaceutically acceptable salts of such compound. Thus, compounds described herein and recited in any of the claims can be in the form of pharmaceutically acceptable salts, or can be formulated as pharmaceutically acceptable salts. Contemplated pharmaceutically acceptable salt forms include, without limitation, mono, bis, tris, tetrakis, and so on. Pharmaceutically acceptable salts are non-toxic in the amounts and concentrations at which they are administered. The preparation of such salts can facilitate the pharmacological use by altering the physical characteristics of a compound without preventing it from exerting its physiological effect. Useful alterations in physical properties include lowering the melting point to facilitate transmucosal administration and increasing the solubility to facilitate administering higher concentrations of the drug. A compound of the disclosure may possess a sufficiently acidic, a sufficiently basic, or both functional groups, and accordingly can react with any of a number of inorganic or organic bases, and inorganic and organic acids, to form a pharmaceutically acceptable salt.

Pharmaceutically acceptable salts include acid addition salts such as those containing chloride, bromide, iodide, hydrochloride, acetate, phenylacetate, acrylate, ascorbate, aspartate, benzoate, 2-phenoxybenzoate, 2-acetoxybenzoate, dinitrobenzoate, hydroxybenzoate, methoxybenzoate, methylbenzoate, bicarbonate, butyne-1,4 dioate, hexyne-1,6-dioate, caproate, caprylate, chlorobenzoate, cinnamate, citrate, decanoate, formate, fumarate, glycolate, gluconate, glucarate, glucuronate, glucose-6-phosphate, glutamate, heptanoate, hexanoate, isethionate, isobutyrate, gamma-hydroxybutyrate, phenylbutyrate, lactate, malate, maleate, hydroxymaleate, methylmaleate, malonate, mandelate, nicotinate, nitrate, isonicotinate, octanoate, oleate, oxalate, pamoate, phosphate, monohydrogenphosphate, dihydrogenphosphate, orthophosphate, metaphosphate, pyrophosphate, 2-phosphoglycerate, 3-phosphoglycerate, phthalate, propionate, phenylpropionate, propiolate, pyruvate, quinate, salicylate, 4-aminosalicylate, sebacate, stearate, suberate, succinate, sulfate, pyrosulfate, bisulfate, sulfite, bisulfite, sulfamate, sulfonate, benzenesulfonate (i.e. besylate), ethanesulfonate (i.e. esylate), ethane-1,2-disulfonate, 2-hydroxyethanesulfonate (i.e. isethionate), methanesulfonate (i.e. mesylate), naphthalene-1-sulfonate, naphthalene-2-sulfonate (i.e. napsylate), propanesulfonate, p-toluenesulfonate (i.e. tosylate), xylenesulfonates, cyclohexylsulfamate, tartrate, and trifluoroacetate. These pharmaceutically acceptable acid addition salts can be prepared using the appropriate corresponding acid.

When acidic functional groups, such as carboxylic acid or phenol are present, pharmaceutically acceptable salts also include basic addition salts such as those containing benzathine, chloroprocaine, choline, ethanolamine, diethanolamine, triethanolamine, t-butylamine, dicyclohexylamine, ethylenediamine, N,N'-dibenzylethylenediamine, meglumine, hydroxyethylpyrrolidine, piperidine, morpholine, piperazine, procaine, aluminum, calcium, copper, iron, lithium, magnesium, manganese, potassium, sodium, zinc, ammonium, and mono-, di-, or tri-alkylamines (e.g. diethylamine), or salts derived from amino acids such as L-histidine, L-glycine, L-lysine, and L-arginine. For example, see Remington's Pharmaceutical Sciences, 19$^{th}$ ed., Mack Publishing Co., Easton, Pa., Vol. 2, p. 1457, 1995. These pharmaceutically acceptable base addition salts can be prepared using the appropriate corresponding base.

Pharmaceutically acceptable salts can be prepared by standard techniques. For example, the free-base form of a compound can be dissolved in a suitable solvent, such as an aqueous or aqueous-alcohol solution containing the appropriate acid and then isolated by evaporating the solution. In another example, a salt can be prepared by reacting the free base and acid in an organic solvent. If the particular compound is an acid, the desired pharmaceutically acceptable salt may be prepared by any suitable method, for example, treatment of the free acid with an appropriate inorganic or organic base.

(d) Other Compound Forms

In the case of agents that are solids, it is understood by those skilled in the art that the compounds and salts may exist in different crystal or polymorphic forms, or may be formulated as co-crystals, or may be in an amorphous form, or may be any combination thereof (e.g. partially crystalline, partially amorphous, or mixtures of polymorphs) all of which are intended to be within the scope of the present disclosure and specified formulae. Whereas salts are formed by acid/base addition, i.e. a free base or free acid of the compound of interest forms an acid/base reaction with a corresponding addition base or addition acid, respectively, resulting in an ionic charge interaction, co-crystals are a new chemical species that is formed between neutral compounds, resulting in the compound and an additional molecular species in the same crystal structure.

In some instances, compounds of the disclosure are complexed with an acid or a base, including base addition salts such as ammonium, diethylamine, ethanolamine, ethylenediamine, diethanolamine, t-butylamine, piperazine, meglumine; acid addition salts, such as acetate, acetylsalicylate, besylate, camsylate, citrate, formate, fumarate, glutarate, hydrochlorate, maleate, mesylate, nitrate, oxalate, phosphate, succinate, sulfate, tartrate, thiocyanate and tosylate; and amino acids such as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine or valine. In combining the compound of the disclosure with the acid or base, an amorphous complex is preferably formed rather than a crystalline material such as a typical salt or co-crystal. In some instances, the amorphous form of the complex is facilitated by additional processing, such as by spray-drying, mechanochemical methods such as roller compaction, or microwave irradiation of the parent compound mixed with the acid or base. Such methods may also include addition of ionic and/or non-ionic polymer systems, including, but not limited to, hydroxypropyl methyl cellulose acetate succinate (HPMCAS) and methacrylic acid copolymer (e.g. Eudragit® L100-55), that further stabilize the amorphous nature of the complex. Such amorphous complexes provide several advantages. For example, lowering of the melting temperature relative to the free base facilitates additional processing, such as hot melt extrusion, to further improve the biopharmaceutical properties of the compound. Also, the amorphous complex is readily friable, which provides improved compression for loading of the solid into capsule or tablet form.

Additionally, the formulae are intended to cover hydrated or solvated as well as unhydrated or unsolvated forms of the identified structures. For example, the indicated compounds include both hydrated and non-hydrated forms. Other examples of solvates include the structures in combination with a suitable solvent, such as isopropanol, ethanol, methanol, dimethyl sulfoxide, ethyl acetate, acetic acid, or ethanolamine.

IV. Formulations and Administration

In another aspect, the present disclosure provides pharmaceutical compositions comprising/including a pharmaceutically acceptable carrier, excipient and/or diluent and a compound of the disclosure described herein or a pharmaceutically acceptable salt or solvate thereof. In an exemplary embodiment, the present disclosure provides a pharmaceutical formulation comprising/including a compound as described herein. In some embodiments, the disclosure provides pharmaceutical composition comprising/including a compound has any of formulas (I'), (I'a), (I), (II), (III), (IV), (V), (V') and any of the subgeneric formulas as described herein, e.g., any of the formulas (I'), (I'a), (I), (II), (III), (IV), (IIIa), (IIIb), (IIIc), (IIId), (IIId), (IIIe), (IIIa-1), (IIIa-2), (IIIa-3), (IIIa-4), (IIIa-5), (IIIa-6), (IIIa-7), (IIIa-8), (IIIb-1), (IIIb-2), (IIIb-3), (IIIb-4), (IIIb-5), (IIIc-1), (IIIc-2), (IIIc-3), (IIIc-4), (IIIc-5), (IIId-1), (IIId-2), (IIId-3), (IIId-4), (IIId-5), (IIIe-1), (IIIe-2), (IIIe-3), (IIIe-4), (IIIe-5), (IVa), (IVa-1), (IVa-2), (IVa-3), (IVa-4), (IVa-5), (IVa-6), (IVa-7), (IVa-8), (IVa-9), (IVa-10), (IVa-1a), (IVa-2a), (IVa-3a), (IVa-4a), (IVa-5a), (IVa-6a), (IVa-7a), (IVa-8a), (IVa-9a), (IVa-10a), (IVa-1b), (IVa-2b), (IVa-5b), (IVa-6b), (IVb), (IVb-1), (IVb-2), (IVb-3), (IVb-4), (IVb-5), (IVb-6), (IVb-7), (IVb-8), (IVc), (IVc-1), (IVc-2), (IVc-3), (IVc-4), (IVc-5), (IVd), (IVd-1), (IVd-2), (IVd-3), (IVd-4), (IVd-5), (IVe), (IVe-1), (IVe-2), (IVe-3), (IVe-4), (IVe-5), (Va), (Va-1), (Va-2), (Va-3), (Va-1a), (Va-2a), (Va-3a), (Va-1a-1), (Va-2a-1), (Va-1b), (Va-2b), (Va-3b), (Va-1b-1), (Va-2b-1), (Va-6), (Va-6a), (Va-6b), (Va-6c) or (Va-6d), and a pharmaceutically acceptable carrier, excipient and/or diluents.

The methods and compounds will typically be used in therapy for human subjects. However, they may also be used to treat similar or identical indications in other animal subjects. Compounds described herein can be administered by different routes, including injection (i.e. parenteral, including intravenous, intraperitoneal, subcutaneous, and intramuscular), oral, transdermal, transmucosal, rectal, or inhalant. Such dosage forms should allow the compound to reach target cells. Other factors are well known in the art, and include considerations such as toxicity and dosage forms that retard the compound or composition from exerting its effects. Techniques and formulations generally may be found in Remington: *The Science and Practice of Pharmacy*, 21$^{st}$ edition, Lippincott, Williams and Wilkins, Philadelphia, Pa., 2005 (hereby incorporated by reference herein).

In some embodiments, compositions will comprise pharmaceutically acceptable carriers or excipients, such as fillers, binders, disintegrants, glidants, lubricants, complexing agents, solubilizers, and surfactants, which may be chosen to facilitate administration of the compound by a particular route. Examples of carriers include calcium carbonate, calcium phosphate, various sugars such as lactose, glucose, or sucrose, types of starch, cellulose derivatives, gelatin, lipids, liposomes, nanoparticles, and the like. Carriers also include physiologically compatible liquids as solvents or for suspensions, including, for example, sterile solutions of water for injection (WFI), saline solution, dextrose solution, Hank's solution, Ringer's solution, vegetable oils, mineral oils, animal oils, polyethylene glycols, liquid paraffin, and the like. Excipients may also include, for example, colloidal silicon dioxide, silica gel, talc, magnesium silicate, calcium silicate, sodium aluminosilicate, magnesium trisilicate, powdered cellulose, macrocrystalline cellulose, carboxymethyl cellulose, cross-linked sodium carboxymethylcellulose, sodium benzoate, calcium carbonate, magnesium carbonate, stearic acid, aluminum stearate, calcium stearate, magnesium stearate, zinc stearate, sodium stearyl fumarate, syloid, stearowet C, magnesium oxide, starch, sodium starch glycolate, glyceryl monostearate, glyceryl dibehenate, glyceryl palmitostearate, hydrogenated vegetable oil, hydrogenated cotton seed oil, castor seed oil mineral oil, polyethylene glycol (e.g. PEG 4000-8000), polyoxyethylene glycol, poloxamers, povidone, crospovidone, croscarmellose sodium, alginic acid, casein, methacrylic acid divinylbenzene copolymer, sodium docusate, cyclodextrins (e.g. 2-hydroxypropyl-.delta.-cyclodextrin), polysorbates (e.g. polysorbate 80), cetrimide, TPGS (d-alpha-tocopheryl polyethylene glycol 1000 succinate), magnesium lauryl sulfate, sodium lauryl sulfate, polyethylene glycol ethers, difatty acid ester of polyethylene glycols, or a polyoxyalkylene sorbitan fatty acid ester (e.g., polyoxyethylene sorbitan ester Tween®), polyoxyethylene sorbitan fatty acid esters, sorbitan fatty acid ester, e.g. a sorbitan fatty acid ester from a fatty acid such as oleic, stearic or palmitic acid, mannitol, xylitol, sorbitol, maltose, lactose, lactose monohydrate or lactose spray dried, sucrose, fructose, calcium phosphate, dibasic calcium phosphate, tribasic calcium phosphate, calcium sulfate, dextrates, dextran, dextrin, dextrose, cellulose acetate, maltodextrin, simethicone, polydextrosem, chitosan, gelatin, HPMC (hydroxypropyl methyl celluloses), HPC (hydroxypropyl cellulose), hydroxyethyl cellulose, and the like.

Pharmaceutical formulations may be presented in unit dose forms containing a predetermined amount of active ingredient per unit dose. Such a unit may contain, for example, 0.5 mg to 1 g, preferably 1 mg to 700 mg, more preferably 5 mg to 100 mg of a compound of the disclosure (as a free-base, solvate (including hydrate) or salt, in any form), depending on the condition being treated, the route of administration, and the age, weight and condition of the patient. Preferred unit dosage formulations are those containing a daily dose, weekly dose, monthly dose, a sub-dose or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including capsules, tablets, liquid-filled capsules, disintegrating tablets, immediate, delayed and controlled release tablets, oral strips, solutions, syrups, buccal and sublingual), rectal, nasal, inhalation, topical (including transdermal), vaginal or parenteral (including subcutaneous, intramuscular, intravenous or intradermal) route. Such formulations may be prepared by any method known in the art of pharmacy, for example by bringing into association the active ingredient with the carrier(s), excipient(s) or diluent. Generally, the carrier, excipient or diluent employed in the pharmaceutical formulation is "non-toxic," meaning that it/they is/are deemed safe for consumption in the amount delivered in the pharmaceutical composition, and "inert" meaning that it/they does/do not appreciably react with or result in an undesired effect on the therapeutic activity of the active ingredient.

In some embodiments, oral administration may be used. Pharmaceutical preparations for oral use can be formulated into conventional oral dosage forms such as discreet units capsules, tablets, and liquid preparations such as syrups, elixirs, and concentrated drops. Compounds described herein may be combined with solid excipients, optionally grinding a resulting mixture, and processing the mixture of granules, after adding suitable auxiliaries, if desired, to obtain, for example, tablets, coated tablets, hard capsules, soft capsules, solutions (e.g. aqueous, alcoholic, or oily solutions) and the like. Suitable excipients are, in particular, fillers such as sugars, including lactose, glucose, sucrose, mannitol, or sorbitol; cellulose preparations, for example, corn starch, wheat starch, rice starch, potato starch, gelatin, gum tragacanth, methyl cellulose, hydroxypropylmethylcellulose, sodium carboxymethylcellulose (CMC), and/or polyvinylpyrrolidone (PVP: povidone); oily excipients, including vegetable and animal oils, such as sunflower oil, olive oil, or cod-liver oil. The oral dosage formulations may also contain disintegrating agents, such as the cross-linked polyvinylpyrrolidone, agar, or alginic acid, or a salt thereof such as sodium alginate; a lubricant, such as talc or magnesium stearate; a plasticizer, such as glycerol or sorbitol; a sweetening such as sucrose, fructose, lactose, or aspartame; a natural or artificial flavoring agent, such as peppermint, oil of wintergreen, or cherry flavoring; or dye-stuffs or pigments, which may be used for identification or characterization of different doses or combinations, such as unit dosages. Also provided are dragee cores with suitable coatings. For this purpose, concentrated sugar solutions may be used, which may optionally contain, for example, gum arabic, talc, poly-vinylpyrrolidone, carbopol gel, polyethylene glycol, and/or titanium dioxide, lacquer solutions, and suitable organic solvents or solvent mixtures. Oral fluids such as solutions, syrups and elixirs can be prepared in dosage unit form so that a given quantity contains a predetermined amount of the compound.

Pharmaceutical preparations that can be used orally include push-fit capsules made of gelatin ("gelcaps"), as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols.

In some embodiments, injection (parenteral administration) may be used, e.g., intramuscular, intravenous, intraperitoneal, and/or subcutaneous. Compounds described herein for injection may be formulated in sterile liquid solutions, preferably in physiologically compatible buffers or solutions, such as saline solution, Hank's solution, or Ringer's solution. Dispersions may also be prepared in non-aqueous solutions, such as glycerol, propylene glycol, ethanol, liquid polyethylene glycols, triacetin, and vegetable oils. Solutions may also contain a preservative, such as methylparaben, propylparaben, chlorobutanol, phenol, sorbic acid, thimerosal, and the like. In addition, the compounds may be formulated in solid form, including, for example, lyophilized forms, and redissolved or suspended prior to use. The formulations may be presented in unit-dose or multi-dose containers, for example sealed ampoules and vials, and may be stored in a freeze-dried (lyophilized) condition requiring only the addition of the sterile liquid carrier, for example water for injection, immediately prior to use.

In some embodiments, transmucosal, topical or transdermal administration may be used. In such formulations of compounds described herein, penetrants appropriate to the barrier to be permeated are used. Such penetrants are generally known in the art, and include, for example, for transmucosal administration, bile salts and fusidic acid derivatives. In addition, detergents may be used to facilitate permeation. Transmucosal administration, for example, may be through nasal sprays or suppositories (rectal or vaginal). Compositions of compounds described herein for topical administration may be formulated as oils, creams, lotions, ointments, and the like by choice of appropriate carriers known in the art. Suitable carriers include vegetable or mineral oils, white petrolatum (white soft paraffin), branched chain fats or oils, animal fats and high molecular weight alcohol (greater than $C_{12}$). In some embodiments, carriers are selected such that the active ingredient is soluble. Emulsifiers, stabilizers, humectants and antioxidants may also be included as well as agents imparting color or fragrance, if desired. Creams for topical application are preferably formulated from a mixture of mineral oil, self-emulsifying beeswax and water in which mixture the active ingredient, dissolved in a small amount of solvent (e.g., an oil), is admixed. Additionally, administration by transdermal means may comprise a transdermal patch or dressing such as a bandage impregnated with an active ingredient and optionally one or more carriers or diluents known in the art. To be administered in the form of a transdermal delivery system, the dosage administration will be continuous rather than intermittent throughout the dosage regimen.

In some embodiments, compounds are administered as inhalants. Compounds described herein may be formulated as dry powder or a suitable solution, suspension, or aerosol. Powders and solutions may be formulated with suitable additives known in the art. For example, powders may include a suitable powder base such as lactose or starch, and solutions may comprise propylene glycol, sterile water, ethanol, sodium chloride and other additives, such as acid, alkali and buffer salts. Such solutions or suspensions may be administered by inhaling via spray, pump, atomizer, or nebulizer, and the like. The compounds described herein may also be used in combination with other inhaled therapies, for example corticosteroids such as fluticasone propionate, beclomethasone dipropionate, triamcinolone acetonide, budesonide, and mometasone furoate; beta agonists such as albuterol, salmeterol, and formoterol; anticholinergic agents such as ipratroprium bromide or tiotropium; vasodilators such as treprostinal and iloprost; enzymes such as DNAase; therapeutic proteins; immunoglobulin antibodies; an oligonucleotide, such as single or double stranded DNA or RNA, siRNA; antibiotics such as tobramycin; muscarinic receptor antagonists; leukotriene antagonists; cytokine antagonists; protease inhibitors; cromolyn sodium; nedocril sodium; and sodium cromoglycate.

The amounts of various compounds to be administered can be determined by standard procedures taking into account factors such as the compound activity (in vitro, e.g. the compound $IC_{50}$ vs. target, or in vivo activity in animal efficacy models), pharmacokinetic results in animal models (e.g. biological half-life or bioavailability), the age, size, and weight of the subject, and the disorder associated with the subject. The importance of these and other factors are well known to those of ordinary skill in the art. Generally, a dose will be in the range of about 0.01 to 50 mg/kg, also about 0.1 to 20 mg/kg of the subject being treated. Multiple doses may be used.

The compounds described herein may also be used in combination with other therapies for treating the same disease. Such combination use includes administration of the compounds and one or more other therapeutics at different times, or co-administration of the compound and one or more other therapies. In some embodiments, dosage may be modified for one or more of the compounds of the disclosure or other therapeutics used in combination, e.g., reduction in the amount dosed relative to a compound or therapy used alone, by methods well known to those of ordinary skill in the art.

It is understood that use in combination includes use with other therapies, drugs, medical procedures etc., where the other therapy or procedure may be administered at different times (e.g. within a short time, such as within hours (e.g. 1, 2, 3, 4-24 hours), or within a longer time (e.g. 1-2 days, 2-4 days, 4-7 days, 1-4 weeks)) than a compound described herein, or at the same time as a compound described herein. Use in combination also includes use with a therapy or medical procedure that is administered once or infrequently, such as surgery, along with a compound described herein administered within a short time or longer time before or after the other therapy or procedure. In some embodiments, the present disclosure provides for delivery of a compound described herein and one or more other drug therapeutics delivered by a different route of administration or by the same route of administration. The use in combination for any route of administration includes delivery of a compound described herein and one or more other drug therapeutics delivered by the same route of administration together in any formulation, including formulations where the two compounds are chemically linked in such a way that they maintain their therapeutic activity when administered. In one aspect, the other drug therapy may be co-administered with a compound described herein. Use in combination by co-administration includes administration of co-formulations or formulations of chemically joined compounds, or administration of two or more compounds in separate formulations within a short time of each other (e.g. within an hour, 2 hours, 3 hours, up to 24 hours), administered by the same or different routes. Co-administration of separate formulations includes co-administration by delivery via one device, for example the same inhalant device, the same syringe, etc., or administration from separate devices within a short time of each other. Co-formulations of a compound described herein and one or more additional drug therapies delivered by the same route includes preparation of the materials together such that they can be administered by one device, including the separate compounds combined in one formulation, or compounds that are modified such that they are chemically joined, yet still maintain their biological activity. Such chemically joined compounds may have a linkage that is substantially maintained in vivo, or the linkage may break down in vivo, separating the two active components.

V. Disease Indications and Modulations of c-Kit Kinase

Exemplary Diseases Associated with c-Kit or Mutant Form of c-Kit

The compounds of formulas (I'), (I'a), (I), (II), (III), (IV), (V), (V'), or any of the subformulas and compounds as described herein are useful for treating disorders related to c-kit e.g., diseases related to unregulated kinase signal transduction, including cell proliferative disorders, fibrotic disorders and metabolic disorders, among others. As described in more detail below and in Lipson et al., U.S. 20040002534 (U.S. application Ser. No. 10/600,868, filed Jun. 23, 2003) which is incorporated herein by reference in its entirety, cell proliferative disorders which can be treated by the present disclosure include cancers, and mast cell proliferative disorders.

The presence of c-kit or mutant c-kit has also been associated with a number of different types of cancers, diseases and conditions, as described below. In addition, the association between abnormalities in c-kit and disease are not restricted to cancer. As such, c-kit has been associated with malignancies, including mast cell tumors, small cell lung cancer, testicular cancer, gastrointestinal stromal tumors (GISTs), metastatic GISTs, glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myelocytic leukemia (AML), acute lymphocytic leukemia, chronic myelogenous leukemia, mastocytosis, melanoma, and canine mast cell tumors, and inflammatory diseases, including asthma, rheumatoid arthritis, allergic rhinitis, multiple sclerosis, inflammatory bowel syndrome, transplant rejection, hypereosinophilia, urticaria pigmentosa (UP), telangiectasia macularis eruptiva perstans (TMEP), systemic mastocytosis, indolent systemic, smoldering systemic, aggressive systemic, mast cell leukemia and mast cell sarcoma. The presence of mutant forms of c-kit has been associated with diseases or conditions, for example, gastrointestinal stromal tumors (GISTs), mast cell leukemia, germ-cell tumor, t-cell lymphoma, mastocytosis, acute lymphocytic leukemia and seminama.

Exemplary Malignant Diseases Associated with c-Kit

Aberrant expression and/or activation of c-kit and/or mutant form of c-kit has been implicated in a variety of cancers (Roskoski, 2005, Biochemical and biophysical Research Comm. 338: 1307-1315). Evidence for a contribution of c-kit to neoplastic pathology includes its association with leukemias and mast cell tumors, small cell lung cancer, testicular cancer, and some cancers of the gastrointestinal tract and central nervous system. In addition, c-kit has been implicated in playing a role in carcinogenesis of the female genital tract (Inoue, et al., 1994, Cancer Res. 54(11): 3049-3053), sarcomas of neuroectodermal origin (Ricotti, et al., 1998, Blood 91:2397-2405), and Schwann cell neoplasia associated with neurofibromatosis (Ryan, et al., 1994, J. Neuro. Res. 37:415-432). It was found that mast cells are involved in modifying the tumor microenvironment and enhancing tumor growth (Yang et al., 2003, J Clin Invest. 112:1851-1861; Viskochil, 2003, J Clin Invest. 112:1791-1793). Thus, c-kit is a useful target in treating neurofibromatosis as well as malignant tumors.

Small cell lung carcinoma: c-kit kinase receptor has been found to be aberrantly expressed in many cases of small cell lung carcinoma (SCLC) cells (Hibi, et al., 1991, Oncogene 6:2291-2296). Thus, as an example, inhibition of c-kit kinase can be beneficial in treatment of SCLC, e.g., to improve the long term survival of patients with SCLC.

Leukemias: SCF binding to the c-kit protects hematopoietic stem and progenitor cells from apoptosis (Lee, et al., 1997, J. Immunol. 159:3211-3219), thereby contributing to colony formation and hematopoiesis. Expression of c-kit is frequently observed in acute myelocytic leukemia (AML), and in some cases of acute lymphocytic leukemia (ALL) (for reviews, see Sperling, et al., 1997, Haemat 82:617-621; Escribano, et al., 1998, Leuk. Lymph. 30:459-466). Although c-kit is expressed in the majority of AML cells, its expression does not appear to be prognostic of disease progression (Sperling, et al, 1997, Haemat 82:617-621). However, SCF protected AML cells from apoptosis induced by chemotherapeutic agents (Hassan, et al., 1996, Acta. Hem. 95:257-262). Inhibition of c-kit by the present disclosure will enhance the efficacy of these agents and can induce apoptosis of AML cells.

The clonal growth of cells from patients with myelodysplastic syndrome (Sawada, et al., 1996, Blood 88:319-327) or chronic myelogenous leukemia (CML) (Sawai, et al., 1996, Exp. Hem. 2:116-122) was found to be significantly enhanced by SCF in combination with other cytokines. CML is characterized by expansion of Philadelphia chromosome positive cells of the marrow (Verfaillie, et al., Leuk. 1998, 12:136-138), which appears to primarily result from inhibition of apoptotic death (Jones, Curr. Opin. Onc. 1997, 9:3-7). The product of the Philadelphia chromosome, p210$^{BCR-ABL}$, has been reported to mediate inhibition of apoptosis (Bedi, et al., Blood 1995, 86:1148-1158). Since p210$^{BCR-ABL}$ and c-kit both inhibit apoptosis and p62$^{dok}$ has been suggested as a substrate (Carpino, et al., Cell 1997, 88:197-204), clonal expansion mediated by these kinases may occur through a common signaling pathway. However, c-kit has also been reported to interact directly with p210$^{BCR-ABL}$(Hallek, et al., Brit. J Haem. 1996, 94:5-16), which suggests that c-kit has a more causative role in CML pathology. Therefore, inhibition of c-kit will be useful in the treatment of the above disorders.

Gastrointestinal cancers: Normal colorectal mucosa does not express c-kit (Bellone, et al., 1997, J. Cell Physiol. 172:1-11). However, c-kit is frequently expressed in colorectal carcinoma (Bellone, et al., 1997, J. Cell Physiol. 172: 1-11), and autocrine loops of SCF and c-kit have been observed in several colon carcinoma cell lines (Toyota, et al., 1993, Turn Biol 14:295-302; Lahm, et al., 1995, Cell Growth & Differ 6:1111-1118; Bellone, et al., 1997, J. Cell Physiol. 172:1-11). Furthermore, disruption of the autocrine loop by the use of neutralizing antibodies (Lahm, et al., 1995, Cell Growth & Differ. 6:1111-1118) and down regulation of c-kit and/or SCF significantly inhibits cell proliferation (Lahm, et al., 1995, Cell Growth & Differ 6:1111-1118; Bellone, et al., 1997, J. Cell Physiol. 172:1-11).

SCF/c-kit autocrine loops have been observed in gastric carcinoma cell lines (Turner, et al., 1992, Blood 80:374-381; Hassan, et al., 1998, Digest. Dis. Science 43:8-14), and constitutive c-kit activation also appears to be important for gastrointestinal stromal tumors (GISTs). GISTs are the most common mesenchymal tumor of the digestive system. More than 90% of GISTs express c-kit, which is consistent with the putative origin of these tumor cells from interstitial cells of Cajal (ICCs) (Hirota, et al., 1998, Science 279:577-580). ICCs are thought to regulate contraction of the gastrointestinal tract, and patients lacking c-kit in their ICCs exhibited a myopathic form of chronic idiopathic intestinal pseudo-obstruction (Isozaki, et al., 1997, Amer. J. of Gast. 9 332-334). The c-kit expressed in GISTs from several different patients was observed to have mutations in the intracellular juxtamembrane domain leading to constitutive activation of c-kit (Hirota, et al., 1998, Science 279:577-580). Hence, inhibition of c-kit kinase will be an efficacious means for the treatment of these cancers.

Overexpression or constitutive activation of Kit mutations have been implicated and associated in gastrointestinal stromal tumors (GISTs) and most GISTs contain oncogenic KIT receptor or PDGFRA receptor tyrosine kinase mutations (Miettinen, et al., 2006, Arch Pathol Lab Med, 130: 14661478; Fletcher, et al., 2007, Current Opinion in Genetics & Development, 17:3-7; and Frost, et al. 2002, Molecular Cancer Therapeutics, 1:1115-1124). Frost, et al, 2002 has shown that D816V KIT mutation is resistant to imatinib, such that additional types of c-kit inhibitors are useful. Many GISTs have activating mutations in the KIT justamembrane regions (Lux, et al., 2000, American Journal Pathology, 156:795). Constitutive activation of the Kit receptor tyrosine kinase is a central pathogenic event in most GISTs and generally results from oncogenic point mutations (Heinrich, et al. 2002, Human Pathology, 33:484-495). Inhibition of wild-type KIT and/or certain mutant KIT isoforms with a small molecule tyrosine kinase inhibitor has become standard of care for treating patient with metastatic GISTs (Schittenhelm, et al. 2006, Cancer Res., 66: 473-481). Therefore, inhibition of c-kit kinase and/or mutant c-kit kinase will be an efficacious means for the treatment of GISTs.

Testicular cancers: Male germ cell tumors have been histologically categorized into seminomas, which retain germ cell characteristics, and nonseminomas which can display characteristics of embryonal differentiation. Both seminomas and nonseminomas are thought to initiate from a preinvasive stage designated carcinoma in situ (CIS) (Murty, et al., 1998, Sem. Oncol. 25:133-144). Both c-kit and SCF have been reported to be essential for normal gonadal development during embryogenesis (Loveland, et al., 1997, J. Endocrinol 153:337-344). Loss of either the receptor or the ligand resulted in animals devoid of germ cells. In postnatal testes, c-kit has been found to be expressed in Leydig cells and spermatogonia, while SCF was expressed in Sertoli cells (Loveland, et al., 1997, J. Endocrinol 153:337-344). Testicular tumors develop from Leydig cells with high frequency in transgenic mice expressing human papilloma virus 16 (HPV16) E6 and E7 oncogenes (Kondoh, et al., 1991, J. Virol. 65:3335-3339; Kondoh, et al., 1994, J. Urol. 152:2151-2154). These tumors express both c-kit and SCF, and an autocrine loop may contribute to the tumorigenesis (Kondoh, et al., 1995, Oncogene 10:341-347) associated with cellular loss of functional p53 and the retinoblastoma gene product by association with E6 and E7 (Dyson, et al., 1989, Science 243:934-937; Werness, et al., 1990, Science 248:76-79; Scheffner, et al., 1990, Cell 63:1129-1136). Defective signaling mutants of SCF (Kondoh, et al., 1995, Oncogene 10:341-347) or c-kit (Li, et al., 1996, Canc. Res. 56:4343-4346) inhibited formation of testicular tumors in mice expressing HPV16 E6 and E7. The c-kit kinase activation is pivotal to tumorigenesis in these animals and thus modulation of the c-kit kinase pathway by the present disclosure will prevent or treat such disorders.

Expression of c-kit in germ cell tumors shows that the receptor is expressed by the majority of carcinomas in situ and seminomas, but c-kit is expressed in only a minority of nonseminomas (Strohmeyer, et al., 1991, Canc. Res. 51:1811-1816; Rajpert-de Meyts, et al., 1994, Int. J. Androl. 17:85-92; Izquierdo, et al., 1995, J. Pathol. 177:253-258; Strohmeyer, et al., 1995, J. Urol. 153:511-515; Bokenmeyer, et al., 1996, J. Cancer Res. Clin. Oncol. 122:301-306; Sandlow, et al., 1996, J. Androl. 17:403-408). Therefore, inhibition of c-kit kinase provides a means for treating these disorders.

CNS cancers: SCF and c-kit are expressed throughout the CNS of developing rodents, and the pattern of expression indicates a role in growth, migration and differentiation of neuroectodermal cells. Expression of both receptor and ligand have also been reported in the adult brain (Hamel, et al., 1997, J. Neuro-Onc. 35:327-333). Expression of c-kit has also been observed in normal human brain tissue (Tada, et al. 1994, J. Neuro 80:1063-1073). Glioblastoma and astrocytoma, which define the majority of intracranial tumors, arise from neoplastic transformation of astrocytes (Levin, et al., 1997, Principles & Practice of Oncology: 2022-2082). Expression of c-kit has been observed in glioblastoma cell lines and tissues (Berdel, et al., 1992, Canc. Res. 52:3498-3502; Tada, et al. 1994, J. Neuro 80:1063-1073; Stanulla, et al., 1995, Act Neuropath 89:158-165).

Cohen, et al., 1994, Blood 84:3465-3472 reported that all 14 neuroblastoma cell lines examined contained c-kit/SCF autocrine loops, and expression of both the receptor and ligand were observed in 45% of tumor samples examined. In two cell lines, anti-c-kit antibodies inhibited cell proliferation, suggesting that the SCF/c-kit autocrine loop contributed to growth (will Cohen, et al., 1994, Blood 84:3465-3472). Hence, c-kit kinase inhibitors can be used to treat these cancers.

Exemplary Mast Cell Diseases Involving c-Kit

Excessive activation of c-kit is also associated with diseases resulting from an overabundance of mast cells. Mastocytosis is the term used to describe a heterogeneous group of disorders characterized by excessive mast cell proliferation (Metcalfe, 1991, J. Invest. Derm 93:2S-4S; Golkar, et al., 1997, Lancet 349:1379-1385). Elevated c-kit expression was reported on mast cells from patients with aggressive mastocytosis (Nagata, et al., 1998, Leukemia 12:175-181).

Additionally, mast cells and eosinophils represent key cells involved in allergy, inflammation and asthma (Thomas, et al., 1996, Gen. Pharmacol 27:593-597; Metcalfe, et al., 1997, Physiol Rev 77:1033-1079; Naclerio, et al., 1997, JAMA 278:1842-1848; Costa, et al., 1997, JAMA 278:1815-1822). SCF, and hence c-kit, directly and indirectly regulates activation of both mast cells and eosinophils, thereby influencing the primary cells involved in allergy and asthma through multiple mechanisms. Because of this mutual regulation of mast cell and eosinophil function, and the role that SCF can play in this regulation, inhibition of c-kit can be used to treat allergy-associated chronic rhinitis, inflammation and asthma.

Mastocytosis: SCF (also known as mast cell growth factor) stimulation of c-kit has been reported to be essential for the growth and development of mast cells (Hamel, et al., 1997, J. Neuro-Onc. 35:327-333; Kitamura, et al., 1995, Int. Arch. Aller. Immunol. 107:54-56). Mice with mutations of c-kit that attenuate its signaling activity have exhibited significantly fewer mast cells in their skin (Tsujimura, 1996, Pathol Int 46:933-938). Excessive activation of c-kit can be associated with diseases resulting from an overabundance of mast cells.

Mastocytosis is limited to the skin in the majority of patients, but can involve other organs in 15-20% of patients (Valent, 1996, Wein/Klin Wochenschr 108:385-397; Golkar, et al., 1997, Lancet 349:1379-1385). Even among patients with systemic mastocytosis, the disease can range from having a relatively benign prognosis to aggressive mastocytosis and mast cell leukemia. (Valent, 1996, Wein/Klin Wochenschr 108:385-397; Golkar, et al., 1997, Lancet 349: 1379-1385). c-kit has been observed on malignant mast cells from canine mast cell tumors (London, et al., 1996, J. Compar. Pathol. 115:399-414), as well as on mast cells from patients with aggressive systemic mastocytosis (Baghestanian, et al., 1996, Leuk.:116-122; Castells, et al., 1996, J. Aller. Clin. Immunol. 98:831-840).

SCF has been shown to be expressed on stromal cells as a membrane-bound protein, and its expression can be induced by fibrogenic growth factors such as PDGF. It has also been shown to be expressed on keratinocytes as a membrane-bound protein in normal skin. However, in the skin of patients with mastocytosis, an increased amount of soluble SCF has been observed (Longley, et al., 1993, New Engl. J. Med. 328:1302-1307).

Mast cell chymase has been reported to cleave membrane-associated SCF to a soluble and biologically active form. This mast cell-mediated process can generate a feedback loop to enhance mast cell proliferation and function (Longley, et al., 1997, Proc. Natl. Acad. Sci. 94:9017-9021), and may be important for the etiology of mastocytosis. Transgenic mice overexpressing a form of SCF that could not be proteolytically released from keratinocytes did not develop mastocytosis, while similar animals expressing normal SCF in keratinocytes exhibited a phenotype resembling human cutaneous mastocytosis (Kunisada, et al., 1998, J. Exp. Med. 187:1565-1573). Formation of large amounts of soluble SCF can contribute to the pathology associated with mastocytosis in some patients and the present disclosure can treat or prevent such disorders by modulating the interaction between SCF and c-kit kinase. Several different mutations of c-kit that resulted in constitutive kinase activity have been found in human and rodent mast cell tumor cell lines (Furitsu, et al., 1993, J. Clin. Invest. 92:1736-1744; Tsujimura, et al., 1994, Blood 9:2619-2626; Tsujimura, et al., 1995, Int. Arch. Aller. Immunol 106:377-385; Tsujimura, 1996, Pathol Int 46:933-938). In addition, activating mutations of the c-kit gene have been observed in peripheral mononuclear cells isolated from patients with mastocytosis and associated hematologic disorders (Nagata, et al., 1998, Mastocytosis Leuk 12:175-181), and in mast cells from a patient with urticaria pigmentosa and aggressive mastocytosis (Longley, et al., 1996, Nat. Gen. 12:312-314). Inhibition of c-kit kinase will therefore prove to have an excellent therapeutic role in the treatment of these disorders.

In some patients, activating mutations of c-kit may be responsible for the pathogenesis of the disease and these patients can be treated, or their diseases prevented, by modulation of the SCF interaction with c-kit kinase. SCF activation of c-kit has been shown to prevent mast cell apoptosis which may be critical for maintaining cutaneous mast cell homeostasis (Iemura, et al., 1994, Amer. J. Pathol 144:321-328; Yee, et al., 1994, J. Exp. Med. 179:1777-1787; Mekori, et al., 1994, J. Immunol 153:2194-2203; Mekori, et al., 1995, Int. Arch. Allergy Immunol. 107:137-138). Inhibition of mast cell apoptosis can lead to the mast cell accumulation associated with mastocytosis. Thus, observation of c-kit activation resulting from overexpression of the receptor, excessive formation of soluble SCF, or mutations of the c-kit gene that constitutively activate its kinase, provides a rationale that inhibition of the kinase activity of c-kit will decrease the number of mast cells and provide benefit for patients with mastocytosis.

For cells with activating c-kit mutations, it was found that inhibitors of c-kit inhibit or even kill the cells (Ma et al., 2000, J Invest Dermatol. 114:392-394), particularly for mutations in the regulatory region (Ma et al., 2002, Blood 99:1741-1744). Ma et al., 2002, also showed that for mutations in the catalytic region, inhibitors STI571 (Gleevec) and SU9529 did not inhibit the cells, such that additional types of c-kit inhibitors are useful. Thus, c-kit inhibitors can be used against both wild-type c-kit as well as c-kit having mutations, e.g., activating mutations in the regulatory region and/or catalytic region.

It has been shown that mastocytosis is characterized by a pathologic increase of mast cells in tissues associated with mutations in KIT (Metcalfe, 2008, Blood, 112:946-956; and Ma, et al., 2002). D816 mutation of c-kit has been detected in patients with mastocytosis (Taylor, et al., 2001, Blood, 98:1195-1199; and Longley, et al. 1999, Proc. Natl. Acad. Sci. 96:1609-14). Inhibition of KIT oncogenic protein $KIT^{D816V}$ with small molecule tyrosine kinase inhibitor is capable of treating patients with systemic mastocytosis (Shah, et al., 2006, Blood, 108:286-291). Thus, c-kit inhibitors can be used in treating patients with mastocytosis.

Asthma & Allergy: Mast cells and eosinophils represent key cells in parasitic infection, allergy, inflammation, and asthma (Thomas, et al., 1996, Gen. Pharmacol 27:593-597; Metcalfe, et al., 1997, Physiol Rev 77:1033-1079; Holgate, 1997, CIBA Found. Symp.; Naclerio, et al, 1997, JAMA 278:1842-1848; Costa, et al., 1997, JAMA 778:1815-1822). SCF has been shown to be essential for mast cell development, survival and growth (Kitamura, et al., 1995, Int. Arch. Aller. Immunol. 107:54-56; Metcalfe, et al., 1997, Physiol Rev 77:1033-1079). In addition, SCF cooperates with the eosinophil-specific regulator, IL-5, to increase the development of eosinophil progenitors (Metcalf, et al., 1998, Proc. Natl. Acad. Sci., USA 95:6408-6412). SCF has also been reported to induce mast cells to secrete factors (Okayama, et al., 1997, Int. Arch. Aller. Immunol. 114:75-77; Okayama, et al., 1998, Eur. J. Immunol. 28:708-715) that promote the survival of eosinophils (Kay, et al., 1997, Int. Arch. Aller. Immunol. 113:196-199), which may contribute to chronic, eosinophil-mediated inflammation (Okayama, et al., 1997, Int. Arch. Aller. Immunol. 114:75-77; Okayama, et al., 1998, Eur. J. Immunol. 28:708-715). In this regard, SCF directly and indirectly regulates activation of both mast cells and eosinophils.

SCF induces mediator release from mast cells, as well as priming these cells for IgE-induced degranulation (Columbo, et al., 1992, J. Immunol 149:599-602) and sensitizing their responsiveness to eosinophil-derived granule major basic protein (Furuta, et al., 1998, Blood 92:1055-1061). Among the factors released by activated mast cells are IL-5, GM-CSF and TNF-□, which influence eosinophil protein secretion (Okayama, et al., 1997, Int. Arch. Aller. Immunol. 114:75-77; Okayama, et al., 1998, Eur. J. Immunol. 28:708-715). In addition to inducing histamine release from mast cells (Luckacs, et al., 1996, J. Immunol. 156: 3945-3951; Hogaboam, et al., 1998, J. Immunol. 160:6166-6171), SCF promotes the mast cell production of the eosinophil chemotactic factor, eotaxin (Hogaboam, et al., 1998, J. Immunol. 160:6166-6171), and eosinophil infiltration (Luckacs, et al., 1996, J. Immunol. 156:3945-3951).

SCF also directly influences the adhesion of both mast cells (Dastych, et al., 1994, J. Immunol. 152:213-219; Kinashi, et al., 1994, Blood 83:1033-1038) and eosinophils (Yuan, et al., 1997, J. Exp. Med. 186:313-323), which in turn, regulates tissue infiltration. Thus, SCF can influence the primary cells involved in allergy and asthma through multiple mechanisms. Currently, corticosteroids are the most effective treatment for chronic rhinitis and inflammation associated with allergy (Naclerio, et al., 1997, JAMA 278:1842-1848; Meltzer, 1997, Aller. 52:33-40). These agents work through multiple mechanisms including reduction of circulating and infiltrating mast cells and eosinophils, and diminished survival of eosinophils associated with inhibition of cytokine production (Meltzer, 1997, Aller. 52:33-40). Steroids have also been reported to inhibit the expression of SCF by fibroblasts and resident connective tissue cells, which leads to diminished mast cell survival (Finotto, et al., 1997, J. Clin. Invest. 99 1721-1728). Because of the mutual regulation of mast cell and eosinophil function, and the role that SCF can play in this regulation, inhibition of c-kit kinase will provide a means to treat allergy-associated chronic rhinitis, inflammation and asthma.

Inflammatory arthritis (e.g. rheumatoid arthritis): Due to the association of mast cells with the arthritic process (Lee et al., 2002, Science 297:1689-1692), c-kit provides a useful target for prevention, delay, and/or treatment of inflammatory arthritis, such as rheumatoid arthritis.

Multiple sclerosis: Mast cells have been shown to play an extensive role in autoimmune diseases, as demonstrated in the mouse model of multiple sclerosis (MS), experimental allergic encephalomyelitis (EAE). Mast cells were indicated to be required for full manifestation of the disease. Secor et al., 2000, J Exp Med 191:813-821. Thus, c-kit also provides a useful target for the prevention, delay, and/or treatment of multiple sclerosis.

Kinase Activity Assays

A number of different assays for kinase activity can be utilized for assaying for active modulators and/or determining specificity of a modulator for a particular kinase or group or kinases. In addition to the assay mentioned in the Examples below, one of ordinary skill in the art will know of other assays that can be utilized and can modify an assay for a particular application. For example, numerous papers concerning kinases describe assays that can be used.

In certain embodiments, compounds of formulas (I'), (I'a), (I), (II), (III), (IV), (V) or (V'), or any of the subformulas or compounds as disclosed herein are active in an assay measuring c-kit and/or mutant c-kit protein kinase activity. In some embodiments, a compound of formulas (I), (II) or any of the subformulas or a compound as described herein has an $IC_{50}$ of less than 10,000 nM, 1,000 nM, less than 500 nM, less than 100 nM, less than 50 nM, less than 20 nM, less than 10 nM, less than 5 nM, or less than 1 nM as determined in a generally accepted c-kit and/or mutant c-kit kinase activity assay. In some embodiments, a compound as described herein has an $IC_{50}$ of less than 10,000 nM, 1,000 nM, less than 500 nM, less than 100 nM, less than 50 nM, less than 20 nM, less than 10 nM, less than 5 nM, or less than 1 nM as determined in a generally accepted mutant c-kit kinase (such as D816F, D816H, D816N, D816Y, D816V, K642E, Y823D, Del 550-558, Del 557-561, N822K, V654A, N822H, Del 550-558+V654A, Del 557-561+V654A, Ins503AY, V560G, 558NP, Del 557-558, Del W559-560, F522C, Del 579, R634W, K642E, T801I, C809G, D820Y, N822K, N822H, Y823D, Y823C and T670I) activity assay. In some embodiments, the assay for measuring c-kit kinase activity and/or mutant c-kit kinase (such as D816F, D816H, D816N, D816Y, D816V, K642E, Y823D, Del 550-558, Del 557-561, N822K, V654A, N822H, Del 550-558+V654A, Del 557-561+V654A, Ins503AY, V560G, 558NP, Del 557-558, Del W559-560, F522C, Del 579, R634W, K642E, T801I, C809G, D820Y, N822K, N822H, Y823D, Y823C and T670I) activity includes an assay (e.g., biochemical or cell-bases assays) such as described in Example 17 or an assay well known in the art similar to those described in Example 17.

In some embodiments, compounds of formulas (I'), (I'a), (I), (II), (III), (IV), (V) or (V'), any of the subformulas as described herein or a compound as described herein are active in an assay measuring c-kit protein kinase activity and/or an assay for measuring mutant c-kit (such as D816V and/or V560G). In some embodiments a compound as described herein has an $IC_{50}$ of less than 10,000 nM, 1,000 nM, less than 500 nM, less than 100 nM, less than 50 nM, less than 20 nM, less than 10 nM, less than 5 nM, or less than 1 nM as determined in a generally accepted c-kit kinase activity assay (including a mutant c-kit kinase activity assay). In some embodiments, a compound as described herein has an $IC_{50}$ of less than 100 nM, less than 10 nM, or less than 1 nM in a D816V and/or V560G mutant c-kit activity assay.

Modulation of c-Kit Kinase

In another aspect, the disclosure provides a method for modulating or inhibiting a c-kit and/or mutant c-kit kinase. The method includes administering to a subject an effective amount of a compound of any of formulas (I'), (I'a), (I), (II), (III), (IV), (V), (V') and any of the subgeneric formulas as described herein, e.g., any of the formulas (I'), (I'a), (I), (II), (III), (IV), (V0, (V'), (IIIa), (IIIb), (IIIc), (IIId), (IIId), (IIIe), (IIIa-1), (IIIa-2), (IIIa-3), (IIIa-4), (IIIa-5), (IIIa-6), (IIIa-7), (IIIa-8), (IIIb-1), (IIIb-2), (IIIb-3), (IIIb-4), (IIIb-5), (IIIc-1), (IIIc-2), (IIIc-3), (IIIc-4), (IIIc-5), (IIId-1), (IIId-2), (IIId-3), (IIId-4), (IIId-5), (IIIe-1), (IIIe-2), (IIIe-3), (IIIe-4), (IIIe-5), (IVa), (IVa-1), (IVa-2), (IVa-3), (IVa-4), (IVa-5), (IVa-6), (IVa-7), (IVa-8), (IVa-9), (IVa-10), (IVa-1a), (IVa-2a), (IVa-3a), (IVa-4a), (IVa-5a), (IVa-6a), (IVa-7a), (IVa-8a), (IVa-9a), (IVa-10a), (IVa-1b), (IVa-2b), (IVa-5b), (IVa-6b), (IVb), (IVb-1), (IVb-2), (IVb-3), (IVb-4), (IVb-5), (IVb-6), (IVb-7), (IVb-8), (IVc), (IVc-1), (IVc-2), (IVc-3), (IVc-4), (IVc-5), (IVd), (IVd-1), (IVd-2), (IVd-3), (IVd-4), (IVd-5), (IVe), (IVe-1), (IVe-2), (IVe-3), (IVe-4), (IVe-5), (Va), (Va-1), (Va-2), (Va-3), (Va-1a), (Va-2a), (Va-3a), (Va-1a-1), (Va-2a-1), (Va-1b), (Va-2b), (Va-3b), (Va-1b-1), (Va-2b-1), (Va-6), (Va-6a), (Va-6b), (Va-6c) or (Va-6d), or a compound set forth in Table 1, Table 2 or Table 3, or a compound of P-2001 to P-2273 and P-2274 to P-2307, or a compound as described herein, or pharmaceutically acceptable salts, hydrates, solvates, tautomers or isomers thereof, or a composition comprising a compound of any of the formulas as described herein, thereby, modulating or inhibiting the c-kit and/or mutant c-kit kinase. In some embodiments, the c-kit is a wild type kit kinase. In other embodiments, the c-kit kinase is a mutant kit kinase having a mutation selected from D816F, D816H, D816N, D816Y, D816V, K642E, Y823D, Del 550-558, Del 557-561, N822K, V654A, N822H, Del 550-558+V654A, Del 557-561+V654A, Ins503AY, V560G, 558NP, Del 557-558, Del W559-560, F522C, Del 579, R634W, K642E, T801I, C809G, D820Y, N822K, N822H, Y823D, Y823C and T670I. In one embodiment, the mutant c-kit has an activating D816V and/or V560G mutation. In some embodiments, the method includes contacting a cell in vivo or in vitro with a compound of formulas (I'), (I'a), (I), (II), (III), (IV), (V), (V') or any of the subformulas as described herein, or a compound as disclosed herein, or pharmaceutically acceptable salts, hydrates, solvates, tautomers or isomers thereof, or a composition comprising a compound of any of the formulas as described herein. In other embodiments, the method includes contacting a mutant c-kit kinase in vivo or in vitro with a compound of formulas (I'), (I'a), (I), (II), (III), (IV), (V), (V') or any of the subformulas as described herein or a compound as disclosed herein or pharmaceutically acceptable salts, hydrates, solvates, tautomers or isomers thereof, or a composition comprising a compound of any of the formulas as described herein.

VI. Methods for Treating Conditions Mediated by c-Kit Kinase

In another aspect, the present disclosure provides a method for treating a subject suffering from or at risk of a c-kit and or a mutant c-kit protein kinase mediated diseases or conditions. The method includes administering to the subject an effective amount of a compound of any of formulas (I'), (I'a), (I), (II), (III), (IV), (V), (V'), (IIIa), (IIIb), (IIIc), (IIId), (IIId), (IIIe), (IIIa-1), (IIIa-2), (IIIa-3), (IIIa-4), (IIIa-5), (IIIa-6), (IIIa-7), (IIIa-8), (IIIb-1), (IIIb-2), (IIIb-3), (IIIb-4), (IIIb-5), (IIIc-1), (IIIc-2), (IIIc-3), (IIIc-4), (IIIc-5), (IIId-1), (IIId-2), (IIId-3), (IIId-4), (IIId-5), (IIIe-1), (IIIe-2), (IIIe-3), (IIIe-4), (IIIe-5), (IVa), (IVa-1), (IVa-2), (IVa-3), (IVa-4), (IVa-5), (IVa-6), (IVa-7), (IVa-8), (IVa-9), (IVa-10), (IVa-1a), (IVa-2a), (IVa-3a), (IVa-4a), (IVa-5a), (IVa-6a), (IVa-7a), (IVa-8a), (IVa-9a), (IVa-10a), (IVa-1b), (IVa-2b), (IVa-5b), (IVa-6b), (IVb), (IVb-1), (IVb-2), (IVb-3), (IVb-4), (IVb-5), (IVb-6), (IVb-7), (IVb-8), (IVc), (IVc-1), (IVc-2), (IVc-3), (IVc-4), (IVc-5), (IVd), (IVd-1), (IVd-2), (IVd-3), (IVd-4), (IVd-5), (IVe), (IVe-1), (IVe-2), (IVe-3), (IVe-4), (IVe-5), (Va), (Va-1), (Va-2), (Va-3), (Va-1a), (Va-2a), (Va-3a), (Va-1a-1), (Va-2a-1), (Va-1b), (Va-2b), (Va-3b), (Va-1b-1), (Va-2b-1), (Va-6), (Va-6a), (Va-6b), (Va-6c) or (Va-6d), or a compound disclosed in the Examples, a compound set forth in Table 1, Table 2 or Table 3, or a compound of P-2001 to P-2273 and P-2274 to P-2307, or a compound as described herein, or pharmaceutically acceptable salts, hydrates, solvates, tautomers or isomers thereof, or a composition comprising a compound of any of the formulas as described herein. In some embodiments, the mutant c-kit kinase has a mutation selected from D816F, D816H, D816N, D816Y, D816V, K642E, Y823D, Del 550-558, Del 557-561, N822K, V654A, N822H, Del 550-558+V654A, Del 557-561+V654A, Ins503AY, V560G, 558NP, Del 557-558, Del W559-560, F522C, Del 579, R634W, K642E, T801I, C809G, D820Y, N822K, N822H, Y823D, Y823C or T670I or combinations thereof. In one embodiment, the mutant c-kit has an activating D816 mutation. In one embodiment, the mutant c-kit has an activating D816V mutation. In another embodiment, the mutant c-kit has a V560G mutation. In yet another embodiment, the mutant c-kit has an activating D816V and V560G mutations. In certain embodiments, the method involves administering to the subject an effective amount of any one or more compound(s) as described herein in combination with one or more other therapies for the disease or condition.

In some embodiments, the disclosure provides a method of suppressing undesired proliferation of tumor cells expressing a D816 (such as D816F, D816H, D816N, D816Y or D816V) and/or V560G mutant c-kit protein kinase. The method includes contacting tumor cells expressing D816 (such as D816F, D816H, D816N, D816Y or D816V) and/or V560G mutant c-kit protein kinase with an effective amount of a compound of any of formulas (I'), (I'a) (I), (II), (III), (IV), (V), (V') or any of the subformulas as described herein, or any compound as described herein, or pharmaceutically acceptable salts, hydrates, solvates, tautomers or isomers thereof, or a composition comprising a compound as described herein. In some instances, the tumor cells expressing D816V and/or V560G mutant c-kit kinase.

In certain embodiments, the disclosure provides a method of treating a c-kit protein kinase D816 (such as D816F, D816H, D816N, D816Y or D816V) and/or V560G mutation-positive patient. The method includes administering to the patient in need thereof an effective amount of a compound of any of formulas (I'), (I'a) (I), (II), (III), (IV), (V), (V') or any of the subformulas as described herein, or any compound as described herein, or pharmaceutically acceptable salts, hydrates, solvates, tautomers or isomers thereof, or a composition comprising a compound as described herein. In some embodiments, the patient is D816V mutation-positive. In other embodiments, the patient is V560G mutation-positive. In some embodiments, the patient is D816V and V560G mutation-positive. In certain instances the patient is suffering from gastrointestinal stromal tumors (GISTs) and/or mastocytosis.

In some embodiments, the diseases or conditions treatable with the compounds of the present disclosure include, but are not limited to, multi-infarct dementia, head injury, spinal cord injury, Alzheimer's disease (AD), Parkinson's disease, seizures and epilepsy; neoplastic diseases including, but not limited to, melanoma, glioma, glioblastoma multiforme, pilocytic astrocytoma, sarcoma, carcinoma (e.g. gastrointestinal, liver, biliary tract, bile duct (cholangiocarcinoma), colorectal, lung, gallbladder, breast, pancreatic, thyroid, renal, ovarian, adrenocortical, prostate), lymphoma (e.g. histiocytic lymphoma) neurofibromatosis, gastrointestinal stromal tumors, acute myeloid leukemia, myelodysplastic syndrome, leukemia, tumor angiogenesis, neuroendocrine tumors such as medullary thyroid cancer, carcinoid, small cell lung cancer, Kaposi's sarcoma, and pheochromocytoma; pain of neuropathic or inflammatory origin, including, but not limited to, acute pain, chronic pain, cancer-related pain, and migraine; cardiovascular diseases including, but not limited to, heart failure, ischemic stroke, cardiac hypertrophy, thrombosis (e.g. thrombotic microangiopathy syndromes), atherosclerosis, and reperfusion injury; inflammation and/or proliferation including, but not limited to, psoriasis, eczema, arthritis and autoimmune diseases and conditions, osteoarthritis, endometriosis, scarring, vascular restenosis, fibrotic disorders, rheumatoid arthritis, inflammatory bowel disease (IBD); immunodeficiency diseases, including, but not limited to, organ transplant rejection, graft versus host disease, and Kaposi's sarcoma associated with HIV; renal, cystic, or prostatic diseases, including, but not limited to, diabetic nephropathy, polycystic kidney disease, nephrosclerosis, glomerulonephritis, prostate hyperplasia, polycystic liver disease, tuberous sclerosis, Von Hippel Lindau disease, medullary cystic kidney disease, nephronophthisis, and cystic fibrosis; metabolic disorders, including, but not limited to, obesity; infection, including, but not limited to Helicobacter pylori, Hepatitis and Influenza viruses, fever, HIV, and sepsis; pulmonary diseases including, but not limited to, chronic obstructive pulmonary disease (COPD) and acute respiratory distress syndrome (ARDS); genetic developmental diseases, including, but not limited to, Noonan's syndrome, Costello syndrome, (facio-cutaneoskeletal syndrome), LEOPARD syndrome, cardiofaciocutaneous syndrome (CFC), and neural crest syndrome abnormalities causing cardiovascular, skeletal, intestinal, skin, hair and endocrine diseases; and diseases associated with muscle regeneration or degeneration, including, but not limited to, sarcopenia, muscular dystrophies (including, but not limited to, Duchenne, Becker, Emery-Dreifuss, Limb-Girdle, Facioscapulohumeral, Myotonic, Oculopharyngeal, Distal and Congenital Muscular Dystrophies), motor neuron diseases (including, but not limited to, amyotrophic lateral sclerosis, infantile progressive spinal muscular atrophy, intermediate spinal muscular atrophy, juvenile spinal muscular atrophy, spinal bulbar muscular atrophy, and adult spinal muscular atrophy), inflammatory myopathies (including, but not limited to, dermatomyositis, polymyositis, and inclusion body myositis), diseases of the neuromuscular junction (including, but not limited to, myasthenia gravis, Lambert-Eaton syndrome, and congenital myasthenic syndrome), myopathies due to endocrine abnormalities (including, but not limited to, hyperthyroid myopathy and hypothyroid myopathy) diseases of peripheral nerve (including, but not limited to, Charcot-Marie-Tooth disease, Dejerine-Sottas disease, and Friedreich's ataxia), other myopathies (including, but not limited to, myotonia congenita, paramyotonia congenita, central core disease, nemaline myopathy, myotubular myopathy, and periodic paralysis), and metabolic diseases of muscle (including, but not limited to, phosphorylase deficiency, acid maltase deficiency, phosphofructokinase deficiency, debrancher enzyme deficiency, mitochondrial myopathy, carnitine deficiency, carnitine palmatyl transferase deficiency, phosphoglycerate kinase deficiency, phosphoglycerate mutase deficiency, lactate dehydrogenase deficiency, and myoadenylate deaminase deficiency). In one embodiment, the disease or condition is selected from the group consisting of melanoma, glioma, glioblastoma multiforme, pilocytic astrocytoma, sarcoma, liver cancer, biliary tract cancer, cholangiocarcinoma, colorectal cancer, lung cancer, gallbladder cancer, breast cancer, pancreatic cancer, thyroid cancer, renal cancer, ovarian cancer, adrenocortical cancer, prostate cancer, histiocytic lymphoma, neurofibromatosis, gastrointestinal stromal tumors, acute myeloid leukemia, myelodysplastic syndrome, leukemia, tumor angiogenesis, medullary thyroid cancer, carcinoid, small cell lung cancer, Kaposi's sarcoma, pheochromocytoma, acute pain, chronic pain, and polycystic kidney disease. In a preferred embodiment, the disease or condition is selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, cholangiocarcinoma, acute pain, chronic pain, and polycystic kidney disease.

In other embodiments, the diseases or conditions treatable with the compounds of the present disclosure include, but are not limited to, ischemic stroke, cerebrovascular ischemia, multi-infarct dementia, head injury, spinal cord injury, Alzheimer's disease, Parkinson's disease, amyotrophic lateral sclerosis, dementia, senile chorea, Huntington's disease, neoplastic disease, complications with neoplastic disease, chemotherapy-induced hypoxia, gastrointestinal stromal tumors, prostate tumors, mast cell tumors, canine mast cell tumors, acute myeloid leukemia, acute lymphocytic leukemia, chronic myeloid leukemia, chronic lymphocytic leukemia, multiple myeloma, melanoma, mastocytosis, glioma, glioblastoma, astrocytoma, neuroblastoma, sarcomas, sarcomas of neuroectodermal origin, leiomyosarcoma, lung carcinoma, breast carcinoma, pancreatic carcinoma, colon carcinoma, hepatocellular carcinoma, renal carcinoma, carcinoma of the female genital tract, squamous cell carcinoma, carcinoma in situ, lymphoma, histiocytic lymphoma, non-Hodgkin's lymphoma, MEN2 syndromes, neurofibromatosis, Schwann cell neoplasia, myelodysplastic syndrome, leukemia, tumor angiogenesis, thyroid cancer, liver cancer, bone cancer, skin cancer, brain cancer, cancer of the central nervous system, pancreatic cancer, lung cancer, small cell lung cancer, non small cell lung cancer, breast cancer, colon cancer, bladder cancer, prostate cancer, gastrointestinal tract cancer, cancer of the endometrium, fallopian tube cancer, testicular cancer, ovarian cancer, pain of neuropathic origin, pain of inflammatory origin, acute pain, chronic pain, migraine, cardiovascular disease, heart failure, cardiac hypertrophy, thrombosis, thrombotic microangiopathy syndromes, atherosclerosis, reperfusion injury, ischemia, cerebrovascular ischemia, liver ischemia, inflammation, polycystic kidney disease, age-related macular degeneration, rheumatoid arthritis, allergic rhinitis, inflammatory bowel disease, ulcerative colitis, Crohn's disease, systemic lupus erythematosis, Sjogren's Syndrome, Wegener's granulomatosis, psoriasis, scleroderma, chronic thyroiditis, Grave's disease, myasthenia gravis, multiple sclerosis, osteoarthritis, endometriosis, dermal scarring, tissue scarring, vascular restenosis, fibrotic disorders, hypereosinophilia, CNS inflammation, pancreatitis, nephritis, atopic dermatitis, hepatitis, immunodeficiency diseases, severe combined immunodeficiency, organ transplant rejection, graft versus host disease, renal disease, prostatic disease, diabetic nephropathy, nephrosclerosis, glomerulonephritis, interstitial nephritis, Lupus nephritis, prostate hyperplasia, chronic renal failure, tubular necrosis, diabetes-associated renal complication, associated renal hypertrophy, type 1 diabetes, type 2 diabetes, metabolic syndrome, obesity, hepatic steatosis, insulin resistance, hyperglycemia, lipolysis obesity, infection, *Helicobacter pylori* infection, Influenza virus infection, fever, sepsis, pulmonary diseases, chronic obstructive pulmonary disease, acute respiratory distress syndrome, asthma, allergy, bronchitis, emphysema, pulmonary fibrosis, genetic developmental diseases, Noonan's syndrome, Crouzon syndrome, acrocephalo-syndactyly type I, Pfeiffer's syndrome, Jackson-Weiss syndrome, Costello syndrome, faciocutaneoskeletal syndrome, leopard syndrome, cardio-faciocutaneous syndrome, neural crest syndrome abnormalities causing cardiovascular, skeletal, intestinal, skin, hair or endocrine diseases, disorders of bone structure or mineralization, osteoporosis, increased risk of fracture, hypercalcemia, bone metastases, Grave's disease, Hirschsprung's disease, lymphoedema, selective T-cell defect, X-linked agammaglobulinemia, diabetic retinopathy, alopecia, erectile dysfunction, and tuberous sclerosis In some embodiments, the disease is selected from the group consisting of mast cell tumors, small cell lung cancer, testicular cancer, gastrointestinal stromal tumors (GISTs), metastatic GISTs, glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myelocytic leukemia, acute lymphocytic leukemia, chronic myelogenous leukemia, mastocytosis, urticaria pigmentosa (UP), telangiectasia macularis eruptiva perstans (TMEP), systemic mastocytosis, indolent systemic, smoldering systemic, aggressive systemic, mast cell leukemia, mast cell sarcoma melanoma, and canine mast cell tumors, and inflammatory diseases, including asthma, rheumatoid arthritis, allergic rhinitis, multiple sclerosis, inflammatory bowel syndrome, transplant rejection, and hypereosinophilia. In certain instances, the disease is a c-kit and or c-kit mutant, such as D816F, D816H, D816N, D816Y, D816V, K642E, Y823D, Del 550-558, Del 557-561, N822K, V654A, N822H, Del 550-558+V654A, Del 557-561+V654A, Ins503AY, V560G, 558NP, Del 557-558, Del W559-560, F522C, Del 579, R634W, K642E, T801I, C809G, D820Y, N822K, N822H, Y823D, Y823C or T670I mutant-mediated disease. In one embodiment, the disease is a D816 (such as D816F, D816H, D816N, D816Y or D816V) mutant mediated disease. In another embodiment, the disease is a D816V mutant mediated disease. In yet another embodiment, the disease is a V560G mutant mediated disease. In another embodiment, the disease is a D816V and V560G mutant mediated disease. In one embodiment, the disease is a cancer, preferably selected from the group consisting of melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract cancer, and cholangiocarcinoma. In one embodiment, the cancer is melanoma, colorectal cancer, thyroid cancer or lung cancer.

In some embodiments, the disclosure provides a method for treating a disease or condition selected from urticaria pigmentosa (UP), telangiectasia macularis eruptiva perstans (TMEP), systemic mastocytosis, indolent systemic, smoldering systemic, aggressive systemic, mast cell leukemia, mast cell sarcoma, GISTs and metastatic GISTs. The method involves administering to the subject in need thereof an effective amount of any one or more compound(s) as described herein, or pharmaceutically acceptable salts, hydrates, solvates, tautomers or isomers thereof, or a composition as described herein.

In some embodiments, the disclosure provides methods for treating any c-kit protein kinase mediated disease or condition, including any c-kit mutant kinase mediated disease or condition in an animal subject in need thereof, wherein the method involves administering to the subject an effective amount of any one or more compound(s) as described herein. In certain embodiments, the method involves administering to the subject an effective amount of any one or more compound(s) as described herein in combination with one or more other therapies for the disease or condition.

In some embodiments, the disclosure provides methods for treating any c-kit D816F, D816H, D816N, D816Y, D816V, K642E, Y823D, Del 550-558, Del 557-561, N822K, V654A, N822H, Del 550-558+V654A, Del 557-561+V654A, Ins503AY, V560G, 558NP, Del 557-558, Del W559-560, F522C, Del 579, R634W, K642E, T801I, C809G, D820Y, N822K, N822H, Y823D, Y823C or T670I mutant protein kinase mediated disease or condition in an animal subject in need thereof, wherein the method involves administering to the subject an effective amount of any one or more compound(s) as described herein. In certain embodiments, the method involves administering to the subject an effective amount of any one or more compound(s) as described herein in combination with one or more other therapies for the disease or condition. In some embodiments, the c-kit mutant protein kinase is c-kit D816 (such as D816F, D816H, D816N, D816Y or D816V) mutant kinase. In one embodiment, the c-kit mutant protein kinase is c-kit D816V mutant. In another embodiment, the c-kit mutant protein kinase is c-kit V560G mutant. In another embodiment, the c-kit mutant protein kinase is c-kit D816V/V560G mutant.

In some embodiments, a compound of any of formulas (I'), (I'a) (I), (II), (III), (IV), (V), (V') or any of the subformulas as described herein, or a compound as described herein, or pharmaceutically acceptable salts, hydrates, solvates, tautomers or isomers thereof, or a composition comprising a compound as described herein is a c-kit and/or mutant c-kit kinase inhibitor and has an $IC_{50}$ of less than 500 nM, less than 100 nM, less than 50 nM, less than 20 nM, less than 10 nM, less than 5 nM, or less than 1 nM as determined in a generally accepted c-kit kinase activity assay. In some embodiments, a compound as described herein will have an $IC_{50}$ of less than 500 nM, less than 100 nM, less than 50 nM, less than 20 nM, less than 10 nM, less than 5 nM, or less than 1 nM with respect to c-kit, c-kit D816V mutant, c-kit V560G mutant or D816V/V560G mutant. In some embodiments, a compound as described herein will selectively inhibit one or more mutant c-kit kinases relative to one or more other mutant c-kit kinases.

In some embodiments, the disclosure provides a method for inhibiting a c-kit mutant protein kinase, such as D816V, V560G or D816V/V560G mutant protein kinase. The method includes contacting a compound of any of formulas (I), (II), or any of the subformulas as described herein, or a compound as described herein, or a composition comprising a compound as described herein, or pharmaceutically acceptable salts, hydrates, solvates, tautomers or isomers thereof with a cell or a c-kit mutant protein kinase either in vitro or in vivo.

In certain embodiments, the disclosure provides use of a compound of any of formulas (I'), (I'a) (I), (II), (III), (IV), (V), (V') or any of the subformulas as described herein, or a compound as described herein, or a composition comprising a compound as described herein, or pharmaceutically acceptable salts, hydrates, solvates, tautomers or isomers thereof in the manufacture of a medicament for the treatment of a disease or condition as described herein. In other embodiments, the disclosure provides a compound of any of formulas (I), (II), or any of the subformulas as described herein, or a compound as described herein, or a composition comprising a compound as described herein, or pharmaceutically acceptable salts, hydrates, solvates, tautomers or isomers thereof for use in treating a disease or condition as described herein.

Combination Therapy

Protein kinase modulators may be usefully combined with another pharmacologically active compound, or with two or more other pharmacologically active compounds, particularly in the treatment of cancer. In one embodiment, the composition includes any one or more compound(s) as described herein along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer.

In some embodiments, the disclosure provides methods for treating a c-kit and/or mutant c-kit protein kinase mediated disease or condition in an animal subject in need thereof, wherein the method involves administering to the subject an effective amount of any one or more compound(s) as described herein, or one or more compounds of any of formulas (I'), (I'a) (I), (II), (III), (IV), (V), (V'), or any of the subformulas as described herein, or pharmaceutically acceptable salts, solvates, tautomers or isomers thereof, or a composition comprising a compound as described herein in combination with one or more other therapeutic agent as described herein. In certain embodiments, the disclosure provides methods for treating a c-kit and/or mutant c-kit protein kinase mediated disease or condition in an animal subject in need thereof, wherein the method involves administering to the subject an effective amount of any one or more compound(s) as described herein, or one or more compounds of any of formula (I'), (I'a) (I), (II), (III), (IV), (V), (V'), or any of the subformulas as described herein, or pharmaceutically acceptable salts, solvates, tautomers or isomers thereof, or a composition comprising a compound as described herein in combination with one or more other therapies for the disease or condition.

In some embodiments, the disclosure provides a composition, e.g., a pharmaceutical composition comprising a compound of any of formulas (I'), (I'a), (I), (II), (III), (IV), (V), (V'), (IIIa), (IIIb), (IIIc), (IIId), (IIId), (IIIe), (IIIa-1), (IIIa-2), (IIIa-3), (IIIa-4), (IIIa-5), (IIIa-6), (IIIa-7), (IIIa-8), (IIIb-1), (IIIb-2), (IIIb-3), (IIIb-4), (IIIb-5), (IIIc-1), (IIIc-2), (IIIc-3), (IIIc-4), (IIIc-5), (IIId-1), (IIId-2), (IIId-3), (IIId-4), (IIId-5), (IIIe-1), (IIIe-2), (IIIe-3), (IIIe-4), (IIIe-5), (IVa), (IVa-1), (IVa-2), (IVa-3), (IVa-4), (IVa-5), (IVa-6), (IVa-7), (IVa-8), (IVa-9), (IVa-10), (IVa-1a), (IVa-2a), (IVa-3a), (IVa-4a), (IVa-5a), (IVa-6a), (IVa-7a), (IVa-8a), (IVa-9a), (IVa-10a), (IVa-1b), (IVa-2b), (IVa-5b), (IVa-6b), (IVb), (IVb-1), (IVb-2), (IVb-3), (IVb-4), (IVb-5), (IVb-6), (IVb-7), (IVb-8), (IVc), (IVc-1), (IVc-2), (IVc-3), (IVc-4), (IVc-5), (IVd), (IVd-1), (IVd-2), (IVd-3), (IVd-4), (IVd-5), (IVe), (IVe-1), (IVe-2), (IVe-3), (IVe-4), (IVe-5), (V), (V'), (Va), (Va-1), (Va-2), (Va-3), (Va-1a), (Va-2a), (Va-3a), (Va-1a-1), (Va-2a-1), (Va-1b), (Va-2b), (Va-3b), (Va-1b-1), (Va-2b-1), (Va-6), (Va-6a), (Va-6b), (Va-6c) or (Va-6d), or a compound disclosed in the Examples, a compound set forth in Table 1, Table 2 or Table 3, or a compound of P-2001 to P2002 and P-2004 to P-2307, or a compound as described herein, or pharmaceutically acceptable salts, hydrates, solvates, tautomers or isomers thereof and one or more other therapeutic agents. In some embodiments, the one or more other therapeutic agents are selected from an alkylating agent, including, but not limiting to, adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosphamide, and uramustine; an antibiotic, including, but not limiting to, aclarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, and zorubicin; an antimetabolite, including, but not limiting to, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, raltitrexed, tegafur-uracil, thioguanine, trimethoprim, trimetrexate, and vidarabine; an immunotherapy, an antibody therapy, including, but not limiting to, alemtuzumab, bevacizumab, cetuximab, galiximab, gemtuzumab, panitumumab, pertuzumab, rituximab, brentuximab, tositumomab, trastuzumab, 90 Y ibritumomab tiuxetan, ipilimumab, tremelimumab and anti-CTLA-4 antibodies; a hormone or hormone antagonist, including, but not limiting to, anastrozole, androgens, buserelin, diethylstilbestrol, exemestane, flutamide, fulvestrant, goserelin, idoxifene, letrozole, leuprolide, magestrol, raloxifene, tamoxifen, and toremifene; a taxane, including, but not limiting to, DJ-927, docetaxel, TPI 287, larotaxel, ortataxel, paclitaxel, DHA-paclitaxel, and tesetaxel; a retinoid, including, but not limiting to, alitretinoin, bexarotene, fenretinide, isotretinoin, and tretinoin; an alkaloid, including, but not limiting to, demecolcine, homoharringtonine, vinblastine, vincristine, vindesine, vinflunine, and vinorelbine; an antiangiogenic agent, including, but not limiting to, AE-941 (GW786034, Neovastat), ABT-510, 2-methoxyestradiol, lenalidomide, and thalidomide; a topoisomerase inhibitor, including, but not limiting to, amsacrine, belotecan, edotecarin, etoposide, etoposide phosphate, exatecan, irinotecan (also active metabolite SN-38 (7-ethyl-10-hydroxy-camptothecin)), lucanthone, mitoxantrone, pixantrone, rubitecan, teniposide, topotecan, and 9-aminocamptothecin; a kinase inhibitor, including, but not liming to, axitinib (AG 013736), dasatinib (BMS 354825), erlotinib, gefitinib, flavopiridol, imatinib mesylate, lapatinib, motesanib diphosphate (AMG 706), nilotinib (AMN107), seliciclib, sorafenib, sunitinib malate, AEE-788, BMS-599626, UCN-01 (7-hydroxystaurosporine), vemurafenib, dabrafenib, PLX3397, selumetinib, and vatalanib; a targeted signal transduction inhibitor including, but not limiting to bortezomib, geldanamycin, and rapamycin; a biological response modifier, including, but not limiting to, imiquimod, interferon-E, and interleukin-2; and other chemotherapeutics, including, but not limiting to 3-AP (3-amino-2-carboxyaldehyde thiosemicarbazone), altrasentan, aminoglutethimide, anagrelide, asparaginase, bryostatin-1, cilengitide, elesclomol, eribulin mesylate (E7389), ixabepilone, lonidamine, masoprocol, mitoguanazone, oblimersen, sulindac, testolactone, tiazofurin, mTOR inhibitors (e.g. sirolimus, temsirolimus, everolimus, deforolimus), PI3K inhibitors (e.g. BEZ235, GDC-0941, XL147, XL765), Cdk4 inhibitors (e.g. PD-332991), Akt inhibitors, Hsp90 inhibitors (e.g. geldanamycin, radicicol, tanespimycin), farnesyltransferase inhibitors (e.g. tipifarnib), and Aromatase inhibitors (anastrozole letrozole exemestane). In one embodiment, the method of treating a cancer involves administering to the subject an effective amount of a composition including any one or more compound(s) of Formulae (I), (II) or any of the subformulas as described herein or a compound as described herein in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-□, interleukin-2, or erlotinib. In another embodiment, the chemotherapeutic agent is a Mek inhibitor. Exemplary Mek inhibitors include, but are not limited to, AS703026, AZD6244 (Selumetinib), AZD8330, BIX 02188, CI-1040 (PD184352), GSK1120212 (JTP-74057), PD0325901, PD318088, PD98059, RDEA119 (BAY 869766), TAK-733 and U0126-EtOH. In another embodiment, the chemotherapeutic agent is a tyrosine kinase inhibitor. Exemplary tyrosine kinase inhibitors include, but are not limited to, AEE788, AG-1478 (Tyrphostin AG-1478), AG-490, Apatinib (YN968D1), AV-412, AV-951(Tivozanib), Axitinib, AZD8931, BIBF1120 (Vargatef), BIBW2992 (Afatinib), BMS794833, BMS-599626, Brivanib (BMS-540215), Brivanib alaninate(BMS-582664), Cediranib (AZD2171), Chrysophanic acid (Chrysophanol), Crenolanib (CP-868569), CUDC-101, CYC116, Dovitinib Dilactic acid (TKI258 Dilactic acid), E7080, Erlotinib Hydrochloride (Tarceva, CP-358774, OSI-774, $NSC_{718781}$), Foretinib (GSK1363089, XL880), Gefitinib (ZD-1839 or Iressa), Imatinib (Gleevec), Imatinib Mesylate, Ki8751, KRN 633, Lapatinib (Tykerb), Linifanib (ABT-869), Masitinib (Masivet, AB1010), MGCD-265, Motesanib (AMG-706), MP-470, Mubritinib(TAK 165), Neratinib (HKI-272), NVP-BHG712, OSI-420 (Desmethyl Erlotinib, CP-473420), OSI-930, Pazopanib HCl, PD-153035 HCl, PD173074, Pelitinib (EKB-569), PF299804, Ponatinib (AP24534), PP121, RAF265 (CHIR-265), Raf265 derivative, Regorafenib (BAY 73-4506), Sorafenib Tosylate (Nexavar), Sunitinib Malate (Sutent), Telatinib (BAY 57-9352), TSU-68 (SU6668), Vandetanib (Zactima), Vatalanib dihydrochloride (PTK787), WZ3146, WZ4002, WZ8040, XL-184 free base (Cabozantinib), XL647, EGFR siRNA, FLT4 siRNA, KDR siRNA, Antidiabetic agents such as metformin, PPAR agonists (rosiglitazone, pioglitazone, bezafibrate, ciprofibrate, clofibrate, gemfibrozil, fenofibrate, indeglitazar), and DPP4 inhibitors (sitagliptin, vildagliptin, saxagliptin, dutogliptin, gemigliptin, alogliptin). In another embodiment, the agent is an EGFR inhibitor. Exemplary EGFR inhibitors include, but are not limited to, AEE-788, AP-26113, BIBW-2992 (Tovok), CI-1033, GW-572016, Iressa, LY2874455, RO-5323441. Tarceva (Erlotinib, OSI-774), CUDC-101 and WZ4002. In one embodiment, the method of treating a cancer involves administering to the subject an effective amount of a composition including any one or more compound(s) as described herein in combination with a chemotherapeutic agent selected from capecitabine, 5-fluorouracil, carboplatin, dacarbazine, gefitinib, oxaliplatin, paclitaxel, SN-38, temozolomide, vinblastine, bevacizumab, cetuximab, interferon-a, interleukin-2, or erlotinib. In some embodiments, a kit protein kinase modulator, particularly a compound of any of formula (I'), (I'a), (I), (II), (III), (IV), (V), or any of the subformulas as described herein, or a compound described herein, or pharmaceutically acceptable salts, solvates, tautomer or isomers thereof, may be administered simultaneously, sequentially or separately in combination with one or more agents as described above.

In some embodiments, the disclosure provides methods for treating a disease or condition mediated by c-kit and/or mutant c-kit kinase, including any mutations thereof, by administering to a subject an effective amount of a composition as described herein, which includes any one or more compound(s) as described herein in combination with one or more other therapeutic agents as described herein. In other embodiments, the disclosure provides methods for treating a disease or condition mediated by c-kit and/or mutant c-kit kinase, including any mutations thereof, by administering to a subject an effective amount of a composition as described herein, which includes any one or more compound(s) as described herein in combination with one or more other suitable therapies for treating the disease or condition.

In some embodiments, compositions are provided that include a therapeutically effective amount of any one or more compound(s) as described herein and at least one pharmaceutically acceptable carrier, excipient, and/or diluent, including combinations of any two or more compounds as described herein. The composition can further include a plurality of different pharmacologically active compounds, which can include a plurality of compounds as described herein. In certain embodiments, the composition can include any one or more compound(s) as described herein along with one or more compounds that are t herapeutically effective for the same disease indication. In one aspect, the composition includes any one or more compound(s) as described herein along with one or more compounds that are therapeutically effective for the same disease indication, wherein the compounds have a synergistic effect on the disease indication. In one embodiment, the composition includes any one or more compound(s) as described herein effective in treating a cancer and one or more other compounds that are effective in treating the same cancer, further wherein the compounds are synergistically effective in treating the cancer. The compounds can be administered simultaneously or sequentially.

In one embodiment, the disclosure provides methods for treating a disease or condition mediated by c-kit mutant kinases, such as D816F, D816H, D816N, D816Y, D816V, K642E, Y823D, Del 550-558, Del 557-561, N822K, V654A, N822H, Del 550-558+V654A, Del 557-561+V654A, Ins503AY, V560G, 558NP, Del 557-558, Del W559-560, F522C, Del 579, R634W, K642E, T801I, C809G, D820Y, N822K, N822H, Y823D, Y823C or T670I mutant kinase, by administering to the subject an effective amount of a composition including any one or more compound(s) as described herein in combination with one or more other suitable therapies as described herein for treating the disease. In one embodiment, the disclosure provides methods for treating a cancer mediated by c-kit mutant kinases, such as D816F, D816H, D816N, D816Y, D816V, K642E, Y823D, Del 550-558, Del 557-561, N822K, V654A, N822H, Del 550-558+V654A, Del 557-561+V654A, Ins503AY, V560G, 558NP, Del 557-558, Del W559-560, F522C, Del 579, R634W, K642E, T801I, C809G, D820Y, N822K, N822H, Y823D, Y823C or T670I mutant by administering to the subject an effective amount of a composition including any one or more compound(s) as described herein. In one embodiment, the disclosure provides methods for treating a cancer mediated by c-kit mutant kinases, such as D816F, D816H, D816N, D816Y, D816V, K642E, Y823D, Del 550-558, Del 557-561, N822K, V654A, N822H, Del 550-558+V654A, Del 557-561+V654A, Ins503AY, V560G, 558NP, Del 557-558, Del W559-560, F522C, Del 579, R634W, K642E, T801I, C809G, D820Y, N822K, N822H, Y823D, Y823C or T670I mutant by administering to the subject an effective amount of a composition including any one or more compound(s) as described herein in combination with one or more suitable anticancer therapies, such as one or more chemotherapeutic drugs or agents as described herein. In one instance, the c-kit mutant kinase is D816V mutant kinase. In another instance, the c-kit mutant kinase is V560G mutant kinase. In yet another instance, the c-kit mutant kinase has both D816V and V560G mutations.

In some embodiments, the disclosure provides a method of treating a cancer as described herein in a subject in need thereof by administering to the subject an effective amount of a compound or a composition including any one or more compound(s) as described herein, in combination with one or more other therapies or medical procedures effective in treating the cancer. Other therapies or medical procedures include suitable anticancer therapy (e.g. drug therapy, vaccine therapy, gene therapy, photodynamic therapy) or medical procedure (e.g. surgery, radiation treatment, hyperthermia heating, bone marrow or stem cell transplant). In one embodiment, the one or more suitable anticancer therapies or medical procedures is selected from treatment with a chemotherapeutic agent (e.g. chemotherapeutic drug), radiation treatment (e.g. x-ray, □-ray, or electron, proton, neutron, or □ particle beam), hyperthermia heating (e.g. microwave, ultrasound, radiofrequency ablation), Vaccine therapy (e.g. AFP gene hepatocellular carcinoma vaccine, AFP adenoviral vector vaccine, AG-858, allogeneic GM-CSF-secretion breast cancer vaccine, dendritic cell peptide vaccines), gene therapy (e.g. Ad5CMV-p53 vector, adenovector encoding MDA7, adenovirus 5-tumor necrosis factor alpha), photodynamic therapy (e.g. aminolevulinic acid, motexafin lutetium), oncolytic viral or bacterial therapy, surgery, or bone marrow and stem cell transplantation. In certain embodiments, the disclosure provides a method of treating a cancer in a subject in need thereof by administering to the subject an effective amount of a compound as described herein and applying a radiation treatment as described herein either separately or simultaneously. In one embodiment, the disclosure provides a method for treating a cancer in a subject in need thereof by administering an effective amount of a compound as described herein to the subject followed by a radiation treatment (e.g. x-ray, □-ray, or electron, proton, neutron, or □ particle beam). In another embodiment, the disclosure provides a method for treating a cancer in a subject in need thereof by applying a radiation treatment (e.g. x-ray, □-ray, or electron, proton, neutron, or □ particle beam) to the subject followed by administering an effective amount of a compound as described herein to the subject. In yet another embodiment, the disclosure provides a method for treating a cancer in a subject in need thereof by administering a compound as described herein and a radiation therapy (e.g. x-ray, □-ray, or electron, proton, neutron, or □ particle beam) to the subject simultaneously.

In another aspect, the disclosure provides kits or containers that include a compound of any of formulas (I'), (I'a) (I), (II), (III), (IV), (V), (V') or any of the subformulas as described herein, or a pharmaceutically acceptable salt thereof, a compound as described herein or a composition thereof as described herein. In some embodiments, the compound or composition is packaged, e.g., in a vial, bottle, flask, which may be further packaged, e.g., within a box, envelope, or bag; the compound or composition is approved by the U.S. Food and Drug Administration or similar regulatory agency for administration to a mammal, e.g., a human; the compound or composition is approved for administration to a mammal, e.g., a human, for a protein kinase mediated disease or condition; the disclosure kit or container may include written instructions for use and/or other indication that the compound or composition is suitable or approved for administration to a mammal, e.g., a human, for a c-kit protein kinase-mediated disease or condition; and the compound or composition may be packaged in unit dose or single dose form, e.g., single dose pills, capsules, or the like.

VII. Examples

The following examples are offered to illustrate, but not to limit the claimed disclosure.

Compounds within the scope of this disclosure can be synthesized as described below, using a variety of reactions known to the skilled artisan. One skilled in the art will also recognize that alternative methods may be employed to synthesize the target compounds of this disclosure, and that the approaches described within the body of this document are not exhaustive, but do provide broadly applicable and practical routes to compounds of interest. In some examples, the mass spectrometry result indicated for a compound may have more than one value due to the isotope distribution of an atom in the molecule, such as a compound having a bromo or chloro substituent.

Certain molecules claimed in this patent can exist in different enantiomeric and diastereomeric forms or one or more hydrogen atoms of the molecules can be replaced by one or more deuterium atoms including perdeuterated analogs, all such variants of these compounds are claimed. Further, it should be noted that the term "deuterated analog" refers to compounds where at least one hydrogen atom has been replaced by a deuterium atom.

Those skilled in the art will also recognize that during standard work up procedures in organic chemistry, acids and bases are frequently used. Salts of the parent compounds are sometimes produced, if they possess the necessary intrinsic acidity or basicity, during the experimental procedures described within this patent.

Example 1:

Preparation of N-[2-(4-fluorophenyl)-1H-pyrrolo[2,3-b]pyridin-5-yl]-3,4-dimethyl-1H-pyrazole-5-carboxamide (P-2024)

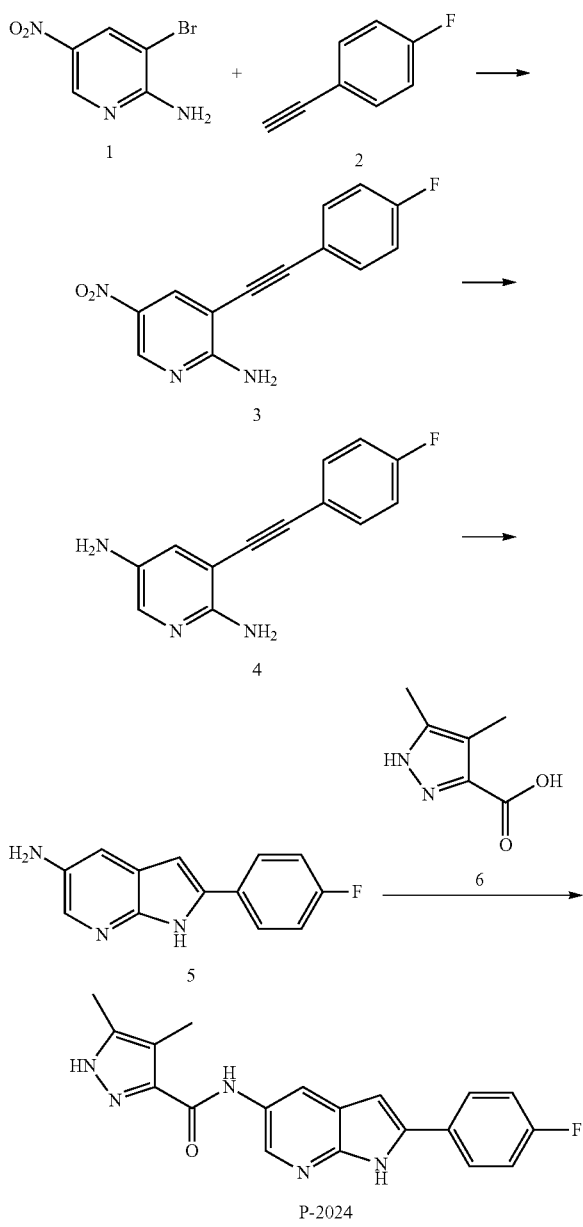

Step 1—Synthesis of 3-((4-fluorophenyl)ethynyl)-5-nitropyridin-2-amine (3): To a suspension of 3-bromo-5-nitropyridin-2-amine (1) (62.63 g, 287 mmol) in tetrahydrofuran (400 mL) and triethylamine (120 mL, 861 mmol) was added 1-ethynyl-4-fluorobenzene 2 (38.0 g, 316 mmol), copper(I) iodide (378 mg, 1.98 mmol) and bis(triphenylphosphine)palladium (II) dichloride (1.39 g, 1.98 mmol). The reaction mixture was purged with nitrogen for 5 minutes at room temperature and heated overnight in a sealed vessel at 50° C. The reaction mixture was cooled down and filtered. The resulting solid was washed with 3:1 heptanes:ethyl acetate (1.6 L), water (500 mL), heptanes (1 L) and dried at 50° C. in a vacuum oven to give crude 3-((4-fluorophenyl)ethynyl)-5-nitropyridin-2-amine 3 (59.27 g) as a golden solid. The data from the $^1$H NMR spectrum was consistent with the structure of the compound and the solid was used in the next step without further purification.

Step 2—Synthesis of 3-((4-fluorophenyl)ethynyl)pyridine-2,5-diamine (4): To 3-((4-fluorophenyl)ethynyl)-5-nitropyridin-2-amine 3 (59.27 g) in tetrahydrofuran (800 mL) and ethyl acetate (800 mL) was added tin(II) chloride (208 g, 0.952 mol) over 90 minutes while heating the reaction to 60° C. After the addition was complete, the reaction was stirred at 60° C. for 2 hours. The reaction mixture was cooled and filtered over Celite (550 g). The Celite was washed with ethyl acetate (3 L) then tetrahydrofuran (5 L) to give compound 4 (55.22 g). The data from the $^1$H NMR spectrum was consistent with the structure of the compound and the compound was used in the next step without further purification.

Step 3-Synthesis of 2-(4-fluorophenyl)-1H-pyrrolo[2,3-b]pyridin-5-amine (5): To N-methyl-2-pyrrolidone (360 mL) at 80° C. was added potassium tert-butoxide (55 g) then crude 3-((4-fluorophenyl)ethynyl)pyridine-2,5-diamine 4 (55.22 g) in N-methyl-2-pyrrolidone (750 mL) over 7 minutes. After 2 hours, the reaction mixture was cooled to room temperature (~22° C.) and water (5.5 L) was added. The aqueous layer was extracted with dichloromethane (~8 L). The organic layers were combined and dried with sodium sulfate, filtered, and concentrated under reduced pressure. The crude material was purified via silica gel (1.5 kg) column chromatography eluting with 0-5% methanol/dichloromethane to give 2-(4-fluorophenyl)-1H-pyrrolo[2,3-b]pyridin-5-amine 5 (4.5 g). $^1$HNMR and MS spectroscopy data were consistent with the desired product.

Step 4—Synthesis of N-[2-(4-fluorophenyl)-1H-pyrrolo[2,3-b]pyridin-5-yl]-3,4-dimethyl-1H-pyrazole-5-carboxamide (P-2024): A mixture of 3,4-dimethyl-1H-pyrazole-5-carboxylic acid 6 (0.11 g, 0.78 mmol) and benzotriazol-1-yl-oxytripyrrolidinophosphonium hexafluorophosphate (0.5 g, 0.96 mmol) in dimethylacetamide (4 mL) was stirred for 30 minutes. To the mixture was added 2-(4-fluorophenyl)-1H-pyrrolo[2,3-b]pyridin-5-amine 5 (0.12 g, 0.53 mmol), followed by N,N-diisopropylethylamine (0.1 mL). The reaction was stirred at room temperature overnight. To the reaction mixture was added acetonitrile and water and the precipitate was collected, washed with ethyl acetate and methanol. It was dried under vacuum to provide compound (P-2024) (85 mg, 46%). MS ESI [M+H+]+=350.1. The data from the $^1$H NMR spectrum was consistent with the structure of the compound.

Exemplary compounds N-[2-(4-fluorophenyl)-1H-pyrrolo[2,3-b]pyridin-5-yl]-3-methyl-1H-pyrazole-5-carboxamide (P-2019); N3-[2-(4-fluorophenyl)-1H-pyrrolo[2,3-b]pyridin-5-yl]benzene-1,3-dicarboxamide (P-2020); 3-(cyanomethyl)-N-[2-(4-fluorophenyl)-1H-pyrrolo[2,3-b]pyridin-5-yl]benzamide (P-2021); 2-chloro-N-[2-(4-fluorophenyl)-1H-pyrrolo[2,3-b]pyridin-5-yl]-6-methyl-benzamide (P-2022); 4-chloro-N-[2-(4-fluorophenyl)-1H-pyrrolo[2,3-b]pyridin-5-yl]-3-methyl-1H-pyrazole-5-carboxamide (P-2023); 3-cyano-N-[2-(4-fluorophenyl)-1H-pyrrolo[2,3-b]pyridin-5-yl]benzamide (P-2025); 3-acetamido-N-[2-(4-fluorophenyl)-1H-pyrrolo[2,3-b]pyridin-5-yl]benzamide (P-2026); N-[2-(4-fluorophenyl)-1H-pyrrolo[2,3-b]pyridin-5-yl]-2H-indazole-4-carboxamide (P-2027); 3-ethyl-N-[2-(4-fluorophenyl)-1H-pyrrolo[2,3-b]pyridin-5-yl]-4-methyl-1H-pyrazole-5-carboxamide (P-2028); N-[2-(4-fluorophenyl)-1H-pyrrolo[2,3-b]pyridin-5-yl]-4-methyl-1H-pyrazole-3-carboxamide (P-2029); N-[2-(4-fluorophenyl)-1H-pyrrolo[2,3-b]pyridin-5-yl]-1H-1,2,4-triazole-5-carboxamide (P-2035); N-[2-(4-fluorophenyl)-1H-pyrrolo[2,3-b]pyridin-5-yl]-5-methyl-2H-triazole-4-carboxamide (P-2037); N-[2-(4-fluorophenyl)-1H-pyrrolo[2,3-b]pyridin-5-yl]-1H-indazole-3-carboxamide (P-2046); N-[2-(4-fluorophenyl)-1H-pyrrolo[2,3-b]pyridin-5-yl]-4,5,6,7-tetrahydro-1H-indazole-3-carboxamide (P-2047); N-[2-(4-fluorophenyl)-1H-pyrrolo[2,3-b]pyridin-5-yl]-1,4,5,6-tetrahydrocyclopenta[c]pyrazole-3-carboxamide (P-2056); N-[2-(4-fluorophenyl)-1H-pyrrolo[2,3-b]pyridin-5-yl]-1,5-dimethyl-pyrazole-3-carboxamide (P-2119); N-[2-(4-fluorophenyl)-1H-pyrrolo[2,3-b]pyridin-5-yl]-3-methyl-1H-1,2,4-triazole-5-carboxamide (P-2131); N-[2-(4-fluorophenyl)-1H-pyrrolo[2,3-b]pyridin-5-yl]-3-propyl-1H-pyrazole-5-carboxamide (P-2132); 3-ethyl-N-[2-(4-fluorophenyl)-1H-pyrrolo[2,3-b]pyridin-5-yl]-1H-pyrazole-5-carboxamide (P-2159); 3-(difluoromethyl)-N-[2-(4-fluorophenyl)-1H-pyrrolo[2,3-b]pyridin-5-yl]-1H-pyrazole-5-carboxamide (P-2172); and 4-chloro-3-ethyl-N-[2-(4-fluorophenyl)-1H-pyrrolo[2,3-b]pyridin-55-yl]-1H-pyrazole-5-carboxamide (P-2173) were prepared according to the synthetic protocols set forth in Scheme 1 and Example 1. The data from the $^1$H NMR spectra and observed molecular weights (Table 1) were consistent with the structures of the compounds.

Example 2

Preparation of 3,4-dimethyl-N-(2-phenyl-1H-pyrrolo[2,3-b]pyridin-5-yl)-1H-pyrazole-5-carboxamide (P-2007)

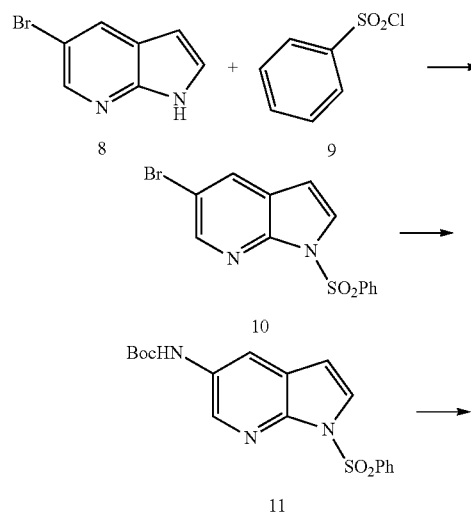

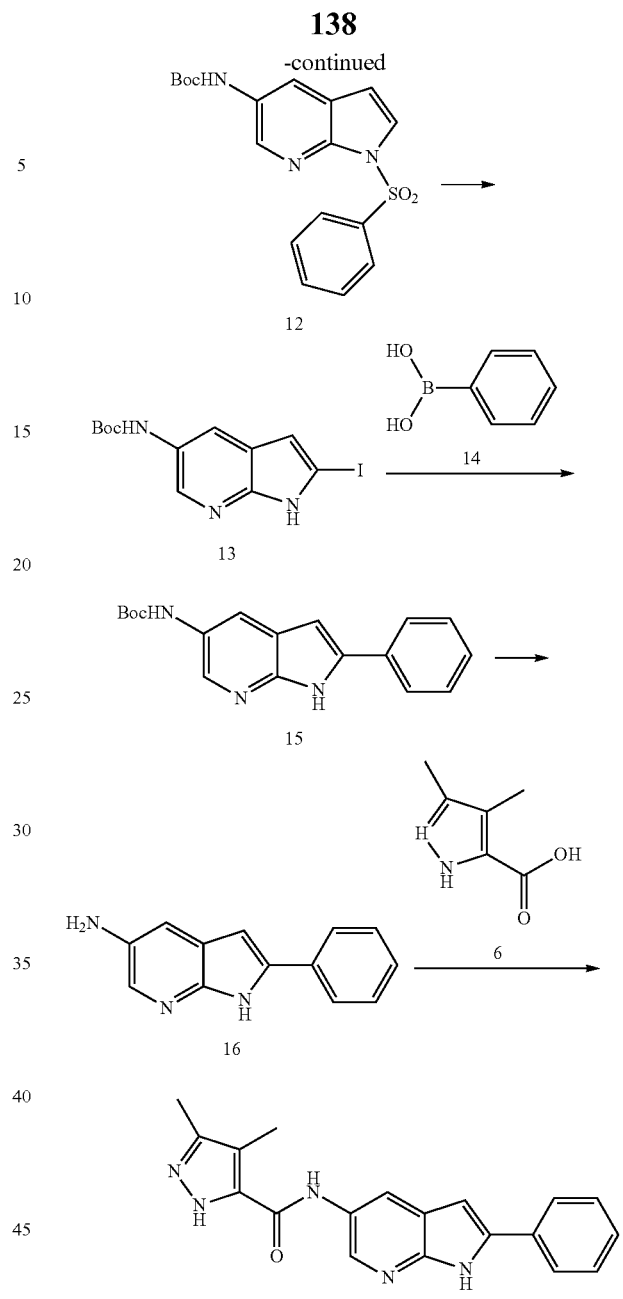

Step 1—Synthesis of 5-bromo-1-(phenylsulfonyl)-1H-pyrrolo[2,3-b]pyridine (10): A solution of 5-bromo-1H-pyrrolo[2,3-b]pyridine 8 (196 g, 994 mmol) in anhydrous tetrahydrofuran (2 L) was cooled to 0° C. and treated with sodium hydride (60% in mineral oil, 49.3 g 1233 mmol) over 30 minutes. After two hours, benzenesulfonyl chloride 9 (153 mL, 1193 mmol) was added dropwise and the reaction was stirred at room temperature overnight. The reaction was quenched with brine (1 L). The layers were separated and the aqueous phase was extracted with ethyl acetate (2×500 mL). The organic layers were combined, dried with sodium sulfate, filtered and concentrated under reduced pressure. The product was triturated with methyl tert-butyl ether to give compound 10 as a tan solid (319 g, 95%). The data from the $^1$H NMR spectrum were consistent with the structure of the compound.

Step 2—Synthesis of tert-butyl (1-(phenylsulfonyl)-1H-pyrrolo[2,3-b]pyridin-5-yl)carbamate (11): A suspension of 5-bromo-1-(phenylsulfonyl)-1H-pyrrolo[2,3-b]pyridine (10) (200 g, 594 mmol), tert-butylcarbamate (118 g, 1009 mmol), cesium carbonate (368 g, 1128 mmol), Xantphos (32 g, 65 mmol), and palladium(II) acetate (10.7 g, 47.5 mmol) in 1,4-dioxane (3 L) was degassed with nitrogen for 10 minutes then, heated at reflux overnight. LC/MS and TLC indicated the reaction was complete. The reaction was diluted with ethyl acetate/tetrahydrofuran (1:1, 1 L) and filtered through Celite. The filtrate was extracted with water (1 L). The layers were separated and the aqueous phase was extracted with ethyl acetate (2×500 mL). The combined organic layers were dried with sodium sulfate, filtered, and concentrated under reduced pressure. The product was triturated with methyl tert-butyl ether to give compound 11 as a tan solid (125 g, 57%). The data from the $^1$H NMR spectrum were consistent with the structure of the compound.

Step 3—Synthesis of tert-butyl (2-iodo-1-(phenylsulfonyl)-1H-pyrrolo[2,3-b]pyridin-5-yl)carbamate (12): To tert-butyl N-[1-(benzenesulfonyl)pyrrolo[2,3-b]pyridin-5-yl]carbamate (0.5 g, 1.34 mmol) in anhydrous tetrahydrofuran (10 mL) at −78° C. was added tert-butyl lithium (1.7 mL, 1.7 M). The resulting mixture was allowed to warm up to -20° C. and then cooled down to −78° C. Iodine (0.4 g, 1.58 mmol) in anhydrous tetrahydrofuran (2 mL) was added and the reaction mixture was allowed to warm up room temperature overnight. The reaction mixture was quenched with aqueous ammonium chloride and extracted with ethyl acetate. The organic layer was collected, washed with aqueous sodium thiosulfate (10%), brine, and dried under sodium sulfate. After removal of drying agent and solvent, the residue was purified by column chromatography to provide compound (12) as an off-white solid (0.38 g, 56%). MS(ESI) [M+H+]+=500.15. The data from the $^1$H NMR spectrum were consistent with the structure of the compound.

Step 4—Synthesis of tert-butyl (2-iodo-1H-pyrrolo[2,3-b]pyridin-5-yl)carbamate (13):To a solution of tert-butyl (2-iodo-1-(phenyl)sulfonyl)-1H-pyrrolo[2,3-b]pyridin-5-yl) carbamate (12) (45 g, 73 mmol) in tetrahydrofuran (600 mL) was added tetrabutylammonium fluoride trihydrate (126 g, 400 mmol). The solution was stirred at room temperature overnight. The reaction mixture was poured into water (500 mL) and extracted with ethyl acetate (2×200 mL). The combined organic layers were dried with sodium sulfate, filtered, and concentrated under reduced pressure. The crude material was triturated with dichloromethane to give compound (13) as an off-white solid (15 g, 59%). The data from the $^1$H NMR spectrum were consistent with the structure of the compound.

Step 5—Synthesis of tert-butyl (2-phenyl-1H-pyrrolo[2,3-b]pyridin-5-yl)carbamate (15): A suspension of tert-butyl (2-iodo-1H-pyrrolo[2,3-b]pyridin-5-yl)carbamate 13 (8.3 g, 23 mmol), phenylboronic acid 14 (3.0 g, 25 mmol), potassium carbonate (9.6 g, 69 mmol) in 1,4-dioxane/water (10:1, 165 mL) was degassed with nitrogen for 10 minutes then, added tetrakis(triphenylphosphine)palladium(0) (1.6 g, 1.4 mmol, 0.06 equiv). The reaction mixture was heated at reflux overnight. LC/MS indicated the reaction was complete. The reaction mixture was diluted with tetrahydrofuran (50 mL) and filtered through Celite. The filtrate was extracted with brine (100 mL). The layers were separated and the aqueous phase was extracted with ethyl acetate (2×100 mL). The organic layers were combined, dried with sodium sulfate, filtered, and concentrated under reduced pressure. The product was triturated with dichloromethane to give compound (15) as a tan solid (5.3 g, 74%). The data from the $^1$H NMR spectrum were consistent with the structure of the compound.

Step 6—Synthesis of 2-phenyl-1H-pyrrolo[2,3-b]pyridin-5-amine (16): To a suspension of tert-butyl (2-phenyl-1H-pyrrolo[2,3-b]pyridin-5-yl)carbamate 15 (5.3 g, 17 mmol) in dichloromethane (60 mL) was added trifluoroacetic acid (12 mL). The solution was stirred at room temperature for two hours, at which time LC/MS indicated the reaction was complete. The reaction was concentrated under reduced pressure. The crude material was suspended in 10% aqueous sodium carbonate (100 mL) and stirred at room temperature for 1 hour. The solid was filtered, washed with water (50 mL), methyl tert-butyl ether (50 mL) and dichloromethane (50 mL) and dried in vacuum at 50° C. Compound 16 was obtained as a tan solid (3.2 g, 89%). The data from the $^1$H NMR spectrum were consistent with the structure of the compound.

Step 7—Synthesis of 3,4-dimethyl-N-(2-phenyl-1H-pyrrolo[2,3-b]pyridin-5-yl)-1H-pyrazole-5-carboxamide (P-2007): A solution of compound 6 (0.09 g, 0.67 mmol) and benzotriazol-1-yl-oxytripyrrolidinophosphonium hexafluorophosphate (0.35 g, 0.67 mmol) in dimethylacetamide (4 mL) was stirred at room temperature for 30 minutes. To this mixture was added 2-phenyl-1H-pyrrolo[2,3-b]pyridin-5-amine (16) (0.08 g, 0.38 mmol) followed by diisopropylethylamine (0.1 mL). The reaction mixture was stirred at room temperature overnight. The reaction mixture was added dropwise to water and the suspension was stirred for 1 hour. The solid was filtered and was purified by preparative HPLC to give compound (P-2007) as white solid (46 mg, 36%). MS ESI [M+H+]+=332.2. $^1$H NMR spectrum was consistent with the structure of the compound.

Exemplary compounds 4-bromo-N-(2-phenyl-1H-pyrrolo [2,3-b]pyridin-5-yl)-1H-pyrazole-5-carboxamide (P-2005); 4-methyl-3-phenyl-N-(2-phenyl-1H-pyrrolo[2,3-b]pyridin-5-yl)-1H-pyrazole-5-carboxamide (P-2008); 3-cyclopropyl-N-(2-phenyl-1H-pyrrolo[2,3-b]pyridin-5-yl)-1H-pyrazole-5-carboxamide (P-2009); 5-fluoro-N-(2-phenyl-1H-pyrrolo [2,3-b]pyridin-5-yl)-1H-indazole-3-carboxamide (P-2010); N-(2-phenyl-1H-pyrrolo[2,3-b]pyridin-5-yl)pyrimidine-4-carboxamide (P-2011); 3-fluoro-N-(2-phenyl-1H-pyrrolo[2,3-b]pyridin-5-yl)pyridine-2-carboxamide (P-2012); 3,5-dimethyl-N-(2-phenyl-1H-pyrrolo[2,3-b]pyridin-5-yl) isoxazole-4-carboxamide (P-2013); N-(2-phenyl-1H-pyrrolo[2,3-b]pyridin-5-yl)pyridazine-3-carboxamide (P-2014); N-(2-phenyl-1H-pyrrolo[2,3-b]pyridin-5-yl)-2H-triazole-4-carboxamide (P-2015); 3-methyl-N-(2-phenyl-1H-pyrrolo[2,3-b]pyridin-5-yl)pyridine-2-carboxamide (P-2016); and 4,5-dimethyl-N-(2-phenyl-1H-pyrrolo[2,3-b] pyridin-5-yl)isoxazole-3-carboxamide (P-2017) were prepared according to the synthetic protocols set forth in Scheme 2 and Example 2. The data from the $^1$H NMR spectra and observed molecular weights (Table 1) were consistent with the structures of the compounds.

Example 3

Preparation of (2-phenyl-1H-pyrrolo[2,3-b]pyridin-5-yl)-(3-pyridyl)methanol (P-2001) and (2-phenyl-1H-pyrrolo[2,3-b]pyridin-5-yl)-(3-pyridyl)methanone (P-2002)

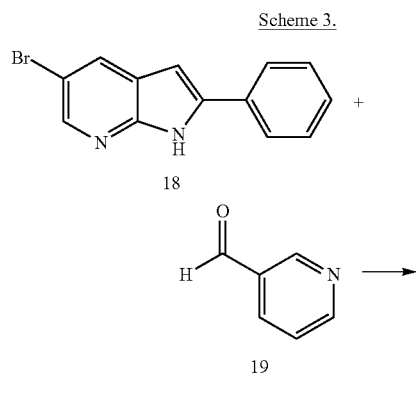

Scheme 3.

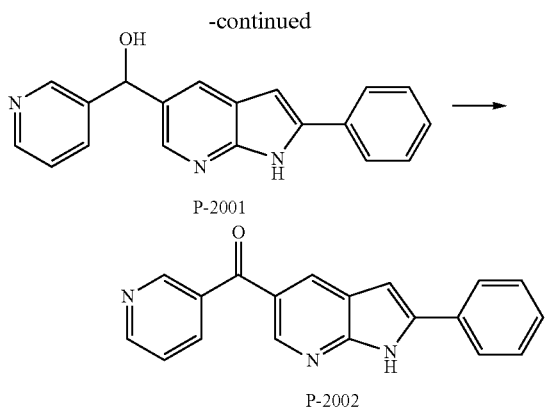

Step 1—Preparation of (2-phenyl-1H-pyrrolo[2,3-b]pyridin-5-yl)-(3-pyridyl)methanol (P-2001): To 5-bromo-2-phenyl-1H-pyrrolo[2,3-b]pyridine (18) (56 mg, 0.21 mmol) in tetrahydrofuran (6 mL) at −78° C. under nitrogen, was added n-butyllithium in tetrahydrofuran (0.21 ml, 2.5 M) slowly. After one hour 3-pyridinecarboxaldehyde (19) (0.02 ml, 0.19 mmol) in tetrahydrofuran (5 mL) was added to the reaction mixture. The reaction mixture was allowed to warm to room temperature (~22° C.) and poured into water and extracted with ethyl acetate. The organic layer was washed with brine, dried over sodium sulfate, and filtered. The filtrate was concentrated and purified with silica gel column chromatography eluting with 20% to 100% ethyl acetate in hexane to provide compound (P-2001) (40 mg, 64.7%). MS (EI) [M+H+]+=301.85. The data from the $^1$H NMR spectrum were consistent with the structure of the compound.

Step 2—Preparation of (2-phenyl-1H-pyrrolo[2,3-b]pyridin-5-yl)-(3-pyridyl)methanone (P-2002): Compound (P-2001) was oxidized with 2-iodobenzoic acid (IBX) in a mixture of tetrahydrofuran and dichloromethane. The reaction mixture was stirred at room temperature for 48 hrs and quenched with water. After aqueous work up, the product was purified with silica gel chromatography eluting with a gradient of dichloromethane and methanol (2-20%) to provide compound (P-2002) (17 mg, 68%). MS ESI [M+H+]+=299.85. The data from the $^1$H NMR spectrum were consistent with the structure of the compound.

Example 4

Preparation of (2-phenyl-1H-pyrrolo[2,3-b]pyridin-5-yl)-(3-pyridyl)methanone (P-2006) and (2-phenyl-1H-pyrrolo[2,3-b]pyridin-5-yl)-(3-pyridyl)methanone (P-2018)

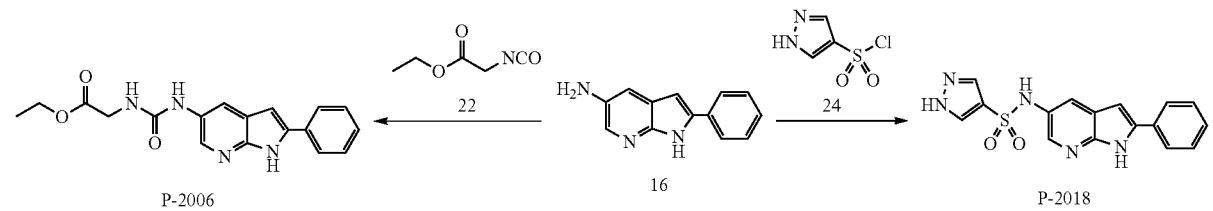

Step 1—Preparation of (2-phenyl-1H-pyrrolo[2,3-b]pyridin-5-yl)-(3-pyridyl)methanone P-2006: To a mixture of 2-phenyl-1H-pyrrolo[2,3-b]pyridin-5-amine 16 (50 mg, 0.24 mmol) and ethyl 3-isocyanatopropanoate 22 (50 mg, 0.35 mmol) in dimethylformamide (3 ml) was added N,N-diisopropylethylamine (0.1 mL). The reaction mixture was stirred at room temperature for 3 hours. The precipitate formed was filtered and washed with a mixture of ethyl acetate and hexanes to provide compound (P-2006) (22 mg, 26%). MS ESI [M+H+]+=352.85. The data from the $^1$H NMR spectrum were consistent with the structure of the compound.

Step 2—Preparation of (2-phenyl-1H-pyrrolo[2,3-b]pyridin-5-yl)-(3-pyridyl)methanone (P-2018): To 2-phenyl-1H-pyrrolo[2,3-b]pyridin-5-amine 16 (15 mg, 0.07 mmol) in pyridine (3 mL) was added 1H-pyrazole-4-sulfonyl chloride 24 (30 mg, 0.18 mmol). The reaction mixture was stirred at room temperature for 2 hours and concentrated. The residue was purified by column chromatography eluting with a gradient of dichloromethane and methanol (0-15%) to provide compound (P-2018) (9 mg, 37%). MS ESI [M+H+]+=340.1. The data from the $^1$H NMR spectrum were consistent with the structure of the compound.

Exemplary compound 2-ethyl-N-[2-(4-fluorophenyl)-1H-pyrrolo[2,3-b]pyridin-5-yl]pyrazole-3-sulfonamide (P-2030) was prepared according to the synthetic protocols set forth in Scheme 4 and Example 4. The data from the $^1$H NMR spectra and observed molecular weights (Table 1) were consistent with the structure of the compound.

Example 5

Preparation of (2-phenyl-1H-pyrrolo[2,3-b]pyridin-5-yl)-(3-pyridyl)methanone (P-2071)

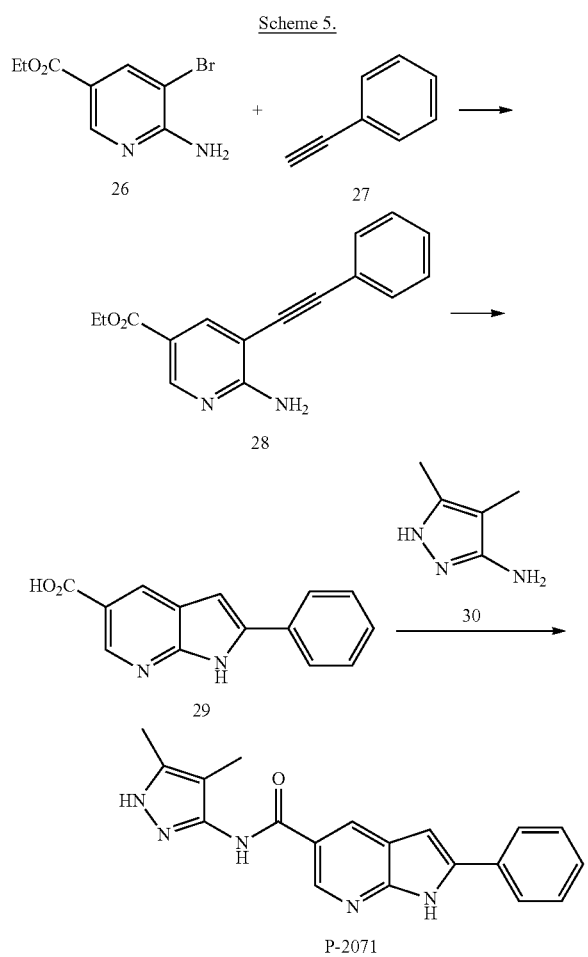

Scheme 5.

Step 1—Synthesis of ethyl 6-amino-5-(phenylethynyl) nicotinate (28): To a solution of ethyl 6-amino-5-bromonicotinate 26 (5.04 g, 20.6 mmol) in tetrahydrofuran (30 mL) was added triethylamine (8.6 mL, 61.7 mmol, 3.0 eq.), copper (I) iodide (23.4 mg, 0.28 mmol), bis(triphenylphosphine)palladium (II) dichloride (190 mg, 0.28 mmol) and phenylacetylene 27 (4.1 mL, 37.6 mmol). The reaction mixture was purged with nitrogen then heated to reflux in a sealed tube. When LCMS indicated a complete reaction, the reaction was cooled, poured into water and extracted with ethyl acetate. The organic layers were combined, dried with sodium sulfate, filtered, and concentrated under reduced pressure. The crude product was triturated with 3:1 heptanes:ethyl acetate to give compound (28) (3.05 g). The filtrate was allowed to stand overnight at room temperature to give additional compound (28) (1.67 g) as a beige solid after washing with heptanes. Total yield: 4.72 g (86% yield). The data from the $^1$H NMR spectrum were consistent with the structure of the compound.

Step 2—Synthesis of 2-phenyl-1H-pyrrolo[2,3-b]pyridine-5-carboxylic acid (29): To compound (28) (40 mg, 0.15 mmol) in N-methylpyrrolidine (1.6 mL) was added potassium tert-butoxide (35 mg, 0.32 mmol, 3.2 eq.). The reaction mixture was heated at 80° C. overnight, cooled to room temperature, added hydrochloric acid (1N, 3 mL) and poured into water (250 mL). The pH of the resulting solution was adjusted using 1N aqueous hydrochloric acid to produce a precipitate. The precipitate was filtered, washed with water and diethyl ether to give compound (29) as an orange-tan solid (30 mg, 71% yield). The data from the $^1$H NMR spectrum were consistent with the structure of the compound.

Step 3—Synthesis of (2-phenyl-1H-pyrrolo[2,3-b]pyridin-5-yl)-(3-pyridyl)methanone (P-2071): To 2-phenyl-1H-pyrrolo[2,3-b]pyridine-5-carboxylic acid 29 (50 mg, 0.21 mmol) in tetrahydrofuran (3 mL) was added benzotriazol-1-yl-oxytripyrrolidinophosphonium hexafluorophosphate (0.12 g, 0.23 mmol) and N,N-diisopropylethylamine (0.2 ml, 1.16 mmol). The suspension was stirred at room temperature for 30 minutes and was added 3, 4-dimethyl-1H-pyrazol-5-amine (30) (28 mg, 0.25 mmol) in N,N-dimethylformamide (1 mL). The reaction mixture was stirred at room temperature overnight and the reaction was quenched with water. The precipitate was collected, washed with ethyl acetate, and purified with silica gel column chromatography to provide compound (P-2071) as a white solid (18 mg, 25%). MS ESI [M+H+]+=331.85. The data from the $^1$H NMR spectrum were consistent with the structure of the compound.

Exemplary compounds N-(3-carbamoylphenyl)-2-phenyl-1H-pyrrolo[2,3-b]pyridine-5-carboxamide (P-2003); and 2-phenyl-N-(1H-pyrazol-3-yl)-1H-pyrrolo[2,3-b]pyridine-5-carboxamide (P-2004) were prepared according to the synthetic protocols set forth in Scheme 5 and Example 5. The data from the $^1$H NMR spectra and observed molecular weights (Table 1) were consistent with the structures of the compounds.

Example 6

Preparation of N-[2-(4-fluorophenyl)pyrazolo[1,5-a]pyrimidin-6-yl]-4,5-dimethyl-1H-pyrazole-3-carboxamide (P-2072) and N-(3-(4-fluorophenyl)-1H-pyrazolo[3,4-b]pyridin-5-yl)-3,4-dimethyl-1H-pyrazole-5-carboxamide (P-2041)

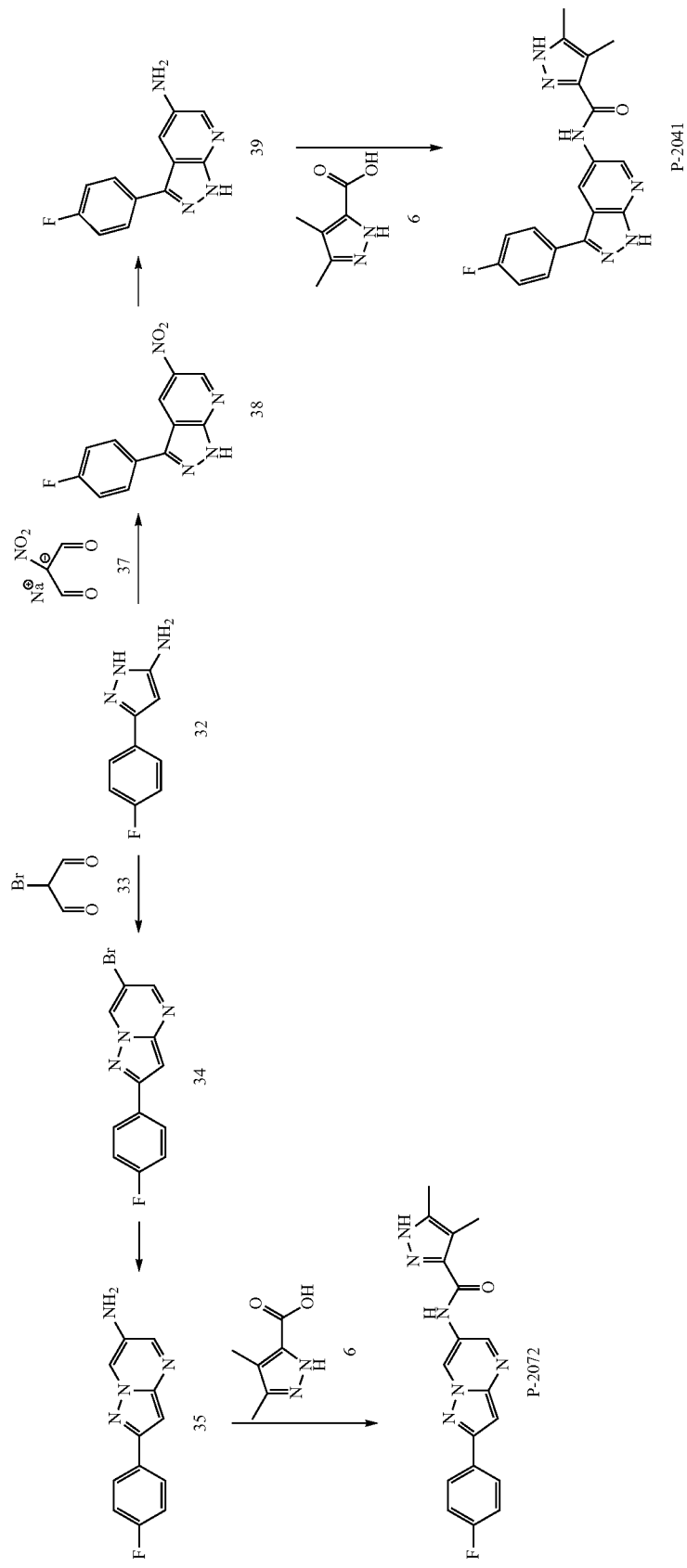

Step 1—Synthesis of 6-bromo-2-(4-fluorophenyl)pyrazolo[1,5-a]pyrimidine (34): To 3-(4-fluorophenyl)-1H-pyrazol-5-amine 32 (75 g, 423 mmol) and bromomalonaldehyde 33 (63.9 g, 423 mmol) in ethanol (652 mL) was added p-toluenesulfonic acid monohydrate (8.05 g, 42.3 mmol). The reaction mixture was heated to reflux overnight. Upon cooling, the reaction mixture was concentrated under reduced pressure to give a crude residue. The residue was dissolved in dichloromethane and purified by silica gel column chromatography eluting with 0-100% ethyl acetate/heptane to give compound 34 (3.6 g, 12.32 mmol, 2.9% yield) as a light yellow solid. The data from the $^1$H NMR spectrum were consistent with the structure of the compound.

Step 2—Synthesis of 2-(4-fluorophenyl)pyrazolo[1,5-a]pyrimidin-6-amine (35): To a mixture of 6-bromo-2-(4-fluorophenyl)pyrazolo[1, 5-a]pyrimidine (34) (4 g, 13.69 mmol), sodium tert-butoxide (1.842 g, 19.17 mmol) and benzophenone imine (2.76 mL, 16.43 mmol) in degassed toluene (45.6 mL) was added 2,2'-bis(diphenylphosphino)-1,1'-binaphthyl (0.294 g, 1.027 mmol) and tris(dibenzylideneacetone)dipalladium(0) (0.313 g, 0.342 mmol). The reaction mixture was heated at 100° C. overnight and was concentrated under reduced pressure to give a crude residue, which was dissolved in tetrahydrofuran (150 mL) and 2N aqueous hydrochloric acid (150 mL) and stirred at room temperature overnight. The reaction mixture was diluted with ethyl acetate and the aqueous layer was separated, basified with saturated aqueous potassium carbonate and extracted with ethyl acetate. The organic layer was concentrated under reduced pressure to give a crude residue. The residue was dissolved in dichloromethane and purified by silica gel column chromatography eluting with 0-10% methanol/dichloromethane and trituration with methyl tert-butyl ether/heptane to give compound (35) (0.05 g, 0.219 mmol, 1.6% yield) as a tan solid. The data from the $^1$H NMR spectrum were consistent with the structure of the compound.

Step 3—Synthesis of N-[2-(4-fluorophenyl)pyrazolo[1,5-a]pyrimidin-6-yl]-4,5-dimethyl-1H-pyrazole-3-carboxamide (P-2072): To 3,4-dimethyl-1H-pyrazole-5-carboxylic acid 6 (35 mg, 0.25 mmol) in dimethylacetamide (4 mL) was added benzotriazol-1-yl-oxytripyrrolidinophosphonium hexafluorophosphate (0.12 g, 0.23 mmol), followed by N,N-diisopropylethylamine (0.2 ml, 1.16 mmol). The suspension was stirred at room temperature for 30 minutes. To this suspension was added 2-(4-fluorophenyl)pyrazolo[1,5-a]pyrimidin-6-amine (35) (22 mg, 0.1 mmol, brownish solid). The reaction mixture was stirred at room temperature overnight and poured into water. The precipitate was collected and purified by column chromatography to provide compound (P-2072) as a pale yellow solid (5 mg, 15%). MS ESI [M+H+]+=351.95. The data from the $^1$H NMR spectrum were consistent with the structure of the compound.

Step 4—Synthesis of 3-(4-fluorophenyl)-5-nitro-1H-pyrazolo[3,4-b]pyridine (38): A yellow suspension of 3-(4-fluorophenyl)-1H-pyrazol-5-amine 32 (10 g, 56.4 mmol) and in-house prepared sodium nitromalonaldehyde monohydrate 37 (9.31 g, 59.3 mmol) in acetic acid (202 mL) were heated at 50° C. overnight. The reaction mixture was diluted with water (10 volumes) and the resulting solid was filtered and washed with more water to give compound 38, which was used directly in the next step. The data from the $^1$H NMR spectrum were consistent with the structure of the compound.

Step 5—Synthesis of 3-(4-fluorophenyl)-1H-pyrazolo[3,4-b]pyridin-5-amine 39: To a reaction vessel containing a solution of 3-(4-fluorophenyl)-5-nitro-1H-pyrazolo[3, 4-b]pyridine 38 (14.57 g, 56.4 mmol) in a mixture of ethanol (500 mL) and tetrahydrofuran (500 mL) was added hydrogen at a pressure of 40 psi. The reaction was stopped after hydrogen consumption ceased. The reaction mixture was filtered through a bed of Celite and the residue was washed with additional tetrahydrofuran. The filtrate was concentrated under reduced pressure to give compound 39 (11.4 g, 50.0 mmol, 89% yield over 2 steps) as a solid. The data from the $^1$H NMR spectrum were consistent with the structure of the compound.

Step 6—Synthesis of N-(3-(4-fluorophenyl)-1H-pyrazolo[3,4-b]pyridin-5-yl)-3,4-dimethyl-1H-pyrazole-5-carboxamide (P-2041): To a solution of 3-(4-fluorophenyl)-1H-pyrazolo[3,4-b]pyridin-5-amine 39 (0.150 g, 0.657 mmol) in N,N-dimethylformamide (3.87 mL) was added a mixture of triethylamine (0.102 mL, 0.723 mmol), 3,4-dimethyl-1H-pyrazole-5-carboxylic acid (0.101 g, 0.723 mmol) and O-(7-azabenzotriazol-1-yl)-N,N,N',N'-tetramethyluronium hexafluorophosphate (0.250 g, 0.657 mmol) and stirred at room temperature overnight. The reaction mixture was then poured into water and extracted with acetate. The organic layer was separated and concentrated under reduced pressure and the resulting residue was dissolved in a minimal amount of dichloromethane and was purified by chromatography eluting with 0-10% methanol/dichloromethane and trituration with methyl tert-butyl ether/heptane to give compound (P-2041) (0.100 g, 0.285 mmol, 43.4% yield) as a light yellow solid. MS ESI [M+H+]+=351.3. The data from the $^1$H NMR spectrum were consistent with the structure of the compound.

Exemplary compounds 3,4-dimethyl-N-(3-methyl-1H-pyrazolo[3,4-b]pyridin-5-yl)-1H-pyrazole-5-carboxamide (P-2040) and 4,5-dimethyl-N-(2-methylpyrazolo[1,5-a]pyrimidin-6-yl)-1H-pyrazole-3-carboxamide (P-2114) were prepared according to the synthetic protocols set forth in Scheme 6 and Example 6. The data from the $^1$H NMR spectra and observed molecular weights (Table 1) were consistent with the structures of the compounds.

Example 7

Preparation of N-[2-(3-fluoroprop-1-ynyl)-1H-pyrrolo[2,3-b]pyridin-5-yl]-3,4-dimethyl-1H-pyrazole-5-carboxamide (P-2063)

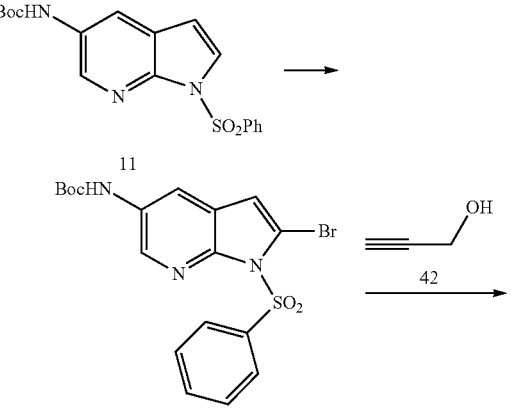

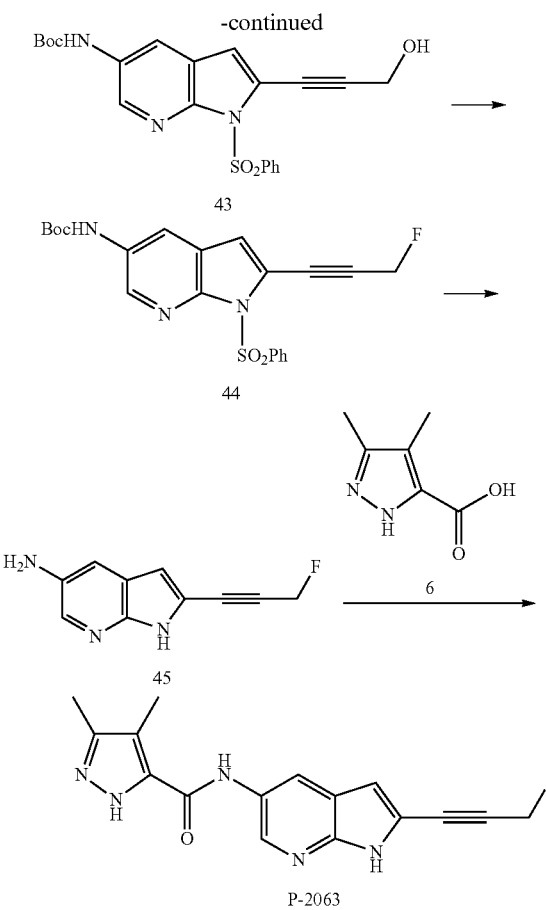

Step 1—Synthesis of tert-butyl N-[1-(benzenesulfonyl)-2-bromo-pyrrolo[2,3-b]pyridin-5-yl]carbamate 41: To tert-butyl N-[1-(benzenesulfonyl)pyrrolo[2,3-b]pyridin-5-yl]carbamate 11 (0.5 g, 1.34 mmol) in anhydrous tetrahydrofuran (10 mL) at −78° C. was added tert-butyl lithium (1.6 mL, 1.7 M). The resulting mixture was allowed to warm up to -20 OC and then cooled down to −78° C. To the mixture was added 1,2-dibromo-1,1,2,2-tetrachloro-ethane (0.22 g, 0.676 mmol) in anhydrous tetrahydrofuran (3 mL) slowly and the reaction mixture was allowed to reach room temperature overnight. The reaction mixture was quenched with aqueous ammonium chloride and extracted with ethyl acetate. The organic layer was collected, washed with brine, and dried under sodium sulfate. Drying agent and solvent were removed and the residue was purified by column chromatography to provide compound 41 as viscous oil, which was solidified into a pale yellow solid (0.24 g, 39%). MS(ESI) [M+H+]+=453.8. The data from the $^1$H NMR spectrum were consistent with the structure of the compound.

Step 2—Synthesis of tert-butyl N-[1-(benzenesulfonyl)-2-(3-hydroxyprop-1-ynyl)pyrrolo[2,3-b]pyridin-5-yl]carbamate 43: To a mixture of tert-butyl N-[1-(benzenesulfonyl)-2-bromo-pyrrolo[2,3-b]pyridin-5-yl]carbamate 41 (250 mg, 0.55 mmol), copper(I) iodide (20 mg, 0.11 mmol) palladium(II) acetate (20 mg, 0.09 mmol) and triphenylphosphine (40 mg, 0.15 mmol) in diethylamine (5 mL) was added propargyl alcohol 42 (0.25 ml, 4.23 mmol). The reaction mixture was stirred at room temperature for 4.5 hours and filtered through Celite and concentrated. The residue was mixed with water and extracted with ethyl acetate. The organic layer was collected, washed with water and brine, and then dried over sodium sulfate. The solvent was removed and the residue was purified by silica gel chromatography eluting with a gradient of ethyl acetate and hexanes (10-100%) to provide compound 43 (100 mg, 34%). MS ESI [M+H+]+=427.9. The data from the $^1$H NMR spectrum were consistent with the structure of the compound.

Step 3—Synthesis of tert-butyl N-[1-(benzenesulfonyl)-2-(3-fluoroprop-1-ynyl)pyrrolo[2,3-b]pyridin-5-yl]carbamate 44: To tert-butyl N-[1-(benzenesulfonyl)-2-(3-hydroxyprop-1-ynyl)pyrrolo[2,3-b]pyridin-5-yl]carbamate 43 (100 mg, 0.23 mmol) in dichloromethane (10 ml) at −10° C. was added bis(2-methoxyethyl)aminosulfur trifluoride (0.08 ml, 0.43 mmol). The reaction mixture was stirred at between −10° C. and 0° C. for 10 minutes and allowed to warm to room temperature. The reaction was quenched with water. The organic layer was collected, washed with water and brine and dried over sodium sulfate. Solvent was removed and residue was purified by chromatography eluting with ethyl acetate and hexanes (20-100%) to provide compound 44. MS ESI [M+H+]+=430.1. The data from the $^1$H NMR spectrum were consistent with the structure of the compound.

Step 4—Synthesis of 2-(3-fluoroprop-1-ynyl)-1H-pyrrolo[2,3-b]pyridin-5-amine (45); To tert-butyl N-[1-(benzenesulfonyl)-2-(3-fluoroprop-1-ynyl)pyrrolo[2,3-b]pyridin-5-yl]carbamate 44 (50 mg, 0.12 mmol) was added potassium hydroxide in methanol (4 ml, 1 M). The reaction was stirred at room temperature for 30 minutes. To the reaction mixture was added hydrochloric acid in dioxane (6 mL, 4 M) and the reaction was stirred at room temperature for three hours. The reaction mixture was concentrated twice from toluene and dried under vacuum to provide compound (45) as a hydrochloric acid salt (30 mg). MS ESI [M+H+]+=190.1. The compound was used for the subsequent reaction without further purification.

Step 5—Synthesis of N-[2-(3-fluoroprop-1-ynyl)-1H-pyrrolo[2,3-b]pyridin-5-yl]-3,4-dimethyl-1H-pyrazole-5-carboxamide (P-2063): To 3,4-dimethyl-1H-pyrazole-5-carboxylic acid 6 (50 mg, 0.36 mmol) in dimethylacetamide (3 mL) was added benzotriazol-1-yl-oxytripyrrolidinophosphonium hexafluorophosphate (200 mg, 0.38 mmol). The reaction mixture was stirred at room temperature for 30 minutes and added 2-(3-fluoroprop-1-ynyl)-1H-pyrrolo[2,3-b]pyridin-5-amine hydrochloride 45 (12 mg, 0.05 mmol) and N,N-diisopropylethylamine (1 mL) and further stirred at room temperature for three hours. The reaction mixture was then purified by chromatography eluting with a gradient of ethyl acetate and hexanes to provide compound (P-2063) (2.2 mg, 13%). MS ESI [M+H+]+=312.1. The data from the $^1$H NMR spectrum were consistent with the structure of the compound.

Exemplary compound N-[2-(3-fluoroprop-1-ynyl)-1H-pyrrolo[2,3-b]pyridin-5-yl]-3-methyl-1H-pyrazole-5-carboxamide (P-2068) was prepared according to the synthetic protocols set forth in Scheme 7 and Example 7. The data from the $^1$H NMR spectra and observed molecular weights (Table 1) were consistent with the structure of the compound.

Example 8 Preparation of N-[2-[3-(benzenesulfonamido)anilino]pyrimidin-5-yl]-3,4-dimethyl-1H-pyrazole-5-carboxamide (P-2053)

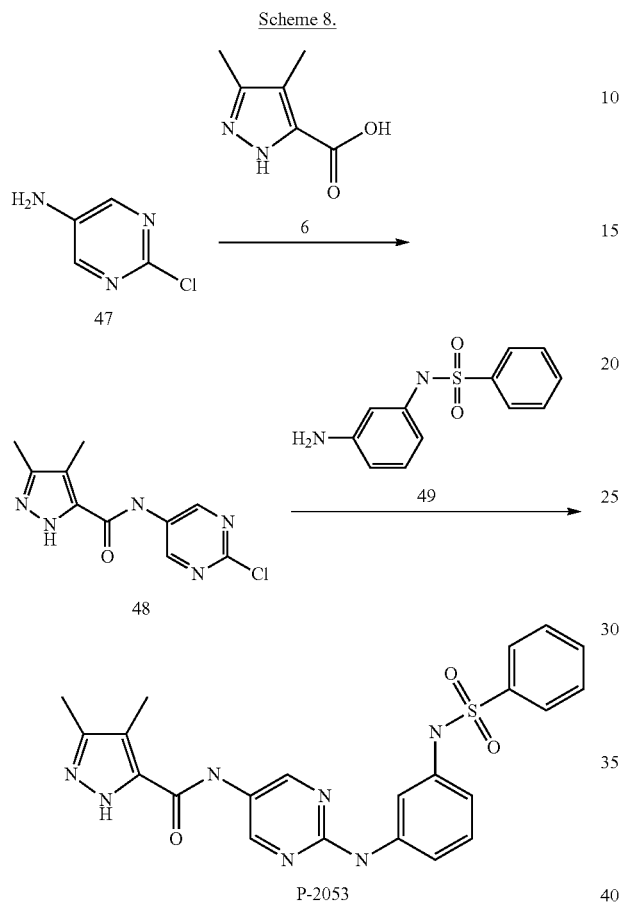

Step 1—Synthesis of N-(2-chloropyrimidin-5-yl)-3,4-dimethyl-1H-pyrazole-5-carboxamide (48); To a 20 mL scintillation vial were added 3,4-dimethyl-1H-pyrazole-5-carboxylic acid 6 (0.6 g, 4.28 mmol) and benzotriazol-1-yloxytripyrrolidinophosphonium hexafluorophosphate (2.4 g, 4.61 mmol) in dimethylacetamide (4 mL) to form a reaction mixture. The reaction mixture was stirred at room temperature for 30 minutes to give solution A. To another 20 mL scintillation vial were added 2-chloropyrimidin-5-amine 47 (0.75 g, 5.79 mmol) and N,N-diisopropylethylamine (0.1 mL) to form a mixture. The mixture was heated at 60° C. to form solution B. The activated acid (solution A) was then added to the amine (solution B). The reaction mixture was stirred at 60° C. overnight and cooled down to room temperature. Water was added to the reaction mixture to form a precipitate, which was collected to provide compound 48 (323 mg, 30%). MS ESI [M+H+]+=251.8.

Step 2—Preparation of N-[2-[3-(benzenesulfonamido)anilino]pyrimidin-5-yl]-3,4-dimethyl-1H-pyrazole-5-carboxamide (P-2053): To a microwave reaction vessel was added N-(2-chloropyrimidin-5-yl)-3,4-dimethyl-1H-pyrazole-5-carboxamide 48 (50 mg, 0.2 mmol), isopropanol(3 mL), N-(3-aminophenyl)benzenesulfonamide 49 (113.64 mg, 0.46 mmol), and aqueous hydrochloric acid (0.1 mL, 37%). The reaction mixture was heated in microwave reactor at 160° C. for 120 minutes. The reaction mixture was purified by silica gel chromatography eluting with a gradient of dichloromethane and methanol (0-15%). The desired fractions were combined to provide compound (P-2053): (41 mg, 45%). MS ESI [M+H+]+=464.3.

Exemplary compounds N-(2-anilinopyrimidin-5-yl)-3,4-dimethyl-1H-pyrazole-5-carboxamide (P-2044); N-(6-anilino-3-pyridyl)-3,4-dimethyl-1H-pyrazole-5-carboxamide (P-2045); N-[2-[3-(ethylsulfamoyl)anilino]pyrimidin-5-yl]-3,4-dimethyl-1H-pyrazole-5-carboxamide (P-2050); 3,4-dimethyl-N-[2-(3-morpholinoanilino)pyrimidin-5-yl]-1H-pyrazole-5-carboxamide (P-2051); 3,4-dimethyl-N-[2-[3-(propylsulfonylamino)anilino]pyrimidin-5-yl]-1H-pyrazole-5-carboxamide (P-2052); 3,4-dimethyl-N-[2-[3-(methylcarbamoyl)anilino]pyrimidin-5-yl]-1H-pyrazole-5-carboxamide (P-2054); and ethyl N-[3-[[5-[(3,4-dimethyl-1H-pyrazole-5-carbonyl)amino]pyrimidin-2-yl]amino]phenyl]carbamate (P-2055) were prepared according to the synthetic protocols set forth in Scheme 8 and Example 8. The data from the $^1$H NMR spectra and observed molecular weights (Table 1) were consistent with the structures of the compounds.

Example 9

Preparation of N-[2-[1-(cyclopropanecarbonyl)-3,6-dihydro-2H-pyridin-4-yl]-1H-pyrrolo[2,3-b]pyridin-5-yl]-4,5-dimethyl-1H-pyrazole-3-carboxamide (P-2043)

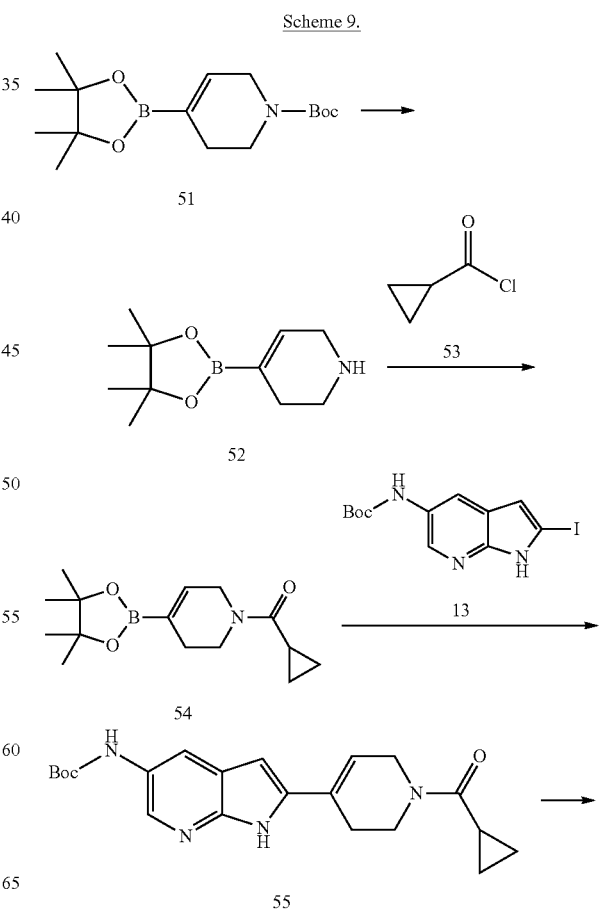

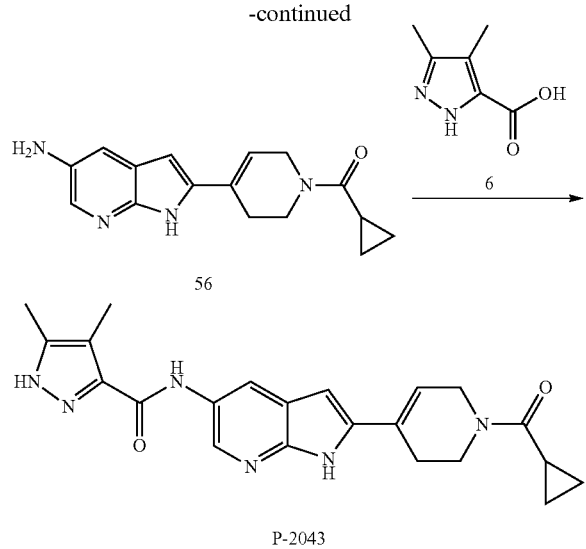

Step 1—Synthesis of N-[2-chloropyrimidin-5-yl]-3,4-dimethyl-1H-pyrazole-5-carboxamide 52: To tert-butyl 4-(4,4,5,5-tetramethyl-1,3,2-dioxaborolan-2-yl)-3,6-dihydro-2H-pyridine-1-carboxylate 51 (3 g, 9.7 mmol) in dichloromethane (5 mL) was added hydrochloric acid in 1,4-dioxane (4 N, 5 mL). The reaction was stirred at room temperature overnight, then concentrated twice from toluene. The residue was washed with ethyl acetate and dried under vacuum to produce compound 52 as an HCl salt (2.3 g, 96%). The data from the $^1$H NMR spectrum were consistent with the structure of the compound.

Step 2—Synthesis of cyclopropyl-[4-(4,4,5,5-tetramethyl-1,3,2-dioxaborolan-2-yl)-3,6-dihydro-2H-pyridin-1-yl]methanone 54: To 4-(4,4,5,5-tetramethyl-1,3,2-dioxaborolan-2-yl)-1,2,3,6-tetrahydropyridine hydrochloride 52 (0.7 g, 2.85 mmol) in acetonitrile (15 mL) was added cyclopropanecarbonyl chloride 53 (0.3 g, 2.87 mmol), followed by N,N-diisopropylethylamine (0.8 mL). The reaction mixture was stirred at room temperature for 3 hours, then passed through a silica gel column (eluting with ethyl acetate and hexanes) to provide crude product in light-colored fractions. The fractions were combined and concentrated. The residue was triturated with a mixture of ethyl acetate and hexanes. The mother liquid was collected and concentrated to provide compound 54 as an orange gel. The compound 54 was used for the subsequent reactions without further purification.

Step 3—Synthesis of tert-butyl N-[2-[1-(cyclopropanecarbonyl)-3,6-dihydro-2H-pyridin-4-yl]-1H-pyrrolo[2,3-b]pyridin-5-yl]carbamate 55: To a microwave reaction vessel were charged with tert-butyl N-(2-iodo-1H-pyrrolo[2,3-b]pyridin-5-yl)carbamate 13 (400 mg, 1.11 mmol), cyclopropyl-[4-(4,4,5,5-tetramethyl-1,3,2-dioxaborolan-2-yl)-3,6-dihydro-2H-pyridin-1-yl]methanone 54 (340 mg, 1.23 mmol), dichloro(1,1-bis(diphenylphosphino)ferrocene)palladium (ii) acetone adduct (68.41 mg, 0.09 mmol) in acetonitrile (6 mL) and potassium carbonate (1N, 3.3 mL). The mixture was irradiated with microwave at 100° C. for 30 minutes. The reaction was quenched with water, neutralized with aqueous hydrochloric acid (5 N), extracted with ethyl acetate, washed with brine, and dried over sodium sulfate. After solvent was removed and salt filtered, the residue was purified by silica gel chromatography eluting with ethyl acetate and hexane to provide compound 55 (102 mg, 24%). The data from the $^1$H NMR spectrum were consistent with the structure of the compound.

Step 4—Synthesis of [4-(5-amino-1H-pyrrolo[2,3-b]pyridin-2-yl)-3,6-dihydro-2H-pyridin-1-yl]-cyclopropyl-methanone 56: To tert-butyl N-[2-[1-(cyclopropanecarbonyl)-3,6-dihydro-2H-pyridin-4-yl]-1H-pyrrolo[2,3-b]pyridin-5-yl]carbamate 55 (102 mg, 0.27 mmol) in dichloromethane was added hydrochloric acid in 1,4-dioxane (4 M, 0.7 mL). The reaction mixture was stirred at room temperature overnight. After solvent was removed, the residue was dried under vacuum to provide compound 56 as a yellow solid (85 mg, 100%). MS ESI [M+H+]+=282. It was used as is without purification.

Step 5—Synthesis of N-[2-[1-(cyclopropanecarbonyl)-3,6-dihydro-2H-pyridin-4-yl]-1H-pyrrolo[2,3-b]pyridin-5-yl]-4,5-dimethyl-1H-pyrazole-3-carboxamide (P-2043): To 4,5-dimethyl-1H-pyrazole-3-carboxylic acid 6 (0.02 g, 0.17 mmol) in acetonitrile (3 mL) was added benzotriazol-1-yl-oxytripyrrolidinophosphonium hexafluorophosphate (0.1 g, 0.19 mmol). The reaction mixture was stirred at room temperature for one hour, and then was added [4-(5-amino-1H-pyrrolo[2,3-b]pyridin-2-yl)-3,6-dihydro-2H-pyridin-1-yl]-cyclopropyl-methanone hydrochloride 56 (0.05 g, 0.16 mmol) and triethylamine (0.03 ml, 0.19 mmol), and stirred at room temperature overnight. The reaction was quenched with water, extracted with ethyl acetate, washed with brine, and dried over sodium sulfate. After solvent was removed, the residue was triturated with ethyl acetate. The solid was collected, washed with methanol and water to provide compound 57 as a white solid (5 mg, 7%). MS ESI [M+H]+=404.9. The data from the $^1$H NMR spectrum were consistent with the structure of the compound.

Exemplary compounds 5-methyl-N-[2-[1-(morpholine-4-carbonyl)-3,6-dihydro-2H-pyridin-4-yl]-1H-pyrrolo[2,3-b]pyridin-5-yl]-1H-pyrazole-3-carboxamide (P-2031); N-[1-(benzenesulfonyl)-2-[1-(morpholine-4-carbonyl)-3,6-dihydro-2H-pyridin-4-yl]pyrrolo[2,3-b]pyridin-5-yl]-3,4-dimethyl-1H-pyrazole-5-carboxamide (P-2033); 3,4-dimethyl-N-[2-[1-(morpholine-4-carbonyl)-3,6-dihydro-2H-pyridin-4-yl]-1H-pyrrolo[2,3-b]pyridin-5-yl]-1H-pyrazole-5-carboxamide (P-2034); 4-chloro-3-methyl-N-[2-[1-(morpholine-4-carbonyl)-3,6-dihydro-2H-pyridin-4-yl]-1H-pyrrolo[2,3-b]pyridin-5-yl]-1H-pyrazole-5-carboxamide (P-2036); 4-chloro-N-[2-[1-(cyclopropanecarbonyl)-3,6-dihydro-2H-pyridin-4-yl]-1H-pyrrolo[2,3-b]pyridin-5-yl]-5-methyl-1H-pyrazole-3-carboxamide (P-2039); and N-[2-[1-(cyclopropanecarbonyl)-3,6-dihydro-2H-pyridin-4-yl]-1H-pyrrolo[2,3-b]pyridin-5-yl]-5-methyl-1H-pyrazole-3-carboxamide (P-2042) were prepared according to the synthetic protocols set forth in Scheme 9 and Example 9. The data from the $^1$H NMR spectra and observed molecular weights (Table 1) were consistent with the structures of the compounds.

Example 10

Preparation of 3,4-dimethyl-N-[2-[1-(2-morpholinoacetyl)-3,6-dihydro-2H-pyridin-4-yl]-1H-pyrrolo[2,3-b]pyridin-5-yl]-1H-pyrazole-5-carboxamide (P-2073)

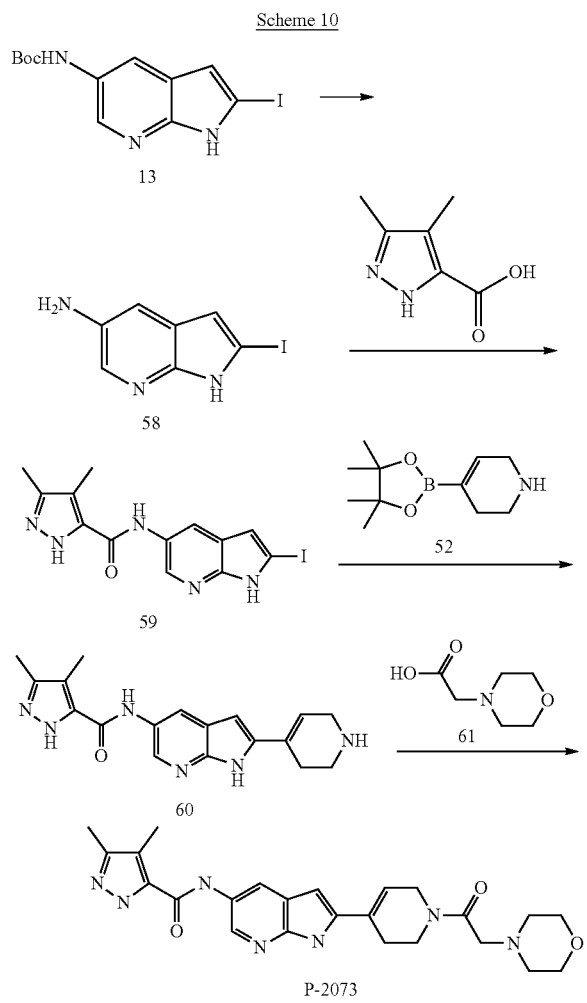

Step 1—Synthesis of 2-iodo-1H-pyrrolo[2,3-b]pyridin-5-amine hydrochloride 58: To tert-butyl 2-iodo-pyrrolo[2,3-b]pyridin-5-yl]carbamate 13 (0.25 g, 0.7 mmol) in dichloromethane (5 mL) was added hydrochloric acid in 1,4-dioxane (3 mL, 4 M). The suspension was stirred at room temperature for three hours. The reaction mixture was concentrated and dried under vacuum to provide compound 58 as hydrochloric acid salt (0.26 g). MS ESI [M+H+]+=260.0. Compound 58 was used for subsequent reactions without purification.

Step 2—Synthesis of N-(2-iodo-1H-pyrrolo[2,3-b]pyridin-5-yl)-3,4-dimethyl-1H-pyrazole-5-carboxamide 59: A solution of 3,4-dimethyl-1H-pyrazole-5-carboxylic acid 6 (0.81 g, 5.79 mmol) and benzotriazol-1-yl-oxytripyrrolidinophosphonium hexafluorophosphate (3.01 g, 5.79 mmol) in dimethylacetamide (20 ml) was stirred at room temperature for one hour. To the reaction mixture was added 2-iodo-1H-pyrrolo[2,3-b]pyridin-5-amine 58 (0.5 g, 1.93 mmol), followed by N,N-diisopropylethylamine (0.67 ml, 3.86 mmol). The reaction mixture was stirred at room temperature for 3 hours, then added dropwise into iced water (200 mL). The resulting suspension was stirred overnight. The solid was collected by filtration, washed with water, and triturated with methanol to provide compound 59 (1.4 g, 96%). MS ESI [M+H+]+=382.05. The compound was used for subsequent reaction without purification.

Step 3—Preparation of 3,4-dimethyl-N-[2-(1,2,3,6-tetrahydropyridin-4-yl)-1H-pyrrolo[2,3-b]pyridin-5-yl]-1H-pyrazole-5-carboxamide 60: To N-(2-iodo-1H-pyrrolo[2,3-b]pyridin-5-yl)-3,4-dimethyl-1H-pyrazole-5-carboxamide 59 (0.15 g, 0.39 mmol) in 1,4-dioxane (3 ml) was added 4-(4,4,5,5-tetramethyl-1,3,2-dioxaborolan-2-yl)-1,2,3,6-tetrahydropyridine hydrochloride 52 (0.19 g, 0.79 mmol), dichloro(1,1-bis(diphenylphosphino)ferrocene)palladium (ii) acetone adduct (0.02 g, 0.03 mmol) and aqueous potassium carbonate (1.2 mL, 1 M). The reaction mixture was heated in a microwave reactor at 130° C. for 20 minutes. The reaction mixture was poured into iced water and the precipitate was collected by filtration, and then triturated with ethyl acetate to provide compound 60 (73 mg, 55%). The compound was used for subsequent reaction without further purification.

Step 4—Preparation of 3,4-dimethyl-N-[2-[1-(2-morpholinoacetyl)-3,6-dihydro-2H-pyridin-4-yl]-1H-pyrrolo[2,3-b]pyridin-5-yl]-1H-pyrazole-5-carboxamide (P-2073); To a solution of 2-morpholinoacetic acid hydrochloride 61 (0.02 g, 0.11 mmol) in dimethylacetamide (2 ml) was added benzotriazol-1-yl-oxytripyrrolidinophosphonium hexafluorophosphate (55.69 mg, 0.11 mmol). The mixture was stirred at room temperature for 40 minutes, then added 3,4-dimethyl-N-[2-(1,2,3,6-tetrahydropyridin-4-yl)-1H-pyrrolo[2,3-b]pyridin-5-yl]-1H-pyrazole-5-carboxamide 60 (0.02 g, 0.07 mmol) and N,N-diisopropylethylamine (0.02 ml, 0.14 mmol). The reaction mixture was stirred at room temperature for two hours. After the reaction was completed as evidenced by LCMS, the reaction mixture was filtered and purified by preparative HPLC to provide compounds (P-2073) (5 mg, 15%). MS (ESI) [M+H]+=464.6. The data from the ¹H NMR spectrum were consistent with the structure of the compound.

Exemplary compound N-[2-[1-(2,3-dihydroxypropanoyl)-3,6-dihydro-2H-pyridin-4-yl]-1H-pyrrolo[2,3-b]pyridin-5-yl]-3,4-dimethyl-1H-pyrazole-5-carboxamide (P-2074) was prepared according to the synthetic protocols set forth in Scheme 10 and Example 10. The data from the ¹H NMR spectra and observed molecular weights (Table 1) were consistent with the structure of the compound.

Example 11

Preparation of 3-methyl-N-(2-morpholino-1H-pyrrolo[2,3-b]pyridin-5-yl)-1H-pyrazole-5-carboxamide (P-2058)

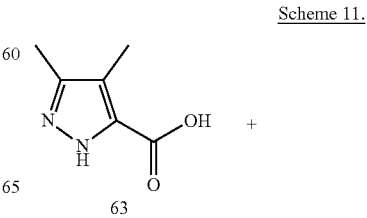

157

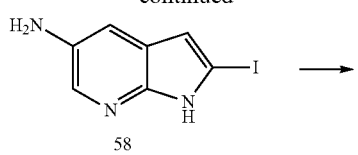

158

Example 12

Preparation of N-[2-(1,3-dimethylpyrazol-4-yl)-1H-pyrrolo[2,3-b]pyridin-5-yl]-4,5-dimethyl-1H-pyrazole-3-carboxamide (P-2038)

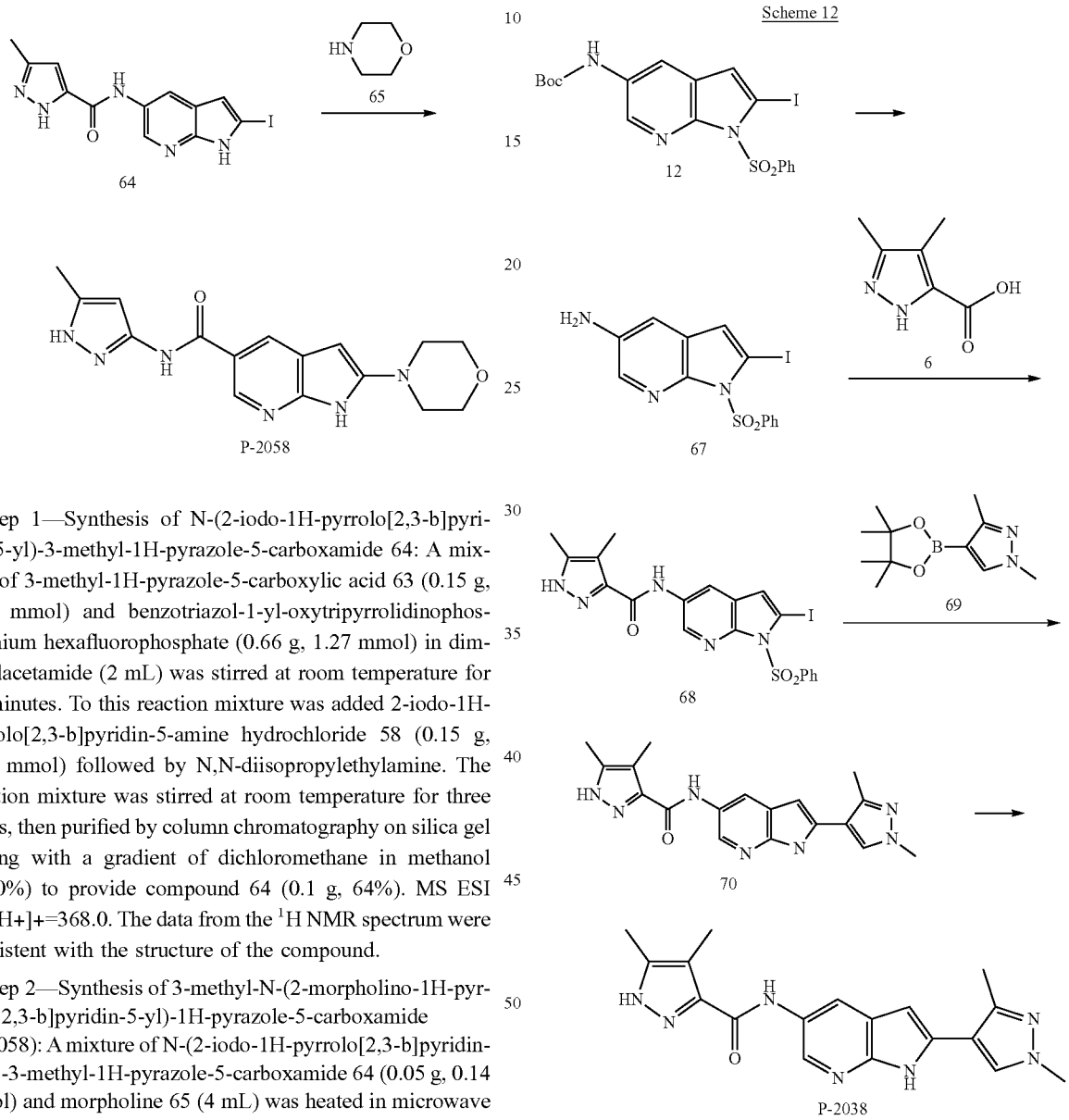

Step 1—Synthesis of N-(2-iodo-1H-pyrrolo[2,3-b]pyridin-5-yl)-3-methyl-1H-pyrazole-5-carboxamide 64: A mixture of 3-methyl-1H-pyrazole-5-carboxylic acid 63 (0.15 g, 1.19 mmol) and benzotriazol-1-yl-oxytripyrrolidinophosphonium hexafluorophosphate (0.66 g, 1.27 mmol) in dimethylacetamide (2 mL) was stirred at room temperature for 30 minutes. To this reaction mixture was added 2-iodo-1H-pyrrolo[2,3-b]pyridin-5-amine hydrochloride 58 (0.15 g, 0.51 mmol) followed by N,N-diisopropylethylamine. The reaction mixture was stirred at room temperature for three hours, then purified by column chromatography on silica gel eluting with a gradient of dichloromethane in methanol (5-20%) to provide compound 64 (0.1 g, 64%). MS ESI [M+H+]+=368.0. The data from the $^1$H NMR spectrum were consistent with the structure of the compound.

Step 2—Synthesis of 3-methyl-N-(2-morpholino-1H-pyrrolo[2,3-b]pyridin-5-yl)-1H-pyrazole-5-carboxamide (P-2058): A mixture of N-(2-iodo-1H-pyrrolo[2,3-b]pyridin-5-yl)-3-methyl-1H-pyrazole-5-carboxamide 64 (0.05 g, 0.14 mmol) and morpholine 65 (4 mL) was heated in microwave reactor at 160° C. for 60 minutes. The reaction mixture was purified by preparative HPLC to provide compound (P-2058) (18 mg, 40%). MS ESI [M+H+]+=327.3. The data from the $^1$H NMR spectrum were consistent with the structure of the compound.

Exemplary compound 3,4-dimethyl-N-(2-pyrrolidin-1-yl-1H-pyrrolo[2,3-b]pyridin-5-yl)-1H-pyrazole-5-carboxamide (P-2115) was prepared according to the synthetic protocols set forth in Scheme 11 and Example 11. The data from the $^1$H NMR spectra and observed molecular weights (Table 1) were consistent with the structure of the compound.

Step 1—Synthesis of 1-(benzenesulfonyl)-2-iodo-pyrrolo[2,3-b]pyridin-5-amine 67: To a solution of tert-butyl N-[1-(benzenesulfonyl)-2-iodo-pyrrolo[2,3-b]pyridin-5-yl]carbamate 12 (0.5 g, 1 mmol) in acetonitrile (5 ml) was added hydrochloric acid in dioxane (10 mL, 4 M). The reaction mixture was stirred at room temperature for four hours. The reaction mixture was concentrated and dried under vacuum to provide compound 67 as hydrochloric acid salt (0.6 g). The compound was used for subsequent reaction without purification.

Step 2—Synthesis of N-[1-(benzenesulfonyl)-2-iodo-pyrrolo[2,3-b]pyridin-5-yl]-4,5-dimethyl-1H-pyrazole-3-carboxamide 68: To 3,4-dimethyl-1H-pyrazole-5-carboxylic acid 6 (0.2 g, 1.43 mmol) in acetonitrile (20 mL) was added o-benzotriazole-N,N,N',N'-tetramethyl-uronium-hexafluorophosphate (0.55 g, 1.45 mmol), followed N,N-diisopropylethylamine (0.5 ml, 2.89 mmol). The suspension was stirred at room temperature for 2 hours to yield a clear solution. To the clear solution was added 1-(benzenesulfonyl)-2-iodo-pyrrolo[2,3-b]pyridin-5-amine hydrochloride 67 (0.4 g, 0.92 mmol) in tetrahydrofuran (1 mL). The reaction mixture was stirred at 40° C. overnight. The reaction mixture was concentrated and the residue was partitioned with ethyl acetate, washed with brine and dried with sodium sulfate. Solvent was removed and the residue was purified by flash chromatography on silica gel to provide product 68 as a pale yellow solid (0.1 g, 21%). MS(ESI) [M+H+]+=522.0. The data from the ¹H NMR spectrum were consistent with the structure of the compound.

Step 3—Synthesis of N-[1-(benzenesulfonyl)-2-(1,3-dimethylpyrazol-4-yl)pyrrolo[2,3-b]pyridin-5-yl]-4,5-dimethyl-1H-pyrazole-3-carboxamide 70: To N-[1-(benzenesulfonyl)-2-iodo-pyrrolo[2,3-b]pyridin-5-yl]-4,5-dimethyl-1H-pyrazole-3-carboxamide 68 (52 mg, 0.1 mmol) in acetonitrile (3 ml) was added 1,3-dimethyl-4-(4,4,5,5-tetramethyl-1,3,2-dioxaborolan-2-yl)pyrazole 69 (26 mg, 0.12 mmol), [1,1'-bis(diphenylphosphino)ferrocene]dichloropalladium(ii) (14 mg, 0.02 mmol) and aqueous potassium carbonate (1 ml, 1 M). The reaction mixture was irradiated with microwave at 100° C. for 15 minutes. The reaction mixture was partitioned with ethyl acetate, washed with brine and dried under sodium sulfate. Drying agent and solvent were removed and the residue was purified by column chromatography to provide product 70 as off-white solid (0.02 g, 36%). MS(ESI) [M+H+]+=490.0. The data from the ¹H NMR spectrum were consistent with the structure of the compound.

Step 4—Synthesis of N-[2-(1,3-dimethylpyrazol-4-yl)-1H-pyrrolo[2,3-b]pyridin-5-yl]-4,5-dimethyl-1H-pyrazole-3-carboxamide (P-2038): To N-[1-(benzenesulfonyl)-2-(1,3-dimethylpyrazol-4-yl)pyrrolo[2,3-b]pyridin-5-yl]-4,5-dimethyl-1H-pyrazole-3-carboxamide 70 (0.02 g, 0.04 mmol) in acetonitrile (2 mL) was added tetrabutylammonium fluoride (0.23 ml, 0.76 mmol). The reaction mixture was stirred at 80° C. for six hours, then was partitioned with ethyl acetate, washed with brine, and dried under sodium sulfate. Drying agent and solvent were removed and the residue was purified by column chromatography on silica gel followed by preparative HPLC to provide compound (P-2038) (5 mg, 35%). MS(ESI) [M+H+]+=349.9. The data from the ¹H NMR spectrum were consistent with the structure of the compound.

Exemplary compound N-[1-(benzenesulfonyl)-2-[1-(morpholine-4-carbonyl)-3,6-dihydro-2H-pyridin-4-yl]pyrrolo[2,3-b]pyridin-5-yl]-3,4-dimethyl-1H-pyrazole-5-carboxamide (P-2033) was prepared according to the synthetic protocols set forth in Scheme 12 and Example 12. The data from the ¹H NMR spectra and observed molecular weights (Table 1) were consistent with the structure of the compound.

Example 13

Preparation of 3,4-dimethyl-N-(2-pyrazol-1-yl-1H-pyrrolo[2,3-b]pyridin-5-yl)-1H-pyrazole-5-carboxamide (P-2112)

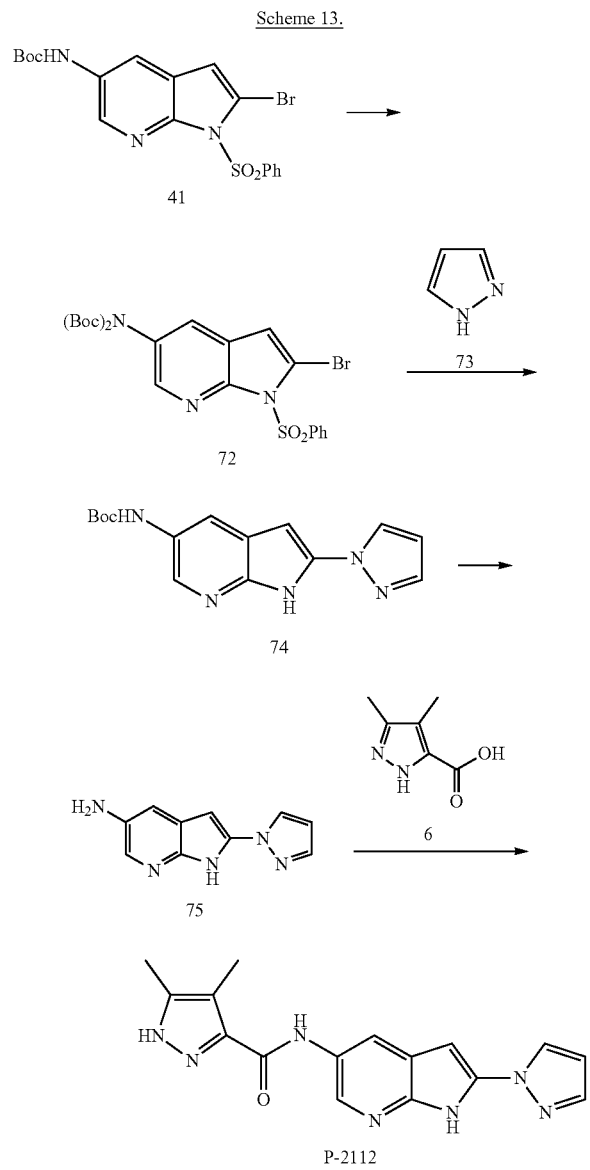

Step 1—Synthesis of tert-butyl N-[1-(benzenesulfonyl)-2-bromo-pyrrolo[2,3-b]pyridin-5-yl]-N-tert-butoxycarbonyl-carbamate 72: To a round bottom flask was added tert-butyl N-[1-(benzenesulfonyl)-2-bromo-pyrrolo[2,3-b]pyridin-5-yl]carbamate 41 (1.2 g, 2.65 mmol), tetrahydrofuran (10 mL), di-tert-butyldicarbonate (1.32 g, 6.07 mmol), 4-dimethylaminopyridine (0.01 g, 0.08 mmol) and N,N-diisopropylethylamine (1.5 ml). The reaction mixture was stirred at room temperature overnight. The mixture was concentrated and the residue was partitioned between water and ethyl acetate. The organic layer was collected, washed with brine and dried over anhydrous sodium sulfate. Solvent was removed and the residue was dried under vacuum to provide compound 72. MS ESI [M+H+]+=554.2. The compound was used for subsequent reaction without further purification.

Step 2—Synthesis of tert-butyl N-(2-pyrazol-1-yl-1H-pyrrolo[2,3-b]pyridin-5-yl)carbamate 74: To a microwave vessel were added tert-butyl N-[1-(benzenesulfonyl)-2-bromo-pyrrolo[2,3-b]pyridin-5-yl]-N-tert-butoxycarbonyl-carbamate 72 (0.4 g, 0.72 mmol), 1H-pyrazole 73 (0.5 g, 7.34 mmol), tris(dibenzylideneacetone)dipalladium(0) (0.05 g, 0.05 mmol) and racemic 2,2'-bis(diphenylphosphino)-1,1'-binaphthyl (0.050 g, 0.08 mmol) and toluene (5 mL). The mixture was stirred at room temperature for 5 minutes, then added potassium tert-butoxide (0.7 g, 6.24 mmol) followed by additional 2 mL of toluene. The mixture was irradiated with microwave at 145° C. for 15 minutes. The mixture was poured into brine and extracted with ethyl acetate. The organic layers were collected and dried over anhydrous sodium sulfate. Solvent was removed and the residue was purified by silica gel column chromatography eluting with a gradient of methanol and dichloromethane (0-20%) to provide compound 74 (0.12 g, 55%). MS ESI [M+H+]+=300.1. The data from the ¹H NMR spectrum were consistent with the structure of the compound.

Step 3—Synthesis of 2-pyrazol-1-yl-1H-pyrrolo[2,3-b]pyridin-5-amine hydrochloride 75: To tert-butyl N-(2-pyrazol-1-yl-1H-pyrrolo[2,3-b]pyridin-5-yl)carbamate 74 (0.12 g, 0 mol) in methylene chloride (4 mL) was added hydrochloric acid in 1,4-dioxane (5 mL, 4N). The reaction mixture was stirred for 30 minutes and concentrated. The residue was dried under vacuum to provide compound 75 (0.13 g, 96%). MS ESI [M+H+]+=199.85. The compound was used for subsequent reaction without purification.

Step 4—Synthesis of 3,4-dimethyl-N-(2-pyrazol-1-yl-1H-pyrrolo[2,3-b]pyridin-5-yl)-1H-pyrazole-5-carboxamide (P-2112): To a 20 mL scintillation vial were added 3,4-dimethyl-1H-pyrazole-5-carboxylic acid 6 (0.1 g, 0.71 mmol), benzotriazol-1-yl-oxytripyrrolidinophosphonium hexafluorophosphate (0.36 g, 0.7 mmol) and dimethylacetamide (2 mL). The reaction mixture was stirred at room temperature for one hour. To the mixture was added 2-pyrazol-1-yl-1H-pyrrolo[2,3-b]pyridin-5-amine hydrochloride 75 (0.13 g, 0.39 mmol) in dimethylacetamide (1 mL) followed by N, N-diisopropylethylamine (1.5 ml, 8.67 mmol). The reaction mixture was stirred at room temperature for two hours and concentrated. The residue was purified by silica gel column chromatography eluting with a gradient of methanol and dichloromethane to provide a product, which was further titrated with a mixture of ethyl acetate and hexanes to provide compound 76 (5 mg, 4%). MS ESI [M+H+]+=322.3. The data from the ¹H NMR spectrum were consistent with the structure of the compound.

Exemplary compound 3-methyl-N-(2-pyrazol-1-yl-1H-pyrrolo[2,3-b]pyridin-5-yl)-1H-pyrazole-5-carboxamide (P-2116) was prepared according to the synthetic protocols set forth in Scheme 13 and Example 13. The data from the ¹H NMR spectra and observed molecular weights (Table 1) were consistent with the structure of the compound.

Example 14

Preparation of N-[2-[2-chloro-5-(trifluoromethoxy)phenyl]-1H-pyrrolo[2,3-b]pyridin-5-yl]-3,4-dimethyl-1H-pyrazole-5-carboxamide (P-2113)

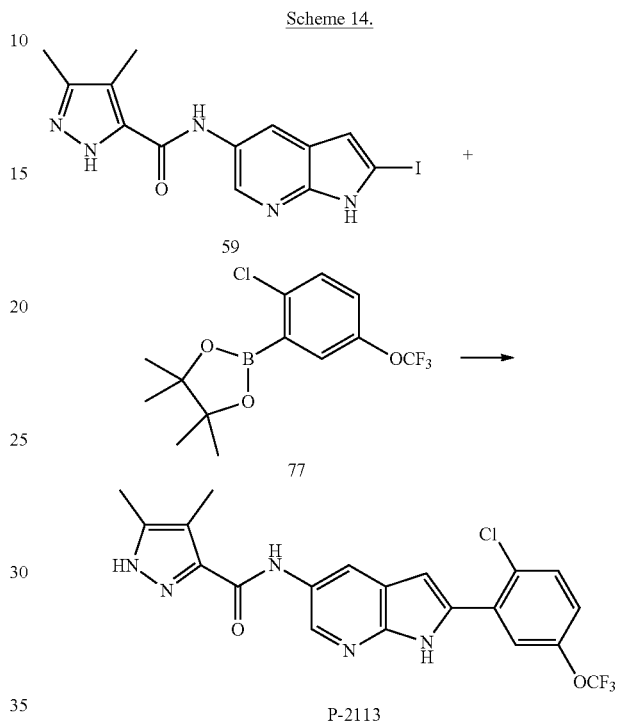

Scheme 14.

P-2113

To a solution of N-(2-iodo-1H-pyrrolo[2,3-b]pyridin-5-yl)-3,4-dimethyl-1H-pyrazole-5-carboxamide 59 (0.05 g, 0.13 mmol), [2-chloro-5-(trifluoromethoxy)phenyl]boronic acid 77 (37.84 mg, 0.16 mmol) and dichloro(1,1-bis(diphenylphosphino)ferrocene)palladium(ii) acetone adduct (7.05 mg, 0.01 mmol) in 1,4-dioxane (3 ml) was added aqueous potassium carbonate (0.4 mL, 1 M). The reaction mixture was irradiated with microwave at 120° C. for 20 minutes. The reaction was quenched with water, neutralized with 1M aqueous hydrochloric acid, and extracted with ethyl acetate. The organic layer washed with brine, dry with sodium sulfate, filtered and concentrated to dryness. The residue was absorbed onto silica gel pad and purified via flash column chromatography (0-10% methanol/dichloromethane). Desired fractions were concentrated to dryness, and then triturated with ethyl acetate to provide compound (P-2113) as an off-white solid (30 mg, 51%). MS ESI [M+H+]+= 450.2. The data from the ¹H NMR spectrum were consistent with the structure of the compound.

Exemplary compounds 4,5-dimethyl-N-[2-(4-morpholinophenyl)-1H-pyrrolo[2,3-b]pyridin-5-yl]-1H-pyrazole-3-carboxamide (P-2059); N-[2-[3-(dimethylamino)phenyl]-1H-pyrrolo[2,3-b]pyridin-5-yl]-3,4-dimethyl-1H-pyrazole-5-carboxamide (P-2064); N-[2-(3,5-dimethylisoxazol-4-yl)-1H-pyrrolo[2,3-b]pyridin-5-yl]-3,4-dimethyl-1H-pyrazole-5-carboxamide (P-2065); 3,4-dimethyl-N-[2-[3-(2-morpholinoethoxy)phenyl]-1H-pyrrolo[2,3-b]pyridin-5-yl]-1H-pyrazole-5-carboxamide (P-2066); 3,4-dimethyl-N-[2-[4-(methylcarbamoyl)phenyl]-1H-pyrrolo[2,3-b]pyridin-5-yl]-1H-pyrazole-5-carboxamide (P-2067); 4,5-dimethyl-N-[2-[2-(4-methylpiperazin-1-yl)-4-pyridyl]-1H-pyrrolo[2,3-b]pyridin-5-yl]-1H-pyrazole-3-carboxamide (P-2069); 4,5-dimethyl-N-[2-(3-morpholinophenyl)-1H-pyrrolo[2,3-b]pyridin-5-yl]-1H-pyrazole-3-carboxamide (P-2070); N-[2-(2-chloro-4-methoxy-phenyl)-1H-pyrrolo[2,3-b]pyridin-5-yl]-3,4-dimethyl-1H-pyrazole-5-carboxamide (P-2075); N-[2-(2-fluoro-4-methoxy-phenyl)-1H-pyrrolo[2,3-b]pyridin-5-yl]-3,4-dimethyl-1H-pyrazole-5-carboxamide; (P-2076); N-[2-(2-chloro-5-methoxy-phenyl)-1H-pyrrolo[2,3-b]pyridin-5-yl]-3,4-dimethyl-1H-pyrazole-5-carboxamide (P-2077); N-[2-(3-fluoro-5-morpholino-phenyl)-1H-pyrrolo[2,3-b]pyridin-5-yl]-3,4-dimethyl-1H-pyrazole-5-carboxamide (P-2078); 3,4-dimethyl-N-[2-(3-pyrrolidin-1-ylphenyl)-1H-pyrrolo[2,3-b]pyridin-5-yl]-1H-pyrazole-5-carboxamide (P-2079); N-[2-(4-aminocyclohexen-1-yl)-1H-pyrrolo[2,3-b]pyridin-5-yl]-3,4-dimethyl-1H-pyrazole-5-carboxamide (P-2080); N-[2-(4-cyano-3-morpholino-phenyl)-1H-pyrrolo[2,3-b]pyridin-5-yl]-3,4-dimethyl-1H-pyrazole-5-carboxamide (P-2081); N-[2-(3-fluoro-2-morpholino-4-pyridyl)-1H-pyrrolo[2,3-b]pyridin-5-yl]-3,4-dimethyl-1H-pyrazole-5-carboxamide (P-2082); N-[2-(1-isobutylpyrazol-4-yl)-1H-pyrrolo[2,3-b]pyridin-5-yl]-3,4-dimethyl-1H-pyrazole-5-carboxamide (P-2083); N-[2-(1,5-dimethylpyrazol-4-yl)-1H-pyrrolo[2,3-b]pyridin-5-yl]-3,4-dimethyl-1H-pyrazole-5-carboxamide (P-2084); N-[2-[4-(dimethylcarbamoyl)phenyl]-1H-pyrrolo[2,3-b]pyridin-5-yl]-3,4-dimethyl-1H-pyrazole-5-carboxamide (P-2085); 3,4-dimethyl-N-[2-[3-(trifluoromethoxy)phenyl]-1H-pyrrolo[2,3-b]pyridin-5-yl]-1H-pyrazole-5-carboxamide (P-2086); N-[2-[3-(dimethylcarbamoyl)phenyl]-1H-pyrrolo[2,3-b]pyridin-5-yl]-3,4-dimethyl-1H-pyrazole-5-carboxamide (P-2087); 3,4-dimethyl-N-[2-(3-pyridyl)-1H-pyrrolo[2,3-b]pyridin-5-yl]-1H-pyrazole-5-carboxamide (P-2088); 3,4-dimethyl-N-[2-(6-morpholino-3-pyridyl)-1H-pyrrolo[2,3-b]pyridin-5-yl]-1H-pyrazole-5-carboxamide (P-2089); N-[2-(6-methoxy-3-pyridyl)-1H-pyrrolo[2,3-b]pyridin-5-yl]-3,4-dimethyl-1H-pyrazole-5-carboxamide (P-2090); 3,4-dimethyl-N-[2-(2-methylthiazol-5-yl)-1H-pyrrolo[2,3-b]pyridin-5-yl]-1H-pyrazole-5-carboxamide (P-2091); N-[2-(4-cyanophenyl)-1H-pyrrolo[2,3-b]pyridin-5-yl]-3,4-dimethyl-1H-pyrazole-5-carboxamide (P-2092); N-[2-(2-fluorophenyl)-1H-pyrrolo[2,3-b]pyridin-5-yl]-3,4-dimethyl-1H-pyrazole-5-carboxamide (P-2093); N-[2-(3-fluorophenyl)-1H-pyrrolo[2,3-b]pyridin-5-yl]-3,4-dimethyl-1H-pyrazole-5-carboxamide (P-2094); N-[2-(3-chlorophenyl)-1H-pyrrolo[2,3-b]pyridin-5-yl]-3,4-dimethyl-1H-pyrazole-5-carboxamide (P-2095); N-[2-(2-chlorophenyl)-1H-pyrrolo[2,3-b]pyridin-5-yl]-3,4-dimethyl-1H-pyrazole-5-carboxamide (P-2096); 3,4-dimethyl-N-[2-(o-tolyl)-1H-pyrrolo[2,3-b]pyridin-5-yl]-1H-pyrazole-5-carboxamide; (P-2097); N-[2-(3-methoxyphenyl)-1H-pyrrolo[2,3-b]pyridin-5-yl]-3,4-dimethyl-1H-pyrazole-5-carboxamide (P-2098); N-[2-(4-methoxyphenyl)-1H-pyrrolo[2,3-b]pyridin-5-yl]-3,4-dimethyl-1H-pyrazole-5-carboxamide (P-2099); N-[2-(3-acetamidophenyl)-1H-pyrrolo[2,3-b]pyridin-5-yl]-3,4-dimethyl-1H-pyrazole-5-carboxamide (P-2100); 3,4-dimethyl-N-[2-[4-(pyrrolidine-1-carbonyl)phenyl]-1H-pyrrolo[2,3-b]pyridin-5-yl]-1H-pyrazole-5-carboxamide (P-2101); N-[2-[4-(3-methoxypropoxy)phenyl]-1H-pyrrolo[2,3-b]pyridin-5-yl]-3,4-dimethyl-1H-pyrazole-5-carboxamide (P-2102); 3,4-dimethyl-N-[2-[4-(4-methylpiperazin-1-yl)phenyl]-1H-pyrrolo[2,3-b]pyridin-5-yl]-1H-pyrazole-5-carboxamide (P-2104); 3,4-dimethyl-N-[2-[4-(thiomorpholine-4-carbonyl)phenyl]-1H-pyrrolo[2,3-b]pyridin-5-yl]-1H-pyrazole-5-carboxamide (P-2105); 3,4-dimethyl-N-[2-[3-(morpholine-4-carbonyl)phenyl]-1H-pyrrolo[2,3-b]pyridin-5-yl]-1H-pyrazole-5-carboxamide (P-2106); 3,4-dimethyl-N-[2-[3-(pyrrolidine-1-carbonyl)phenyl]-1H-pyrrolo[2,3-b]pyridin-5-yl]-1H-pyrazole-5-carboxamide (P-2107); N-[2-(2-cyclopropyl-4-pyridyl)-1H-pyrrolo[2,3-b]pyridin-5-yl]-3,4-dimethyl-1H-pyrazole-5-carboxamide (P-2108); N-[2-(2-methoxy-4-pyridyl)-1H-pyrrolo[2,3-b]pyridin-5-yl]-3,4-dimethyl-1H-pyrazole-5-carboxamide (P-2109); 3,4-dimethyl-N-[2-(2-morpholino-4-pyridyl)-1H-pyrrolo[2,3-b]pyridin-5-yl]-1H-pyrazole-5-carboxamide (P-2110); N-[2-[4-(methanesulfonamido)phenyl]-1H-pyrrolo[2,3-b]pyridin-5-yl]-3,4-dimethyl-1H-pyrazole-5-carboxamide (P-2111); N-[2-[3-[4-(cyclopropanecarbonyl)piperazin-1-yl]phenyl]-1H-pyrrolo[2,3-b]pyridin-5-yl]-3,4-dimethyl-1H-pyrazole-5-carboxamide (P-2118); N-[2-(4-cyano-3-pyrrolidin-1-ylphenyl)-1H-pyrrolo[2,3-b]pyridin-5-yl]-3,4-dimethyl-1H-pyrazole-5-carboxamide (P-2120); 3,4-dimethyl-N-[2-[3-(methylsulfamoyl)phenyl]-1H-pyrrolo[2,3-b]pyridin-5-yl]-1H-pyrazole-5-carboxamide (P-2121); N-[2-(4-chlorophenyl)-1H-pyrrolo[2,3-b]pyridin-5-yl]-3,4-dimethyl-1H-pyrazole-5-carboxamide; (P-2122); 3,4-dimethyl-N-[2-(6-methyl-3-pyridyl)-1H-pyrrolo[2,3-b]pyridin-5-yl]-1H-pyrazole-5-carboxamide (P-2123); 3,4-dimethyl-N-[2-(4-pyridyl)-1H-pyrrolo[2,3-b]pyridin-5-yl]-1H-pyrazole-5-carboxamide (2124); 3,4-dimethyl-N-[2-(4-pyrrolidin-1-ylphenyl)-1H-pyrrolo[2,3-b]pyridin-5-yl]-1H-pyrazole-5-carboxamide (P-2125); 3,4-dimethyl-N-[2-[3-(propylsulfonylamino)phenyl]-1H-pyrrolo[2,3-b]pyridin-5-yl]-1H-pyrazole-5-carboxamide (P-2126); N-[2-(3-cyanophenyl)-1H-pyrrolo[2,3-b]pyridin-5-yl]-3,4-dimethyl-1H-pyrazole-5-carboxamide (P-2128); N-[2-(2-fluoro-3-methoxy-phenyl)-1H-pyrrolo[2,3-b]pyridin-5-yl]-3,4-dimethyl-1H-pyrazole-5-carboxamide (P-2129); 3,4-dimethyl-N-[2-(m-tolyl)-1H-pyrrolo[2,3-b]pyridin-5-yl]-1H-pyrazole-5-carboxamide (P-2130); N-[2-(6-acetamido-3-pyridyl)-1H-pyrrolo[2,3-b]pyridin-5-yl]-3,4-dimethyl-1H-pyrazole-5-carboxamide (P-2133); N-[2-[3-(butylcarbamoylamino)phenyl]-1H-pyrrolo[2,3-b]pyridin-5-yl]-3,4-dimethyl-H-pyrazole-5-carboxamide (P-2134); N-[2-(2-methoxyphenyl)-1H-pyrrolo[2,3-b]pyridin-5-yl]-3,4-dimethyl-1H-pyrazole-5-carboxamide (P-2135); 3,4-dimethyl-N-[2-(2-methyl-3-pyridyl)-1H-pyrrolo[2,3-b]pyridin-5-yl]-1H-pyrazole-5-carboxamide (P-2136); N-[2-(4-acetamidophenyl)-1H-pyrrolo[2,3-b]pyridin-5-yl]-3,4-dimethyl-1H-pyrazole-5-carboxamide (P-2137); 3,4-dimethyl-N-[2-[4-(morpholine-4-carbonyl)phenyl]-1H-pyrrolo[2,3-b]pyridin-5-yl]-1H-pyrazole-5-carboxamide (P-2138); N-[2-(2,4-dimethylthiazol-5-yl)-1H-pyrrolo[2,3-b]pyridin-5-yl]-3,4-dimethyl-1H-pyrazole-5-carboxamide (P-2139); N-[2-[1-(difluoromethyl)pyrazol-4-yl]-1H-pyrrolo[2,3-b]pyridin-5-yl]-3,4-dimethyl-1H-pyrazole-5-carboxamide (P-2140); 3,4-dimethyl-N-[2-[2-(trifluoromethyl)-3-pyridyl]-1H-pyrrolo[2,3-b]pyridin-5-yl]-1H-pyrazole-5-carboxamide (P-2176); N-[2-(2-ethyl-4-pyridyl)-1H-pyrrolo[2,3-b]pyridin-5-yl]-3,4-dimethyl-1H-pyrazole-5-carboxamide (P-2177); N-[2-(6-ethyl-3-pyridyl)-1H-pyrrolo[2,3-b]pyridin-5-yl]-3,4-dimethyl-1H-pyrazole-5-carboxamide (P-2178); N-[2-(2,3-dihydro-[1,4]dioxino[2,3-b]pyridin-8-yl)-1H-pyrrolo[2,3-b]pyridin-5-yl]-3,4-dimethyl-H-pyrazole-5-carboxamide (P-2179); 3,4-dimethyl-N-[2-[2-(trifluoromethyl)phenyl]-1H-pyrrolo[2,3-b]pyridin-5-yl]-1H-pyrazole-5-carboxamide (P-2180); N-[2-(2,4-dimethylphenyl)-1H-pyrrolo[2,3-b]pyridin-5-yl]-3,4-dimethyl-1H-pyrazole-5-carboxamide (P-2181); 3,4-dimethyl-N-[2-[2-(trifluoromethoxy)phenyl]-1H-pyrrolo[2,3-b]pyridin-5-yl]-1H-pyrazole-5-carboxamide (P-2182);

N-[2-(5-methoxy-3-pyridyl)-1H-pyrrolo[2,3-b]pyridin-5-yl]-3,4-dimethyl-1H-pyrazole-5-carboxamide (p-2183); 3,4-dimethyl-N-[2-(5-methyl-3-pyridyl)-1H-pyrrolo[2,3-b]pyridin-5-yl]-1H-pyrazole-5-carboxamide (P-2184); N-[2-(4-methoxy-3-pyridyl)-1H-pyrrolo[2,3-b]pyridin-5-yl]-3,4-dimethyl-1H-pyrazole-5-carboxamide (P-2185); and compounds P-2144, P-2146, P-2147, P-2148, P-2149, P-2153, P-2154, p-2155, P-2156, P-2157, P-2158, P-2160, P-2161, P-2163, P-2164, P-2166, P-2167, P-2168, P-2169, P-2170, P-2171 and P-2174 were prepared according to the synthetic protocols set forth in Scheme 14 and Example 14. The data from the ¹H NMR spectra and observed molecular weights (Table 1) were consistent with the structures of the compounds. In addition, compounds P-2238, P-2239, P-2240, P-2241, P-2242, P-2243, P-2244, P-2245, P-2246, P-2247, P-2248, P-2249, P-2250, P-2251, P-2252, P-2253, P-2254, P-2255, P-2256, P-2257, P-2258, P-2259, P-2260, P-2261, P-2262, P-2263, P-2264, P-2265, P-2266 and P-2267 can be prepared according to the synthetic routes set forth in Example 14 and Scheme 14.

Example 15

Preparation of N-[2-(4-dimethylphosphorylphenyl)-1H-pyrrolo[2,3-b]pyridin-5-yl]-3,4-dimethyl-1H-pyrazole-5-carboxamide (P-2127)

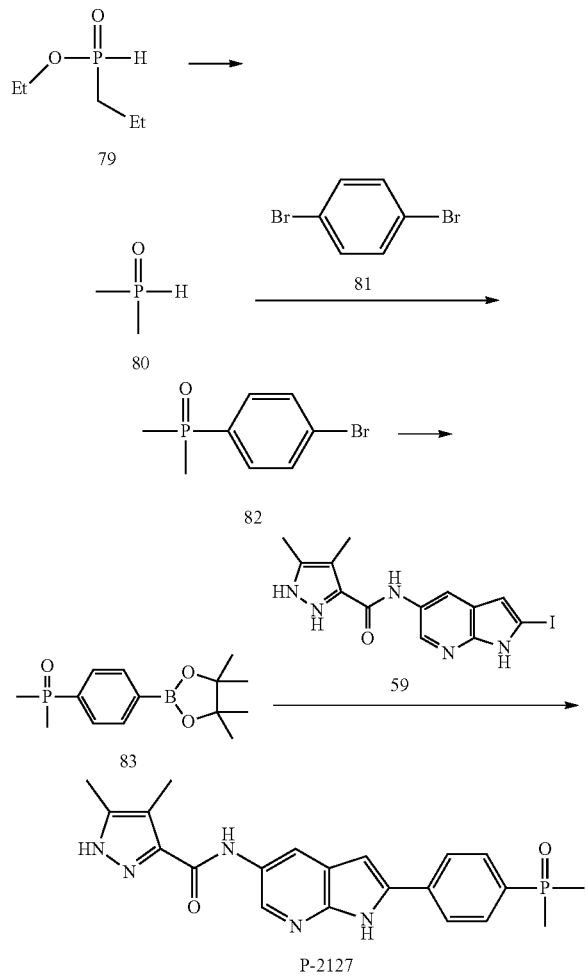

Step 1—Synthesis of methylphosphonoylmethane (80): In round bottom flask, methylmagnesium chloride in tetrahydrofuran (20 ml, 3 M) was chilled with an ice water bath. 1-ethoxyphosphonoyloxyethane 79 (2.58 ml, 20 mmol) in tetrahydrofuran (5 ml) was added dropwise. The reaction mixture was allowed to stir from 0 OC to room temperature for 5 hours. Saturated sodium bicarbonate (20 mL) was added into the reaction mixture slowly, followed by methanol (20 mL). Precipitate was formed and reaction mixture was allowed to stir at room temperature overnight. Salt formed was filtered and the filtrate was concentrated under reduced pressure. The reaction mixture was dried under vacuum to afford a clear semi solid/oil (80). ¹H NMR [D₂O] spectrum was consistent with the desired product.

Step 2—Synthesis of 1-bromo-4-dimethylphosphorylbenzene (82); In a pressure vessel, 1,4-dibromobenzene 81 (4 g, 16.96 mmol), methylphosphonoylmethane (80) (5.5 g, 70.67 mmol), tetrakis(triphenylphosphine)palladium (0) (0.98 g, 0.85 mmol) and triethylamine (9.45 ml, 67.82 mmol) were dissolved in acetonitrile (40 ml). The reaction was stirred at 90° C. overnight. The reaction mixture was cooled to room temperature and concentrated. The residue was loaded onto silica gel and purified via silica gel chromatography to provide crude compound 82 as a yellowish solid (2.1 g). The solid was used for subsequent reaction without further purification. MS(ESI) [M+H+]+=232.7/234.7. ¹H NMR spectrum was consistent with the structure of the compound.

Step 3—Synthesis of 2-(4-dimethylphosphorylphenyl)-4,4,5,5-tetramethyl-1,3,2-dioxaborolane 83: To a solution of 1-bromo-4-dimethylphosphoryl-benzene 82 (2.1 g, 9.01 mmol) in 1,4 dioxane (50 ml) in a pressure vessel were added 4,4,5,5-tetramethyl-2-(4,4,5,5-tetramethyl-1,3,2-dioxaborolan-2-yl)-1,3,2-dioxaborolane (4.58 g, 18.02 mmol), potassium acetate (2.99 ml, 47.76 mmol) and 1,1'-bis(diphenylphosphino)ferrocene-palladium(ii)dichloride dichloromethane complex (0.99 ml, 1.17 mmol). The mixture was stirred at 90° C. for four hours. The reaction mixture was cooled down and filtered through Celite. The filtrate was concentrated to dryness. A third of the material was loaded onto silica gel and purified via silica gel chromatography to provide compound 83 (350 mg). MS(ESI) [M+H+]+= 280.80. Compound 83 was used for subsequent reaction without further purification.

Step 4: Synthesis of N-[2-(4-dimethylphosphorylphenyl)-1H-pyrrolo[2,3-b]pyridin-5-yl]-3,4-dimethyl-1H-pyrazole-5-carboxamide (P-2127): To a suspension of 2-(4-dimethylphosphorylphenyl)-4,4,5,5-tetramethyl-1,3,2-dioxaborolane 83 (60 mg, 0.21 mmol) in 1,4 dioxane (3 mL) were added N-(2-iodo-1H-pyrrolo[2,3-b]pyridin-5-yl)-3,4-dimethyl-1H-pyrazole-5-carboxamide 59 (163.3 mg, 0.43 mmol), 1,1'-Bis(diphenylphosphino)ferrocene-palladium(ii) dichloride dichloromethane complex (0.01 g, 0.01 mmol) and an aqueous potassium carbonate solution (0.64 ml, 1 M). The reaction mixture was irradiated with microwave at 110° C. for 20 minutes. The reaction mixture was filtered and the precipitate was collected and triturated with a mixture of methanol and acetonitrile to provide product (P-2127) as an off white solid (33 mg, 37.8%). MS(ESI) [M+H+]+=408.30. ¹H NMR spectrum and mass spectroscopy data were consistent with the structure of the compound.

Example 16

Preparation of N-[(4-chloro-5-methyl-1H-pyrazol-3-yl)methyl]-2-(4-fluorophenyl)-1H-pyrrolo[2,3-b]pyridin-5-amine (P-2141) and Preparation of 2-(4-fluorophenyl)-N-[(5-methyl-1H-pyrazol-3-yl)methyl]-1H-pyrrolo[2,3-b]pyridin-5-amine (P-2142)

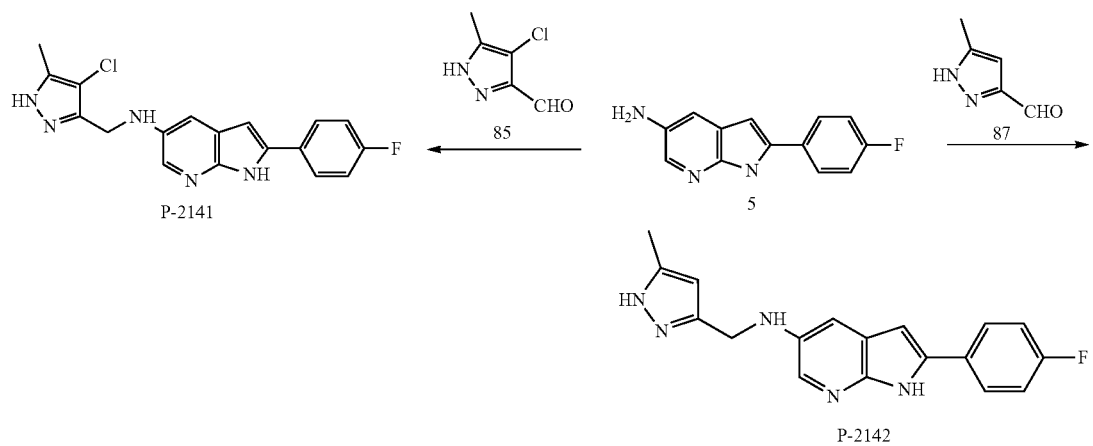

Step 1—Preparation of N-[(4-chloro-5-methyl-1H-pyrazol-3-yl)methyl]-2-(4-fluorophenyl)-1H-pyrrolo[2,3-b]pyridin-5-amine (P-2141): To 4-chloro-5-methyl-1H-pyrazole-3-carbaldehyde 85 (0.16 g, 1.1 mmol) in tetrahydrofuran (5 mL) was added 2-(4-fluorophenyl)-1H-pyrrolo[2,3-b]pyridin-5-amine 5 (0.4 g, crude) and sodium borohydride (84 mg, 1.34 mmol). The reaction mixture was stirred at room temperature for three days. The reaction mixture was quenched with water, extracted with ethyl acetate. The organic layer was collected, washed by brine and dried under sodium sulfate. Drying agent and solvent were removed and the residue was purified by silica gel column chromatography followed by preparative HPLC to provide product as a yellow solid (P-2141) (48 mg, 12%). MS(ESI) [M+H+]+=355.95. $^1$HNMR spectrum and mass spectroscopy data were consistent with the structure of the compound.

Step 2—Preparation of 2-(4-fluorophenyl)-N-[(5-methyl-1H-pyrazol-3-yl)methyl]-1H-pyrrolo[2,3-b]pyridin-5-amine (P-2142): To a mixture of 2-(4-fluorophenyl)-1H-pyrrolo[2,3-b]pyridin-5-amine 5 (46 mg, 0.2 mmol) and 5-methyl-1H-pyrazole-3-carbaldehyde 87 (58 mg, 0.53 mmol) in acetonitrile (3 mL) was added trifluoroacetic acid (0.1 ml, 1.3 mmol), followed by triethylsilane (0.1 ml, 0.63 mmol). The reaction mixture was stirred at room temperature overnight. The reaction mixture was concentrated. The residue was dissolved in a mixture of water and saturated sodium bicarbonate solution and then was extracted with ethyl acetate. The organic layer was collected, washed with brine, and dried under sodium sulfate. After removal of drying agent and solvent, the residue was purified by column chromatography to provide compound (P-2142) as a tan solid (28 mg, 43%). MS(ESI) [M+H+]+=453.75. $^1$H NMR spectrum and mass spectroscopy data were consistent with the structure of the compound.

Example 17

Preparation of 3,4-dimethyl-N-(2-phenylthiazolo[5,4-b]pyridin-6-yl)-1H-pyrazole-5-carboxamide (P-2144)

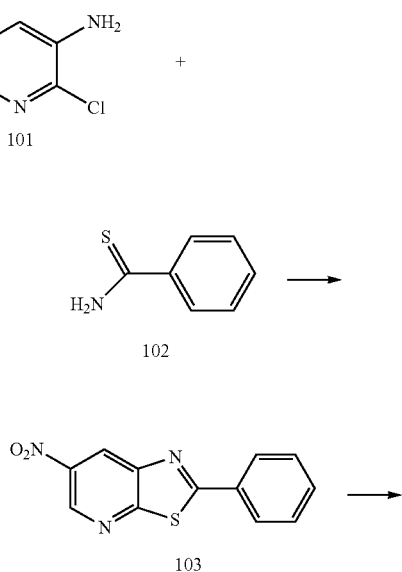

169

-continued

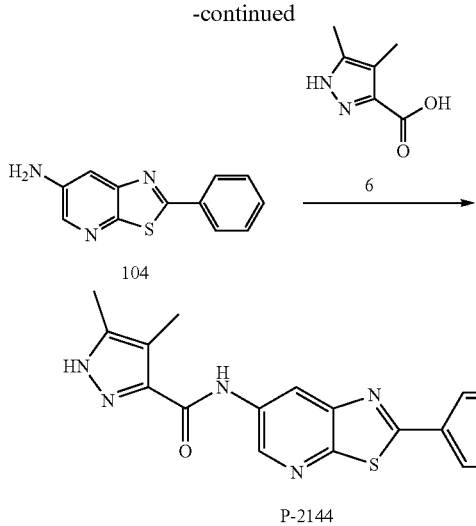

Step 1—Synthesis of 6-nitro-2-phenyl-thiazolo[5,4-b]pyridine (103): In a pressure vessel, 2-chloro-3,5-dinitropyridine 101 (2.5 g, 12.04 mmol) and benzenecarbothioamide 102 (6.6 g, 48.18 mmol) were dissolved in sulfolane (20 ml, 209.87 mmol). The mixture was heated to 100° C. and stirred overnight. The reaction mixture was the cooled to room temperature, quenched with brine, extracted with ethyl acetate and washed with brine. The organic layer was dried with sodium sulfate. After removal of solvent, the residue was triturated with methanol, filtered, and the filter cake was washed with hexane. The solid was triturated again with methanol to afford the product as a brown solid 103 (0.46 g, 14.7%).

Step 2—Synthesis of 2-phenylthiazolo[5,4-b]pyridin-6-amine 104: To a round bottom flask containing 6-nitro-2-phenyl-thiazolo[5,4-b]pyridine 103 (30 mg, 0.116 mmol) in aqueous hydrochloric acid (12N, 1 mL) and methanol (1 mL) was added iron (30 mg). The reaction mixture was stirred at 80° C. for 2 hours, cooled to room temperature, filtered over celite and washed with methanol and dichloromethane. The filtrate was concentrated to half volume, diluted with water, neutralized with sodium bicarbonate and extracted with ethyl acetate. The organic layer was washed with brine and dried with sodium sulfate. After removal of solvent, the residue was dried under vacuum to provide 2-phenylthiazolo[5,4-b]pyridin-6-amine 104 as a yellowish solid (93 mg, 98%).

Step 3—Synthesis of 3, 4-dimethyl-N-(2-phenylthiazolo[5,4-b]pyridin-6-yl)-1H-pyrazole-5-carboxamide 105: To a scintillation were added 3,4-dimethyl-1H-pyrazole-5-carboxylic acid 6 (0.03 g, 0.21 mmol) and (O-(7-azabenzotriazol-1-yl)-N,N,N',N'-tetramethyluronium hexafluorophosphate) (0.1 g, 0.26 mmol) in dimethylacetamide (3 ml). The reaction mixture was stirred at room temperature for one hour. To this mixture were then added 2-phenylthiazolo[5,4-b]pyridin-6-amine 104 (30 mg, 0.13 mmol) and triethylamine (0.04 ml, 0.26 mmol). The reaction mixture was stirred at room temperature overnight. The reaction was quenched with water, extracted with ethyl acetate and washed with brine. The organic layer was dried with sodium sulfate. After removal of solvent, the residue was purified by reverse phase column chromatography to provide compound (P-2144) as a fluffy white solid (6.3 mg, 13.7%). MS (ESI) [M+H+]+=349.85. $^1$H NMR and mass spectroscopy data were consistent with the desired product.

170

Example 18

Preparation of N-[2-(2-fluorophenyl)-3H-imidazo[4,5-b]pyridin-6-yl]-3,4-dimethyl-1H-pyrazole-5-carboxamide (P-2152)

Scheme 18.

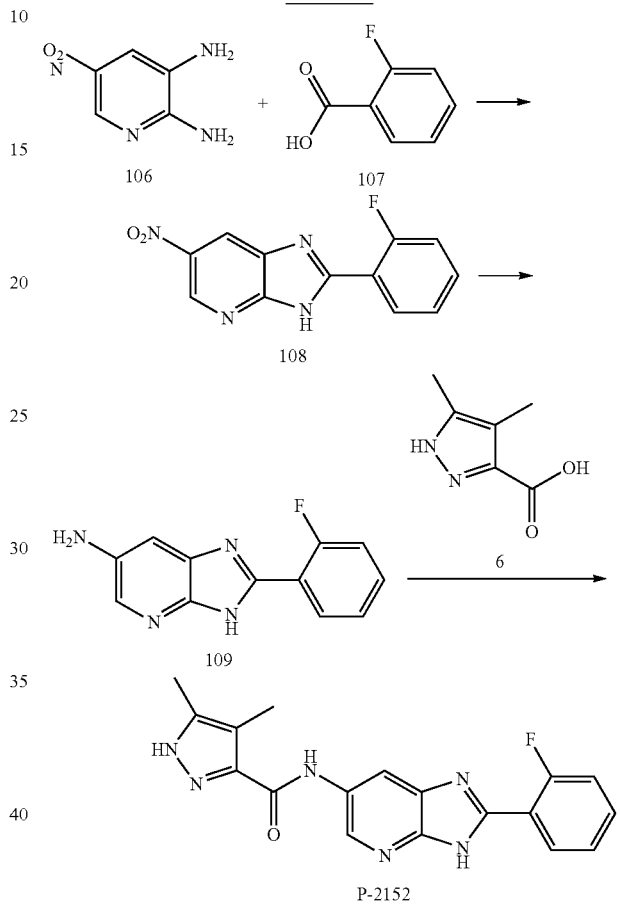

Step 1—Synthesis of 2-(2-fluorophenyl)-6-nitro-3H-imidazo[4,5-b]pyridine (108): To a pressure vessel containing 5-nitropyridine-2,3-diamine 106 (125 mg, 0.8 mmol) and 2-fluorobenzoic acid 107 (112.17 mg, 0.8 mmol) was added Eaton's reagent (2 ml, 12.73 mmol). The reaction mixture was stirred at 150° C. The mixture was cooled to room temperature and quenched with water. The precipitate was collected and dried under vacuum to provide compound 108. The compound was used for subsequent reaction without purification.

Step 2—Synthesis of 2-(2-fluorophenyl)-3H-imidazo[4,5-b]pyridin-6-amine (109): To a pressure vessel charged with 2-(2-fluorophenyl)-6-nitro-3H-imidazo[4,5-b]pyridine 108 (100 mg, 0.38 mmol), aqueous hydrochloric acid (12N, 3 mL), and methanol (3 mL) was added iron (22 mg). The reaction mixture was stirred at 80° C. for two hours, cooled to room temperature, filtered over celite, and washed with methanol and dichloromethane. The filtrate was concentrated to half volume, diluted with water, neutralized to with sodium bicarbonate and extracted with ethyl acetate. The organic layer was washed with brine and dried with sodium sulfate. After removal of solvent, the residue was dried under vacuum to provide compound 109 as a yellow solid (60 mg, 68.4%). The compound was used for subsequent reaction without purification.

Step 3—Synthesis of N-[2-(2-fluorophenyl)-3H-imidazo [4,5-b]pyridin-6-yl]-3,4-dimethyl-1H-pyrazole-5-carboxamide (P-2152): To a scintillation vial were added 3,4-dimethyl-1H-pyrazole-5-carboxylic acid 6 (44 mg, 0.32 mmol) and (O-(7-azabenzotriazol-1-yl)-N,N,N',N'-tetramethyluronium hexafluorophosphate) (0.15 g, 0.39 mmol) in dimethylacetamide (3 ml). The reaction mixture was stirred at room temperature for one hour, then added 2-(2-fluorophenyl)-3H-imidazo[4,5-b]pyridin-6-amine 109 (45 mg, 0.2 mmol) and N,N-diisopropylethylamine (0.07 ml, 0.39 mmol). The mixture was stirred at room temperature overnight, quenched with water, extracted with ethyl acetate, and washed with brine. The organic layer was collected and dried with sodium sulfate. After removal of solvent, the residue was purified by column chromatography and further triturated with methanol to afford compound (P-2152) as an off-white solid (22 mg, 30%). MS (ESI) [M+H+]+=351.1. ¹H NMR and mass spectroscopy data were consistent with the desired product.

Exemplary compounds 3,4-dimethyl-N-(2-phenyl-3H-imidazo[4,5-b]pyridin-6-yl)-1H-pyrazole-5-carboxamide (P-2145), 4-chloro-3-methyl-N-(2-phenyl-3H-imidazo[4,5-b]pyridin-6-yl)-1H-pyrazole-5-carboxamide (P-2150) and 3-methyl-N-(2-phenyl-3H-imidazo[4,5-b]pyridin-6-yl)-1H-pyrazole-5-carboxamide (P-2151) were prepared according to the synthetic protocols set forth in Scheme 18 and Example 18. The data from the ¹H NMR spectra and observed molecular weights (Table 1) were consistent with the structures of the compounds.

Example 19

Preparation of tert-butyl 4-[3-[5-[(3,4-dimethyl-1H-pyrazole-5-carbonyl)amino]-1H-pyrazolo[3,4-b]pyridin-3-yl]phenyl]piperazine-1-carboxylate (P-2162) and 3,4-dimethyl-N-[3-(3-piperazin-1-ylphenyl)-1H-pyrazolo[3,4-b]pyridin-5-yl]-1H-pyrazole-5-carboxamide (P-2165)

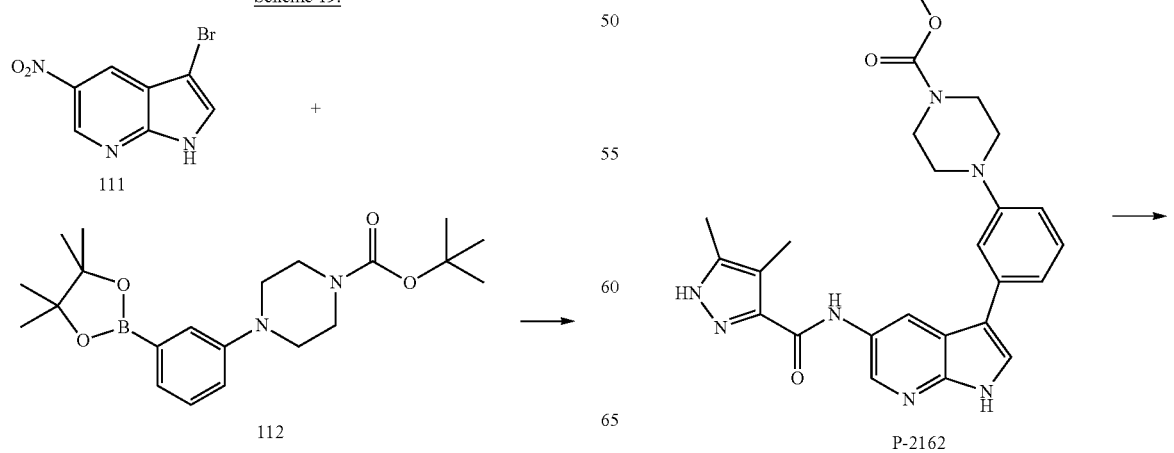

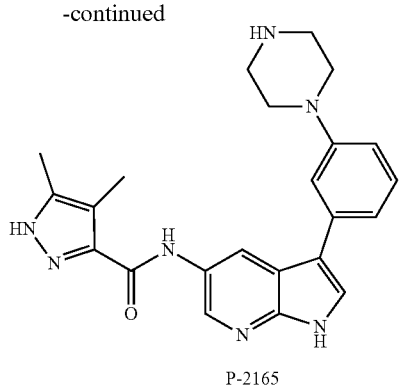

P-2165

Step 1—Synthesis of tert-butyl 4-[3-(5-nitro-1H-pyrazolo[3,4-b]pyridin-3-yl)phenyl]piperazine-1-carboxylate (113): To 3-bromo-5-nitro-1H-pyrazolo[3,4-b]pyridine 111 (0.1 g, 0.41 mmol) in acetonitrile (3 ml) were added tert-butyl 4-[3-(4,4,5,5-tetramethyl-1,3,2-dioxaborolan-2-yl)phenyl]piperazine-1-carboxylate 112 (0.2 g, 0.52 mmol), [1,1'-bis(diphenylphosphino)ferrocene]dichloropalladium(ii) (12 mg, 0.016 mmol), and aqueous potassium carbonate (1 ml, 1 M). The reaction mixture was irradiated in microwave at 120° C. for 20 minutes and at 150° C. for 170 minutes. The reaction mixture was poured into water and extracted with ethyl acetate. The organic layer was washed by brine and dried under sodium sulfate. After removal of drying agent and solvent, the residue was purified by silica gel column chromatography to provide compound 113 as a brownish solid (58 mg, 23%). MS(ESI) [M−H−]−=423.20.

Step 2—Synthesis of tert-butyl 4-[3-(5-amino-1H-pyrazolo[3,4-b]pyridin-3-yl)phenyl]piperazine-1-carboxylate (114): To tert-butyl 4-[3-(5-nitro-1H-pyrazolo[3,4-b]pyridin-3-yl)phenyl]piperazine-1-carboxylate 113 (58 mg, 0.14 mmol) in a mixture of methanol (2 ml) and methylene chloride (2 ml) was added palladium on carbon (5 mg, 10%, wet). The reaction mixture was stirred under a balloon of hydrogen at room temperature overnight. After removal of catalyst and solvent, the residue was dried under vacuum to provide compound 114 as a brownish solid (46 mg, 85%). MS(ESI) [M−H+]−=395.25. The compound was used for the subsequent reaction without purification.

Step 3—Synthesis of tert-butyl 4-[3-[5-[(3,4-dimethyl-1H-pyrazole-5-carbonyl)amino]-1H-pyrazolo[3,4-b]pyridin-3-yl]phenyl]piperazine-1-carboxylate (P-2162): To 4,5-dimethyl-1H-pyrazole-3-carboxylic acid 6 (30 mg, 0.21 mmol) in N,N-dimethylamide (4 mL) was added benzotriazol-1-yl-oxytripyrrolidinophosphonium hexafluorophosphate (0.115 g, 0.22 mmol), followed by N,N-diisopropylethylamine (0.1 ml, 0.58 mmol). The suspension was stirred at room temperature for 60 minutes. To this suspension was added tert-butyl 4-[3-(5-amino-1H-pyrazolo[3,4-b]pyridin-3-yl)phenyl]piperazine-1-carboxylate 114 (46 mg, 0.12 mmol) in N,N-dimethylamide (1 mL). The reaction mixture was stirred at room temperature for two days, then quenched with water and extracted with ethyl acetate. The organic layer was collected, washed with brine and dried under sodium sulfate. After removal of drying agent and solvent, the residue was purified by column chromatography and preparative HPLC to provide compound 115 as a white solid (12 mg, 10%). MS(ESI) [M+H+]+=517.4. The data from the $^1$H NMR spectrum was consistent with the structure of the compound.

Step 4—Preparation of 3,4-dimethyl-N-[3-(3-piperazin-1-ylphenyl)-1H-pyrazolo[3,4-b]pyridin-5-yl]-1H-pyrazole-5-carboxamide (P-2165): To tert-butyl 4-[3-[5-[(3,4-dimethyl-1H-pyrazole-5-carbonyl)amino]-1H-pyrazolo[3,4-b]pyridin-3-yl]phenyl]piperazine-1-carboxylate 115 (8 mg, 0.02 mmol) in tetrahydrofuran (1 mL) was added hydrochloric acid in dioxane (0.4 ml, 4 M). The reaction mixture was stirred at room temperature overnight. The reaction mixture was quenched with water and extracted with ethyl acetate. The organic layer was collected, washed with brine, and dried under sodium sulfate. After removal of drying agent and solvent, the residue was purified by preparative HPLC to provide compound 116 as white solid (2 mg, 28%). MS(ESI) [M+H+]+=417.15. $^1$H NMR and MS were consistent with the desired product.

Exemplary compounds 4,5-dimethyl-N-(3-(6-(piperazin-1-yl)pyridin-2-yl)-1H-pyrrolo[2,3-b]pyridin-5-yl)-1H-pyrazole-3-carboxamide (P-2190); 4,5-dimethyl-N-(3-(6-(piperazin-1-yl)pyridin-2-yl)-1H-pyrrolo[2,3-b]pyridin-5-yl)-1H-pyrazole-3-carboxamide (P-2191); 4,5-dimethyl-N-(3-(6-morpholinopyridin-2-yl)-1H-pyrrolo[2,3-b]pyridin-5-yl)-1H-pyrazole-3-carboxamide (P-2192); and 4,5-dimethyl-N-(3-(2-morpholinopyridin-4-yl)-1H-pyrrolo[2,3-b]pyridin-5-yl)-1H-pyrazole-3-carboxamide (P-2193) can be prepared according to the synthetic protocols set forth in Scheme 19 and Example 19.

Example 20

Preparation of 3,4-dimethyl-N-[2-[3-methyl-1-(oxetan-3-yl)pyrazol-4-yl]-1H-pyrrolo[2,3-b]pyridin-5-yl]-1H-pyrazole-5-carboxamide (P-2168)

Scheme 20.

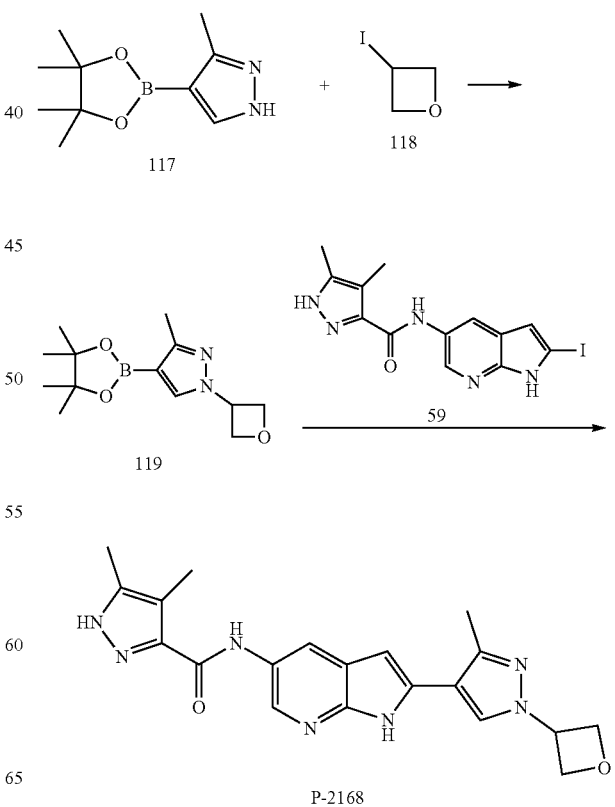

P-2168

Step 1—Synthesis of 3-methyl-1-(oxetan-3-yl)-4-(4,4,5,5-tetramethyl-1,3,2-dioxaborolan-2-yl)pyrazole (119): Into a round bottom flask was placed 3-methyl-4-(4,4,5,5-tetramethyl-1,3,2-dioxaborolan-2-yl)-1H-pyrazole 117 (0.7 g, 3.36 mmol) in dimethylformamide (10 ml), and cooled in an ice-water bath. Sodium hydride (60% in mineral oil, 0.34 g, 8.41 mmol) was added and the mixture was stirred for 60 minutes. To this mixture was added 3-iodooxetane 118 (0.3 ml, 3.49 mmol) under nitrogen dropwise. The reaction was allowed to warm to room temperature and stirred overnight. The reaction was quenched with methanol and concentrated to dryness. The resulting liquid crude product solidified to a toffee consistency 119. The material was used for subsequent reaction without purification. MS ESI [M+H+]+= 264.8.

Step 2—Synthesis of 3,4-dimethyl-N-[2-[3-methyl-1-(oxetan-3-yl)pyrazol-4-yl]-1H-pyrrolo[2,3-b]pyridin-5-yl]-1H-pyrazole-5-carboxamide (2168): Into a microwave vessel were placed N-(2-iodo-1H-pyrrolo[2,3-b]pyridin-5-yl)-3,4-dimethyl-1H-pyrazole-5-carboxamide 59 (0.05 g, 0.13 mmol) and 3-methyl-1-(oxetan-3-yl)-4-(4,4,5,5-tetramethyl-1,3,2-dioxaborolan-2-yl)pyrazole 119 (0.18 g, crude), [1,1'-bis(diphenylphosphino)ferrocene]dichloropalladium (II) (0.01 g, 0.02 mmol) and 1,4 dioxane (3 mL). To this mixture was added potassium carbonate (1M aqueous solution, 0.8 ml) and the reaction was irradiated at 110° C. for 20 minutes. After filtration, the mixture was purified with preparative HPLC eluting with a gradient of acetonitrile:water and 0.1% formic acid to produce compound (P-2168) as a main product. MS (ESI) [M+H+]+=392.2. $^1$H NMR and mass spectroscopy were consistent with the desired product.

The exemplary compounds N-(2-(1-(1-acetylazetidin-3-yl)-3-methyl-1H-pyrazol-4-yl)-1H-pyrrolo[2,3-b]pyridin-5-yl)-4,5-dimethyl-1H-pyrazole-3-carboxamide (P-2194); N-(2-(1-(azetidin-3-yl)-3-methyl-1H-pyrazol-4-yl)-1H-pyrrolo[2,3-b]pyridin-5-yl)-4,5-dimethyl-1H-pyrazole-3-carboxamide (P-2195); 4,5-dimethyl-N-(2-(5-methyl-1-(oxetan-3-yl)-1H-pyrazol-4-yl)-1H-pyrrolo[2,3-b]pyridin-5-yl)-1H-pyrazole-3-carboxamide (P-2196); N-(2-(1-(azetidin-3-yl)-5-methyl-1H-pyrazol-4-yl)-1H-pyrrolo[2,3-b]pyridin-5-yl)-4,5-dimethyl-1H-pyrazole-3-carboxamide (P-2197); 4,5-dimethyl-N-(2-(5-methyl-1-(piperidin-4-yl)-1H-pyrazol-4-yl)-1H-pyrrolo[2,3-b]pyridin-5-yl)-1H-pyrazole-3-carboxamide (p-2198); N-(2-(1-(1-acetylpiperidin-4-yl)-5-methyl-1H-pyrazol-4-yl)-1H-pyrrolo[2,3-b]pyridin-5-yl)-4,5-dimethyl-1H-pyrazole-3-carboxamide (P-2199); N-(2-(1-(1-(cyclopropanecarbonyl)piperidin-4-yl)-5-methyl-1H-pyrazol-4-yl)-1H-pyrrolo[2,3-b]pyridin-5-yl)-4,5-dimethyl-1H-pyrazole-3-carboxamide (P-2200); 4,5-dimethyl-N-(2-(3-methyl-1-(piperidin-4-yl)-1H-pyrazol-4-yl)-1H-pyrrolo[2,3-b]pyridin-5-yl)-1H-pyrazole-3-carboxamide (P-2201); N-(2-(1-(1-acetylpiperidin-4-yl)-3-methyl-1H-pyrazol-4-yl)-1H-pyrrolo[2,3-b]pyridin-5-yl)-4,5-dimethyl-1H-pyrazole-3-carboxamide (P-2202); and N-(2-(1-(1-(cyclopropanecarbonyl)piperidin-4-yl)-3-methyl-1H-pyrazol-4-yl)-1H-pyrrolo[2,3-b]pyridin-5-yl)-4,5-dimethyl-1H-pyrazole-3-carboxamide (P-2203) can be prepared according to the synthetic protocols set forth in Scheme 20 and Example 20.

Example 21

Preparation of N-[2-(4-fluorophenyl)-1H-pyrrolo[2,3-b]pyridin-5-yl]-3,4-dimethyl-1H-pyrazole-5-carboxamide (P-2024)

Scheme 21.

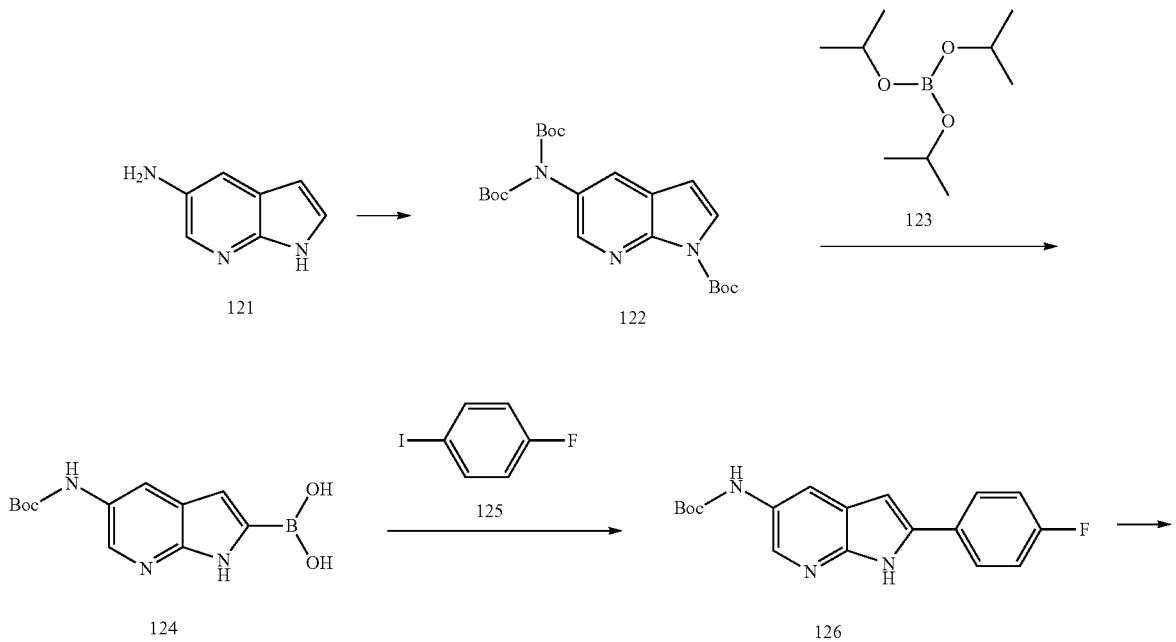

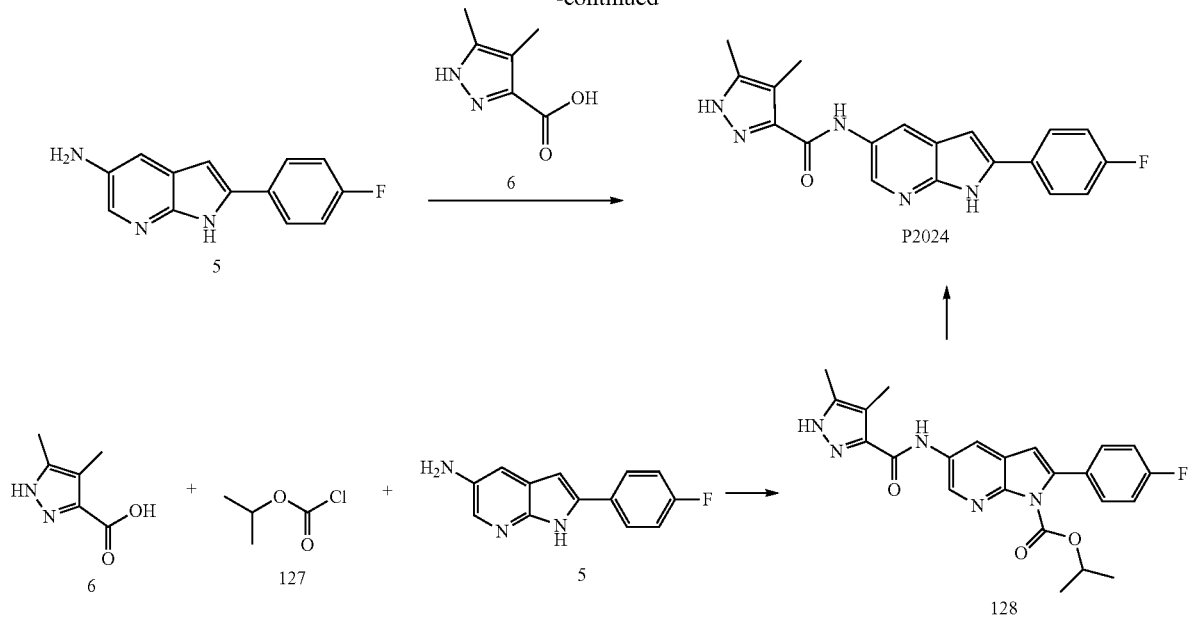

Step 1—Preparation of tert-butyl 5-[bis(tert-butoxycarbonyl)amino]pyrrolo[2,3-b]pyridine-1-carboxylate 122: Into a round bottom flask were placed 1H-pyrrolo[2,3-b]pyridin-5-amine 121 (1 g, 7.51 mmol), di-tert-butyldicarbonate (6.5 g, 29.78 mmol), 4-dimethylaminopyridine (0.03 g, 0.23 mmol) and N,N-diisopropylethylamine (5 ml, 28.71 mmol) in tetrahydrofuran (20 mL). The reaction was stirred at room temperature overnight, then concentrated. The residue was mixed with water and brine and extracted with ethyl acetate. The organic layers were dried over anhydrous sodium sulfate and evaporated to dryness. The resulting solid was purified by silica gel chromatography to provide compound 122 (0.73 g, 22%) MS ESI [M+H+]+=434.3. $^1$H NMR and mass spectroscopy data were consistent with the desired product.

Step 2—Preparation of [5-(tert-butoxycarbonylamino)-1H-pyrrolo[2,3-b]pyridin-2-yl]boronic acid 124: To an ice cold solution of tert-butyl 5-[bis(tert-butoxycarbonyl)amino]pyrrolo[2,3-b]pyridine-1-carboxylate 122 (0.38 g, 0.88 mmol) and tryisopropylborate 123 (2 ml, 8.67 mmol) in tetrahydrofuran (5 mL) under an atmosphere of nitrogen was added a solution of 2M lithium diisopropylamide (3.6 ml). The reaction mixture was stirred at 0° C. for one hour, after which the reaction was let stirred at room temperature for an additional hour. The mixture was quenched with 2N HCl and placed on silica and concentrated to dryness. The crude was purified by silica gel chromatography eluting with a gradient of methanol: methylene chloride (0-30%) to provide compound 124 (0.1 g, 41%). Analytical data were consistent with the desired product.

Step 3—Preparation of tert-butyl N-[2-(4-fluorophenyl)-1H-pyrrolo[2,3-b]pyridin-5-yl]carbamate (126): Into a microwave vessel were placed [5-(tert-butoxycarbonylamino)-1H-pyrrolo[2,3-b]pyridin-2-yl]boronic acid 124 (0.1 g, 0.36 mmol), 1-fluoro-4-iodo-benzene (0.09 g, 0.4 mmol), [1,1'-bis(diphenylphosphino)ferrocene]dichloropalladium(II) (50 mg, 0.06 mmol) and 1,4 Dioxane (4 mL). Potassium carbonate (1M aqueous solution, 1 mL) was added and the reaction was irradiated at 80° C. for 10 minutes. The mixture was placed on silica and purified with silica gel chromatography eluting with a gradient of ethyl acetate: hexanes (20-100%) to provide compound 126 (0.02 g, 17%). MS ESI [M+H+]+=327.8. Analytical data were consistent with the desired product.

Step 4—Preparation of 2-(4-fluorophenyl)-1H-pyrrolo[2,3-b]pyridin-5-amine 5: To tert-butyl N-[2-(4-fluorophenyl)-1H-pyrrolo[2,3-b]pyridin-5-yl]carbamate 125 (0.02 g, 0.06 mmol) in methylene chloride (2 mL) was added hydrochloric acid in 1,4-dioxane (4 mL, 4N) and aqueous hydrochloric acid (50 µL, 12N). The reaction was stirred at room temperature for two hours and concentrated. The residue was dried under vacuum to provide crude compound 5, which was used without purification. MS ESI [M+H+]+=227.7. Analytical data were consistent with the desired product.

Step 5—Preparation of N-[2-(4-fluorophenyl)-1H-pyrrolo[2,3-b]pyridin-5-yl]-4,5-dimethyl-1H-pyrazole-3-carboxamide (P2034): To a solution of 3,4-dimethyl-1H-pyrazole-5-carboxylic acid 6 (0.03 g, 0.21 mmol) in dimethylacetamide (2 mL) was added benzotriazol-1-yl-oxytripyrrolidinophosphonium hexafluorophosphate (0.11 g, 0.21 mmol) and the mixture was stirred at room temperature for 30 minutes. 2-(4-Fluorophenyl)-1H-pyrrolo[2,3-b]pyridin-5-amine hydrochloride 5 (16 mg, 0.06 mmol) was added, followed by N,N-diisopropylethylamine (0.5 ml, 2.89 mmol). The reaction mixture was stirred at room temperature for an hour and purified by preparative HPLC to provide compound (P-2034) (5 mg, 21%). MS ESI [M+H+]+=350.15. $^1$H NMR and mass spectroscopy data were consistent with the desired product.

Step 6—Preparation of isopropyl 5-[(4,5-dimethyl-1H-pyrazole-3-carbonyl)amino]-2-(4-fluorophenyl)pyrrolo[2,3-b]pyridine-1-carboxylate (128): To 4,5-dimethyl-1H-pyrazole-3-carboxylic acid 6 (69.3 mg, 0.49 mmol) in N-methylmorpholine (2 mL) at −20° C. was added isopropyl carbonochloridate 127 (0.5 ml, 1.0 M in toluene, 0.5 mmol) dropwise. The mixture was stirred at −20° C. for 10 minutes. To this mixture was then added 2-(4-fluorophenyl)-1H-pyrrolo[2,3-b]pyridin-5-amin 5 (105 mg, 0.46 mmol)N-methylmorpholine (2 mL). The reaction mixture was stirred −20° C. for 20 minutes and was allowed to warm up to room temperature. It was then stirred at room temperature overnight. Solvent was removed and the residue was partitioned between ethyl acetate and saturated sodium bicarbonate. The organic layers were collected, washed with brine, and dried under sodium sulfate. After removal of drying agent and solvent, the residue was purified by column chromatography to provide compound 128 (32 mg, 15.9%). MS ESI [M+H+]+=435.90. $^1$H NMR and MS were consistent with the desired product.

Step 7—Preparation of N-[2-(4-fluorophenyl)-1H-pyrrolo[2,3-b]pyridin-5-yl]-4,5-dimethyl-1H-pyrazole-3-carboxamide (P-2034): To isopropyl 5-[(4,5-dimethyl-1H-pyrazole-3-carbonyl)amino]-2-(4-fluorophenyl)pyrrolo[2,3-b]pyridine-1-carboxylate 128 (20 mg, 0.046 mmol) in methanol (2 mL) was added potassium hydroxide (8 mg, 0.14 mmol). The reaction mixture was stirred at room temperature overnight, concentrated, placed in water and brine and extracted with ethyl acetate. The organic layers were dried over anhydrous sodium sulfate. After removal of drying agent and solvent, the residue was purified by silica gel chromatography to provide compound (P-2034) (12 mg, 74%). MS ESI [M+H+]+=350.1.

Example 22

Preparation of N-[2-(2-cyclopropyl-4-pyridyl)-1H-pyrrolo[2,3-b]pyridin-5-yl]-4,5-dimethyl-1H-pyrazole-3-carboxamide (P-2108)

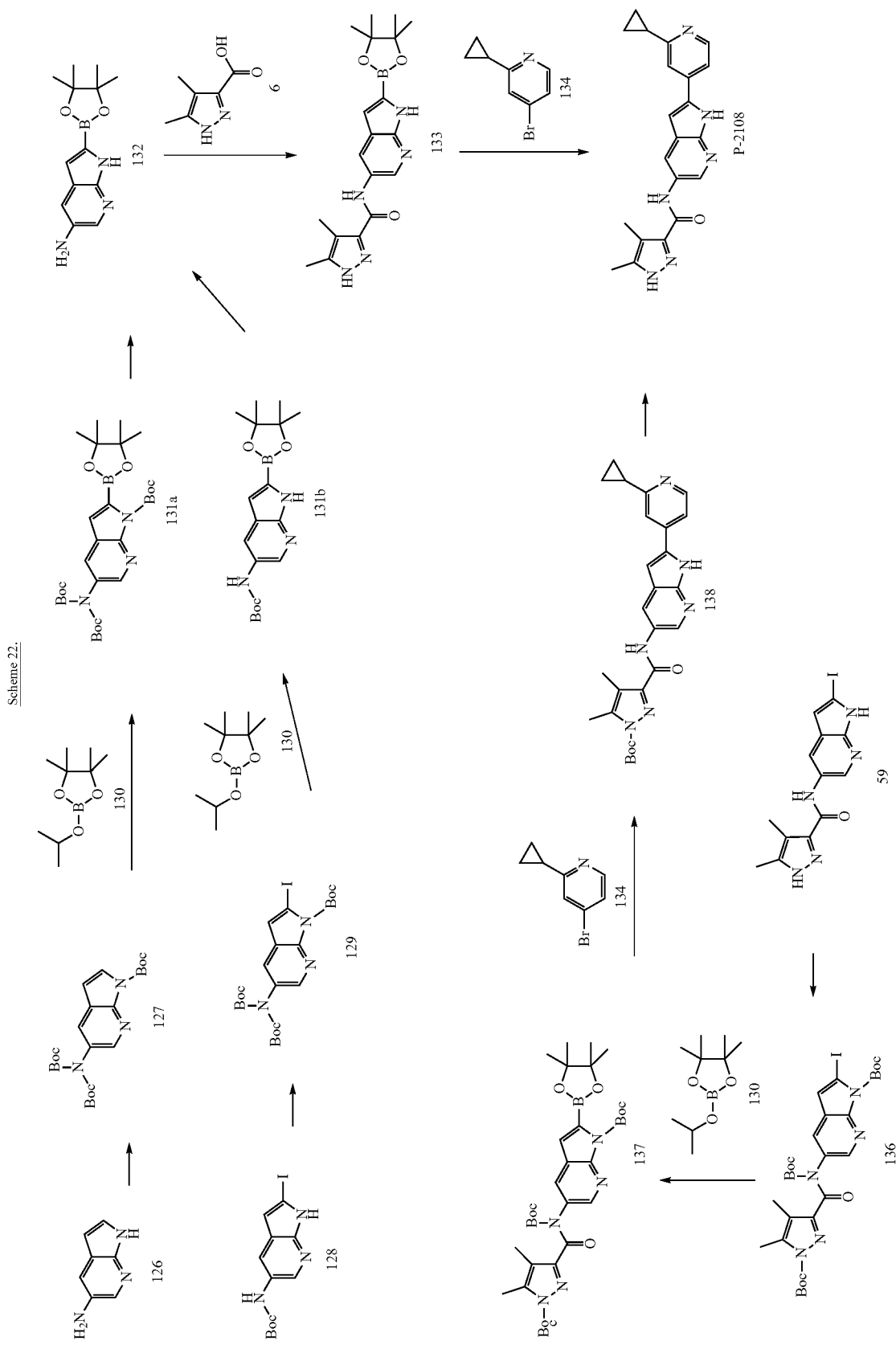

Step 1—Synthesis of tert-butyl 5-[bis(tert-butoxycarbonyl)amino]-2-iodo-pyrrolo[2,3-b]pyridine-1-carboxylate (127): To a round bottom flask were placed 1H-pyrrolo[2,3-b]pyridin-5-amine 126 (1 g, 7.51 mmol), di-tert-butyldicarbonate (6.5 g, 29.78 mmol), 4-dimethylaminopyridine (0.03 g, 0.23 mmol) and N,N-diisopropylethylamine (5 ml, 28.71 mmol) in tetrahydrofuran (20 mL). The reaction mixture was stirred at room temperature overnight and concentrated. The residue was partitioned between ethyl acetate and water. The organic layers were collected, washed with brine, and dried with sodium sulfate. After removal of drying agent and solvent, the residue was purified by column chromatography on silica gel eluting with a gradient of ethyl acetate: hexanes to provide compound 127 (0.73 g, 22%). MS (ESI) [M+H]+=434.3. $^1$H NMR and mass spectroscopy data were consistent with the desired product.

Step 2—Synthesis of tert-butyl 5-[bis(tert-butoxycarbonyl)amino]-2-(4,4,5,5-tetramethyl-1,3,2-dioxaborolan-2-yl)pyrrolo[2,3-b]pyridine-1-carboxylate (131a): To an ice cold tert-butyl 5-[bis(tert-butoxycarbonyl)amino]-2-iodo-pyrrolo[2,3-b]pyridine-1-carboxylate 127 (0.1 g, 0.23 mmol) and isopropoxy-(4,4,5,5-tetramethyl-1,3-dioxolan-2-yl)borane (0.091 g, 0.49 mmol) in tetrahydrofuran (3 ml) was added lithium diisopropylamide (2 M, 0.23 ml, 0.46 mmol). The mixture was stirred at 0° C. for one hour. The reaction was quenched with aqueous hydrochloric acid. The reaction mixture was poured into water and extracted with dichloromethane. Organic layer was washed with brine and dried over sodium sulfate. After removal of solvent, the residue was purified with silica gel column chromatography to provide compound 131a. MS (ESI) [M+H]+=559.80. Analytical data were consistent with the desired product.

Step 3—Synthesis of 2-(4,4,5,5-tetramethyl-1,3,2-dioxaborolan-2-yl)-1H-pyrrolo[2,3-b]pyridin-5-amine (132): To tert-butyl 5-[bis(tert-butoxycarbonyl)amino]-2-(4,4,5,5-tetramethyl-1,3,2-dioxaborolan-2-yl)pyrrolo[2,3-b]pyridine-1-carboxylate 131a (1 eq.) in tetrahydrofuran (THF) was added hydrochloric acid (1 to 10 eq.). The reaction mixture was stirred at room temperature overnight. Solvent was removed and the residue was partitioned between ethyl acetate and saturated sodium bicarbonate. The organic layer was washed with brine and dried over sodium sulfate. After removal of solvent, the residue was dried under vacuum to provide compound 132.

Step 4—Synthesis of tert-butyl 5-[bis(tert-butoxycarbonyl)amino]-2-iodo-pyrrolo[2,3-b]pyridine-1-carboxylate (129): Into a round bottom flask were placed tert-butyl N-(2-iodo-1H-pyrrolo[2,3-b]pyridin-5-yl)carbamate 128 (0.8 g, 2.23 mmol), di-tert-butyldicarbonate (1 g, 4.58 mmol), 4-dimethylaminopyridine (0.01 g, 0.08 mmol) and N,N-diisopropylethylamine (1 ml, 5.74 mmol) in tetrahydrofuran (20 mL). The reaction mixture was stirred at room temperature overnight. The mixture was concentrated and the residue was partitioned between ethyl acetate and water. The organic layers were collected, washed with brine, and dried under sodium sulfate. After removal of drying agent and solvent, the residue was dried under vacuum to provide compound 129, which was used for the subsequent reaction without purification. MS (ESI) [M+H]+=560.25.

Step 5—Synthesis of tert-butyl N-[2-(4,4,5,5-tetramethyl-1,3,2-dioxaborolan-2-yl)-1H-pyrrolo[2,3-b]pyridin-5-yl]carbamate (131b): To tert-butyl 5-[bis(tert-butoxycarbonyl)amino]-2-iodo-pyrrolo[2,3-b]pyridine-1-carboxylate 129 (0.1 g, 0.23 mmol) in tetrahydrofuran (3 ml) was added butyl lithium (1.6 M, 0.6 ml, 0.9 mmol). The mixture was stirred at room temperature for 20 minutes. To this mixture was added isopropoxy-(4,4,5,5-tetramethyl-1,3-dioxolan-2-yl)borane 130 (0.1 g, 0.53 mmol) in tetrahydrofuran (2 ml) slowly. The resulting mixture was stirred at room temperature for three hours and then overnight. The reaction mixture was poured into water, and extracted with ethyl acetate. The organic layer was washed with brine, dried over sodium sulfate. After removal of solvent, the residue was purified with silica gel column chromatography to provide compound 131 as off-white solid (16 mg, 16%). MS (ESI) [M+H]+=359.9.

Step 6—Synthesis of 2-(4,4,5,5-tetramethyl-1,3,2-dioxaborolan-2-yl)-1H-pyrrolo[2,3-b]pyridin-5-amine (132): To tert-butyl N-[2-(4,4,5,5-tetramethyl-1,3,2-dioxaborolan-2-yl)-1H-pyrrolo[2,3-b]pyridin-5-yl]carbamate 131 (14 mg, 0.04 mmol) in tetrahydrofuran (1 ml) was added hydrochloric acid in dioxane (0.5 mL, 4 M). The reaction mixture was stirred at room temperature overnight. Solvent was removed and the residue was partitioned between an appropriate solvent (ethyl acetate or dichloromethane), water and saturated sodium bicarbonate. The organic layer is collected and dried over sodium sulfate. After removal of solvent, the residue was dried under vacuum to provide crude compound 132 as a tan solid (8 mg, 67%), which was used for the subsequent reaction without purification. MS (ESI) [M+H]+=259.8.

Step 7—Synthesis of 4,5-dimethyl-N-[2-(4,4,5,5-tetramethyl-1,3,2-dioxaborolan-2-yl)-1H-pyrrolo[2,3-b]pyridin-5-yl]-1H-pyrazole-3-carboxamide (133): To 3,4-dimethyl-1H-pyrazole-5-carboxylic acid 6 (1 eq.) in an appropriate amount of solvent such as dimethylacetamide, tetrahydrofuran, acetonitrile, or N,N-dimethylformamide are added benzotriazol-1-yl-oxytripyrrolidinophosphonium hexafluorophosphate (1 eq.) or o-benzotriazole-N,N,N',N'-tetramethyl-uronium-hexafluoro-phosphate (1 eq.) and N-hydroxybenzotriazole (1 eq.), followed by N,N-diisopropylethylamine (1 eq.) or triethylamine (1 eq.). The mixture is stirred at room temperature from 30 minutes to a few hours. To this mixture is added 2-(4,4,5,5-tetramethyl-1,3,2-dioxaborolan-2-yl)-1H-pyrrolo[2,3-b]pyridin-5-amine 132 (1 eq.) and N,N-diisopropylethylamine (1 eq.) or triethylamine (1 eq.). The reaction mixture is stirred at room temperature from one hour to 2-3 days. Heating can be used to if needed. The reaction mixture is partitioned between an organic solvent (including, but not limiting to, hexanes, benzene, ethyl acetate, and dichloromethane) and water. The organic layer is collected and dried over sodium sulfate. After removal of drying agent and solvent, the residue is purified by chromatography to produce compound 133.

Step 8—Synthesis of N-[2-(2-cyclopropyl-4-pyridyl)-1H-pyrrolo[2,3-b]pyridin-5-yl]-4,5-dimethyl-1H-pyrazole-3-carboxamide (P-2108): To a mixture of 4,5-dimethyl-N-[2-(4,4,5,5-tetramethyl-1,3,2-dioxaborolan-2-yl)-1H-pyrrolo[2,3-b]pyridin-5-yl]-1H-pyrazole-3-carboxamide 133 (1 eq.), 4-bromo-2-cyclopropyl-pyridine 134 (1 eq.), [1,1'-bis(diphenylphosphino)ferrocene]dichloropalladium(ii) or tetrakis(triphenylphosphine)palladium(O) (0.1 eq.) in an appropriate amount of solvent (e.g. acetonitrile or tetrahydrofuran, or dioxane) is added an appropriate amount of aqueous potassium carbonate solution (1M). The reaction mixture is irradiated in microwave at a temperature ranging from 90° C. to 180° C. for about 10 minutes to 2-3 hours. The reaction mixture is partitioned between water and an organic solvent (including, but not limiting to, hexanes, ethyl acetate and dichloromethane). The organic layer is collected, washed by brine and dried under sodium sulfate. After removal of drying agent and solvent, the residue was purified by chromatography to provide compound 135.

Step 9—Synthesis of tert-butyl 5-[tert-butoxycarbonyl-(1-tert-butoxycarbonyl-4,5-dimethyl-pyrazole-3-carbonyl)amino]-2-iodo-pyrrolo[2,3-b]pyridine-1-carboxylate (136): Into a round bottom flask were placed N-(2-iodo-1H-pyrrolo[2,3-b]pyridin-5-yl)-3,4-dimethyl-1H-pyrazole-5-carboxamide 59 (0.5 g, 1.31 mmol), di-tert-Butyldicarbonate (1.15 g, 5.25 mmol), and 4-dimethylaminopyridine (0.02 g, 0.13 mmol) in tetrahydrofuran (18 ml). N,N-diisopropylethylamine (0.8 ml, 4.59 mmol) was added and the mixture was stirred at room temperature overnight. The reaction mixture was poured into water and extracted with ethyl acetate. The organic layer was washed by brine and dried under sodium sulfate. After removal of drying agent and solvent, the residue was purified by silica gel column chromatography (0-10% methanol/dichloromethane, 12G) to provide compound 136 as a white brittle foam (700 mg. 78.3%). MS (ESI) [M+H+]=682.4. $^1$H NMR and mass spectroscopy data were consistent with the structure of the desired product.

Step 10—Synthesis of tert-butyl 5-[tert-butoxycarbonyl-(1-tert-butoxycarbonyl-4,5-dimethyl-pyrazole-3-carbonyl)amino]-2-(4,4,5,5-tetramethyl-1,3,2-dioxaborolan-2-yl)pyrrolo[2,3-b]pyridine-1-carboxylate (137): To tert-butyl 5-[tert-butoxycarbonyl-(1-tert-butoxycarbonyl-4,5-dimethyl-pyrazole-3-carbonyl)amino]-2-iodo-pyrrolo[2,3-b]pyridine-1-carboxylate 136 (50 mg, 0.073 mmol) and isopropoxy-(4,4,5,5-tetramethyl-1,3-dioxolan-2-yl)borane 130 (0.03 g, 0.15 mmol) in tetrahydrofuran (3 ml) at −20° C. was added lithium diisopropylamide (2 M, 0.15 ml, 0.3 mmol) in tetrahydrofuran (1 ml). The mixture was allowed to warm up to room temperature slowly and stirred at room temperature overnight. The reaction was quenched with aqueous hydrochloric acid. The mixture was poured into water, and extracted with ethyl acetate. The organic layer was washed with brine and dried over sodium sulfate. After removal of solvent, the residue was purified with silica gel column chromatography to provide compound 137. MS (ESI) [M+H+]=682.5.

Step 11—Synthesis of tert-butyl 3-[[2-(2-cyclopropyl-4-pyridyl)-1H-pyrrolo[2,3-b]pyridin-5-yl]carbamoyl]-4,5-dimethyl-pyrazole-1-carboxylate (138): To a mixture of tert-butyl 5-[tert-butoxycarbonyl-(1-tert-butoxycarbonyl-4,5-dimethyl-pyrazole-3-carbonyl)amino]-2-(4,4,5,5-tetramethyl-1,3,2-dioxaborolan-2-yl)pyrrolo[2,3-b]pyridine-1-carboxylate 137 (1 eq.), 4-bromo-2-cyclopropyl-pyridine 134 (1 eq.), [1,1'-bis(diphenylphosphino)ferrocene]dichloropalladium(ii) or tetrakis(triphenylphosphine)palladium(0) (0.1 eq.) in an appropriate amount of solvent (e.g. acetonitrile or tetrahydrofuran, or dioxane) is added an appropriate amount of aqueous potassium carbonate solution (1M). The reaction mixture is irradiated in microwave at temperature ranging from 90 to 180° C. for 10 minutes to 2-3 hours. The reaction mixture is partitioned between water and an appropriate solvent (ethyl acetate or dichloromethane). The organic layer is collected, washed with brine and dried under sodium sulfate. After removal of drying agent and solvent, the residue is purified by chromatography to provide compound 138.

Step 12—Synthesis of N-[2-(2-cyclopropyl-4-pyridyl)-1H-pyrrolo[2,3-b]pyridin-5-yl]-4,5-dimethyl-1H-pyrazole-3-carboxamide (P-2108): To tert-butyl 3-[[2-(2-cyclopropyl-4-pyridyl)-1H-pyrrolo[2,3-b]pyridin-5-yl]carbamoyl]-4,5-dimethyl-pyrazole-1-carboxylate 138 (1 eq.) in an appropriate amount of tetrahydrofuran is added hydrochloric acid (1 to 10 eq.). The reaction mixture is stirred at room temperature overnight. Solvent was removed and the residue is partitioned between an appropriate solvent (ethyl acetate or dichloromethane), water and saturated sodium bicarbonate. The organic layer is collected, washed with brine, and dried over sodium sulfate. After removal of drying agent and solvent, the residue is purified by chromatography to provide compound 135.

The exemplary compounds N-(2-(2-(cyclopropylamino)pyridin-4-yl)-1H-pyrrolo[2,3-b]pyridin-5-yl)-4,5-dimethyl-1H-pyrazole-3-carboxamide (P-2204); N-(2-(3-chloro-2-(cyclopropanecarboxamido)pyridin-4-yl)-1H-pyrrolo[2,3-b]pyridin-5-yl)-4,5-dimethyl-1H-pyrazole-3-carboxamide (P-2205); N-(2-(2-(cyclopropanecarboxamido)pyridin-4-yl)-1H-pyrrolo[2,3-b]pyridin-5-yl)-4,5-dimethyl-1H-pyrazole-3-carboxamide (P-2206); N-(2-(2-(1-(cyclopropanecarbonyl)piperidin-4-yl)pyridin-4-yl)-1H-pyrrolo[2,3-b]pyridin-5-yl)-4,5-dimethyl-1H-pyrazole-3-carboxamide (P-2207); 4,5-dimethyl-N-(2-(2-(pyrrolidin-1-yl)pyridin-4-yl)-1H-pyrrolo[2,3-b]pyridin-5-yl)-1H-pyrazole-3-carboxamide (P-2208); 4,5-dimethyl-N-(2-(2-(piperidin-1-yl)pyridin-4-yl)-1H-pyrrolo[2,3-b]pyridin-5-yl)-1H-pyrazole-3-carboxamide (P-2209); 4,5-dimethyl-N-(2-(2-(4-methylpiperidin-1-yl)pyridin-4-yl)-1H-pyrrolo[2,3-b]pyridin-5-yl)-1H-pyrazole-3-carboxamide (P-2210); 4,5-dimethyl-N-(2-(2-(piperidin-4-yl)pyridin-4-yl)-1H-pyrrolo[2,3-b]pyridin-5-yl)-1H-pyrazole-3-carboxamide (P-2211); N-(2-(2-(4-hydroxypiperidin-1-yl)pyridin-4-yl)-1H-pyrrolo[2,3-b]pyridin-5-yl)-4,5-dimethyl-1H-pyrazole-3-carboxamide (P-2212); and N-(2-(2-(3-hydroxypiperidin-1-yl)pyridin-4-yl)-1H-pyrrolo[2,3-b]pyridin-5-yl)-4,5-dimethyl-1H-pyrazole-3-carboxamide (P-2213) can be prepared according to the synthetic protocols set forth in Example 22 and Scheme 22.

Example 23

Preparation of 4,5-dimethyl-N-[2-[2-(4-methylsulfonylpiperazin-1-yl)-4-pyridyl]-1H-pyrrolo[2,3-b]pyridin-5-yl]-1H-pyrazole-3-carboxamide (P-2189)

Scheme 23.

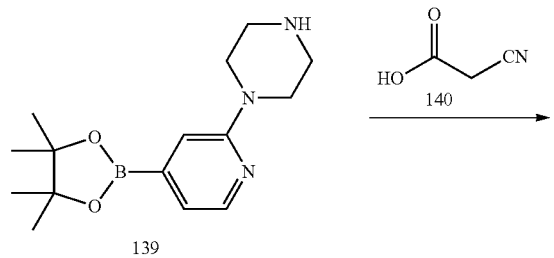

139

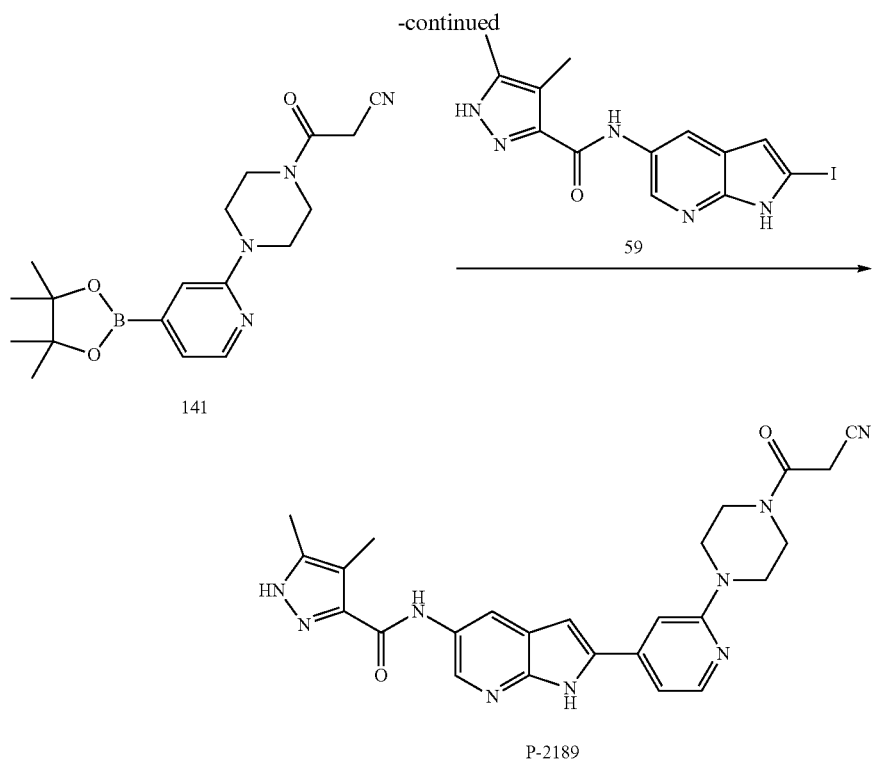

Step 1—Synthesis of 3-oxo-3-[4-[4-(4,4,5,5-tetramethyl-1,3,2-dioxaborolan-2-yl)-2-pyridyl]piperazin-1-yl]propanenitrile (141): To 2-cyanoacetic acid 140 (0.1 g, 1.18 mmol) in tetrahydrofuran (3 ml) was added O-benzotriazole-N,N,N',N'-tetramethyl-uronium-hexafluoro-phosphate (0.48 ml, 1.32 mmol) and N,N-diisopropylethylamine (0.4 ml, 2.31 mmol). The reaction mixture was stirred at room temperature for 30 minutes. To the mixture was added 1-[4-(4,4,5,5-tetramethyl-1,3,2-dioxaborolan-2-yl)-2-pyridyl]piperazine 139 (0.2 g, 0.69 mmol) in tetrahydrofuran (1 ml). The reaction mixture was stirred at room temperature overnight and concentrated. The residue was partitioned between ethyl acetate and water. The organic layers were collected, washed with brine, and dried under sodium sulfate. After removal of drying agent and solvent, the residue was dried under vacuum to provide crude compound 141 (0.35 g), which was used for the subsequent reaction without purification.

Step 2—Synthesis of 4,5-dimethyl-N-[2-[2-(4-methylsulfonylpiperazin-1-yl)-4-pyridyl]-1H-pyrrolo[2,3-b]pyridin-5-yl]-1H-pyrazole-3-carboxamide (P-2189):To N-(2-iodo-1H-pyrrolo[2,3-b]pyridin-5-yl)-3,4-dimethyl-1H-pyrazole-5-carboxamide 59 (0.1 g, 0.26 mmol) in acetonitrile (3 ml) was added 3-oxo-3-[4-[4-(4,4,5,5-tetramethyl-1,3,2-dioxaborolan-2-yl]-2-pyridyl]piperazin-1-yl]propanenitrile 141 (0.2 g, crude), [1,1'-bis(diphenylphosphino)ferrocene]dichloropalladium(ii) (15 mg, 0.019 mmol), and aqueous potassium carbonate (1 ml, 1 M). The reaction mixture was irradiated in microwave at 130° C. for 30 minutes. The residue was partitioned between ethyl acetate and water. The organic layers were collected, washed with brine, and dried under sodium sulfate. After removal of drying agent and solvent, the residue was purified by preparative HPLC to provide compound (P-2189) as a yellow solid (35 mg, 25%). MS (ESI) [M+H+]−+=484.30. $^1$H NMR and mass spectroscopy data were consistent with the desired product.

Exemplary compounds 3,4-dimethyl-N-[2-[2-(4-methylsulfonylpiperazin-1-yl)-4-pyridyl]-1H-pyrrolo[2,3-b]pyridin-5-yl]-1H-pyrazole-5-carboxamide (P-2186) and N-[2-[2-[4-(cyclopropanecarbonyl)piperazin-1-yl]-4-pyridyl]-1H-pyrrolo[2,3-b]pyridin-5-yl]-3,4-dimethyl-1H-pyrazole-5-carboxamide (P-2187) were prepared according to the synthetic protocols set forth in Example 23 and Scheme 23. $^1$HNMR and mass spectroscopy data were consistent with the structures of the compounds. The compounds N-(2-(2-(4-acetylpiperazin-1-yl)pyridin-4-yl)-1H-pyrrolo[2,3-b]pyridin-5-yl)-4,5-dimethyl-1H-pyrazole-3-carboxamide (P-2214) and 4,5-dimethyl-N-(2-(2-(4-(3-methylbut-2-enoyl)piperazin-1-yl)pyridin-4-yl)-1H-pyrrolo[2,3-b]pyridin-5-yl)-1H-pyrazole-3-carboxamide (P-2215) can also be prepared via the synthetic routes outlined in Example 23 and Scheme 23.

Example 24

Preparation of N-cyclopropyl-4-[5-[(3,4-dimethyl-1H-pyrazole-5-carbonyl)amino]-1H-pyrrolo[2,3-b]pyridin-2-yl]pyridine-2-carboxamide (P-2175)

Scheme 24.

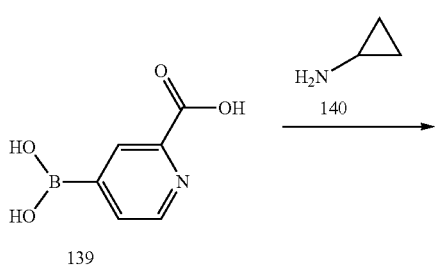

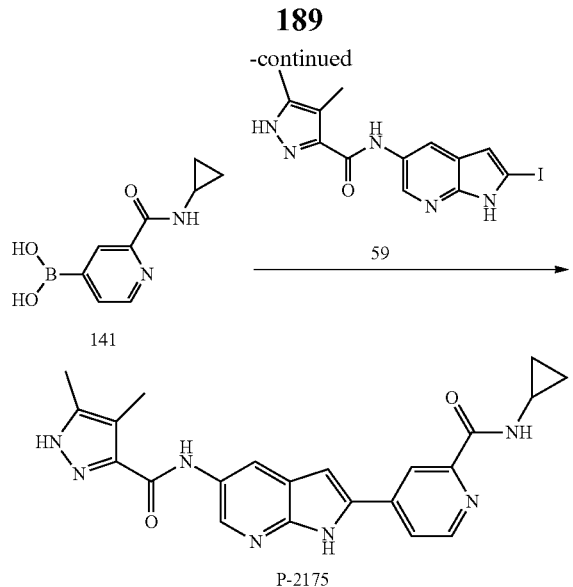

Step 1—Preparation of [2-(cyclopropylcarbamoyl)-4-pyridyl]boronic acid (141): To a round bottom flask were added 4-boronopyridine-2-carboxylic acid 139 (120 mg, 0.72 mmol), 1-(3-dimethylaminopropyl)-3-ethylcarbodiimide hydrochloride (0.28 g, 1.44 mmol), and 1-hydroxybenzotriazole (0.19 g, 1.44 mmol) in dimethylacetamide (3 ml). The mixture was stirred at room temperature for 40 minutes, then added cyclopropanamine (0.06 ml, 1.44 mmol) followed by N,N-diisopropylethylamine (0.25 ml, 1.44 mmol). The reaction mixture was stirred at room temperature for three hours, poured into water and extracted with ethyl acetate. The organic layer was washed by brine and dried under sodium sulfate. After removal of drying agent and solvent, the residue was dried under vacuum to provide compound 141 (60 mg, 40.5%). The compound was used for the subsequent reaction without purification.

Step 2—Preparation of N-cyclopropyl-4-[5-[(3,4-dimethyl-1H-pyrazole-5-carbonyl)amino]-1H-pyrrolo[2,3-b]pyridin-2-yl]pyridine-2-carboxamide (P-2175): Into a microwave vessel were placed N-(2-iodo-1H-pyrrolo[2,3-b]pyridin-5-yl)-3,4-dimethyl-1H-pyrazole-5-carboxamide 59 (60 mg, 0.16 mmol), [2-(cyclopropylcarbamoyl)-4-pyridyl]boronic acid 141 (0.06 g, 0.31 mmol) [1,1'-bis(diphenylphosphino)ferrocene]dichloropalladium(ii) (0.01 g, 0.01 mmol) and 1,4 dioxane (3 mL). To the mixture was further added aqueous potassium carbonate solution (0.47 ml, 1M) and the reaction was irradiated in microwave at 130° C. for 30 minutes. Additional equivalences of [2-(cyclopropylcarbamoyl)-4-pyridyl]boronic acid, [1,1'-bis(diphenylphosphino)ferrocene]dichloropalladium(II), and aqueous potassium carbonate solution (0.47 ml, 1M) were added and the reaction mixture was irradiated in microwave at 135° C. for another 30 minutes. The reaction mixture was neutralized with 1N aqueous hydrochloric acid, poured into water and extracted with ethyl acetate. The organic layer was washed by brine and dried under sodium sulfate. After removal of drying agent and solvent, the residue was purified by silica gel column chromatography and triturated with methanol to afford compound (P-2175) as a white solid (5.5 mg, 8.4%). MS (ESI) [M+H+]$^+$=415.85. $^1$H NMR and mass spectroscopy data were consistent with the structure of the compound.

Exemplary compounds 4,5-dimethyl-N-(2-(2-(morpholine-4-carbonyl)pyridin-4-yl)-1H-pyrrolo[2,3-b]pyridin-5-yl)-1H-pyrazole-3-carboxamide (P-2216); 4,5-dimethyl-N-(2-(2-(4-methylpiperazine-1-carbonyl)pyridin-4-yl)-1H-pyrrolo[2,3-b]pyridin-5-yl)-1H-pyrazole-3-carboxamide(P-2217); 4,5-dimethyl-N-(2-(2-(pyrrolidine-1-carbonyl)pyridin-4-yl)-1H-pyrrolo[2,3-b]pyridin-5-yl)-1H-pyrazole-3-carboxamide (P-2218); 4,5-dimethyl-N-(2-(2-(thiomorpholine-4-carbonyl)pyridin-4-yl)-1H-pyrrolo[2,3-b]pyridin-5-yl)-1H-pyrazole-3-carboxamide (P-2219); 4-(5-(4,5-dimethyl-1H-pyrazole-3-carboxamido)-1H-pyrrolo[2,3-b]pyridin-2-yl)-N-(2-methoxyethyl)picolinamide (P-2220); 4-(5-(4,5-dimethyl-1H-pyrazole-3-carboxamido)-1H-pyrrolo[2,3-b]pyridin-2-yl)-N-(2-(dimethylamino)ethyl)picolinamide (P-2221); 4-(5-(4,5-dimethyl-1H-pyrazole-3-carboxamido)-1H-pyrrolo[2,3-b]pyridin-2-yl)-N-(2-methoxyethyl)picolinamide (P-2222); 4-(5-(4,5-dimethyl-1H-pyrazole-3-carboxamido)-1H-pyrrolo[2,3-b]pyridin-2-yl)-N-methoxypicolinamide (P-2223); 4-(5-(4,5-dimethyl-1H-pyrazole-3-carboxamido)-1H-pyrrolo[2,3-b]pyridin-2-yl)-N,N-dimethylpicolinamide (P-2224); 4-(5-(4,5-dimethyl-1H-pyrazole-3-carboxamido)-1H-pyrrolo[2,3-b]pyridin-2-yl)-N-(2-morpholinoethyl)picolinamide (P-2225); 4-(5-(4,5-dimethyl-1H-pyrazole-3-carboxamido)-1H-pyrrolo[2,3-b]pyridin-2-yl)-N-(2-(4-methylpiperazin-1-yl)ethyl)picolinamide (P-2226); N-(2-cyanoethyl)-4-(5-(4,5-dimethyl-1H-pyrazole-3-carboxamido)-1H-pyrrolo[2,3-b]pyridin-2-yl)picolinamide (P-2227); 4-(5-(4,5-dimethyl-1H-pyrazole-3-carboxamido)-1H-pyrrolo[2,3-b]pyridin-2-yl)-N-isobutylpicolinamide (P-2228); 4-(5-(4,5-dimethyl-1H-pyrazole-3-carboxamido)-1H-pyrrolo[2,3-b]pyridin-2-yl)-N-isopropylpicolinamide (P-2229); and 4-(5-(4,5-dimethyl-1H-pyrazole-3-carboxamido)-1H-pyrrolo[2,3-b]pyridin-2-yl)-N,N-diethylpicolinamide (P-2230) can be prepared according to the synthetic protocols set forth in Example 24 and Scheme 24.

Example 25

Preparation of 5-methyl-N-(2-phenyl-1H-pyrrolo[2,3-b]pyridin-5-yl)-4-(trifluoromethyl)-1H-pyrazole-3-carboxamide (P-2190)

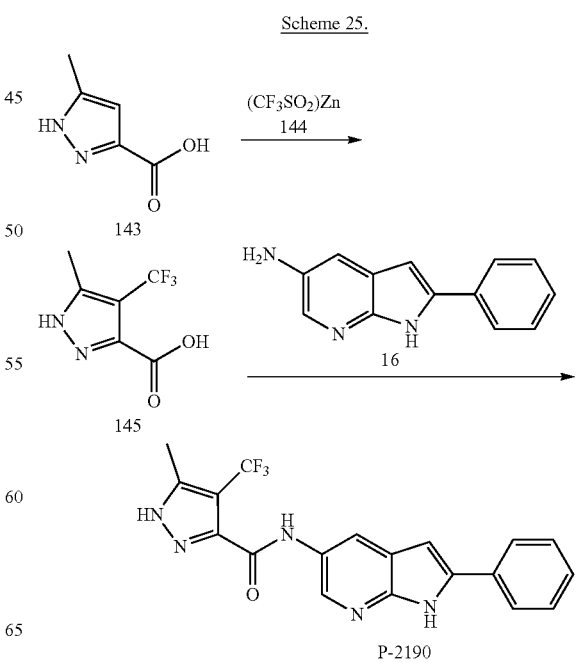

Step 1—Preparation of 5-methyl-4-(trifluoromethyl)-1H-pyrazole-3-carboxylic acid (145): To a mixture of bis(trifluoromethylsulfonyl)zinc (0.15 g, 0.45 mmol) and 5-methyl-1H-pyrazole-3-carboxylic acid 143 (0.05 g, 0.4 mmol) in dichloromethane (2 mL) was added water (0.5 mL), followed by tert-butyl hydroperoxide (0.3 ml, 70% solution in water, 2 mmol). The reaction mixture was allowed to warm up to room temperature and was stirred for two hours and then overnight. The reaction mixture was stirred at 50° C. for three days. The reaction mixture was partitioned between dichloromethane and water. The organic layer was collected and dried over sodium sulfate. After removal of drying agent and solvent, the residue was purified by preparative HPLC to provide compound 145 as a white solid (5 mg, 6.5%). MS(ESI) [M+H+]+=194.70. $^1$H NMR and mass spectroscopy data were consistent with the structure of the compound.

Step 2—Preparation of 5-methyl-4-(trifluoromethyl)-1H-pyrazole-3-carboxylic acid (P-2190): To 5-methyl-4-(trifluoromethyl)-1H-pyrazole-3-carboxylic acid (1 eq.) 145 in an appropriate amount of solvent such as dimethylacetamide, tetrahydrofuran, acetonitrile, or N,N-dimethylformamide are added benzotriazol-1-yl-oxytripyrrolidinophosphonium hexafluorophosphate (1 eq.) or o-benzotriazole-N,N,N',N'-tetramethyl-uronium-hexafluoro-phosphate (1 eq.) and N-hydroxybenzotriazole (1 eq.), followed by N,N-diisopropylethylamine (1 eq.) or triethylamine (1 eq.). The mixture is stirred at room temperature from 30 minutes to a few hours. To this mixture is added 2-(4-phenyl)-1H-pyrrolo[2,3-b]pyridin-5-amine hydrochloride 16 (1 eq.) and N,N-diisopropylethylamine (1 eq.) or triethylamine (1 eq.). The reaction mixture is stirred at room temperature from one hour to 2-3 days. Heating can be used if needed. The reaction mixture is partitioned between an organic solvent (ethyl acetate, dichloromethane, etc.) and water. The organic layer is collected and dried over sodium sulfate. After removal drying agent and solvent, the residue is purified by chromatography or/and preparative HPLC to provide compound P-2190.

Exemplary compounds 4-methyl-N-(2-phenyl-1H-pyrrolo[2,3-b]pyridin-5-yl)-5-(trifluoromethyl)-1H-pyrazole-3-carboxamide (P-2231); 4-chloro-N-(2-phenyl-1H-pyrrolo[2,3-b]pyridin-5-yl)-5-(trifluoromethyl)-1H-pyrazole-3-carboxamide (P-2232); 5-chloro-N-(2-phenyl-1H-pyrrolo[2,3-b]pyridin-5-yl)-4-(trifluoromethyl)-1H-pyrazole-3-carboxamide (P-2233); 5-(difluoromethyl)-4-methyl-N-(2-phenyl-1H-pyrrolo[2,3-b]pyridin-5-yl)-1H-pyrazole-3-carboxamide (P-2234); 4-(difluoromethyl)-5-methyl-N-(2-phenyl-1H-pyrrolo[2,3-b]pyridin-5-yl)-1H-pyrazole-3-carboxamide (P-2235); 5-chloro-4-(difluoromethyl)-N-(2-phenyl-1H-pyrrolo[2,3-b]pyridin-5-yl)-1H-pyrazole-3-carboxamide (P-2236); and 4-chloro-5-(difluoromethyl)-N-(2-phenyl-1H-pyrrolo[2,3-b]pyridin-5-yl)-1H-pyrazole-3-carboxamide (P-2237) can be prepared according to the synthetic protocols set forth in Example 25 and Scheme 25.

Compounds listed in Table 1 below, e.g., compounds P-2001 to P-2189 were prepared according to the protocols set forth in Examples 1 to 25 and Schemes 1 to 25. The $^1$H NMR and mass spectroscopy data were consistent with the structures of the compounds.

TABLE 1

| No. | Compound | Name | MS(ESI) [M + H+]+ or [M − H+]− observed |
|---|---|---|---|
| P-2001 |  | (2-phenyl-1H-pyrrolo[2,3-b]pyridin-5-yl)-(3-pyridyl)methanol | 301.8 |
| P-2002 |  | (2-phenyl-1H-pyrrolo[2,3-b]pyridin-5-yl)-(3-pyridyl)methanone | 299.8 |
| P-2003 |  | N-(3-carbamoylphenyl)-2-phenyl-1H-pyrrolo[2,3-b]pyridine-5-carboxamide | 355.1* |

TABLE 1-continued

| No. | Compound | Name | MS(ESI) [M + H+]+ or [M − H+]− observed |
|---|---|---|---|
| P-2004 | | 2-phenyl-N-(1H-pyrazol-3-yl)-1H-pyrrolo[2,3-b]pyridine-5-carboxamide | 304.1 |
| P-2005 | | 4-bromo-N-(2-phenyl-1H-pyrrolo[2,3-b]pyridin-5-yl)-1H-pyrazole-5-carboxamide | 384.0 |
| P-2006 | | ethyl 3-[(2-phenyl-1H-pyrrolo[2,3-b]pyridin-5-yl)carbamoylamino]propanoate | 352.8 |
| P-2007 | | 3,4-dimethyl-N-(2-phenyl-1H-pyrrolo[2,3-b]pyridin-5-yl)-1H-pyrazole-5-carboxamide | 332.2 |
| P-2008 | | 4-methyl-3-phenyl-N-(2-phenyl-1H-pyrrolo[2,3-b]pyridin-5-yl)-1H-pyrazole-5-carboxamide | 394.2 |
| P-2009 | | 3-cyclopropyl-N-(2-phenyl-1H-pyrrolo[2,3-b]pyridin-5-yl)-1H-pyrazole-5-carboxamide | 344.1 |

TABLE 1-continued

| No. | Compound | Name | MS(ESI) [M + H+]+ or [M − H+]− observed |
|---|---|---|---|
| P-2010 | | 5-fluoro-N-(2-phenyl-1H-pyrrolo[2,3-b]pyridin-5-yl)-1H-indazole-3-carboxamide | 372.1 |
| P-2011 | | N-(2-phenyl-1H-pyrrolo[2,3-b]pyridin-5-yl)pyrimidine-4-carboxamide | 316.1 |
| P-2012 | | 3-fluoro-N-(2-phenyl-1H-pyrrolo[2,3-b]pyridin-5-yl)pyridine-2-carboxamide | 333.1 |
| P-2013 | | 3,5-dimethyl-N-(2-phenyl-1H-pyrrolo[2,3-b]pyridin-5-y)isoxazole-4-carboxamide | 333.1 |
| P-2014 | | N-(2-phenyl-1H-pyrrolo[2,3-b]pyridin-5-yl)pyridazine-3-carboxamide | 316.1 |
| P-2015 | | N-(2-phenyl-1H-pyrrolo[2,3-b]pyridin-5-yl)-2H-triazole-4-carboxamide | 305.1 |
| P-2016 | | 3-methyl-N-(2-phenyl-1H-pyrrolo[2,3-b]pyridin-5-yl)pyridine-2-carboxamide | 329.1 |

TABLE 1-continued

| No. | Compound | Name | MS(ESI) [M + H+]+ or [M − H+]− observed |
|---|---|---|---|
| P-2017 | | 4,5-dimethyl-N-(2-phenyl-1H-pyrrolo[2,3-b]pyridin-5-yl)isoxazole-3-carboxamide | 333.3 |
| P-2018 | | N-(2-phenyl-1H-pyrrolo[2,3-b]pyridin-5-yl)-1H-pyrazole-4-sulfonamide | 340.1 |
| P-2019 | | N-[2-(4-fluorophenyl)-1H-pyrrolo[2,3-b]pyridin-5-yl]-3-methyl-1H-pyrazole-5-carboxamide | 335.8 |
| P-2020 | | N3-[2-(4-fluorophenyl)-1H-pyrrolo[2,3-b]pyridin-5-yl]benzene-1,3-dicarboxamide | 375.2 |
| P-2021 | | 3-(cyanomethyl)-N-[2-(4-fluorophenyl)-1H-pyrrolo[2,3-b]pyridin-5-yl]benzamide | 371.1 |
| P-2022 | | 2-chloro-N-[2-(4-fluorophenyl)-1H-pyrrolo[2,3-b]pyridin-5-yl]-6-methyl-benzamide | 380.1 |
| P-2023 | | 4-chloro-N-[2-(4-fluorophenyl)-1H-pyrrolo[2,3-b]pyridin-5-yl]-3-methyl-1H-pyrazole-5-carboxamide | 369.75 |

TABLE 1-continued

| No. | Name | MS(ESI) [M + H+]+ or [M − H+]− observed |
|---|---|---|
| P-2024 | N-[2-(4-fluorophenyl)-1H-pyrrolo[2,3-b]pyridin-5-yl]-3,4-dimethyl-1H-pyrazole-5-carboxamide | 350.1 |
| P-2025 | 3-cyano-N-[2-(4-fluorophenyl)-1H-pyrrolo[2,3-b]pyridin-5-yl]benzamide | 357.1 |
| P-2026 | 3-acetamido-N-[2-(4-fluorophenyl)-1H-pyrrolo[2,3-b]pyridin-5-yl]benzamide | 389.0 |
| P-2027 | N-[2-(4-fluorophenyl)-1H-pyrrolo[2,3-b]pyridin-5-yl]-2H-indazole-4-carboxamide | 370.1 |
| P-2028 | 3-ethyl-N-[2-(4-fluorophenyl)-1H-pyrrolo[2,3-b]pyridin-5-yl]-4-methyl-1H-pyrazole-5-carboxamide | 364.25 |
| P-2029 | N-[2-(4-fluorophenyl)-1H-pyrrolo[2,3-b]pyridin-5-yl]-4-methyl-1H-pyrazole-3-carboxamide | 336.2 |
| P-2030 | 2-ethyl-N-[2-(4-fluorophenyl)-1H-pyrrolo[2,3-b]pyridin-5-yl]pyrazole-3-sulfonamide | 386.05 |

TABLE 1-continued

| No. | Name | MS(ESI) [M + H+]+ or [M − H+]− observed |
|---|---|---|
| P-2031 | 5-methyl-N-[2-[1-(morpholine-4-carbonyl)-3,6-dihydro-2H-pyridin-4-yl]-1H-pyrrolo[2,3-b]pyridin-5-yl]-1H-pyrazole-3-carboxamide | 435.9 |
| P-2032 | 3,4-dimethyl-N-(1H-pyrrolo[2,3-b]pyridin-5-yl)-1H-pyrazole-5-carboxamide | 256.1 |
| P-2033 | N-[1-(benzenesulfonyl)-2-[1-(morpholine-4-carbonyl)-3,6-dihydro-2H-pyridin-4-yl]pyrrolo[2,3-b]pyridin-5-yl]-3,4-dimethyl-1H-pyrazole-5-carboxamide | 589.95 |
| P-2034 | 3,4-dimethyl-N-[2-[1-(morpholine-4-carbonyl)-3,6-dihydro-2H-pyridin-4-yl]-1H-pyrrolo[2,3-b]pyridin-5-yl]1H-pyrazole-5-carboxamide | 449.95 |
| P-2035 | N-[2-(4-fluorophenyl)-1H-pyrrolo[2,3-b]pyridin-5-yl]-1H-1,2,4-triazole-5-carboxamide | 322.95 |
| P-2036 | 4-chloro-3-methyl-N-[2-[1-(morpholine-4-carbonyl)-3,6-dihydro-2H-pyridin-4-yl]-1H-pyrrolo[2,3-b]pyridin-5-yl]-1H-pyrazole-5-carboxamide | 470 |

TABLE 1-continued

| No. | Compound | Name | MS(ESI) [M + H+]+ or [M − H+]− observed |
|---|---|---|---|
| P-2037 | | N-[2-(4-fluorophenyl)-1H-pyrrolo[2,3-b]pyridin-5-yl]-5-methyl-2H-triazole-4-carboxamide | 337.2 |
| P-2038 | | N-[2-(1,3-dimethylpyrazol-4-yl)-1H-pyrrolo[2,3-b]pyridin-5-yl]-3,4-dimethyl-1H-pyrazole-5-carboxamide | 349.9 |
| P-2039 | | 4-chloro-N-[2-[1-(cyclopropanecarbonyl)-3,6-dihydro-2H-pyridin-4-yl]-1H-pyrrolo[2,3-b]pyridin-5-yl]-5-methyl-1H-pyrazole-3-carboxamide | 424.9 |
| P-2040 | | 3,4-dimethyl-N-(3-methyl-1H-pyrazolo[3,4-b]pyridin-5-yl)-1H-pyrazole-5-carboxamide | 271.2 |
| P-2041 | | N-[3-(4-fluorophenyl)-1H-pyrazolo[3,4-b]pyridin-5-yl]-3,4-dimethyl-1H-pyrazole-5-carboxamide | 351.3 |
| P-2042 | | N-[2-[1-(cyclopropanecarbonyl)-3,6-dihydro-2H-pyridin-4-yl]-1H-pyrrolo[2,3-b]pyridin-5-yl-5-methyl-1H-pyrazole-3-carboxamide | 390.9 |

TABLE 1-continued

| No. | Compound | Name | MS(ESI) [M + H+]+ or [M − H+]− observed |
|---|---|---|---|
| P-2043 | | N-[2-[1-(cyclopropanecarbonyl)-3,6-dihydro-2H-pyridin-4-yl]-1H-pyrrolo[2,3-b]pyridin-5-yl]-4,5-dimethyl-1H-pyrazole-3-carboxamide | 404.9 |
| P-2044 | | N-(2-anilinopyrimidin-5-yl)-3,4-dimethyl-1H-pyrazole-5-carboxamide | 309.1 |
| P-2045 | | N-(6-anilino-3-pyridyl)-3,4-dimethyl-1H-pyrazole-5-carboxamide | 308.5 |
| P-2046 | | N-[2-(4-fluorophenyl)-1H-pyrrolo[2,3-b]pyridin-5-yl]-1H-indazole-3-carboxamide | 372.35 |
| P-2047 | | N-[2-(4-fluorophenyl)-1H-pyrrolo[2,3-b]pyridin-5-yl]-4,5,6,7-tetrahydro-1H-indazole-3-carboxamide | 376.45 |
| P-2048 | | 3,4-dimethyl-N-[2-[1-(4-piperidyl)pyrazol-4-yl]-1H-pyrrolo[2,3-b]pyridin-5-yl]-1H-pyrazole-5-carboxamide | 405.2 |

TABLE 1-continued

| No. | Compound | Name | MS(ESI) [M + H+]+ or [M − H+]− observed |
|---|---|---|---|
| P-2049 | | N-(2-chloro-1H-pyrrolo[2,3-b]pyridin-5-yl)-3,4-dimethyl-1H-pyrazole-5-carboxamide | 289.95 |
| P-2050 | | N-[2-[3-(ethylsulfamoyl)anilino]pyrimidin-5-yl]-3,4-dimethyl-1H-pyrazole-5-carboxamide | 415.9 |
| P-2051 | | 3,4-dimethyl-N-[2-(3-morpholinoanilino)pyrimidin-5-yl]-1H-pyrazole-5-carboxamide | 394.5 |
| P-2052 | | 3,4-dimethyl-N-[2-[3-(propylsulfonylamino)anilino]pyrimidin-5-yl]-1H-pyrazole-5-carboxamide | 430.4 |
| P-2053 | | N-[2-]3-(benzenesulfonamido)anilino]pyrimidin-5-yl]-3,4-dimethyl-1H-pyrazole-5-carboxamide | 464.3 |
| P-2054 | | 3,4-dimethyl-N-[2-]3-(methylcarbamoyl)anilino]pyrimidin-5-yl]-1H-pyrazole-5-carboxamide | 365.9 |

TABLE 1-continued

| No. | Compound | Name | MS(ESI) [M + H+]+ or [M − H+]− observed |
|---|---|---|---|
| P-2055 | | ethyl N-[3-[[5-[(3,4-dimethyl-1H-pyrazole-5-carbonyl)amino]pyrimidin-2-yl]amino]phenyl]carbamate | 396.4 |
| P-2056 | | N[2-(4-fluorophenyl)-1H-pyrrolo[2,3-b]pyridin-5-yl]-1,4,5,6-tetrahydrocyclopenta[c]pyrazole-3-carboxamide | 361.9 |
| P-2057 | | 4-chloro-3-methyl-N-[2-(1-methylsulfonyl-3,6-dihydro-2H-pyridin-4-yl)-1H-pyrrolo[2,3-b]pyridin-5-yl]-1H-pyrazole-5-carboxamide | 434.9 |
| P-2058 | | 3-methyl-N-(2-morpholino-1H-pyrrolo[2,3-b]pyridin-5-yl)-1H-pyrazole-5-carboxamide | 327.3 |
| P-2059 | | 4,5-dimethyl-N-[2-(4-morpholinophenyl)-1H-pyrrolo[2,3-b]pyridin-5-yl]-1H-pyrazole-3-carboxamide | 417.2 |
| P-2060 | | 4-chloro-N-[2-[1-(cyclopropanecarbonyl)-2,5-dihydropyrrol-3-yl]-1H-pyrrolo[2,3-b]pyridin-5-yl]-3-methyl-1H-pyrazole-5-carboxamide | 412.0 |
| P-2061 | | N-[2-(1-acetyl-3,6-dihydro-2H-pyridin-4-yl)-1H-pyrrolo[2,3-b]pyridin-5-yl]-4-chloro-3-methyl-1H-pyrazole-5-carboxamide | 398.9 |

TABLE 1-continued

| No. | Compound | Name | MS(ESI) [M + H+]+ or [M − H+]− observed |
|---|---|---|---|
| P-2062 | | 4-chloro-3-methyl-N-[2-[1-(morpholine-4-carbonyl)-2,5-dihydropyrrol-3-yl]-1H-pyrrolo[2,3-b]pyridin-5-yl]-1H-pyrazole-5-carboxamide | 456.0 |
| P-2063 | | N-[2-(3-fluoroprop-1-ynyl)-1H-pyrrolo[2,3-b]pyridin-5-yl]-3,4-dimethyl-1H-pyrazole-5-carboxamide | 312.25 |
| P-2064 | | N-[2-[3-(dimethylamino)phenyl]-1H-pyrrolo[2,3-b]pyridin-5-yl]-3,4-dimethyl-1H-pyrazole-5-carboxamide | 374.95 |
| P-2065 | | N-[2-(3,5-dimethylisoxazol-4-yl)-1H-pyrrolo[2,3-b]pyridin-5-yl]-3,4-dimethyl-1H-pyrazole-5-carboxamide | 351.5 |
| P-2066 | | 3,4-dimethyl-N-[2-[3-(2-morpholinoethoxy)phenyl]-1H-pyrrolo[2,3-b]pyridin-5-yl]-1H-pyrazole-5-carboxamide | 461.1 |
| P-2067 | | 3,4-dimethyl-N-[2-[4-(methylcarbamoyl)phenyl]-1H-pyrrolo[2,3-b]pyridin-5-yl]-1H-pyrazole-5-carboxamide | 388.9 |

TABLE 1-continued

| No. | Compound | Name | MS(ESI) [M + H+]+ or [M − H+]− observed |
|---|---|---|---|
| P-2068 | | N-[2-(3-fluoroprop-1-ynyl)-1H-pyrrolo[2,3-b]pyridin-5-yl]-3-methyl-1H-pyrazole-5-carboxamide | 298 |
| P-2069 | | 4,5-dimethyl-N-[2-[2-(4-methylpiperazin-1-yl)-4-pyridyl]-1H-pyrrolo[2,3-b]pyridin-5-yl]-1H-pyrazole-3-carboxamide | 431.3 |
| P-2070 | | 4,5-dimethyl-N-[2-(3-morpholinophenyl)-1H-pyrrolo[2,3-b]pyridin-5-yl]-1H-pyrazole-3-carboxamide | 417.25 |
| P-2071 | | N-(4,5-dimethyl-1H-pyrazol-3-yl)-2-phenyl-1H-pyrrolo[2,3-b]pyridine-5-carboxamide | 331.9 |
| P-2072 | | N-[2-(4-fluorophenyl)pyrazolo[1,5-a]pyrimidin-6-yl]-4,5-dimethyl-1H-pyrazole-3-carboxamide | 352.0 |
| P-2073 | | 3,4-dimethyl-N-[2-[1-(2-morpholinoacetyl)-3,6-dihydro-2H-pyridin-4-yl]-1H-pyrrolo[2,3-b]pyridin-5-yl]-1H-pyrazole-5-carboxamide | 464.6 |

TABLE 1-continued

| No. | Compound | Name | MS(ESI) [M + H+]+ or [M − H+]− observed |
|---|---|---|---|
| P-2074 | | N-[2-[1-(2,3-dihydroxypropanoyl)-3,6-dihydro-2H-pyridin-4-yl]-1H-pyrrolo[2,3-b]pyridin-5-yl]-3,4-dimethyl-1H-pyrazole-5-carboxamide | 425.2 |
| P-2075 | | N-[2-(2-chloro-4-methoxy-phenyl)-1H-pyrrolo[2,3-b]pyridin-5-yl]-3,4-dimethyl-1H-pyrazole-5-carboxamide | 396.2 |
| P-2076 | | N-[2-(2-fluoro-4-methoxy-phenyl)-1H-pyrrolo[2,3-b]pyridin-5-yl]-3,4-dimethyl-1H-pyrazole-5-carboxamide | 380.3 |
| P-2077 | | N-[2-(2-chloro-5-methoxy-phenyl)-1H-pyrrolo[2,3-b]pyridin-5-yl]-3,4-dimethyl-1H-pyrazole-5-carboxamide | 395.9 |
| P-2078 | | N-[2-(3-fluoro-5-morpholino-phenyl)-1H-pyrrolo[2,3-b]pyridin-5-yl]-3,4-dimethyl-1H-pyrazole-5-carboxamide | 435.3 |
| P-2079 | | 3,4-dimethyl-N-[2-(3-pyrrolidin-1-ylphenyl)-1H-pyrrolo[2,3-b]pyridin-5-yl]-1H-pyrazole-5-carboxamide | 401.4 |

TABLE 1-continued

| No. | Name | MS(ESI) [M + H+]+ or [M − H+]− observed |
|---|---|---|
| P-2080 | N-[2-(4-aminocyclohexen-1-yl)-1H-pyrrolo[2,3-b]pyridin-5-yl]-3,4-dimethyl-1H-pyrazole-5-carboxamide | 351.3 |
| P-2081 | N-[2-(4-cyano-3-morpholino-phenyl)-1H-pyrrolo[2,3-b]pyridin-5-yl]-3,4-dimethyl-1H-pyrazole-5-carboxamide | 442.2 |
| P-2082 | N-[2-(3-fluoro-2-morpholino-4-pyridyl)-1H-pyrrolo[2,3-b]pyridin-5-yl]-3,4-dimethyl-1H-pyrazole-5-carboxamide | 435.9 |
| P-2083 | N-[2-(1-isobutylpyrazol-4-yl)-1H-pyrrolo[2,3-b]pyridin-5-yl]-3,4-dimethyl-1H-pyrazole-5-carboxamide | 378.4 |
| P-2084 | N-[2-(1,5-dimethylpyrazol-4-yl)-1H-pyrrolo[2,3-b]pyridin-5-yl]-3,4-dimethyl-1H-pyrazole-5-carboxamide | 350.3 |
| P-2085 | N-[2-[4-(dimethylcarbamoyl)phenyl]-1H-pyrrolo[2,3-b]pyridin-5-yl]-3,4-dimethyl-1H-pyrazole-5-carboxamide | 403.3 |

TABLE 1-continued

| No. | Compound | Name | MS(ESI) [M + H+]+ or [M − H+]− observed |
|---|---|---|---|
| P-2086 | | 3,4-dimethyl-N-[2-[3-(trifluoromethoxy)phenyl]-1H-pyrrolo[2,3-b]pyridin-5-yl]-1H-pyrazole-5-carboxamide | 416.2 |
| P-2087 | | N-[2-[3-(dimethylcarbamoyl)phenyl]-1H-pyrrolo[2,3-b]pyridin-5-yl]-3,4-dimethyl-1H-pyrazole-5-carboxamide | 403.3 |
| P-2088 | | 3,4-dimethyl-N-[2-(3-pyridyl)-1H-pyrrolo[2,3-b]pyridin-5-yl]-1H-pyrazole-5-carboxamide | 333.3 |
| P-2089 | | 3,4-dimethyl-N-[2-(6-morpholino-3-pyridyl)-1H-pyrrolo[2,3-b]pyridin-5-yl]-1H-pyrazole-5-carboxamide | 418.3 |
| P-2090 | | N-[2-(6-methoxy-3-pyridyl)-1H-pyrrolo[2,3-b]pyridin-5-yl]-3,4-dimethyl-1H-pyrazole-5-carboxamide | 363.3 |
| P-2091 | | 3,4-dimethyl-N-[2-(2-methylthiazol-5-yl)-1H-pyrrolo[2,3-b]pyridin-5-yl]-1H-pyrazole-5-carboxamide | 353.1 |
| P-2092 | | N-[2-(4-cyanophenyl)-1H-pyrrolo[2,3-b]pyridin-5-yl]-3,4-dimethyl-1H-pyrazole-5-carboxamide | 357.3 |

TABLE 1-continued

| No. | Compound | Name | MS(ESI) [M + H+]+ or [M − H+]− observed |
|---|---|---|---|
| P-2093 | | N-[2-(2-fluorophenyl)-1H-pyrrolo[2,3-b]pyridin-5-yl]-3,4-dimethyl-1H-pyrazole-5-carboxamide | 350.1 |
| P-2094 | | N-[2-(3-fluorophenyl)-1H-pyrrolo[2,3-b]pyridin-5-yl]-3,4-dimethyl-1H-pyrazole-5-carboxamide | 350.4 |
| P-2095 | | N-[2-(3-chlorophenyl)-1H-pyrrolo[2,3-b]pyridin-5-yl]-3,4-dimethyl-1H-pyrazole-5-carboxamide | 366.3 |
| P-2096 | | N-[2-(2-chlorophenyl)-1H-pyrrolo[2,3-b]pyridin-5-yl]-3,4-dimethyl-1H-pyrazole-5-carboxamide | 366.0 |
| P-2097 | | 3,4-dimethyl-N-[2-(o-tolyl)-1H-pyrrolo[2,3-b]pyridin-5-yl]-1H-pyrazole-5-carboxamide | 346.2 |
| P-2098 | | N-[2-(3-methoxyphenyl)-1H-pyrrolo[2,3-b]pyridin-5-yl]-3,4-dimethyl-1H-pyrazole-5-carboxamide | 362.4 |
| P-2099 | | N-[2-(4-methoxyphenyl)-1H-pyrrolo[2,3-b]pyridin-5-yl]-3,4-dimethyl-1H-pyrazole-5-carboxamide | 362.4 |

TABLE 1-continued

| No. | Name | MS(ESI) [M + H+]+ or [M − H+]− observed |
|---|---|---|
| P-2100 | N-[2-(3-acetamidophenyl)-1H-pyrrolo[2,3-b]pyridin-5-yl]-3,4-dimethyl-1H-pyrazole-5-carboxamide | 389.4 |
| P-2101 | 3,4-dimethyl-N-[2-[4-(pyrrolidine-1-carbonyl)phenyl]-1H-pyrrolo[2,3-b]pyridin-5-yl]-1H-pyrazole-5-carboxamide | 429.4 |
| P-2102 | N-[2-[4-(3-methoxypropoxy)phenyl]-1H-pyrrolo[2,3-b]pyridin-5-yl]-3,4-dimethyl-1H-pyrazole-5-carboxamide | 420.4 |
| P-2104 | 3,4-dimethyl-N-[2-[4-(4-methylpiperazin-1-yl)phenyl]-1H-pyrrolo[2,3-b]pyridin-5-yl]-1H-pyrazole-5-carboxamide | 430.6 |
| P-2105 | 3,4-dimethyl-N-[2-[4-(thiomorpholine-4-carbonyl)phenyl]-1H-pyrrolo[2,3-b]pyridin-5-yl]-1H-pyrazole-5-carboxamide | 461.2 |
| P-2106 | 3,4-dimethyl-N-[2-[3-(morpholine-4-carbonyl)phenyl]-1H-pyrrolo[2,3-b]pyridin-5-yl]-1H-pyrazole-5-carboxamide | 445.3 |

TABLE 1-continued

| No. | Compound | Name | MS(ESI) [M + H+]+ or [M − H+]− observed |
|---|---|---|---|
| P-2107 | | 3,4-dimethyl-N-[2-[3-(pyrrolidine-1-carbonyl)phenyl]-1H-pyrrolo[2,3-b]pyridin-5-yl]-1H-pyrazole-5-carboxamide | 429.4 |
| P-2108 | | N-[2-(2-cyclopropyl-4-pyridyl)-1H-pyrrolo[2,3-b]pyridin-5-yl]-3,4-dimethyl-1H-pyrazole-5-carboxamide | 373.2 |
| P-2109 | | N-[2-(2-methoxy-4-pyridyl)-1H-pyrrolo[2,3-b]pyridin-5-yl]-3,4-dimethyl-1H-pyrazole-5-carboxamide | 363.3 |
| P-2110 | | 3,4-dimethyl-N-[2-(2-morpholino-4-pyridyl)-1H-pyrrolo[2,3-b]pyridin-5-yl]-1H-pyrazole-5-carboxamide | 418.3 |
| P-2111 | | N-[2-[4-(methanesulfonamido)phenyl]-1H-pyrrolo[2,3-b]pyridin-5-yl]-3,4-dimethyl-1H-pyrazole-5-carboxamide | 425.2 |
| P-2112 | | 3,4-dimethyl-N-(2-pyrazol-1-yl-1H-pyrrolo[2,3-b]pyridin-5-yl)-1H-pyrazole-5-carboxamide | 322.3 |

TABLE 1-continued

| No. | Compound | Name | MS(ESI) [M + H+]+ or [M − H+]− observed |
|---|---|---|---|
| P-2113 | | N-[2-[2-chloro-5-(trifluoromethoxy)phenyl]-1H-pyrrolo[2,3-b]pyridin-5-yl]-3,4-dimethyl-1H-pyrazole-5-carboxamide | 450.2 |
| P-2114 | | 4,5-dimethyl-N-(2-methylpyrazolo[1,5-a]pyrimidin-6-yl)-1H-pyrazole-3-carboxamide | 271.0 |
| P-2115 | | 3,4-dimethyl-N-(2-pyrrolidin-1-yl-1H-pyrrolo[2,3-b]pyridin-5-yl)-1H-pyrazole-5-carboxamide | 325.2 |
| P-2116 | | 3-methyl-N-(2-pyrazol-1-yl-1H-pyrrolo[2,3-b]pyridin-5-yl)-1H-pyrazole-5-carboxamide | 308.1 |
| P-2117 | | N-[2-[4-(methanesulfonamido)phenyl]-1H-pyrrolo[2,3-b]pyridin-5-yl]-3,4-dimethyl-1H-pyrazole-5-carboxamide | 425.2 |
| P-2118 | | N-[2-[3-[4-(cyclopropanecarbonyl)piperazin-1-yl]phenyl]-1H-pyrrolo[2,3-b]pyridin-5-yl]-3,4-dimethyl-1H-pyrazole-5-carboxamide | 484.4 |

TABLE 1-continued

| No. | Name | MS(ESI) [M + H+]+ or [M − H+]− observed |
|---|---|---|
| P-2119 | N-[2-(4-fluorophenyl)-1H-pyrrolo[2,3-b]pyridin-5-yl]-1,5-dimethyl-pyrazole-3-carboxamide | 350.4 |
| P-2120 | N-[2-(4-cyano-3-pyrrolidin-1-yl-phenyl)-1H-pyrrolo[2,3-b]pyridin-5-yl]-3,4-dimethyl-1H-pyrazole-5-carboxamide | 426.0 |
| P-2121 | 3,4-dimethyl-N-[2-[3-(methylsulfamoyl)phenyl]-1H-pyrrolo[2,3-b]pyridin-5-yl]-1H-pyrazole-5-carboxamide | 425.2 |
| P-2122 | N-[2-(4-chlorophenyl)-1H-pyrrolo[2,3-b]pyridin-5-yl]-3,4-dimethyl-1H-pyrazole-5-carboxamide | 366.1 |
| P-2123 | 3,4-dimethyl-N-[2-(6-methyl-3-pyridyl)-1H-pyrrolo[2,3-b]pyridin-5-yl]-1H-pyrazole-5-carboxamide | 347.2 |
| P-2124 | 3,4-dimethyl-N-[2-(4-pyridyl)-1H-pyrrolo[2,3-b]pyridin-5-yl]-1H-pyrazole-5-carboxamide | 333.2 |
| P-2125 | 3,4-dimethyl-N-[2-(4-pyrrolidin-1-ylphenyl)-1H-pyrrolo[2,3-b]pyridin-5-yl]-1H-pyrazole-5-carboxamide | 401.2 |

TABLE 1-continued

| No. | Compound | Name | MS(ESI) [M + H+]+ or [M − H+]− observed |
|---|---|---|---|
| P-2126 | | 3,4-dimethyl-N-[2-[3-(propylsulfonylamino)phenyl]-1H-pyrrolo[2,3-b]pyridin-5-yl]-1H-pyrazole-5-carboxamide | 453.3 |
| P-2127 | | N-[2-(4-dimethylphosphorylphenyl)-1H-pyrrolo[2,3-b]pyridin-5-yl]-3,4-dimethyl-1H-pyrazole-5-carboxamide | 408.3 |
| P-2128 | | N-[2-(3-cyanophenyl)-1H-pyrrolo[2,3-b]pyridin-5-yl]-3,4-dimethyl-1H-pyrazole-5-carboxamide | 357.2 |
| P-2129 | | N-[2-(2-fluoro-3-methoxy-phenyl)-1H-pyrrolo[2,3-b]pyridin-5-yl]-3,4-dimethyl-1H-pyrazole-5-carboxamide | 380.4 |
| P-2130 | | 3,4-dimethyl-N-[2-(m-tolyl)-1H-pyrrolo[2,3-b]pyridin-5-yl]-1H-pyrazole-5-carboxamide | 346.2 |
| P-2131 | | N-[2-(4-fluorophenyl)-1H-pyrrolo[2,3-b]pyridin-5-yl]-3-methyl-1H-1,2,4-triazole-5-carboxamide | 335 |

TABLE 1-continued

| No. | Compound | Name | MS(ESI) [M + H+]+ or [M − H+]− observed |
|---|---|---|---|
| P-2132 | | N-[2-(4-fluorophenyl)-1H-pyrrolo[2,3-b]pyridin-5-yl]-3-propyl-1H-pyrazole-5-carboxamide | 364.15 |
| P-2133 | | N-[2-(6-acetamido-3-pyridyl)-1H-pyrrolo[2,3-b]pyridin-5-yl]-3,4-dimethyl-1H-pyrazole-5-carboxamide | 390.2 |
| P-2134 | | N-[2-[3-(butylcarbamoylamino)phenyl]-1H-pyrrolo[2,3-b]pyridin-5-yl]-3,4-dimethyl-1H-pyrazole-5-carboxamide | 446.3 |
| P-2135 | | N-[2-(2-methoxyphenyl)-1H-pyrrolo[2,3-b]pyridin-5-yl]-3,4-dimethyl-1H-pyrazole-5-carboxamide | 362.2 |
| P-2136 | | 3,4-dimethyl-N-[2-(2-methyl-3-pyridyl)-1H-pyrrolo[2,3-b]pyridin-5-yl]-1H-pyrazole-5-carboxamide | 347.15 |
| P-2137 | | N-[2-(4-acetamidophenyl)-1H-pyrrolo[2,3-b]pyridin-5-yl]-3,4-dimethyl-1H-pyrazole-5-carboxamide | 389.4 |

TABLE 1-continued

| No. | Compound | Name | MS(ESI) [M + H+]+ or [M − H+]− observed |
|---|---|---|---|
| P-2138 | | 3,4-dimethyl-N-[2-[4-(morpholine-4-carbonyl)phenyl]-1H-pyrrolo[2,3-b]pyridin-5-yl]-1H-pyrazole-5-carboxamide | 445.3 |
| P-2139 | | N-[2-(2,4-dimethylthiazol-5-yl)-1H-pyrrolo[2,3-b]pyridin-5-yl]-3,4-dimethyl-1H-pyrazole-5-carboxamide | 367.2 |
| P-2140 | | N-[2-[1-(difluoromethyl)pyrazol-4-yl]-1H-pyrrolo[2,3-b]pyridin-5-yl]-3,4-dimethyl-1H-pyrazole-5-carboxamide | 372 |
| P-2141 | | N-[(4-chloro-3-methyl-1H-pyrazol-5-yl)methyl]-2-(4-fluorophenyl)-1H-pyrrolo[2,3-b]pyridin-5-amine | 356 |
| P-2142 | | 2-(4-fluorophenyl)-N-[(3-methyl-1H-pyrazol-5-yl)methyl]-1H-pyrrolo[2,3-b]pyridin-5-amine | 322 |
| P-2143 | | N-[2-(4-fluorophenyl)-1H-pyrrolo[2,3-b]pyridin-5-yl]-1H-pyrazole-5-carboxamide | 322.1 |
| P-2144 | | 3,4-dimethyl-N-(2-phenylthiazolo[5,4-b]pyridin-6-yl)-1H-pyrazole-5-carboxamide | 349.9 |

TABLE 1-continued

| No. | Compound | Name | MS(ESI) [M + H+]+ or [M − H+]− observed |
|---|---|---|---|
| P-2145 | | 3,4-dimethyl-N-(2-phenyl-3H-imidazo[4,5-b]pyridin-6-yl)-1H-pyrazole-5-carboxamide | 333.1 |
| P-2146 | | N-[2-(3-fluoro-2-methyl-phenyl)-1H-pyrrolo[2,3-b]pyridin-5-yl]-3,4-dimethyl-1H-pyrazole-5-carboxamide | 364.2 |
| P-2147 | | N-[2-(3-chloro-2-methyl-phenyl)-1H-pyrrolo[2,3-b]pyridin-5-yl]-3,4-dimethyl-1H-pyrazole-5-carboxamide | 380.2 |
| P-2148 | | N-[2-[4-(cyclopropylcarbamoyl)phenyl]-1H-pyrrolo[2,3-b]pyridin-5-yl]-3,4-dimethyl-1H-pyrazole-5-carboxamide | 415.3 |
| P-2149 | | 3,4-dimethyl-N-[2-[4-[(3-methyloxetan-3-yl)methoxy]phenyl]-1H-pyrrolo[2,3-b]pyridin-5-yl]-1H-pyrazole-5-carboxamide | 432.3 |
| P-2150 | | 4-chloro-3-methyl-N-(2-phenyl-3H-imidazo[4,5-b]pyridin-6-yl)-1H-pyrazole-5-carboxamide | 353.0 |
| P-2151 | | 3-methyl-N-(2-phenyl-3H-imidazo[4,5-b]pyridin-6-yl)-1H-pyrazole-5-carboxamide | 319.1 |

TABLE 1-continued

| No. | Name | MS(ESI) [M + H+]+ or [M − H+]− observed |
|---|---|---|
| P-2152 | N-[2-(2-fluorophenyl)-3H-imidazo[4,5-b]pyridin-6-yl]-3,4-dimethyl-1H-pyrazole-5-carboxamide | 351.1 |
| P-2153 | N-[2-(2-ethoxypyrimidin-5-yl)-1H-pyrrolo[2,3-b]pyridin-5-yl]-3,4-dimethyl-1H-pyrazole-5-carboxamide | 378.2 |
| P-2154 | N-[2-(2-isopropylpyrimidin-5-yl)-1H-pyrrolo[2,3-b]pyridin-5-yl]-3,4-dimethyl-1H-pyrazole-5-carboxamide | 376.2 |
| P-2155 | N-[2-(2-cyclopropylpyrimidin-5-yl)-1H-pyrrolo[2,3-b]pyridin-5-yl]-3,4-dimethyl-1H-pyrazole-5-carboxamide | 374.1 |
| P-2156 | N-[2-(4-fluorophenyl)-1H-pyrrolo[2,3-b]pyridin-5-yl]-3-(trifluoromethyl)-1H-pyrazole-5-carboxamide | 390.0 |
| P-2157 | N-[2-[2-(cyclopropylamino)pyrimidin-5-yl]-1H-pyrrolo[2,3-b]pyridin-5-yl]-3,4-dimethyl-1H-pyrazole-5-carboxamide | 389.3 |
| P-2158 | 3,4-dimethyl-N-[2-(2-morpholinopyrimidin-5-yl)-1H-pyrrolo[2,3-b]pyridin-5-yl]-1H-pyrazole-5-carboxamide | 419.3 |

TABLE 1-continued

| No. | Name | MS(ESI) [M + H+]+ or [M − H+]− observed |
|---|---|---|
| P-2159 | 3-ethyl-N-[2-(4-fluorophenyl)-1H-pyrrolo[2,3-b]pyridin-5-yl]-1H-pyrazole-5-carboxamide | 350.2 |
| P-2160 | 3,4-dimethyl-N-[2-[2-(4-methylpiperazin-1-yl)pyrimidin-5-yl]-1H-pyrrolo[2,3-b]pyridin-5-yl]-1H-pyrazole-5-carboxamide | 432.3 |
| P-2161 | N-[2-(4-cyano-2-methyl-phenyl)-1H-pyrrolo[2,3-b]pyridin-5-yl]-3,4-dimethyl-1H-pyrazole-5-carboxamide | 371.0 |
| P-2162 | tert-butyl 4-[3-[5-[(3,4-dimethyl-1H-pyrazole-5-carbonyl)amino]-1H-pyrazolo[3,4-b]pyridin-3-yl]phenyl]piperazine-1-carboxylate | 517.4 |
| P-2163 | N-[2-(2-isopropyl-4-pyridyl)-1H-pyrrolo[2,3-b]pyridin-5-yl]-3,4-dimethyl-1H-pyrazole-5-carboxamide | 374.9 |
| P-2164 | 3,4-dimethyl-N-[2-(2,3,4,5,6-pentadeuteriophenyl)-1H-pyrrolo[2,3-b]pyridin-5-yl]-1H-pyrazole-5-carboxamide | 336.9 |

TABLE 1-continued

| No. | Compound | Name | MS(ESI) [M + H+]+ or [M − H+]− observed |
|---|---|---|---|
| P-2165 | | 3,4-dimethyl-N-[2-(1,3,5-trimethylpyrazol-4-yl)-1H-pyrrolo[2,3-b]pyridin-5-yl]-1H-pyrazole-5-carboxamide | 364.2 |
| P-2166 | | 3,4-dimethyl-N-[3-(3-piperazin-1-ylphenyl)-1H-pyrazolo[3,4-b]pyridin-5-yl]-1H-pyrazole-5-carboxamide | 417.2 |
| P-2167 | | N-[2-(3,5-dimethyl-1H-pyrazol-4-yl)-1H-pyrrolo[2,3-b]pyridin-5-yl]-3,4-dimethyl-1H-pyrazole-5-carboxamide | 350.2 |
| P-2168 | | 3,4-dimethyl-N-[2-[3-methyl-1-(oxetan-3-yl)pyrazol-4-yl]-1H-pyrrolo[2,3-b]pyridin-5-yl]-1H-pyrazole-5-carboxamide | 392.2 |
| P-2169 | | N-[2-(6-methoxy-2-methyl-3-pyridyl)-1H-pyrrolo[2,3-b]pyridin-5-yl]-3,4-dimethyl-1H-pyrazole-5-carboxamide | 377.1 |
| P-2170 | | N-[2-(2-methoxy-6-methyl-3-pyridyl)-1H-pyrrolo[2,3-b]pyridin-5-yl]-3,4-dimethyl-1H-pyrazole-5-carboxamide | 375.3 |

TABLE 1-continued

| No. | Compound | Name | MS(ESI) [M + H+]+ or [M − H+]− observed |
|---|---|---|---|
| P-2171 | | N-[2-(3-chloro-2-methoxy-4-pyridyl)-1H-pyrrolo[2,3-b]pyridin-5-yl]-3,4-dimethyl-1H-pyrazole-5-carboxamide | 396.9 |
| P-2172 | | 3-(difluoromethyl)-N-[2-(4-fluorophenyl)-1H-pyrrolo[2,3-b]pyridin-5-yl]-1H-pyrazole-5-carboxamide | 372.1 |
| P-2173 | | 4-chloro-3-ethyl-N-[2-(4-fluorophenyl)-1H-pyrrolo[2,3-b]pyridin-5-yl]-1H-pyrazole-5-carboxamide | 383.8 |
| P-2174 | | N-[2-[4-fluoro-3-(2H-tetrazol-5-yl)phenyl]-1H-pyrrolo[2,3-b]pyridin-5-yl]-3,4-dimethyl-1H-pyrazole-5-carboxamide | 417.8 |
| P-2175 | | N-cyclopropyl-4-[5-[(3,4-dimethyl-1H-pyrazole-5-carbonyl)amino]-1H-pyrrolo[2,3-b]pyridin-2-yl]pyridine-2-carboxamide | 415.9 |

TABLE 1-continued

| No. | Compound | Name | MS(ESI) [M + H+]+ or [M − H+]− observed |
|---|---|---|---|
| P-2176 | | 3,4-dimethyl-N-[2-[2-(trifluoromethyl)-3-pyridyl]-1H-pyrrolo[2,3-b]pyridin-5-yl]-1H-pyrazole-5-carboxamide | 401.2 |
| P-2177 | | N-[2-(2-ethyl-4-pyridyl)-1H-pyrrolo[2,3-b]pyridin-5-yl]-3,4-dimethyl-1H-pyrazole-5-carboxamide | 361.2 |
| P-2178 | | N-[2-(6-ethyl-3-pyridyl)-1H-pyrrolo[2,3-b]pyridin-5-yl]-3,4-dimethyl-1H-pyrazole-5-carboxamide | 361.2 |
| P-2179 | | N-[2-(2,3-dihydro-[1,4]dioxino[2,3-b]pyridin-8-yl)-1H-pyrrolo[2,3-b]pyridin-5-yl]-3,4-dimethyl-1H-pyrazole-5-carboxamide | 391.3 |
| P-2180 | | 3,4-dimethyl-N-[2-[2-(trifluoromethyl)phenyl]-1H-pyrrolo[2,3-b]pyridin-5-yl]-1H-pyrazole-5-carboxamide | 400.3 |
| P-2181 | | N-[2-(2,4-dimethylphenyl)-1H-pyrrolo[2,3-b]pyridin-5-yl]-3,4-dimethyl-1H-pyrazole-5-carboxamide | 360.3 |

TABLE 1-continued

| No. | Compound | Name | MS(ESI) [M + H+]+ or [M − H+]− observed |
|---|---|---|---|
| P-2182 | | 3,4-dimethyl-N-[2-[2-(trifluoromethoxy)phenyl]-1H-pyrrolo[2,3-b]pyridin-5-yl]-1H-pyrazole-5-carboxamide | 416.2 |
| P-2183 | | N-[2-(5-methoxy-3-pyridyl)-1H-pyrrolo[2,3-b]pyridin-5-yl]-3,4-dimethyl-1H-pyrazole-5-carboxamide | 363.3 |
| P-2184 | | 3,4-dimethyl-N-[2-(5-methyl-3-pyridyl)-1H-pyrrolo[2,3-b]pyridin-5-yl]-1H-pyrazole-5-carboxamide | 347.1 |
| P-2185 | | N-[2-(4-methoxy-3-pyridyl)-1H-pyrrolo[2,3-b]pyridin-5-yl]-3,4-dimethyl-1H-pyrazole-5-carboxamide | 363.3 |
| P-2186 | | 3,4-dimethyl-N-[2-[2-(4-methylsulfonylpiperazin-1-yl)-4-pyridyl-1H-pyrrolo[2,3-b]pyridin-5-yl]-1H-pyrazole-5-carboxamide | 494.9 |

TABLE 1-continued

| No. | Compound | Name | MS(ESI) [M + H+]+ or [M − H+]− observed |
|---|---|---|---|
| P-2187 | | N-[2-[2-[4-(cyclopropanecarbonyl)piperazin-1-yl]-4-pyridyl]-1H-pyrrolo[2,3-b]pyridin-5-yl]-3,4-dimethyl-1H-pyrazole-5-carboxamide | 485.0 |
| P-2188 | | N-(2-iodo-1H-pyrrolo[2,3-b]pyridin-5-yl)-3,4-dimethyl-1H-pyrazole-5-carboxamide | 381.9 |
| P-2189 | | N-[2-[2-[4-(2-cyanoacetyl)piperazin-1-yl]-4-pyridyl]-1H-pyrrolo[2,3-b]pyridin-5-yl]-3,4-dimethyl-1H-pyrazole-5-carboxamide | 484.3 |

*MS(ESI) [M − H]− observed.

Exemplary compounds of the present disclosure as set forth in Table 2, e.g., compounds P-2190 to P-2273 were prepared according to the protocols set forth in Examples 1 to 25 and Schemes 1 to 25. The $^1$H NMR and mass spectroscopy data were consistent with the structures of the compounds.

TABLE 2

| No. | Compound | Name | MS(ESI) [M + H+]+ observed |
|---|---|---|---|
| P-2190 | | 4,5-dimethyl-N-(3-(6-(piperazin-1-yl)pyridin-2-yl)-1H-pyrrolo[2,3-b]pyridin-5-yl)-1H-pyrazole-3-carboxamide | |

TABLE 2-continued

| No. | Compound | Name | MS(ESI) [M + H+]+ observed |
|---|---|---|---|
| P-2191 | | 4,5-dimethyl-N-(3-(6-(piperazin-1-yl)pyridin-2-yl)-1H-pyrrolo[2,3-b]pyridin-5-yl)-1H-pyrazole-3-carboxamide | |
| P-2192 | | 4,5-dimethyl-N-(3-(6-morpholinopyridin-2-yl)-1H-pyrrolo[2,3-b]pyridin-5-yl)-1H-pyrazole-3-carboxamide | |
| P-2193 | | 4,5-dimethyl-N-(3-(2-morpholinopyridin-4-yl)-1H-pyrrolo[2,3-b]pyridin-5-yl)-1H-pyrazole-3-carboxamide | |
| P-2194 | | N-(2-(1-(1-acetylazetidin-3-yl)-3-methyl-1H-pyrazol-4-yl)-1H-pyrrolo[2,3-b]pyridin-5-yl)-4,5-dimethyl-1H-pyrazole-3-carboxamide | |
| P-2195 | | N-(2-(1-(azetidin-3-yl)-3-methyl-1H-pyrazol-4-yl)-1H-pyrrolo[2,3-b]pyridin-5-yl)-4,5-dimethyl-1H-pyrazole-3-carboxamide | |

TABLE 2-continued

| No. | Compound | Name | MS(ESI) [M + H+]+ observed |
|---|---|---|---|
| P-2196 | | 4,5-dimethyl-N-(2-(5-methyl-1-(oxetan-3-yl)-1H-pyrazol-4-yl)-1H-pyrrolo[2,3-b]pyridin-5-yl)-1H-pyrazole-3-carboxamide | |
| P-2197 | | N-(2-(1-(azetidin-3-yl)-5-methyl-1H-pyrazol-4-yl)-1H-pyrrolo[2,3-b]pyridin-5-yl)-4,5-dimethyl-1H-pyrazole-3-carboxamide | |
| P-2198 | | 4,5-dimethyl-N-(2-(5-methyl-1-(piperidin-4-yl)-1H-pyrazol-4-yl)-1H-pyrrolo[2,3-b]pyridin-5-yl)-1H-pyrazole-3-carboxamide | |
| P-2199 | | N-(2-(1-(1-acetylpiperidin-4-yl)-5-methyl-1H-pyrazol-4-yl)-1H-pyrrolo[2,3-b]pyridin-5-yl)-4,5-dimethyl-1H-pyrazole-3-carboxamide | |
| P-2200 | | N-(2-(1-(1-(cyclopropanecarbonyl)piperidin-4-yl)-5-methyl-1H-pyrazol-4-yl)-1H-pyrrolo[2,3-b]pyridin-5-yl)-4,5-dimethyl-1H-pyrazole-3-carboxamide | |
| P-2201 | | 4,5-dimethyl-N-(2-(3-methyl-1-(piperidin-4-yl)-1H-pyrazol-4-yl)-1H-pyrrolo[2,3-b]pyridin-5-yl)-1H-pyrazole-3-carboxamide | |

TABLE 2-continued

| No. | Compound | Name | MS(ESI) [M + H+]+ observed |
|---|---|---|---|
| P-2202 | | N-(2-(1-(1-acetylpiperidin-4-yl)-3-methyl-1H-pyrazol-4-yl)-1H-pyrrolo[2,3-b]pyridin-5-yl)-4,5-dimethyl-1H-pyrazole-3-carboxamide | |
| P-2203 | | N-(2-(1-(1-(cyclopropanecarbonyl)piperidin-4-yl)-3-methyl-1H-pyrazol-4-yl)-1H-pyrrolo[2,3-b]pyridin-5-yl)-4,5-dimethyl-1H-pyrazole-3-carboxamide | |
| P-2204 | | N-(2-(2-(cyclopropylamino)pyridin-4-yl)-1H-pyrrolo[2,3-b]pyridin-5-yl)-4,5-dimethyl-1H-pyrazole-3-carboxamide | |
| P-2205 | | N-(2-(3-chloro-2-(cyclopropanecarboxamido)pyridin-4-yl)-1H-pyrrolo[2,3-b]pyridin-5-yl)-4,5-dimethyl-1H-pyrazole-3-carboxamide | |
| P-2206 | | N-(2-(2-(cyclopropanecarboxamido)pyridin-4-yl)-1H-pyrrolo[2,3-b]pyridin-5-yl)-4,5-dimethyl-1H-pyrazole-3-carboxamide | |
| P-2207 | | N-(2-(2-(1-(cyclopropanecarbonyl)piperidin-4-yl)pyridin-4-yl)-1H-pyrrolo[2,3-b]pyridin-5-yl)-4,5-dimethyl-1H-pyrazole-3-carboxamide | |

TABLE 2-continued

| No. | Compound | Name | MS(ESI) [M + H+]+ observed |
|---|---|---|---|
| P-2208 | | 4,5-dimethyl-N-(2-(2-(pyrrolidin-1-yl)pyridin-4-yl)-1H-pyrrolo[2,3-b]pyridin-5-yl)-1H-pyrazole-3-carboxamide | |
| P-2209 | | 4,5-dimethyl-N-(2-(2-(piperidin-1-yl)pyridin-4-yl)-1H-pyrrolo[2,3-b]pyridin-5-yl)-1H-pyrazole-3-carboxamide | |
| P-2210 | | 4,5-dimethyl-N-(2-(2-(4-methylpiperidin-1-yl)pyridin-4-yl)-1H-pyrrolo[2,3-b]pyridin-5-yl)-1H-pyrazole-3-carboxamide | |
| P-2211 | | 4,5-dimethyl-N-(2-(2-(piperidin-4-yl)pyridin-4-yl)-1H-pyrrolo[2,3-b]pyridin-5-yl)-1H-pyrazole-3-carboxamide | |
| P-2212 | | N-(2-(2-(4-hydroxypiperidin-1-yl)pyridin-4-yl)-1H-pyrrolo[2,3-b]pyridin-5-yl)-4,5-dimethyl-1H-pyrazole-3-carboxamide | |
| P-2213 | | N-(2-(2-(3-hydroxypiperidin-1-yl)pyridin-4-yl)-1H-pyrrolo[2,3-b]pyridin-5-yl)-4,5-dimethyl-1H-pyrazole-3-carboxamide | |

TABLE 2-continued

| No. | Compound | Name | MS(ESI) [M + H+]+ observed |
|---|---|---|---|
| P-2214 | | N-(2-(2-(4-acetylpiperazin-1-yl)pyridin-4-yl)-1H-pyrrolo[2,3-b]pyridin-5-yl)-4,5-dimethyl-1H-pyrazole-3-carboxamide | |
| P-2215 | | 4,5-dimethyl-N-(2-(2-(4-(3-methylbut-2-enoyl)piperazin-1-yl)pyridin-4-yl)-1H-pyrrolo[2,3-b]pyridin-5-yl)-1H-pyrazole-3-carboxamide | |
| P-2216 | | 4,5-dimethyl-N-(2-(2-(morpholine-4-carbonyl)pyridin-4-yl)-1H-pyrrolo[2,3-b]pyridin-5-yl)-1H-pyrazole-3-carboxamide | |
| P-2217 | | 4,5-dimethyl-N-(2-(2-(4-methylpiperazine-1-carbonyl)pyridin-4-yl)-1H-pyrrolo[2,3-b]pyridin-5-yl)-1H-pyrazole-3-carboxamide | |
| P-2218 | | 4,5-dimethyl-N-(2-(2-(pyrrolidine-1-carbonyl)pyridin-4-yl)-1H-pyrrolo[2,3-b]pyridin-5-yl)-1H-pyrazole-3-carboxamide | |
| P-2219 | | 4,5-dimethyl-N-(2-(2-(thiomorpholine-4-carbonyl)pyridin-4-yl)-1H-pyrrolo[2,3-b]pyridin-5-yl)-1H-pyrazole-3-carboxamide | |

TABLE 2-continued

| No. | Compound | Name | MS(ESI) [M + H+]+ observed |
|---|---|---|---|
| P-2220 | | 4-(5-(4,5-dimethyl-1H-pyrazole-3-carboxamido)-1H-pyrrolo[2,3-b]pyridin-2-yl)-N-(2-methoxyethyl)picolinamide | |
| P-2221 | | 4-(5-(4,5-dimethyl-1H-pyrazole-3-carboxamido)-1H-pyrrolo[2,3-b]pyridin-2-yl)-N-(2-(dimethylamino)ethyl)picolinamide | |
| P-2222 | | 4-(5-(4,5-dimethyl-1H-pyrazole-3-carboxamido)-1H-pyrrolo[2,3-b]pyridin-2-yl)-N-(2-methoxyethyl)picolinamide | |
| P-2223 | | 4-(5-(4,5-dimethyl-1H-pyrazole-3-carboxamido)-1H-pyrrolo[2,3-b]pyridin-2-yl)-N-methoxypicolinamide | |
| P-2224 | | 4-(5-(4,5-dimethyl-1H-pyrazole-3-carboxamido)-1H-pyrrolo[2,3-b]pyridin-2-yl)-N,N-dimethylpicolinamide | |
| P-2225 | | 4-(5-(4,5-dimethyl-1H-pyrazole-3-carboxamido)-1H-pyrrolo[2,3-b]pyridin-2-yl)-N-(2-morpholinoethyl)picolinamide | |
| P-2226 | | 4-(5-(4,5-dimethyl-1H-pyrazole-3-carboxamido)-1H-pyrrolo[2,3-b]pyridin-2-yl)-N-(2-(4-methylpiperazin-1-yl)ethyl)picolinamide | |

TABLE 2-continued

| No. | Compound | Name | MS(ESI) [M + H+]+ observed |
|---|---|---|---|
| P-2227 | | N-(2-cyanoethyl)-4-(5-(4,5-dimethyl-1H-pyrazole-3-carboxamido)-1H-pyrrolo[2,3-b]pyridin-2-yl)picolinamide | |
| P-2228 | | 4-(5-(4,5-dimethyl-1H-pyrazole-3-carboxamido)-1H-pyrrolo[2,3-b]pyridin-2-yl)-N-isobutylpicolinamide | |
| P-2229 | | 4-(5-(4,5-dimethyl-1H-pyrazole-3-carboxamido)-1H-pyrrolo[2,3-b]pyridin-2-yl)-N-isopropylpicolinamide | |
| P-2230 | | 4-(5-(4,5-dimethyl-1H-pyrazole-3-carboxamido)-1H-pyrrolo[2,3-b]pyridin-2-yl)-N,N-diethylpicolinamide | |
| P-2231 | | 4-methyl-N-(2-phenyl-1H-pyrrolo[2,3-b]pyridin-5-yl)-5-(trifluoromethyl)-1H-pyrazole-3-carboxamide | |
| P-2232 | | 4-chloro-N-(2-phenyl-1H-pyrrolo[2,3-b]pyridin-5-yl)-5-(trifluoromethyl)-1H-pyrazole-3-carboxamide | |
| P-2233 | | 5-chloro-N-(2-phenyl-1H-pyrrolo[2,3-b]pyridin-5-yl)-4-(trifluoromethyl)-1H-pyrazole-3-carboxamide | |

TABLE 2-continued

| No. | Compound | Name | MS(ESI) [M + H+]+ observed |
|---|---|---|---|
| P-2234 | | 5-(difluoromethyl)-4-methyl-N-(2-phenyl-1H-pyrrolo[2,3-b]pyridin-5-yl)-1H-pyrazole-3-carboxamide | |
| P-2235 | | 4-(difluoromethyl)-5-methyl-N-(2-phenyl-1H-pyrrolo[2,3-b]pyridin-5-yl)-1H-pyrazole-3-carboxamide | |
| P-2236 | | 5-chloro-4-(difluoromethyl)-N-(2-phenyl-1H-pyrrolo[2,3-b]pyridin-5-yl)-1H-pyrazole-3-carboxamide | |
| P-2237 | | 4-chloro-5-(difluoromethyl)-N-(2-phenyl-1H-pyrrolo[2,3-b]pyridin-5-yl)-1H-pyrazole-3-carboxamide | |
| P-2238 | | N-(2-(2-methoxypyridin-3-yl)-1H-pyrrolo[2,3-b]pyridin-5-yl)-4,5-dimethyl-1H-pyrazole-3-carboxamide | 363.3 |
| P-2239 | | N-(2-(2-ethoxypyridin-3-yl)-1H-pyrrolo[2,3-b]pyridin-5-yl)-4,5-dimethyl-1H-pyrazole-3-carboxamide | 377.1 |
| P-2240 | | N-(2-(2-(difluoromethoxy)pyridin-3-yl)-1H-pyrrolo[2,3-b]pyridin-5-yl)-4,5-dimethyl-1H-pyrazole-3-carboxamide | 399.1 |

TABLE 2-continued

| No. | Compound | Name | MS(ESI) [M + H+]+ observed |
|---|---|---|---|
| P-2241 | 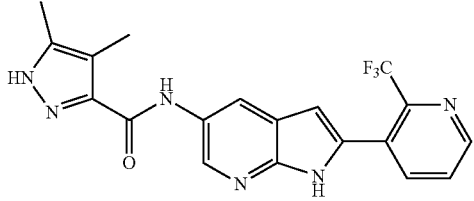 [SMILES: Cc1[nH]nc(C(=O)Nc2cnc3[nH]c(-c4cccnc4C(F)(F)F)cc3c2)c1C] | 4,5-dimethyl-N-(2-(2-(trifluoromethyl)pyridin-3-yl)-1H-pyrrolo[2,3-b]pyridin-5-yl)-1H-pyrazole-3-carboxamide | |
| P-2242 | 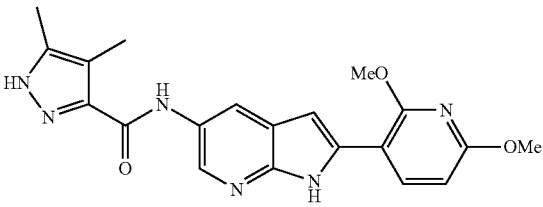 [SMILES: COc1ccc(-c2cc3cc(NC(=O)c4n[nH]c(C)c4C)cnc3[nH]2)c(OC)n1] | N-(2-(2,6-dimethoxypyridin-3-yl)-1H-pyrrolo[2,3-b]pyridin-5-yl)-4,5-dimethyl-1H-pyrazole-3-carboxamide | 393.4 |
| P-2243 |  | N-(2-(5-cyclopropylpyridin-3-yl)-1H-pyrrolo[2,3-b]pyridin-5-yl)-4,5-dimethyl-1H-pyrazole-3-carboxamide | 373.2 |
| P-2244 | 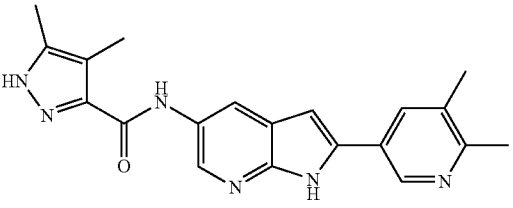 [SMILES: Cc1cc(-c2cc3cc(NC(=O)c4n[nH]c(C)c4C)cnc3[nH]2)cnc1C] | N-(2-(5,6-dimethylpyridin-3-yl)-1H-pyrrolo[2,3-b]pyridin-5-yl)-4,5-dimethyl-1H-pyrazole-3-carboxamide | |
| P-2245 | 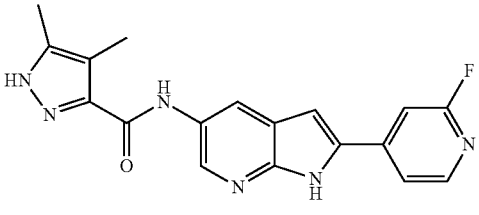 [SMILES: Cc1[nH]nc(C(=O)Nc2cnc3[nH]c(-c4ccnc(F)c4)cc3c2)c1C] | N-(2-(2-fluoropyridin-4-yl)-1H-pyrrolo[2,3-b]pyridin-5-yl)-4,5-dimethyl-1H-pyrazole-3-carboxamide | 393.4 |
| P-2246 | 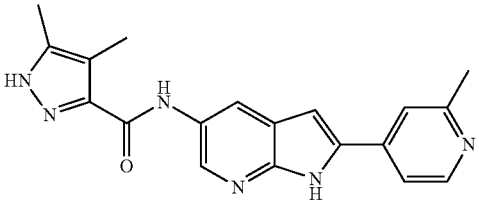 [SMILES: Cc1cc(-c2cc3cc(NC(=O)c4n[nH]c(C)c4C)cnc3[nH]2)ccn1] | 4,5-dimethyl-N-(2-(2-methylpyridin-4-yl)-1H-pyrrolo[2,3-b]pyridin-5-yl)-1H-pyrazole-3-carboxamide | 347.1 |
| P-2247 | 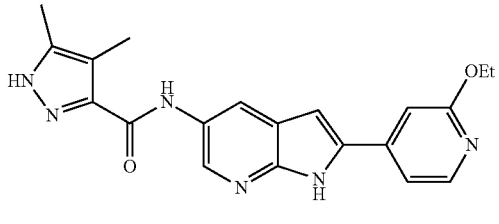 [SMILES: CCOc1cc(-c2cc3cc(NC(=O)c4n[nH]c(C)c4C)cnc3[nH]2)ccn1] | N-(2-(2-ethoxypyridin-4-yl)-1H-pyrrolo[2,3-b]pyridin-5-yl)-4,5-dimethyl-1H-pyrazole-3-carboxamide | 377.1 |

TABLE 2-continued

| No. | Name | MS(ESI) [M + H+]+ observed |
|---|---|---|
| P-2248 | N-(2-(2-isopropoxypyridin-4-yl)-1H-pyrrolo[2,3-b]pyridin-5-yl)-4,5-dimethyl-1H-pyrazole-3-carboxamide | 391.3 |
| P-2249 | N-(2-(3-chloro-2-methoxypyridin-4-yl)-1H-pyrrolo[2,3-b]pyridin-5-yl)-4,5-dimethyl-1H-pyrazole-3-carboxamide | |
| P-2250 | N-(2-(3-chloropyridin-4-yl)-1H-pyrrolo[2,3-b]pyridin-5-yl)-4,5-dimethyl-1H-pyrazole-3-carboxamide | |
| P-2251 | 4,5-dimethyl-N-(2-(3-methylpyridin-4-yl)-1H-pyrrolo[2,3-b]pyridin-5-yl)-1H-pyrazole-3-carboxamide | 347.1 |
| P-2252 | 4,5-dimethyl-N-(2-(2-(pyrrolidin-1-yl)pyridin-4-yl)-1H-pyrrolo[2,3-b]pyridin-5-yl)-1H-pyrazole-3-carboxamide | 402.1 |
| P-2253 | N-(2-(5-fluoropyridin-3-yl)-1H-pyrrolo[2,3-b]pyridin-5-yl)-4,5-dimethyl-1H-pyrazole-3-carboxamide | 351.3 |
| P-2254 | 4,5-dimethyl-N-(2-(5-(trifluoromethyl)pyridin-3-yl)-1H-pyrrolo[2,3-b]pyridin-5-yl)-1H-pyrazole-3-carboxamide | 401.2 |

TABLE 2-continued

| No. | Compound | Name | MS(ESI) [M + H+]+ observed |
|---|---|---|---|
| P-2255 | | N-(2-(6-cyclopropylpyridin-3-yl)-1H-pyrrolo[2,3-b]pyridin-5-yl)-4,5-dimethyl-1H-pyrazole-3-carboxamide | 373.2 |
| P-2256 | | N-(2-(5-ethylpyridin-3-yl)-1H-pyrrolo[2,3-b]pyridin-5-yl)-4,5-dimethyl-1H-pyrazole-3-carboxamide | 361.2 |
| P-2257 | | N-(2-(2-(difluoromethyl)phenyl)-1H-pyrrolo[2,3-b]pyridin-5-yl)-4,5-dimethyl-1H-pyrazole-3-carboxamide | |
| P-2258 | | N-(2-(4-chloro-2-methylphenyl)-1H-pyrrolo[2,3-b]pyridin-5-yl)-4,5-dimethyl-1H-pyrazole-3-carboxamide | |
| P-2259 | | N-(2-(4-fluoro-2-methylphenyl)-1H-pyrrolo[2,3-b]pyridin-5-yl)-4,5-dimethyl-1H-pyrazole-3-carboxamide | 364.2 |
| P-2260 | | N-(2-(2,4-difluorophenyl)-1H-pyrrolo[2,3-b]pyridin-5-yl)-4,5-dimethyl-1H-pyrazole-3-carboxamide | 368.1 |
| P-2261 | | N-(2-(3-cyano-2,4-difluorophenyl)-1H-pyrrolo[2,3-b]pyridin-5-yl)-4,5-dimethyl-1H-pyrazole-3-carboxamide | |

TABLE 2-continued

| No. | Compound | Name | MS(ESI) [M + H+]+ observed |
|---|---|---|---|
| P-2262 | | N-(2-(4-fluoro-2,3-dimethylphenyl)-1H-pyrrolo[2,3-b]pyridin-5-yl)-4,5-dimethyl-1H-pyrazole-3-carboxamide | |
| P-2263 | | N-(2-(2-(difluoromethoxy)phenyl)-1H-pyrrolo[2,3-b]pyridin-5-yl)-4,5-dimethyl-1H-pyrazole-3-carboxamide | 398.2 |
| P-2264 | | N-(2-(2-(difluoromethoxy)-3-fluorophenyl)-1H-pyrrolo[2,3-b]pyridin-5-yl)-4,5-dimethyl-1H-pyrazole-3-carboxamide | |
| P-2265 | | N-(2-(3,6-dihydro-2H-pyran-4-yl)-1H-pyrrolo[2,3-b]pyridin-5-yl)-4,5-dimethyl-1H-pyrazole-3-carboxamide | |
| P-2266 | | 4,5-dimethyl-N-(2-(2,2,6,6-tetramethyl-1,2,3,6-tetrahydropyridin-4-yl)-1H-pyrrolo[2,3-b]pyridin-5-yl)-1H-pyrazole-3-carboxamide | 393.3 |
| P-2267 | | N-(2-(2,2-difluorobenzo[d][1,3]dioxol-4-yl)-1H-pyrrolo[2,3-b]pyridin-5-yl)-4,5-dimethyl-1H-pyrazole-3-carboxamide | |
| P-2268 | | N-[2-[2-(difluoromethoxy)-4-fluoro-phenyl]-1H-pyrrolo[2,3-b]pyridin-5-yl]-3,4-dimethyl-1H-pyrazole-5-carboxamide | 416.2 |

TABLE 2-continued

| No. | Name | MS(ESI) [M + H+]+ observed |
|---|---|---|
| P-2269 | N-[2-(6-fluoro-3-pyridyl)-1H-pyrrolo[2,3-b]pyridin-5-yl]-3,4-dimethyl-1H-pyrazole-5-carboxamide | 351.3 |
| P-2270 | N-[2-(5-cyano-3-pyridyl)-1H-pyrrolo[2,3-b]pyridin-5-yl]-3,4-dimethyl-1H-pyrazole-5-carboxamide | 358.2 |
| P-2271 | N-[2-(3,6-dihydro-2H-pyran-4-yl)-1H-pyrrolo[2,3-b]pyridin-5-yl]-3,4-dimethyl-1H-pyrazole-5-carboxamide | 338.4 |
| P-2272 | 3-[5-[(3,4-dimethyl-1H-pyrazole-5-carbonyl)amino]-1H-pyrrolo[2,3-b]pyridin-2-yl]pyridine-4-carboxamide | 376.2 |
| P-2273 | N-[2-(2,3-dihydrobenzofuran-7-yl)-1H-pyrrolo[2,3-b]pyridin-5-yl]-3,4-dimethyl-1H-pyrazole-5-carboxamide | 374.1 |

Exemplary compounds of the present disclosure as set forth in Table 3, e.g., compounds P-2274 to P-2307 were prepared according to the protocols set forth in Examples 1 to 25 and Schemes 1 to 25. The ¹H NMR and mass spectroscopy data were consistent with the structures of the compounds

TABLE 3

| No. | Compound | Name | MS(ESI) [M + H+]+ observed |
|---|---|---|---|
| P-2274 | | 3,4-dimethyl-N-[2-(3-piperazin-1-ylphenyl)-1H-pyrrolo[2,3-b]pyridin-5-yl]-1H-pyrazole-5-carboxamide | 416.0 |
| P-2275 | | 4-fluoro-N-[2-(4-fluorophenyl)-1H-pyrrolo[2,3-b]pyridin-5-yl]-3-methyl-1H-pyrazole-5-carboxamide | 355.0 |
| P-2276 | | N-[2-[3-(isobutylcarbamoyl)phenyl]-1H-pyrrolo[2,3-b]pyridin-5-yl]-3,4-dimethyl-1H-pyrazole-5-carboxamide | 431.0 |
| P-2277 | | N-[2-(4-chloro-2-methyl-phenyl)-1H-pyrrolo[2,3-b]pyridin-5-yl]-3,4-dimethyl-1H-pyrazole-5-carboxamide | 380.1 |
| P-2278 | | N-[2-(3-chloro-4-pyridyl)-1H-pyrrolo[2,3-b]pyridin-5-yl]-3,4-dimethyl-1H-pyrazole-5-carboxamide | 367.2 |
| P-2279 | | N-[2-(4-fluoro-2,3-dimethyl-phenyl)-1H-pyrrolo[2,3-b]pyridin-5-yl]-3,4-dimethyl-1H-pyrazole-5-carboxamide | 378.3 |

TABLE 3-continued

| No. | Compound | Name | MS(ESI) [M + H+]+ observed |
|---|---|---|---|
| P-2280 | | N-[2-(2,6-difluoro-3-pyridyl)-1H-pyrrolo[2,3-b]pyridin-5-yl]-3,4-dimethyl-1H-pyrazole-5-carboxamide | 369.0 |
| P-2281 | | N-[2-(2,2-difluoro-1,3-benzodioxol-4-yl)-1H-pyrrolo[2,3-b]pyridin-5-yl]-3,4-dimethyl-1H-pyrazole-5-carboxamide | 412.0 |
| P-2282 | | N-[2-(5,6-dimethyl-3-pyridyl)-1H-pyrrolo[2,3-b]pyridin-5-yl]-3,4-dimethyl-1H-pyrazole-5-carboxamide | 361.2 |
| P-2283 | | N-[2-(6-fluoro-2-methyl-3-pyridyl)-1H-pyrrolo[2,3-b]pyridin-5-yl]-3,4-dimethyl-1H-pyrazole-5-carboxamide | 365.1 |
| P-2284 | | N-[2-(4-methoxy-2,3-dimethyl-phenyl)-1H-pyrrolo[2,3-b]pyridin-5-yl]-3,4-dimethyl-1H-pyrazole-5-carboxamide | 390.4 |
| P-2285 | | tert-butyl 3-[4-[5-[(3,4-dimethyl-1H-pyrazole-5-carbonyl)amino]-1H-pyrrolo[2,3-b]pyridin-2-yl]-3-methyl-pyrazol-1-yl]azetidine-1-carboxylate | 491.4 |

TABLE 3-continued

| No. | Name | MS(ESI) [M + H+]+ observed |
|---|---|---|
| P-2286 | N-[2-[1-(azetidin-3-yl)-3-methyl-pyrazol-4-yl]-1H-pyrrolo[2,3-b]pyridin-5-yl]-3,4-dimethyl-1H-pyrazole-5-carboxamide | 391.0 |
| P-2287 | 3-(difluoromethyl)-N-[2-(4-fluorophenyl)-1H-pyrrolo[2,3-b]pyridin-5-yl]-4-methyl-1H-pyrazole-5-carboxamide | 386.1 |
| P-2288 | N-(2-iodo-1H-pyrrolo[2,3-b]pyridin-5-yl)-2H-indazole-4-carboxamide | 403.9 |
| P-2289 | N-(2-phenyl-1H-pyrrolo[2,3-b]pyridin-5-yl)-2H-indazole-4-carboxamide | 353.9 |
| P-2290 | methyl 3-[(2-phenyl-1H-pyrrolo[2,3-b]pyridin-5-yl)carbamoyl]benzoate | 372.1 |
| P-2291 | 3-[(2-phenyl-1H-pyrrolo[2,3-b]pyridin-5-yl)carbamoyl]benzoic acid | 357.8 |
| P-2292 | 4-[5-[(3,4-dimethyl-1H-pyrazole-5-carbonyl)amino]-1H-pyrrolo[2,3-b]pyridin-2-yl]-2-fluoro-benzoic acid | 394.3 |

TABLE 3-continued

| No. | Compound | Name | MS(ESI) [M + H+]+ observed |
|---|---|---|---|
| P-2293 | | 2-[3-[5-[(3,4-dimethyl-1H-pyrazole-5-carbonyl)amino]-1H-pyrrolo[2,3-b]pyridin-2-yl]phenyl]acetic acid | 390.4 |
| P-2294 | | 1-[4-[5-[(3,4-dimethyl-1H-pyrazole-5-carbonyl)amino]-1H-pyrrolo[2,3-b]pyridin-2-yl]phenyl]cyclopropanecarboxylic acid | 416.2 |
| P-2295 | | 2-[4-[5-[(3,4-dimethyl-1H-pyrazole-5-carbonyl)amino]-1H-pyrrolo[2,3-b]pyridin-2-yl]phenyl]acetic acid | 390.4 |
| P-2296 | | 4-[5-[(3,4-dimethyl-1H-pyrazole-5-carbonyl)amino]-1H-pyrrolo[2,3-b]pyridin-2-yl]-2-methyl-benzoic acid | 390.4 |
| P-2297 | | 3-[5-[(3,4-dimethyl-1H-pyrazole-5-carbonyl)amino]-1H-pyrrolo[2,3-b]pyridin-2-yl]-2-methyl-benzoic acid | 390.4 |

TABLE 3-continued

| No. | Compound | Name | MS(ESI) [M + H+]+ observed |
|---|---|---|---|
| P-2298 | | 1-methyl-N-(2-phenyl-1H-pyrrolo[2,3-b]pyridin-5-yl)indazole-4-carboxamide | 367.8 |
| P-2299 | | N-(2-phenyl-1H-pyrrolo[2,3-b]pyridin-5-yl)-1H-indole-4-carboxamide | 352.8 |
| P-2300 | | N-(2-phenyl-1H-pyrrolo[2,3-b]pyridin-5-yl)-1H-benzimidazole-4-carboxamide | 353.8 |
| P-2301 | | N-(2-methyl-1H-pyrrolo[2,3-b]pyridin-5-yl)-2H-indazole-4-carboxamide | 291.8 |
| P-2302 | | 3,4-dimethyl-N-(2-methyl-1H-pyrrolo[2,3-b]pyridin-5-yl)-1H-pyrazole-5-carboxamide | 270.0 |
| P-2303 | | 4-[(2-phenyl-1H-pyrrolo[2,3-b]pyridin-5-yl)carbamoyl]benzoic acid | 358.2 |
| P-2304 | | N,3,4-trimethyl-N-(2-phenyl-1H-pyrrolo[2,3-b]pyridin-5-yl)-1H-pyrazole-5-carboxamide | 346.2 |

TABLE 3-continued

| No. | Compound | Name | MS(ESI) [M + H+]+ observed |
|---|---|---|---|
| P-2305 | | N-[2-(2,3-dihydro-1,4-benzodioxin-5-yl)-1H-pyrrolo[2,3-b]pyridin-5-yl]-3,4-dimethyl-1H-pyrazole-5-carboxamide | 389.8 |
| P-2306 | | tert-butyl 4-[4-[5-[(3,4-dimethyl-1H-pyrazole-5-carbonyl)amino]-1H-pyrrolo[2,3-b]pyridin-2-yl]pyrazol-1-yl]piperidine-1-carboxylate | 506.2 |
| P-2307 | | N-[2-(cyclohexen-1-yl)-1H-pyrrolo[2,3-b]pyridin-5-yl]-3,4-dimethyl-1H-pyrazole-5-carboxamide | 336.0 |

Example 26

Compound Properties

While the inhibitory activity of the compounds on any c-kit kinase and mutants thereof is important to their activity in treating of disease, the compounds described herein show favorable properties that provide advantages as a pharmaceutical as well.

The compounds described herein are useful for treating disorders related to c-kit and mutants thereof, e.g., diseases related to unregulated kinase signal transduction, including cell proliferative disorders, fibrotic disorders and metabolic disorders, among others. As described in more detail below and in Lipson et al., U.S. 2004/0002534 (U.S. application Ser. No. 10/600,868, filed Jun. 23, 2003) which is incorporated herein by reference in its entirety, cell proliferative disorders which can be treated by the present disclosure include cancers, and mast cell proliferative disorders.

The presence of c-kit or mutant(s) of c-kit has also been associated with a number of different types of cancers. In addition, the association between abnormalities in c-kit and disease are not restricted to cancer. As such, c-kit has been associated with malignancies, including mast cell tumors, small cell lung cancer, testicular cancer, gastrointestinal stromal tumors (GISTs), glioblastoma, astrocytoma, neuroblastoma, carcinomas of the female genital tract, sarcomas of neuroectodermal origin, colorectal carcinoma, carcinoma in situ, Schwann cell neoplasia associated with neurofibromatosis, acute myelocytic leukemia, acute lymphocytic leukemia, chronic myelogenous leukemia, mastocytosis, melanoma, and canine mast cell tumors, and inflammatory diseases, including asthma, rheumatoid arthritis, allergic rhinitis, multiple sclerosis, inflammatory bowel syndrome, transplant rejection, and hypereosinophilia.

Exemplary c-Kit Biochemical Assay

Assays for biochemical cell-based activity of c-kit kinase are known in the art, for example, as described in U.S. Pat. Nos. 7,498,342 and 7,846,941, the disclosures of which are hereby incorporated by reference as it relates to such assays. The c-kit (or kinase domain thereof) is an active kinase in AlphaScreen. $IC_{50}$ values are determined with respect to inhibition of c-Kit kinase activity, where inhibition of phosphorylation of a peptide substrate is measured as a function of compound concentration. Compounds to be tested were dissolved in DMSO to a concentration of 20 mM. These were diluted 30 µl into 120 µl of DMSO (4 mM) and 1 µl was added to an assay plate. These were then serially diluted 1:3 (50 µl to 100 µl DMSO) for a total of 8 points. Plates were prepared such that each kinase reaction is 20 µl in 1× kinase buffer (50 mM HEPES, pH 7.2, 5 mM $MgCl_2$, 5 mM $MnCl_2$, 0.01% NP-40, 0.2% BSA), 5% DMSO and 10 gM ATP. Substrate was 100 nM biotin-(E4Y)3 (Open Source Biotech, Inc.). C-kit kinase was at 0.1 ng per sample. After incubation of the kinase reaction for 1 hour at room temperature, 5 µl of donor beads (Streptavidin coated beads (Perkin Elmer Life Science) final concentration 1 µg/ml) in stop buffer (50 mM EDTA in 1× kinase buffer) was added, the sample was mixed and incubated for 20 minutes at room temperature before adding 5 µl of acceptor beads (PY20 coated beads (Perkin Elmer Life Science) final concentration 1 µg/ml) in stop buffer. The samples were incubated for 60 minutes at room temperature and the signal per well was read on AlphaQuest reader. Phosphorylated substrate results in binding of the PY20 antibody and association of the donor and acceptor beads such that signal correlates with kinase activity. The signal vs. compound concentration was used to determine the $IC_{50}$.

Compounds were also tested using a similar assay with a 10-fold higher ATP concentration. For these samples, compounds to be tested were dissolved in DMSO to a concentration of 20 mM. These were diluted 30 µl into 120 µl of DMSO (4 mM) and 1 µl was added to an assay plate. These were then serially diluted 1:3 (50 µl to 100 µl DMSO) for a total of 8 points. Plates were prepared such that each kinase reaction is 20 µl in 1× kinase buffer (25 mM HEPES, pH 7.5, 2 mM MgCl$_2$, 2 mM MnCl$_2$, 0.01% Tween-20, 1 mM DTT, and 0.001% BSA), 5% DMSO and 100 gM ATP. Substrate was 30 nM biotin-(E4Y)10 (Upstate Biotech, Cat#12-440). C-kit kinase was at 1 ng per sample. After incubation of the kinase reaction for 1 hour at room temperature, 5 µl of donor beads (Streptavidin coated beads (Perkin Elmer Life Science) final concentration 10 µg/ml) in stop buffer (25 mM HEPES pH 7.5, 100 mM EDTA, 0.3% BSA) was added, the sample was mixed and incubated for 20 minutes at room temperature before adding 5 µl of acceptor beads (PY20 coated beads (Perkin Elmer Life Science) final concentration 10 µg/ml) in stop buffer. The samples were incubated for 60 minutes at room temperature and the signal per well was read on AlphaQuest or Envision reader (Perkin Elmer Life Science). Phosphorylated substrate results in binding of the PY20 antibody and association of the donor and acceptor beads such that signal correlates with kinase activity. The signal vs. compound concentration was used to determine the IC$_{50}$.

The c-kit enzyme used in the above assay was either obtained from Cell Signaling Technology (Cat. #7754) or was prepared as follows: A plasmid encoding kit (DNA and encoded protein sequences shown below) was engineered using common polymerase chain reaction (PCR) methods. Complementary DNA cloned from various human tissues were purchased from Invitrogen, and these were used as substrates in the PCR reactions. Specific custom synthetic oligonucleotide primers were designed to initiate the PCR product, and also to provide the appropriate restriction enzyme cleavage sites for ligation with the plasmids. The entire sequence encoding the enzyme was made through a gene synthesis procedure, using custom synthetic oligonucleotides covering the entire coding sequence (Invitrogen, see below).

The plasmid used for ligation with the kinase-encoding inserts was derivative of pET (Novagen) for expression using E. coli. The Kit kinase was engineered to include a Histidine tag for purification using metal affinity chromatography. The kinase-encoding plasmid was engineered as bicistronic mRNA to co-express a second protein that modifies the kinase protein during its expression in the host cell. Protein tyrosine phosphatase 1B (PTP), was co-expressed for dephosphorylation of the phospho-Tyrosines.

For protein expression, the plasmid containing the Kit gene was transformed into E. coli strains BL21(DE3)RIL and transformants selected for growth on LB agar plates containing appropriate antibiotics. Single colonies were grown overnight at 37° C. in 200 mL TB (Terrific broth) media. 16×1 L of fresh TB media in 2.8 L flasks were inoculated with 10 mL of overnight culture and grown with constant shaking at 37° C. Once cultures reached an absorbance of 1.0 at 600 nm, IPTG was added and cultures were allowed to grow for a further 12 to 18 hrs at temperatures ranging from 12-30° C. Cells were harvested by centrifugation and pellets frozen at −80° C. until ready for lysis.

For protein Purification; frozen E. coli cell pellets were resuspended in lysis buffer and lysed using standard mechanical methods. Protein was purified via poly-Histidine tags using immobilized metal affinity purification IMAC. The Kit kinase was purified using a 3 step purification process utilizing; IMAC, size exclusion chromatography and ion exchange chromatography. The poly-Histidine tag was removed using Thrombin (Calbiochem).

Compounds were assayed using a similar assay to that described above, using in a final reaction volume of 25 µl: c-Kit (h) (5-10 mU) in 8 mM MOPS pH 7.0, 0.2 mM EDTA, 10 mM MnCl$_2$, 0.1 mg/ml poly (Glu, Tyr) 4:1, 10 mM MgAcetate and γ-$^{33}$P-ATP (approximately 500 cpm/pmol), with appropriate concentrations of compound. Incubated for 40 minutes at room temperature and stopped by addition of 5 µl of 3% phosphoric acid. Spotted 10 µl of each sample onto Filtermat A and washed 3x with 75 mM phosphoric acid, once with methanol, dried and measured on scintillation counter (performed at Upstate USA, Charlottesville, Va.).

Exemplary c-Kit Mutant Biochemical Assay

The c-kit mutant D816V (or kinase domain thereof) is an active kinase in AlphaScreen. IC$_{50}$ values are determined with respect to inhibition of c-Kit mutant D816V kinase activity, where inhibition of phosphorylation of a peptide substrate is measured as a function of compound concentration. Compounds to be tested were dissolved in DMSO to a concentration of 20 mM. These were diluted 30 µl into 120 µl of DMSO (4 mM) and 1 µl was added to an assay plate. These were then serially diluted 1:3 (50 µl to 100 µl DMSO) for a total of 8 points. Plates were prepared such that each kinase reaction is 20 µl in 1× kinase buffer (25 mM HEPES, pH 7.2, 8 mM MgCl$_2$, 2 mM MnCl$_2$, 50 mM NaCl, 0.01% Brij, 1 mM DTT, 0.01% BSA), 5% DMSO and 10 µM ATP. Substrate was 30 nM biotin-(E4Y)10 (EMD Millipore, Cat#12-440). C-kit mutant D816V kinase was at 0.75 ng per sample. After incubation of the kinase reaction for 30 minutes at room temperature, 5 µl of donor beads (Streptavidin coated beads (Perkin Elmer Life Science) final concentration 7.5 µg/ml) in stop buffer (25 mM Hepes pH 7.5, 100 mM EDTA, 0.01% BSA) was added, the sample was mixed and incubated for 20 minutes at room temperature before adding 5 µl of acceptor beads (PY20 coated beads (Perkin Elmer Life Science) final concentration 7.5 ug/ml) in stop buffer. The samples were incubated for 60 minutes at room temperature and the signal per well was read on EnVision reader. Phosphorylated substrate results in binding of the PY20 antibody and association of the donor and acceptor beads such that signal correlates with kinase activity. The signal vs. compound concentration was used to determine the IC$_{50}$.

Protein Expression and Purification

Recombinant c-kit mutant D816V (residues 551-934, kinase insertion domain residues 694-753 deleted) with a 6x-histidine N-terminal tag was expressed in E. coli Arctic Express (DE3) RIL (Stratagene). Cells were grown in Terrific Broth (TB) media to an OD$_{600}$ of 0.6 at 37° C. at which temperature was reduced to 10° C., protein was induced with 1.0 mM IPTG for 18 hours and harvested by centrifugation at 8000×g for 20 minutes. Cells were re-suspended in 0.1M KPO$_4$ pH 8.0, 250 mM NaCl, 10% Glycerol, 0.75% NP-40, 25 mM Imidazole, 5 mM BME with 0.2 mg/ml Lysosyme, 2.0 mM PMSF, 25 µg/ml DNAse I, incubated in ice for 30 minutes and lyzed with a cell disruptor (MicroFluidics). The lysate was clarified by centrifugation at 20,000×g for 2 hours. The protein was captured with Talon resin (Clontech). Contaminating proteins were washed off with 25 mM Tris-HCl pH 8.3, 250 mM NaCl, 15% Glycerol, 1% Triton X-100, and protein eluted using 100 mM EDTA. The protein was further purified using Gel Filtration column 26/600 Superdex 200 (GE) in 50 mM Tris-HCl, pH 8.0, 250 mM NaCl, 15% Glycerol, 5 mM BME. The protein was aliquoted and flash-frozen in liquid Nitrogen.

Exemplary Cell-Based Assays of c-Kit Mutant Kinase Activity

The c-Kit mutant D816V inhibitors were assessed using an engineered BaF3-FL KIT D816V or BaF3-FL KIT V560G/D816V cell line. The BaF3-FL KIT D816V cell lines were created by introduction of KIT mutant (D816V) full length constructs that render the cells dependent on the introduced kinase for growth. Inhibitors of c-Kit mutant D816V kinase reduce or eliminate the mediated c-kit mutant D816V kinase activation, resulting in reduced cell proliferation of the BaF3-FL Kit mutant D816V cells. This inhibition is measured by the effect of compound concentration on cell growth to assess $IC_{50}$ values. BaF3-FL KIT D816V cells were seeded at $1\times10^4$ cells per well of a 96 well cell culture plate in 50 µl of cell culture medium of RPMI Medium 1X (Invitrogen #11875-093) supplemented with 10% FBS (Invitrogen #10438), 1% Non Essential Amino Acids(Invitrogen #11140), 1% Penicillin Streptomycin (Invitrogen #15140), 1% L-Glutamine (Invitrogen #25030-081). Compounds were dissolved in DMSO at a concentration of 5 mM and were serially diluted 1:3 for a total of eight points and added to the cells to a final maximum concentration of 10 µM in 100 µl cell culture medium (final concentration 0.2% DMSO). Cells were also treated with Dasatinib as a positive control. The cells were incubated at 37° C., 5% $CO_2$ for three days. ATPlite Buffer (Perkin Elmer #6016739) and substrate were equilibrated to room temperature, and enzyme/substrate Recombinant Firefly Luciferase/ D-Luciferin was reconstituted. The cell plates were equilibrated to room temperature for 30 minutes, then lysed by addition of 25 uL per well of the ATPlite Reagent. The plate was mixed for 5 minutes on a plate shaker to lyse the cells. The plates were read on a Tecan Safire using Luminescence protocol modified to read 0.1 s per well. The luminescence reading assesses the ATP content, which correlates directly with cell number such that the reading as a function of compound concentration is used to determine the $IC_{50}$ value.

Plasmids P75635 and P75565 were engineered for mammalian cell expression. In both plasmids, full-length human v-kit Hardy-Zuckerman 4 feline sarcoma viral oncogene homolog gene (NCBI accession NM_000222, KIT, residues M1-V976) was subcloned into the pCI-Neo vector (Promega E1841). Plasmid P75635 contains the mutation of residue Aspartic acid 816 to Valine. Plasmid P75565 contains the double mutation of residues Valine 560 to Glycine and Aspartic acid 816 to Valine. The pCI-neo Mammalian Expression Vector carries the human cytomegalovirus (CMV) immediate-early enhancer/promoter region to promote constitutive expression of KIT and contains the neomycin phosphotransferase gene, a selectable marker.

It is understood that the results of these assays may vary as assay conditions are varied. Inhibition levels determined under the conditions described herein represent a relative activity for the compounds tested under the specific conditions employed. The cell based assays are likely to show variability due to the complexity of the system and the sensitivity thereof to any changes in the assay conditions. As such, some level of inhibition in the cell based assays is indicative of the compounds having some inhibitory activity for those cells, whereas lack of inhibition below the threshold of the highest concentration tested does not necessarily indicate that the compound has no inhibitory activity on the cells, only that under the conditions tested, no inhibition is observed. In some instances, the compounds were not tested in all of the assays, or assay results were not valid.

The following table provides data indicating the c-kit and c-kit D816V biochemical inhibitory activity for exemplary compounds as described herein. In the table below, activity in the kit and kit mutant assays is provided as follows: +++=0.0001<$IC_{50}$<1 µM; ++=1 µM<$IC_0$<10 µM; +=10 µM<$IC_{50}$<200 µM.

| Compound number | Biochemical activity ($IC_{50}$ µM) Kit | Biochemical activity ($IC_{50}$ µM) Kit D816V |
|---|---|---|
| P-2003 | | + |
| P-2005 | ++ | +++ |
| P-2007 | +++ | +++ |
| P-2009 | | + |
| P-2010 | + | + |
| P-2011 | | + |
| P-2012 | +++ | ++ |
| P-2013 | +++ | + |
| P-2015 | ++ | ++ |
| P-2016 | ++ | ++ |
| P-2017 | | + |
| P-2018 | + | + |
| P-2019 | + | +++ |
| P-2020 | ++ | |
| P-2021 | | + |
| P-2023 | ++ | +++ |
| P-2024 | + | +++ |
| P-2025 | | + |
| P-2026 | +++ | + |
| P-2027 | +++ | ++ |
| P-2029 | +++ | +++ |
| P-2030 | ++ | + |
| P-2031 | +++ | +++ |
| P-2032 | + | ++ |
| P-2033 | + | +++ |
| P-2034 | +++ | +++ |
| P-2036 | +++ | +++ |
| P-2037 | ++ | +++ |
| P-2038 | +++ | +++ |
| P-2039 | +++ | +++ |
| P-2040 | + | +++ |
| P-2041 | | +++ |
| P-2042 | +++ | +++ |
| P-2043 | +++ | +++ |
| P-2044 | + | +++ |
| P-2045 | + | +++ |
| P-2046 | + | +++ |
| P-2047 | + | +++ |
| P-2048 | +++ | +++ |
| P-2049 | + | +++ |
| P-2050 | + | ++ |
| P-2051 | +++ | +++ |
| P-2052 | ++ | +++ |
| P-2053 | ++ | +++ |
| P-2054 | ++ | +++ |
| P-2055 | ++ | +++ |
| P-2056 | | +++ |
| P-2057 | +++ | +++ |
| P-2058 | + | +++ |
| P-2059 | +++ | +++ |
| P-2060 | +++ | +++ |
| P-2061 | +++ | +++ |
| P-2062 | +++ | +++ |
| P-2063 | | +++ |
| P-2064 | +++ | +++ |
| P-2065 | ++ | +++ |
| P-2066 | | +++ |
| P-2067 | ++ | +++ |
| P-2068 | | ++ |
| P-2069 | ++ | +++ |
| P-2070 | ++ | +++ |
| P-2071 | | + |
| P-2072 | | ++ |
| P-2073 | ++ | +++ |
| P-2074 | +++ | +++ |
| P-2075 | | +++ |
| P-2076 | | +++ |
| P-2077 | | ++ |

| Compound number | Biochemical activity (IC$_{50}$ μM) Kit | Biochemical activity (IC$_{50}$ μM) Kit D816V |
|---|---|---|
| P-2078 |  | +++ |
| P-2079 | ++ | +++ |
| P-2080 | ++ | +++ |
| P-2081 | ++ | +++ |
| P-2112 | ++ | +++ |
| P-2113 |  | ++ |
| P-2114 |  | ++ |
| P-2115 |  | ++ |
| P-2116 | + | ++ |
| P-2118 | + | +++ |
| P-2120 |  | +++ |
| P-2121 |  | +++ |
| P-2122 |  | +++ |
| P-2123 |  | +++ |
| P-2144 | ++ | ++ |
| P-2145 |  | +++ |
| P-2146 |  | +++ |
| P-2148 | +++ | +++ |
| P-2149 |  | +++ |
| P-2150 |  | +++ |
| P-2151 |  | ++ |
| P-2152 |  | +++ |
| P-2153 |  | +++ |
| P-2154 |  | +++ |
| P-2155 |  | +++ |
| P-2157 |  | +++ |
| P-2158 |  | +++ |
| P-2159 |  | +++ |
| P-2160 | ++ | +++ |
| P-2161 |  | +++ |
| P-2162 | +++ | ++ |
| P-2163 | +++ | +++ |
| P-2164 | ++ | +++ |
| P-2165 | +++ | ++ |
| P-2166 | +++ | +++ |
| P-2167 | +++ | +++ |
| P-2168 | +++ | +++ |
| P-2169 |  | +++ |
| P-2172 |  | ++ |
| P-2174 | ++ | +++ |
| P-2175 |  | +++ |
| P-2176 | + | +++ |
| P-2177 | +++ | +++ |
| P-2178 | + | +++ |
| P-2179 | ++ | +++ |
| P-2180 | ++ | +++ |
| P-2181 | + | +++ |
| P-2182 | ++ | +++ |
| P-2183 | + | +++ |
| P-2184 | ++ | +++ |
| P-2185 |  | +++ |
| P-2186 | ++ | +++ |
| P-2187 | ++ | +++ |
| P-2188 |  | ++ |
| P-2189 | +++ | +++ |
| P-2268 | ++ | +++ |
| P-2269 |  | +++ |
| P-2270 | + | +++ |
| P-2271 | +++ | +++ |
| P-2272 | + | +++ |
| P-2273 | + | +++ |
| P-2274 | +++ | +++ |
| P-2275 |  | +++ |
| P-2276 |  | +++ |
| P-2277 | + | +++ |
| P-2278 | + | +++ |
| P-2279 | + |  |
| P-2280 | + | +++ |
| P-2281 | + | +++ |
| P-2282 | ++ | +++ |
| P-2283 |  | +++ |
| P-2284 | ++ | +++ |
| P-2285 | +++ | +++ |
| P-2286 | +++ | +++ |
| P-2287 |  | +++ |
| P-2288 |  | ++ |
| P-2289 | +++ | ++ |
| P-2290 | + | + |
| P-2291 | + | + |
| P-2292 | +++ | +++ |
| P-2293 | +++ | +++ |
| P-2294 | +++ | +++ |
| P-2295 | +++ | +++ |
| P-2296 | +++ | +++ |
| P-2297 | +++ | +++ |
| P-2301 | + |  |

Compounds P-2001 to P-2102, P-2104 to P-2116 and P-2118 to P-2189, e.g., compounds P-2001, P-2002, P-2004, P-2005, P-2006, P-2007, P-2008, P-2012, P-2013, P-2014, P-2015, P-2016, P-2019, P-2020, P-2022, P-2023, P-2024, P-2026, P-2027, P-2028, P-2029, P-2030, P-2031, P-2032, P-2033, P-2034, P-2035, P-2036, P-2037, P-2038, P-2039, P-2040, P-2041, P-2042, P-2043, P-2044, P-2045, P-2046, P-2047, P-2048, P-2049, P-2050, P-2051, P-2052, P-2053, P-2054, P-2055, P-2056, P-2057, P-2058, P-2059, P-2060, P-2061, P-2062, P-2063, P-2064, P-2065, P-2066, P-2067, P-2068, P-2069, P-2070, P-2072, P-2073, P-2074, P-2075, P-2076, P-2077, P-2078, P-2079, P-2080, P-2081, P-2082, P-2083, P-2084, P-2085, P-2086, P-2087, P-2088, P-2089, P-2090, P-2091, P-2092, P-2093, P-2094, P-2095, P-2096, P-2097, P-2098, P-2099, P-2100, P-2101, P-2102, P-2104, P-2105, P-2106, P-2107, P-2108, P-2109, P-2110, P-2111, P-2112, P-2113, P-2114, P-2115, P-2116, P-2117, P-2118, P-2119, P-2120, P-2121, P-2122, P-2123, P-2124, P-2125, P-2126, P-2127, P-2128, P-2129, P-2130, P-2131, P-2132, P-2133, P-2134, P-2135, P-2136, P-2137, P-2138, P-2139, P-2140, P-2141, P-2142, P-2144, P-2145, P-2146, P-2147, P-2148, P-2149, P-2150, P-2151, P-2152, P-2153, P-2154, P-2155, P-2156, P-2157, P-2158, P-2159, P-2160, P-2161, P-2162, P-2163, P-2164, P-2165, P-2166, P-2167, P-2168, P-2169, P-2170, P-2171, P-2172, P-2173, P-2174, P-2175, P-2176, P-2177, P-2178, P-2179, P-2180, P-2181, P-2182, P-2183, P-2184, P-2185, P-2186, P-2187, P-2188 and P-2189 had IC$_{50}$ of less than 10 μM in at least one of the c-kit cell assays described above in Example 26.

Compounds P-2190 to P-2267, e.g., compounds P-2190, P-2191, P-2192, P-2193, P-2194, P-2195, P-2196, P-2197, P-2198, P-2199, P-2200, P-2201, P-2202, P-2203, P-2204, P-2205, P-2206, P-2207, P-2208, P-2209, P-2210, P-2211, P-2212, P-2213, P-2214, P-2215, P-2216, P-2217, P-2218, P-2219, P-2220, P-2221, P-2222, P-2223, P-2224, P-2225, P-2226, P-2227, P-2228, P-2229, P-2230, P-2231, P-2232, P-2233, P-2234, P-2235, P-2236, P-2237, P-2238, P-2239, P-2240, P-2241, P-2242, P-2243, P-2244, P-2245, P-2246, P-2247, P-2248, P-2249, P-2250, P-2251, P-2252, P-2253, P-2254, P-2255, P-2256, P-2257, P-2258, P-2259, P-2260, P-2261, P-2262, P-2263, P-2264, P-2265, P-2266, and P-2267 demonstrate IC$_{50}$ of less than 10 μM in at least one of the c-kit cell assays described above in Example 26.

Compounds P-2268 to P-2307, e.g., compounds P-2268, P-2269, P-2270, P-2271, P-2272, P-2273, P-2274, P-2275, P-2276, P-2277, P-2278, P-2279, P-2280, P-2281, P-2282, P-2283, P-2284, P-2285, P-2286, P-2287, P-2288, P-2289, P-2290, P-2291, P-2292, P-2293, P-2294, P-2295, P-2296, P-2297, P-2298, P-2299, P-2300, P-2301, P-2302, P-2303, P-2304, P-2305, P-2306, and P-2307 had an IC$_{50}$ of less than 10 μM in at least one of the c-kit cell assays described above in Example 26.

Pharmacokinetic properties of compounds as described herein (including any solid forms or formulations thereof), e.g., compounds P-2001, P-2002, P-2004 to P-2273 and P-2274 to P-2307 are assessed in male Sprague Dawley rats or male Beagle dogs. Rats are dosed daily with compound either by IV injections via surgically implanted jugular catheters or by oral gavage (PO). Each compound is prepared as a 20 mg/mL stock solution in dimethyl sulfoxide, which is further diluted to provide the dosing stock at the desired concentration for the IV or PO formulations. For IV dosing, the dosing stock is diluted into a 1:1:8 mixture of Solutol®:ethanol:water. For PO dosing, the dosing stock is diluted into 1% methylcellulose. In a cassette format (or each compound, solid form thereof or formulation thereof is done individually), compounds are diluted to 0.5 mg/mL each for IV dosing and 0.4 mg/mL each for PO dosing and dosed at 1 mg/kg (2 mL/kg) or 2 mg/kg (5 mL/kg), respectively. For IV dosed animals, tail vein blood samples are collected with lithium heparin anticoagulant at 5, 15, 30, and 60 minutes and 4, 8, and 24 hours post dosing each day. For PO dosed animals, tail vein blood samples are collected with lithium heparin anticoagulant at 30 minutes, 1, 2, 4, 8 and 24 hours post dosing each day. Dogs are dosed daily by oral capsules in a suitable formulation at 50 mg/mL. Cephalic vein blood samples are collected with lithium heparin anticoagulant at 30 minutes, 1, 2, 4, 8 and 24 hours post dosing each day. All samples are processed to plasma and frozen for later analysis of each compound by LC/MS/MS. Plasma levels as a function of time are plotted to assess the AUC (ng*hr/mL). Compounds according to the present disclosure preferably show improved pharmacokinetic properties relative to previously described compounds, i.e. they have substantially higher values for one or more of AUC, Cmax and half-life relative to previously described compounds.

All patents, patent applications and other references cited in the specification are indicative of the level of skill of those skilled in the art to which the disclosure pertains, and are incorporated by reference in their entireties, including any tables and figures, to the same extent as if each reference had been incorporated by reference in its entirety individually.

One skilled in the art would readily appreciate that the present disclosure is well adapted to obtain the ends and advantages mentioned, as well as those inherent therein. The methods, variances, and compositions described herein as presently representative of preferred embodiments are exemplary and are not intended as limitations on the scope of the disclosure. Changes therein and other uses will occur to those skilled in the art, which are encompassed within the spirit of the disclosure, are defined by the scope of the claims.

While this disclosure has been disclosed with reference to specific embodiments, it is apparent that other embodiments and variations of this disclosure may be devised by others skilled in the art without departing from the true spirit and scope of the disclosure.

In addition, where features or aspects of the disclosure are described in terms of Markush groups or other grouping of alternatives, those skilled in the art will recognize that the disclosure is also thereby described in terms of any individual member or subgroup of members of the Markush group or other group.

Also, unless indicated to the contrary, where various numerical values are provided for embodiments, additional embodiments are described by taking any two different values as the endpoints of a range. Such ranges are also within the scope of the described disclosure.

---

SEQUENCE LISTING

```
SEQ ID NO: 1 Sequence NP_000213
Met Arg Gly Ala Arg Gly Ala Trp Asp Phe Leu Cys Val Leu Leu Leu Leu Arg Val Gln Thr Gly
Ser Ser Gln Pro Ser Val Ser Pro Gly Glu Pro Ser Pro Ser Ile His Pro Gly Lys Ser Asp Leu Ile Val
Arg Val Gly Asp Glu Ile Arg Leu Leu Cys Thr Asp Pro Gly Phe Val Lys Trp Thr Phe Glu Ile Leu
Asp Glu Thr Asn Glu Asn Lys Gln Asn Glu Trp Ile Thr Glu Lys Ala Glu Ala Thr Asn Thr Gly Lys
Tyr Thr Cys Thr Asn Lys His Gly Leu Ser Asn Ser Ile Tyr Val Phe Val Arg Asp Pro Ala Lys Leu Phe
Leu Val Asp Arg Ser Leu Tyr Gly Lys Glu Asp Asn Asp Thr Leu Val Arg Cys Pro Leu Thr Asp Pro
Glu Val Thr Asn Tyr Ser Leu Lys Gly Cys Gln Gly Lys Pro Leu Pro Lys Asp Leu Arg Phe Ile Pro
Asp Pro Lys Ala Gly Ile Met Ile Lys Ser Val Lys Arg Ala Tyr His Arg Leu Cys Leu His Cys Ser Val
Asp Gln Glu Gly Lys Ser Val Leu Ser Glu Lys Phe Ile Leu Lys Val Arg Pro Ala Phe Lys Ala Val Pro
Val Val Ser Val Ser Lys Ala Ser Tyr Leu Leu Arg Glu Gly Glu Glu Phe Thr Val Thr Cys Thr Ile Lys
Asp Val Ser Ser Ser Val Tyr Ser Thr Trp Lys Arg Glu Asn Ser Gln Thr Lys Leu Gln Glu Lys Tyr Asn
Ser Trp His His Gly Asp Phe Asn Tyr Glu Arg Gln Ala Thr Leu Thr Ile Ser Ser Ala Arg Val Asn Asp
Ser Gly Val Phe Met Cys Tyr Ala Asn Asn Thr Phe Gly Ser Ala Asn Val Thr Thr Thr Leu Glu Val
Val Asp Lys Gly Phe Ile Asn Ile Phe Pro Met Ile Asn Thr Thr Val Phe Val Asn Asp Gly Glu Asn Val
Asp Leu Ile Val Glu Tyr Glu Ala Phe Pro Lys Pro Glu His Gln Gln Trp Ile Tyr Met Asn Arg Thr Phe
Thr Asp Lys Trp Glu Asp Tyr Pro Lys Ser Glu Asn Glu Ser Asn Ile Arg Tyr Val Ser Glu Leu His Leu
Thr Arg Leu Lys Gly Thr Glu Gly Gly Thr Tyr Thr Phe Leu Val Ser Asn Ser Asp Val Asn Ala Ala Ile
Ala Phe Asn Val Tyr Val Asn Thr Lys Pro Glu Ile Leu Thr Tyr Asp Arg Leu Val Asn Gly Met Leu
Gln Cys Val Ala Ala Gly Phe Pro Glu Pro Thr Ile Asp Trp Tyr Phe Cys Pro Gly Thr Glu Gln Arg Cys
Ser Ala Ser Val Leu Pro Val Asp Val Gln Thr Leu Asn Ser Ser Gly Pro Pro Phe Gly Lys Leu Val Val
Gln Ser Ser Ile Asp Ser Ser Ala Phe Lys His Asn Gly Thr Val Glu Cys Lys Ala Tyr Asn Asp Val Gly
Lys Thr Ser Ala Tyr Phe Asn Phe Ala Phe Lys Gly Asn Asn Lys Glu Gln Ile His Pro His Thr Leu Phe
Thr Pro Leu Leu Ile Gly Phe Val Ile Val Ala Gly Met Met Cys Ile Ile Val Met Ile Leu Thr Tyr Lys
Tyr Leu Gln Lys Pro Met Tyr Glu Val Gln Trp Lys Val Val Glu Glu Ile Asn Gly Asn Asn Tyr Val
Tyr Ile Asp Pro Thr Gln Leu Pro Tyr Asp His Lys Trp Glu Phe Pro Arg Asn Arg Leu Ser Phe Gly Lys
Thr Leu Gly Ala Gly Ala Phe Gly Lys Val Val Glu Ala Thr Ala Tyr Gly Leu Ile Lys Ser Asp Ala Ala
Met Thr Val Ala Val Lys Met Leu Lys Pro Ser Ala His Leu Thr Glu Arg Glu Ala Leu Met Ser Glu
Leu Lys Val Leu Ser Tyr Leu Gly Asn His Met Asn Ile Val Asn Leu Leu Gly Ala Cys Thr Ile Gly
Gly Pro Thr Leu Val Ile Thr Glu Tyr Cys Cys Tyr Gly Asp Leu Leu Asn Phe Leu Arg Arg Lys Arg
Asp Ser Phe Ile Cys Ser Lys Gln Glu Asp His Ala Glu Ala Ala Leu Tyr Lys Asn Leu Leu His Ser Lys
Glu Ser Ser Cys Ser Asp Ser Thr Asn Glu Tyr Met Asp Met Lys Pro Gly Val Ser Tyr Val Val Pro Thr
Lys Ala Asp Lys Arg Arg Ser Val Arg Ile Gly Ser Tyr Ile Glu Arg Asp Val Thr Pro Ala Ile Met Glu
Asp Asp Glu Leu Ala Leu Asp Leu Glu Asp Leu Leu Ser Phe Ser Tyr Gln Val Ala Lys Gly Met Ala
Phe Leu Ala Ser Lys Asn Cys Ile His Arg Asp Leu Ala Ala Arg Asn Ile Leu Leu Thr His Gly Arg Ile
Thr Lys Ile Cys Asp Phe Gly Leu Ala Arg Asp Ile Lys Asn Asp Ser Asn Tyr Val Val Lys Gly Asn
Ala Arg Leu Pro Val Lys Trp Met Ala Pro Glu Ser Ile Phe Asn Cys Val Tyr Thr Phe Glu Ser Asp Val
```

SEQUENCE LISTING

Trp Ser Tyr Gly Ile Phe Leu Trp Glu Leu Phe Ser Leu Gly Ser Ser Pro Tyr Pro Gly Met Pro Val Asp
Ser Lys Phe Tyr Lys Met Ile Lys Glu Gly Phe Arg Met Leu Ser Pro Glu His Ala Pro Ala Glu Met Tyr
Asp Ile Met Lys Thr Cys Trp Asp Ala Asp Pro Leu Lys Arg Pro Thr Phe Lys Gln Ile Val Gln Leu Ile
Glu Lys Gln Ile Ser Glu Ser Thr Asn His Ile Tyr Ser Asn Leu Ala Asn Cys Ser Pro Asn Arg Gln Lys
Pro Val Val Asp His Ser Val Arg Ile Asn Ser Val Gly Ser Thr Ala Ser Ser Ser Gln Pro Leu Leu Val
His Asp Asp Val

SEQ ID NO: 2 Sequence NM_000222

```
   1 gatcccatcg cagctaccgc gatgagaggc gctcgcggcg cctgggattt tctctgcgtt
  61 ctgctcctac tgcttcgcgt ccagacaggc tcttctcaac catctgtgag tccaggggaa
 121 ccgtctccac catccatcca tccaggaaaa tcagacttaa tagtccgcgt gggcgacgag
 181 attaggctgt tatgcactga tccgggcttt gtcaaatgga cttttgagat cctggatgaa
 241 acgaatgaga ataagcagaa tgaatggatc acggaaaagg cagaagccac caacaccggc
 301 aaatacacgt gcaccaacaa aacgggctta agcaattcca tttatgtgtt tgttagagat
 361 cctgccaagc ttttccttgt tgaccgctcc ttgtatggga agaagacaa cgacacgctg
 421 gtccgctgtc ctctcacaga cccagaagtg accaattatt ccctcaaggg gtgccagggg
 481 aagcctcttc ccaaggactt gaggtttatt cctgacccca aggcgggcat catgatcaaa
 541 agtgtgaaac gcgcctacca tcggctctgt ctgcattgtt ctgtggacca ggagggcaag
 601 tcagtgctgt cggaaaaatt catcctgaaa gtgaggccag ccttcaaagc tgtgcctgtt
 661 gtgtctgtgt ccaaagcaag ctatcttctt agggaagggg aagaattcac agtgacgtgc
 721 acaataaaag atgtgtctag ttctgtgtac tcaacgtgga aaagagaaaa cagtcagact
 781 aaactacagg agaatataa tagctggcat cacggtgact tcaattatga acgtcaggca
 841 acgttgacta tcagttcagc gagagttaat gattctggag tgttcatgtg ttatgccaat
 901 aatactttttg gatcagcaaa tgtcacaaca accttggaaa tagtagataa aggattcatt
 961 aatatcttcc ccatgataaa cactacagta tttgtaaacg atggagaaaa tgtagatttg
1021 attgttgaat atgaagcatt ccccaaacct gaacaccagc agtggatcta tatgaacaga
1081 accttcactg ataaatggga agattatccc aagtctgaga tgaaagtaa tatcagatac
1141 gtaagtgaac ttcatctaac gagattaaaa ggcaccgaag gaggcactta cacattccta
1201 gtgtccaatt ctgacgtcaa tgctgccata gcatttaatg tttatgtgaa tacaaaacca
1261 gaaatcctga cttacgacag gctcgtgaat ggcatgctcc aatgtgtggc agcaggattc
1321 ccagagccca caatagattg gtattttgt ccaggaactg agcagagatg ctctgcttct
1381 gtactgccag tggatgtgca gacactaaac tcatctgggc caccgttttgg aaagctagtg
1441 gttcagagtt ctatagattc tagtgcattc aagcacaagt gcacggttga atgtaaggct
1501 tacaacgatg tgggcaagac ttctgcctat ttttaacttttg catttaaagg taacaacaaa
1561 gagcaaatcc atccccacac cctgttcact cctttgctga ttggtttcgt aatcgtagct
1621 ggcatgatgt gcattattgt gatgattctg acctacaaat atttacagaa acccatgtat
1681 gaagtacagt ggaaggttgt tgaggagata aatggaaaca attatgttta catagaccca
1741 acacaacttc cttatgatca caaatggagg tttcccagaa acaggctgag ttttgggaaa
1801 accctgggtg ctggagcttt cgggaaggtt gttgaggcaa ctgcttatgg cttaattaag
1861 tcagatgcgg ccatgactgt cgctgtaaag atgctcaagc cgagtgccca tttgacagaa
1921 cgggaagccc tcatgtctga actcaaagtc ctgagttacc ttggtaatca catgaatatt
1981 gtgaatctac ttggagcctg caccattgga gggcccaccc tggtcattac agaatattgt
2041 tgctatggtg atcttttgaa ttttttgaga agaaacgtg attcatttat ttgttcaaag
2101 caggaagatc atgcagaagc tgcactttat aagaatcttc tgcattcaaa ggagtcttcc
2161 tgcagcgata gtactaatga gtacatggac atgaaacctg gagtttctta tgttgtccca
2221 accaaggccg acaaaaggag atctgtgaga ataggctcat acatagaaag agatgtgact
2281 cccgccatca tggaggatga cgagttggcc ctagacttag aagacttgct gagcttttct
2341 taccaggtgg caaagggcat ggcttcctc gcctccaaga attgtattca cagagacttg
2401 gcagccagaa atatcctcct tactcatggt cggatcacaa agatttgtga ttttggtcta
2461 gccagagaca tcaagaatga ttctaattat gtggttaaag aaacgctcg actacctgtg
2521 aagtggatgg cacctgaaag cattttcaac tgtgtataca cgtttgaaag tgacgtctgg
2581 tcctatggga tttttctttg ggagctgttc tctttaggaa gcagcccta tcctggaatg
2641 ccggtcgatt ctaagttcta caagatgatc aaggaaggct tccggatgct cagccctgaa
2701 cacgcacctg ctgaaatgta tgacataatg aagacttgct gggatgcaga tccctaaaa
2761 agaccaacat tcaagcaaat tgttcagcta attgagaagc agatttcaga gagcaccaat
2821 catatttact ccaacttagc aaactgcagc cccaaccgac agaagcccgt ggtagaccat
2881 tctgtgcgga tcaattctgt cggcagcacc gcttcctcct cccagcctct gcttgtgcac
2941 gacgatgtct gagcagaatc agtgtttggg tcacccctcc aggaatgatc tcttctttttg
3001 gcttccatga tggttatttt cttttcttttc aacttgcatc caactccagg atagtgggca
3061 ccccactgca atcctgtctt tctgagcaca ctttagtggc cgatgatttt tgtcatcagc
3121 caccatccta ttgcaaaggt tccaactgta tatattccca atagcaacgt agcttctacc
3181 atgaacagaa aacattctga tttggaaaaa gagagggagg tatggactgg gggccagagt
3241 cctttccaag gcttctccaa ttctgcccaa aaatatggtt gatagtttac ctgaataaat
3301 ggtagtaatc acagttggcc ttcagaacca tccatagtag tatgatgata caagattaga
3361 agctgaaaac ctaagtcctt tatgtggaaa acagaacatc attagaacaa aggacagagt
3421 atgaacacct gggcttaaga aatctagtat ttcatgctgg gaatagacta taggccatga
3481 aaaaaatgat ccccaagtgt gaacaaaaga tgctcttctg tggacactg catgagcttt
3541 tatactaccg acctggttttt taaatagagt ttgctattag agcattgaat tggagagaag
3601 gcctccctag ccagcacttg tatatacgca tctataaatt gtccgtgttc atacatttga
3661 ggggaaaaca ccataaggtt tcgttctctgt atacaaccct ggcattatgt ccactgtgta
3721 tagaagtaga ttaagagcca tataagtttg aaggaaacag ttaataccat ttttttaagga
3781 aacaatataa ccacaaagca cagttgaac aaaatctcct cttttagctg atgaacttat
3841 tctgtagatt ctgtggaaca agcctatcag cttcagaatg gcattgtact caatggattt
3901 gatgctgttt gacaaagtta ctgattcact gcatggctcc cacaggagtg ggaaaacact
3961 gccatccttag tttggattct tatgtagcag gaaataaagt ataggtttag cctccttcgc
4021 aggcatgtcc tggacaccgg gccagatctct atatatgtgt atgtacgttt gtatgtgtgt
4081 agacaaatat ttggaggggt attttttgccc tgagtccaag agggtccttt agtacctgaa
```

-continued

SEQUENCE LISTING

```
4141 aagtaacttg gctttcatta ttagtactgc tcttgtttct tttcacatag ctgtctagag
4201 tagcttacca gaagcttcca tagtggtgca gaggaagtgg aaggcatcag tccctatgta
4261 tttgcagttc acctgcactt aaggcactct gttatttaga ctcatcttac tgtacctgtt
4321 ccttagacct tccataatgc tactgtctca ctgaaacatt taaattttac ccttagact
4381 gtagcctgga tattattctt gtagtttacc tctttaaaaa caaaacaaaa caaaacaaaa
4441 aactccccct cctcactgcc caatataaaa ggcaaatgtg tacatggcag agtttgtgtg
4501 ttgtcttgaa agattcaggt atgttgcctt tatggtttcc cccttctaca tttcttagac
4561 tacatttaga gaactgtggc cgttatctgg aagtaaccat ttgcactgga gttctatgct
4621 ctcgcacctt tccaaagtta acagattttg gggttgtgtt gtcacccaag agattgttgt
4681 ttgccatact ttgtctgaaa aattcctttg tgtttctatt gacttcaatg atagtaagaa
4741 aagtggttgt tagttataga tgtctaggta cttcaggggc acttcattga gagttttgtc
4801 ttgccatact ttgtctgaaa aattcctttg tgtttctatt gacttcaatg atagtaagaa
4861 aagtggttgt tagttataga tgtctaggta cttcaggggc acttcattga gagttttgtc
4921 aatgtctttt gaatattccc aagcccatga gtccttgaaa atattttta tatatacagt
4981 aactttatgt gtaaatacat aagcggcgta agtttaaagg atgttggtgt tccacgtgtt
5041 ttattcctgt atgttgtcca attgttgaca gttctgaaga attc
```

What is claimed is:

1. A method for treating a subject suffering from a disease or condition selected from Alzheimer's disease (AD), Parkinson's disease, melanoma, glioma, glioblastoma multiforme, pilocytic astrocytoma, sarcoma, gastrointestinal carcinoma, liver cancer, biliary tract carcinoma, bile duct carcinoma, colorectal cancer, lung cancer, gallbladder cancer, breast cancer, pancreatic cancer, thyroid cancer, renal cancer, ovarian cancer, adrenocortical carcinoma, prostate cancer, lymphoma, neurofibromatosis, gastrointestinal stromal tumors, acute myeloid leukemia, myelodysplastic syndrome, leukemia, tumor angiogenesis, medullary thyroid cancer, carcinoid, small cell lung cancer, Kaposi's sarcoma, pheochromocytoma, cancer-related pain and mastocytosis, said method comprising administering to the subject in need thereof an effective amount of a compound having Formula (IV):

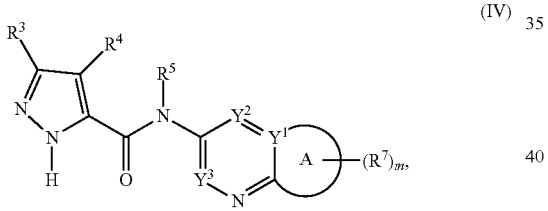

(IV)

or a pharmaceutically acceptable salt, a solvate, a tautomer, a stereoisomer, or a deuterated analog thereof, wherein:

ring A is a 5-membered fused heteroaryl ring having from 1-3 heteroatoms as ring members selected from O, N, or S;

each $R^7$ is independently selected from $C_{1-6}$alkyl, deuterated $C_{1-6}$alkyl, $C_{1-6}$alkoxy, $C_{2-6}$alkenyl, $C_{2-6}$alkynyl, —$X^1$-aryl, aryl-$C_{1-4}$alkylene-$X^1$—, heteroaryl-$C_{1-4}$alkylene-$X^1$—, $C_{3-6}$cycloalkyl-$X^1$—, $C_{3-6}$cycloalkyl-$C_{1-4}$alkylene-$X^1$—, $C_{3-6}$cycloalkenyl-$X^1$—, $CH_2$=CH—$X^1$, $C_{3-6}$cycloalkyl-$C_{2-4}$alkenylene-$X^1$—, $C_{3-6}$cycloalkyl-$C_{2-4}$alkynylene-$X^1$—, heterocyclyl-$X^1$—, heterocyclyl-$C_{1-4}$alkylene-$X^1$— or $R^8$, wherein $R^8$ is selected from halogen, —CN, —OH, —$NH_2$, —$NO_2$, —C(O)OH, —C(S)OH, —C(O)$NH_2$, —C(S)$NH_2$, —S(O)$_2NH_2$, —NHC(O)$NH_2$, —NHC(S)$NH_2$, —NHS(O)$_2NH_2$, —C(NH)$NH_2$, —$OR^a$, —$SR^a$, —OC(O)$R^a$, —OC(S)$R^a$, —C(O)$R^a$, —C(S)$R^a$, —C(S)$OR^a$, —S(O)$R^a$, —S(O)$_2R^a$, —C(O)$NHR^a$, —C(S)$NHR^a$, —C(O)$NR^aR^a$, —C(S)$NR^aR^a$, —S(O)$_2NHR^a$, —S(O)$_2NR^aR^a$, —C(NH)$NHR^a$, —C(NH)$NR^aR^a$, —NHC(O)$R^a$, —NHC(S)$R^a$, —$NR^aC(O)R^a$, —$NR^aC(S)R^a$, —NHS(O)$_2R^a$, —$NR^aS(O)_2R^a$, —NHC(O)$NHR^a$, —NHC(S)$NHR^a$, —$NR^aC(O)NH_2$, —$NR^aC(S)NH_2$, —$NR^aC(O)NHR^a$, —$NR^aC(S)NHR^a$, —NHC(O)$NR^aR^a$, —NHC(S)$NR^aR^a$, —$NR^aC(O)NR^aR^a$, —$NR^aC(S)NR^aR^a$, —NHS(O)$_2NHR^a$, —$NR^aS(O)_2NH_2$, —$NR^aS(O)_2NHR^a$, —NHS(O)$_2NR^aR^a$, —$NR^aS(O)_2NR^aR^a$, —$NHR^a$, or —$NR^aR^a$, wherein each $R^a$ is independently selected from $C_{1-6}$alkyl, aryl, aryl-$C_{1-2}$alkyl, $C_{3-6}$cycloalkyl, $C_{3-6}$cycloalkyl-$C_{1-4}$alkyl, heteroaryl, heteroaryl-$C_{1-4}$alkyl, heterocycloalkyl, or heterocycloalkyl-$C_{1-4}$alkyl, wherein each $R^a$ is further optionally substituted with 1-3 $R^b$ substituents independently selected from $C_{1-6}$alkyl, $C_{1-6}$alkoxy, halogen, $C_{1-6}$ haloalkyl, or $C_{1-6}$ haloalkoxy; wherein $X^1$ is a bond or —C(O)— and wherein $R^7$ is optionally substituted with from 1-5 $R^9$ members selected from halogen, —CH=$CH_2$, —CN, —OH, —$NH_2$, —$NO_2$, —C(O)OH, —C(S)OH, —C(O)$NH_2$, —C(S)$NH_2$, —S(O)$_2NH_2$, —NHC(O)$NH_2$, —NHC(S)$NH_2$, —NHS(O)$_2NH_2$, —C(NH)$NH_2$, —$OR^c$, —$SR^c$, —OC(O)$R^c$, —OC(S)$R^c$, —P(=O)$HR^c$, —P(=O)$R^cR^c$, —PH(=O)$OR^c$, —P(=O)$(OR^c)_2$, —OP(=O)$(OR^c)_2$, —C(O)$R^c$, —C(S)$R^c$, —C(O)$OR^c$, —C(S)$OR^c$, —S(O)$R^c$, —S(O)$_2R^c$, —C(O)$NHR^c$, —C(S)$NHR^c$, —C(O)$NR^cR^c$, —C(S)$NR^cR^c$, —S(O)$_2NHR^c$, —S(O)$_2NR^cR^c$, —C(NH)$NHR^c$, —C(NH)$NR^cR^c$, —NHC(O)$R^c$, —NHC(S)$R^c$, —$NR^cC(O)R^c$, —$NR^cC(S)R^c$, —NHS(O)$_2R^c$, —$NR^cS(O)_2R^c$, —NHC(O)$NHR^c$, —NHC(S)$NHR^c$, —$NR^cC(O)NH_2$, —$NR^cC(S)NH_2$, —$NR^cC(O)NHR^c$, —$NR^cC(S)NHR^c$, —NHC(O)$NR^cR^c$, —NHC(S)$NR^cR^c$, —$NR^cC(O)NR^cR^c$, —$NR^cC(S)NR^cR^c$, —NHS(O)$_2NHR^c$, —$NR^cS(O)_2NH_2$, —$NR^cS(O)_2NHR^c$, —NHS(O)$_2NR^cR^c$, —$NR^cS(O)_2NR^cR^c$, —$NHR^c$, $R^c$, or —$NR^cR^c$; or two adjacent $R^9$ substituents, together with the atoms to which they are attached, form a 5 or 6-membered ring having from 0-2 heteroatoms selected from O, N, or S;

wherein each $R^c$ is independently selected from $C_{1-6}$alkyl, aryl, aryl-$C_2$alkyl, $C_{3-6}$cycloalkyl, $C_{3-6}$cycloalkyl-$C_{1-4}$alkyl, heteroaryl, heteroaryl-$C_{1-4}$alkyl, heterocycloalkyl, or heterocycloalkyl-$C_{1-4}$alkyl, wherein each $R^c$ is further optionally substituted with from 1-3 $R^d$ groups independently selected from —CN, —OH, —N($R^e$)($R^e$), —$NO_2$, —C(O)OH, —C(O)$NH_2$, —S(O)$_2NH_2$, —NHC(O)$NH_2$, —C(NH)$NH_2$, —OC(O)$R^e$, —OC(S)$R^e$, —C(O)$R^e$, —C(S)$R^e$, —C(O)$OR^e$, —P(=O)$HR^e$, —P(=O)$R^eR^e$, —PH(=O)$OR^e$, —P(=O)$(OR^e)_2$, —OP(=O)$(OR^e)_2$, —S(O)$_2R^e$, —C(O)$NHR^e$, $C_{1-6}$alkyl, $C_{1-6}$alkoxy, halogen, $C_{1-6}$ haloalkyl, or $C_{1-6}$ haloalkoxy, wherein each $R^e$ is independently $C_{1-6}$alkyl;

or two adjacent $R^7$ substituents together with the atoms to which they are attached form a 4-, 5-, or 6-membered carbocyclic ring or heterocyclic ring having from 1-2 heteroatoms as ring members selected from O, N, or S;

$Y^2$ is C—$R^{10}$, wherein $R^{10}$ is H, $C_{1-6}$alkyl, $C_{1-6}$alkoxy, $C_{2-6}$alkenyl, $C_{2-6}$alkynyl, aryl-$C_{1-4}$alkyl-, heteroaryl-$C_{1-4}$ alkyl-, $C_{3-6}$cycloalkyl-$C_{1-4}$alkyl-, $C_{3-6}$cycloalkenyl-$C_{1-4}$alkyl-, $CH_2$=CH—$X^2$—, $C_{3-6}$cycloalkyl-$C_{2-4}$alkenylene-$X^2$—, $C_{3-6}$cycloalkyl-$C_{2-4}$alkynylene-$X^2$—, heterocyclyl-$C_{1-4}$alkyl-, or $R^8$, each of which is optionally substituted with from 1-5 $R^9$ groups; wherein $X^2$ is $C_{1-4}$alkylene, —O—, —S—, or —NH—;

$R^3$ and $R^4$ are each independently selected from H, halogen, $C_{1-6}$ alkyl, $C_{1-4}$haloalkyl, $C_{1-4}$haloalkoxy, cyclopropyl, phenyl, —CN, CN—$CH_2$—, $C_{1-6}$alkoxy, or $R^g$; or $R^3$ and $R^4$ are taken together with the atoms to which they are attached form an optionally substituted 4 to 8-membered ring having from 0-2 heteroatoms as ring members selected from O, N, or S;

wherein $R^g$ is —OH, —$NH_2$, —$NO_2$, —C(O)OH, —C(S) OH, —C(O)$NH_2$, —C(S)$NH_2$, —S(O)$_2NH_2$, —NHC(O)$NH_2$, —NHC(S)$NH_2$, —NHS(O)$_2NH_2$, —C(NH) $NH_2$, —$OR^h$, —$SR^h$, —OC(O)$R^h$, —OC(S)$R^h$, —C(O)$R^h$, —C(S)$R^h$, —C(O)$OR^h$, —C(S)$OR^h$, —S(O)$R^h$, —S(O)$_2R^h$, —C(O)$NHR^h$, —C(S)$NHR^h$, —C(O)$NR^hR^h$, —C(S)$NR^hR^h$, —S(O)$NHR^h$, —S(O)$_2NR^hR^h$, —C(NH)$NHR^h$, —C(NH)$NR^hR^h$, —NHC(O)$R^h$, —NHC(S)$R^h$, —$NR^h$C(O)$R^h$, —$NR^h$C(S)$R^h$, —NHS(O)$_2R^h$, —$NR^h$S(O)$_2R^h$, —NHC(O) $NHR^h$, —NHC(S)$NHR^h$, —$NR^h$C(O)$NH_2$, —$NR^h$C(S)$NH_2$, —$NR^h$C(O)$NHR^h$, —$NR^h$C(S)$NHR^h$, —NHC(O)$NR^hR^h$, —NHC(S)$NR^hR^h$, —$NR^h$C(O) $NR^hR^h$, —$NR^h$C(S)$NR^hR^h$, —NHS(O)$_2NHR^h$, —$NR^h$S(O)$_2NH_2$, —$NR^h$S(O)$_2NHR^h$, —NHS(O)$_2$ $NR^hR^h$, —$NR^h$S(O)$_2NR^hR^h$, —$NHR^h$, or —$NR^hR^h$, wherein each $R^h$ is independently H or Ca-2alkyl;

$R^5$ is H or $C_{1-4}$alkyl;

$Y^1$ is N or C;

$Y^3$ is CH; and the subscript m is 0, 1, or 2.

2. The method according to claim 1, wherein the compound is of Formula (IVa), (IVb), (IVc), or (IVd):

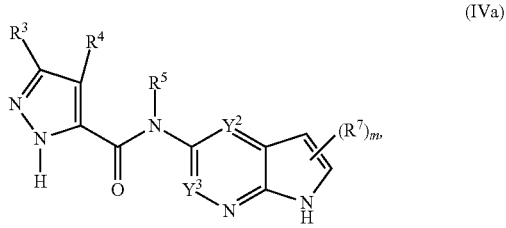

(IVa)

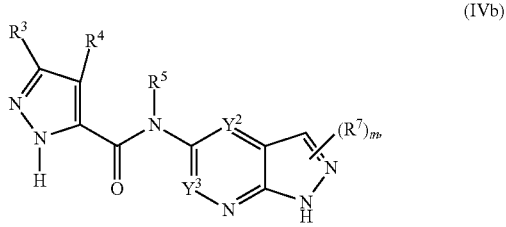

(IVb)

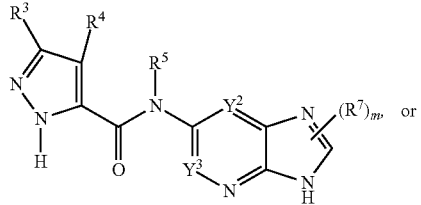

(IVc)

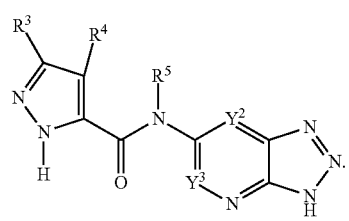

(IVd)

3. The method according to claim 1, wherein the compound is of Formula (IVa-2):

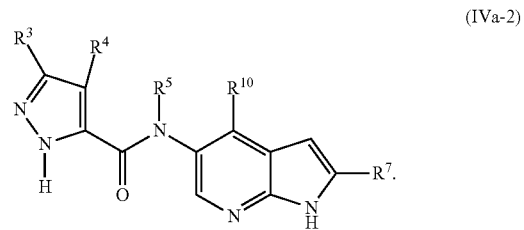

(IVa-2)

4. The method according to claim 3, wherein $R^{10}$ is H.

5. The method according to claim 3, wherein $R^3$ and $R^4$ are each independently H, halogen, $C_{1-6}$alkyl, $C_{1-6}$alkoxy, cyclopropyl, —CN, $C_{1-4}$haloalkyl, or $C_{1-4}$haloalkoxy; or $R^3$ and $R^4$ are taken together with the atoms to which they are attached form an optionally substituted fused 4 to 8-membered ring having from 0-2 heteroatoms selected from N or S.

6. The method according to claim 3, wherein $R^3$ and $R^4$ are each independently selected from H, Br, Cl, methyl, ethyl, cyclopropyl, —CN, $CF_3$, $CHF_2$, $CH_2F$, —$OCH_3$, —$OCF_3$, —$OCHF_2$ or —$OCH_2F$, $CNCH_2$—, $NH_2C(O)$—, $CH_3NHCO$—, or $CH_3C(O)NH$—; or $R^3$ and $R^4$ are taken together with the atoms to which they are attached form a fused ring selected from benzene, pyridine, pyrimidine, pyrazine, pyridazine, cyclobutane, cyclopentane, cyclohexane, cycloheptane, cyclopentene, cyclohexene, cyclooctane, or cyclooctatriene, each of which is optionally substituted.

7. The method according to claim 3, wherein $R^7$ is selected from halogen, —CN, $C_{1-6}$alkyl, $C_{1-6}$alkoxy, $C_{2-6}$alkenyl, $C_{2-6}$ alkynyl, $C_{3-6}$ cycloalkyl, $C_{3-6}$ cycloalkyl-$C_{1-4}$alkyl, aryl, aryl-$C_{1-4}$alkyl, heteroaryl, heteroaryl-$C_{1-4}$ alkyl, heterocyclyl or heterocyclyl-$C_{1-4}$alkyl, —C(O)—$R^a$, —C(O)$NHR^a$, —C(O)$NR^aR^a$, —NHC(O)$R^a$, —NHC(O) $NHR^a$, —NHC(O)$NR^aR^a$, —$NR^aR^a$, —$NHR^a$, —OC(O) $R^a$, —$SO_2R^a$, —$NHSO_2R^a$, —$NHSO_2NHR^a$, —$NHSO_2NR^aR^a$, —$SO_2NHR^a$, or —$SO_2NR^aR^a$, wherein at each occurrence $R^7$ is optionally substituted with from 1-4 $R^9$ members, wherein each $R^9$ is independently selected from halogen, —CN, $C_{1-6}$alkyl, $C_{1-6}$alkoxy, $C_{1-6}$ haloalkyl, $C_{1-6}$ haloalkoxy, $C_{3-6}$cycloalkyl, $C_{3-6}$ cycloalkyl-$C_{1-4}$alkyl, aryl, aryl-$C_{1-2}$alkyl, heteroaryl, heteroaryl-$C_{1-4}$ alkyl, heterocyclyl, or heterocyclyl-$C_{1-4}$alkyl or the two adjacent $R^9$ substituents on an aromatic ring are taken together to form a 5 or 6-membered ring having from 0-2 heteroatoms selected from O, N, or S.

8. The method according to claim 3, wherein $R^7$ is vinyl, ethynyl, deuterated $C_{1-6}$alkyl, $C_{1-6}$alkyl, halogen, $C_{1-6}$alkoxy, 2-cyclopropylethynyl, 2-pyridyl, 3-pyridyl, 4-pyridyl, phenyl, benzyl, 1-pyrazolyl, 3-pyrazolyl, 4-pyrazolyl, 2-oxazolyl, 4-oxazolyl, 5-oxazolyl, 3-isoxazolyl, 4-isoxazolyl, 5-isoxazolyl, 2-thiozolyl, 4-thiozolyl, 5-thiozolyl, 2-pyrimidinyl, 4-pyrimidinyl, 5-pyrimidinyl, 2-pyrazinyl, 3-pyridazinyl, 4-pyridazinyl, cyclopropyl, cyclopropylmethyl, cyclopropylcarbonyl, cyclobutyl, cyclobutylmethyl, cyclopentyl, cyclopentylmethyl, cyclohexyl, cyclohexylmethyl, benzoyl, phenylcarbamoyl, 1-piperidinyl, 2-piperidinyl, 3-piperidinyl, 4-piperidinyl, 1-piperazinyl, 2-piperazinyl, 4-morpholinyl, 4-thiomorpholinyl, 1-cyclopentenyl, 1-cyclohexenyl, 1,2,3,6-tetrahydropyridin-4-yl, 1,2,3,6-tetrahydropyridin-5-yl, 2,5-dihydro-1H-pyrrol-3-yl, 2,5-dihydro-pyrrol-1-yl, 2,3-dihydro-1,4-benzodioxin-5-yl, 1,3-benzodioxol-4-yl, 1,3-benzodioxol-5-yl, indan-1-yl, indan-2-yl, 1,2-benzoxazolyl, or 1,3-benzoxazolyl, each of which is optionally substituted with from 1-4 $R^9$ members.

9. The method according to claim 3, wherein $R^7$ is selected from Cl, Br, phenyl, 4-fluorophenyl, 2-fluorophenyl, 3-fluorophenyl, 2-pyridyl, 3-pyridyl, 4-pyridyl, 1-cyclopropylcarbonyl-1,2,3,6-tetrahydropyridin-4-yl, 1-morpholinocarbonyl, 1,2,3,6-tetrahydropyridin-4-yl, 1,2,3,6-tetrahydropyridin-5-yl, 1,3-dimethyl-pyrazol-4-yl, 1-(4-piperidinyl)pyrazol-4-yl, 3,4-dimethyl-1H-pyrazol-5-yl, 1-(cyclopropylcarbonyl)-2,5-dihydro-pyrrol-3-yl, 3-fluoropropynyl, or 3,5-dimethyl-isoxazol-4-yl, 5-thiazolyl, each of which is optionally substituted with from 1-3 substituents independently selected from F, Cl, —$CH_3$, ethyl, propyl, isopropyl, 2-methylpropyl, $CD_3$, —$OCH_3$, CN, $CH_2F$, —$CF_2H$, $CF_3$, $CF_3O$—, $CHF_2O$—, $CH_2FO$—, $NH_2$, —$N(CH_3)_2$, —$NHCH_3$, $CH_3CONH$—, $NH_2C(O)$—, $CH_3NHC(O)$—, $(CH_3)_2NC(O)$—, cyclopropyl, 1-cyanocyclopropyl, 4-morpholinyl, 4-morpholinylmethyl, 4-thiomorpholinyl, 4-morpholinylcarbonyl, 4-thiomorpholinylcarbonyl, 4-morpholinylmethylcarbonyl, 4-thiomorpholinylmethylcarbonyl, cyclopropylcarbonyl, cyclobutylcarbonyl, cyclopentylcarbonyl, cyclohexylcarbonyl, —PH(=O)($C_{1-4}$alkyl), —P(=O)($C_{1-4}$alkyl)$_2$, —PH(=O)(O$C_{1-4}$alkyl), —P(=O)(O$C_{1-4}$alkyl)$_2$, —OP(=O)(O$C_{1-4}$alkyl)$_2$, 4-piperidinyl, 4-piperidinylcarbonyl, 1-piperidinylcarbonyl, 1-piperazinylcarbonyl, t-butoxycarbonyl, 2-(4-morpholinyl)-ethyl, 2-(4-morpholinyl)-ethoxy, 1,2-dihydroxyethylcarbonyl, 3-methoxypropoxy, 1-pyrrolidinyl, phenyl-$SO_2NH$—, $C_{1-4}$alkyl-$SO_2NH$—, cyclopropyl-$SO_2NH$—, p-$CH_3C_6H_4SO_2NH$—, $NH_2SO_2$—, $C_{1-4}$alkyl-$NHSO_2$—, ($C_{1-4}$alkyl)$_2NSO_2$—, $C_{1-4}$alkyl-NHC(O)—, $C_{1-4}$alkyl-C(O)—, $C_{1-4}$alkyl-$SO_2$—, 4-morpholinyl-$C_{1-4}$alkoxy, or 1-pyrrolidinylcarbonyl.

10. The method according to claim 3, wherein $R^5$ is H.

11. A method for treating a subject suffering from disease or condition selected from Alzheimer's disease (AD), Parkinson's disease, melanoma, glioma, glioblastoma multiforme, pilocytic astrocytoma, sarcoma, gastrointestinal carcinoma, liver cancer, biliary tract carcinoma, bile duct carcinoma, colorectal cancer, lung cancer, gallbladder cancer, breast cancer, pancreatic cancer, thyroid cancer, renal cancer, ovarian cancer, adrenocortical carcinoma, prostate cancer, lymphoma, neurofibromatosis, gastrointestinal stromal tumors, acute myeloid leukemia, myelodysplastic syndrome, leukemia, tumor angiogenesis, medullary thyroid cancer, carcinoid, small cell lung cancer, Kaposi's sarcoma, pheochromocytoma, cancer-related pain and mastocytosis, said method comprising administering to the subject in need thereof an effective amount of a compound of structure:

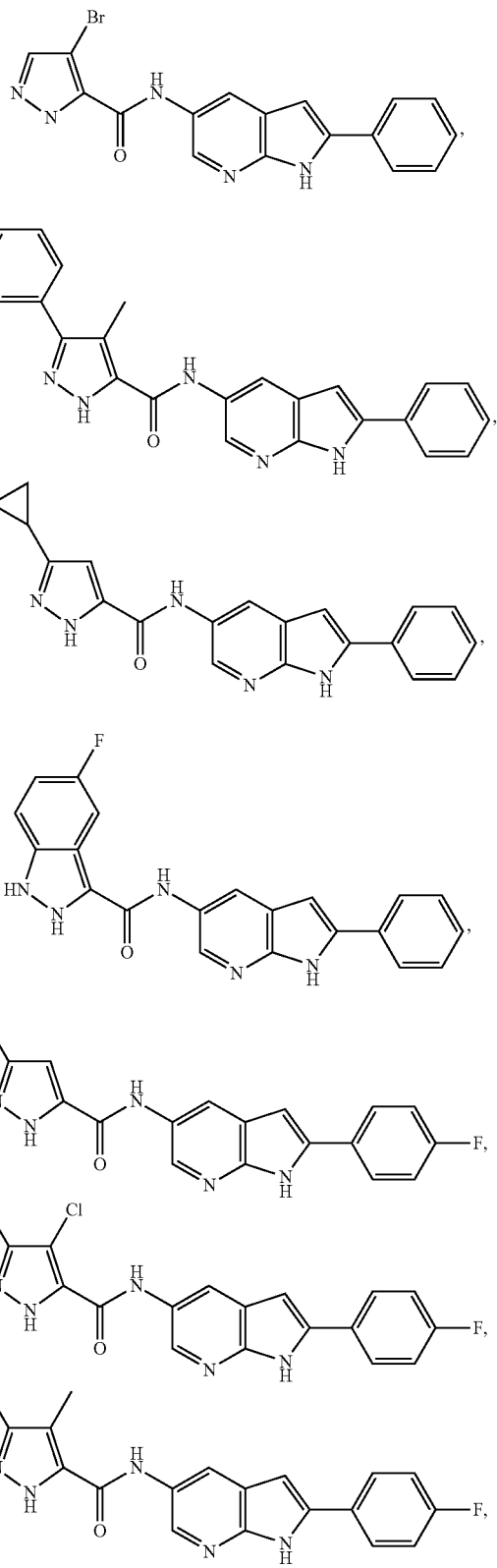

317
-continued
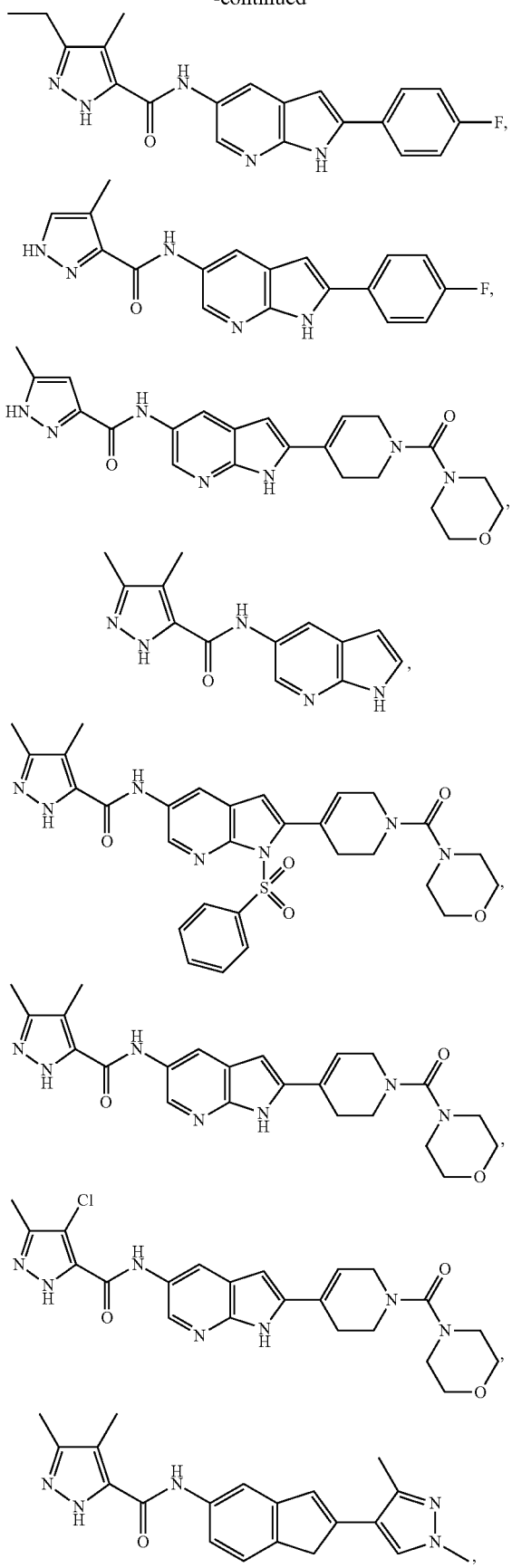
318
-continued
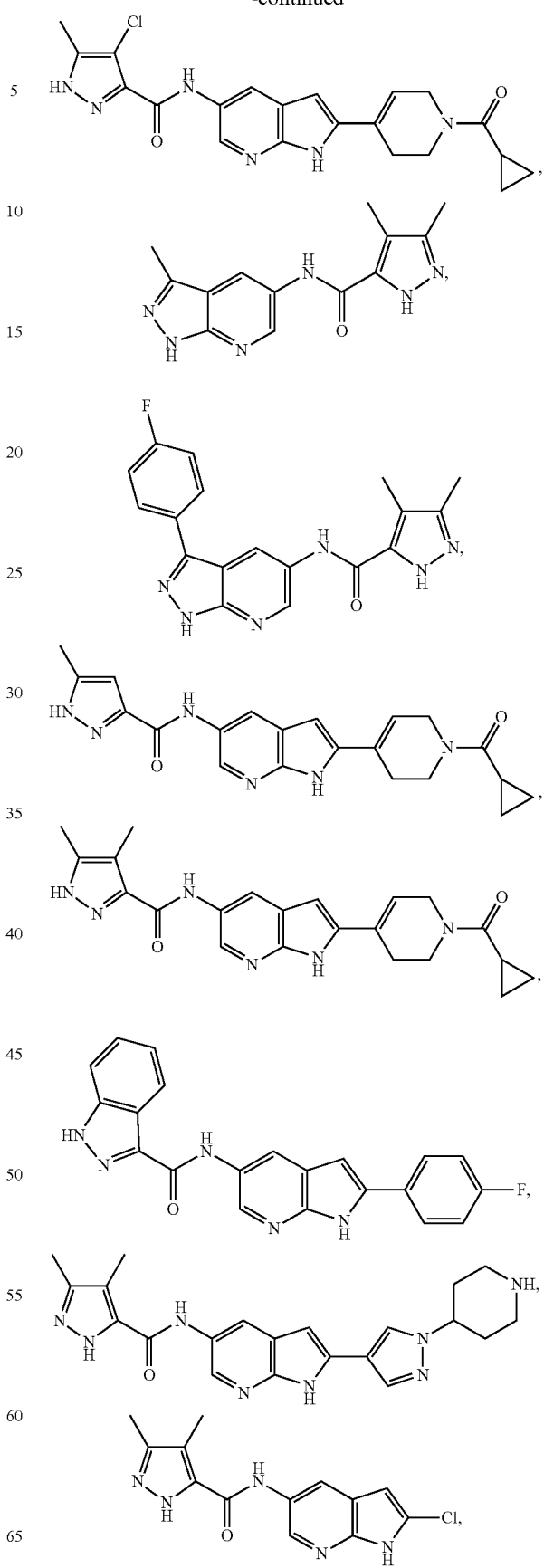

319
-continued
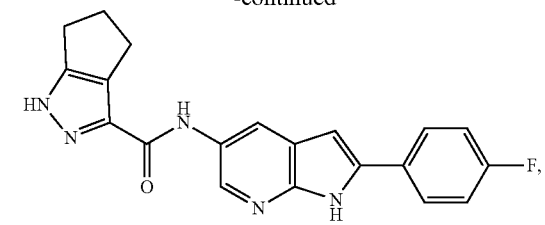
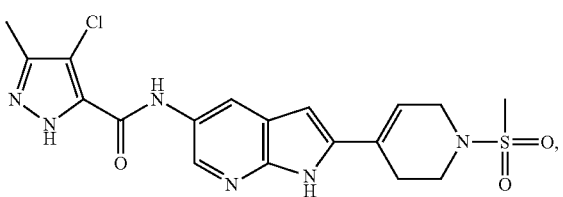
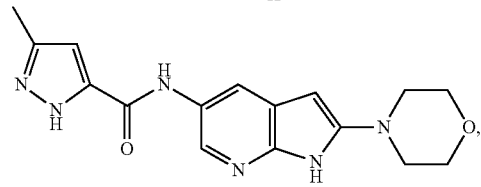
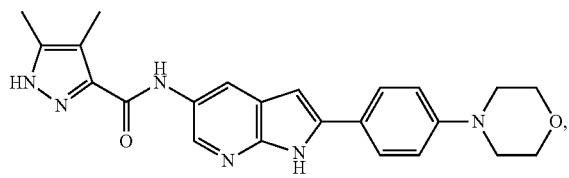
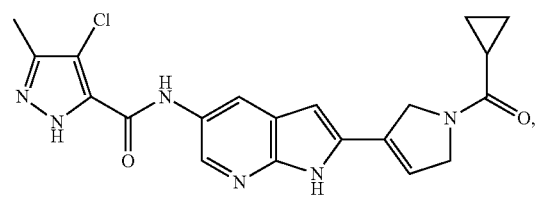
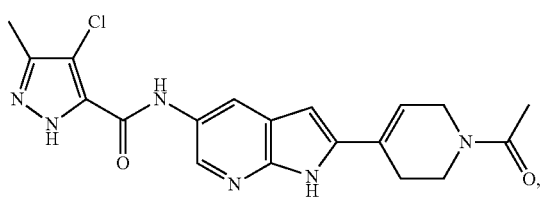
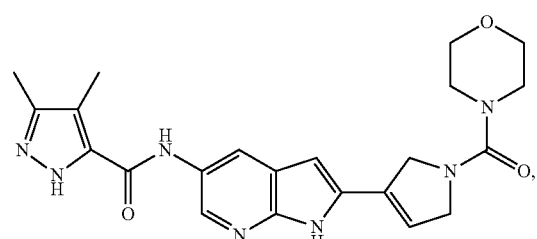
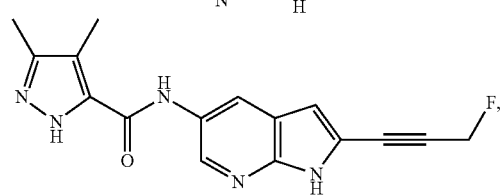
320
-continued
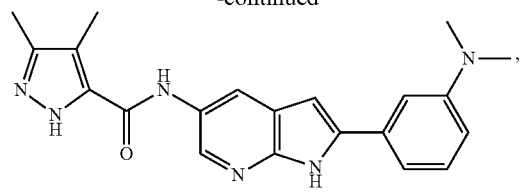
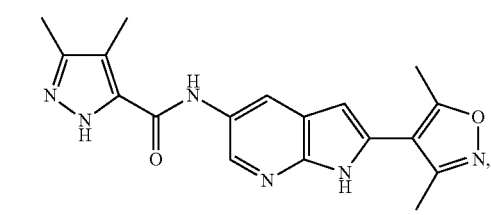
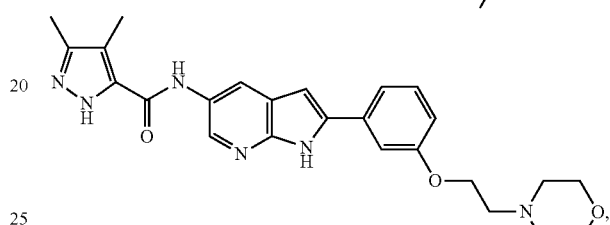
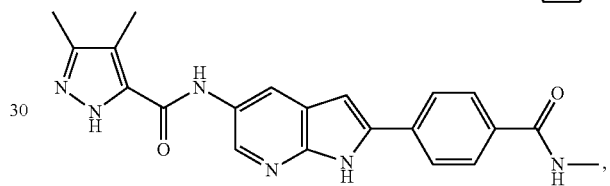
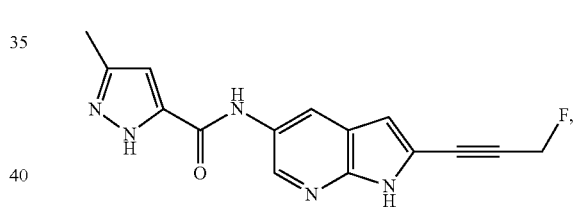
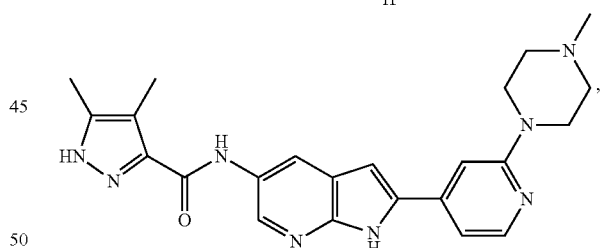
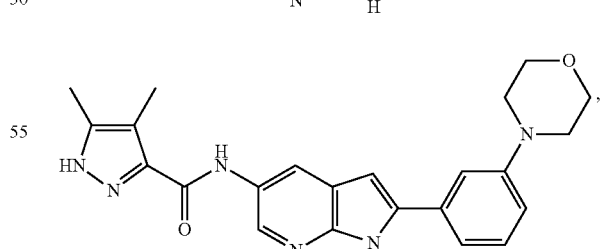
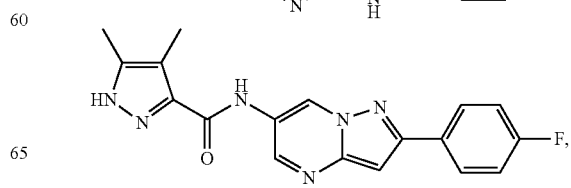

-continued

323
-continued
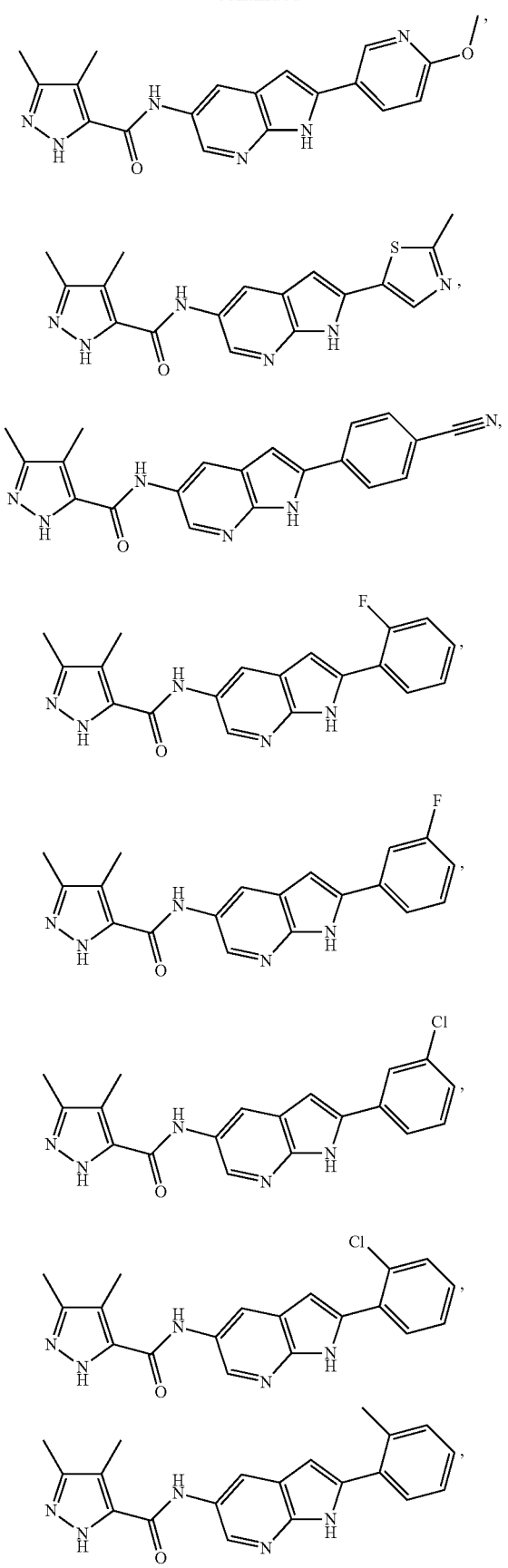
324
-continued
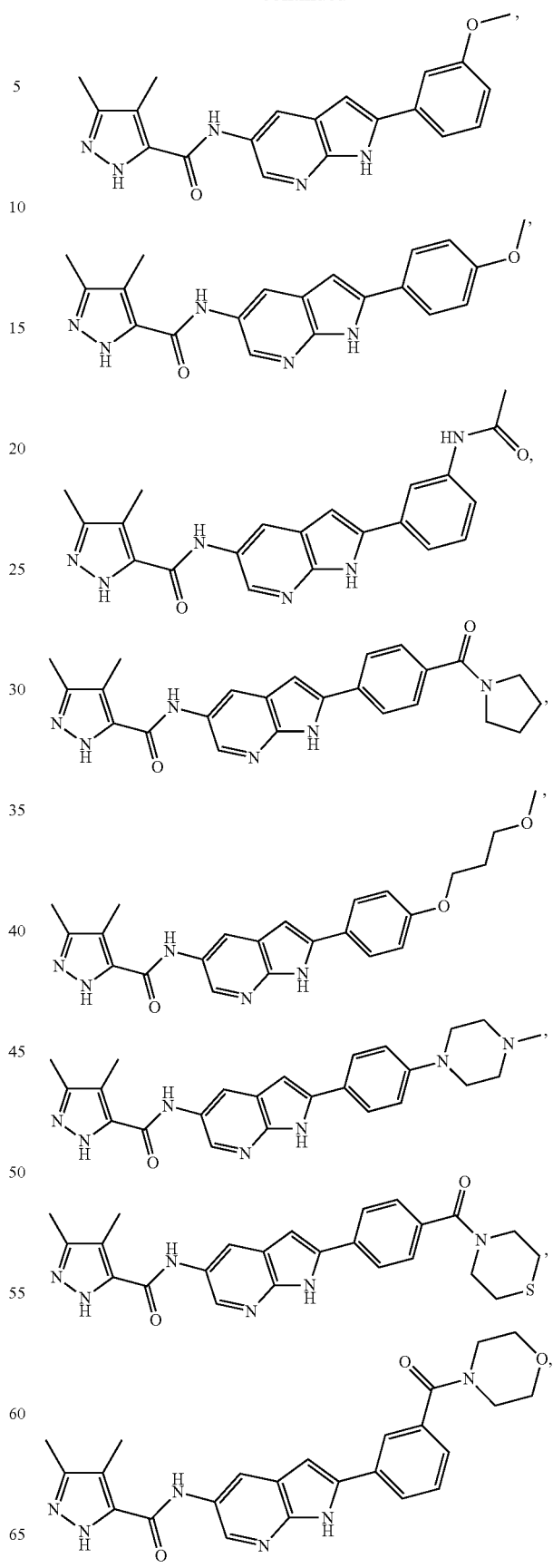

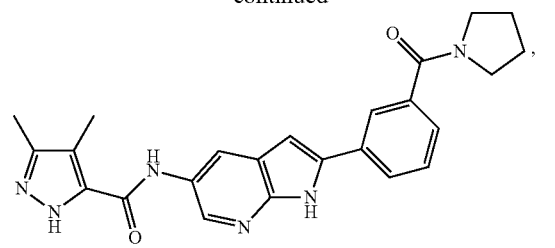
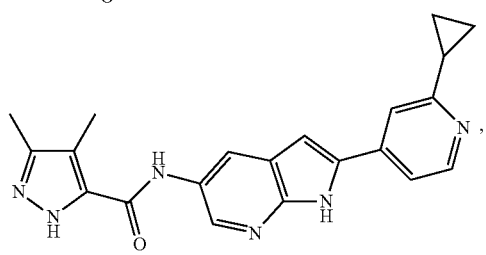
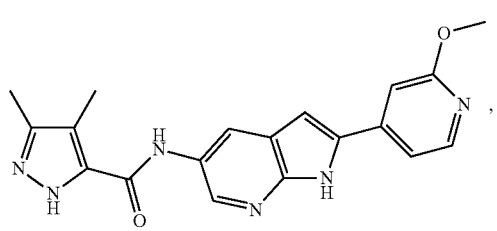
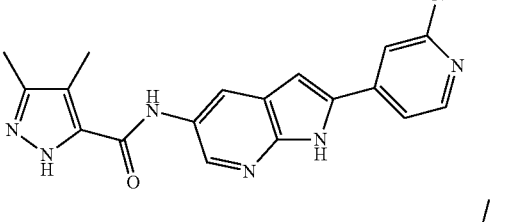
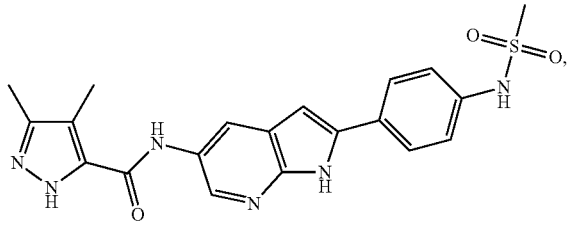
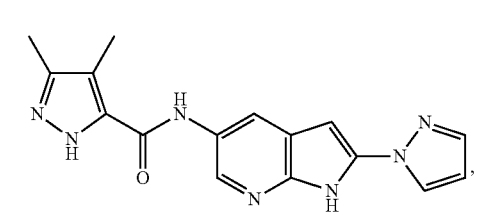
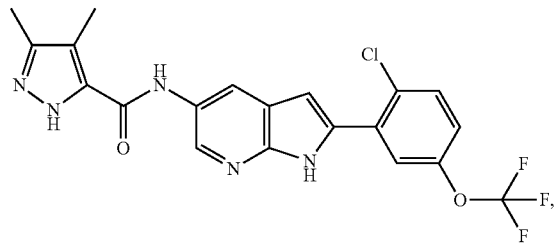
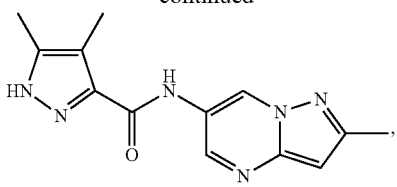
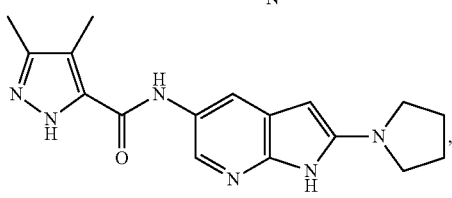
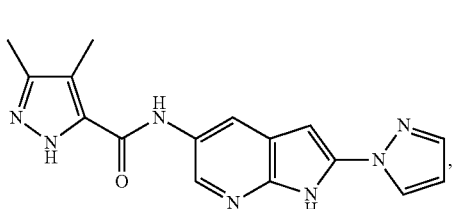
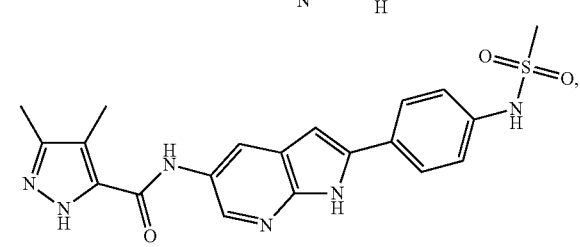
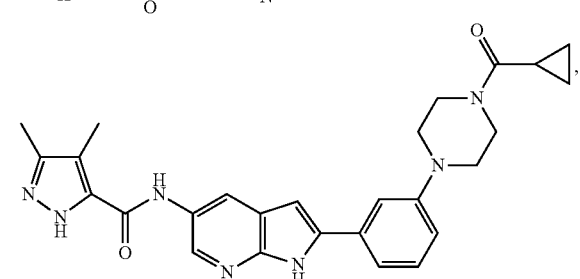
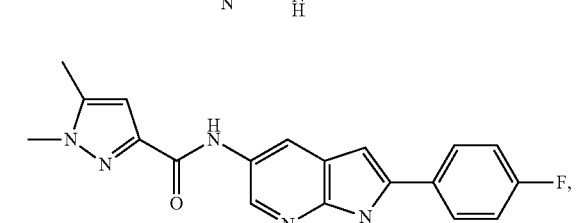
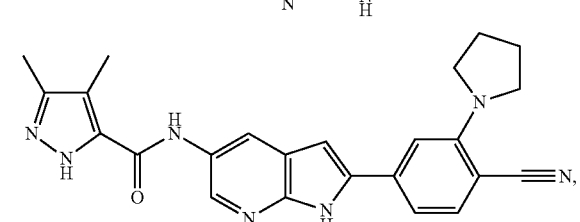
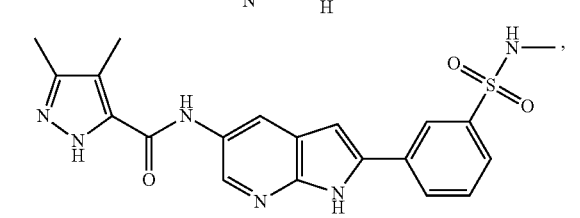

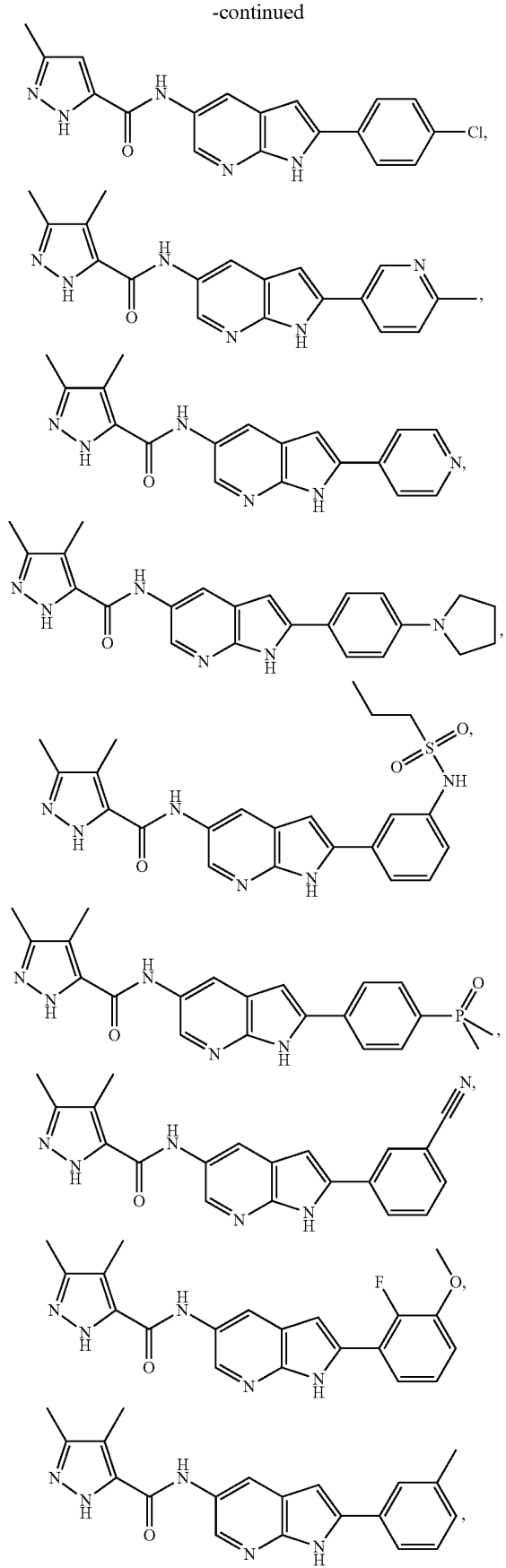
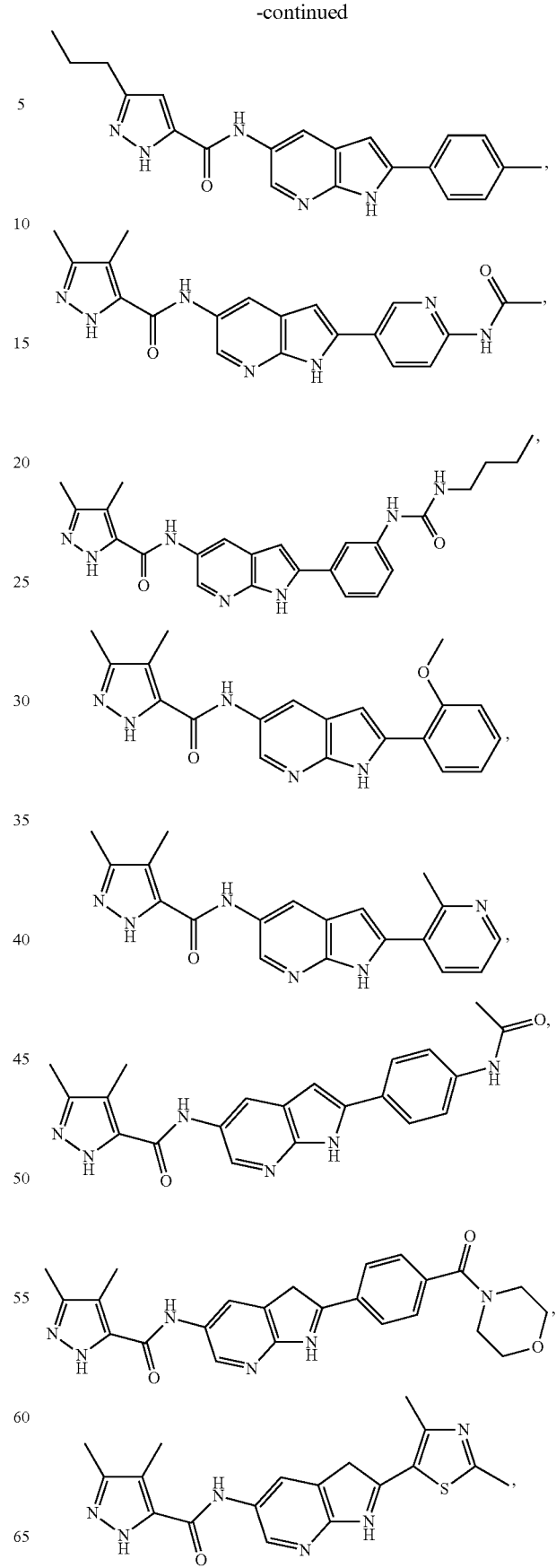

-continued
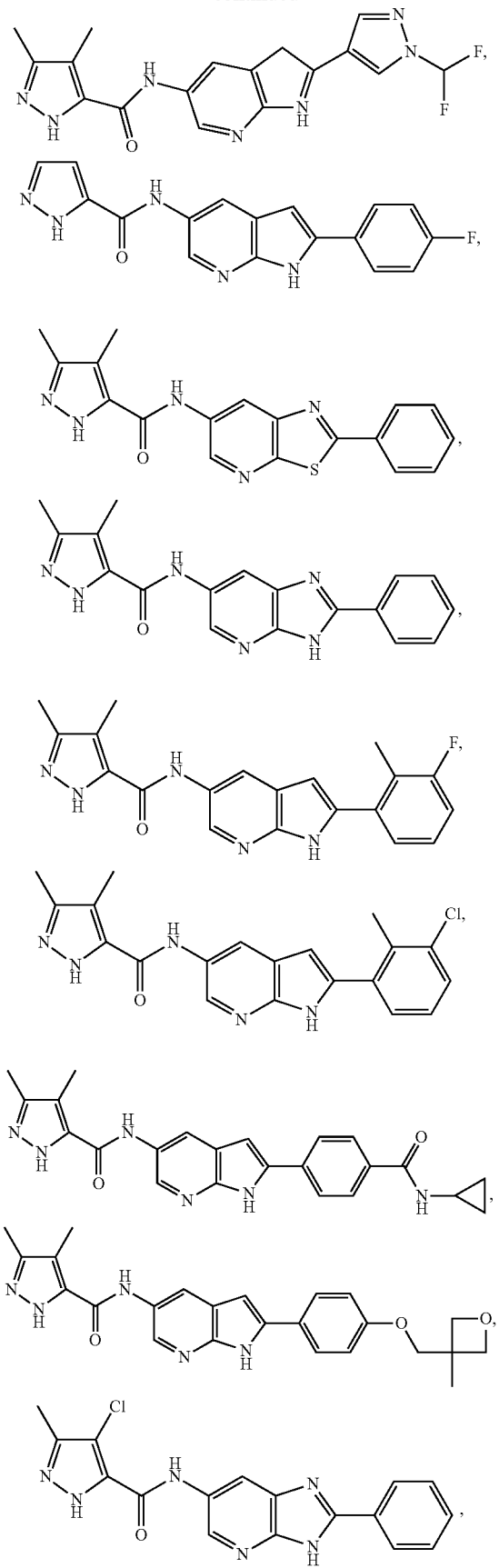
-continued
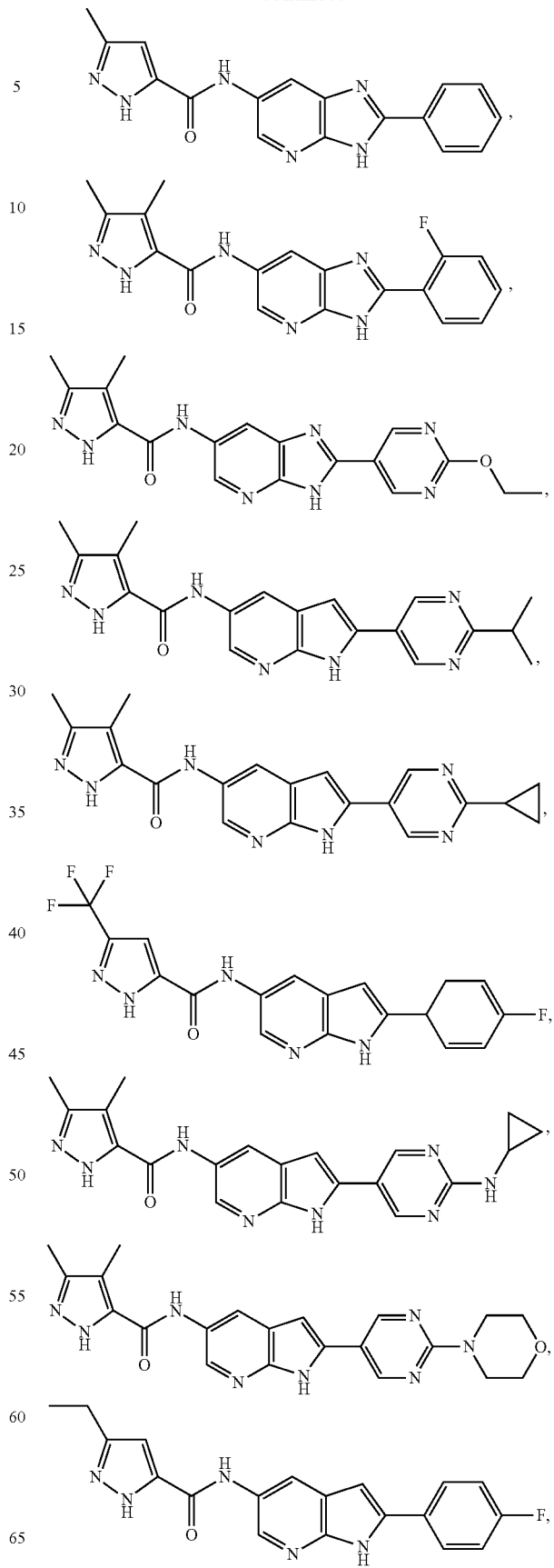

331
-continued
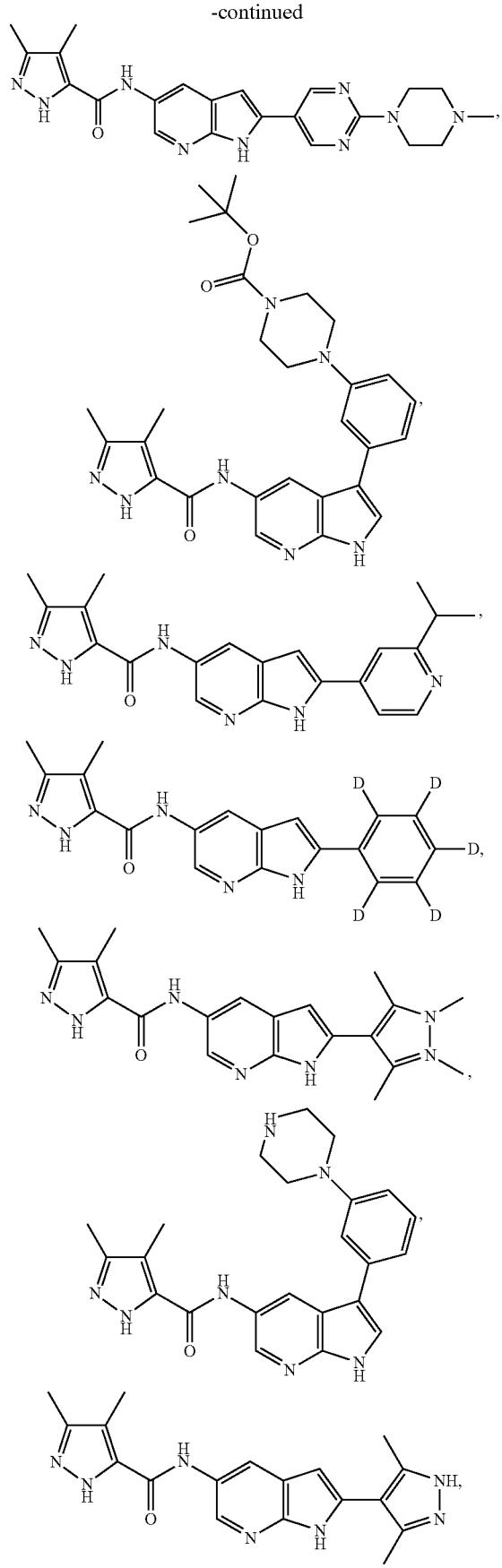
332
-continued
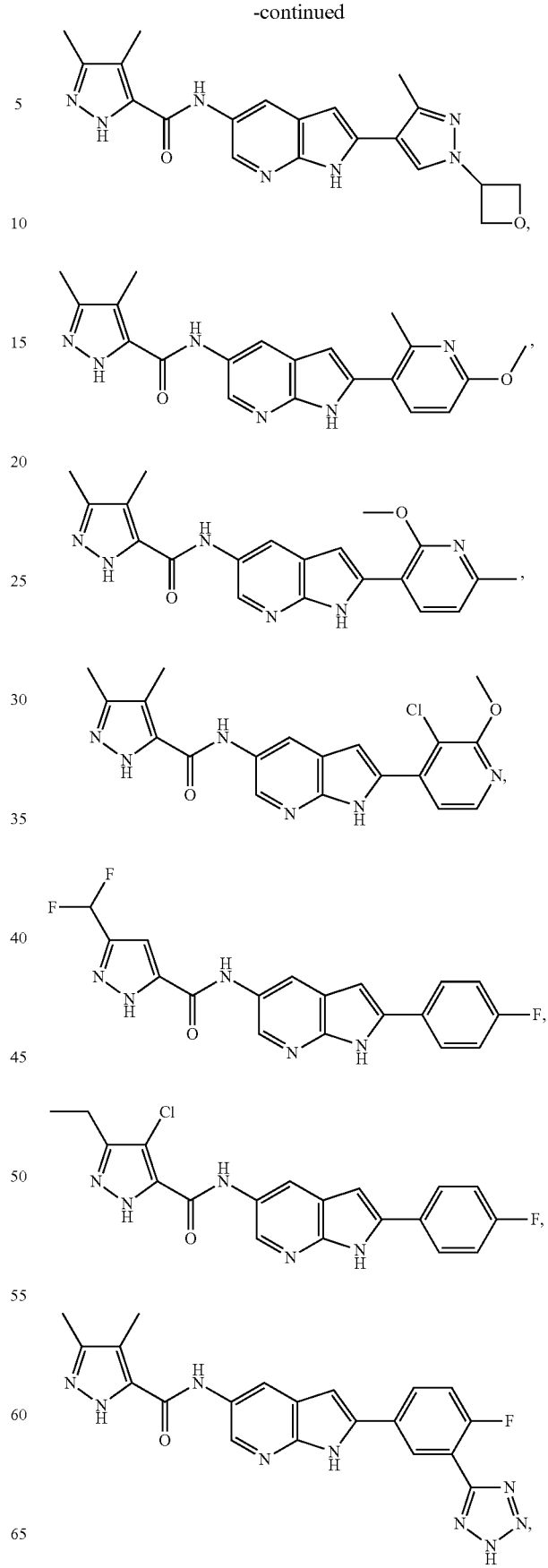

333
-continued
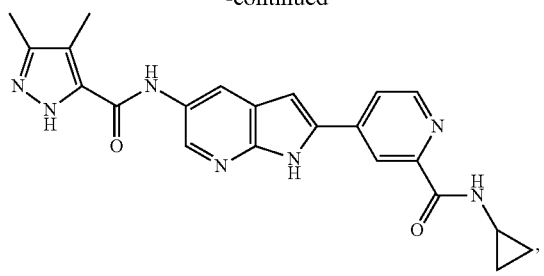
334
-continued
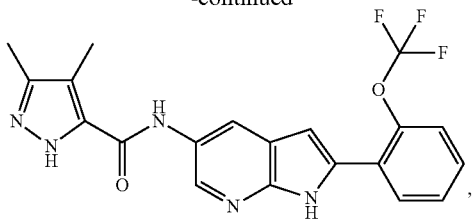
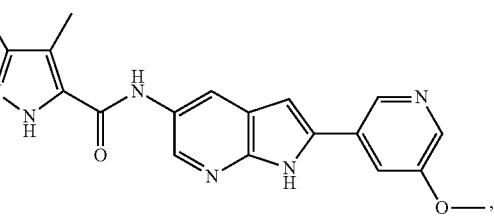
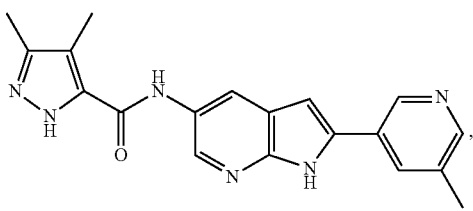
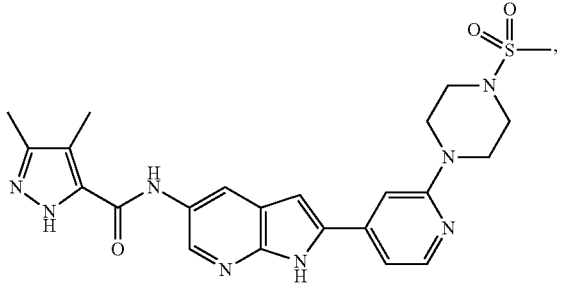
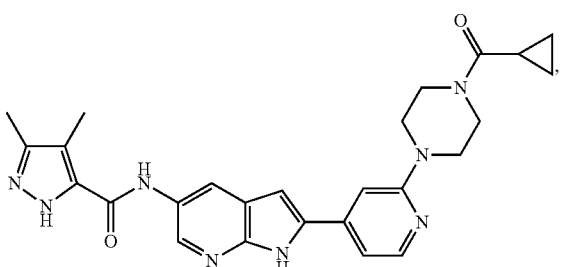
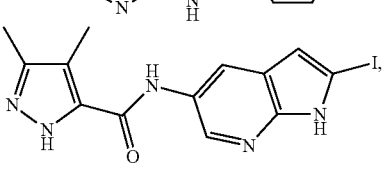

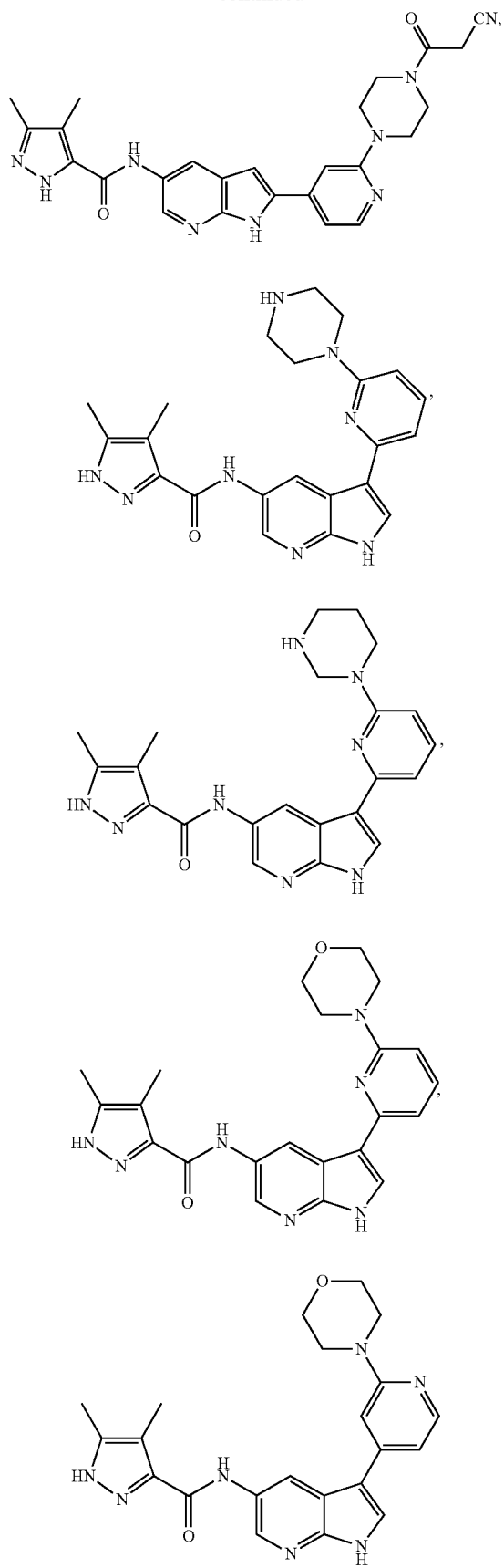
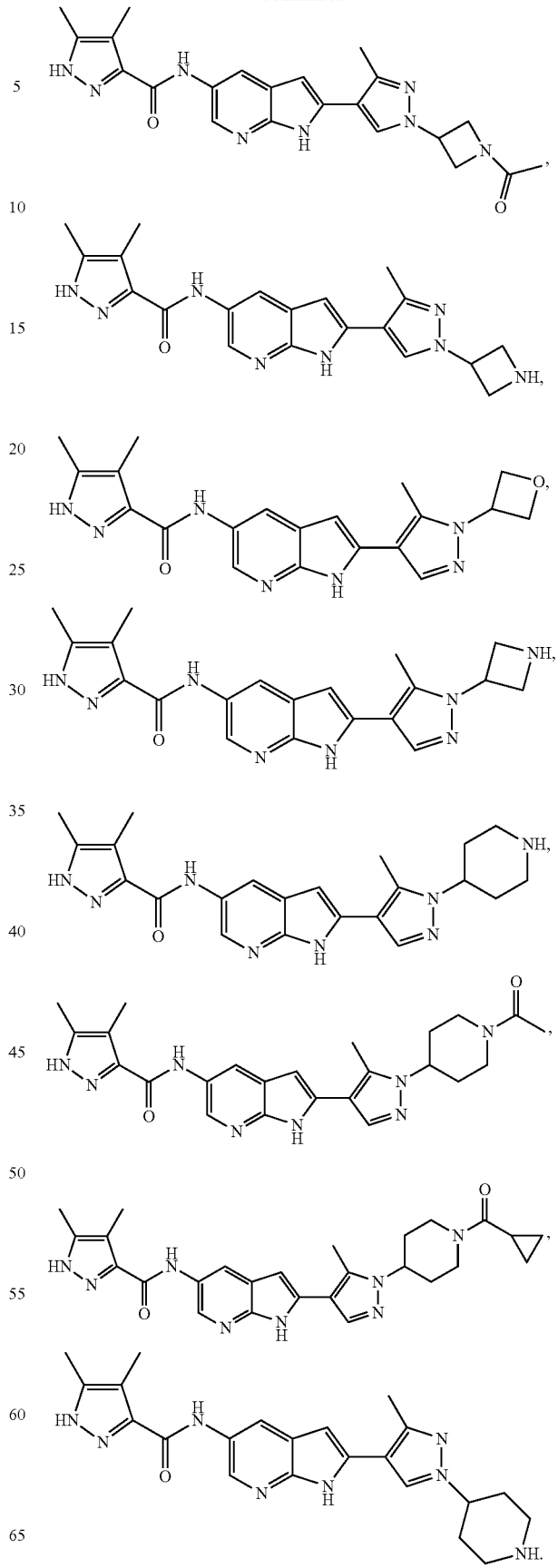

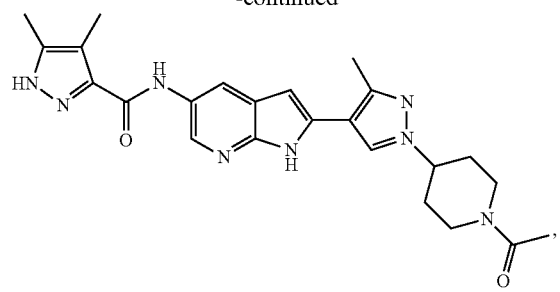
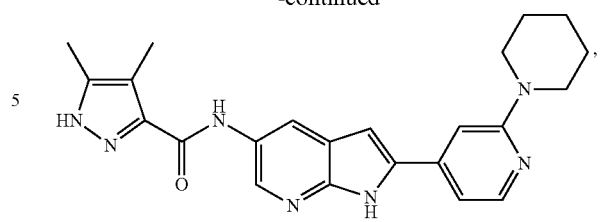
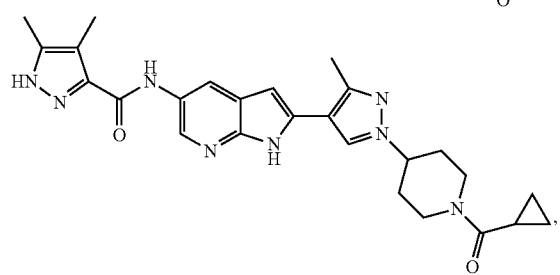
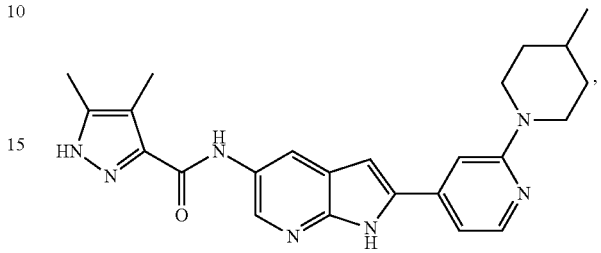
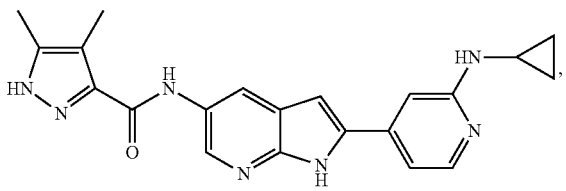
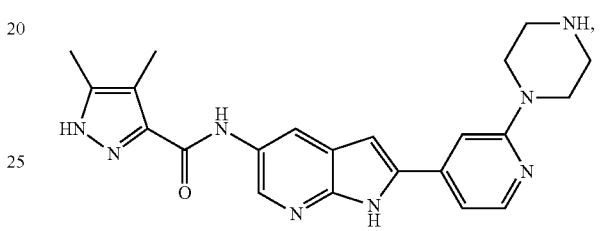
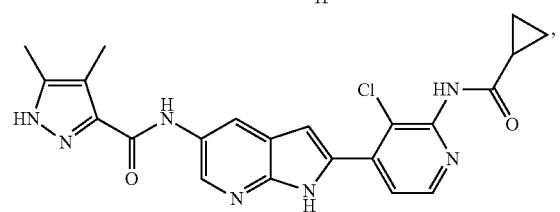
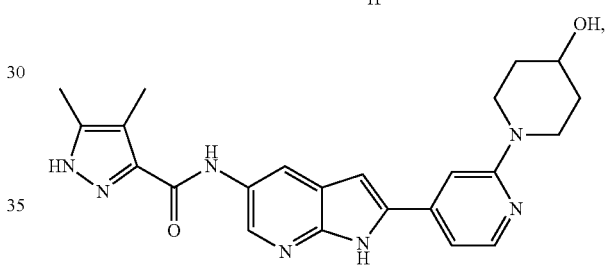
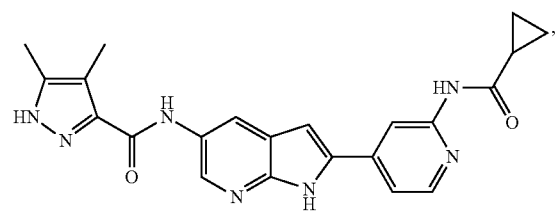
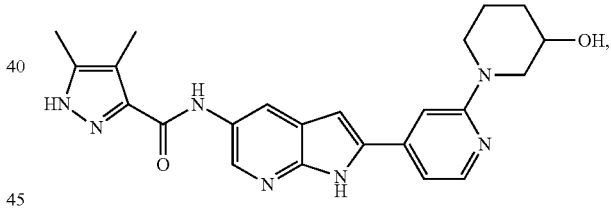
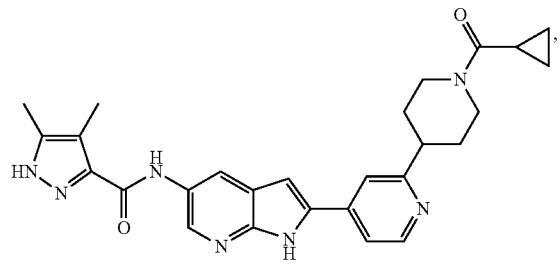
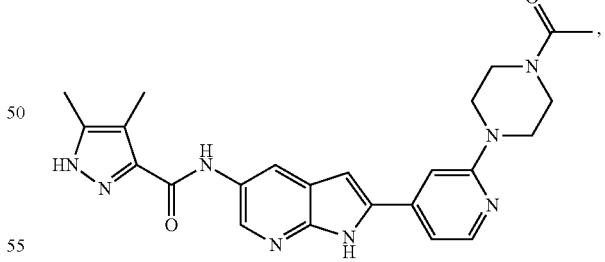
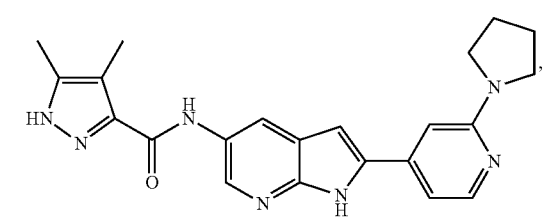
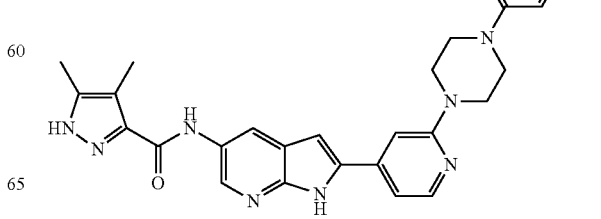

339
-continued
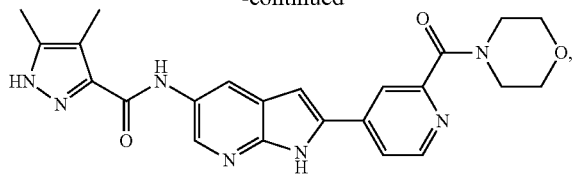,
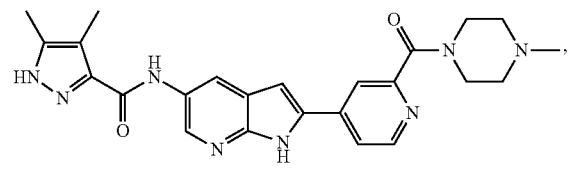,
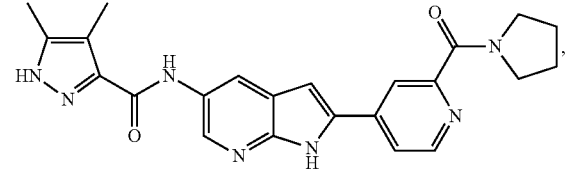,
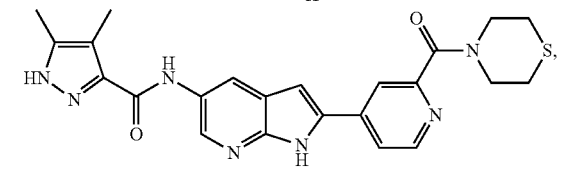,
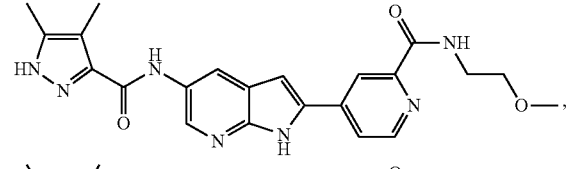,
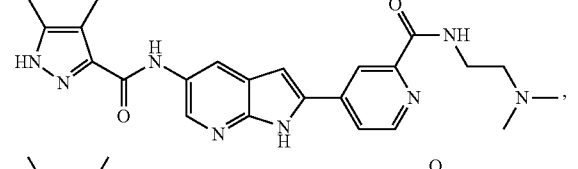,
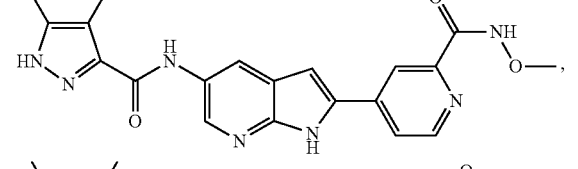,
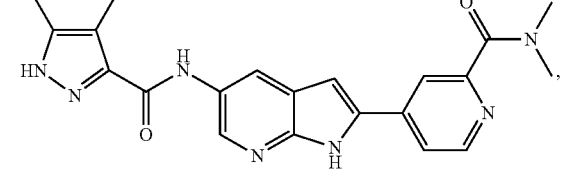,
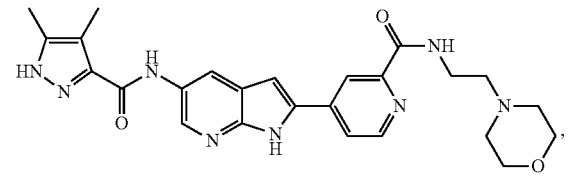,
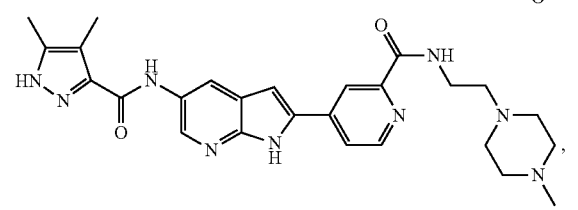,
340
-continued
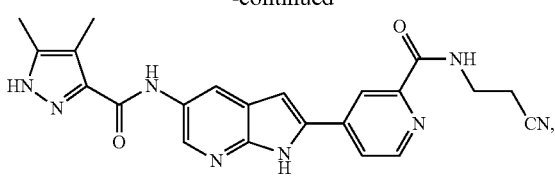,
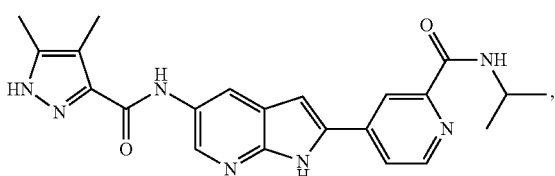,
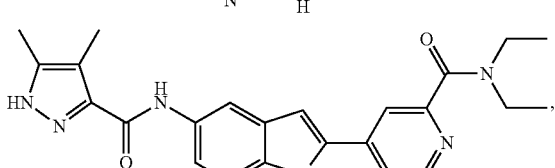,
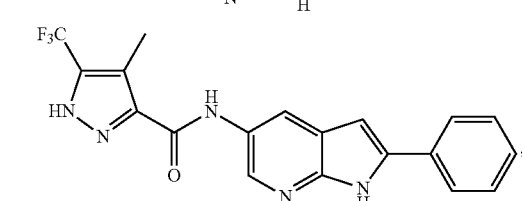,
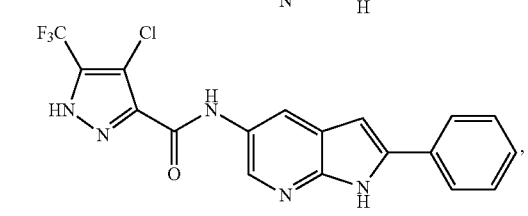,
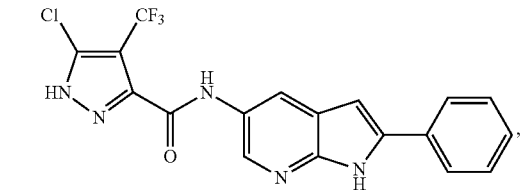,
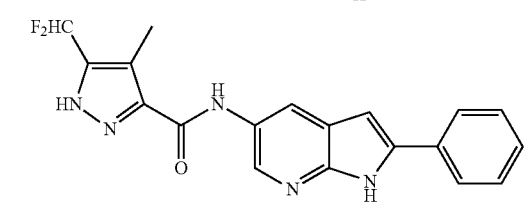,
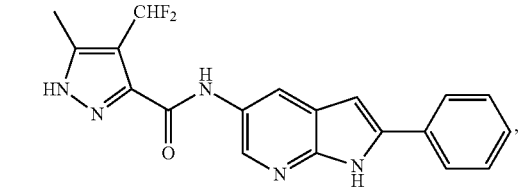,
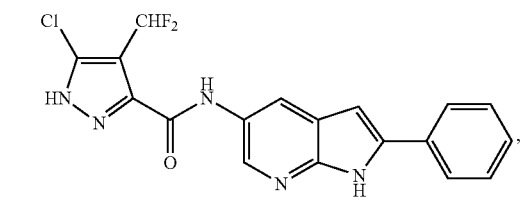, 341
-continued
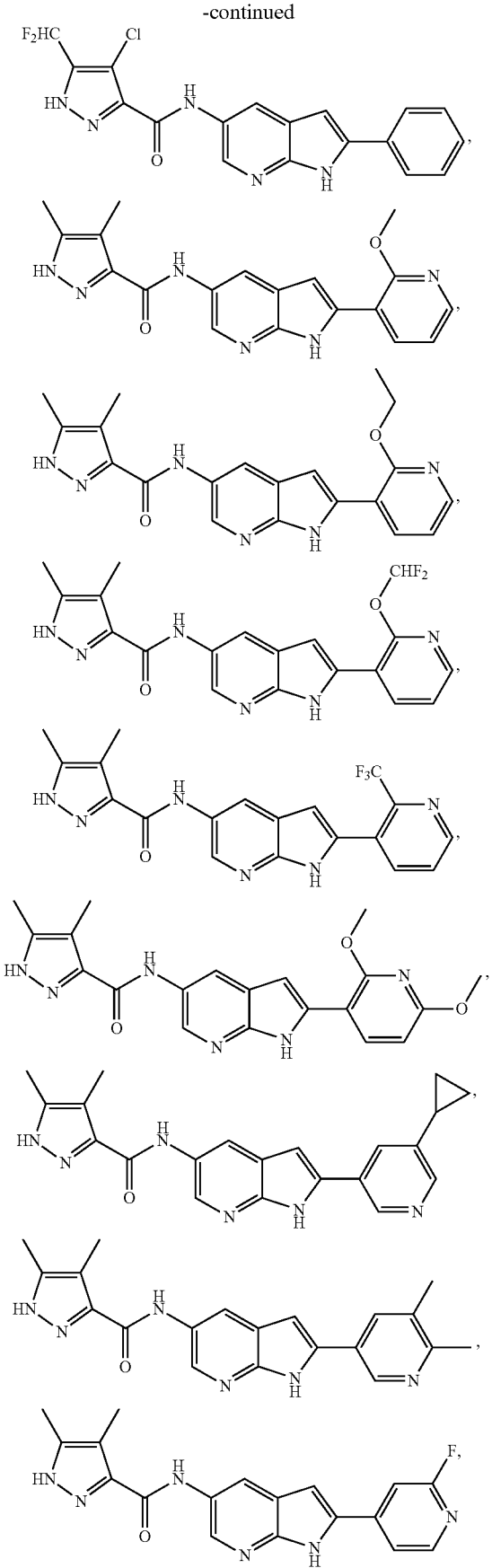
342
-continued
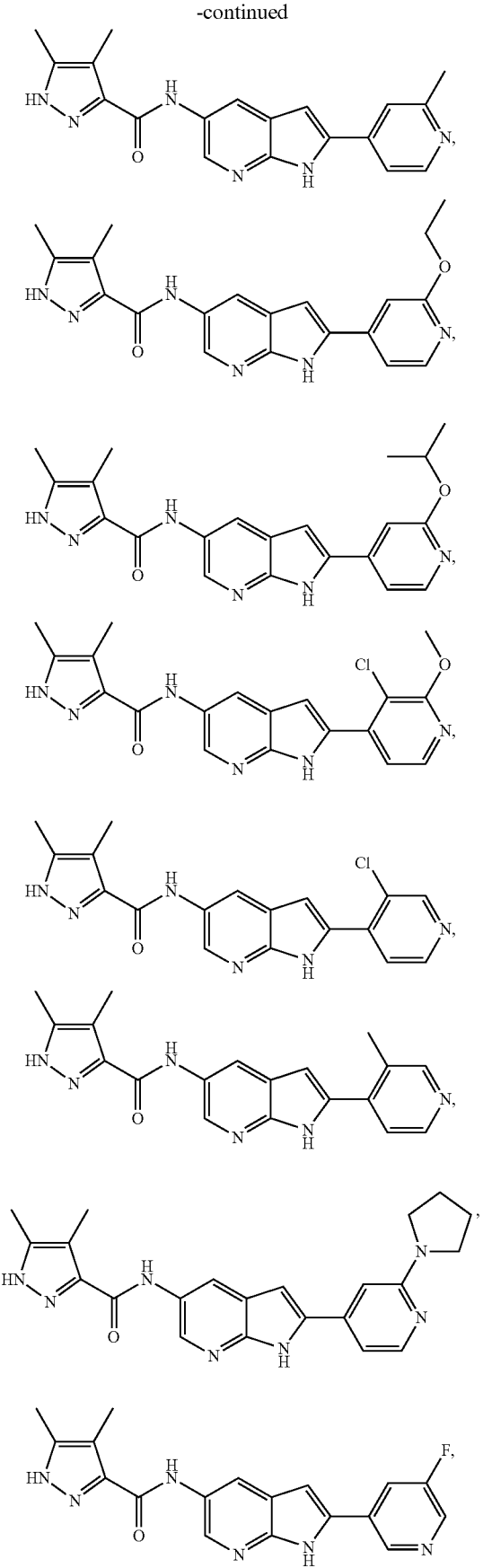

-continued

-continued
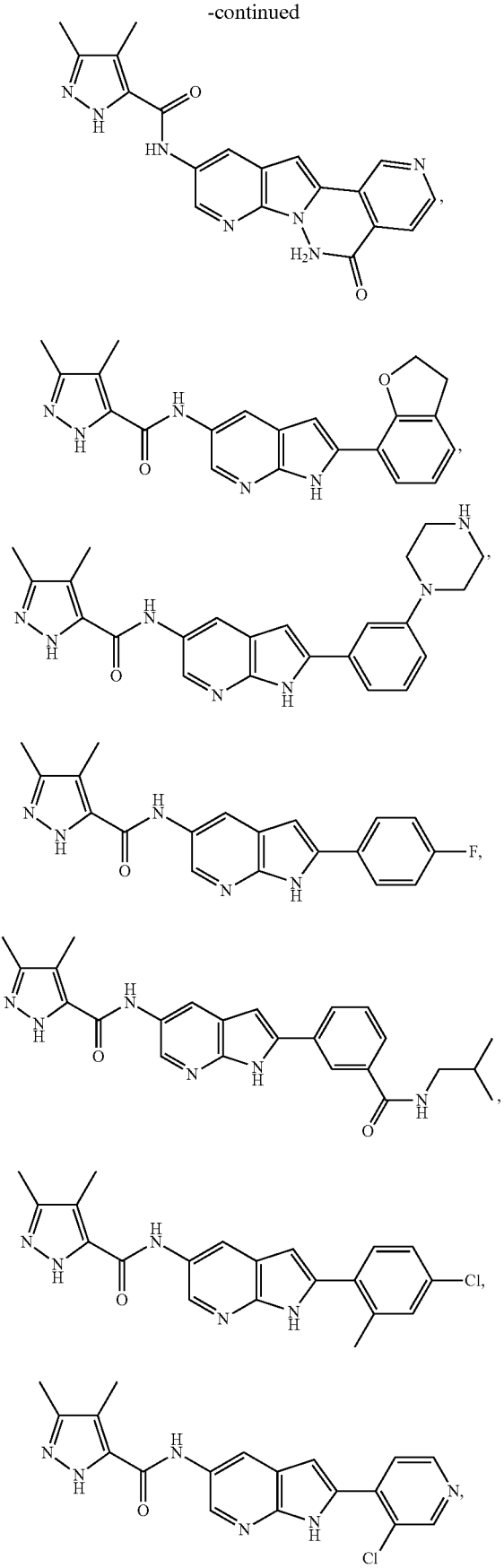
-continued
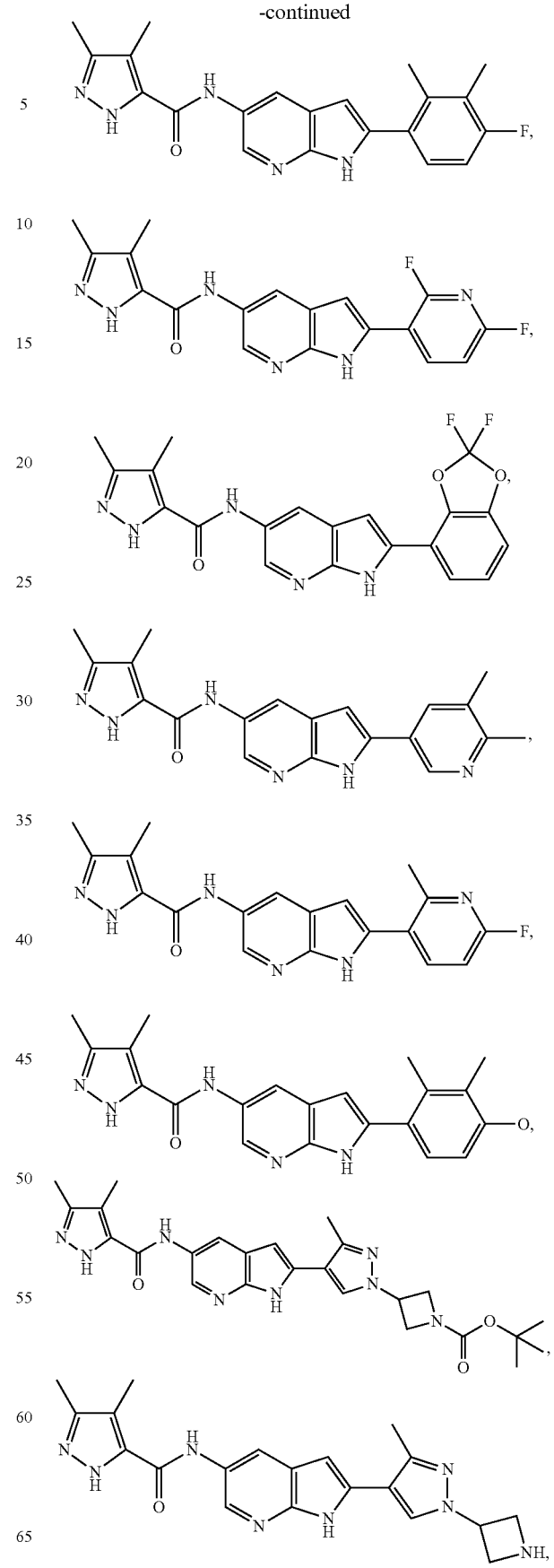

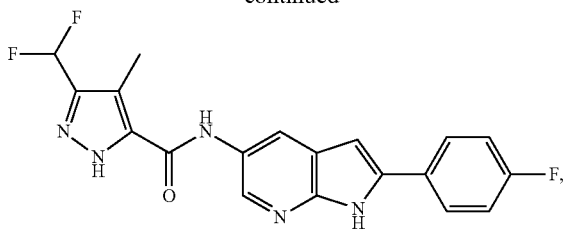
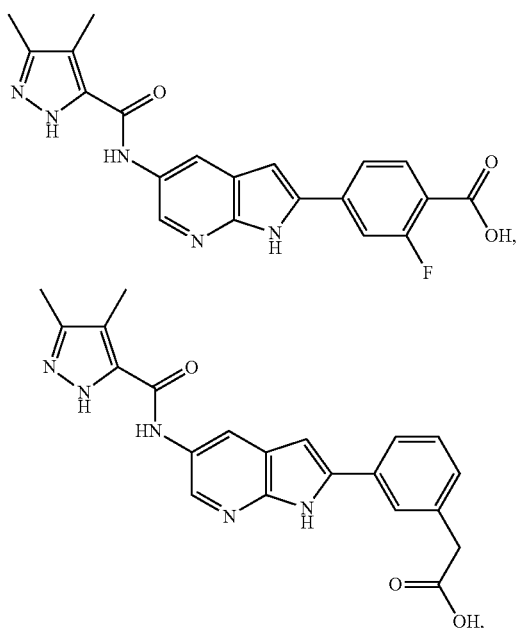
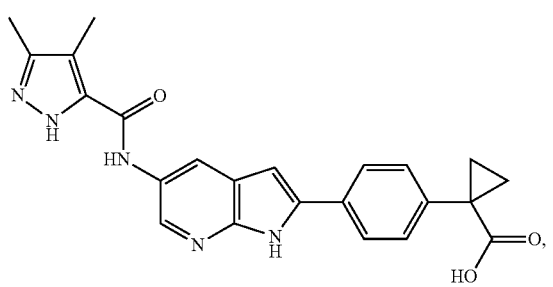
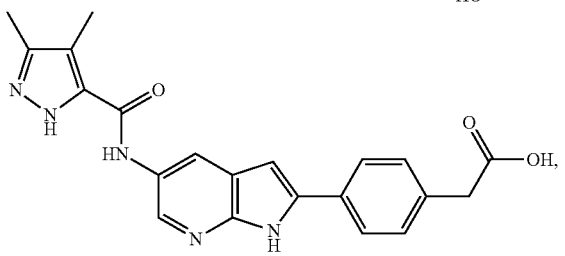
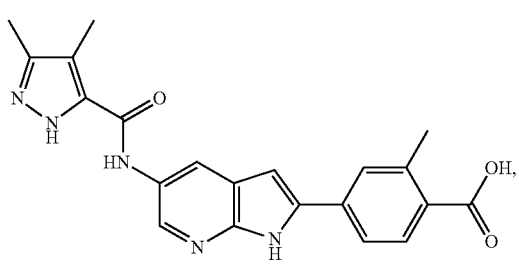
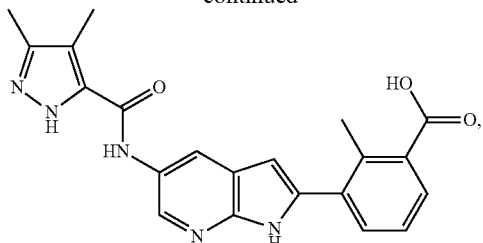
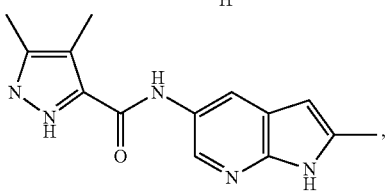
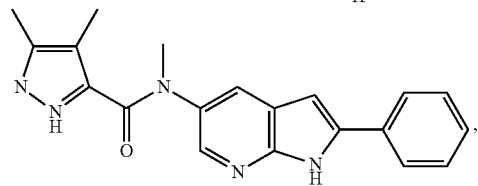
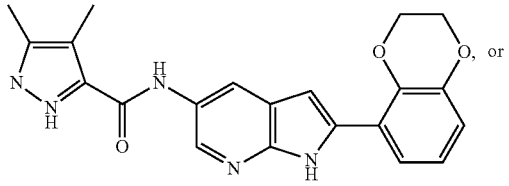
or a pharmaceutically acceptable salt thereof.
12. The method according to claim 3, wherein the compound has the following structure:
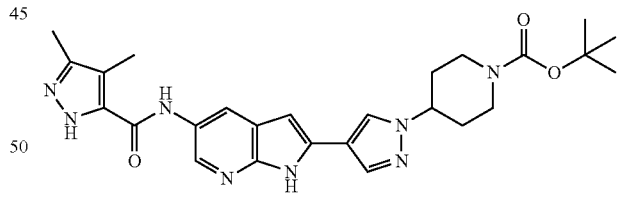
or a pharmaceutically acceptable salt-thereof.
13. The method according to claim 3, wherein the compound has the following structure:
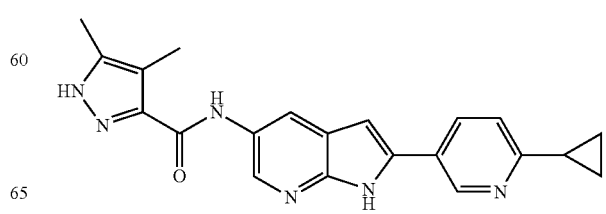
or a pharmaceutically acceptable salt thereof.

14. The method according to claim 3, wherein the compound has the following structure

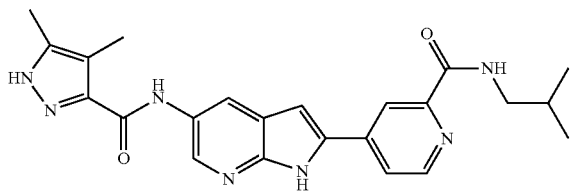 [SMILES: Cc1[nH]nc(C(=O)Nc2cnc3[nH]c(-c4ccnc(C(=O)NCC(C)C)c4)cc3c2)c1C]

or a pharmaceutically acceptable salt thereof.

15. The method according to claim 3, wherein the compound has the following structure:

or a pharmaceutically acceptable salt thereof.

16. The method according to claim 3, wherein the compound has the following structure:

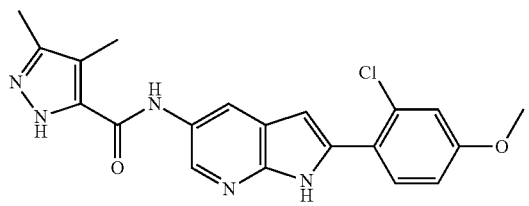 [SMILES: COc1ccc(-c2cc3cc(NC(=O)c4[nH]nc(C)c4C)cnc3[nH]2)c(Cl)c1]

or a pharmaceutically acceptable salt thereof.

17. The method according to claim 3, wherein the compound has the following structure:

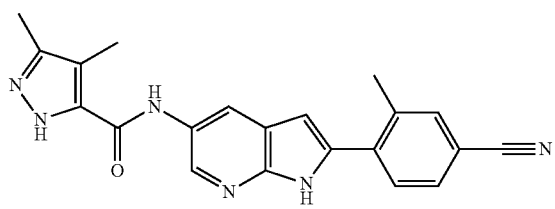 [SMILES: Cc1cc(C#N)ccc1-c1cc2cc(NC(=O)c3[nH]nc(C)c3C)cnc2[nH]1]

or a pharmaceutically acceptable salt thereof.

18. The method according to claim 11, wherein the disease or condition is melanoma, glioma, glioblastoma multiforme, pilocytic astrocytoma, colorectal cancer, thyroid cancer, lung cancer, ovarian cancer, prostate cancer, liver cancer, gallbladder cancer, gastrointestinal stromal tumors, biliary tract carcinoma or cancer-related pain.

19. The method according to any one of claims 12-17, wherein the disease or condition is acute myeloid leukemia, gastrointestinal stromal tumors, or mastocytosis.

20. The method according to claim 1, further comprising administering to the subject a therapeutic agent in combination with the compound having Formula IV, where the therapeutic agent is adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosfamide, uramustine, clarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, zorubicin, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, raltitrexed, tegafur-uracil, thioguanine, trimethoprim, trimetrexate, vidarabine, alemtuzumab, bevacizumab, cetuximab, galiximab, gemtuzumab, panitumumab, pertuzumab, rituximab, brentuximab, tositumomab, trastuzumab, 90 Y ibritumomab tiuxetan, ipilimumab, tremelimumab, anti-CTLA-4 antibodies, anastrozole, androgens, buserelin, diethylstilbestrol, exemestane, flutamide, fulvestrant, goserelin, idoxifene, letrozole, leuprolide, magestrol, raloxifene, tamoxifen, toremifene, DJ-927, docetaxel, TPI 287, larotaxel, ortataxel, paclitaxel, DHA-paclitaxel, tesetaxel, alitretinoin, bexarotene, fenretinide, isotretinoin, tretinoin, demecolcine, homoharringtonine, vinblastine, vincristine, vindesine, vinflunine, vinorelbine; GW786034, neovastat, ABT-510, 2-methoxyestradiol, lenalidomide, thalidomide; a topoisomerase inhibitor, amsacrine, belotecan, edotecarin, etoposide, etoposide phosphate, exatecan, irinotecan, lucanthone, mitoxantrone, pixantrone, rubitecan, teniposide, topotecan, 9-aminocamptothecin; axitinib, dasatinib, erlotinib, gefitinib, flavopiridol, imatinib mesylate, lapatinib, motesanib diphosphate, nilotinib, seliciclib, sorafenib, sunitinib malate, AEE-788, BMS-599626, 7-hydroxystaurosporine, vemurafenib, dabrafenib, PLX3397, selumetinib, and vatalanib, bortezomib, geldanamycin, rapamycin, imiquimod, interferon, interleukin-2; 3-amino-2-carboxyaldehyde thiosemicarbazone, altrasentan, aminoglutethimide, anagrelide, asparaginase, bryostatin-1, cilengitide, elesclomol, eribulin mesylate, ixabepilone, lonidamine, masoprocol, mitoguanazone, oblimersen, sulindac, testolactone, tiazofurin, mTOR inhibitors, PI3K inhibitors, Cdk4 inhibitors, Akt inhibitors, Hsp90 inhibitors, farnesyltransferase inhibitors, or Aromatase inhibitors.

21. The method according to claim 11, further comprising administering to the subject a therapeutic agent in combination with the compound, where the therapeutic agent is adozelesin, altretamine, bendamustine, bizelesin, busulfan, carboplatin, carboquone, carmofur, carmustine, chlorambucil, cisplatin, cyclophosphamide, dacarbazine, estramustine, etoglucid, fotemustine, hepsulfam, ifosfamide, improsulfan, irofulven, lomustine, mannosulfan, mechlorethamine, melphalan, mitobronitol, nedaplatin, nimustine, oxaliplatin, piposulfan, prednimustine, procarbazine, ranimustine, satraplatin, semustine, streptozocin, temozolomide, thiotepa, treosulfan, triaziquone, triethylenemelamine, triplatin tetranitrate, trofosfamide, uramustine, clarubicin, amrubicin, bleomycin, dactinomycin, daunorubicin, doxorubicin, elsamitrucin, epirubicin, idarubicin, menogaril, mitomycin, neocarzinostatin, pentostatin, pirarubicin, plicamycin, valrubicin, zorubicin, aminopterin, azacitidine, azathioprine, capecitabine, cladribine, clofarabine, cytarabine, decitabine, floxuridine, fludarabine, 5-fluorouracil, gemcitabine, hydroxyurea, mercaptopurine, methotrexate, nelarabine, pemetrexed, raltitrexed, tegafur-uracil, thioguanine, trimethoprim, trimetrexate, vidarabine, alemtuzumab, bevacizumab, cetuximab, galiximab, gemtuzumab, panitumumab, pertuzumab, rituximab, brentuximab, tositumomab, trastuzumab, 90 Y ibritumomab tiuxetan, ipilimumab, tremelimumab, anti-CTLA-4 antibodies, anastrozole, androgens, buserelin, diethylstilbestrol, exemestane, flutamide, fulvestrant, goserelin, idoxifene, letrozole, leuprolide, magestrol, raloxifene, tamoxifen, toremifene, DJ-927, docetaxel, TPI 287, larotaxel, ortataxel, paclitaxel, DHA-paclitaxel, tesetaxel, alitretinoin, bexarotene, fenretinide, isotretinoin, tretinoin, demecolcine, homoharringtonine, vinblastine, vincristine, vindesine, vinflunine, vinorelbine; GW786034, neovastat, ABT-510, 2-methoxyestradiol, lenalidomide, thalidomide; a topoisomerase inhibitor, amsacrine, belotecan, edotecarin, etoposide, etoposide phosphate, exatecan, irinotecan, lucanthone, mitoxantrone, pixantrone, rubitecan, teniposide, topotecan, 9-aminocamptothecin; axitinib, dasatinib, erlotinib, gefitinib, flavopiridol, imatinib mesylate, lapatinib, motesanib diphosphate, nilotinib, seliciclib, sorafenib, sunitinib malate, AEE-788, BMS-599626, 7-hydroxystaurosporine, vemurafenib, dabrafenib, PLX3397, selumetinib, and vatalanib, bortezomib, geldanamycin, rapamycin, imiquimod, interferon, interleukin-2; 3-amino-2-carboxyaldehyde thiosemicarbazone, altrasentan, aminoglutethimide, anagrelide, asparaginase, bryostatin-1, cilengitide, elesclomol, eribulin mesylate, ixabepilone, lonidamine, masoprocol, mitoguanazone, oblimersen, sulindac, testolactone, tiazofurin, mTOR inhibitors, PI3K inhibitors, Cdk4 inhibitors, Akt inhibitors, Hsp90 inhibitors, farnesyltransferase inhibitors, or Aromatase inhibitors.

\* \* \* \* \*

SEQUENCE LISTING

<160> NUMBER OF SEQ ID NOS: 3

<210> SEQ ID NO 1
<211> LENGTH: 976
<212> TYPE: PRT
<213> ORGANISM: Homo sapiens

<400> SEQUENCE: 1

```
Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
                20                  25                  30

Glu Pro Ser Pro Pro Ser Ile His Pro Gly Lys Ser Asp Leu Ile Val
            35                  40                  45

Arg Val Gly Asp Glu Ile Arg Leu Leu Cys Thr Asp Pro Gly Phe Val
        50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
    130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
    210                 215                 220

Glu Gly Glu Glu Phe Thr Val Thr Cys Thr Ile Lys Asp Val Ser Ser
225                 230                 235                 240
```

-continued

Ser Val Tyr Ser Thr Trp Lys Arg Glu Asn Ser Gln Thr Lys Leu Gln
            245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
            275                 280                 285

Met Cys Tyr Ala Asn Asn Thr Phe Gly Ser Ala Asn Val Thr Thr Thr
            290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
            325                 330                 335

Tyr Glu Ala Phe Pro Lys Pro Glu His Gln Gln Trp Ile Tyr Met Asn
            340                 345                 350

Arg Thr Phe Thr Asp Lys Trp Glu Asp Tyr Pro Lys Ser Glu Asn Glu
            355                 360                 365

Ser Asn Ile Arg Tyr Val Ser Glu Leu His Leu Thr Arg Leu Lys Gly
            370                 375                 380

Thr Glu Gly Gly Thr Tyr Thr Phe Leu Val Ser Asn Ser Asp Val Asn
385                 390                 395                 400

Ala Ala Ile Ala Phe Asn Val Tyr Val Asn Thr Lys Pro Glu Ile Leu
            405                 410                 415

Thr Tyr Asp Arg Leu Val Asn Gly Met Leu Gln Cys Val Ala Ala Gly
            420                 425                 430

Phe Pro Glu Pro Thr Ile Asp Trp Tyr Phe Cys Pro Gly Thr Glu Gln
            435                 440                 445

Arg Cys Ser Ala Ser Val Leu Pro Val Asp Val Gln Thr Leu Asn Ser
            450                 455                 460

Ser Gly Pro Pro Phe Gly Lys Leu Val Val Gln Ser Ser Ile Asp Ser
465                 470                 475                 480

Ser Ala Phe Lys His Asn Gly Thr Val Glu Cys Lys Ala Tyr Asn Asp
            485                 490                 495

Val Gly Lys Thr Ser Ala Tyr Phe Asn Phe Ala Phe Lys Gly Asn Asn
            500                 505                 510

Lys Glu Gln Ile His Pro His Thr Leu Phe Thr Pro Leu Leu Ile Gly
            515                 520                 525

Phe Val Ile Val Ala Gly Met Met Cys Ile Ile Val Met Ile Leu Thr
            530                 535                 540

Tyr Lys Tyr Leu Gln Lys Pro Met Tyr Glu Val Gln Trp Lys Val Val
545                 550                 555                 560

Glu Glu Ile Asn Gly Asn Asn Tyr Val Tyr Ile Asp Pro Thr Gln Leu
            565                 570                 575

Pro Tyr Asp His Lys Trp Glu Phe Pro Arg Asn Arg Leu Ser Phe Gly
            580                 585                 590

Lys Thr Leu Gly Ala Gly Ala Phe Gly Lys Val Val Glu Ala Thr Ala
            595                 600                 605

Tyr Gly Leu Ile Lys Ser Asp Ala Ala Met Thr Val Ala Val Lys Met
            610                 615                 620

Leu Lys Pro Ser Ala His Leu Thr Glu Arg Glu Ala Leu Met Ser Glu
625                 630                 635                 640

Leu Lys Val Leu Ser Tyr Leu Gly Asn His Met Asn Ile Val Asn Leu
            645                 650                 655

Leu Gly Ala Cys Thr Ile Gly Gly Pro Thr Leu Val Ile Thr Glu Tyr
                660                 665                 670

Cys Cys Tyr Gly Asp Leu Leu Asn Phe Leu Arg Arg Lys Arg Asp Ser
            675                 680                 685

Phe Ile Cys Ser Lys Gln Glu Asp His Ala Glu Ala Ala Leu Tyr Lys
        690                 695                 700

Asn Leu Leu His Ser Lys Glu Ser Ser Cys Ser Asp Ser Thr Asn Glu
705                 710                 715                 720

Tyr Met Asp Met Lys Pro Gly Val Ser Tyr Val Pro Thr Lys Ala
                725                 730                 735

Asp Lys Arg Arg Ser Val Arg Ile Gly Ser Tyr Ile Glu Arg Asp Val
            740                 745                 750

Thr Pro Ala Ile Met Glu Asp Asp Glu Leu Ala Leu Asp Leu Glu Asp
        755                 760                 765

Leu Leu Ser Phe Ser Tyr Gln Val Ala Lys Gly Met Ala Phe Leu Ala
770                 775                 780

Ser Lys Asn Cys Ile His Arg Asp Leu Ala Ala Arg Asn Ile Leu Leu
785                 790                 795                 800

Thr His Gly Arg Ile Thr Lys Ile Cys Asp Phe Gly Leu Ala Arg Asp
                805                 810                 815

Ile Lys Asn Asp Ser Asn Tyr Val Val Lys Gly Asn Ala Arg Leu Pro
            820                 825                 830

Val Lys Trp Met Ala Pro Glu Ser Ile Phe Asn Cys Val Tyr Thr Phe
        835                 840                 845

Glu Ser Asp Val Trp Ser Tyr Gly Ile Phe Leu Trp Glu Leu Phe Ser
850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
                885                 890                 895

Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
        915                 920                 925

Ser Glu Ser Thr Asn His Ile Tyr Ser Asn Leu Ala Asn Cys Ser Pro
930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
                965                 970                 975

<210> SEQ ID NO 2
<211> LENGTH: 5084
<212> TYPE: DNA
<213> ORGANISM: Homo sapiens

<400> SEQUENCE: 2
gatcccatcg cagctaccgc gatgagaggc gctcgcggcg cctgggattt tctctgcgtt     60
ctgctcctac tgcttcgcgt ccagacaggc tcttctcaac catctgtgag tcaggggaa    120 ccgtctccac catccatcca tccaggaaaa tcagacttaa tagtccgcgt gggcgacgag    180
attaggctgt tatgcactga tccgggcttt gtcaaatgga cttttgagat cctggatgaa    240
acgaatgaga ataagcagaa tgaatggatc acggaaaagg cagaagccac caacaccggc    300
aaatacacgt gcaccaacaa acacggctta agcaattcca tttatgtgtt tgttagagat    360

```
cctgccaagc ttttccttgt tgaccgctcc ttgtatggga aagaagacaa cgacacgctg    420
gtccgctgtc ctctcacaga cccagaagtg accaattatt ccctcaaggg gtgccagggg    480
aagcctcttc ccaaggactt gaggtttatt cctgacccca aggcgggcat catgatcaaa    540
agtgtgaaac gcgcctacca tcggctctgt ctgcattgtt ctgtggacca ggagggcaag    600
tcagtgctgt cggaaaaatt catcctgaaa gtgaggccag ccttcaaagc tgtgcctgtt    660
gtgtctgtgt ccaaagcaag ctatcttctt agggaagggg aagaattcac agtgacgtgc    720
acaataaaag atgtgtctag ttctgtgtac tcaacgtgga aaagagaaaa cagtcagact    780
aaactacagg agaaatataa tagctggcat cacggtgact tcaattatga acgtcaggca    840
acgttgacta tcagttcagc gagagttaat gattctggag tgttcatgtg ttatgccaat    900
aatacttttg gatcagcaaa tgtcacaaca accttggaag tagtagataa aggattcatt    960
aatatcttcc ccatgataaa cactacagta tttgtaaacg atggagaaaa tgtagatttg   1020
attgttgaat atgaagcatt ccccaaacct gaacaccagc agtggatcta tatgaacaga   1080
accttcactg ataaatggga agattatccc aagtctgaga tgaaagtaa tatcagatac    1140 gtaagtgaac ttcatctaac gagattaaaa ggcaccgaag gaggcactta cacattccta   1200
gtgtccaatt ctgacgtcaa tgctgccata gcatttaatg tttatgtgaa tacaaaacca   1260
gaaatcctga cttacgacag gctcgtgaat ggcatgctcc aatgtgtggc agcaggattc   1320
ccagagccca aatagattg gtatttttgt ccaggaactg agcagagatg ctctgcttct   1380
gtactgccag tggatgtgca gacactaaac tcatctgggc caccgtttgg aaagctagtg   1440
gttcagagtt ctatagattc tagtgcattc aagcacaatg gcacggttga atgtaaggct   1500
tacaacgatg tgggcaagac ttctgcctat tttaactttg catttaaagg taacaacaaa   1560
gagcaaatcc atccccacac cctgttcact cctttgctga ttggtttcgt aatcgtagct   1620
ggcatgatgt gcattattgt gatgattctg acctacaaat atttacagaa acccatgtat   1680
gaagtacagt ggaaggttgt tgaggagata aatggaaaca attatgttta catagaccca   1740
acacaacttc cttatgatca caatgggag tttcccagaa acaggctgag tttgggaaa    1800 accctgggtg ctggagcttt cgggaaggtt gttgaggcaa ctgcttatgg cttaattaag   1860
tcagatgcgg ccatgactgt cgctgtaaag atgctcaagc cgagtgccca tttgacagaa   1920
cgggaagccc tcatgtctga actcaaagtc ctgagttacc ttggtaatca catgaatatt   1980
gtgaatctac ttgagcctg caccattgga gggcccaccc tggtcattac agaatattgt    2040
tgctatggta tcttttgaa ttttttgaga agaaaacgtg attcatttat ttgttcaaag   2100
caggaagatc atgcagaagc tgcactttat aagaatcttc tgcattcaaa ggagtcttcc   2160
tgcagcgata gtactaatga gtacatggac atgaaacctg gagtttctta tgttgtccca   2220
accaaggccg acaaaggag atctgtgaga ataggctcat acatagaaag agatgtgact   2280
cccgccatca tggaggatga cgagttggcc ctagacttag aagacttgct gagcttttct   2340
taccaggtgg caaagggcat ggcttttctc gcctccaaga attgtattca cagagacttg   2400
gcagccagaa atatcctcct tactcatggt cggatcacaa agatttgtga ttttggtcta   2460
gccagagaca tcaagaatga ttctaattat gtggttaaag aaacgctcg actacctgtg   2520 aagtggatgg cacctgaaag cattttcaac tgtgtataca cgtttgaaag tgacgtctgg   2580
tcctatggga ttttctttg ggagctgttc tctttaggaa gcagcccta tcctggaatg    2640 ccggtcgatt ctaagttcta caagatgatc aaggaaggct tccggatgct cagccctgaa   2700
cacgcacctg ctgaaatgta tgacataatg aagacttgct gggatgcaga tcccctaaaa   2760
```

-continued

```
agaccaacat tcaagcaaat tgttcagcta attgagaagc agatttcaga gagcaccaat    2820
catatttact ccaacttagc aaactgcagc cccaaccgac agaagcccgt ggtagaccat    2880
tctgtgcgga tcaattctgt cggcagcacc gcttcctcct cccagcctct gcttgtgcac    2940
gacgatgtct gagcagaatc agtgtttggg tcacccctcc aggaatgatc tcttcttttg    3000
gcttccatga tggttatttt ctttctttc aacttgcatc caactccagg atagtgggca     3060
ccccactgca atcctgtctt tctgagcaca ctttagtggc cgatgatttt tgtcatcagc    3120
caccatccta ttgcaaaggt tccaactgta tatattccca atagcaacgt agcttctacc    3180
atgaacagaa aacattctga tttggaaaaa gagagggagg tatggactgg gggccagagt    3240
cctttccaag gcttctccaa ttctgcccaa aaatatggtt gatagtttac ctgaataaat    3300
ggtagtaatc acagttggcc ttcagaacca tccatagtag tatgatgata caagattaga    3360
agctgaaaac ctaagtcctt tatgtggaaa acagaacatc attagaacaa aggacagagt    3420
atgaacacct gggcttaaga aatctagtat ttcatgctgg gaatgagaca taggccatga    3480
aaaaaatgat ccccaagtgt gaacaaaaga tgctcttctg tggaccactg catgagcttt    3540
tatactaccg acctggtttt taaatagagt ttgctattag agcattgaat tggagagaag    3600
gcctccctag ccagcacttg tatatacgca tctataaatt gtccgtgttc atacatttga    3660
ggggaaaaca ccataaggtt tcgtttctgt atacaaccct ggcattatgt ccactgtgta    3720
tagaagtaga ttaagagcca tataagtttg aaggaaacag ttaataccat tttttaagga    3780
aacaatataa ccacaaagca cagtttgaac aaaatctcct cttttagctg atgaacttat    3840
tctgtagatt ctgtggaaca agcctatcag cttcagaatg gcattgtact caatggatt     3900
gatgctgttt gacaaagtta ctgattcact gcatggctcc cacaggagtg ggaaaacact    3960
gccatcttag tttggattct tatgtagcag gaaataaagt ataggtttag cctccttcgc    4020
aggcatgtcc tggacaccgg gccagtatct atatatgtgt atgtacgttt gtatgtgtgt    4080
agacaaatat ttggaggggt attttttgccc tgagtccaag agggtccttt agtacctgaa   4140
aagtaacttg gctttcatta ttagtactgc tcttgtttct tttcacatag ctgtctagag    4200
tagcttacca gaagcttcca tagtggtgca gaggaagtgg aaggcatcag tccctatgta    4260
tttgcagttc acctgcactt aaggcactct gttatttaga ctcatcttac tgtacctgtt    4320
ccttagacct tccataatgc tactgtctca ctgaaacatt taaattttac cctttagact    4380
gtagcctgga tattattctt gtagtttacc tctttaaaaa caaacaaaa caaacaaaa      4440
aactccccctt cctcactgcc aatataaaa ggcaaatgtg tacatggcag agtttgtgtg    4500
ttgtcttgaa agattcagt atgttgcctt tatggtttcc cccttctaca tttcttagac    4560
tacatttaga gaactgtggc cgttatctgg aagtaaccat ttgcactgga gttctatgct    4620
ctcgcacctt tccaaagtta acagatttg gggttgtgtt gtcacccaag agattgttgt    4680
ttgccatact ttgtctgaaa aattcctttg tgtttctatt gacttcaatg atagtaagaa    4740
aagtggttgt tagttataga tgtctaggta cttcaggggc acttcattga gagttttgtc    4800
ttgccatact ttgtctgaaa aattcctttg tgtttctatt gacttcaatg atagtaagaa    4860
aagtggttgt tagttataga tgtctaggta cttcaggggc acttcattga gagttttgtc    4920
aatgtcttt gaatattccc aagcccatga gtccttgaaa atattttta tatatacagt      4980
aactttatgt gtaaatacat aagcggcgta agtttaaagg atgttggtgt tccacgtgtt    5040
ttattcctgt atgttgtcca attgttgaca gttctgaaga attc                     5084
```

```
<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 3

His His His His His His
1               5
```